US009175260B2

(12) United States Patent
Dalton et al.

(10) Patent No.: US 9,175,260 B2
(45) Date of Patent: Nov. 3, 2015

(54) EARLY MESODERM CELLS, A STABLE POPULATION OF MESENDODERM CELLS THAT HAS UTILITY FOR GENERATION OF ENDODERM AND MESODERM LINEAGES AND MULTIPOTENT MIGRATORY CELLS (MMC)

(75) Inventors: Stephen Dalton, Athens, GA (US); David Reynolds, Athens, GA (US)

(73) Assignee: The University of Georgia Research Foundation, Inc., Athens, GA (US)

(*) Notice: Subject to any disclaimer, the term of this patent is extended or adjusted under 35 U.S.C. 154(b) by 1013 days.

(21) Appl. No.: 12/449,237

(22) PCT Filed: Jan. 30, 2008

(86) PCT No.: PCT/US2008/001222
§ 371 (c)(1),
(2), (4) Date: Jan. 29, 2010

(87) PCT Pub. No.: WO2008/094597
PCT Pub. Date: Aug. 7, 2008

(65) Prior Publication Data
US 2010/0166713 A1 Jul. 1, 2010

Related U.S. Application Data

(60) Provisional application No. 60/898,204, filed on Jan. 30, 2007, provisional application No. 60/994,354, filed on Sep. 19, 2007.

(51) Int. Cl.
| *C12N 5/02* | (2006.01) |
| *C12N 5/00* | (2006.01) |
| *C12N 5/071* | (2010.01) |
| *A61K 35/12* | (2015.01) |
| *C12N 5/07* | (2010.01) |
| *C12N 5/073* | (2010.01) |
| *C12N 5/0735* | (2010.01) |

(52) U.S. Cl.
CPC ............ *C12N 5/0603* (2013.01); *C12N 5/0606* (2013.01); *C12N 2500/99* (2013.01); *C12N 2501/155* (2013.01); *C12N 2501/16* (2013.01); *C12N 2501/195* (2013.01); *C12N 2501/415* (2013.01); *C12N 2501/70* (2013.01); *C12N 2506/02* (2013.01)

(58) Field of Classification Search
CPC .................. C12N 2501/195; C12N 2501/155; C12N 2501/70; C12N 5/0603; C12N 2501/415; C12N 2506/02; C12N 5/0606; C12N 2501/16
See application file for complete search history.

(56) References Cited

U.S. PATENT DOCUMENTS

| 4,557,264 A | 12/1985 | Hinsch |
| 5,567,612 A | 10/1996 | Vacanti et al. |
| 5,759,830 A | 6/1998 | Vacanti et al. |
| 5,770,417 A | 6/1998 | Vacanti et al. |
| 5,843,780 A | 12/1998 | Thomson |
| 6,022,743 A | 2/2000 | Naughton et al. |
| 6,306,424 B1 | 10/2001 | Vyakarnam et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,509,369 B2 | 1/2003 | Scott et al. |
| 6,534,084 B1 | 3/2003 | Vyakarnam et al. |
| 6,599,323 B2 | 7/2003 | Melican et al. |
| 6,626,950 B2 | 9/2003 | Brown et al. |
| 6,642,048 B2 | 11/2003 | Xu et al. |
| 6,656,488 B2 | 12/2003 | Yi et al. |
| 6,793,945 B2 | 9/2004 | Bathurst et al. |
| 2002/0072117 A1 | 6/2002 | Xu et al. |
| 2004/0062753 A1 | 4/2004 | Rezania et al. |
| 2004/0132729 A1 | 7/2004 | Salituro et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2005/0148070 A1 | 7/2005 | Thomson et al. |
| 2005/0233446 A1 | 10/2005 | Parsons et al. |
| 2006/0003446 A1 | 1/2006 | Keller |
| 2006/0030042 A1 | 2/2006 | Brinvanlou |

(Continued)

FOREIGN PATENT DOCUMENTS

| WO | 2005014799 A1 | 2/2005 |
| WO | 2005065354 A2 | 7/2005 |

(Continued)

OTHER PUBLICATIONS

Verfaillie et al. Hematology (Am Soc Hematol Educ Program). 2002;:369-91.*
Hoffman et al. Nature Biotech., 23(6): 699-708, 2005.*
Meijer et al., Trends in Pharmacological Sciences, 25(9): 471-480, 2004.*
Mikels et al., Oncogene, 25: 7461-7468, 2006.*
Ducy et al., Kidney International, 57: 2207-2214, 2000.*
Shimasaki et al., Endocrine Reviews, 25(1): 72-101, 2004.*
Lu et al. Defined culture conditions of human embryonic stem cells. Proceedings of the National Academy of Sciences USA 2006, 103(15), 5688-5693.
Moretti et al. Multipotent Embryonic Isl1+ Progenitor Cells Lead to Cardiac, Smooth Muscle, and Endothelial Cell Diversification. Cell 2006, 127, 1151-1165.

(Continued)

*Primary Examiner* — Thaian N Ton
(74) *Attorney, Agent, or Firm* — Henry D. Coleman; R. Neil Sudol

(57) ABSTRACT

The present invention relates to the production of multipotent migratory cell (MMCs) which can be differentiated into mesoderm or endoderm lineages. Multipotent Migratory Cells (MMC) are stable and robust and can be passaged at least 20 times (perhaps indefinitely), can be recovered after freezing, reamplified and differentiated into multiple lineages. They are therefore storage stable. The method of producing these cells points to a way to generate a multipotent cell type (mesendoderm) from blastocycts for the generation of therapeutically useful cell types without going through a classical hESC state. The production of multipotent migratory cells, mesendoderm cells and mesoderm cells (Isl1+) is also described.

40 Claims, 52 Drawing Sheets

(56) References Cited

U.S. PATENT DOCUMENTS

| | | | |
|---|---|---|---|
| 2006/0147435 A1 | 7/2006 | Moon et al. | |
| 2006/0246446 A1 | 11/2006 | Evans | |
| 2007/0010011 A1 | 1/2007 | Parsons et al. | |
| 2007/0254359 A1* | 11/2007 | Rezania et al. | 435/325 |
| 2008/0226558 A1 | 9/2008 | Keller | |
| 2009/0181453 A1 | 7/2009 | Keller | |
| 2009/0269314 A1 | 10/2009 | Keller | |

FOREIGN PATENT DOCUMENTS

| | | |
|---|---|---|
| WO | 2005086845 A2 | 9/2005 |
| WO | 2007143193 A1 | 12/2007 |
| WO | 2008054819 A2 | 5/2008 |
| WO | 2008094597 A2 | 8/2008 |
| WO | 2010011352 A2 | 1/2010 |

OTHER PUBLICATIONS

Sato et al. Maintenance of pluripotency in human and mouse embryonic stem cells through activation of Wnt signaling by a pharmacological GSK-3-specific inhibitor. Nature Medicine 2004, 10(1), 55-63.

Lindsley et al. Canonical Wnt signaling is required for development of embryonic stem cell-derived mesoderm. Development 2006, 133, 3787-3796.

Dravid et al. Defining the Role of Wnt/beta-Catenin Signaling in the Survival, Proliferation, and Self-Renewal of Human Embryonic Stem Cells. Stem Cells 2005, 23, 1489-1501.

Schuldiner et al. Effects of eight growth factors on the differentiation of cells derived from human embryonic stem cells. Proceedings of the National Academy of Sciences USA 2000, 97,11307-11312.

Bakre et al. Generation of Multipotential Mesendodermal Progenitors from Mouse Embryonic Stem Cells via Sustained Wnt Pathway Activation. Journal of Biological Chemistry 2007, 282, 31703-31712.

McLean et al. Activin A Efficiently Specifies Definitive Endoderm from Human Embryonic Stem Cells Only When Phosphatidylinositol 3-Kinase Signaling Is Suppressed. Stem Cells 2007, 25, 29-38.

Amit et al. Human Feeder Layers for Human Embryonic Stem Cells, Biology of Reproduction 2003, 68, 2150-2156.

Carpenter et al. Characterization and Differentiation of Human Embryonic Stem Cells. Cloning and Stem Cells 2003, 5(1), 79-88.

Carpenter et al. Properties of Four Human Embryonic Stem Cell Lines Maintained in a Feeder-Free Culture System. Developmental Dynamics 2004, 229, 243-258.

Cheon et al. Defomed Feeder-Free Culture System of Human Embryonic Stem Cells. Biology of Reproduction 2006, 74, 611—Retraction.

Cooper et al. Biochemical properties of a keratan sulphate/chondroitin sulphate proteoglycan expressed in primate pluripotent stem cells. Journal of Anatomy 2002, 200, 259-265.

Draper et al. Surface antigens of human embryonic stem cells: changes upon differentiation in culture. Journal of Anatomy 2002, 200, 249-258.

Ginis et al. Differences between human and mouse embryonic stem cells. Developmental Biology 2004, 269, 360-380.

Inzunza et al. Derivation of Human Embryonic Stem Cell Lines in Serum Replacement Medium Using Postnatal Human Fibroblasts as Feeder Cells. Stem Cells 2005, 23, 544-549.

Levenstein et al. Basic Fibroblast Growth Factor Support of Human Embryonic Stem Cell Self-Renewal. Stem Cells 2006, 24, 568-574.

Ludwig et al. Derivation of human embryonic stem cells in defined conditions. Nature Biotechnology 2006, 24, 185-187.

Miyamoto et al. Human Placenta Feeder Layers Support Undifferentiated Growth of Primate Embryonic Stem Cells. Stem Cells 2004, 23, 433-440.

Oka et al. CD9 is Associated with Leukemia Inhibitory Factor-mediated Maintenance of Embryonic Stem Cells. Molecular Biology of the Cell 2002, 13, 1274-1281.

Rathjen et al. Formation of a primitive ectoderm like cell population,EPL cells, from ES cells in response to biologically derived factors. Journal of Cell Science 1999, 112, 601-612.

Reubinoff et al. Embryonic stem cell lines from human blastocysts: somatic differentiation in vitro. Nature Biotechnology 2000, 18, 399-404.

Richards et al. Comparative Evaluation of Various Human Feeders for Prolonged Undifferentiated Growth of Human Embryonic Stem Cells. Stem Cells 2003, 21,546-556.

Stojkovic et al. An Autogeneic Feeder Cell System That Efficiently Supports Growth of Undiffereniated Human Embryonic Stem Cells. Stem Cells 2005, 23, 306-314.

Takahashi et al. Induction of Pluripotent Stem Cells from Mouse Embryonic and Adult Fibroblast Cultures by Defined Factors. Cell 2006, 126, 663-676.

Tesar et al. New cell lines from mouse epiblast share defining features with human embryonic stem cells. Nature 2007, 448, 196-202.

Thomson et al. Isolation of a primate embryonic stem cell line. Proceedings of the National Academy of Sciences USA 1995, 92, 7844-7848.

Vacanti et al. Selective cell Transplantation Using Bioabsorbable Artificial Polymers as Matricies. Journal of Pediatric Surgery 1988, 23, 3-9.

Vunjak-Novakovic et al. Dynamic Cell Seeding of Polymer Scaffolds for Cartilage Tissue Engineering. Biotechnology Prog. 1998, 14, 193-202.

Wang et al. Derivation and Growing Human Embryonic Stem Cells on Feeders Derived from Themselves. Stem Cells 2005, 23, 1221-1227.

Wang et al. Self-renewal of human embryonic stem cells requires insulin-like growth factor-1 receptor and ERBB2 receptor signaling. Bloood 2007, 1 10, 4111-4119.

Xu et al. Immortalized Fibroblast-Like Cells Derived from Human Embryonic Stem Cells Support Undifferentiated Cell Growth. Stem Cells 2004, 22, 972-980.

Yang et al. Novel cell immobilization method utilizing centrifugal force to achieve high-density hepatocyte culture in porous scaffold. J. Biomed. Mater. Res. 2001, 55(3), 379-386.

Glover (Editor). DNA Cloning a Practical Approach vols. 1-2, 1985, IRL Press Limited, Oxford, England.

Hames and Higgins (Editors). Nucleic Acid Hybridisation a Practical Approach, 1985, IRL Press Limited, Oxford, England.

Maniatis, Fritsch and Sambrook. Molecular Cloning a Laboratory Manual, 1982, Cold Spring Harbor Laboratory, Cold Spring Harbor, New York.

Miller. Experiments in Molecular Genetics, 1972, Cold Spring Harbor Laboratory, Cold Spring Harbor, New York.

Old and Primrose. Principles of Gene Manipulation an Introduction to Genetic Engineering, 1981, University of Califomia Press, Berkeley, California.

Schleif and Wensink. Practical Methods in Molecular Biology, 1981, Springer-Verlag New York, Inc., New York, New York.

Rieger, Michaelis and Green. Glossary of Genetics Classical and Molecular Fifth Edition, 1991, Springer-Verlag, New York, New York.

Sambrook, Fritsch and Maniatis. Molecular Cloning a Laboratory Manual Second Edition, 1989, Cold Spring Harbor Laboratory Press, Plainview, New York.

Setlow and Hollaender (Editors). Genetic Engineering Principles and Methods vols. 1-4, 1979-1982, Plenum Press, New York, New York.

Thomson et al. Primate Embryonic Stem Cells. In: Current Topics in Developmental Biology (1988, Academic Press, New York) vol. 38, pp. 133-165.

Wu (Editor). Methods in Enzymology vol. 68 Recombinant DNA, 1979, Academic Press (Elsevier Inc.) New York.

Wu (Editor). Methods in Enzymology vol. 218 Recombinant DNA Part 1, 1993, Academic Press (Elsevier Inc.) New York.

Wu, Grossman and Moldave (Editors). Methods in Enzymology vol. 65 Recombinant DNA Part C, 1980, Academic Press (Elsevier Inc.) New York.

Wu, Grossman and Moldave (Editors). Methods in Enzymology vol. 100 Recombinant DNA Part B, 1983, Academic Press (Elsevier Inc.) New York.

(56) References Cited

OTHER PUBLICATIONS

Wu, Grossman and Moldave (Editors). Methods in Enzymology vol. 101 Recombinant DNA Part C, 1983, Academic Press (Elsevier Inc.) New York.

Murashow, A.K. et al., Directed Differentiation of Embryonic Stem Cells into Dorsal Neurons, The FASB Journal express article, Nov. 1999, p. 1-18.

Thomson, J.A. et a., Embryonic Stem Cell Lines Derived from Human Blastocysts, *Science*, Nov. 1998, vol. 282, p. 1145-1148.

Lindsey, R.C., et al., Canonical Wnt Signaling is Required for Development of Embryonic Stem Cell-Derived Mesoderm, *Development*, 2006, p. 3787-3796.

Wang, G. et al, Noggin and bFGF Cooperate to Mainteain the Pluripotency of Human Embryonic Stem Cells in the Absence of Feeder Layers, *Biochem. and Biophys. Res. Comm.*, 2005, vol. 330, p. 934-942.

Sato, N., et al., Manipulation of Self-Renewal in Human Embryonic Stem Cells Through a Novel Pharmocological GSK-3 Inhibitor, *Methods in Mol. Biology*, Ed. Turksen, 2006, vol. 331, p. 115-128.

Xiao, L. et al., Activin A Maintains Self-Renewal and Regulates Fibrobast Growth Factor, Wnt, and Bone Morphogenic Protein Pathways in Human Embryonic Stem Cells, *Stem Cells*, 2006, vol. 24, p. 1476-1486.

Capsi, O. et al., Potential Applications of Human Embryonic Stem Cell-Derived Cardiomyocytes, *Ann. N.Y. Acad. Sci.*, 2004, col. 1015, p. 285-298.

Gepstein, L., Derivation and Applications of Human Embryonic Stem Cells, *Circ. Res.*, 2002, vol. 91, p. 866-876.

* cited by examiner

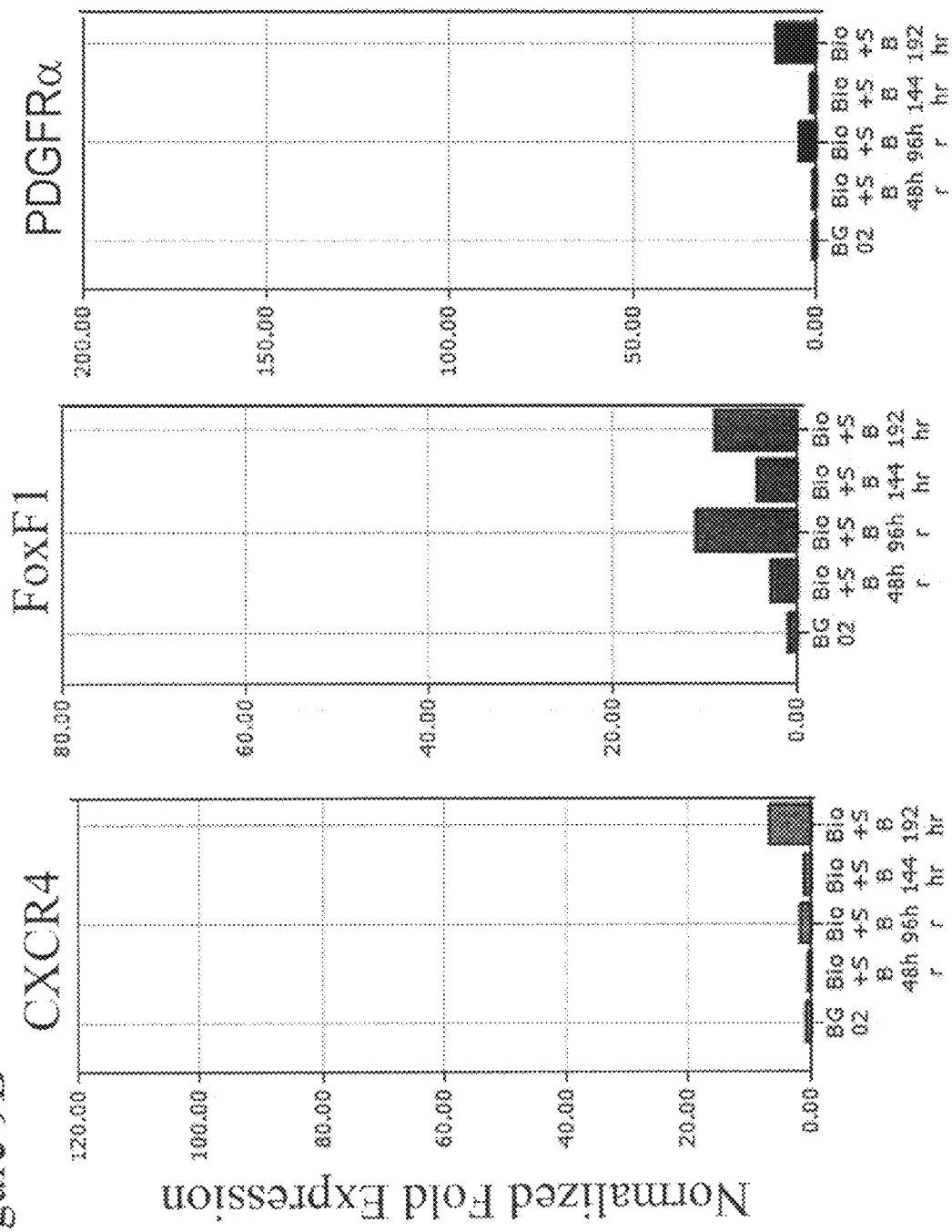

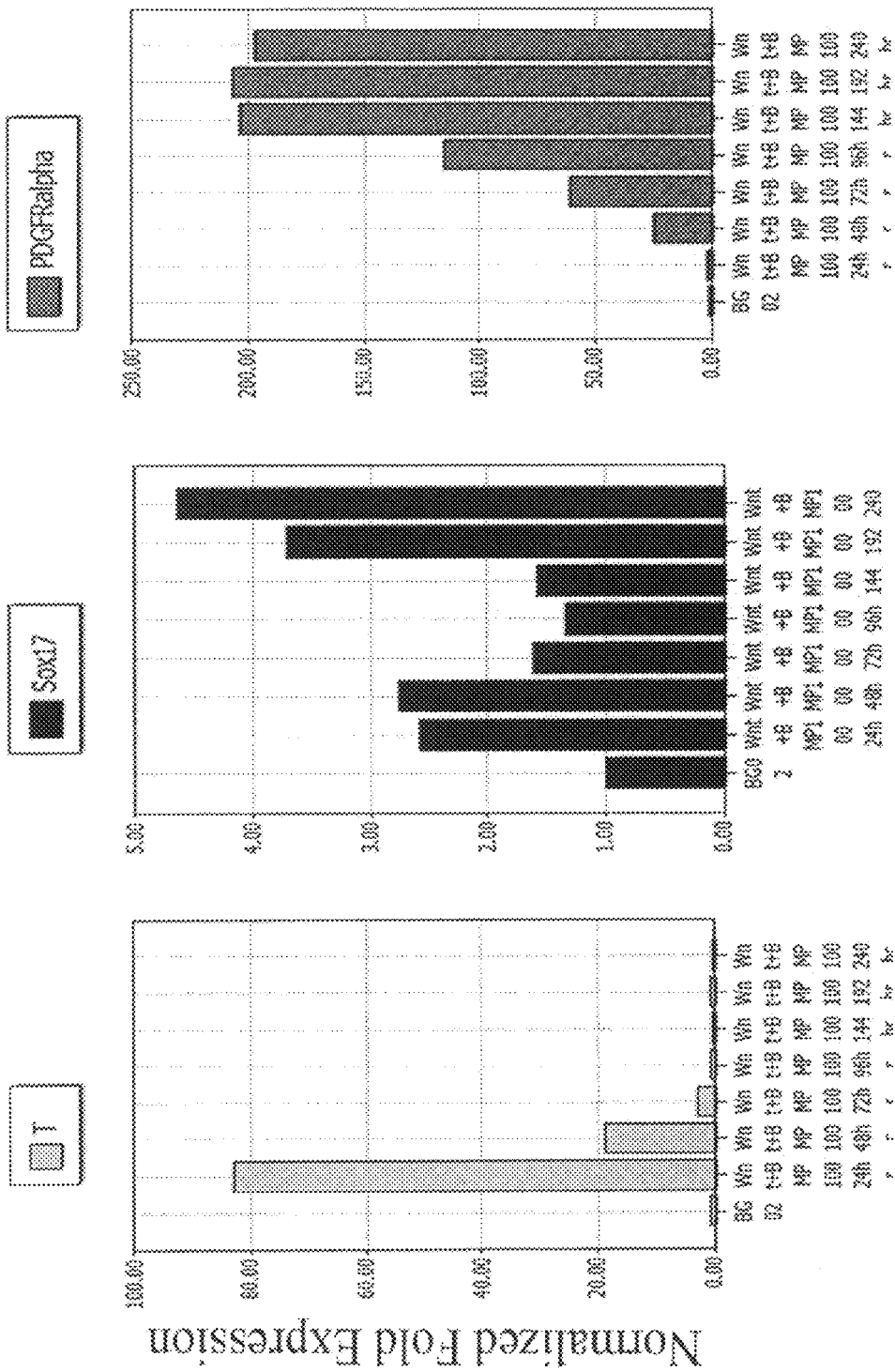

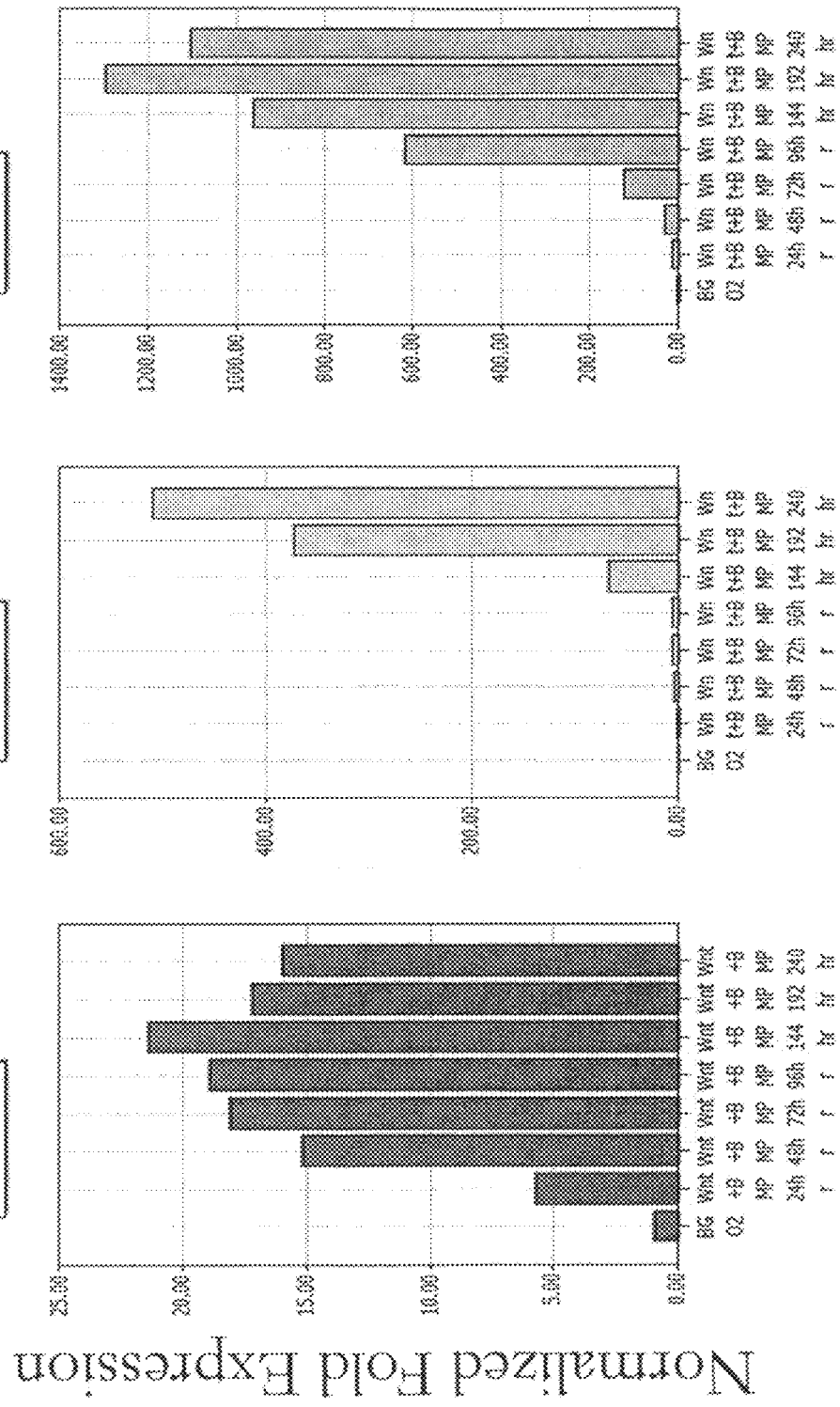

BIO + BMP4 MEF-CM 5 days, 20x

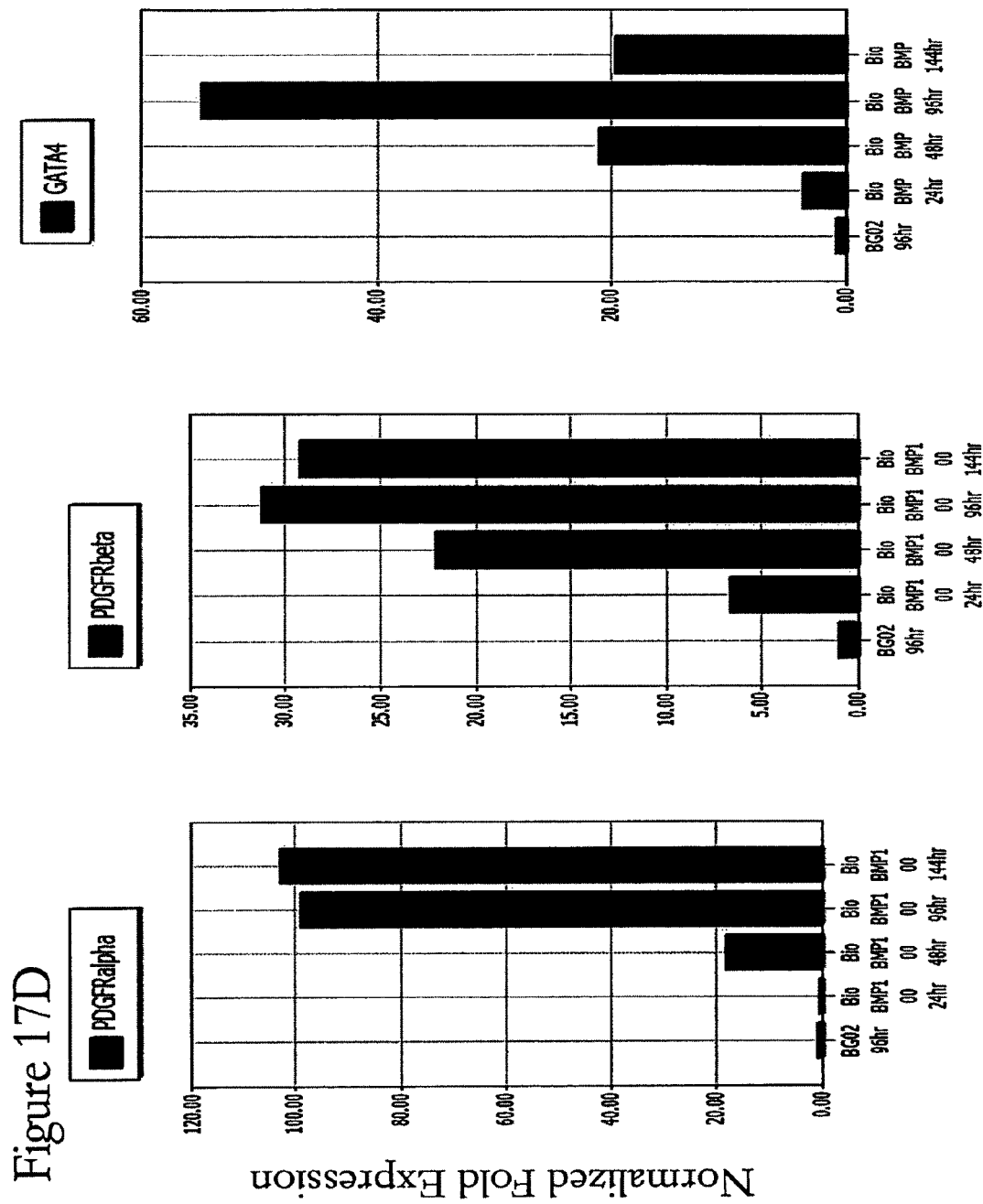

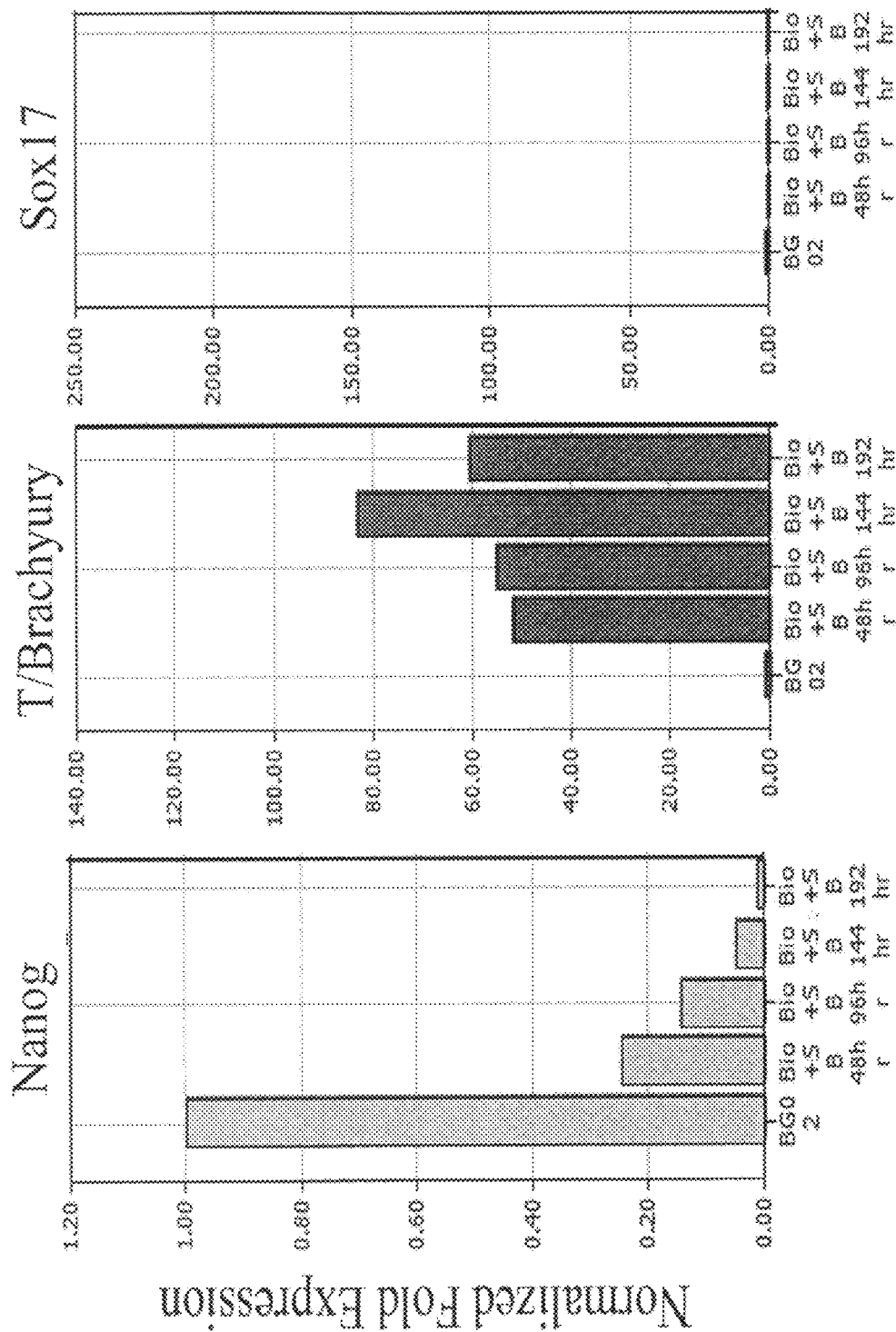

A.

B.

Pre Freeze

Post Freeze

C.

Post Sort

CXCR4 sorted cells

MMC P19

EARLY MESODERM CELLS, A STABLE POPULATION OF MESENDODERM CELLS THAT HAS UTILITY FOR GENERATION OF ENDODERM AND MESODERM LINEAGES AND MULTIPOTENT MIGRATORY CELLS (MMC)

RELATED APPLICATIONS

This application claims the benefit of priority of provisional applications U.S. 60/898,204, filed Jan. 30, 2007 and U.S. 60/994,354, filed Sep. 19, 2007, both of which applications are incorporated by reference in their entirety herein.

FIELD OF THE INVENTION

The present invention relates to the generation of early mesoderm cells from primate Pluripotent Stem cells (pPSCs), especially including hESCs, and new methods for mesoderm differentiation. These approaches can generate a key multipotent precursor that has potential to form cardiac, smooth muscle and endothelial lineages. This approach works for all hESC lines, including BG01 and BG02.

The present invention also relates to the production of a stable multipotent migratory cell (MMC) which can be differentiated into mesoderm or endoderm lineages. MMCs can be passaged at least 20 times (perhaps indefinitely), can be recovered after freezing, reamplified and differentiated into multiple lineages. The method of producing these cells points to a way to generate a multipotent cell type (MMC) from blastocycts for the generation of therapeutically useful cell types without going through a classical hESC state.

The invention also relates to methods of making mesendoderm cells from pPSCs, especially hESCs, methods of making defined definitive endoderm cells, methods of making MMCs, methods of making mesoderm precursors (IMPs) and cellular therapeutics for cardiovascular disease.

BACKGROUND OF THE INVENTION

Human embryonic stem cells (hESC's) (markers for hESCs include SSEA3, SSEA4, TRA-1-60, TRA-1-81 antigens, Nanog, Oct4) are a pluripotent population of cells that can be differentiated into cells derived from all three embryonic germ layers and extraembryonic lineages. This property of hESC's has important implications in cell therapy (e.g. diabetes, heart disease, neurodegenerative diseases), drug discovery and developmental modeling.

Other pluripotent cell types have been identified in mouse. Primitive ectoderm like (EPL; Rathjen et al., 1999, J. Cell Sci) cells were shown to form from mESC's with the ability to dedifferentiate into mESC's. Recently, a new mouse cell, post-implantation epiblast stem cells (EpiSC; Tesar et al., Nature 448: 196-202; 2007) was identified that shares characteristics of hESC's (Nanog+ Sox2+Oct4+). All of these pluripotent cell types from mouse can generate the three embryonic germ layer in vitro or in a teratoma assay.

Epiblast stem cells (EpiScs) and induced pluripotent stem cells (iPS) fit into the broad pluripotent cell category and in concept, the technology described in the application could apply to these and other pluripotent cell types (ie, primate pluripotent cells). EpiSc epiblast stem cells are isolated from early post-implantation stage embryos and express Oct4 and are pluripotent (Tesar et al, Nature, Vol 448, p. 196 12 Jul. 2007). Induced pluripotent stem cells (iPS cells) are made by dedifferentiating adult skin fibroblasts or, other adult somatic cells, back to a pluripotent state by retroviral transduction of four genes (c-myc, Klf4, Sox2, Oct4) (Takahashi and Yamanaka, Cell 126, 663-676, Aug. 25, 2006).

The advantage of developing other non-ESC, self renewing, pluripotent/multipotent stem cells would help in improve developmental models, improve directed differentiation into adult cells and allow more efficient and less costly approaches to conventional methods.

SUMMARY OF THE INVENTION

Figure 1:
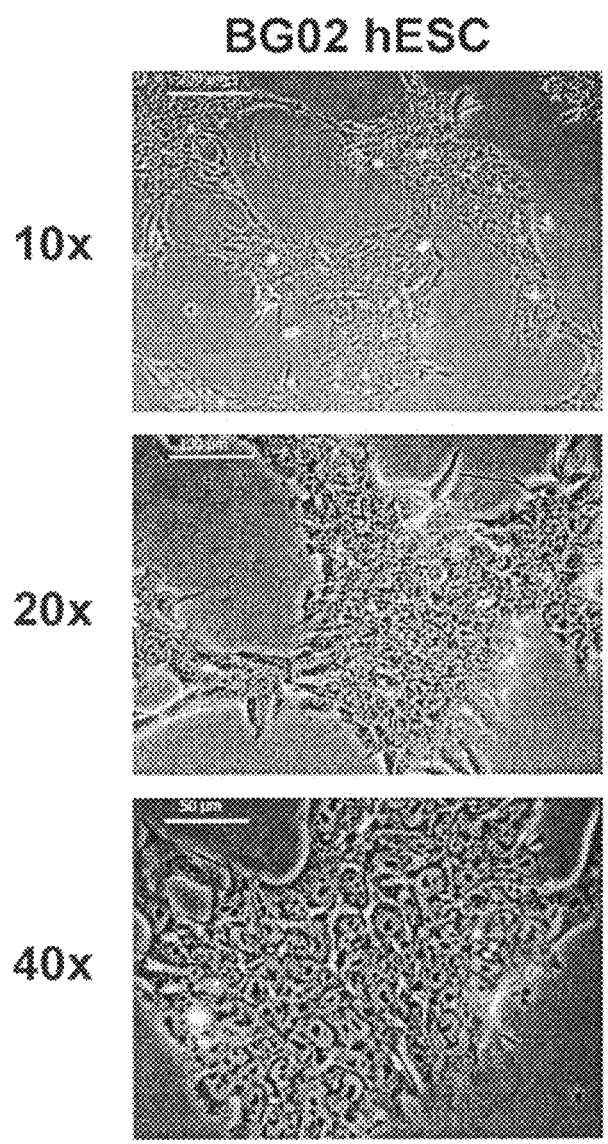
FIG. 1. Bright field pictures of BG02 hESCs grown on matrigel in defined media. 10×, 2×, 40× magnification.

In a first aspect, the present invention relates to a novel method for generating a mesendoderm cell population comprising exposing pPSCs (especially hESCs) to a differentiation medium comprising effective amounts of at least one GSK inhibitor (preferably GSK3) such as BIO, or related compound (as otherwise described herein), including a Wnt protein (wingless protein, e.g., Wnt3a; among others) or a related protein for a period sufficient (generally ranging from about 18 hours to about 72 hours or more) to produce a mesendoderm cell population, which may be isolated and passaged, stored (cryopreservation) or further differentiated (as indicated hereinbelow) to produce a mesoderm (Isl+) precursor cell.

In a second aspect, the present invention relates to a novel method for generating a mesoderm (Isl+) cell population comprising exposing pPSCs (especially hES Cs) to a differentiation medium comprising effective amounts of at least one GSK inhibitor such as BIO, or related compound (as otherwise described herein), including a Wnt protein (wingless protein, e.g., Wnt3a, among others) or a related protein, for a period sufficient (generally ranging from about 18 hours to about 36 hours, preferably about 1-2 days) to produce a mesendoderm cell population, optionally isolating said mesendoderm cell population, and subsequently exposing the mesendoderm cell population produced in the first step to a differentiation medium comprising effective amounts of a GSK inhibitor such as BIO, or related compound (as otherwise described herein), including a Wnt protein (wingless protein, e.g., Wnt3a, among others) or a related protein in combination with effective amounts of bone morphogenic protein (BMP-2, BMP-4, BMP-6, BMP-7) for a period sufficient (generally ranging from about 2-9 days, about 3-6 days, about 3-5 days, about 72-132 hours, about 120-130 hours) to produce a mesoderm Isl1+ cell (islet one cardiovascular progenitor cell). It is noted here that in certain embodiments, GSK inhibitor may be eliminated from the differentiation medium such that mesendoderm may be differentiated to mesoderm cells using effective amounts of BMP in the absence of a GSK inhibitor.

The isolated mesendoderm cells are capable of being further differentiated to mesoderm Isl1+ cells which have the potential to be differentiated to form cardiac, smooth muscle and endothelial lineages or to endoderm cells. The basic approach for forming mesendoderm cells or mesoderm Isl1+ cells works for virtually all pPSCs, especially including hESC cell lines, including BG01 and BG02 cell lines, among others.

Mesoderm (Isl1+) cells may be differentiated into cardiomyocytes (cardiac muscle cell) using methods which are standard in the art. These cardiomyocytes may be used for therapy in treating cardiovascular disease including myocardial infarction (infracted heart) and other cardiovascular disease.

Mesoderm (Isl+) cells may also be differentiated to vascular smooth muscle cells by passaging the cells every 5-6 days in cell differentiation medium containing effective concentrations of a GSK inhibitor (preferably, Wnt3a) in combination with a bone morphogenic protein (BMP4). These vascular smooth muscle cells produced by the present invention may be used to treat ischemic vascular disorders and to repair blood vessels.

In an alternative embodiment, the present invention relates to the production of a stable population of multipotent mesenchymal migratory cells (referred to as multipotent migratory cells or MMCs). In this aspect of the invention, pPSCs, especially hESCs, are grown in a differentiation medium which comprises an effective amount of a GSK inhibitor (preferably, a GSK3 inhibitor such as BIO or a related GSK3 inhibitor such as a wingless protein as otherwise described herein, for example Wnt 3a) and an effective amount of an Activin A inhibitor (antagonist) such as SB-431542 (Sigma), follistatin, follistatin gene related protein (FGRP, available from R and D Systems), BMP and Activin membrane bound inhibitor (BAMBI), anti-BAMBI (monoclonal antibody), Smad7 (Mothers Against Decapentaplegic Homolog 7), TGF RI inhibitor (Calbiochem) and/or a bone morphogenic protein antagonist (BMP antagonist) such as noggin, sclerostin, gremlin (Dmr gremlin) and uterine sensitization associated gene 1 protein (USAG-1, SOST11), among others. In this aspect of the invention, the production of a novel multipotent migratory cell is effected by exposing pPSCs (especially hESC's) in a differentiation medium as otherwise described herein to a GSK inhibitor and an Activin A inhibitor and/or a BMP inhibitor for a period of about 3 days to 12 days, about 4 days to 9 days, about 5 days to 8 days, about 6 days to 8 days about 7 days. These cells, which are stable MMCs may be collected and stored (cryopreserved), or passaged numerous times (for at least 20 up to an infinite number of passages). These cells are self-renewing. These MMCs are multipotent and may be further differentiated to numerous mature cell populations including endoderm cells and/or mesoderm cells using techniques which are otherwise described herein. MMCs can also be isolated from inner cell mass stage embryos or fetal tissue.

The present invention also relates to a population of isolated Multipotent Migratory Cells (MMCs) which are multipotent and self renewing. These cells can be grown over extended periods (through numerous generations) while maintaining their marker profile and so appear to be self-renewing. These cells can be differentiated into multiple cell types including endoderm and mesoderm and are therefore multipotent. These cells therefore have significant developmental plasticity. These cells are not however, hESCs based on marker profiling. This represents the first example of an alternate multipotent cell derived from hESCs. These cells are isolated and stored (cryopreservation).

MMC's according to the present invention have the following characteristics:
They are multipotent and self renewing;
They can be differentiated into multiple cell types including endoderm and mesoderm;
They are dynamic cells which can alternate between MMCs (E-cad−Oct4−Nanog−SSEA3−CXCR4+) and an alternative cell type which his E-cad+Oct4+Nanog+ SSEA3−CXCR4+ (high density (epithelial sheet))— have significant developmental plasticity
Based upon marker profiling—these cells are not hESC's.
MMCs according to the present invention are stable, may be passaged at least 20 times without affecting viability of the cell line and may be stored using standard cryopreservation techniques well known in the art. MMCs according to the invention may be stored, shipped and used in remote locations (to the initial production of cells).

DETAILED DESCRIPTION OF THE INVENTION

The following terms shall be used to describe the present invention.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific conditions, or specific methods, etc., as such may, of course, vary, and the numerous modifications and variations therein will be apparent to those skilled in the art.

Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering Principles and Methods, Vols. 1-4, Plenum Press, New York. Abbreviations and nomenclature, where employed, are deemed standard in the field and commonly used in professional journals such as those cited herein.

The term "primate Pluripotent Stem Cells", of which "human Embryonic Stem Cells" or hESCs are a subset, are derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm and ectoderm), according to a standard art-accepted test, such as the ability to form teratomas in 8-12 week old SCID mice. The term includes both established lines of stem cells of various kinds, and cells obtained from primary tissue that are pluripotent in the manner described.

Included in the definition of pluripotent or pPS cells (pPSCs) are embryonic cells of various types, especially including human embryonic stem cells (hESCs), described by Thomson et al. (Science 282: 1145, 1998); as well as embryonic stem cells from other primates, such as Rhesus stem cells (Thomson et al., Proc. Natl. Acad. Sci. USA 92: 7844, 1995). Other types of pluripotent cells are also included in the term. Human Pluripotent Stem Cells includes stem cells which may be obtained from human umbilical cord or placental blood as well as human placental tissue. Any cells of primate origin that are capable of producing progeny that are derivatives of all three germinal layers are included, regardless of whether they were derived from embryonic tissue, fetal, or other sources. The pPS cells are preferably not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells in the population will often be surrounded by neighboring cells that are differentiated.

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines WA01, WA07, and WA099 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.), as well as normal human embryonic stem cell lines such as WA01, WA07, WA09 (WiCell) and BG01, BG02 (BresaGen, Athens, Ga.).

Epiblast stem cells (EpiScs) and induced pluripotent stem cells (iPS) fall within the broad definition of pluripotent cells hereunder and in concept, the technology described in the present application could apply to these and other pluripotent cell types (ie, primate pluripotent cells) as set forth above. EpiScs are isolated from early post-implantation stage embryos. They express Oct4 and are pluripotent. See, Tesar et al, Nature, Vol 448, p. 196 12 Jul. 2007. iPS cells are made by dedifferentiating adult somatic cells back to a pluripotent state by retroviral transduction of four genes (c-myc, Klf4, Sox2, Oct4). See, Takahashi and Yamanaka, Cell 126, 663-676, Aug. 25, 2006.

Human embryonic stem cells may be prepared by methods which are described in the present invention as well as in the art as described for example, by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

The term "embryonic stem cell" refers to pluripotent cells, preferably of primates, including humans, which are isolated from the blastocyst stage embryo. Human embryonic stem cell refers to a stem cell from a human and are preferably used in aspects of the present invention which relate to human therapy or diagnosis. The following phenotypic markers are expressed by human embryonic stem cells:

SSEA-3, SSEA-4, TRA-1-60, TRA-1-81, CD9, alkaline phosphatase, Oct 4, Nanog, Rex 1, Sox2 and TERT. See Ginis, et al., Dev. Biol, 269(2), 360-380 (2004); Draper, et al., J. Anat., 200 (Pt. 3), 249-258, (2002); Carpenter, et al., Cloning Stem Cells, 5(1), 79-88 (2003); Cooper, et al., J. Anat., 200 (Pt. 3), 259-265 (2002); Oka, et al., Mol. Biol. Cell, 13(4), 1274-81 (2002); and Carpenter, et al., Dev. Dyn., 229(2), 243-258 (2004). While any primate pluripotent stem cells (pPSCs), including especially human embryonic stem cells can be used in the present methods to produce mesendoderm cells, mesoderm Isl1+ cells and multipotent migratory cells (MMCs) according to the present invention, preferred pPSCs for use in the present invention include human embryonic stem cells, including those from the cell lines BG01 and BG02, as well as numerous other available stem cell lines.

The term "differentiation" is used to describe a process wherein an unspecialized ("uncommitted") or less specialized cell acquires the features of a more specialized cell such as, for example, a multipotent migratory cell, a mesendoderm cell, a mesoderm cell, a nerve cell, a muscle cell or other cell. The term "differentiated" includes the process wherein a multipotent stem cell, including a hESC, becomes a more specialized intermediate cell such as a progenitor cell, where a more specialized intermediate cell (MMC, mesendoderm cell or mesoderm cell) becomes an even more specifialized cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

The terms "multipotent migratory cells" "multipotent mesenchymal cells" or "MMCs" are used interchangeably to refer to a cell or cells produced according to the present invention. MMCs are dynamic multipotent cells which are characterized as being E-cad−Oct4−Nanog−SSEA3−CXCR4+, they are of low to medium density and are migratory. They are storage stable and may be passaged for numerous generations and still remain viable. They have significant developmental plasticity. They are not hESCs based on marker profiling.

MMCs according to the present invention may be stabilized for storage in the presence of effective amounts of a GSK inhibitor and an Activin A inhibitor. BMP inhibitors, such as Noggin, can also be used in combination with GSK inhibitors and Activin A inhibitors. These cells may be differentiated to mesoderm cells or definitive endoderm cells, among numerous others.

The multipotent mesenchymal cell (MMC) according to the present invention have one or more (at least 4, at least 5 at least 6, at least 10, preferably all) of the following characteristics:

it can be cultured for at least 20 passages as a stable cell population cells appear mesenchymal when plated at low density and grow into a sheet at high density can be produced from a range of hESC lines including BG01, BG02, WA09

MMCs can be frozen and cryogenically preserved by standard methods

MMCs can be recovered after cryogenic storage, recovered and differentiated

MMCs can be passaged with high plating efficiency (greater than 50% plating efficiency—50% of cells passaged successfully seed down and survive)

do not exhibit the SSEA3 and SSEA4 antigens on their cell surface do not express hESC markers such as Oct4, Nanog MMCs can express CXCR4 on their surface MMCs express the following transcripts at high levels Zic1, HoxA9, HoxD4, HoxA5, HoxC10, HoxD3, Pax6, N-CAM, CXCR4

MMCs are not mesendoderm because they do not express T/brachyury or eomesodermin E-cadherin negative MMCs do not express Sox17, Isl1, musashi, nestin at appreciable levels by Q-PCR analysis retain a normal karyotype during passaging exhibit a migratory, mesenchymal phenotype have multipotent differentiation capacity (including mesoderm, endoderm)

do not form teratomas when injected into SCID mice can be isolated from inner cell mass embryos and fetal tissue see microarray data for a more complete description of MMC genes expression profiles As used herein the terms "mesoderm (Isl1+) cell", mesoderm-derived Isl1+ multipotent progenitor cell or "IMP" are used interchangeably to describe mesoderm Isl1+ cells which are produced according to methods of the present invention from pPSCs (especially hESCs), mesendoderm cells or MMCs.

Mesoderm (Isl1+) cells (Islet 1+ multipotent progenitors or IMPS) have the following characteristics:
 express Isl1, Tbx20, Nkx2.5, Fgf10, GATA4, KDR (Flk1), FoxF1, PDGFRα
 karyotypically normal
 do not express Oct4, Nanog, T, eomesodermin
 can differentiate into cardiomyocytes, smooth muscle cells and endothelial cells Microarray was performed on the formation of IMPs. hESCs were cultured in defined media plus Wnt3a (25 ng/ml) and BMP4 (100 ng/ml) for 6 days. Samples were taken at 0, 24 hr, 48 hr, 72 hr, 96 hr, 144 hr for mRNA extraction and subsequent microarray analysis. The microarray analysis is summarised in a table attached to this document. (IMP microarray)

As used herein, the terms "differentiation medium", "cell differentiation medium", "culture media", "basal cell medium", "basal cell media" or "basal media" or "stabilizing medium" are used synonymously to describe a cellular growth medium in which (depending upon the additional components used) the hESCs, mesendoderm cells, mesoderm cells or multipotent migratory cells (MMCs) are produced, grown/cultured or alternatively, differentiated into more mature cells. Differentiation media are well known in the art and comprise at least a minimum essential medium plus one or more optional components such as growth factors, including fibroblast growth factor (FGF), ascorbic acid, glucose, non-essential amino acids, salts (including trace elements), glutamine, insulin (where indicated and not excluded), Activin A, transferrin, beta mercaptoethanol, and other agents well known in the art and as otherwise described herein. Preferred media includes basal cell media which contains between 1% and 20% (preferably, about 2-10%) fetal calf serum, or for defined medium (preferred) an absence of fetal calf serum and KSR, but including bovine serum albumin (about 1-5%, preferably about 2%). Preferred differentiation medium is defined and is serum free. In certain embodiments wherein MMCs are produced and Activin A inhibitor is used, the medium may eliminate or substantially reduce the amount of Activin A.

Other agents which optionally may be added to differentiation medium according to the present invention include, for example, nicotinamide, members of TGF-β family, including TGF-β 1, 2, and 3, Activin A, nodal, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and H (GLP-I and II), GLP-1 and GLP-2 mimetobody, Exendin-4, parathyroid hormone, insulin, progesterone, aprotinin, hydrocortisone, ethanolamine, epidermal growth factor (EGF), gastrin I and II, copper chelators such as, for example, triethylene pentamine, forskolin, Na-Butyrate, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, Calif.), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, heregulin, or combinations thereof, among a number of other components. Each of these components, when included, are included in effective amounts.

By way of further example, suitable media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029. Preferred embodiments of media used in the present invention are as otherwise described herein.

A particularly preferred differentiation medium for growing/culturing pPSCs (especially, hESCs) and for differentiating cells in the present invention is DMEM/F12 (50:50) which contains about 2% proalbumin (albumin; Millipore/Serologicals), 1× Pen/Strep, 1×NEAA, 1× Trace Elements A, B, C (Mediatech), Ascorbic Acid (10-100 ng/ml, about 25-65 ng/ml, about 50 ng/ml), about 0.1 mM (0.025-0.5 mM) β-Mercaptoethanol (Gibco), about 2-10 ng/ml, about 5-9 ng/ml, about 8 ng/ml bFGF (Sigma), 200 ng/ml (5-500 ng/ml) LR-IGF (referred to as IGF-I; JRH Biosciences), 10 ng/ml Activin A (about 1 ng/ml to no more than about 20 ng/ml) and 10 ng/ml (about 1-20 ng/ml or more) Heregulin. It is noted that Activin A or Activin A signaling is not required for the production of multipotent migratory cells MMCs, and mesendoderm cells but may be included (where included, Activin A is preferably included in low concentrations, generally below about 20 ng/ml), especially when producing mesoderm (Isl+) cells. In contrast, about 20 ng/ml to about 100 ng/ml or more of Activin A or "high concentrations of Activin A" is used for producing definitive endoderm cells. Alternatively, mouse embryonic fibroblast-conditioned media (MEF-CM) with similar componentry to DMEM/F12 may also be used to passage hESC and to produce mesendoderm cells, mesoderm cells (mesoderm Isl1+ cells) and multipotent migratory cells (MMCs) according to the present invention.

Differentiation media useful in the present invention are commercially available and can be supplemented with commercially available components, available from Invitrogen Corp. (GIBCO), Cell Applications, Inc. and Biological Industries, Beth HaEmek, Israel, among numerous other commercial sources, including Calbiochem. In preferred embodiments at least one differentiation agent such as fibroblast growth factor (FGF), LR-IGF (an analogue of insulin-like growth factor) and Heregulin (preferably all three in effective amounts) is added to the cell media in which a stem cell is cultured and differentiated into a multipotent migratory cell, a mesendoderm cell or a mesoderm cell (or even definitive endoderm cells from MMCs). One of ordinary skill in the art will be able to readily modify the cell media to produce any one or more of the target cells pursuant to the present invention. Cell differentiation medium is essentially synonymous with basal cell medium but is used within the context of a differentiation process and includes cell differentiation agents to differentiate cells into other cells. Stabilizing medium is a basal cell medium which is used either before or after a differentiation step in order to stabilize a cell line for further use. Culture media is essentially the same as stabilizing medium, but refers to media in which a pluripotent or other cell line is grown or cultured prior to differentiation. In general; as used herein, cell differentiation medium and stabilizing medium may include essentially similar components of a basal cell medium, but are used within different contexts and may include slightly different components in order to effect the intended result of the use of the medium. In the case of MMCs, especially MMCs which are storage stable, the inclusion of effective amounts of Activin A signaling inhibitors as otherwise disclosed herein in combination with an effective amount of a GSK inhibitor as otherwise described herein in cell media may be used to differentiate and to stabilize the MMCs, i.e., prevent their further differentiation and allow for storage stability of the cell populations. BMP inhibitors may be used in conjunction with Activin A inhibitors and GSK inhibitors for this purpose.

Pluripotent stem cells also may be cultured on a layer of feeder cells that support the pluripotent stem cells in various ways which are described in the art. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium. These approaches are well known in the art. In preferred aspects of the present invention, the cells are grown in feeder cell free medium.

Approaches for culturing cells on a layer of feeder cells are well known in the art. For example, Reubinoff et al. (*Nature Biotechnology* 18: 399-404 (2000)) and Thompson et al. (*Science* 6 Nov. 1998: Vol. 282. no. 5391, pp. 1145-1147) disclose the culture of pluripotent stem cell lines from human blastocysts using a mouse embryonic fibroblast feeder cell layer. Richards et al, (*Stem Cells* 21: 546-556, 2003) evaluated a panel of 11 different human adult, fetal and neonatal feeder cell layers for their ability to support human pluripotent stem cell culture. Richards et al, states: "human embryonic stem cell lines cultured on adult skin fibroblast feeders retain human embryonic stem cell morphology and remain pluripotent". US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer. In another example, Wang et al (Stem Cells 23: 1221-1227, 2005) disclose methods for the long-term growth of human pluripotent stem cells on feeder cell layers derived from human embryonic stem cells. In another example, Stojkovic et al (Stem Cells 2005 23: 306-314, 2005) disclose a feeder cell system derived from the spontaneous differentiation of human embryonic stem cells. In a further example, Miyamoto et al (+22: 433-440, 2004) disclose a source of feeder cells obtained from human placenta. Amit et al (*Biol. Reprod* 68: 2150-2156, 2003) discloses a feeder cell layer derived from human foreskin. In another example, Inzunza et al (Stem Cells 23: 544-549, 2005) disclose a feeder cell layer from human postnatal foreskin fibroblasts.

Approaches for culturing pPSCs in media, especially feeder-free media, are well known in the art. U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure." In another example, WO2005014799 discloses conditioned medium for the maintenance, proliferation and differentiation of mammalian cells. In still another example, Xu et al (*Stem Cells* 22: 972-980, 2004) discloses conditioned medium obtained from human embryonic stem cell derivatives that have been genetically modified to over express human telomerase reverse transcriptase. In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (*BioReprod DOI:* 10.1095/biolreprod. 105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal. In another example, Levenstein et al (*Stem Cells* 24: 568-574, 2006) disclose methods for the long-term culture of human embryonic stem cells in the absence of fibroblasts or conditioned medium, using media supplemented with bFGF. In still another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells. In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In still another example, WO2005086845 discloses a method for maintenance of an undifferentiated stem cell, said method comprising exposing a stem cell to a member of the transforming growth factor-beta (TGF.beta.) family of proteins, a member of the fibroblast growth factor (FGF) family of proteins, or nicotinamide (NIC) in an amount sufficient to maintain the cell in an undifferentiated state for a sufficient amount of time to achieve a desired result.

The cells are preferably grown on a cellular support or matrix, as adherent monolayers, rather than as embryoid bodies or in suspension. In the present invention, the use of Matrigel as a cellular support is preferred. Cellular supports preferably comprise at least one differentiation protein. The term "differentiation protein" or "substrate protein" is used to describe a protein which is used to grow cells and/or to promote differentiation (also preferably attachment) of an embryonic stem cell or mesendoderm, mesoderm or multipotent migratory cell (MMC). Differentiation proteins which are preferably used in the present invention include, for example, an extracellular matrix protein, which is a protein found in the extracellular matrix, such as laminin, tenascin, thrombospondin, and mixtures thereof, which exhibit growth promoting and contain domains with homology to epidermal growth factor (EGF) and exhibit growth promoting and differentiation activity. Other differentiation proteins which may be used in the present invention include for example, collagen, fibronectin, vibronectin, polylysine, polyornithine and mixtures thereof. In addition, gels and other materials such as methylcellulose of other gels which contain effective concentrations of one or more of these embryonic stem cell differentiation proteins may also be used. Exemplary differentiation proteins or materials which include these differentiation proteins include, for example, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), BD™ PuraMatrix™ Peptide Hydrogel, Collagen I, Collagen I High Concentration (HC), Collagen II (Bovine), Collagen III, Collagen IV, Collagen V, and Collagen VI, among others. The preferred material for use in the present invention includes Matrigel™ and Geltrex™.

A preferred composition/material which contains one or more differentiation or substrate proteins is BD Matrigel™ Basement Membrane Matrix. This is a solubilized basement membrane preparation extracted from the Engelbreth-Holm-Swarm (EHS) mouse sarcoma, a tumor rich in ECM proteins. Its major component is laminin, followed by collagen IV, heparan sulfate, proteoglycans, entactin and nidogen.

The pluripotent stem cells are preferably plated onto the differentiation or substrate protein. The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

As used herein, the term "activate" refers to an increase in expression of a marker such as Isl or an upregulation of the activity of Isl or a marker associated with a blood cell; vascular cells (endothelial cells), kidney cells, bone and muscle cells. These cells have utility in treating heart disease, kidney degeneration, the repair of bone and vascular degeneration.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "express" refers to the transcription of a polynucleotide or translation of a polypeptide (including a marker) in a cell, such that levels of the molecule are measurably higher in or on a cell that expresses the molecule than they are in a cell that does not express the molecule. Methods to measure the expression of a molecule are well known to those of ordinary skill in the art, and include without limitation, Northern blotting, RT-PCT, in situ hybridization, Western blotting, and immunostaining.

As used herein, the term "Markers" describe nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

As used herein, the term "contacting" (i.e., contacting a cell with a compound) is intended to include incubating the compound and the cell together in vitro (e.g., adding the compound to cells in culture). The term "contacting" is not intended to include the in vivo exposure of cells to a differentiation agent that may occur naturally in a subject (i.e., exposure that may occur as a result of a natural physiological process). The step of contacting the cell with differentiation medium and one or more growth factors (BMP or other) and inhibitors (inhibitors of GSK, Activin A (signaling) or BMP (signaling)) as otherwise described herein can be conducted in any suitable manner. For example, the cells may be treated in adherent culture as an adherent layer, as embryoid bodies or in suspension culture, although the use of adherent layers are preferred because they provide an efficient differentiation process oftentimes providing differentiation to a target cell population (mesendoderm, mesoderm or multipotent migratory cells) of 90% or more. It is understood that the cells contacted with the differentiation agent may be further treated with other cell differentiation environments to stabilize the cells, or to differentiate the cells further, for example to produce islet cells.

In the case of producing definitive endoderm cells from mesendoderm cells and/or MMCs, the cells are differentiated in a medium as otherwise disclosed herein comprising effective amounts of Activin A (about 20 ng/ml to about 100 ng/ml or more) and optionally an effective amount of an inhibitor of PI3kinase signaling, as otherwise disclosed herein. It is noted that one or more of nodal, TGFβ, or other TGF components may be used in place of or in addition to the Activin A. Also, the removal of factors which influence/promote PI3 kinase signaling such as IGF-I and heregulin from the differentiation medium may also be used instead of/in addition to the inclusion of a PI3kinase inhibitor.

As used herein, the term "differentiation agent" refers to any compound or molecule that induces a cell such as hESC's, mesendoderm cells, multipotent migratory cells (MMCs) or Isl1+ multipotent progenitors (IMPS) to partially or terminally differentiate, wherein said differentiation is due at least in part to inhibition of GSK, to the inclusion of bone morphogenic protein (BMP-2, BMP-4, BMP-6 or BMP-7) such as in the differentiation of hESCs to mesendoderm or mesoderm Isl1+ cells, or alternatively, the inhibition of GSK and the inhibition of Activin A and/or the inhibition of bone morphogenic protein to produce multipotent migratory cells (MMCs), or the addition of Activin A to produce endoderm. While the differentiation agent may be as described below, the term is not limited thereto. The term "differentiation agent" as used herein includes within its scope a natural or synthetic molecule or molecules which exhibit(s) similar biological activity.

The term "effective" is used to describe an amount of a component, compound or compositions which is used or is included in context in an amount and for a period sufficient to produce an intended effect. By way of example, an effective amount of a differentiation agent is that amount which, in combination with other components, in a differentiation medium will produce the differentiated cells desired.

The term "bone morphogenic protein" or BMP is used to describe a differentiation agent which is used in the present invention, in combination with other components as otherwise described herein, to differentiate hESCs or mesendoderm cells to mesoderm Isl1+ cells. Any one of BMP-2, BMP-4, BMP-6 or BMP-7 (BMP-2 or BMP-4 being preferred) may be used in effective amounts to assist the differentiation process. BMP may be used in amounts ranging from about 1 ng/ml to about 500 ng/ml or more, about 25 to about 500 ng/ml, about 25 to about 250 ng/ml, about 50 to about 150 ng/ml; about 75 to about 125 ng/ml, about 100 ng/ml.

The term "GSK inhibitor" is used to describe a compound which inhibits GSK (especially GSK3, including GSK3a or GSK3β). Examples of preferred GSK inhibitors for use in the present invention include one or more of the following, all available from Calbiochem:

BIO (2'Z,3'E)-6-Bromoindirubin-3'-oxime (GSK3 Inhibitor IX);
BIO-Acetoxime (2'Z,3'E)-6-Bromoindirubin-3'-acetoxime (GSK3 Inhibitor X);
(5-Methyl-1H-pyrazol-3-yl)-(2-phenylquinazolin-4-yl) amine (GSK3-Inhibitor XIII);
Pyridocarbazole-cyclopenadienylruthenium complex (GSK3β Inhibitor XV);
TDZD-8 4-Benzyl-2-methyl-1,2,4-thiadiazolidine-3,5-dione (GSK3β Inhibitor I);
2-Thio(3-iodobenzyl)-5-(1-pyridyl)[1,3,4]-oxadiazole (GSK3β Inhibitor II);
OTDZT 2,4-Dibenzyl-5-oxothiadiazolidine-3-thione (GSK3β Inhibitor III);
α-4-Dibromoacetophenone (GSK3β Inhibitor VII);
AR-A014418 N-(4-Methoxybenzyl)-N'-(5-nitro-1,3-thiazol-2-yl)urea (GSK-3β Inhibitor VIII);
3-(1-(3-Hydroxypropyl)-1H-pyrrolo[2,3-b]pyridin-3-yl]-4-pyrazin-2-yl-pyrrole-2,5-dione (GSK-3β Inhibitor XI);
TWS119 pyrrolopyrimidine compound (GSK3β Inhibitor XII);
L803 H-KEAPPAPPQSpP-NH$_2$ or its Myristoylated form (GSK3β Inhibitor XIII); and
2-Chloro-1-(4,5-dibromo-thiophen-2-yl)-ethanone (GSK3β Inhibitor VI).

In addition, numerous wingless proteins or Wnt proteins function similar to GSK inhibitors and in particular, GSK inhibitors according to the present invention. They are therefore subsumed under the term GSK inhibitors. Exemplary Wnt proteins which may be used in the present invention include one or more of Wnt1, Wnt2, Wnt3, Wnt3a, Wnt4, Wnt10, Wnt 14, Wnt14b, Wnt15, and Wnt16, among other Wnt proteins. The use of Wnt3a is preferred.

Preferred GSK inhibitors for use in the present invention include, BIO (GSK-3 IX) and Wnt3a.

GSK inhibitors are useful in all aspects of the invention which relate to the differentiation and formation of mesendoderm cells, mesoderm cells, multipotent migratory cells (MMCs) and even definitive endoderm cells. When used, they are used in effective amounts, in concentrations (depending upon the molecular weight of the inhibitors used) of about 0.001 to about 100 μM or more, about 0.05 to about 75 μM, about 0.1 to about 50 μM, about 0.25 to about 35 μM, about 0.5 to about 25 μM. In the case of the use of BIO, this GSK inhibitor is used in the differentiation medium in an amount ranging from about 0.05 to about 50 μM, about 0.1 to about 10 μM, about 0.5 to about 5 μM, about 1-3 μM. When a Wnt protein is used, the amount of Wnt which is used ranges from about 1 to about 100 ng/ml, about 5 to about 50 ng/ml, about 10 to about 35 ng/ml, about 20 to about 30 ng/ml, about 25 ng/ml.

The term "Activin A inhibitor" is used to describe compounds or components which optionally are added to a differentiation medium to inhibit the effects of Activin A in the differentiation process and when used, produce multipotent migratory cells (MMCs) from hESCs. In order to produce MMCs from hESCs, the differentiation agent comprises an effective amount of a GSK inhibitor (preferably, a GSK3 inhibitor, such as BIO or other GSK3 inhibitor) and an Activin A inhibitor plus or minus a bone morphogenic protein (BMP) inhibitor.

Exemplary Activin A inhibitors for use in the present invention include, for example, SB-431542 (Sigma), follistatin, follistatin gene related protein (FGRP, available from R and D Systems), BMP and Activin Membrane Bound Inhibitor (BAMBI), anti-BAMBI (monoclonal antibody), Smad7 (Mothers Against Decapentaplegic Homolog 7) and TGF RI inhibitor (Calbiochem), among others. Activin A inhibitors are used in the present invention in effective amounts, generally within the range of about 0.001 to about 100 μM or more, about 0.05 to about 75 μM, about 0.1 to about 50 μM, about 0.25 to about 35 μM, about 0.5 to about 25 μM.

The term "bone morphogenic protein inhibitor" or "BMP inhibitor" is used to describe a compound or component which, when added in effective amounts to a differentiation medium to inhibit the effects of bone morphogenic protein in differentiating hESCs to multipotent migratory cells (MMCs). Exemplary BMP inhibitors include, for example, noggin, sclerostin, gremlin (Drm/Gremlin) and USAG-1, among others. The amount of BMP inhibitor used is an effective amount, generally (depending upon the molecular weight and effectiveness of the inhibitor used) falling within the range of about 0.01 ng/ml to about 500 ng/ml or more, about 0.1 to about 350 ng/ml, about 0.5 to about 250 ng/ml, about 1 to about 500 ng/ml, about 5 to about 250 ng/ml, about 50 to about 150 ng/ml, about 75 to about 125 ng/ml, about 100 ng/ml.

The term "inhibitor of the PI3-kinase pathway" or "inhibitor of PI3-kinase signaling" refers to any molecule or compound that decreases the activity of PI3-kinase or at least one molecule downstream of PI3-kinase in a cell contacted with the inhibitor. These inhibitors are preferred inhibitors for preparing definitive endoderm cells from mesendoderm cells and/or multipotent migratory cells according to the present invention. The term encompasses, e.g., PI3-kinase antagonists, antagonists of the PI3-kinase signal transduction cascade, compounds that decrease the synthesis or expression of endogenous PI3-kinase, compounds that decrease release of endogenous PI3-kinase, and compounds that inhibit activators of PI3-kinase activity. In certain embodiments of the foregoing, the inhibitor is selected from the group consisting of Rapamycin, LY 294002, wortmannin, lithium chloride, Akt inhibitor I, Akt inhibitor II (SH-5), Akt inhibitor III (SH-6), NL-71-101, and mixtures of the foregoing. Akt inhibitor I, II, Akt III, and NL-71-101 are commercially available from Calbiochem. In other embodiments, the inhibitor is selected from the group consisting of Rapamycin and LY 294002. In a further preferred embodiment, the inhibitor comprises LY 294002. In another embodiment, the inhibitor comprises Akt1-II. It is understood that combinations of inhibitors may be used to elicit the desired differentiation effect. The ultimate result is production of substantial quantities of definitive endoderm cells which may be used for the production of pancreatic endoderm cells and/or liver endoderm cells as us disclosed in international application no. PCT/US2007/013137, filed 4 Jun. 2007, published as WO 2007/143193, relevant portions of which are incorporated by reference herein.

As used herein when referring to a cell, cell line, cell culture or population of cells within context, the term "isolated" refers to being substantially separated from the natural source of the cells such that the cell, cell line, cell culture, or population of cells are capable of being cultured in vitro. Alternatively, and depending upon context, the term "isolated" means that a cell population is separated from the differentiation medium and culture flask so that the cell population may be stored (cryopreservation). In addition, the term "isolating" may be used to refer to the physical selection of one or more cells out of a group of two or more cells, wherein the cells are selected based on cell morphology and/or the expression of various markers.

The term "passaged" is used to describe the process of splitting cells and transferring them to a new cell vial for further growth/regrowth. The preferred adherent cells (or even embryoid bodies) according to the present invention may be passaged using enzymatic (Accutase™ or collagenase) passage, manual passage (mechanical, with, example, a spatula or other soft mechanical utensil or device) and other non-enzymatic methods, such as cell dispersal buffer As used herein, the term "contacting" (i.e., contacting a hESC, mesendoderm, mesoderm or multipotent migratory cell, with a compound) is intended to include incubating the compound and the cell together in vitro (e.g., adding the compound to cells in culture). The term "contacting" is not intended to include the in vivo exposure of cells to growth factors and/or other differentiation agents or inhibitors that may occur naturally in a subject (i.e., exposure that may occur as a result of a natural physiological process). The step of contacting the cell with the growth factors and/or inhibitors in differentiation medium pursuant to the present invention can be conducted in any suitable manner. For example, the cells may be treated in adherent culture, as embryoid bodies or in suspension culture. It is understood that the cells contacted with the differentiation agent(s) and/or inhibitors may be further treated with other cell differentiation environments to stabilize the cells, or to differentiate the cells further, for example to produce definitive endoderm cells, blood cells, vascular cells (endothelial cells), kidney cells, bone and muscle cells, including cardiac muscle cells. These cells have utility in regenerative medicine to treat heart disease, kidney degeneration, repair of bone and vascular degeneration.

Applicant has demonstrated that culturing hESCs with an effective amount of a GSK inhibitor (in particular, BIO) in combination with an effective amount of bone morphogenic protein (BMP-2, BMP-4, BMP-6, BMP-7) will produce mesoderm cells (Isl1+).

The present invention contemplates a composition comprising a population of isolated differentiated mammalian cells, in particular, human mesendoderm cells, mesoderm (Isl1+) cells and/or multipotent migratory cells (MMCs), wherein the cells are differentiated from hESCs (or, in the case of mesoderm (Isl1+) cells, mesendoderm cells as well) in vitro, and wherein greater than approximately 30% of the cells express markers for mesendoerm cells, mesoderm (Isl1+) cells or MMCs. In one embodiment of the invention, greater than approximately 35%, 40%, 45%, 50%, 55%, 60%, 65%, 67%, 70%, 72%, 74%, 75%, 76%, 77%, 78%, 79%, 80%, 90% or greater than 90% of the cells are mesoderm cells. Preferably, at the composition comprises a population of cells at least 50% of which express Pdx1 and/or Isl1, up to 70-80% or more. Mesendoderm cells are cells which expresses one or more of the markers CD48, eomesodermin (EOMES), T/Brachyury, Wnt3a, and GSC.

The invention further contemplates a composition comprising a population of isolated mesoderm Isl1+, NRx2.5, Tbx20, Fgf10 cells, wherein the cells are produced in an in vitro culture, and wherein greater than approximately 35%, 40%, 45%, 50%, 55%, 60%, 65%, 67%, 70%, 72%, 74%, 75%, 76%, 77%, 78%, 79% or even 80% or 90% or 90+% of the cells are mesoderm (Isl1+) cells.

The invention further contemplates a composition comprising a population of isolated multipotent migratory cells, wherein the cells are produced in an in vitro culture, and wherein greater than approximately 35%, 40%, 45%, 50%, 55%, 60%, 65%, 67%, 70%, 72%, 74%, 75%, 76%, 77%, 78%, 79% or even 80% or 90% or 90+% of the cells are MMCs.

The invention further encompasses a method of differentiating hESCs into mesendoderm cells comprising (a) providing hESCs, and (b) contacting the hESCS with an effective amount of a GSK inhibitor (preferably, GSK3) in a cell differentiation medium to produce mesendoderm cells, and (c) optionally, isolating said mesendoderm cells. To produce mesendoderm cells, hESC's are differentiated in the above conditions for a period ranging from about 18 hours to about 72 hours, preferably about 1-2 days.

The invention further encompasses a method of differentiating hESCs into mesoderm (Isl1+) cells comprising: (a) providing hESCs, (b) contacting the hESCs with an effective amount of a GSK inhibitor in a cell differentiation medium for a period ranging for a period ranging from about 18 hours to about 72 hours, preferably about 1-2 days, and thereafter (c) contacting said cells obtained from step (b) to a an effective amount of a bone morphogenic protein (BMP-2, BMP-4, BMP-6, BMP-7) and optionally, a GSK inhibitor as otherwise described herein, in a cell differentiation medium for a period ranging from about 2-9 days, about 3-6 days, about 3-5 days, about 72-132 hours, about 120-130 hours to produce a mesoderm (Isl1+) cells, and optionally, collecting said mesoderm (Isl1+) cells, storing (cryopreservation) said mesoderm cells and further differentiating said mesoderm cells to produce cardiac and smooth muscle tissue, endothelial lineages or endoderm cells. It is noted that in step c, the inclusion of the GSK inhibitor is not required, but is preferred.

The invention further encompasses a method of differentiating mesendoderm cells into mesoderm (Isl1+) cells comprising (a) providing mesendoderm cells, (b) contacting the mesendoderm cells with an effective amount of a bone morphogenic protein (BMP-2, BMP-4, BMP-6, BMP-7) and optionally, a GSK inhibitor, in a cell differentiation medium for a period ranging from about 2-9 days, about 3-6 days, about 3-5 days, about 72-132 hours, about 120-130 hours to produce a mesoderm (Isl1+) cells, and optionally, collecting said mesoderm (Isl1+) cells, storing (cryopreservation) said mesoderm cells and further differentiating said mesoderm cells to produce cardiac and smooth muscle tissue, endothelial lineages or endoderm cells. Note here that the inclusion of the GSK inhibitor is optional and preferred.

The invention also relates to a method of differentiation hESCs into multipotent migratory cells (MMCs) comprising a) providing hESCs and b) contacting the hESCs with an effective amount of a GSK inhibitor in combination with an effective amount of an Activin A inhibitor and/or a BMP inhibitor for a period ranging from about 4 day to 12 days, about 4 days to 9 days, about 5 days to 8 days, about 6 days to 8 days, about 7 days. The resulting MMCs may be collected and stored (cryopreservation), or passaged numerous times to produce stable MMC's which are self-renewing. These MMCs may be further differentiated to numerous mature cell populations including endoderm cells and/or mesoderm cells using techniques which are otherwise described herein. MMCs may be used to produce mesoderm (Isl1+) cells using the general method used to produce mesoderm (Isl1+) from mesendoderm cells. In this method, MMCs are grown in a cell differentiation medium in combination with an effective amount of BMP and optionally, a GSK inhibitor (as well as removing the Activin A and/or BMP inhibitor used to produce MMCs) for a period ranging from about 2 days to 12 days, 3 to 9 days, 4 to 8 days, etc. MMCs may also be used to produce definitive endoderm cells as otherwise described herein.

In further differentiating MMCs to mesoderm cell populations and/or definitive endoderm populations, the Activin A inhibitors and, where used, BMP inhibitors used to differentiate hESCs to MMCs are removed and the MMCs are grown in conditions (effective amounts of BMP, such as BMP-2, BMP-4, BMP-6, BMP-7 and optionally, a GSK inhibitor such as BIO or Wnt3a) which produce mesoderm Isl1+ cells or conditions (effective amounts of Activin A or equivalent compounds (nodal, TGFβ, or other TGF components) and optionally, a PI3K inhibitor and/or elimination of components IGF-I and/or heregulin) which produce definitive endoderm cells or other conditions which result in mesoderm or definitive endoderm cell populations. Methods and conditions for producing definitive endoderm cells from hESCs, which may be used for producing definitive endoderm cells from MMCs under the present invention, are taught for example, in PCT/US2007/013137, published as WO 2007/143193, relevant portions of which are incorporated by reference herein.

In addition, MMCs according to the present invention may be differentiated to produce a population of definitive endoderm cells using Activin A, optionally in the presence of a PI3K inhibitor in a cell differentiation medium (preferably DMEM/F12) with added components. It is noted that one or more of nodal, TGFβ, or other TGF components may be used in place of or in addition to the Activin A. Also, the removal of factors which influence/promote PI3 kinase signaling such as IGF-I and heregulin from the differentiation medium may also be used instead of, or in addition to, the inclusion of a PI3kinase inhibitor.

The definitive endoderm cells may be isolated and stored after being produced, or alternatively, may be used to produce pancreatic endoderm cells and/or pancreatic β cells. Definitive endoderm cells are exposed to DMEM/F12, optionally including FCS (preferably, about 10%) in the presence of retinoic acid at a concentration ranging from about 0.05 μg/ml to about 25 μg/ml, or about 0.1 μg/ml to about 2 μg/ml and Fgf10 (25 ng/ml, about 1-75, about 5-50, about 15-35, about 20-30 ng/ml) for a further day or more (preferably, two days) wherein pancreatic endoderm cells may be isolated. The pancreatic endoderm cells may be further differentiated into pancreatic β cells using an effective concentration of retinoic acid (concentrations as set forth above) and Fgf10 for a further number of days (about 10-24 days) to provide pancreatic cells.

Liver endoderm cells may be produced from definitive endoderm cells by differentiating definitive endoderm cells in the absence of retinoic acid but with an effective amount of fibroblast growth factor (Fgf10) for a period of at least about 2 days, at least about 4 days, at least about 5 days, at least about 6 days, at least about 8 days, at least about 10 days, about 10-24 days) whereupon liver endoderm cells are produced instead of pancreatic endoderm cells and optionally isolated for further use.

In the present invention, prior to differentiation to mesendoderm cells, mesoderm cells (Isl1+) or MMCs, the pPSCs (especially, hESCs) are grown/cultured in a cell differentiation medium by contact with an appropriate differentiation agents/inhibitors as otherwise described herein. It is contemplated that the hESCs are differentiated by contact with the differentiation agents/inhibitors in differentiation medium to produce mesendoderm cells, mesoderm cells (Isl1+) or MMCs, accordingly, as otherwise taught herein. In one embodiment, the cells may be dissociated to an essentially single cell culture prior to being contacted with the differentiation agents in basal cell media. The cells are grown preferably as adherent monolayers to efficiently allow contact of the differentiation agent/inhibitors with the cells and the adherent layer can be dissociated using a protease, such as, but not limited to, Accutase™. In one embodiment, the cells are contacted with the differentiation agent(s)/inhibitors after being plated for between approximately 12 hours to approximately 10 days or more, after being plated for between approximately 12 hours to approximately 72 hours, after being plated for approximately 24 hours to 72 hours, after being plated for approximately 18 hours to 36 hours, or as otherwise described herein. In one embodiment, the cells are contacted with the differentiation agents and/or inhibitors as otherwise described herein for greater than approximately 18 hours, for greater than approximately 24 hours, for greater than approximately 48 hours, for greater than approximately 72 hours, for greater than approximately 96 hours, for greater than approximately 150 hours, for approximately 136 to approximately 152 hours, for approximately 144 hours or as otherwise described herein. After exposure to the cell medium containing differentiation agent(s)/inhibitor(s), the resulting cells obtained (generally as adherent monolayers or alternatively, as embryoid bodies) may be separated directly (Accutase™ treated) and then further passaged to regenerate a population of cells or to further differentiate the cells to another cell population.

In certain embodiments, the hESCs, mesendorm cells, mesoderm (Isl1+) cells, or MMCs to be further differentiated are plated at a concentration of less than approximately $2.5 \times 10^6$ cells/35 mm dish, of at least approximately $2.5 \times 10^4$ cells/35 mm dish, between approximately $2.5 \times 10^5$ to approximately $2 \times 10^6$ cells/35 mm dish, between approximately $5 \times 10^5$ to approximately $2 \times 10^6$ cells/35 mm dish, of less than approximately $2 \times 10^6$ cells/35 mm dish, or at a density of greater than $4 \times 10^5$ cells/35 mm dish. In certain preferred aspects, the cells to be differentiated are plated at a concentration of approximately $7.5 \times 10^5$ cells/35 mm dish.

In producing mesendoderm, mesoderm (Isl1+) cells or MMCs from hESCs, as a first step in certain embodiments of the present invention, the present invention further encompasses the use of a composition for culturing cells to produce an adherent monolayer of hESCs. The hESC's are grown as adherent monolayers on a cellular support, preferably Matrigel, in defined cellular media (no serum or KSR). The cellular media, in addition to typical components as otherwise described herein, also preferably comprise an effective amount of one or more of the following components in effective amounts: ascorbic acid, transferrin, β-Mercaptoethanol (Gibco), fibroblast growth factor (FGF), LR-IGF, Activin A, and heregulin, and preferably all of these components. The cellular media in which adherent layers (or embryoid bodies) of hESCs are grown to be used as starting cell populations for differentiation may be varied within the teachings of the art.

The hESC's produced above, are then plated onto cellular support and differentiated in a differentiation medium (as otherwise described herein) in effective amounts of differentiation agents and/or inhibitors. The cells are preferably grown as adherent monolayers. In the case of mesendoderm cells, hESCs are contacted with a differentiation medium comprising an effective amount of a GSK inhibitor as otherwise herein (preferably BIO or Wnt3a) for an appropriate period of time (as otherwise described herein, ranging from about 18 hours to about 72 hours) to produce a mesendoderm cell population. In the case of mesoderm cells, hESCs are contacted with a differentiation medium comprising an effective amount of a GSK inhibitor as otherwise herein (preferably BIO or Wnt3a) in combination with a bone morphogenic protein (BMP-2, BMP-4, BMP-6, BMP-7) for an appropriate period of time to produce a mesoderm (Isl1+) cell population (longer duration differentiation—about 5-10 days, about 4-8 days, about 5-7 days, about 6 days, about 140-150 hours).

In a further embodiment, the cell culture medium may be a conditioned medium (MEF-CM). The conditioned medium can be obtained from a feeder layer. It is contemplated that the feeder layer may comprise fibroblasts, and in one embodiment, comprises embryonic fibroblasts. Preferably, the medium is feeder cell free.

In a particularly preferred embodiment, the differentiation medium for producing mesendoderm cells, mesoderm (Isl1+) cells or MMCs comprises DMEM/F12 (50/50), approximately 2% probumin (albumin), antibiotics (1× Pen/Strep 1×NEAA), Trace Elements A, B, C (e.g., 1× from Mediatech), Ascorbic acid (e.g. about 50 μg/ml), Transferrin (e.g. about 10 μml), β-Mercaptoethanol (about 0.1 mM), bFGF (e.g. about 8 ng/ml), LR-IGF (e.g., about 200 ng/ml), Activin A (e.g., about 10 ng/ml) and Heregulin (e.g., about 10 ng/ml). Note that Activin A and Heregulin may be removed for production of multipotent migratory cells (MMCs). Of course, one or more of the above-components may be left out of the differentiation medium as taught by the art, but the full componentry as set forth is preferred for use in the present invention.

The present cells also provide potential for use in bioassays to identify molecules which impact (promote, inhibit or influence) differentiation of cells. The first step in the differentiation of the present cells provides a great chance to study epithelial to mesenchymal transition, especially in the progession of cancer, as part of tumor metastasis. Thus, the methods and populations of cells according to the present invention provide exceptional systems to both understand EMT at the molecular level and identify new drug targets and also to screen for small molecules that block EMT under conditions that promote EMT (BIO). Given that cells can be grown in 96/384 well plates this could easily be done, rapid drug-screening may be used to identify potential molecules which block or inhibit EMT and may represent potentially valuable anticancer agents.

With respect to MMCs, this is a stable population of cells growing in defined media with multi-potent differentiation capabilities. These cells may be particularly useful for screening for molecules that promote or inhibit differentiation or promote and specify differentiation to one lineage or another.

Therapies

The population of cells and/or methods which are described herein may provide useful therapies in the treatment of disease and/or conditions associated with the cells.

In a first aspect, the present invention provides a method for treating a patient suffering from a cardiovascular disorder. This method comprises culturing pluripotent stem cells, differentiating the pluripotent stem cells in vitro into cardiovascular muscle cells (cardiomyocytes) and implanting an effective amount of the cardiovascular muscle cells into a patient in need thereof. Alternatively, a method of treating cardiovascular disease, including an infarction, in a patient comprises administering into the heart tissue of a patient in need of therapy thereof an effective amount of mesoderm (Isl1+) cells.

In another aspect, the present invention provides a method for treating damaged or ischemic vascular tissue (blood vessels) in a patient in need thereof, comprising administering to the blood vessels to be repaired an effective amount of mesoderm (Isl1+) cells. In an alternative embodiment, mesoderm (Isl1+) cells are differentiated to smooth muscle cells by passaging the cells for a period of at least about 5-6 days in a cell differentiation medium comprising an effective amount of a GSK inhibitor (preferably Wnt3a) in combination with BMP (BMP4) and the smooth muscle cells obtained therefore are administered (implanted) to the site of structural vascular damage in the patient in order to treat/repair same.

In another aspect, the present invention provides a method for treating a patient suffering from, or at risk of developing, Type1 diabetes. This method involves culturing pluripotent stem cells, differentiating the pluripotent stem cells in vitro into a β-cell lineage, and implanting the cells of a β-cell lineage into a patient.

In yet another aspect, this invention provides a method for treating a patient suffering from, or at risk of developing, Type 2 diabetes. This method involves culturing pluripotent stem cells, differentiating the cultured cells in vitro into a β-cell lineage, and implanting the cells of a β-cell lineage into the patient.

If appropriate, the patient can be further treated with pharmaceutical agents or bioactives that facilitate the survival and function of the transplanted cells. These agents may include, for example, insulin, members of the TGF-β family (TGF-β 1, 2, and 3) bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others. Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells, prior to transplantation into a recipient. Alternatively, the pluripotent stem cells may be transplanted into a recipient in an undifferentiated or partially differentiated state. Further differentiation may take place in the recipient.

Mesoderm (Isl1+) cells and/or cardiovascular muscle cells may be implanted as dispersed cells or formed into clusters that may be infused directly into the heart or hepatic portal vein. Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response and implanted into an appropriate site in a recipient. The implantation sites include, within context, the heart, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants, immunosuppressants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In another aspect, this invention provides a method for treating a patient suffering from, or at risk of developing cardiovascular disease or diabetes. This method involves culturing pluripotent stem cells, differentiating the cultured cells in vitro into a cardiovascular muscle cell lineage or β-cell, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells or which may otherwise be used to treat diabetes or cardiovascular disease or dysfunction.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656,488, U.S. Published Application 2004/0062753 A1, U.S. Pat. No. 4,557,264 and U.S. Pat. No. 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945. The support may also be incorporated with at least one pharmaceutical compound that is an inhibitor of fibrosis, such as, for example, compounds disclosed in U.S. Pat. No. 6,331,298. The support may also be incorporated with at least one pharmaceutical compound that is capable of enhancing angiogenesis, such as, for example, compounds disclosed in U.S. Published Application 2004/0220393 and U.S. Published Application 2004/0209901. The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β 1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-α, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention may be understood more readily by reference to the following detailed description of the preferred embodiments of the invention and the Examples included herein. However, before the present compositions and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art.

EXAMPLES

The following examples are provided to further describe the present invention. It is noted that the following examples are not to be construed as limiting the present invention in any way.

All of the examples are applicable to (but not restricted to) multiple hESC lines including BG01, BG02, WA09.

Example 1

Culture of Human Embryonic Stem Cells (a) Human Embryonic Stem Cells

Figure 2:
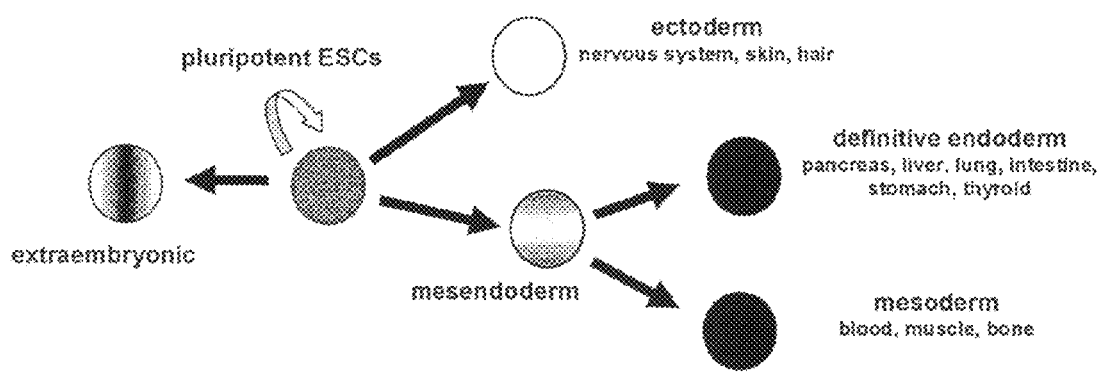
FIG. 2. Schematic of potential hESC cell fate decisions showing ectoderm, mesoderm, endoderm and extra-embryonic lineages.

Human embryonic stem cells (hESCs; FIG. 1) are derived from the inner cell mass (ICM) of blastocyst stage, late pre-implantation embryos. Their strength as an experimental tool for developmental biologists comes from their ability to self-renew and to differentiate into the three embryonic germ layers (ectoderm, endoderm and mesoderm) and extra-embryonic lineages in response to specification signals (FIG. 2). Since the properties and behavior of hESCs recapitulate many embryonic processes, they can be used to understand the development of pluripotent cells in the epiblast and the mechanisms underpinning differentiation into the germ layers at gastrulation. They are also a source of material for the generation of therapeutically useful cell types.

(b) Methods for Growing hESC.

Methods: hESCs expressing markers such as the POU domain transcription factor Oct4 are preferably grown in mouse embryonic feeder conditioned medium MEF-CM or defined media using Matrigel as a growth matrix (for example). Cells are typically plated at 1–1.5×10$^6$ per 60 mm dish. Cells are passaged every 4-5 days at a split of ~1:4 to 1:10.

(i) Mouse Embryo Fibroblast Conditioned Media (MEF-CM)

hESCs can be grown on Matrigel (BD Biosciences; 1:20-1:200 dilution is preferred) or other matrices that support hESC maintenance in mouse embryo fibroblast conditioned media (MEF-CM) in the presence of Fgf2 (McLean et al. Stem Cells 25: 29). Cells can be passaged by a variety of methods using enzymatic (trypsin, Accutase™, collagenase), manual passage (mechanical) and non-enzymatic methods. Cells are plated at a density of 1.5×10$^6$ per 60 mm dish and passaged every 4-5 days at a split of 1:4-1:10.

(ii) Defined Conditions (DC)

(a) Defined media for routine culture of hESCs is purchased from Invitrogen as StemPro® (Wang et al., Blood 110: 4111). The media is used according to the manufacturer's recommendations except that Accutase™ is used for passaging cells as single cell suspensions. We routinely produce this formulation ourselves when we require to modify its constituents for differentiation experiments. The following represents this formulation and is capable of maintaining hESCs in a pluripotent state. The following defined, serum free media conditions work well but are not restricted to this specific formulation and involves feeder-free culture: DMEM:F12 (Gibco), 2% BSA (Seriologicals, #82-047-3), 1× Pen/Strep (Gibco), 1× non-essential amino acids (Gibco), 1× Trace Elements A, B and C (Cellgro; #99-182-C1, #99-176-C1, #99-175-C1), 50 ug/ml Ascorbic Acid (Sigma, #A4034), 10 ug/ml Transferrin (Gibco, #11107-018), 0.1 nM beta-mercaptoethanol, 8 ng/ml Fgf2 (Sigma, #F0291), 200 ng/ml LR-IGF (JRH Biosciences, #85580), 10 ng/ml Activin A (R&D Systems, #338-AC), 10 ng/ml Heregulin beta (Peprotech; #100-03).

(b) hESCs can also be cultured in additional commercially available defined media formulations such as mTeSR1 (BD/Stem Cell Technologies; Ludwig et al., Nat. Biotechnol. 24:185), according to the manufacturer's recommendations. Accutase™ passaging is also used in conjunction with this media.

c. Differentiation Capacity of hESCs hESCs have the capacity to differentiate into each of the three embryonic germ layers (ectoderm, endoderm and mesoderm) in addition to extra-embryonic lineages (FIG. 2). They are therefore a starting point from which to generate a wide variety of therapeutically useful cell types.

Example 2

Methods for Generation of Mesendoderm Cells

Figure 3:
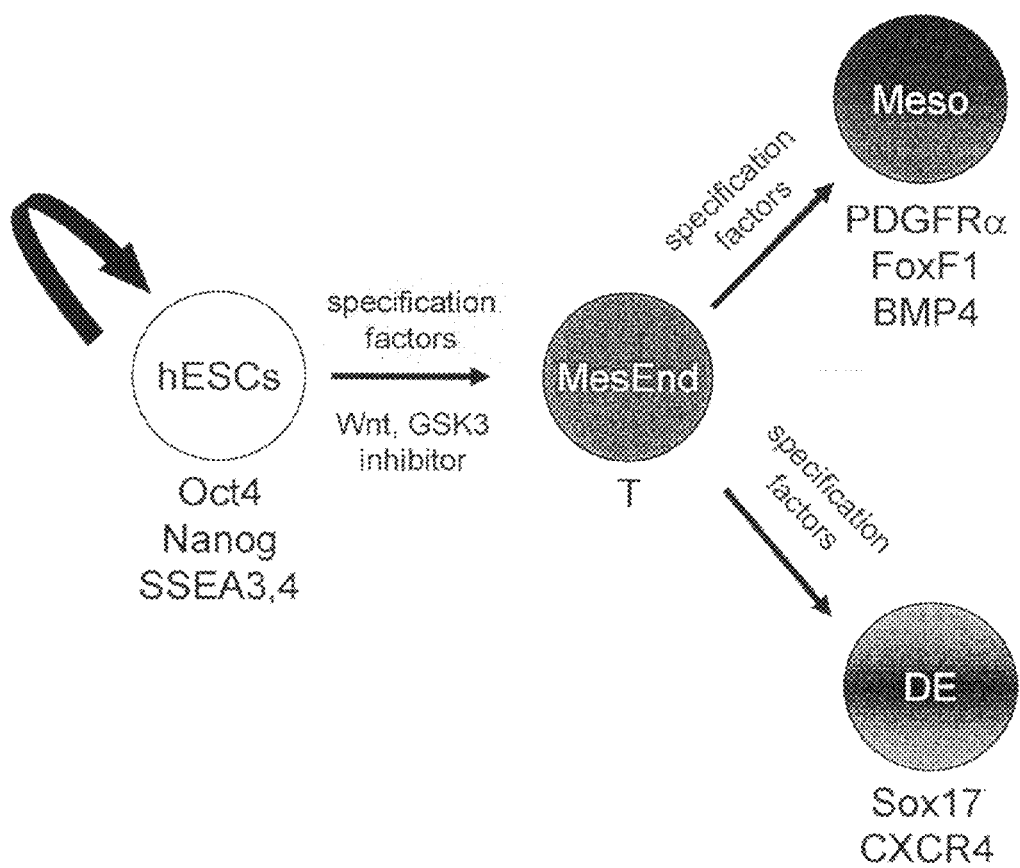
FIG. 3. Schematic showing differentiation pathway leading to formation of T+ mesendoderm which can further differentiate into mesoderm (meso) or definitive endoderm (DE).

Differentiation of hESC towards mesoderm and endoderm involves transition through a T+/Brachyury+ mesendoderm intermediate cell type by addition of differentiation inducing factors such as Wnt3a and GSK inhibitors (FIG. 3).

(a) Using Wnt to Generate Mesendoderm from hESCs

This method involves the differentiation of hESCs to mesendoderm by addition of the canonical Wnt signaling molecule Wnt3a.

Figure 4A:
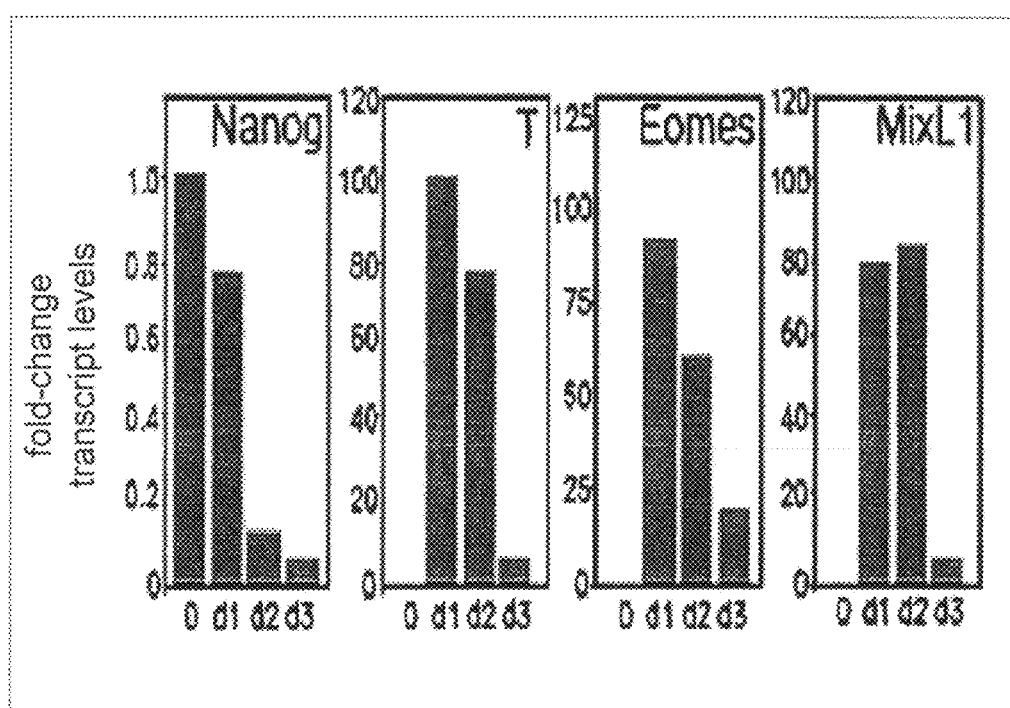
FIG. 4. Formation of mesendoderm under defined media conditions following addition of Wnt3a to BG01 hESCs. (A) Q-PCR analysis of Nanog, T, Eomes and MixL1 transcripts following addition of Wnt3a (25 ng/ml) over a 3 day period. (B) Immunostaining of cells treated with Wnt3a for 2 days (48 hours)—panels show staining for E-cadherin, Nanog, T, β-catenin and Snail for untreated (hESCs) and treated (+Wnt3a) samples.
Figure 4B:
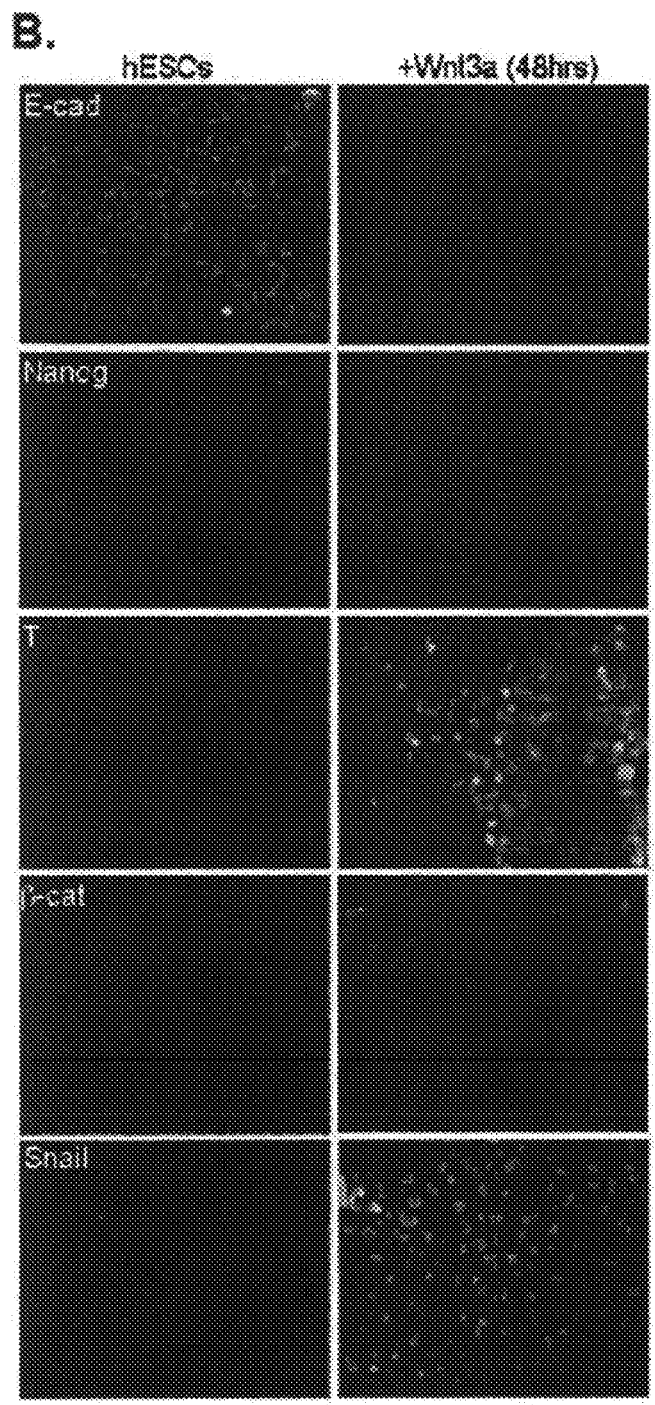

(a-i) Generation of Mesendoderm Using Wnt3a in the Presence of Low Activin A Containing Media hESCs (BG01) were plated as per the conditions specified in Example 1 in defined media. After ~16-24 hours, human Wnt3a (25 ng/ml; R&D Systems) was added to cultures. Q-PCR analysis showed that Nanog transcripts had decreased by 48 hours; T, Eomes and MixL1 mRNA levels increased over 1-2 days, then decreased by day 5 (FIG. 4A). Immunostaining was used to determine that, after 48 hours, E-cadherin and Nanog are downregulated. During this time frame, β-catenin and Snail accumulate in the nucleus and T/brachyury levels are increased (FIG. 4B). Together with the Q-PCR data, these results indicate that Wnt3a caused hESCs to differentiate to mesendoderm, involving an epithelial to mesenchymal transition.

Figure 5:
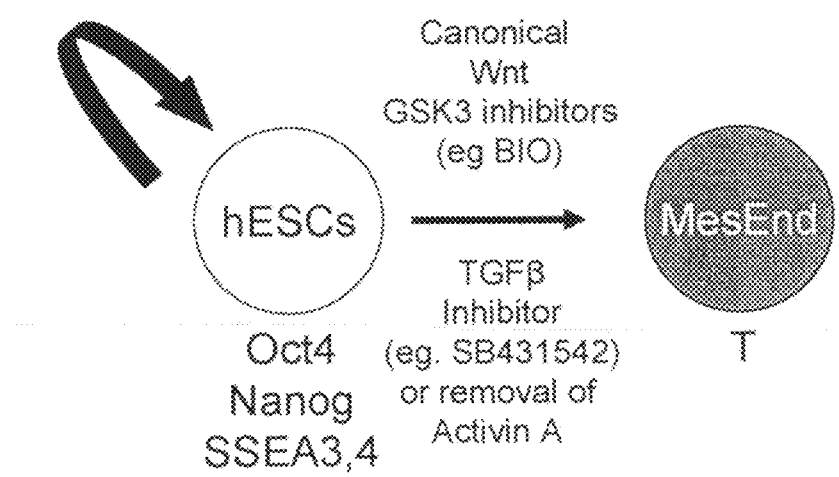
FIG. 5. Model showing formation of mesendoderm in the presence of canonical Wnt signals in the absence of TGFβ signaling.

(a-ii) Generation of Mesendoderm Using Wnt3a in the Absence of Activin A Signaling.

hESCs can be differentiated to mesendoderm by addition of Wnt3a (25 ng/ml) in defined media supplemented with SB431542 (20 µM). This is possible because hESC differentiation to mesendoderm does not require Activin A signaling but, is dependent on activation of the canonical Wnt signaling pathway (FIG. 5).

(a-iii) Generation of Mesendoderm Using Wnt3a in Media Containing No Activin A.

hESCs can be differentiated to mesendoderm by addition of Wnt3a (25 ng/ml) in defined media or MEF-CM lacking Activin A. This is possible because hESC differentiation to mesendoderm does not require Activin A signaling but, is dependent on activation of the canonical Wnt signaling pathway (FIG. 5).

(a-iv) Generation of Mesendoderm Using Wnt3a in the Absence of Activin A in the Presence of SB431542.

hESCs can be differentiated to mesendoderm by addition of Wnt3a (25 ng/ml) in defined media lacking Activin A in the presence of the Activin A signaling inhibitor SB431542. This is possible because hESC differentiation to mesendoderm does not require Activin A signaling.

(b) Generation of Mesendoderm from hESCS Using Inhibitors of GSK

This method involves the differentiation of hESCs to mesendoderm by addition of the GSK inhibitor BIO ((2'Z, 3'E)-6-Bromoindirubin-3'-oxime; GSK3 inhibitor IX, Calbiochem).

Figure 6A:
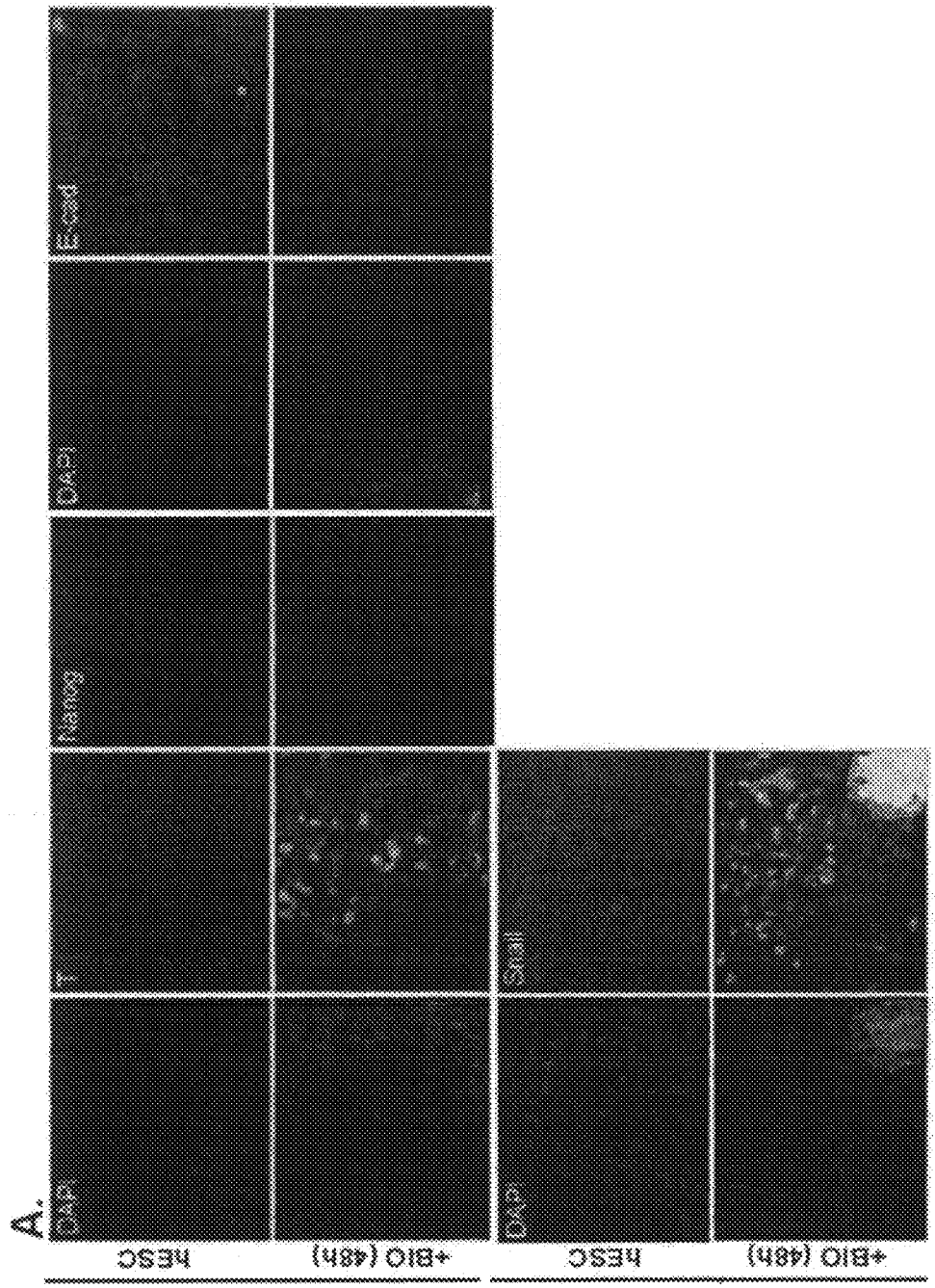
FIG. 6. (A) Formation of mesendoderm following treatment of BG02 hESCs grown in defined media on. Matrigel with BIO for 48 hours. Immunostaining shows staining for T, Nanog, E-cadherin and Snail in untreated hESCs and BIO treated cells. DAPI was used to stain DNA. (B) Q-PCR analysis of Nanog, T, MixL1 transcripts following treatment of hESCs with BIO, over 48 hours.
Figure 6B:
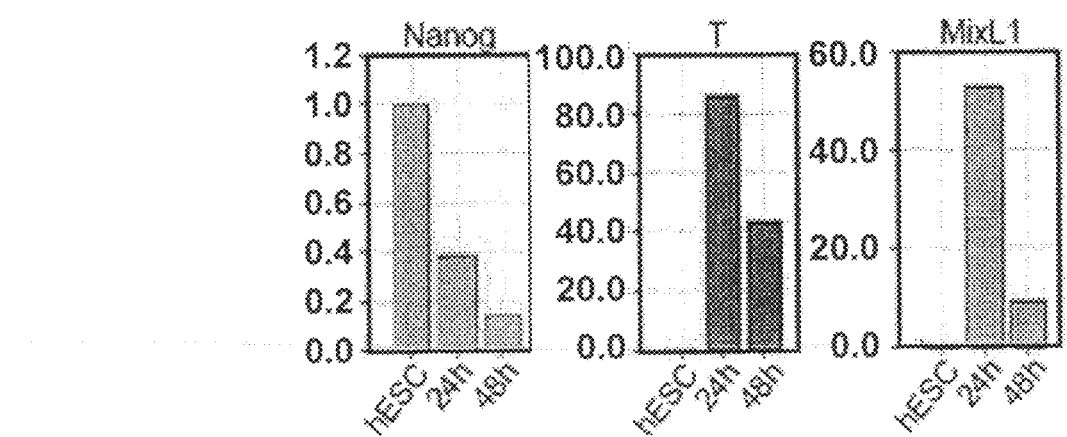

(b-i) Generation of Mesendoderm from hESCS Using BIO in Defined Media hESCs (BG01) were plated as per the conditions specified in Example 1 in defined media. After ~16-24 hours, BIO (2 µM) was added to cultures. Q-PCR analysis showed that Nanog transcripts had decreased by 48 hours; T and MixL1 mRNA levels increased over the first 24 hours then decreased thereon (FIG. 6). Immunostaining was used to determine that, after 48 hours, E-cadherin and Nanog are downregulated. During this time frame, Snail accumulates in the nucleus and T/brachyury levels are increased (FIG. 6). Together with the Q-PCR data, these results indicate that BIO caused hESCs to differentiate to mesendoderm, involving an epithelial to mesenchymal transition.

(b-ii) Addition of the GSK Inhibitor, Bio, to hESCS Grown in MEF-CM hESCs (BG02) grown in MEF-CM on Matrigel coated plates, were passaged in MEF-CM plus BIO (2 µM) over 4 days. The first experiment shows cells passaged with trypsin.

Figure 7:
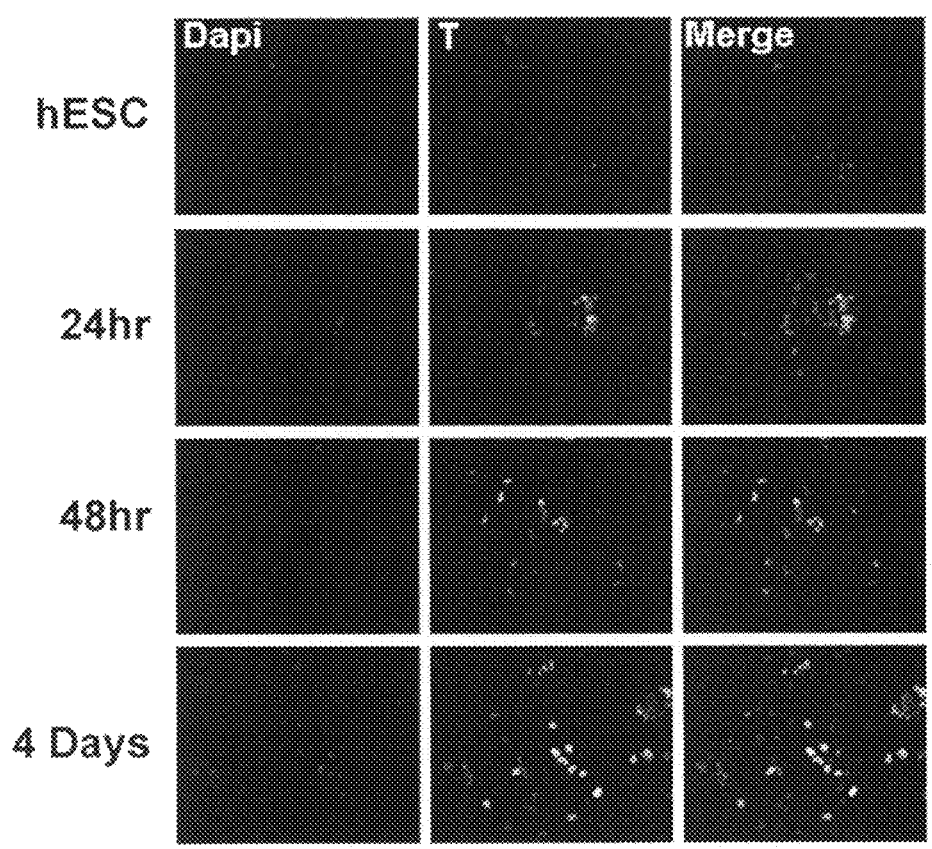
FIG. 7. Trypsin passaged BG01 hESCs grown on Matrigel in MEF-CM were treated with BIO (2 μM) for up to 4 days. Cells were immunostained, probing for (A) T and (B) E-cadherin, Oct4. Merged images are also shown. DAPI was used to detect DNA.
Figure 7:
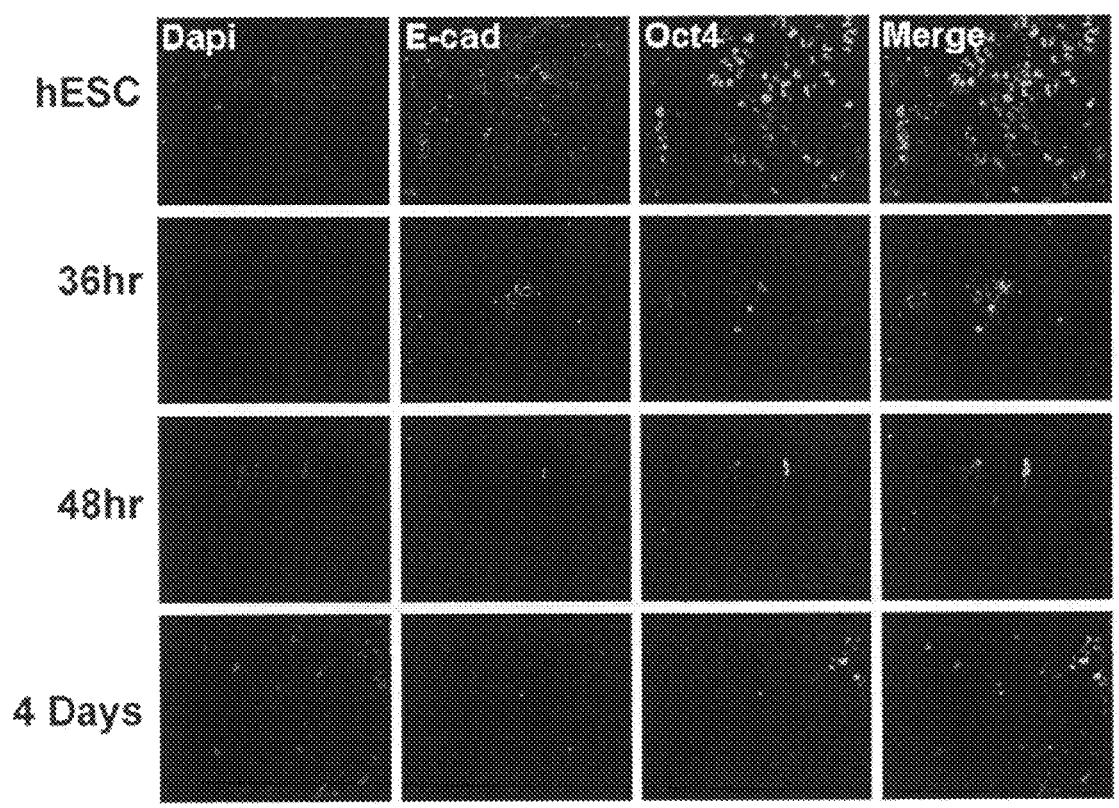
Figure 8:
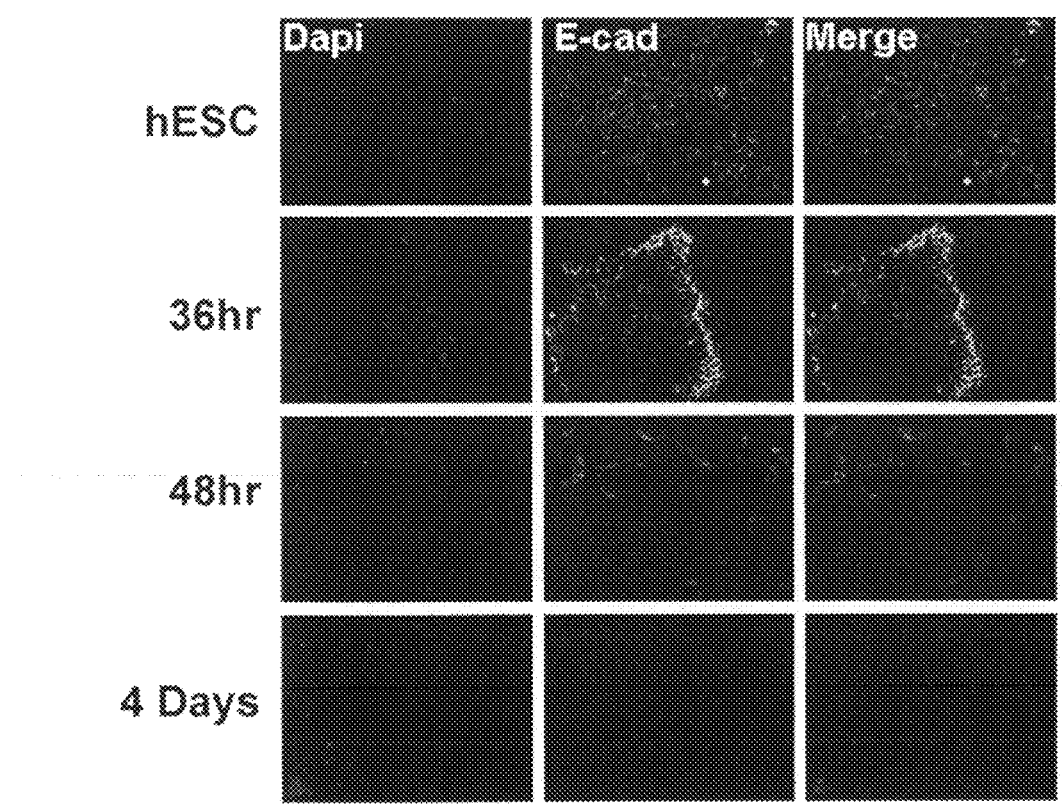
FIG. 8. Collagenase passaged BG01 hESCs grown on Matrigel in MEF-CM were treated with BIO (2 μM) for up to 4 days. Cells were immunostained, probing for (A) E-cadherin and (B) T and Nanog. Merged images are also shown. DAPI was used to detect DNA.
Figure 8:
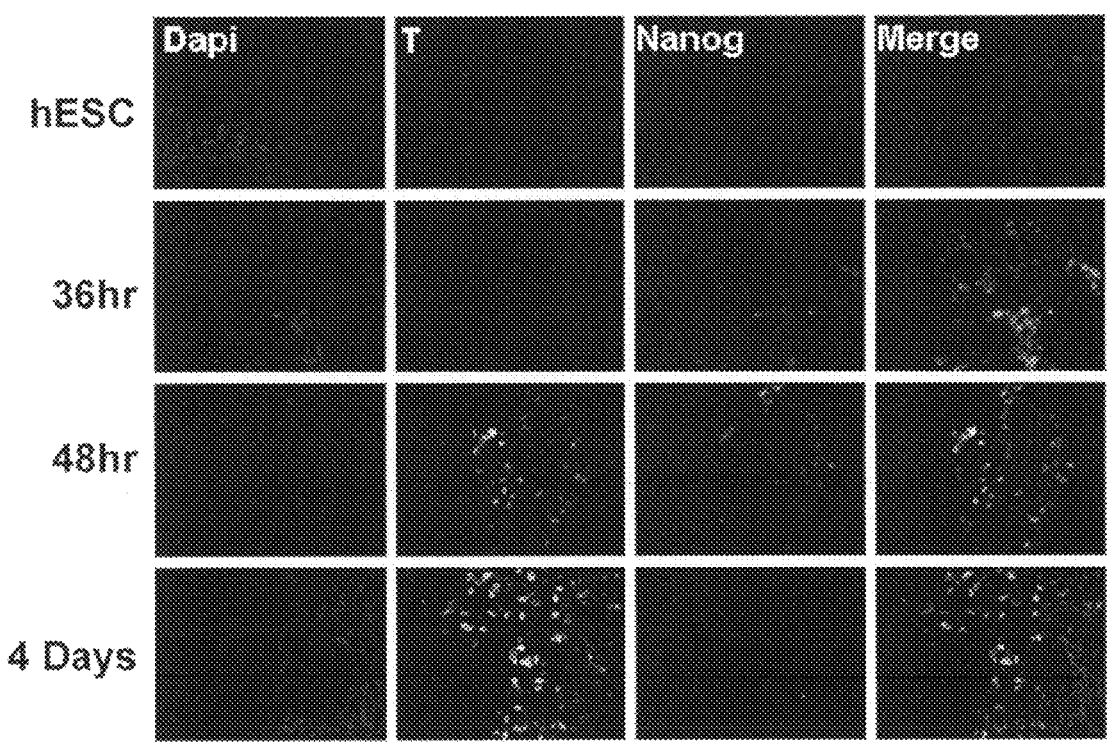

In this experiment BIO treatment caused downregulation of Oct4 and E-cadherin and, upregulation of T/Brachyury (FIG. 7A, B). This is indicative that BIO treatment promotes an epithelial to mesenchymal transition and differentiation to mesendoderm. The second experiment shows a similar experiment where BIO was added to hESCs cultured in MEF-CM, this time passaged with collagenase. BIO treatment caused a downregulation of Nanog and E-cadherin and, upregulation of T/Brachyury (FIG. 8A, B). These results are again indicative that GSK inhibition by BIO causes mesendoderm differentiation and is associated with an epithelial to mesenchymal transition.

Figure 9A:
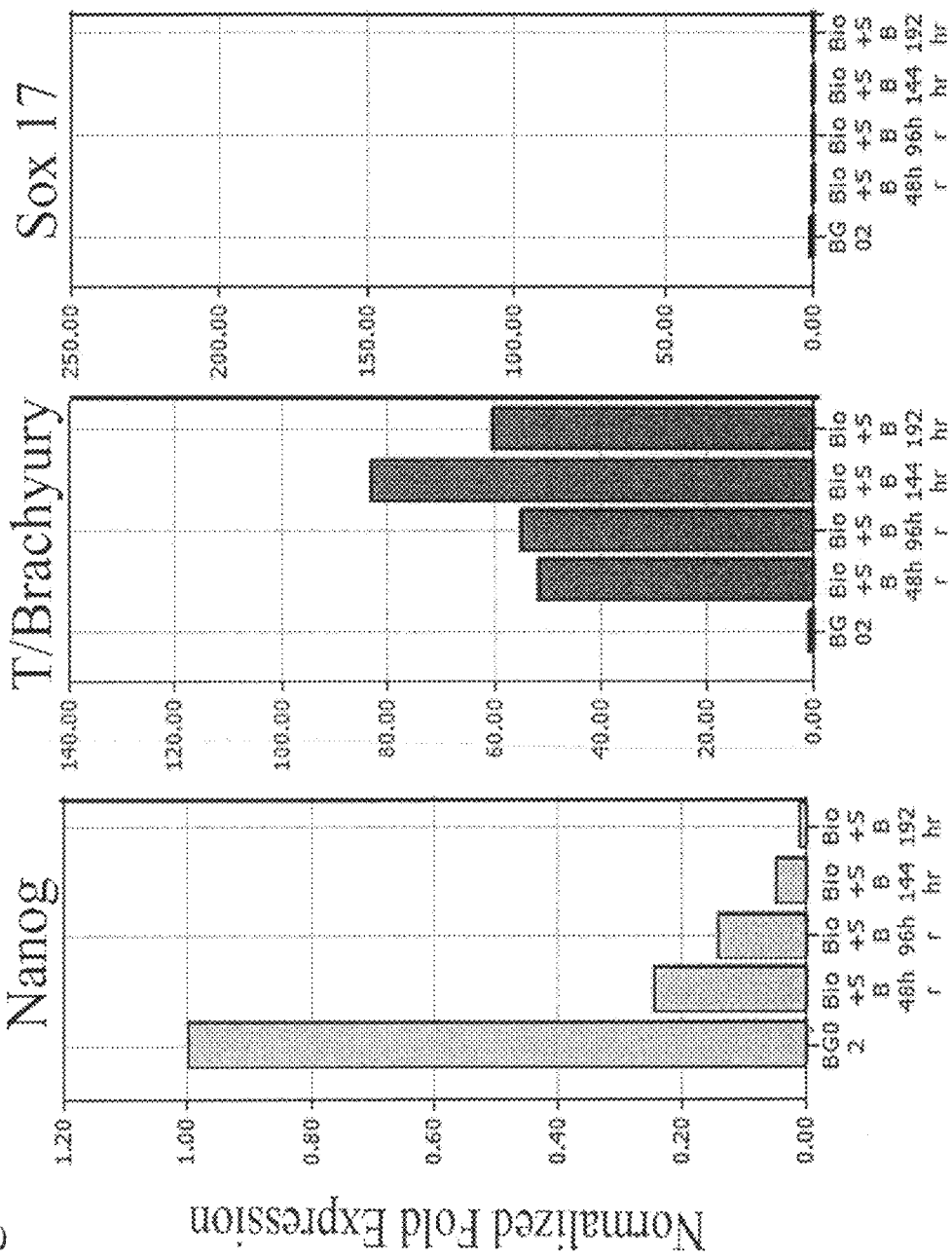
FIG. 9. Formation of mesendoderm in the presence of BIO and SB431542. Q-PCR analysis of hESCs treated with BIO (2 μM) and SB431542 (20 μM) for up to 8 days. Message levels for (A) Nanog, T, Sox 17, and CXCR4, FoxF1 and (B) PDGFRalpha are shown.

(b-iii) Differentiation to Mesendoderm by Addition of the GSK Inhibitor, BIO, and SB431542 hESCs (BG02) grown on Matrigel in defined media were passaged with Accutase™ into defined media supplemented with BIO (2 µM) and SB431542 (20 µM). Q-PCR analysis was used to monitor differentiation of these cells over an 8 day period. This data showed that BIO/SB431542 treatment caused a decrease in Nanog transcripts within 24-48 hours, indicating loss of pluripotency (FIG. 9). After 24 hours T/Brachyury transcript levels were significantly elevated and remained so for the duration of the time course. Markers for mesoderm (FoxF1, PDGFRalpha) and endoderm (Sox17, CXCR4) did not change significantly during this time course (FIG. 9). These results indicate that BIO can promote differentiation of hESCs into mesendoderm, in the absence of Activin A signaling, due to inhibition by SB431542.

(b-iv) Differentiation of hESCS to Mesendoderm by Treatment with GSK Inhibitors, in Media Lacking Activin A.

hESCs can be differentiated to mesendoderm by addition of BIO to hESCs growing in either MEF-CM or defined media lacking Activin A. This is based on our previous work showing that mesendoderm differentiation is independent of Activin A signaling and that BIO can promote an EMT/mesendoderm differentiation in MEF-CM and defined media (FIG. 5).

(b-v) Differentiation of hESCS to Mesendoderm by Treatment with GSK Inhibitors, in Media Containing High Activin A.

hESCs can be differentiated to mesendoderm by addition of BIO to hESCs growing in either MEF-CM or defined media with high levels of Activin A (100 ng/ml). This is based on our previous work showing that mesendoderm differentiation is independent of Activin A signaling and that BIO can promote an EMT/mesendoderm differentiation in MEF-CM and defined media.

Example 3

Methods for Generation of Mesoderm-Derived Isl1+ Multipotent Progenitors (IMPs)

Figure 10:
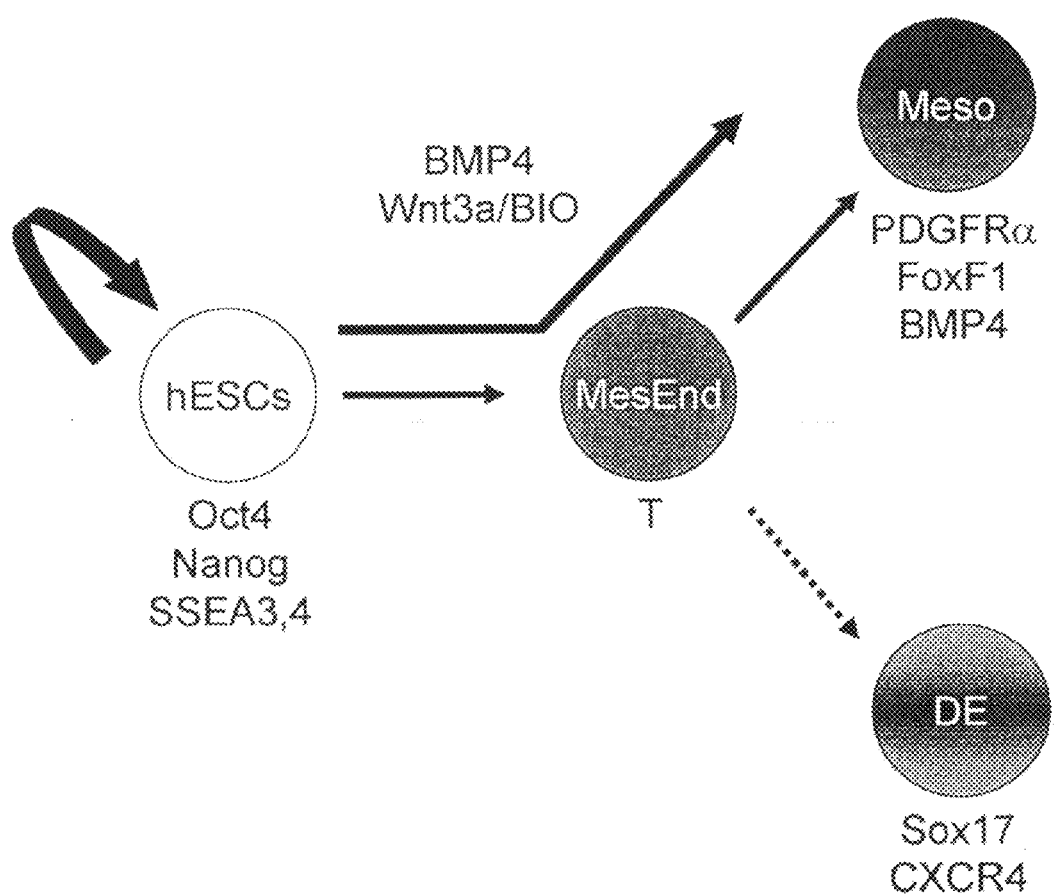
FIG. 10. Schematic showing formation of mesoderm through a mesendoderm intermediate following treatment of hESCs with BMP4 and Wnt3a/BIO.

This Example describes a method for generation of a mesoderm-derived Isl1+ multipotent progenitor (IMP) cell type that has ability to differentiate into cardiomyocytes, smooth muscle cells or endothelial cells. This cell type differentiates along a pathway through the mesendoderm state and then to mesoderm (FIG. 10).

(a) Generation of an Isl1+ Multipotent Progenitor (IMP) by Addition of Wnt3a and BMP4 to hESC Cultures.

Figure 11B:
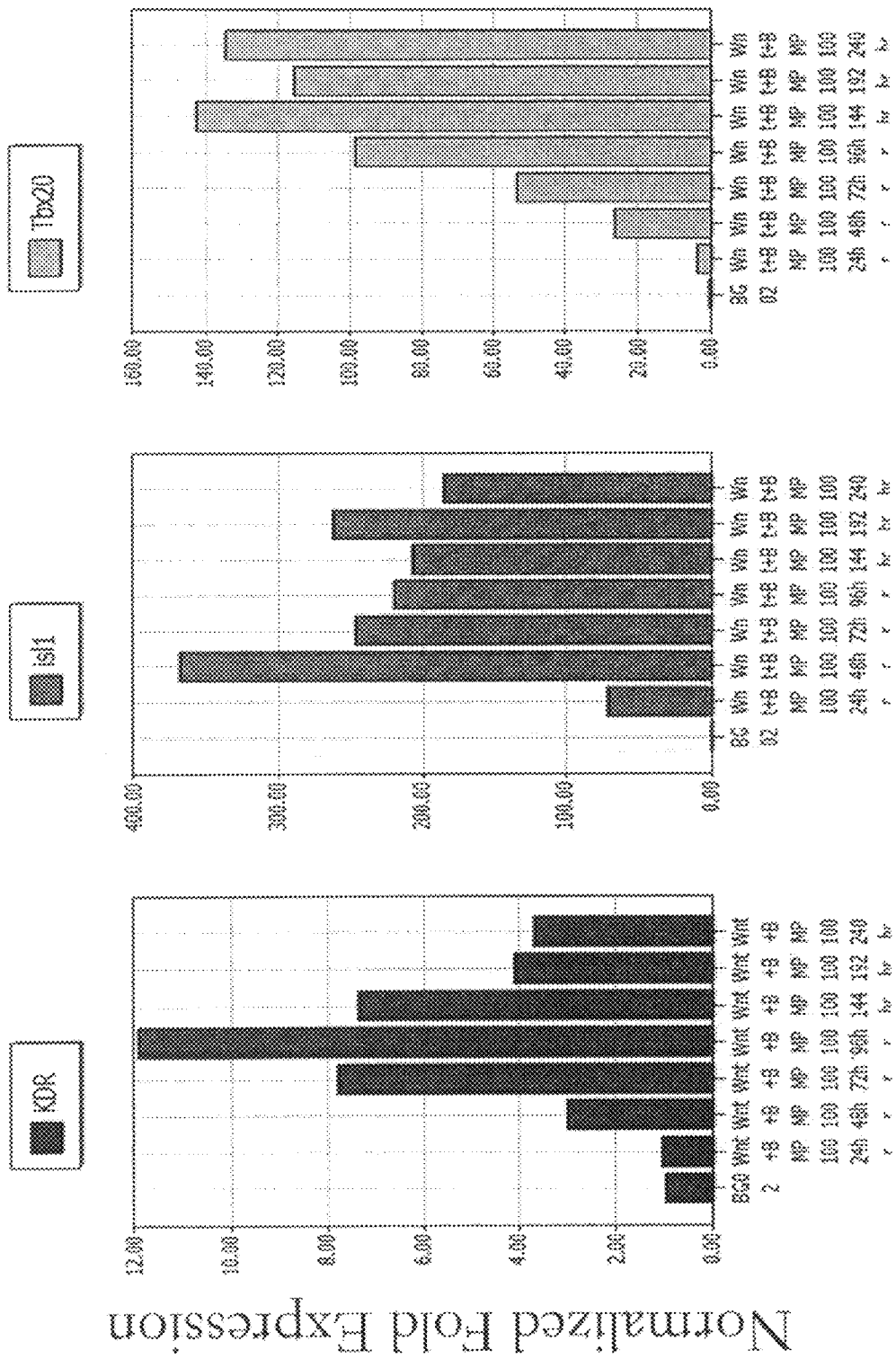
FIG. 11. Differentiation of hESCs to Isl1+ multipotent progenitors (IMP) cells following treatment with Wnt3a (25 ng/ml) and BMP4 (100 ng/ml) over a 10 day period. Transcripts analysis for (A) T, Sox17, PDGFRalpha, (B) KDR, Isl1, Tbx20, and (C) GATA4, VE-cadherin and cTNT are shown.
Figure 12:
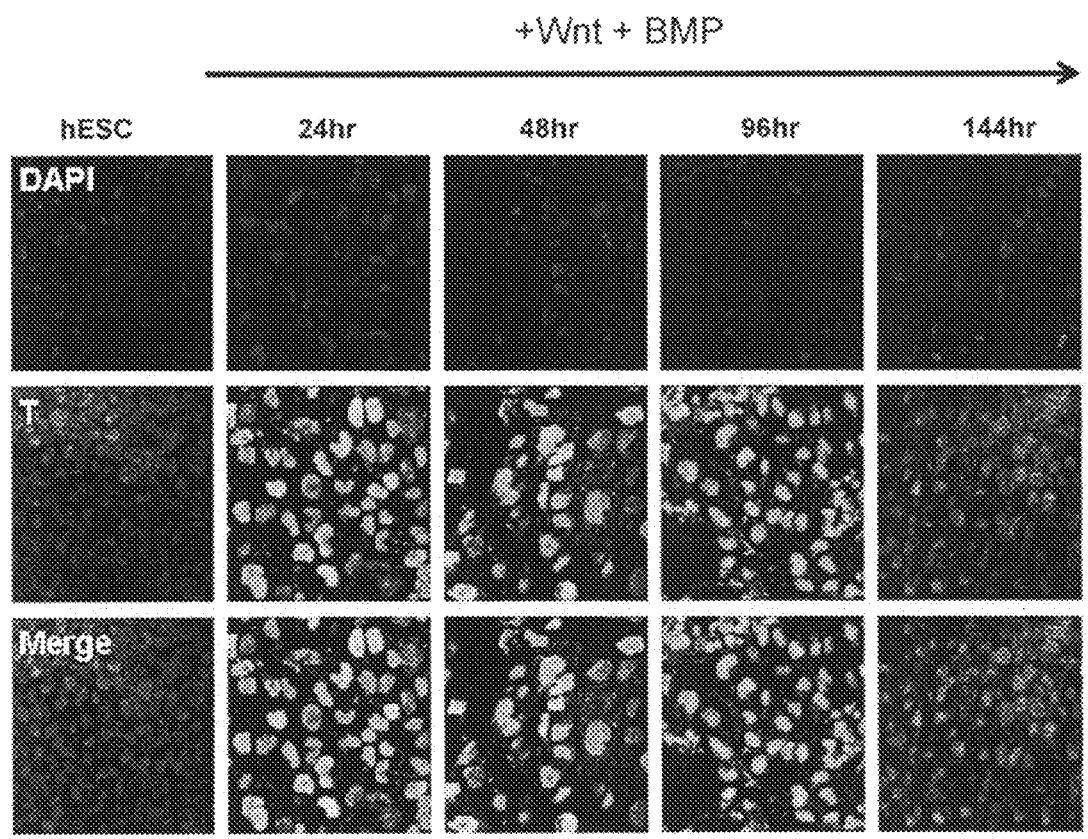
FIG. 12. Transition of hESCs through a T+ state following treatment with Wnt3a (25 ng/ml) and BMP4 (100 ng/ml) over a 144 hour time frame. Immunostaining for T is shown. DAPI is used to indicate DNA. Merge represent DAPI/T staining superimposed.
Figure 13:
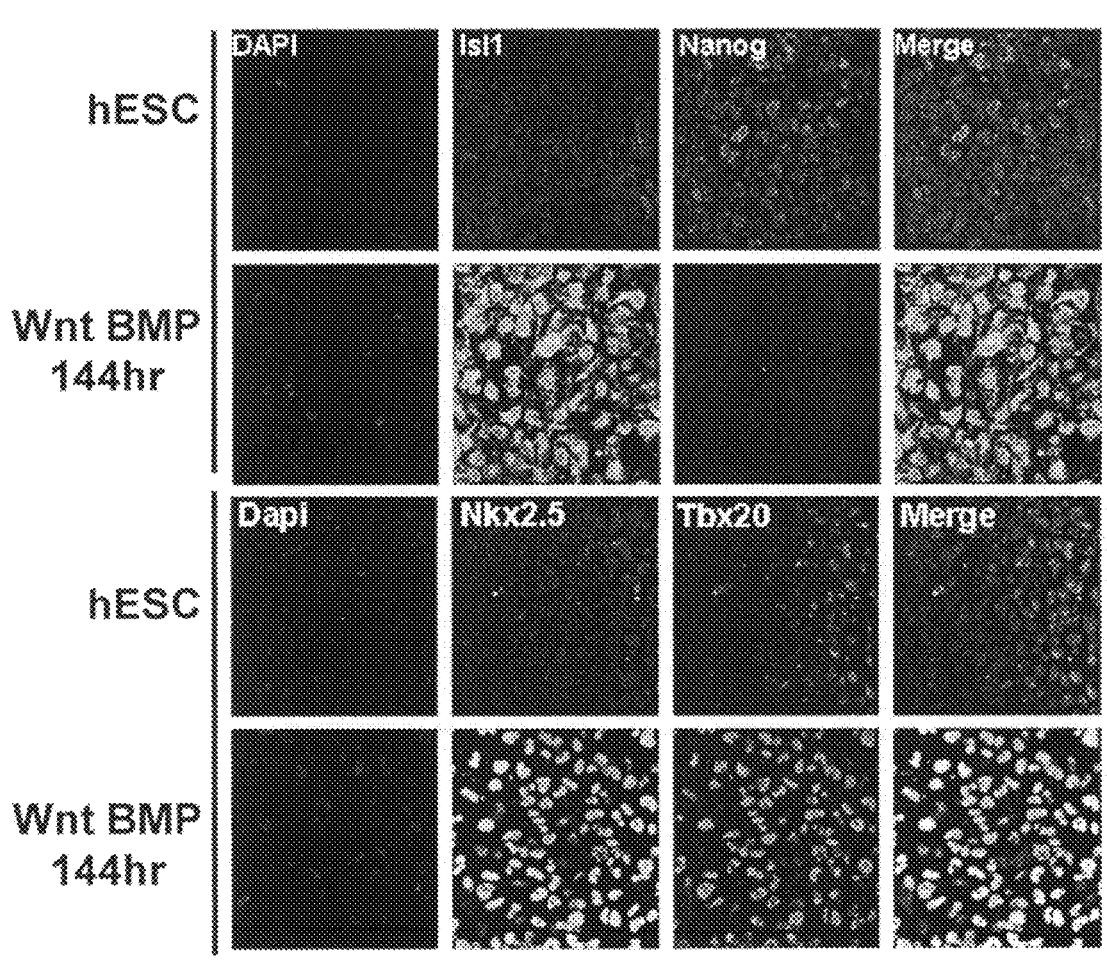
FIG. 13. Differentiation of hESCs to an Isl1+ state following treatment with Wnt3a (25 ng/ml) and BMP4 (100 ng/ml) over a 144 hour time frame. Cells were stained for Isl1, Nanog, Nkx2.5 and Tbx20. DAPI is shown to indicate DNA. Merge represents DAPI staining with Nanog/Isl1 or Nkx2.5/Tbx20.
Figure 14:
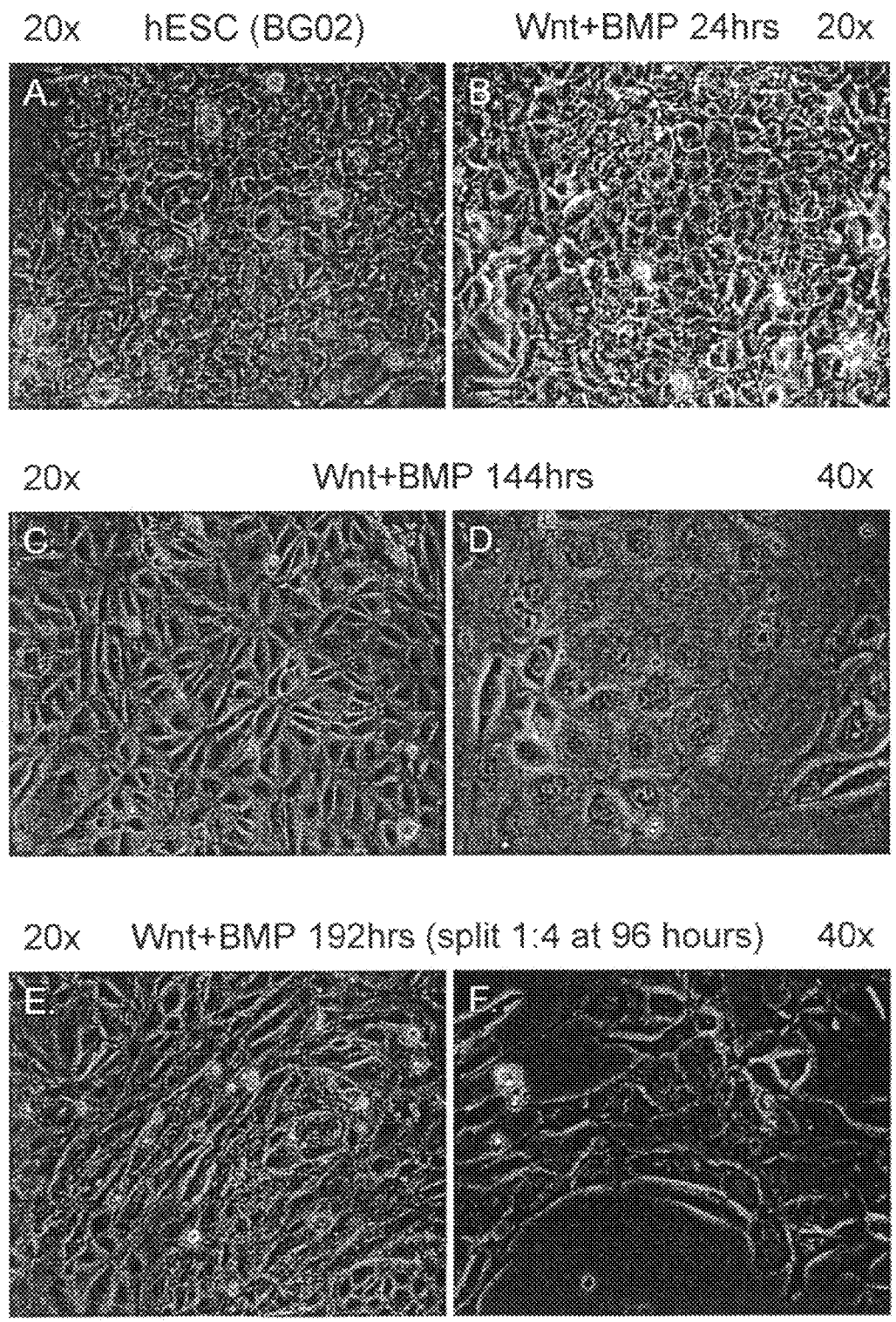
FIG. 14. Bright field images of, hESCs (BG02) and Wnt3a (25 ng/ml), BMP4 (100 ng/ml) treated cells at indicated time points A. Embryonic Stem Cells, B. at 24 Hours, C and D at 144 Hours, E and F at 192 Hours (split 1:4 at 96 Hours). Magnification of images are indicated.

BG02 hESCs grown in StemPro® defined media were passaged with Accutase™ and plated onto Matrigel coated dishes ($1.0 \times 10^6$ cells per 60 mm dish) as described in Example 1, except that media was supplemented with BMP4 (100 ng/ml, R&D Systems) plus human Wnt3a (R&D Systems). Media was replaced every day. Q-PCR analysis was performed over 240 hours (10 days) to evaluate differentiation. This analysis showed that mesendoderm markers such as T were elevated at 24 hours post-treatment but decreased thereafter (FIG. 11). After 24 hours treatment, transcript markers indicative of mesoderm differentiation were significantly upregulated (Isl1, PDGFRalpha, KDR, Tbx20, GATA4) (FIG. 11). Immunostaining revealed that over 24-96 hours post-treatment, most cells stained positive for T but this decreased by 144 hours (FIG. 12). After 6 days treatment (144 hours) with BMP4 and Wnt3a, >90% of cells stained positive for Nkx2.5, Isl1 and Tbx20 (FIG. 13). This gene expression profile is indicative of multipotent Isl1+ progenitor cells of the secondary heart field (Laugwitz et al., Development 135: 193-205). Differentiation to Isl1+ cells is accompanied by a distinctive cell morphology change (FIG. 14).

(b) Generation of an Isl1+ Multipotent Progenitor (IMP) by Addition of Wnt3a for Days 1-3 Followed by Addition of BMP4.

Figure 15:
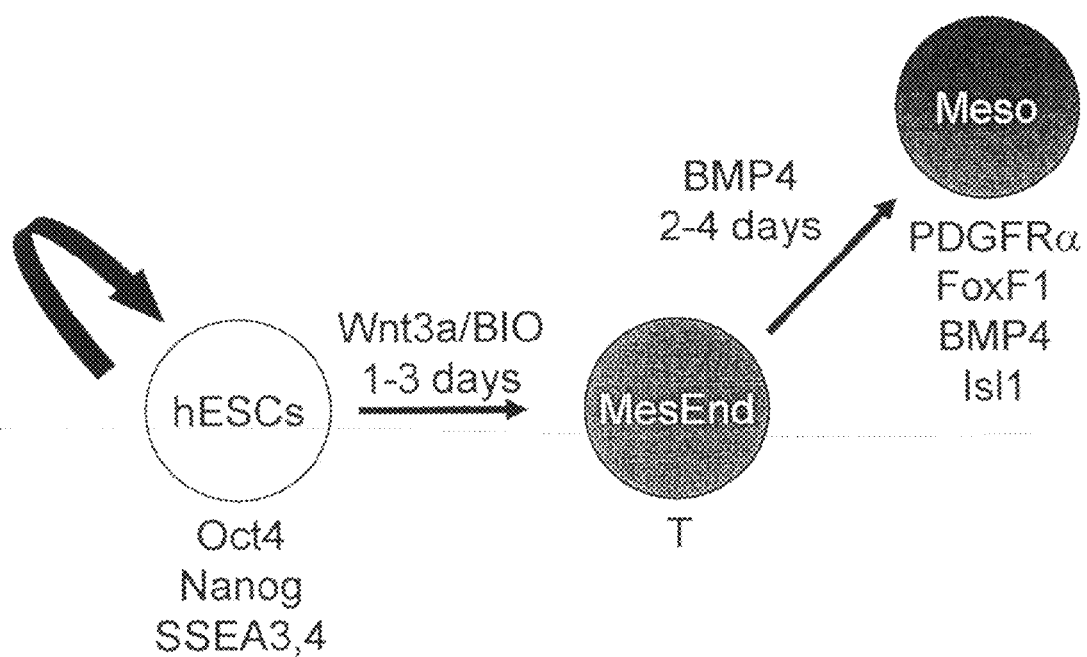
FIG. 15. Schematic illustrating the pathway as hESCs differentiate towards mesendoderm (MesEnd) and then mesoderm (meso). The first step involving treatment with Wnt3a/BIO for 1-3 days followed by treatment with BMP4 for an additional 2-4 days.

Isl1+ mesoderm cells can be generated by treatment of hESCs, grown in either MEF-CM or defined media, with Wnt3a for the initial 1-3 days followed by addition of BMP4 for a further 2-4 days (FIG. 15).

(c) Generation of an Isl1+ Multipotent Progenitor (IMP) by Addition of BMP4 and GSK Inhibitors Such as Bio to hESCS in MEF-CM.

Figure 16:
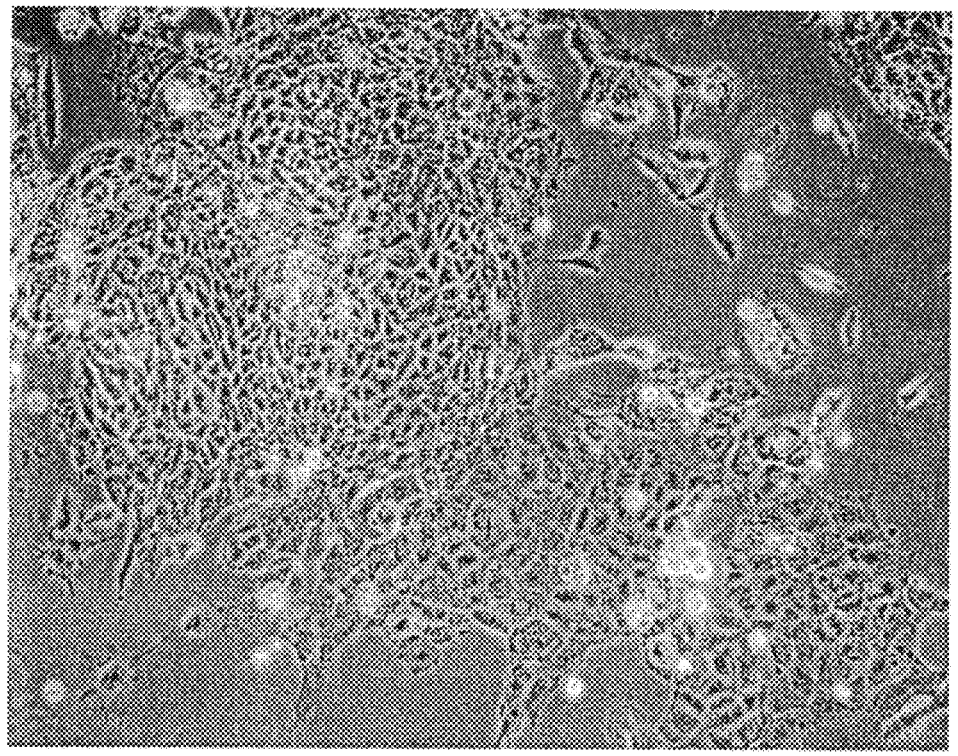
FIG. 16. Bright field image of hESCs treated with BIO (2 µM) and BMP4 (100 ng/ml) for 5 days. In this case hESCs were grown on Matrigel in MEF-CM. Magnification is indicated.
Figure 17A:
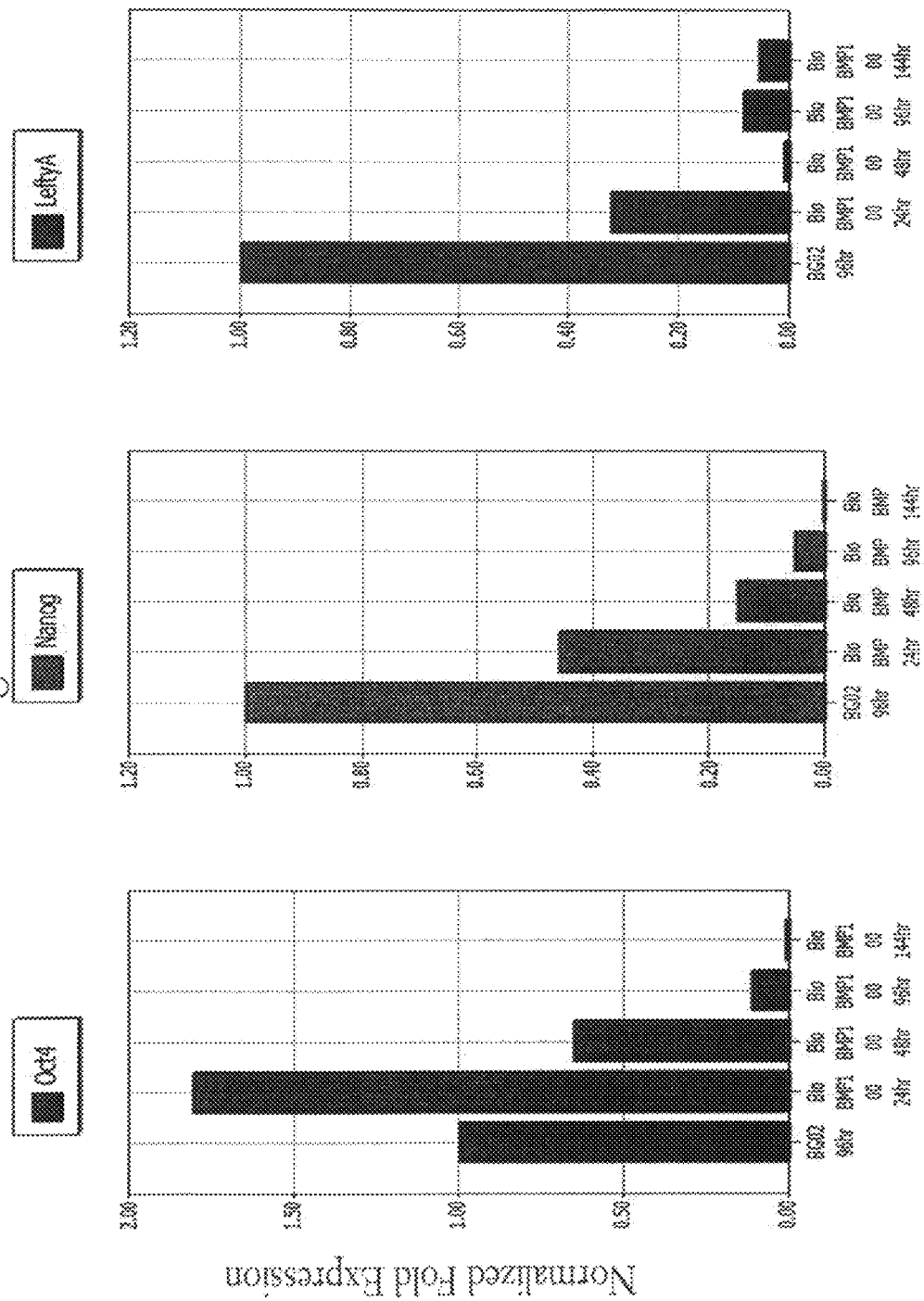
FIG. 17. Generation of Isl1+ multipotent progenitors (IMPS) following treatment of hESCs (BG02) over a 6 day period with BIO (2 µM) and BMP4 (100 ng/ml). Q-PCR analysis shows transcript levels for A. Oct4, Nanog, Lefty A, B. T, MixL1, Goosecoid, C. Sox17, CXCR4, FoxF1, D. PDGFRalpha, PDGFRbeta, GATA4, E. Tbx20 and Isl1 over the time-course.
Figure 17B:
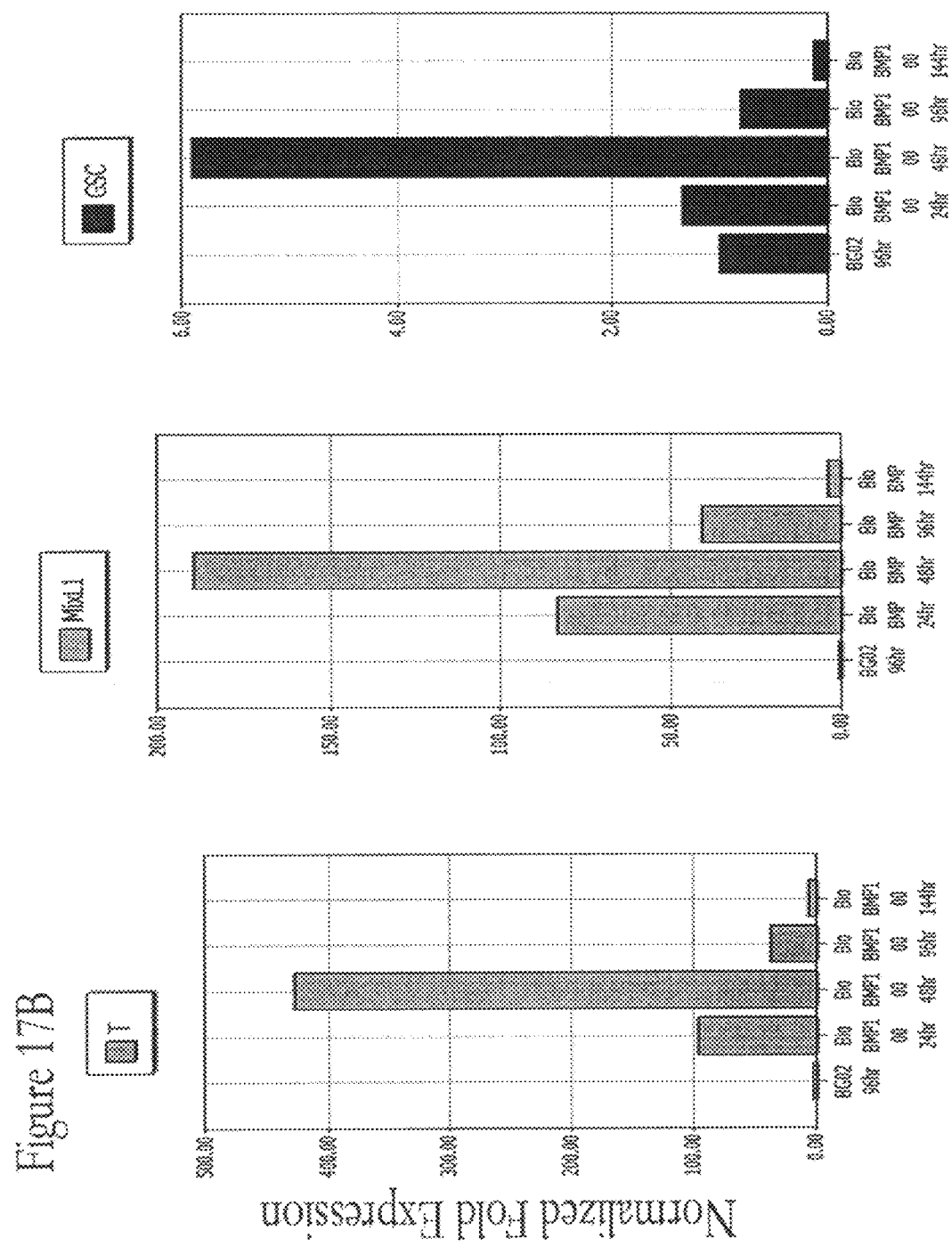
Figure 17C:
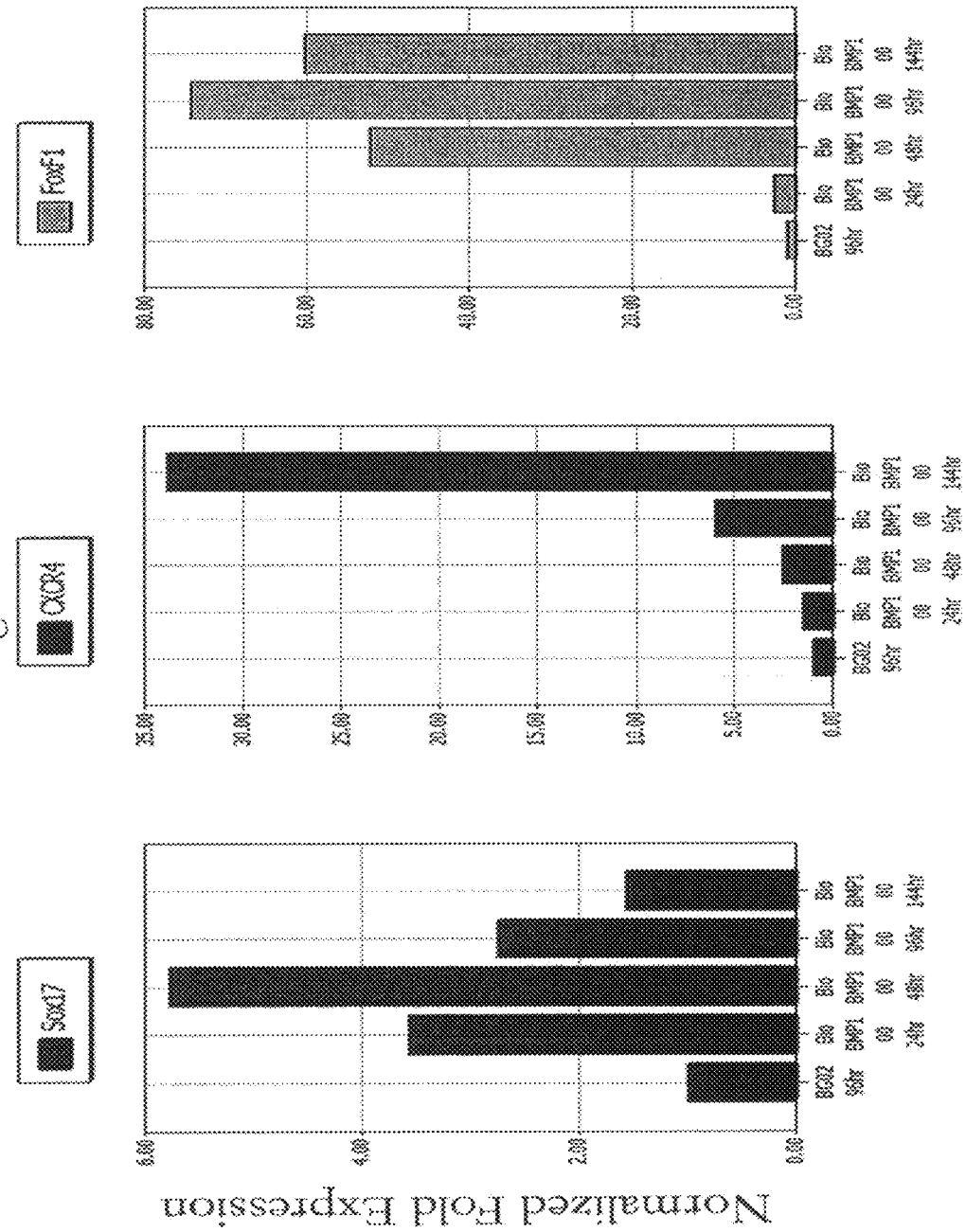
Figure 17E:
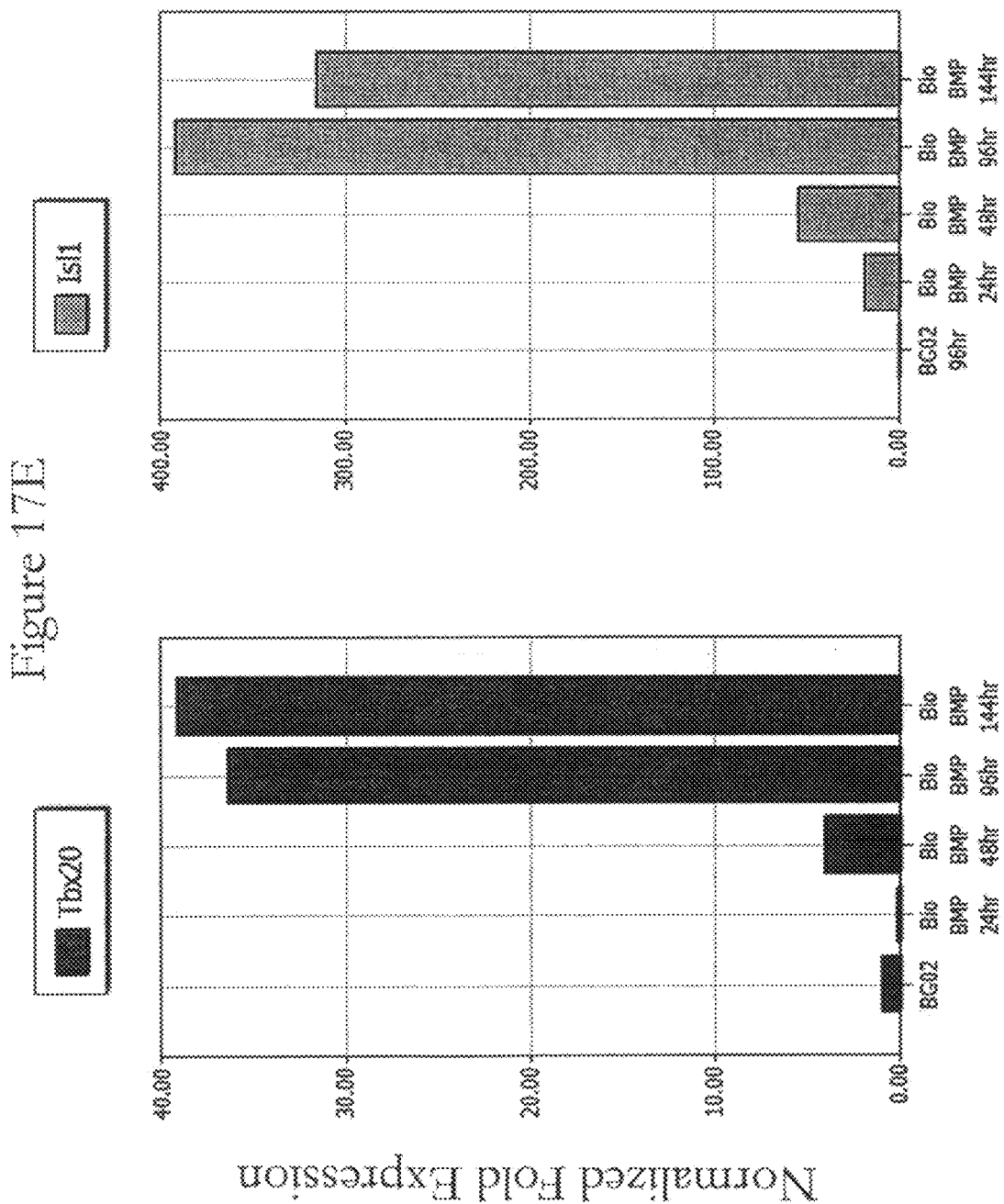

BG02 hESCs grown on Matrigel in MEF-CM were passaged with trypsin and $1.5 \times 10^6$ cells per 60 mm dish seeded back onto Matrigel in MEF-CM supplemented with BIO (2 µM) plus BMP4 (100 ng/ml). Media was replaced every day. Q-PCR analysis was performed over 240 hours (10 days) to evaluate differentiation. Compared to hESCs (FIG. 1), treated cells underwent a change in morphology indicative of differentiation (FIG. 16). Analysis of transcript levels by Q-PCR showed that hESC markers Nanog, Oct4, Lefty A declined by ~48 hours and mesendoderm markers (T, MixL1) peaked at 48 hours but declined by 96 hours. As mesendoderm marker levels decreased, markers for early mesoderm (FoxF1, GATA4, Isl1, Tbx20, PDGFRalpha, PDGFRbeta) became elevated from 24-48 hours onwards (FIG. 17). These markers are indicative of the formation of IMPs.

(d) Generation of an Isl1+ Multipotent Progenitor (Imp) by Addition of BMP4 and GSK Inhibitors Such as BIO to hESCs Cultured in Defined Media.

hESCs can be differentiated to an Isl1+ progenitor by addition of BMP4 and BIO to hESCs cultured in defined media. 6 days of treatment with BMP4 and BIO (FIG. 10).

(d) Generation of an Isl1+ Multipotent Precursor by Addition of GSK Inhibitors, such as BIO, for 1-3 Days Followed by Addition of BMP4.

Isl1+ mesoderm cells can be generated from hESCs grown in MEF-CM or defined media by addition of GSK inhibitors, such as BIO, for 1-3 days followed by addition of BMP4 for a further 2-4 days (FIG. 15).

(e) Generation of an Isl1+ Multipotent Progenitor (IMP) by Addition of Wnt3a and BMP4 and TGFβ Signaling Inhibitors (Such as SB431542) to hESC Cultures.

Figure 18:
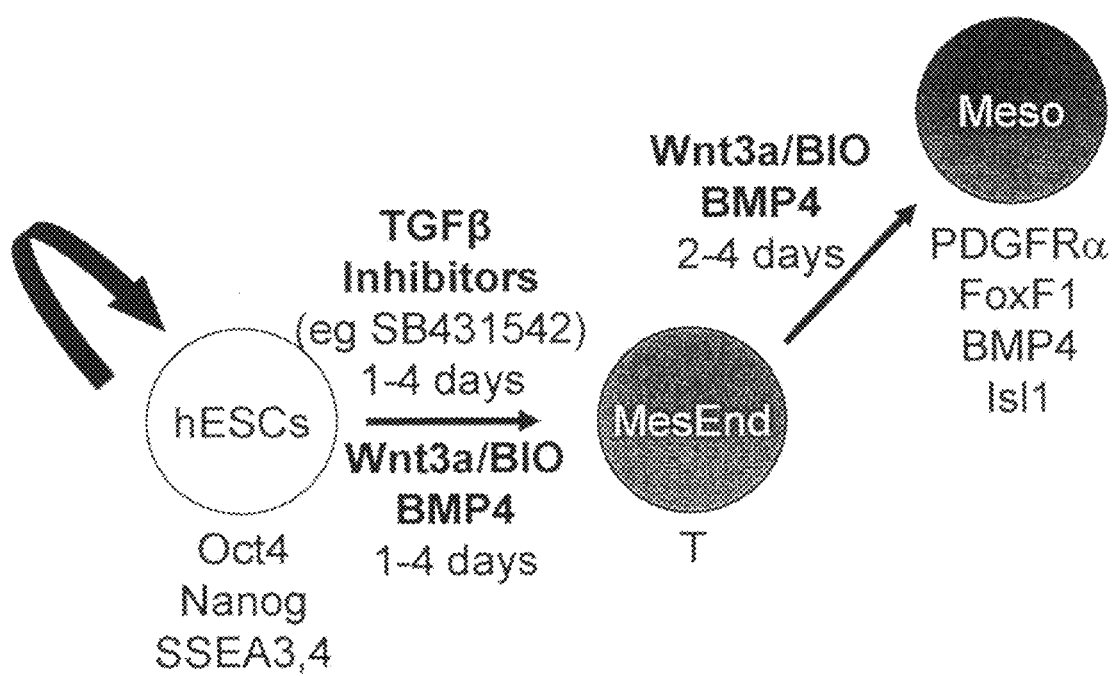
FIG. 18. Schematic showing the pathway of hESC differentiation to mesendoderm and then to mesoderm. hESCs differentiate to mesendoderm in the presence of TGFβ inhibitors such as SB431542 and Wnt3a/BIO and BMP4 (1-4 days). Differentiation of mesendoderm to mesoderm is shown in the presence of Wnt3a/BIO and BMP4 over 2-4 days.

Isl1+ mesoderm cells can be generated from hESCs, grown in MEF-CM or defined media, by addition of Wnt3a, BMP4 and TGFβ inhibitors (such as SB431542) for 1-4 days followed by the removal of TGFβ inhibitors and continued culture with Wnt3a and BMP4 for a further 2-4 days (FIG. 18).

(f) Generation of an Isl1+ Multipotent Progenitor (IMP) by Addition of Wnt3a and TGFβ Signaling Inhibitors (Such as SB431542) for Days 1-4 Followed by Addition of BMP4.

Figure 19:
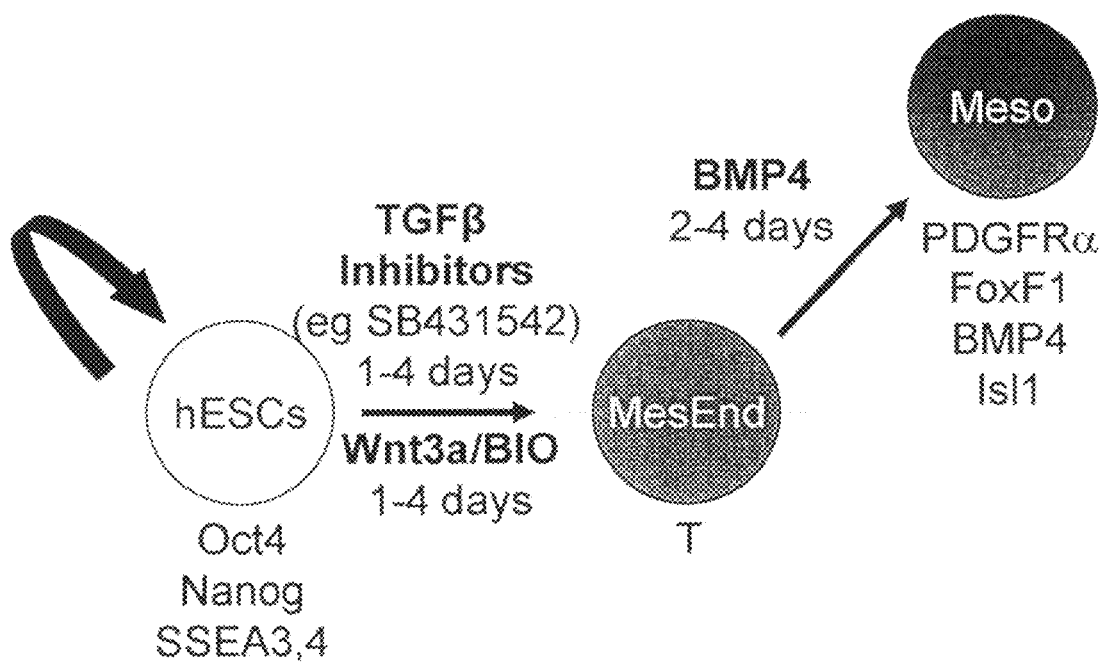
FIG. 19. Schematic showing the pathway of hESC differentiation to mesendoderm and then to mesoderm. hESCs differentiate to mesendoderm in the presence of TGFβ inhibitors such as SB431542 and Wnt3a/BIO (1-4 days). Differentiation of mesendoderm to mesoderm is shown in the presence of BMP4 over 2-4 days.

Isl1+ mesoderm cells can be generated from hESCs, grown in MEF-CM or defined media, by addition of Wnt3a and TGFβ inhibitors (such as SB431542) for 1-4 days followed by addition of BMP4 for a further 2-4 days (FIG. 19).

(g) Generation of an Isl1+ Multipotent Progenitor (IMP) by Addition of Wnt3a for Days 1-3 Followed by Addition of BMP4 and SB431542.

Isl1+ mesoderm cells can be generated from hESCs, grown in mEF-CM or defined media, by addition of Wnt3a and SB431542 for 1-3 days followed by addition of BMP4 for a further 2-4 days.

Example 4

Figure 20:
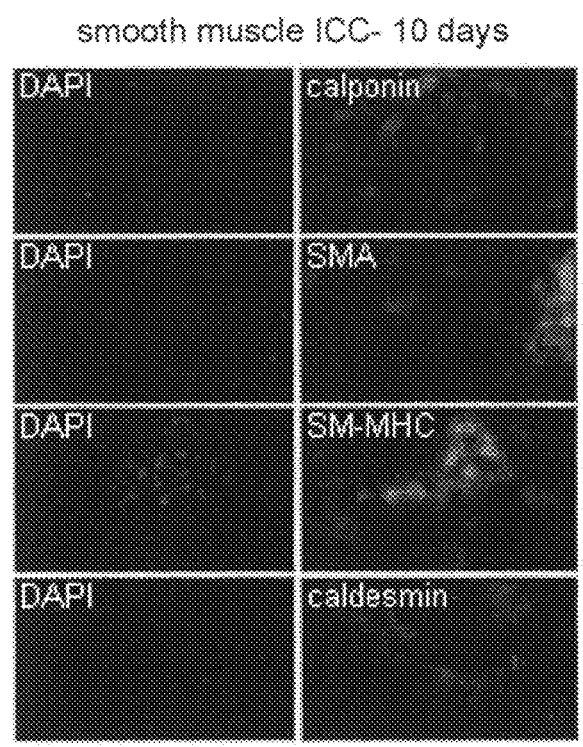
FIG. 20. hESCs were differentiated on Matrigel to IMPs for 6 days in Wnt3a (25 ng/ml), BMP4 (100 ng/ml) containing media for 6 days. Cells were passaged at a 1:5 ratio at day 6, then plated onto matrigel in defined media containing the same concentrations of Wnt3a and BMP4 for a further 10 days. Cells were immunostained for smooth muscle markers calponin, smooth muscle actin (SMA), smooth muscle myosin heavy chain (SM-MHC) and caldesmin. DAPI was used to stain DNA.

IMPs can Differentiate into the Cardiac Lineages, Endothelial Cells, Cardiomyocytes and Smooth Muscle Cells (a) Generation of Smooth Muscle Cell from IMPs.

hESCs were grown in defined media in the presence of Wnt3a (25 ng/ml) and BMP4 (100 ng/ml) for 6 days. The cells were split at 1:4-1:6 into the same media for a further 4 days. The cells were fixed and stained for smooth muscle markers smooth muscle actin, calponin, caldesmin and SM-MHC (FIG. 20). The majority of the cells did stain for these smooth muscle markers.

(b) Generation of Cardiomyocytes and Endothelial Cells from IMPs.

Figure 21:
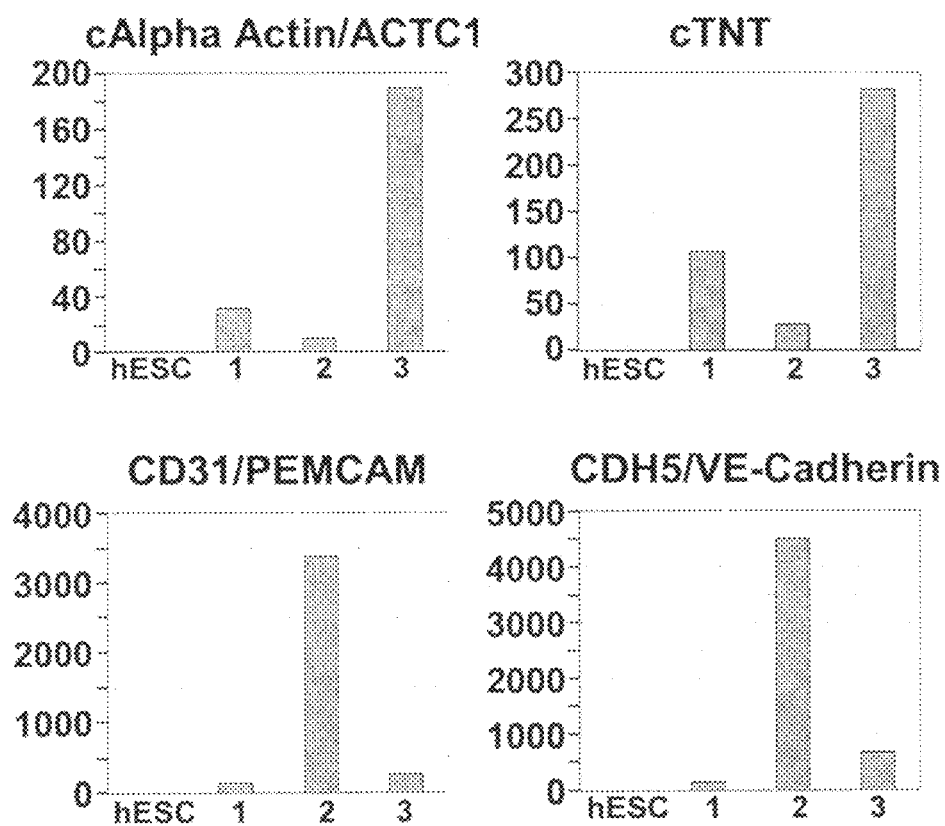
FIG. 21. Generation of cardiomyocytes and endothelial cells from Isl1+ multipotent progenitors (IMPs). The cells were treated in 3 variations of the method to make IMPs for 6 days. Treatment one; hESCs were grown in defined media with Activin A (100 ng/ml) for the first 24 hrs, Wnt3a (25 ng/ml) for Day 1-4 and BMP4 (100 ng/ml) for Day 2-6. Treatment two; hESCs were grown in defined media minus IGF-I, heregulin and FGF2 with Wnt3a (25 ng/ml) for days 1-2 and BMP4 (100 ng/ml) for days 2-6. The cells were then grown in defined media for a further 14 days. Q-PCR analysis was performed for the markers cardiac alpha actin/ACTC1, cTNT, CD31/PECAM1 and CDH5/VE-cadherin.

IMPs were made via three different treatments. Treatment one; hESCs were grown in defined media with Activin A (100 ng/ml) for the first 24 hrs, Wnt3a (25 ng/ml) for Day 1-4 and BMP4 (100 ng/ml) for Day 2-6. Treatment two; hESCs (BG02) were grown in defined media minus IGF-I, Heregulin and FGF2 with Wnt3a (25 ng/ml) for days 1-2 and BMP4 (100 ng/ml) for days 2-6. Treatment 3; hESCs were grown in defined media with Activin A (100 ng/ml) for the first 24 hrs, Wnt3a (25 ng/ml) for Day 1-2 and BMP4 (10 ng/ml) for Day 2-6. At the end of day 6 the cells were put into defined media for a further 14 days. The cells were collected and Q-PCR analysis showed treatment 2 produced endothelial cell markers (CD31/Pecam1 and CDH5/VE-cadherin) and treatment 3 cardiomyocyte markers (ACTC1/Cardiac Alpha Actin and cTNT) (FIG. 21). These results show that IMP cells can differentiate into cardiomyocytes and endothelial cells.

Example 5

Composition of Matter for a Mesoderm-Derived Isl1+ Multipotent Progenitor (IMP)

Islet 1+ multipotent progenitors (IMPs) have the following characteristics:
express Isl1, Tbx20, Nkx2.5, Fgf10, GATA4, KDR (MO, FoxF1, PDGFRα
karyotypically normal
do not express Oct4, Nanog, T, eomesodermin
can differentiate into cardiomyocytes, smooth muscle cells and endothelial cells
do not form teratomas when injected into the hind limb muscle of SCID mice Microarray was performed on the formation of IMPS. hESCs were cultured in defined media plus Wnt3a (25 ng/ml) and BMP4 (100 ng/ml) for 6 days. Samples were taken at 0, 24 hr, 48 hr, 72 hr, 96 hr, 144 hr for mRNA extraction and subsequent microarray analysis. The microarray analysis is summarised in a table attached to this document. (IMP microarray)

Example 6

IMP Cells can be Used as a Cell Therapeutic for Cardiovascular Disease; Heart and Vasculature Because of their ability to differentiate into the key cell lineages comprising the cardiovasculature, IMP cells can be used as a cell therapeutic. For example, they can be used to regenerate damaged mycocardium when transplanted by someone skilled in the art. They can also be used to repair damaged vasculature by someone skilled in the art.

Example 7

Methods for making Definitive Enoderm (DE)

(a) Generation of DE with Treatment of hESC with Wnt and TGFβ (such as SB431542) Followed by High Activin A.

Figure 22:
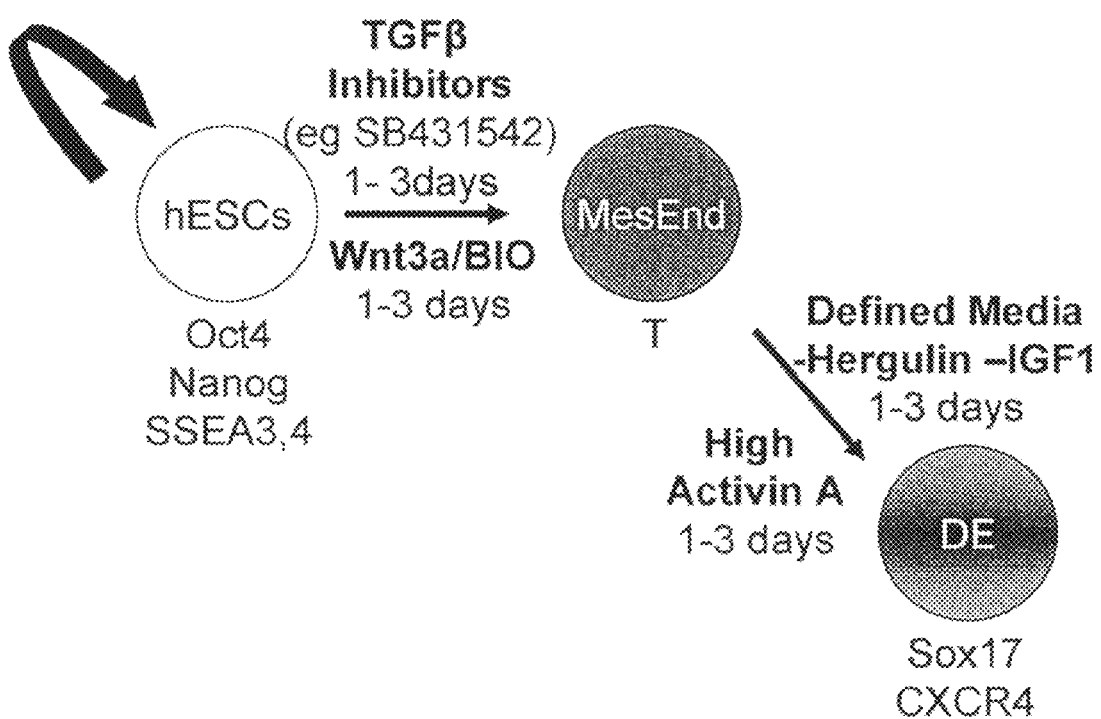
FIG. 22. Schematic showing differentiation of hESCs to definitive endoderm (DE) through a mesendoderm (MesEnd) intermediate state. hESCs in defined media are treated with TGFβ inhibitors such as SB431542, Wnt3a/BIO for 1-3 days then switched to defined media containing high levels of Activin A (100 ng/ml) but without IGF-I and heregulin for a further 1-3 days.

DE can be formed through the addition of Wnt3a and SB431542 for 1-3 days to defined hESC media followed by their removal along with IGF-I and heregulin and the addition of high Activin (50-100 ng/ml) for a further 1-3 days. hESC's would be passaged onto Matrigel coated plates or equivalent (FIG. 22).

(b) Generation of De with Treatment of hESC's with GSK Inhibitor (BIO) and High concentration of Activin A.

Figure 23:
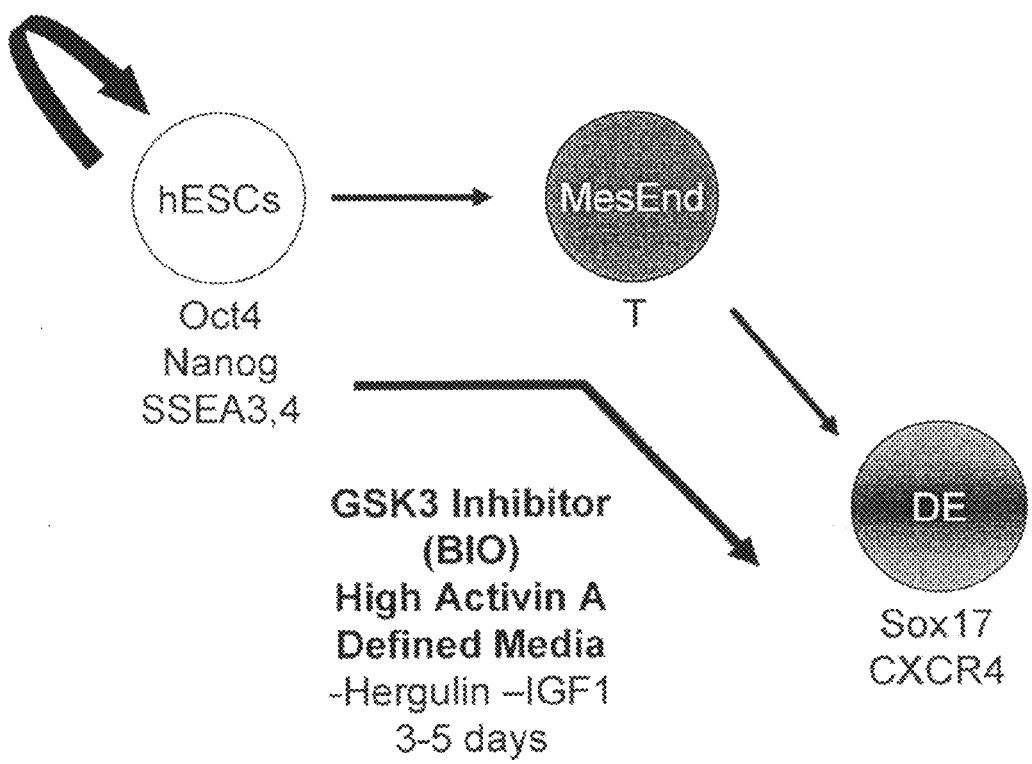
FIG. 23. Schematic showing differentiation of hESCs to definitive endoderm (DE) through a mesendoderm (MesEnd) intermediate state. hESCs in defined media are treated with BIO in the presence of high Activin A (100 ng/ml) and in the absence of IGF-I and heregulin for 3-5 days.

The formation of DE from hESC can be accomplished through the addition of BIO (2-5 μM) and a high concentration of Activin A (50-100 ng/ml) to hESC defined media (minus IGF-I and heregulin) for 3-5 days (FIG. 23). hESC's would be passaged onto Matrigel coated plates or equivalent.

(c) DE Formation with the Treatment of hESC in the Presence of BIO and a Low Concentration of Activin A (10 ng/ml).

Figure 24:
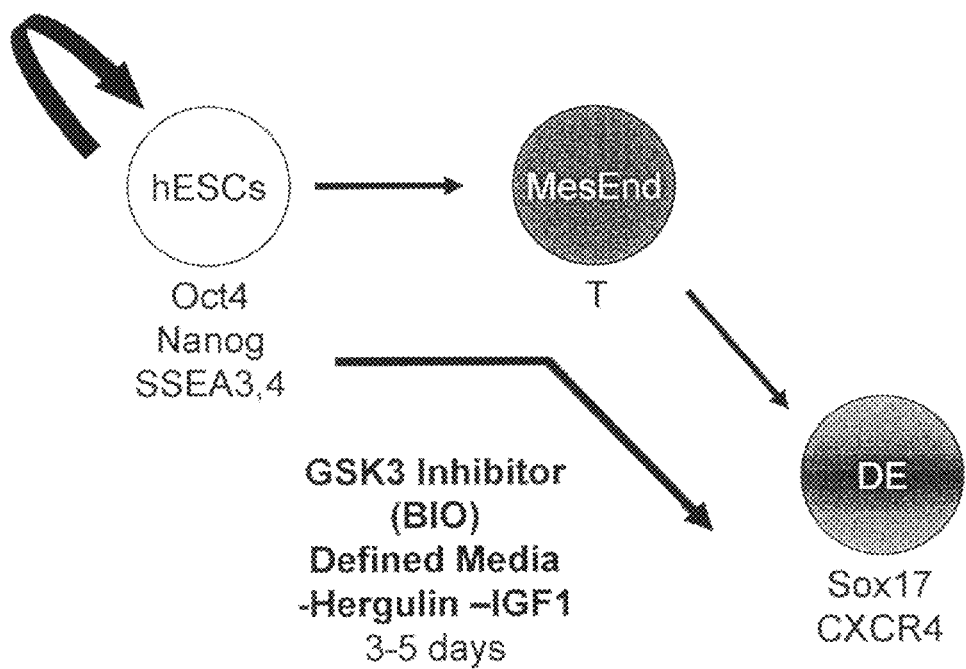
FIG. 24. Schematic showing differentiation of hESCs to definitive endoderm (DE) through a mesendoderm (MesEnd) intermediate state. hESCs in defined media are treated with BIO in the presence of low levels of Activin A (10 ng/ml), in the absence of IGF-I and heregulin for 3-5 days.
Figure 25A:
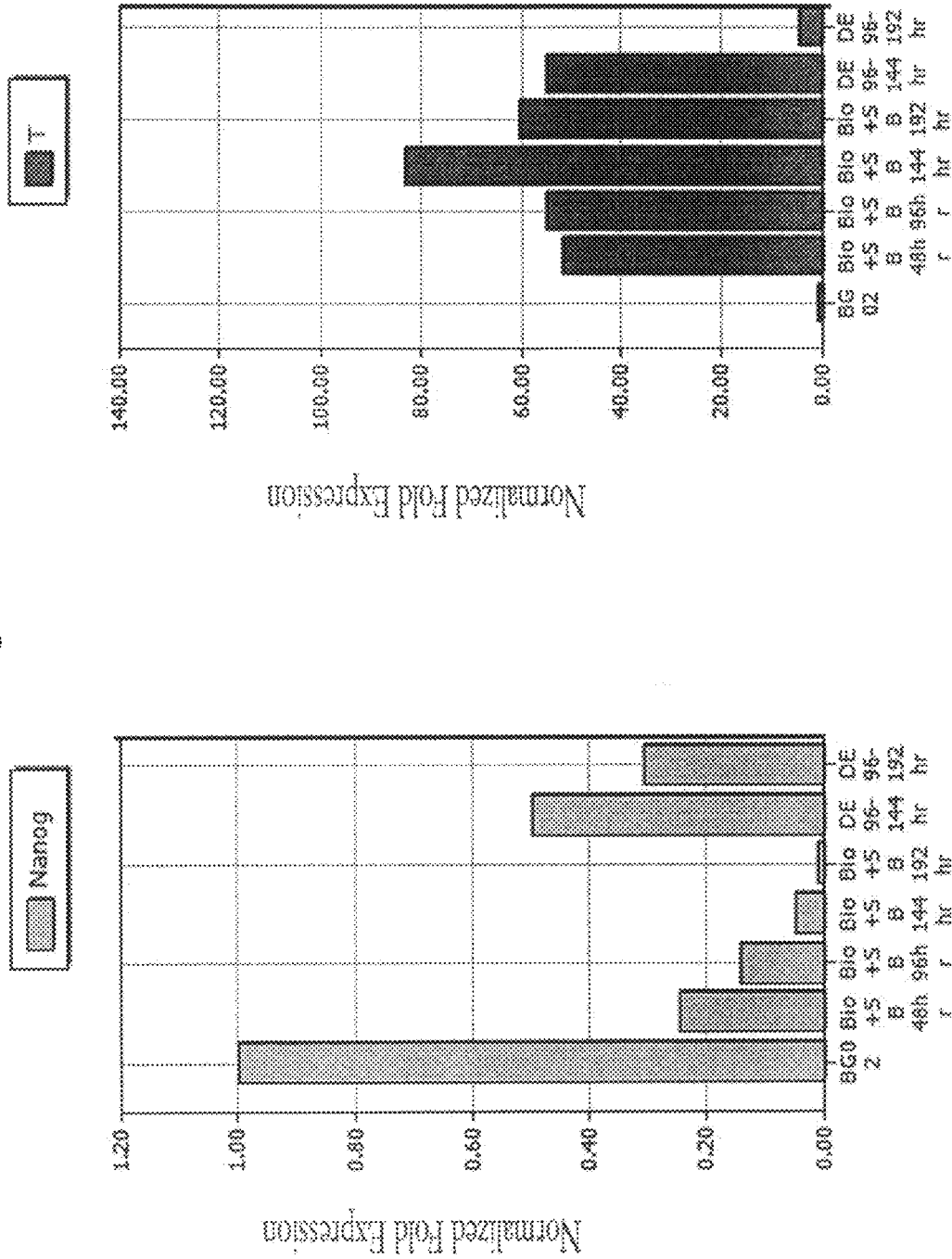
FIG. 25. Formation of definitive endoderm (DE), from hESCs (BG02) grown in defined media on Matrigel, through the addition of BIO (2 µM) and SB431542 (20 µM) for 4 days followed by treatment with high levels of Activin A (100 ng/ml) in the absence of heregulin and IGF-I for a further 4 days. Q-PCR analysis of transcripts for A. Nanog, T, B. Sox17, CXCR4, C. FoxF1 and PDGFRalpha are shown.
Figure 25B:
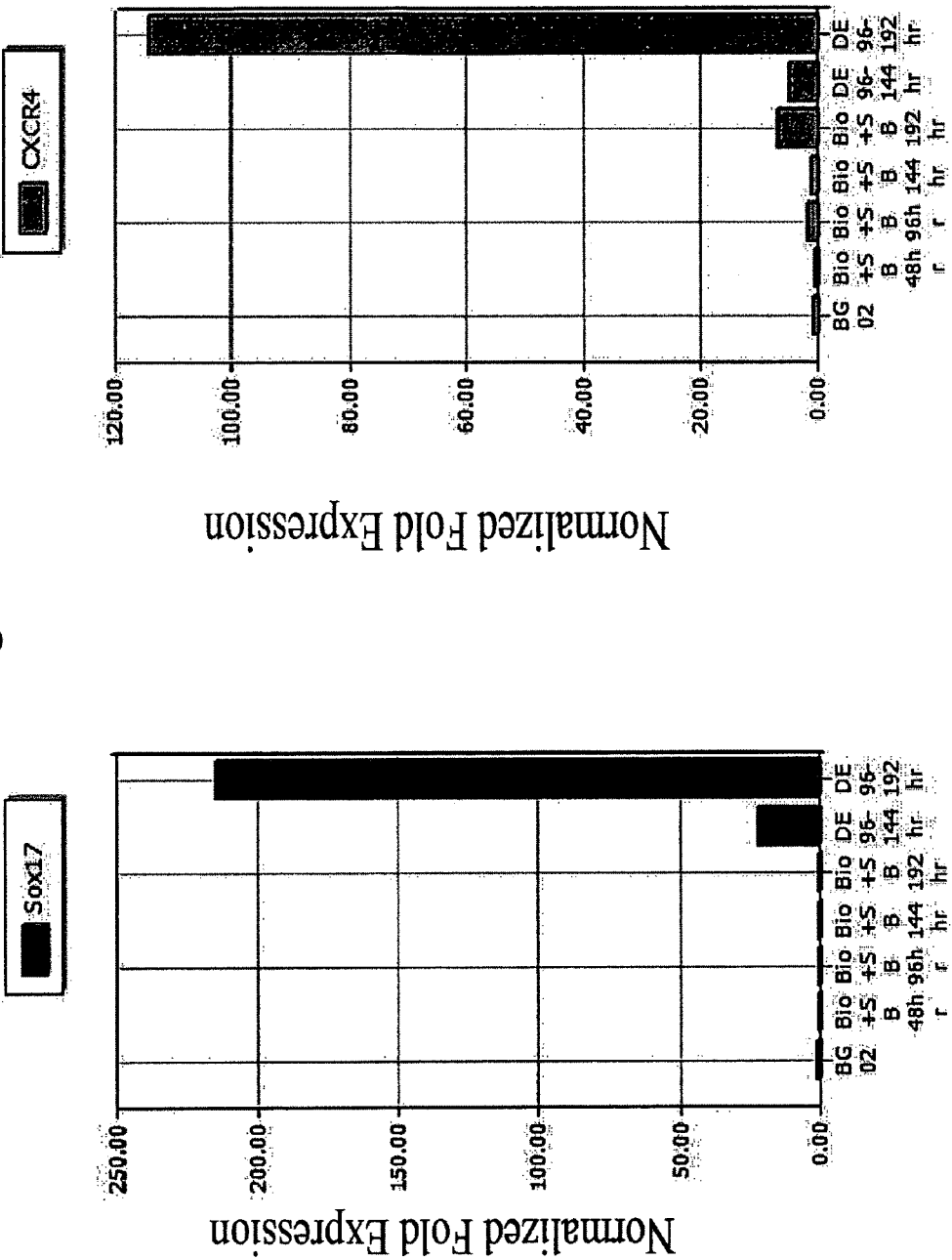
Figure 25C:
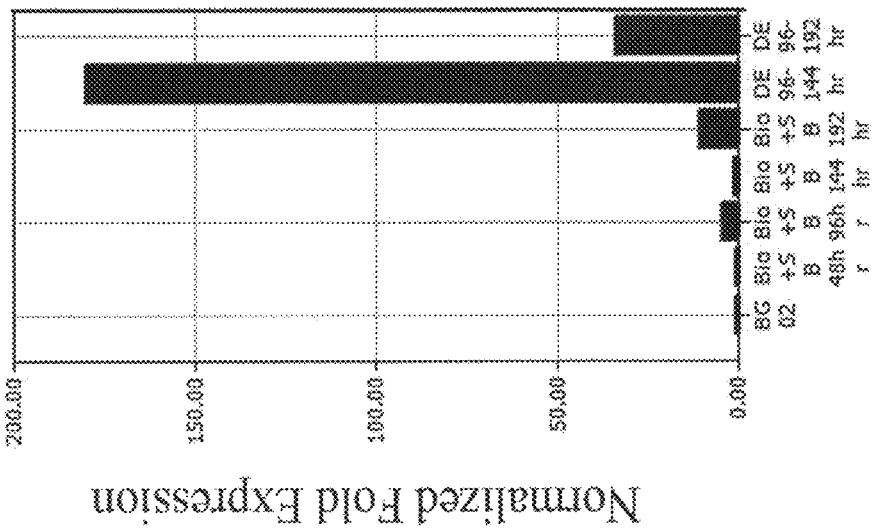
Figure 25C:
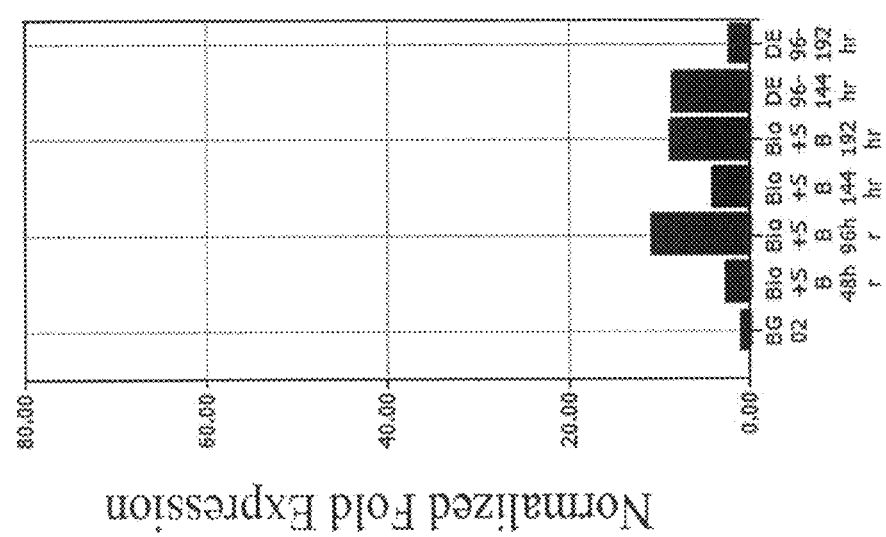

DE can be formed through the addition of BIO (2-5 μM) to hESC defined media minus IGF-I and heregulin for 3-5 days (FIG. 24). hESC's would be passaged onto Matrigel coated plates or equivalent.

(d) Formation of DE from hESC Through the Addition of BIO for 1-3 Days Followed by the Addition of Activin A for 1-3 Days.

The generation of DE can be accomplished through the addition of BIO (2 μM) to hESC defined media for 1-3 days to reach the mesendoderm stage, followed by its removal along with IGF-I and Heregulin and the addition of Activin A for 1-3 days (FIG. 22). hESC's would be passaged onto Matrigel coated plates or equivalent.

(e) The Generation of DE Through the Addition of BIO and SB431542 for 1-4 Days Followed by High Activin A Treatment.

hESC were taken and grown in defined media in the presence of BIO (2 μM) and SB431542 (20 μM) for 4 days. The cells were then split 1-4 into the same media or defined media minus IGF-I and heregulin and with additional Activin A (100 ng/ml) for an additional 4 days (FIG. 22). Samples (BG02) were taken every 2 days up to 8 days for Q-PCR analysis. The first step of BIO/SB431542 differentiated the cells to a T/brachrury positive, Nanog, Sox17 and CXCR4 negative cell within the first 2 days. This cell type persisted in the presence of BIO/SB431542. Once the cells were switched to defined media (minus IGF-I and Heregulin) plus Activin A (100 ng/ml), they further differentiated into DE, evidenced by the upregulation of DE markers Sox17 and CXCR4, and the absence of the mesoderm marker FoxF1 (FIG. 25). hESC's would be passaged onto Matrigel coated plates or equivalent.

Example 8

Methods for Generation of Multipotent Mesenchymal Cells (MMCs)

Figure 26B:
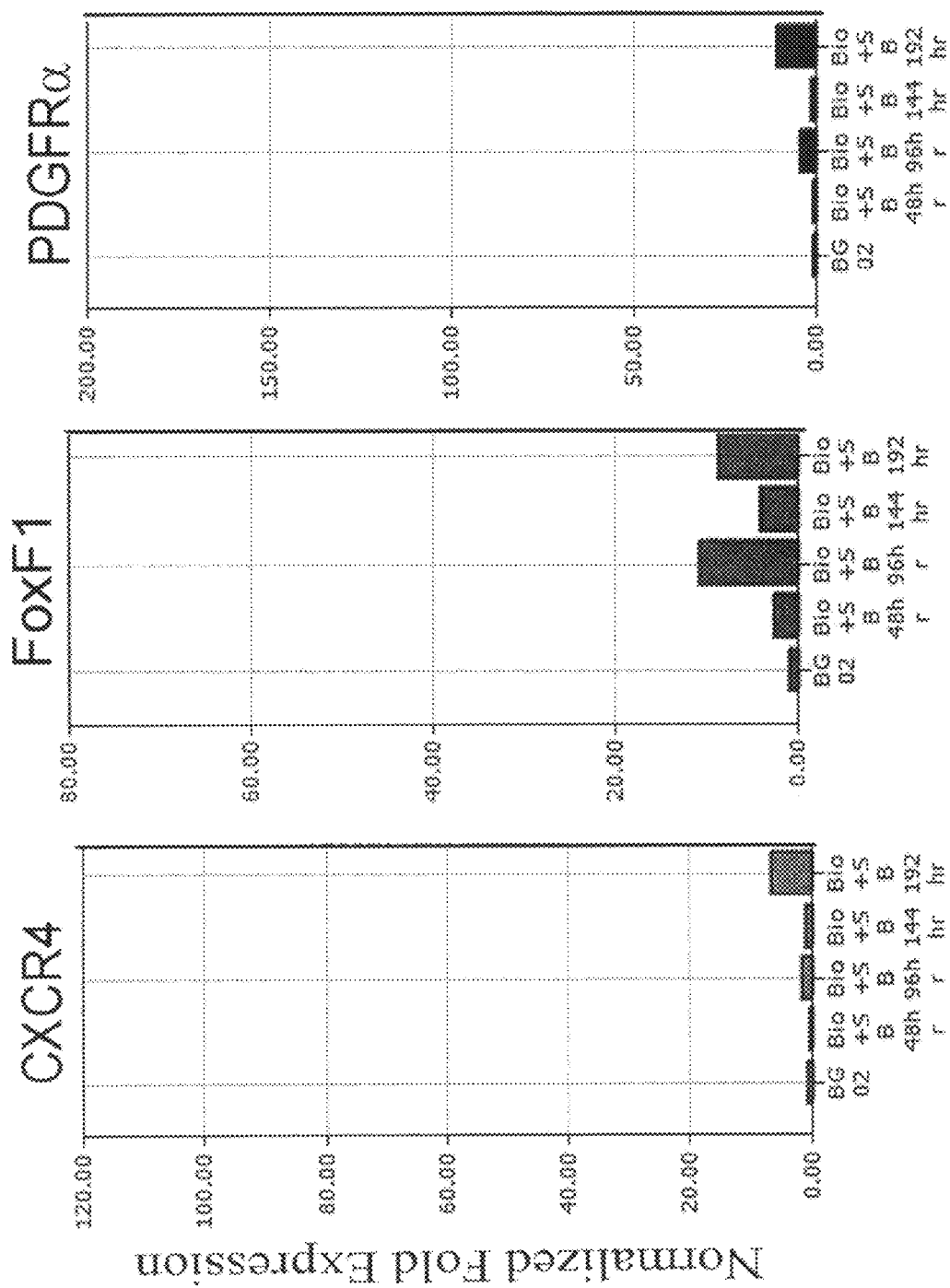
FIG. 26. Formation of multipotent mesenchymal cells (MMCs) following treatment of hESCs (BG02) with BIO (2 µM) and SB431542 (20 µM) over an 8 day time frame. Q-PCR analysis of transcript levels are shown for A. Nanog, T, Sox17, B. CXCR4, FoxF1 and PDGFRalpha.
Figure 27:
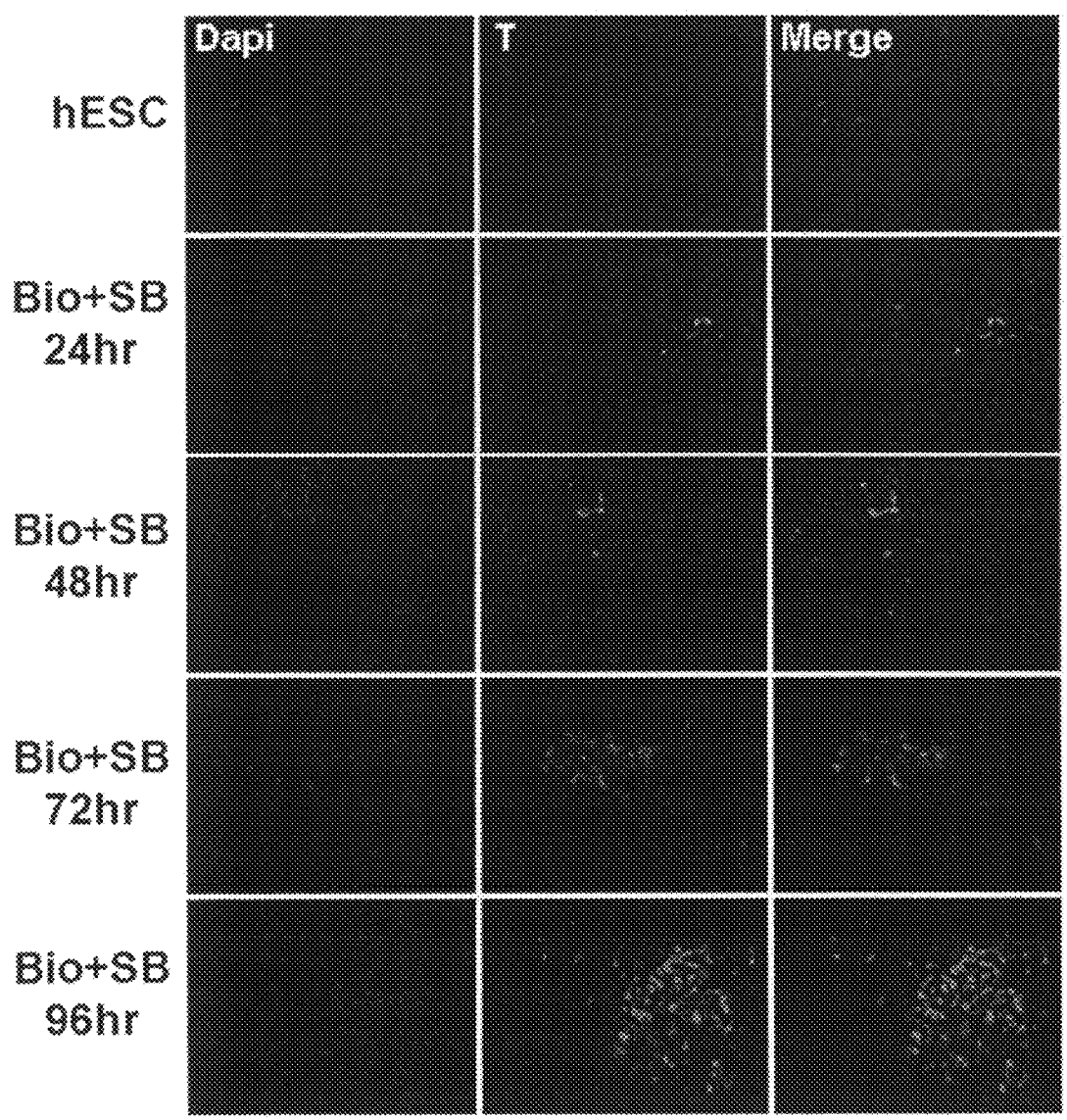
FIG. 27. Formation of multipotent mesenchymal cells (MMCs) following treatment of hESCs (BG02) with BIO (2 µM) and SB431542 (20 µM) over 4 days. DAPI Immunostaining for (A) T, (B) Oct4 and Nanog and, (C) E-cadherin are shown along with DAPI staining for DNA and merged data.
Figure 27:
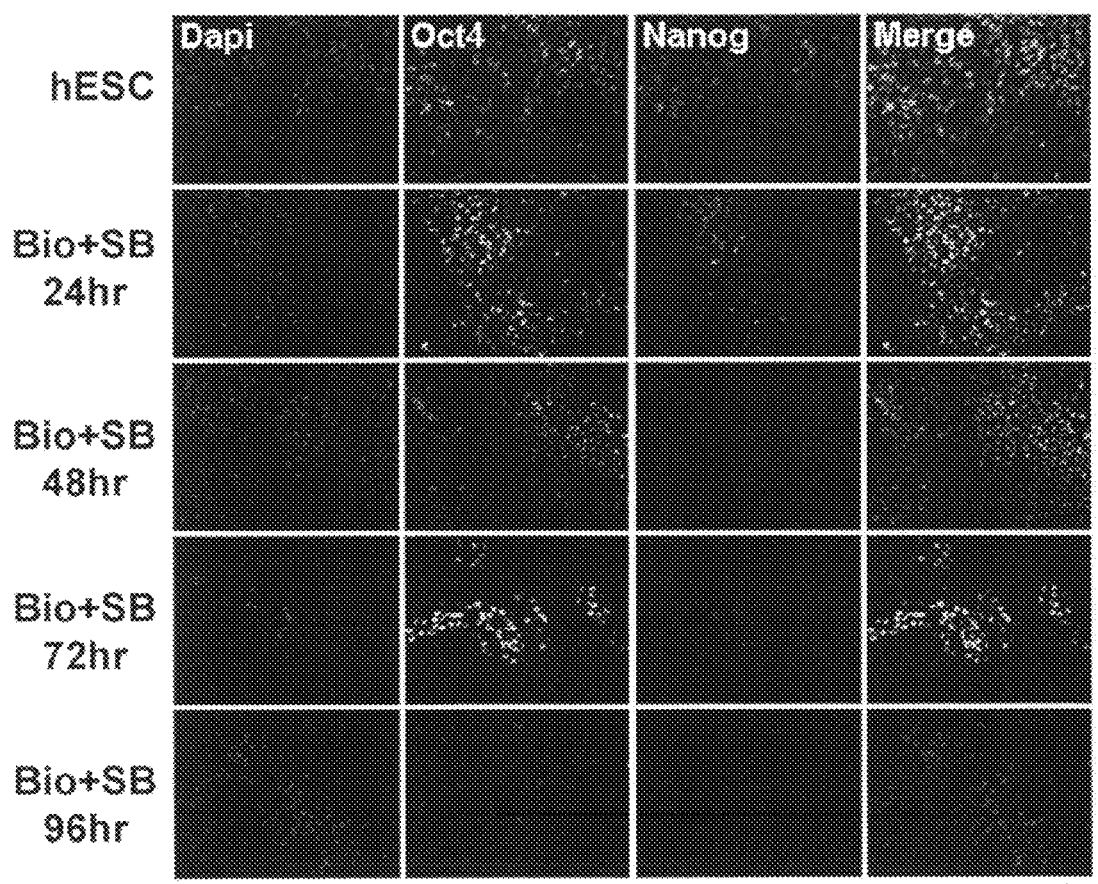
Figure 27:
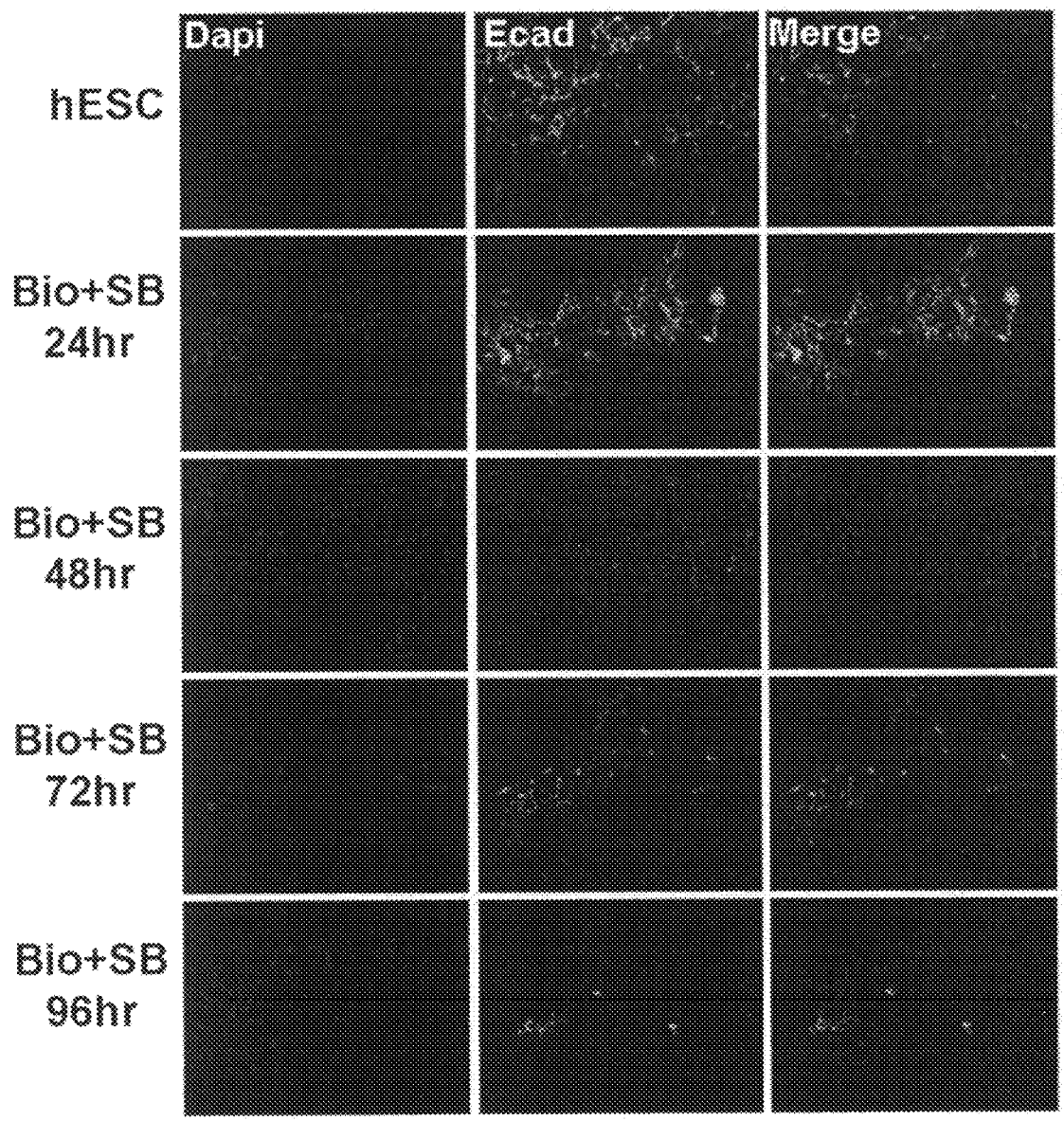
Figure 28:
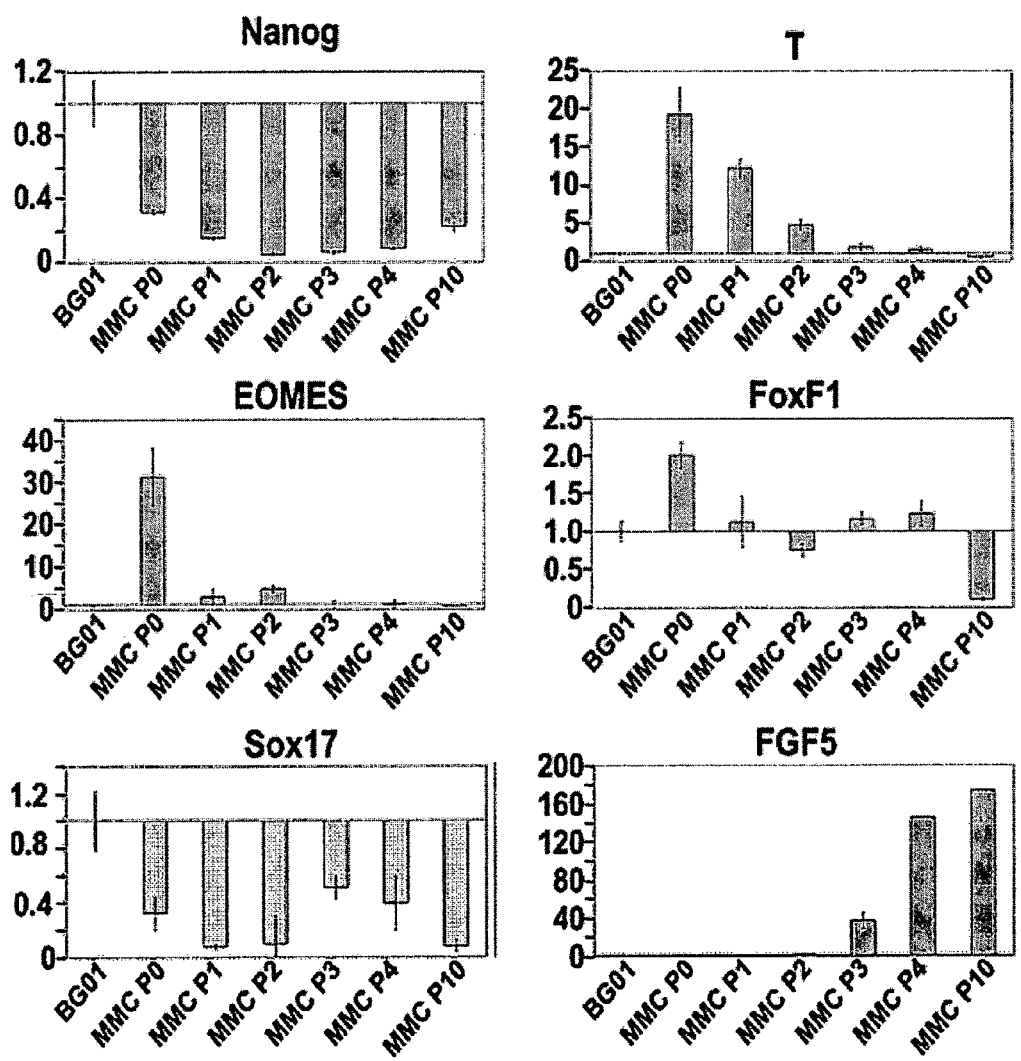
FIG. 28. Multipotent mesenchymal cells (MMCs) were continually grown in defined media containing BIO (2 µM) and SB431542 (20 µM) for up to 10 passages. Cells were passaged every five days with Accutase™ (Innovative Cell Technologies) at a split of 1:5. Q-PCR analysis shows transcript levels for Nanog, T, Eomes, FoxF1, Sox17 and Fgf5 over different passages and in hESCs (BG01).
Figure 29:
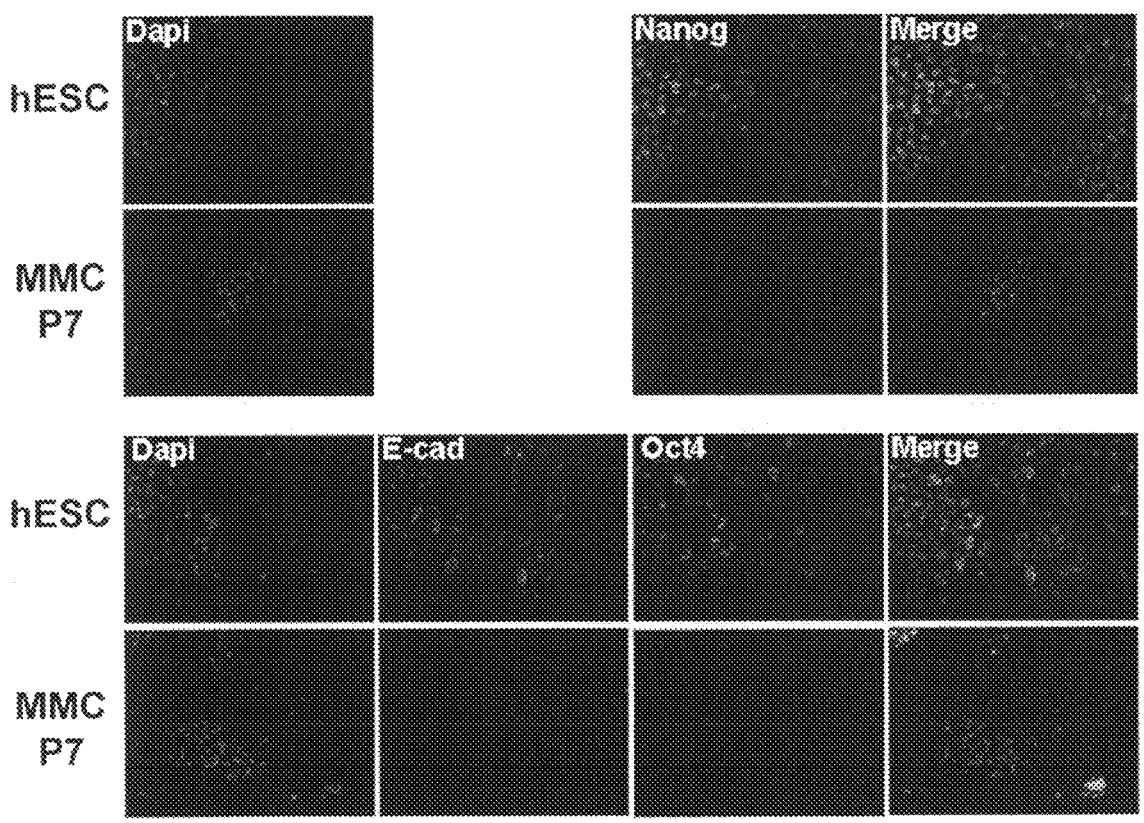
FIG. 29. Multipotent mesenchymal cells (MMCs) derived from BG02 hESCs grown to P7 do not show expression of pluripotent hESC markers such as E-cadherin, Nanog and Oct4. DAPI staining indicates DNA. Merge images for DAPI with Nanog or E-cadherin/Oct4 are shown.
Figure 30:
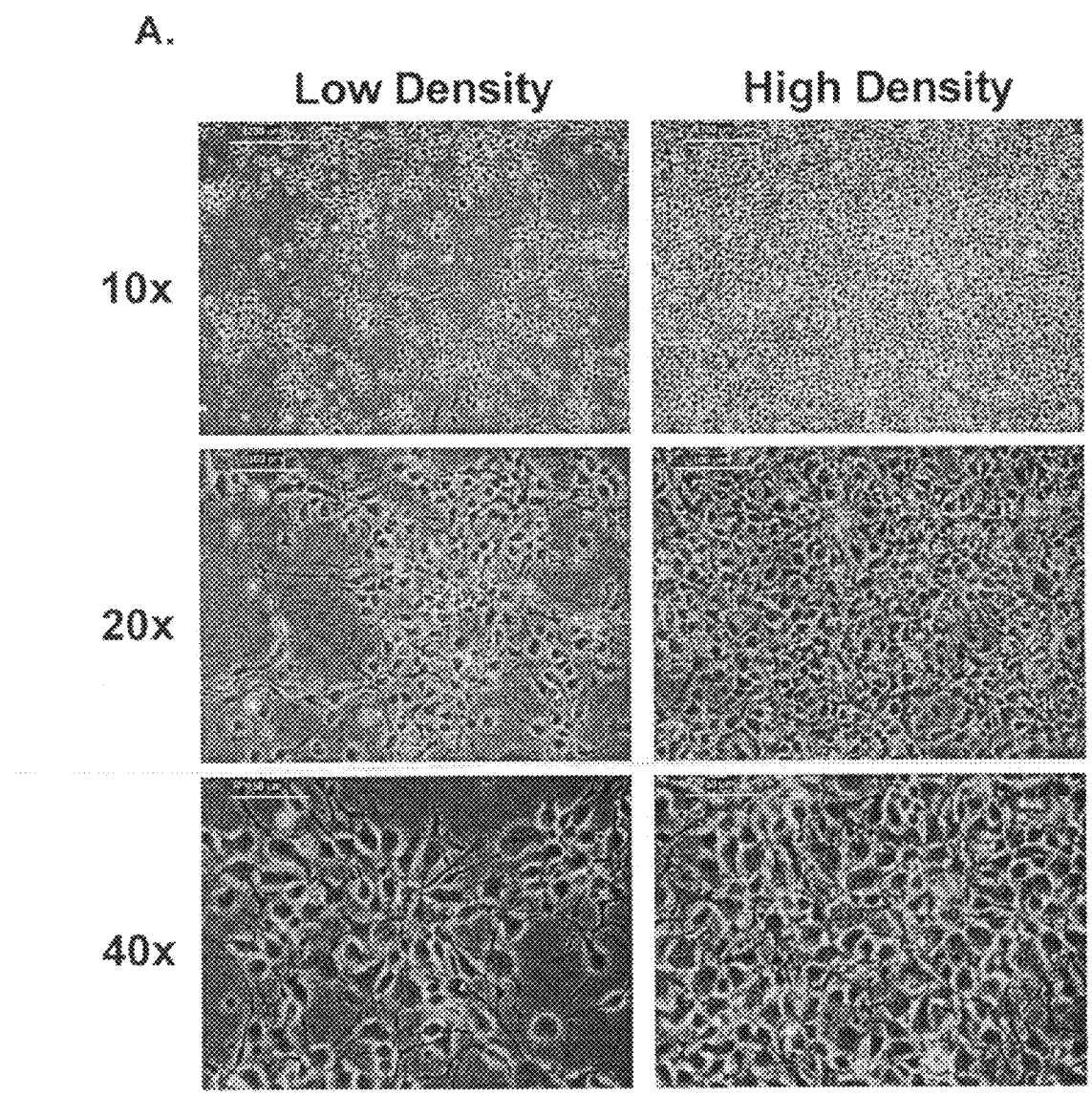
FIG. 30. (A) Bright field images of multipotent mesenchymal cells (MMCs) derived from hESCs (BG02) grown in defined media in the presence of BIO (2 µM) and SB431542 (20 µM) for 20 passages. Cells are shown 3 days post-plating (low density) and 6 days post-plating (high density). Magnification of images is indicated. (B) P14 MMCs generated from BG02 hESCs were cryopreserved, thawed and replated under previously described conditions for maintenance of MMCs. Bright field images of precryopreserved MMCs (P14) and cryorecovered MMCs are shown. (C) P14 MMCs were stained with an APC-conjugated anti-CXCR4 antibody and subject to FACS (fluorescence activated cell sorting). CXCR4+ cells recovered from FACS were plated under standard MMC culture conditions and shown as a bright field picture 5 days post-sorting.
Figure 30:
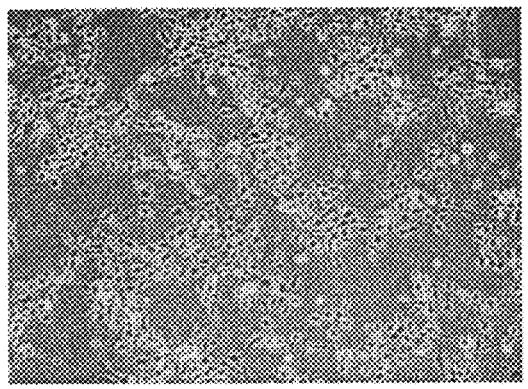
Figure 30:
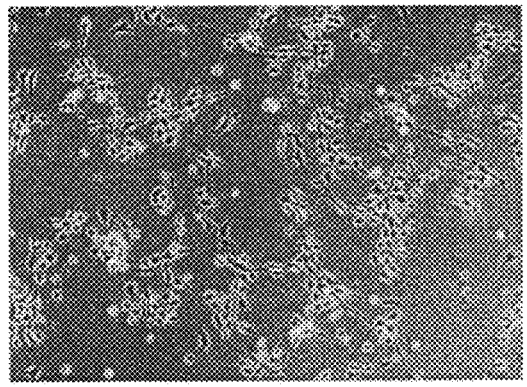
Figure 30:
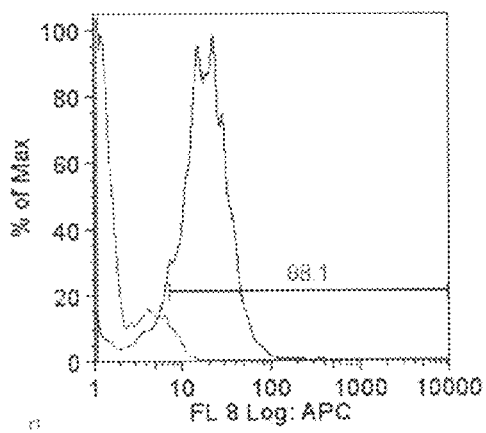
Figure 30:
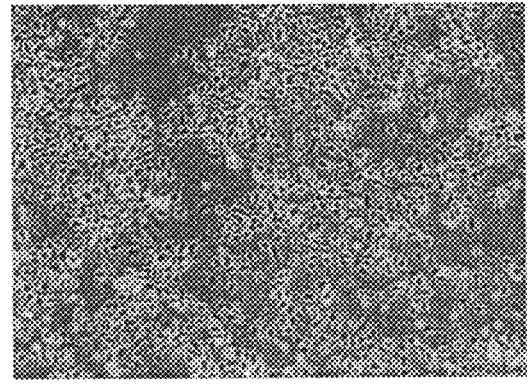

BG02 hESCs grown in StemPro® defined media were passaged with Accutase™ and plated onto Matrigel coated dishes ($1.0 \times 10^6$ cells per 60 mm dish) as described in Example 1, except that media was supplemented with BIO (2 µM) plus SB431542 (20 µM; Sigma). Media was replaced every day and cells were passaged every 5-6 days with Accutase™, with a 1:5-1:10 split at each passage. When cultured under these conditions, the pluripotency marker Nanog decreased during the first passage (P0) and T transcript levels increased whereas Sox17, FoxF1, CXCR4 and PDGFRalpha remained low (FIG. 26). ~90% of cells stained +ve for T 4 days after treatment with BIO and SB431542, indicting they transitioned through a mesendoderm state at some point (FIG. 27A). During this time Nanog, Oct4 and E-cad were significantly downregulated, as indicated by immunostraining (FIG. 27B, C). The disappearance of E-cadherin is indicative that cells underwent an epithelial to mesenchymal transition, consistent with the differentiation into mesendoderm. Upon continued passage, T expression (as determined by Q-PCR) decreased over P1-P10 and the pluripotency marker Nanog did not reappear (FIG. 28). This was confirmed by immunostaining where P7 cells did not express Nanog, Oct4 or E-cadherin, in contrast to hESCs (FIG. 29). Mesoderm and endoderm markers did not increase during this time frame. To establish the cell fate of BIO/SB431542 treated cells we continually passaged them under the same conditions and found they maintained robust proliferative activity for over 20 passages with maintenance of morphology (FIG. 30A). MMCs were cryopreserved, using standard methods, and recovered with a plating efficiency of >10%. The growth characteristics and morphology of cryorecovered MMCs were indistinguishable from that of the precryopreserved MMCs (FIG. 30B).

In MMCs produced from BG02 hESCs, CXCR4 antibodies were used to enrich for a CXCR4+ population, demonstrating that MMCs can be subject to fluorescence activated cell sorting (FACS), replated and amplified (FIG. 30C).

Figure 31A:
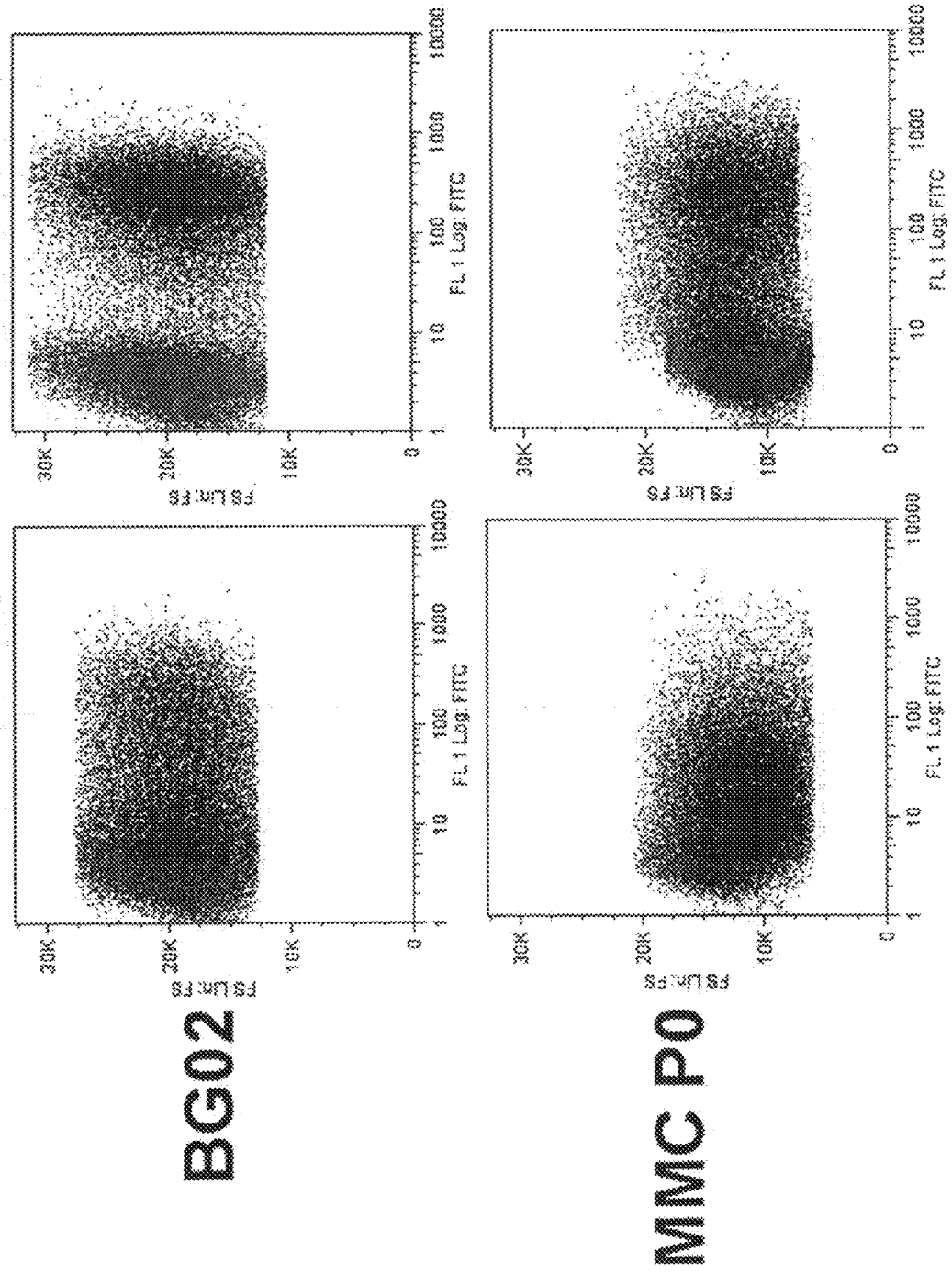
FIG. 31A, B, C. Analysis of SSEA3 and SSEA4 cell surface markers in hESCs (BG02) grown in defined media and multipotent mesenchymal cells (MMCs) grown in defined media with BIO (2 µM) and SB431542 (20 µM). MMC passage number is indicated (A-C). Flow cytometry analysis is shown where MMCs and hESCs are stained with antibodies for SSEA3 and SSEA4. IC, antibody isotype control is shown.
Figure 31B:
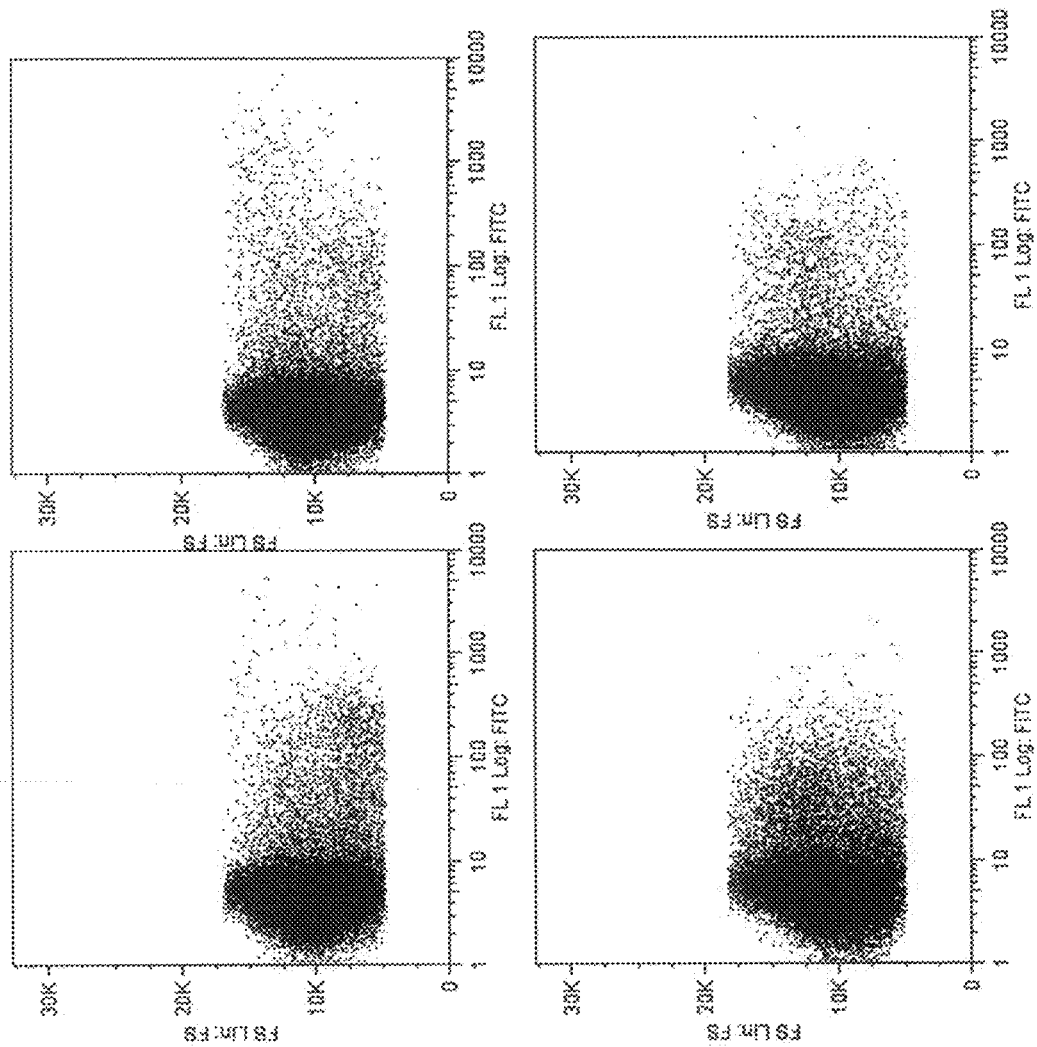
Figure 31C:
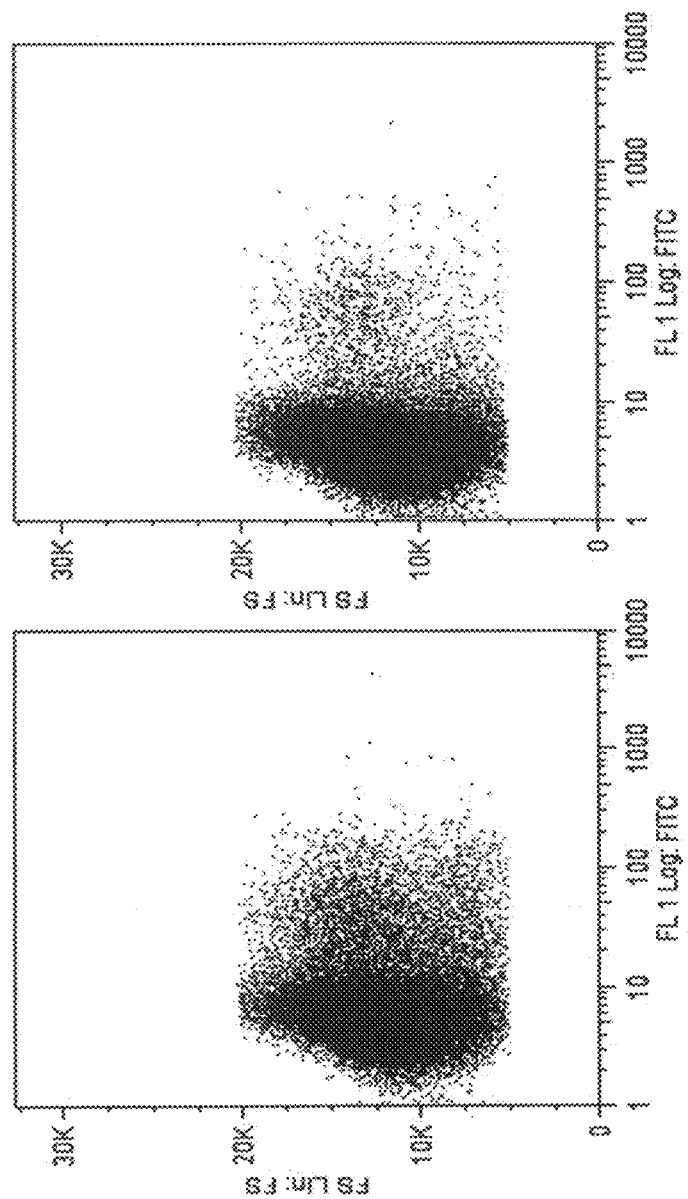

Flow cytometry analysis indicates that hESCs treated with BIO/SB431542 lose the cell surface markers SSEA3 and SSEA4, indicative of differentiation away from the pluripotent hESC state (FIG. 31). Treated cells maintained from P0-P19 continued to exhibit an absence of SSEA3 and SSEA4 (FIG. 31). Treated cells are therefore not hESCs by this criteria.

Figure 32:
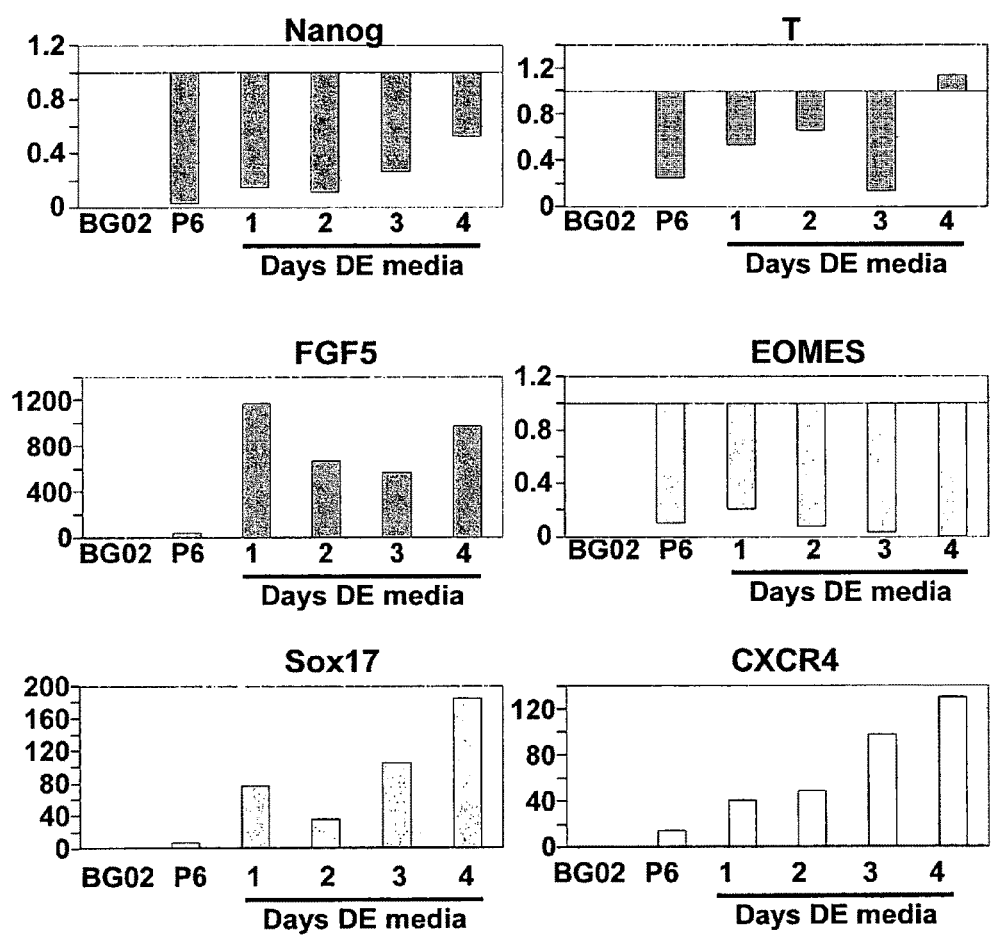
FIG. 32. Multipotent mesenchymal cells (MMCs) were grown to passage 6 in defined media plus BIO (2 µM) and SB431542 (20 µM). MMCs were then plated onto Matrigel in defined media lacking IGF-I and heregulin but with high levels of Activin A (100 ng/ml) for 4 days. Q-PCR analysis is shown where transcripts for Nanog, T, Ffg5, Eomes, Sox17 and CXCR4 are shown.

Despite monitoring the appearance of markers for mesoderm and endoderm from P0-P3 cells (for example) we observed no obvious signs of differentiation into these lineages, indicating that BIO/SB431542 treatment had arrested the cells at a stage of development before markers for these lineages appear. We consider these cells to be pre-mesoderm and pre-endoderm but no longer hESCs. This raised the possibility that these cells retained a multipotent differentiation potential that could be manifested following removal of BIO/SB431542 and by addition of cell differentiation factors. To test the possibility that the cells in BIO/SB431542-containing media could be further differentiated into endoderm, we grew cells for 6 passages in BIO/SB431542, then removed BIO/SB431542, and IGF-I, heregulin (two activators of PI3K activity) from the media and supplemented with Activin A to 100 ng/ml. These are conditions that support differentiation of hESCs to definitive endoderm. Over a 4 day period following the switch to the endoderm differentiation conditions we observed increases in Sox17 and CXCR4 transcripts while Nanog, T and eomesodermin transcripts remained low (FIG. 32). These results indicate that the cells passaged in BIO/SB431542 retained the potential to generate endoderm and, could be induced to differentiate into endoderm when cultured under the appropriate conditions. We propose that the BIO/SB431542 treated cells could also be differentiated into mesoderm and perhaps other lineages (ectoderm) if exposed to the appropriate specification factors. For example, we believe that BIO/SB431542-treated cells could be converted to mesoderm cells if BIO/SB431542 was removed and BMP4 was added to the media.

Figure 33:
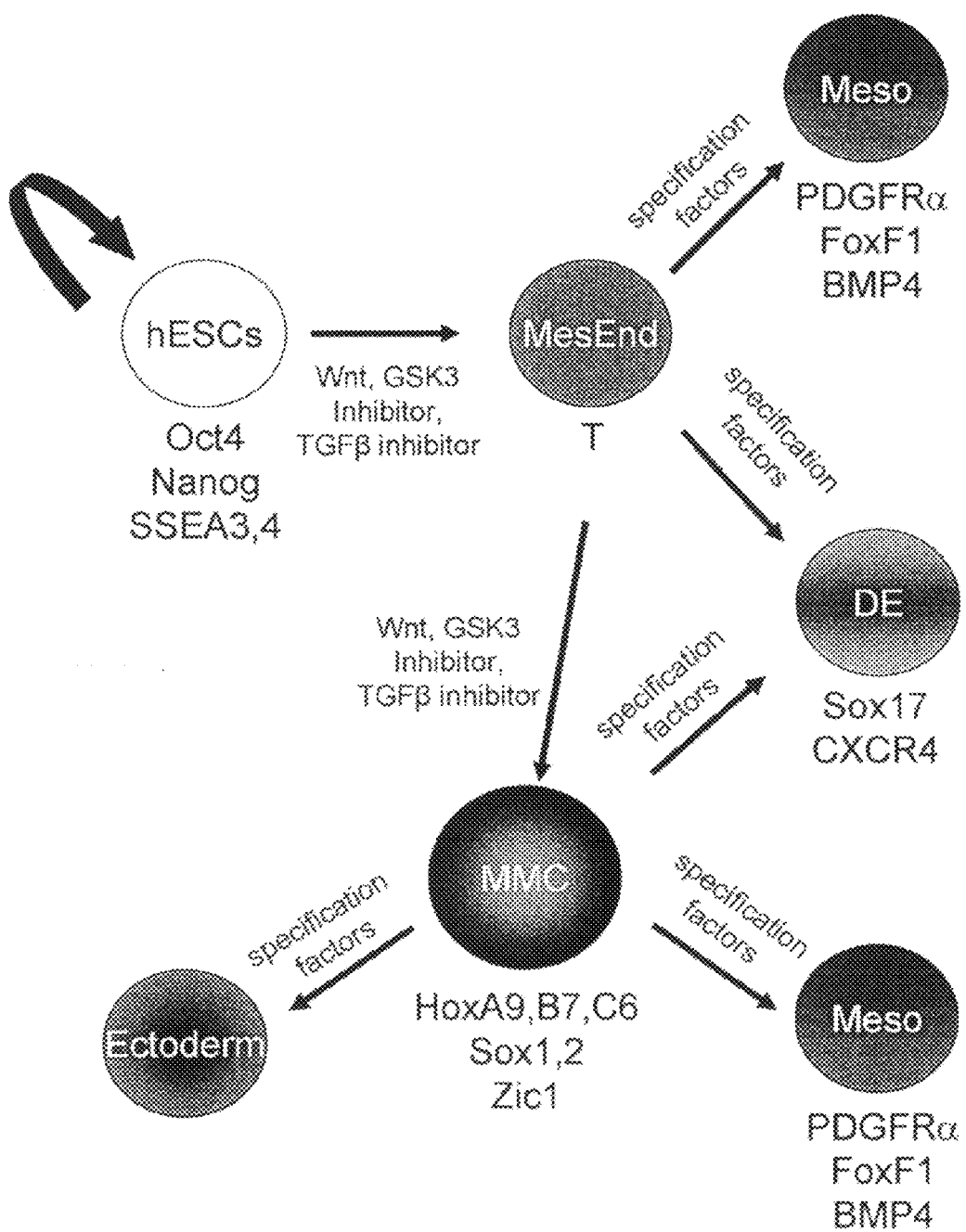
FIG. 33. Schematic showing the formation of multipotent mesenchymal cells (MMCs) from hESCs and the potential cell types they are capable of differentiating into.

Treatment of hESCs with BIO/SB431542 resulted in the production of a self-renewing population with stable characteristics that could be differentiated into endoderm and probably mesoderm. Because of its mesenchymal nature we call this cell type a multipotent mesenchymal cell (MMC) (FIG. 33).

Example 9

Composition of Matter for Multipotent Mesenchymal Cells (MMCs)

The multipotent mesenchymal cell (MMC) we described has the following characteristics:
- it can be cultured for at least 20 passages as a stable cell population
- cells appear mesenchymal when plated at low density and grow into a sheet at high density
- can be produced from a range of hESC lines including BG01, BG02, WA09
- MMCs can be frozen and cryogenically preserved by standard methods
- MMCs can be recovered after cryogenic storage, recovered and differentiated
- MMCs can be passaged with high plating efficiency
- do not exhibit the SSEA3 and SSEA4 antigens on their cell surface
- do not express hESC markers such as Oct4, Nanog
- MMCs can express CXCR4 on their surface
- MMCs express the following transcripts Zic1, HoxA9, HoxD4, HoxC6, N-CAM
- MMCs are not mesendoderm because they do not express T/brachyury or eomesodermin
- E-cadherin negative
- MMCs do not express Sox17, Isl1, musashi, nestin at high levels
- retain a normal karyotype during passaging
- exhibit a migratory, mesenchymal phenotype
- have multipotent differentiation capacity (including mesoderm, endoderm)
- do not form teratomas when injected into SCID mice
- see microarray data for a more complete description of MMC genes expression profiles Appendix 1

Microarray Data for Multipotent Mesenchymal Cells (MMC)

Formation and maintenance of MMC following treatment of BG02 hESCs with BIO (2μM) and SB431542 (20μM) in defined media for 5 days. The MMCs were split at a 1:5 ratio and replated in the same conditions of matrigel plated dishes for 19 passages. mRNA samples were taken for hESCs (one sample) and MMCs at passage 0 (P0), 4 (P4), 13 (P13) and 19 (P19) for microarray analysis. MMCs were sorted at passage 14 for the cell surface receptor CXCR4 and replated for a further 4 passages before collection for microarray analysis. The following table is a summary of the microarray analysis showing the fold changes as log ratios.

Appendix 1

| MMC P13 | | | MMC P19 | | |
|---|---|---|---|---|---|
| Est Log Ratio | Gene Symbol | Gene Descriptor | Est Log Ratio | Gene Symbol | Gene Descriptor |
| -11.42 | HESRG | embryonic stem cell related protein | -12.47 | HESRG | embryonic stem cell related protein |
| -11.40 | LOC645682 | POU domain, class 5, transcription factor 1 pse | -11.79 | NANOG | Nanog homeobox |
| -11.07 | NANOG | Nanog homeobox | 11.24 | IL13RA2 | interleukin 13 receptor, alpha 2 |
| -10.63 | CLDN6 | claudin 6 | -11.12 | KRT18 | keratin 18 |
| -10.46 | RBM35A | RNA binding motif protein 35A | -10.85 | LOC645682 | POU domain, class 5, transcription factor 1 pse |
| -10.37 | DPPA4 | developmental pluripotency associated 4 | -10.67 | LOC642559 | POU domain, class 5, transcription factor 1 pse |
| -10.36 | RBM35A | RNA binding motif protein 35A | -10.54 | CDH1 | cadherin 1, type 1, E-cadherin (epithelial) |
| -10.19 | — | Transcribed locus | -10.49 | CLDN6 | claudin 6 |
| -10.01 | DPPA4 | developmental pluripotency associated 4 | -10.39 | TACSTD1 | tumor-associated calcium signal transducer 1 |
| -10.00 | SCNN1A | sodium channel, nonvoltage-gated 1 alpha | -10.25 | SCNN1A | sodium channel, nonvoltage-gated 1 alpha |
| 9.99 | IL13RA2 | interleukin 13 receptor, alpha 2 | -10.15 | TDGF1 /// TDGF3 | teratocarcinoma-derived growth factor 1 /// tera |
| -9.92 | TDGF1 /// TDGF3 | teratocarcinoma-derived growth factor 1 /// tera | -10.12 | C14orf29 | chromosome 14 open reading frame 29 |
| -9.83 | F11R | F11 receptor | -9.82 | DPPA4 | developmental pluripotency associated 4 |
| -9.63 | — | Transcribed locus | -9.80 | RBM35A | RNA binding motif protein 35A |
| 9.54 | PTPRN2 | protein tyrosine phosphatase, receptor type, N | 9.72 | HOXA9 | homeobox A9 |
| 9.49 | SOX1 | SRY (sex determining region Y)-box 1 | -9.69 | DSP | desmoplakin |
| -9.49 | — | — | -9.68 | KRT19 | keratin 19 |
| 9.44 | FOLH1 | folate hydrolase (prostate-specific membrane a | -9.60 | PRAC | small nuclear protein PRAC |
| 9.43 | EN2 | engrailed homolog 2 | -9.43 | ZFP42 | zinc finger protein 42 homolog (mouse) |
| 9.35 | NR2F1 | Nuclear receptor subfamily 2, group F, membe | 9.43 | EN2 | engrailed homolog 2 |
| 9.34 | ZIC1 | Zic family member 1 (odd-paired homolog, Dro | -9.42 | DPPA4 | developmental pluripotency associated 4 |
| -9.33 | CLDN7 | claudin 7 | 9.42 | TRIM48 | tripartite motif-containing 48 |
| 9.33 | FLJ20366 | hypothetical protein FLJ20366 | 9.41 | NR2F1 | Nuclear receptor subfamily 2, group F, membe |
| -9.25 | CDH1 | cadherin 1, type 1, E-cadherin (epithelial) | -9.41 | L1TD1 | LINE-1 type transposase domain containing 1 |
| 9.25 | HOXA9 | homeobox A9 | -9.39 | — | Transcribed locus |
| -9.22 | — | — | -9.32 | F11R | F11 receptor |
| -9.22 | LOC642559 | POU domain, class 5, transcription factor 1 pse | 9.30 | FOLH1 | folate hydrolase (prostate-specific membrane a |
| -9.20 | IL8 | interleukin 8 | 9.28 | — | — |
| 9.16 | — | — | 9.28 | PTPRN2 | protein tyrosine phosphatase, receptor type, N |
| -9.08 | ZFP42 | zinc finger protein 42 homolog (mouse) | 9.27 | FLJ20366 | hypothetical protein FLJ20366 |
| -9.06 | ZFP42 | zinc finger protein 42 homolog (mouse) | -9.26 | RBM35A | RNA binding motif protein 35A |
| -9.04 | C14orf29 | chromosome 14 open reading frame 29 | 9.23 | ZIC1 | Zic family member 1 (odd-paired homolog, Dro |
| -9.01 | L1TD1 | LINE-1 type transposase domain containing 1 | -9.21 | GNAS | GNAS complex locus |
| 8.99 | PTPRN2 | protein tyrosine phosphatase, receptor type, N | 9.20 | — | — |
| 8.97 | HES5 | hairy and enhancer of split 5 (Drosophila) | -9.15 | GARNL4 | GTPase activating Rap/RanGAP domain-like 4 |
| -8.93 | CDA | cytidine deaminase | -9.11 | IFITM1 | interferon induced transmembrane protein 1 (9 |
| 8.90 | TRIM48 | tripartite motif-containing 48 | -9.04 | POU5F1 /// POU5F | POU domain, class 5, transcription factor 1 /// F |
| -8.89 | KRT19 | keratin 19 | 8.99 | TMEM16C | transmembrane protein 16C |
| -8.87 | GARNL4 | GTPase activating Rap/RanGAP domain-like 4 | 8.98 | PTPRN2 | protein tyrosine phosphatase, receptor type, N |
| -8.81 | — | Transcribed locus | -8.89 | CR1L | complement component (3b/4b) receptor 1-like |
| -8.75 | NTS | neurotensin | -8.88 | GPR64 | G protein-coupled receptor 64 |
| -8.72 | — | — | -8.87 | — | — |
| -8.68 | IFITM1 | interferon induced transmembrane protein 1 (9 | -8.85 | LSR | lipolysis stimulated lipoprotein receptor |
| 8.68 | PDE1A | phosphodiesterase 1A, calmodulin-dependent | -8.85 | COL1A2 | collagen, type I, alpha 2 |
| 8.66 | NCALD | neurocalcin delta /// neurocalcin delta | 8.82 | EPHA3 | EPH receptor A3 |
| 8.63 | LUM | lumican | 8.82 | SOX1 | SRY (sex determining region Y)-box 1 |
| 8.62 | EN1 | engrailed homolog 1 | -8.80 | — | — |
| -8.61 | KRT18 | keratin 18 | -8.80 | SEMA6A | sema domain, transmembrane domain (TM), a |
| -8.61 | TACSTD1 | tumor-associated calcium signal transducer 1 | 8.75 | HES5 | hairy and enhancer of split 5 (Drosophila) |
| -8.61 | — | Homo sapiens, Similar to otoconin 90, clone IM | -8.73 | LEFTY1 | left-right determination factor 1 |
| 8.60 | FOLH1 | folate hydrolase (prostate-specific membrane a | -8.72 | DPPA2 | developmental pluripotency associated 2 |
| -8.58 | IFITM1 | interferon induced transmembrane protein 1 (9 | 8.72 | NCALD | neurocalcin delta /// neurocalcin delta |
| -8.52 | CR1L | complement component (3b/4b) receptor 1-like | -8.70 | CLDN6 | claudin 6 |
| -8.46 | CDH3 | cadherin 3, type 1, P-cadherin (placental) | -8.62 | IFITM1 | interferon induced transmembrane protein 1 (9 |
| -8.46 | — | — | -8.61 | POU5F1 /// POU5F | POU domain, class 5, transcription factor 1 /// F |
| 8.44 | EPHA3 | EPH receptor A3 | -8.51 | VSNL1 | visinin-like 1 |
| -8.44 | — | — | 8.47 | — | — |
| 8.42 | — | — | 8.45 | HOXC6 | homeobox C6 |
| -8.40 | POU5F1 /// POU5F | POU domain, class 5, transcription factor 1 /// F | -8.44 | CDH1 | cadherin 1, type 1, E-cadherin (epithelial) |
| 8.33 | — | — | -8.41 | LEFTY2 | left-right determination factor 2 |
| -8.28 | ZFP42 | zinc finger protein 42 | -8.41 | — | — |
| -8.18 | — | — | -8.39 | — | Transcribed locus |
| 8.18 | — | Transcribed locus | -8.38 | PRSS8 | protease, serine, 8 (prostasin) |
| 8.17 | — | CDNA clone IMAGE:4811567 | 8.36 | FOLH1 | folate hydrolase (prostate-specific membrane a |
| 8.12 | TKTL1 | transketolase-like 1 | -8.35 | ZFP42 | zinc finger protein 42 |
| -8.09 | — | — | -8.35 | CCDC4 | coiled-coil domain containing 4 |
| -7.99 | POU5F1 /// POU5F | POU domain, class 5, transcription factor 1 /// F | -8.25 | ZNF206 | zinc finger protein 206 |
| 7.99 | — | — | -8.25 | — | Homo sapiens, Similar to otoconin 90, clone IM |
| -7.91 | — | — | -8.17 | FOXH1 | forkhead box H1 |

Appendix 1

| | | | |
|---|---|---|---|
| -7.91 LEFTY1 | left-right determination factor 1 | -8.11 SPINT1 | serine peptidase inhibitor, Kunitz type 1 |
| -7.89 CR1 /// CR1L | complement component (3b/4b) receptor 1, inc | 8.07 — | — |
| -7.84 PRAC | small nuclear protein PRAC | -7.97 GALNT3 | UDP-N-acetyl-alpha-D-galactosamine:polypep |
| -7.84 LCK | lymphocyte-specific protein tyrosine kinase | -7.97 ZYG11A | zyg-11 homolog A (C. elegans) |
| -7.82 CDH1 | cadherin 1, type 1, E-cadherin (epithelial) | -7.94 LECT1 | leukocyte cell derived chemotaxin 1 |
| -7.82 — | — | -7.93 GLB1L3 | galactosidase, beta 1 like 3 |
| 7.81 HOXD4 | homeobox D4 | -7.89 LOC728342 | Hypothetical protein LOC728342 |
| 7.79 RFX4 | regulatory factor X, 4 (influences HLA class II e | -7.89 ZFP42 | zinc finger protein 42 homolog (mouse) |
| -7.78 CLDN6 | claudin 6 | -7.88 — | CDNA FLJ30478 fis, clone BRAWH1000167 |
| -7.76 TMEM30B | transmembrane protein 30B | -7.81 CALB1 | calbindin 1, 28kDa |
| -7.74 CYP26A1 | cytochrome P450, family 26, subfamily A, polyp | -7.80 HEY2 | hairy/enhancer-of-split related with YRPW moti |
| 7.70 NR2F2 | nuclear receptor subfamily 2, group F, member | -7.79 CYP26A1 | cytochrome P450, family 26, subfamily A, poly |
| -7.69 — | Homo sapiens, Similar to otoconin 90, clone IM | -7.75 TNNT1 | troponin T type 1 (skeletal, slow) |
| 7.64 GPR56 | G protein-coupled receptor 56 | -7.73 — | — |
| -7.61 GNAS | GNAS complex locus | 7.73 PCDH8 | protocadherin 8 |
| 7.61 NTRK2 | neurotrophic tyrosine kinase, receptor, type 2 | 7.72 — | — |
| 7.61 PCDH8 | protocadherin 8 | 7.72 RFX4 | regulatory factor X, 4 (influences HLA class II e |
| -7.58 DPPA2 | developmental pluripotency associated 2 | -7.72 APOE | apolipoprotein E |
| 7.55 HOXC6 | homeobox C6 | -7.71 COL1A1 | collagen, type I, alpha 1 |
| -7.54 ZNF206 | zinc finger protein 206 | -7.70 RARRES2 | retinoic acid receptor responder (tazarotene ind |
| 7.52 HOXA5 | homeobox A5 | -7.69 TFPI | tissue factor pathway inhibitor (lipoprotein-asso |
| -7.49 VSNL1 | visinin-like 1 | -7.69 APOC1 | apolipoprotein C-I |
| -7.48 IL8 | interleukin 8 | 7.68 — | — |
| 7.48 — | — | -7.66 MT1F | metallothionein 1F (functional) |
| -7.48 — | — | 7.65 PDE1A | phosphodiesterase 1A, calmodulin-dependent |
| -7.47 ALDH1A3 | aldehyde dehydrogenase 1 family, member A3 | -7.65 LCK | lymphocyte-specific protein tyrosine kinase |
| 7.46 EPHA3 | EPH receptor A3 | 7.63 EN1 | engrailed homolog 1 |
| -7.45 EPHA1 | EPH receptor A1 | -7.62 — | — |
| 7.44 SOX1 | SRY (sex determining region Y)-box 1 | -7.59 — | Transcribed locus |
| -7.41 MTAC2D1 | membrane targeting (tandem) C2 domain conta | -7.58 CDA | cytidine deaminase |
| 7.41 HOXB8 | homeobox B8 | -7.55 CLDN7 | claudin 7 |
| 7.41 HOXD3 | homeobox D3 | 7.53 HOXB8 | homeobox B8 |
| -7.40 LEFTY2 | left-right determination factor 2 | -7.50 — | — |
| -7.40 SPINT1 | serine peptidase inhibitor, Kunitz type 1 | 7.47 GPR56 | G protein-coupled receptor 56 |
| 7.39 — | — | -7.46 — | — |
| 7.39 — | — | 7.46 SCUBE2 | signal peptide, CUB domain, EGF-like 2 |
| 7.38 PDE1A | phosphodiesterase 1A, calmodulin-dependent | -7.45 ERBB3 | v-erb-b2 erythroblastic leukemia viral oncogene |
| -7.35 TNFSF11 | tumor necrosis factor (ligand) superfamily, mer | -7.43 SEMA6A | sema domain, transmembrane domain (TM), a |
| -7.33 TFPI | tissue factor pathway inhibitor (lipoprotein-asso | -7.42 CARD10 | caspase recruitment domain family, member 1 |
| 7.33 PDE1A | phosphodiesterase 1A, calmodulin-dependent | -7.40 LOC388638 | hypothetical LOC388638 |
| 7.33 — | — | 7.40 — | — |
| -7.32 ITPR3 | inositol 1,4,5-triphosphate receptor, type 3 | -7.39 FLJ20273 | RNA-binding protein |
| 7.31 HOXB7 | homeobox B7 | -7.39 OCIAD2 | OCIA domain containing 2 |
| -7.31 ARHGAP8 /// LOC5 | Rho GTPase activating protein 8 /// PRR5-ARH | 7.38 — | — |
| -7.30 SPINT2 | serine peptidase inhibitor, Kunitz type, 2 | 7.36 — | — |
| -7.28 ZD52F10 | dermokine | 7.36 DKFZP686A01247 | hypothetical protein |
| 7.28 ASCL1 | achaete-scute complex homolog 1 (Drosophila) | 7.34 — | — |
| -7.28 S100A11 | S100 calcium binding protein A11 | -7.33 CRLF1 | cytokine receptor-like factor 1 |
| -7.26 GUCA1A | guanylate cyclase activator 1A (retina) | -7.32 — | Homo sapiens, Similar to otoconin 90, clone IM |
| 7.26 NR2F2 | nuclear receptor subfamily 2, group F, member | -7.30 NTS | neurotensin |
| -7.25 HBA2 | hemoglobin, alpha 2 /// hemoglobin, alpha 2 | 7.29 HOXB7 | homeobox B7 |
| 7.24 LONRF2 | LON peptidase N-terminal domain and ring fing | 7.27 NR2F2 | nuclear receptor subfamily 2, group F, member |
| -7.21 GALNT3 | UDP-N-acetyl-alpha-D-galactosamine:polypep | -7.26 ABHD9 | abhydrolase domain containing 9 |
| -7.21 HLA-DPB2 | major histocompatibility complex, class II, DP b | 7.26 — | — |
| -7.19 WDR72 | WD repeat domain 72 | -7.25 ITPR3 | inositol 1,4,5-triphosphate receptor, type 3 |
| 7.19 ELAVL3 | ELAV (embryonic lethal, abnormal vision, Dros | -7.25 — | — |
| -7.17 COL9A3 | collagen, type IX, alpha 3 | -7.25 GNA14 | guanine nucleotide binding protein (G protein), |
| 7.17 POU3F2 | POU domain, class 3, transcription factor 2 | -7.25 UTF1 | undifferentiated embryonic cell transcription fac |
| -7.15 RAB17 | RAB17, member RAS oncogene family | -7.24 GLOXD1 | glyoxalase domain containing 1 |
| -7.12 ZNF206 | zinc finger protein 206 | 7.23 PLAGL1 | pleiomorphic adenoma gene-like 1 |
| -7.11 DPPA5 | developmental pluripotency associated 5 | -7.23 AP1M2 | adaptor-related protein complex 1, mu 2 subun |
| 7.10 HOXB6 | homeobox B6 | 7.23 — | — |
| 7.10 — | — | -7.21 COL9A3 | collagen, type IX, alpha 3 |
| 7.07 — | — | 7.21 HOXD4 | homeobox D4 |
| -7.06 — | — | -7.20 — | Transcribed locus |
| 7.06 NTRK2 | neurotrophic tyrosine kinase, receptor, type 2 | 7.20 HOXB7 | homeobox B7 |
| -7.05 — | — | -7.19 RAB25 | RAB25, member RAS oncogene family |
| -7.05 C10orf96 | chromosome 10 open reading frame 96 | -7.18 PPL | periplakin |
| 7.05 EMP1 | epithelial membrane protein 1 | 7.17 — | — |
| 7.04 — | — | 7.16 — | — |
| 7.04 DKFZP686A01247 | hypothetical protein | 7.15 HOXA9 | homeobox A9 |
| -7.03 — | CDNA FLJ12557 fis, clone NT2RM4000783 | -7.15 — | — |
| -7.02 ACSM3 | acyl-CoA synthetase medium-chain family mer | -7.15 — | — |
| 7.02 TFAP2B | transcription factor AP-2 beta (activating enhar | -7.14 MGC16044 | hypothetical protein MGC16044 |
| 7.01 SOX1 | SRY (sex determining region Y)-box 1 | -7.14 — | CDNA FLJ12557 fis, clone NT2RM4000783 |
| -6.99 GLOXD1 | glyoxalase domain containing 1 | -7.14 SPINT2 | serine peptidase inhibitor, Kunitz type, 2 |
| 6.98 — | — | 7.13 HOXD3 | homeobox D3 |
| -6.98 CRLF1 | cytokine receptor-like factor 1 | -7.11 — | — |
| -6.98 LSR | lipolysis stimulated lipoprotein receptor | -7.11 EPPK1 | epiplakin 1 |

Appendix 1

| | | | | |
|---|---|---|---|---|
| 6.98 | MEIS1 | Meis1, myeloid ecotropic viral integration site 1 | 7.10 | — | Homo sapiens, clone IMAGE:5019307, mRNA |
| -6.97 | — | CDNA FLJ35259 fis, clone PROST2004251 | 7.10 | NR2F2 | nuclear receptor subfamily 2, group F, member |
| 6.97 | HOXD10 | homeobox D10 | -7.09 | SEMA6A | sema domain, transmembrane domain (TM), a |
| -6.95 | CCDC4 | coiled-coil domain containing 4 | 7.09 | — | — |
| 6.95 | — | — | -7.08 | S100A11 | S100 calcium binding protein A11 |
| 6.94 | — | — | -7.07 | ARHGAP8 /// LOC5 | Rho GTPase activating protein 8 /// PRR5-ARH |
| 6.94 | — | CDNA FLJ39179 fis, clone OCBBF2004147 | -7.06 | KRT8 | keratin 8 /// keratin 8 |
| 6.93 | — | — | -7.06 | — | CDNA FLJ12624 fis, clone NT2RM4001754 |
| -6.92 | FXYD5 | FXYD domain containing ion transport regulato | -7.04 | GALNT6 | UDP-N-acetyl-alpha-D-galactosamine:polypep |
| -6.91 | BST2 | bone marrow stromal cell antigen 2 | 7.03 | — | Transcribed locus, moderately similar to XP_4 |
| -6.89 | KRT8 | keratin 8 /// keratin 8 | -7.01 | CR1 /// CR1L | complement component (3b/4b) receptor 1, inc |
| -6.89 | CXCL12 | chemokine (C-X-C motif) ligand 12 (stromal cel | 7.01 | FAM70A | family with sequence similarity 70, member A |
| 6.87 | HOXA9 | homeobox A9 | 6.98 | — | — |
| -6.86 | AP1M2 | adaptor-related protein complex 1, mu 2 subun | 6.98 | — | — |
| -6.85 | SMPDL3B | sphingomyelin phosphodiesterase, acid-like 3B | 6.96 | — | — |
| -6.84 | ERBB3 | v-erb-b2 erythroblastic leukemia viral oncogene | 6.96 | PLAGL1 | pleiomorphic adenoma gene-like 1 |
| 6.84 | DCAMKL2 | doublecortin and CaM kinase-like 2 | -6.96 | S100A10 | S100 calcium binding protein A10 |
| -6.83 | NODAL | nodal homolog (mouse) | -6.95 | — | — |
| 6.82 | SCUBE2 | signal peptide, CUB domain, EGF-like 2 | -6.94 | CDH3 | cadherin 3, type 1, P-cadherin (placental) |
| -6.81 | EPPK1 | epiplakin 1 | 6.93 | — | — |
| 6.80 | GLIS3 | GLIS family zinc finger 3 | 6.90 | TKTL1 | transketolase-like 1 |
| -6.80 | EFEMP1 | EGF-containing fibulin-like extracellular matrix | -6.87 | MYL9 | myosin, light chain 9, regulatory |
| -6.79 | HIST1H2BD | Histone cluster 1, H2bd | -6.85 | GAL | galanin |
| 6.78 | HOXB7 | homeobox B7 | -6.85 | — | — |
| 6.77 | — | — | -6.84 | HAPLN1 | hyaluronan and proteoglycan link protein 1 |
| -6.76 | EDG7 | Endothelial differentiation, lysophosphatidic aci | -6.82 | — | — |
| -6.75 | LOC391020 | similar to Interferon-induced transmembrane p | -6.81 | MTAC2D1 | membrane targeting (tandem) C2 domain cont |
| -6.75 | CBR3 | carbonyl reductase 3 | 6.80 | — | CDNA clone IMAGE:4811567 |
| -6.75 | KIAA1244 | KIAA1244 | -6.79 | COL1A2 | collagen, type I, alpha 2 |
| -6.75 | C20orf42 | chromosome 20 open reading frame 42 | 6.77 | LOC145786 | hypothetical protein LOC145786 |
| -6.73 | LOC440132 | LOC440132 | -6.77 | LOC255480 | hypothetical protein LOC255480 |
| 6.73 | HOXB7 | homeobox B7 | -6.75 | MT1E | metallothionein 1E (functional) |
| 6.72 | KIAA1713 | KIAA1713 | -6.75 | LOC153469 | hypothetical protein LOC153469 |
| 6.72 | PLAGL1 | pleiomorphic adenoma gene-like 1 | 6.75 | LONRF2 | LON peptidase N-terminal domain and ring fing |
| 6.72 | — | — | -6.75 | — | — |
| 6.72 | CACNG4 | calcium channel, voltage-dependent, gamma s | 6.75 | — | — |
| -6.72 | PPL | periplakin | -6.75 | NUDT16P | nudix (nucleoside diphosphate linked moiety X) |
| 6.72 | — | — | 6.74 | — | — |
| 6.72 | — | — | 6.73 | HOXC9 | homeobox C9 |
| 6.71 | — | — | 6.73 | SOX1 | SRY (sex determining region Y)-box 1 |
| 6.71 | — | Transcribed locus, moderately similar to XP_4 | -6.73 | ITGB1BP3 | integrin beta 1 binding protein 3 |
| -6.71 | — | — | -6.70 | CHST9 | carbohydrate (N-acetylgalactosamine 4-0) sulfo |
| -6.71 | FLJ25801 | hypothetical protein FLJ25801 | -6.68 | TFPI | tissue factor pathway inhibitor (lipoprotein-asso |
| -6.70 | — | Transcribed locus | -6.68 | C1orf172 | chromosome 1 open reading frame 172 |
| -6.70 | FLJ14712 | hypothetical protein FLJ14712 | 6.68 | FLJ21986 | hypothetical protein FLJ21986 |
| -6.69 | DPPA3 | developmental pluripotency associated 3 | 6.67 | HOXB3 | homeobox B3 |
| -6.69 | RAB25 | RAB25, member RAS oncogene family | 6.66 | — | Homo sapiens, clone IMAGE:5019307, mRNA |
| -6.69 | VENTX | VENT homeobox homolog (Xenopus laevis) | -6.66 | HEPH | hephaestin |
| 6.68 | — | — | 6.66 | ST8SIA1 | ST8 alpha-N-acetyl-neuraminide alpha-2,8-sial |
| -6.67 | PRSS8 | protease, serine, 8 (prostasin) | 6.66 | — | CDNA FLJ39179 fis, clone OCBBF2004147 |
| 6.67 | PLAGL1 | pleiomorphic adenoma gene-like 1 | -6.65 | MT1H | metallothionein 1H |
| -6.66 | TRPC6 | transient receptor potential cation channel, sub | 6.64 | DKFZP686A01247 | hypothetical protein |
| -6.65 | FLJ20273 | RNA-binding protein | 6.64 | HOXB7 | homeobox B7 |
| 6.64 | — | Transcribed locus | -6.64 | CALB1 | calbindin 1, 28kDa |
| -6.62 | FXYD5 | FXYD domain containing ion transport regulato | -6.64 | — | — |
| -6.61 | C21orf105 | chromosome 21 open reading frame 105 | -6.63 | ARHGEF5 | Rho guanine nucleotide exchange factor (GEF) |
| 6.61 | — | — | -6.62 | NRK | Nik related kinase |
| -6.61 | GLB1L3 | galactosidase, beta 1 like 3 | -6.62 | VENTX | VENT homeobox homolog (Xenopus laevis) |
| -6.61 | TNNT1 | troponin T type 1 (skeletal, slow) | -6.62 | LOC391020 | similar to Interferon-induced transmembrane p |
| 6.61 | PDE1A | phosphodiesterase 1A, calmodulin-dependent | 6.60 | — | — |
| 6.60 | HOXA10 | homeobox A10 | -6.58 | TMEM30B | transmembrane protein 30B |
| 6.58 | SCN3A | sodium channel, voltage-gated, type III, alpha | 6.57 | POU3F2 | POU domain, class 3, transcription factor 2 |
| -6.58 | AP1M2 | adaptor-related protein complex 1, mu 2 subun | -6.56 | — | Transcribed locus |
| -6.58 | ZYG11A | zyg-11 homolog A (C. elegans) | 6.56 | EPHA3 | EPH receptor A3 |
| -6.55 | HDCMA18P | HDCMA18P protein | 6.55 | LRRC17 | leucine rich repeat containing 17 |
| 6.55 | PTPRN2 | protein tyrosine phosphatase, receptor type, N | -6.54 | EPHA1 | EPH receptor A1 |
| 6.53 | HOXB3 | homeobox B3 | -6.53 | FLJ44186 | FLJ44186 protein |
| 6.51 | NAP5 | Nck-associated protein 5 | 6.53 | MEGF11 | multiple EGF-like-domains 11 |
| -6.50 | B3GNT7 | UDP-GlcNAc:betaGal beta-1,3-N-acetylglucosa | 6.52 | CRB1 | crumbs homolog 1 (Drosophila) |
| 6.48 | — | — | -6.52 | PPAP2C | phosphatidic acid phosphatase type 2C |
| 6.48 | HOXD11 | homeobox D11 | -6.51 | LOC645745 | metallothionein 1H-like protein |
| -6.48 | FLJ36748 | hypothetical protein FLJ36748 | 6.51 | ASCL1 | achaete-scute complex homolog 1 (Drosophila |
| 6.47 | — | — | -6.49 | EPPK1 | epiplakin 1 |
| -6.47 | LOC255480 | hypothetical protein LOC255480 | 6.49 | HOXA5 | homeobox A5 |
| 6.47 | TCF8 | transcription factor 8 (represses interleukin 2 e | -6.48 | TLE2 | transducin-like enhancer of split 2 (E(sp1) hom |
| -6.47 | — | Transcribed locus | -6.46 | FLJ40125 | hypothetical protein FLJ40125 |
| -6.46 | HEY2 | hairy/enhancer-of-split related with YRPW moti | -6.46 | BCL11B | B-cell CLL/lymphoma 11B (zinc finger protein) |
| -6.46 | — | — | -6.45 | OLFM1 | olfactomedin 1 |
| -6.45 | LOC388638 | hypothetical LOC388638 | -6.45 | ACSM3 | acyl-CoA synthetase medium-chain family mer |

Appendix 1

| Value | Gene | Description |
|---|---|---|
| 6.44 | MAP2 | microtubule-associated protein 2 |
| 6.43 | ZNF536 | zinc finger protein 536 |
| 6.42 | HOXC9 | homeobox C9 |
| 6.42 | SMYD2 | SET and MYND domain containing 2 |
| 6.41 | PDE1A | phosphodiesterase 1A, calmodulin-dependent |
| 6.41 | ABCC9 | ATP-binding cassette, sub-family C (CFTR/MR |
| 6.40 | — | — |
| 6.39 | COL2A1 | collagen, type II, alpha 1 (primary osteoarthritis |
| -6.38 | — | — |
| -6.37 | FOXH1 | forkhead box H1 |
| -6.36 | EDIL3 | EGF-like repeats and discoidin I-like domains 3 |
| -6.36 | MUC4 | mucin 4, cell surface associated |
| -6.35 | CYP2S1 | cytochrome P450, family 2, subfamily S, polype |
| 6.34 | — | Homo sapiens, clone IMAGE:5019307, mRNA |
| -6.34 | PCSK9 | proprotein convertase subtilisin/kexin type 9 |
| -6.34 | GNA14 | guanine nucleotide binding protein (G protein), |
| 6.33 | TKTL1 | transketolase-like 1 |
| 6.33 | TCF8 | transcription factor 8 (represses interleukin 2 e |
| -6.33 | — | — |
| -6.33 | — | — |
| -6.33 | — | — |
| 6.33 | — | — |
| -6.33 | — | Transcribed locus |
| -6.31 | NPW | neuropeptide W |
| -6.31 | FGD5 | FYVE, RhoGEF and PH domain containing 5 |
| -6.31 | GLS2 | glutaminase 2 (liver, mitochondrial) |
| -6.30 | — | MRNA full length insert cDNA clone EUROIMA |
| -6.28 | TFPI | tissue factor pathway inhibitor (lipoprotein-assc |
| -6.28 | TNMD | tenomodulin |
| 6.28 | COL3A1 | collagen, type III, alpha 1 (Ehlers-Danlos syndr |
| -6.27 | FLJ44186 | FLJ44186 protein |
| 6.27 | LOC286411 | hypothetical protein LOC286411 |
| 6.25 | DKFZP686A01247 | hypothetical protein |
| 6.25 | — | — |
| 6.24 | IRX5 | iroquois homeobox protein 5 |
| -6.24 | HPGD | hydroxyprostaglandin dehydrogenase 15-(NAD |
| -6.23 | S100A10 | S100 calcium binding protein A10 |
| -6.23 | NR5A2 | nuclear receptor subfamily 5, group A, member |
| 6.22 | C4orf18 | chromosome 4 open reading frame 18 |
| 6.21 | LOC613266 | hypothetical LOC613266 |
| -6.20 | SEMG1 | semenogelin I |
| 6.19 | MAP6 | microtubule-associated protein 6 |
| 6.19 | FHOD3 | formin homology 2 domain containing 3 |
| 6.18 | TMEM16C | transmembrane protein 16C |
| 6.17 | ST8SIA1 | ST8 alpha-N-acetyl-neuraminide alpha-2,8-sial |
| -6.17 | CST1 | cystatin SN |
| -6.17 | B3GNT7 | UDP-GlcNAc:betaGal beta-1,3-N-acetylglucosa |
| -6.16 | ITGB1BP3 | integrin beta 1 binding protein 3 |
| 6.16 | — | — |
| -6.16 | MGC16044 | hypothetical protein MGC16044 |
| -6.15 | — | Homo sapiens, Similar to otoconin 90, clone IM |
| -6.14 | LOC388494 | hypothetical gene supported by AL365406; BC |
| 6.14 | HOXA2 | homeobox A2 |
| 6.13 | HOXD10 | homeobox D10 |
| -6.12 | — | — |
| -6.11 | GPR160 | G protein-coupled receptor 160 |
| -6.11 | UTF1 | undifferentiated embryonic cell transcription fac |
| -6.11 | ABHD9 | abhydrolase domain containing 9 |
| 6.11 | HOXC10 | homeobox C10 |
| 6.11 | CRB2 | crumbs homolog 2 (Drosophila) |
| -6.10 | FOXA2 | forkhead box A2 |
| 6.08 | ZBTB16 | zinc finger and BTB domain containing 16 |
| 6.08 | CSPG3 | chondroitin sulfate proteoglycan 3 (neurocan) |
| 6.07 | ITGB8 | integrin, beta 8 |
| 6.07 | — | Homo sapiens, clone IMAGE:5019307, mRNA |
| -6.06 | GAL3ST1 | galactose-3-O-sulfotransferase 1 |
| 6.05 | FOLH1 | folate hydrolase (prostate-specific membrane a |
| 6.05 | FLJ41747 | hypothetical gene supported by AK123741 |
| 6.04 | LOC387856 | similar to expressed sequence AI836003 |
| 6.03 | JAM2 | junctional adhesion molecule 2 |
| -6.03 | ARHGEF5 | Rho guanine nucleotide exchange factor (GEF) |
| -6.03 | LOC728342 | Hypothetical protein LOC728342 |
| -6.02 | ANXA3 | annexin A3 |
| 6.02 | DKFZP686A01247 | hypothetical protein |
| -6.00 | LCK | lymphocyte-specific protein tyrosine kinase |
| -6.00 | GABRP | gamma-aminobutyric acid (GABA) A receptor, |
| -6.00 | ARHGAP8 /// LOC5 | Rho GTPase activating protein 8 /// PRR5-ARH |
| -6.00 | TLE2 | transducin-like enhancer of split 2 (E(sp1) hom |
| 5.99 | DCC | deleted in colorectal carcinoma |
| -6.44 | FOXH1 | forkhead box H1 |
| -6.43 | PITX2 | paired-like homeodomain transcription factor 2 |
| 6.43 | MEIS1 | Meis1, myeloid ecotropic viral integration site 1 |
| -6.42 | — | — |
| -6.41 | RAB17 | RAB17, member RAS oncogene family |
| -6.41 | RUNX1T1 | runt-related transcription factor 1; translocated |
| 6.41 | — | — |
| -6.40 | EPS8L2 | EPS8-like 2 |
| -6.40 | B3GNT7 | UDP-GlcNAc:betaGal beta-1,3-N-acetylglucos |
| -6.40 | — | — |
| 6.39 | PRDM13 | PR domain containing 13 |
| -6.39 | NODAL | nodal homolog (mouse) |
| -6.38 | PHF11 /// RP13-36( | PHD finger protein 11 /// cancer/testis antigen ( |
| -6.38 | PACSIN3 | protein kinase C and casein kinase substrate i |
| -6.37 | C21orf105 | chromosome 21 open reading frame 105 |
| -6.37 | — | — |
| 6.37 | CSPG3 | chondroitin sulfate proteoglycan 3 (neurocan) |
| 6.36 | — | Transcribed locus |
| 6.36 | PAX6 | paired box gene 6 (aniridia, keratitis) |
| 6.36 | HOXA1 | homeobox A1 |
| -6.36 | HEY2 | hairy/enhancer-of-split related with YRPW moti |
| -6.35 | CBR3 | carbonyl reductase 3 |
| -6.35 | GATA6 | GATA binding protein 6 |
| -6.35 | ZD52F10 | dermokine |
| -6.33 | B3GNT7 | UDP-GlcNAc:betaGal beta-1,3-N-acetylglucosa |
| -6.33 | — | — |
| 6.30 | TCF8 | transcription factor 8 (represses interleukin 2 e |
| 6.30 | — | — |
| -6.30 | PCSK9 | proprotein convertase subtilisin/kexin type 9 |
| 6.30 | HOXB6 | homeobox B6 |
| 6.29 | UGT2B4 | UDP glucuronosyltransferase 2 family, polypep |
| -6.28 | — | — |
| 6.27 | — | — |
| 6.26 | — | — |
| 6.25 | — | — |
| 6.25 | — | — |
| 6.25 | MAP2 | microtubule-associated protein 2 |
| -6.24 | HDCMA18P | HDCMA18P protein |
| 6.23 | NAP5 | Nck-associated protein 5 |
| -6.22 | CD1D | CD1d molecule /// CD1d molecule |
| -6.22 | TPD52L1 | tumor protein D52-like 1 |
| -6.22 | SEMG1 | semenogelin I |
| -6.22 | C1orf85 | chromosome 1 open reading frame 85 |
| -6.21 | — | — |
| -6.21 | — | MRNA full length insert cDNA clone EUROIMA |
| -6.21 | TNNI3 | troponin I type 3 (cardiac) |
| 6.20 | SMYD2 | SET and MYND domain containing 2 |
| 6.20 | ABCB1 | ATP-binding cassette, sub-family B (MDR/TAP |
| 6.20 | CRYBA1 | crystallin, beta A1 |
| -6.19 | ETS1 | v-ets erythroblastosis virus E26 oncogene hom |
| 6.19 | PRSS23 | Protease, serine, 23 |
| -6.19 | FLJ20273 | RNA-binding protein |
| -6.19 | FGD5 | FYVE, RhoGEF and PH domain containing 5 |
| -6.19 | SRY | sex determining region Y |
| -6.18 | RBM35B | RNA binding motif protein 35B |
| 6.18 | PDE1A | phosphodiesterase 1A, calmodulin-dependent |
| -6.17 | RPL39L | ribosomal protein L39-like |
| -6.16 | — | — |
| -6.15 | — | — |
| -6.14 | SLFN12 | schlafen family member 12 |
| 6.13 | KIAA1713 | KIAA1713 |
| -6.13 | — | Transcribed locus |
| -6.13 | PPP1R1A | protein phosphatase 1, regulatory (inhibitor) su |
| -6.12 | NFIA | nuclear factor I/A |
| 6.12 | NDP | Norrie disease (pseudoglioma) |
| -6.12 | HBA1 /// HBA2 | hemoglobin, alpha 1 /// hemoglobin, alpha 2 |
| 6.11 | LUM | lumican |
| 6.11 | JAM2 | junctional adhesion molecule 2 |
| -6.09 | COL1A2 | Collagen, type I, alpha 2 |
| -6.09 | BST2 | bone marrow stromal cell antigen 2 |
| 6.09 | — | — |
| 6.08 | GPR85 | G protein-coupled receptor 85 |
| 6.08 | — | Clone 24626 mRNA sequence |
| 6.08 | FRZB | frizzled-related protein |
| -6.07 | FAM46B | family with sequence similarity 46, member B |
| 6.06 | PKNOX2 | PBX/knotted 1 homeobox 2 |
| -6.05 | — | — |
| -6.05 | PIK3R5 | phosphoinositide-3-kinase, regulatory subunit 5 |
| 6.04 | SYNE1 | spectrin repeat containing, nuclear envelope 1 |

Appendix 1

| Value | Gene | Description |
|---|---|---|
| 5.99 | LHFP | lipoma HMGIC fusion partner |
| -5.99 | RIPK4 | receptor-interacting serine-threonine kinase 4 |
| -5.99 | TLE2 | transducin-like enhancer of split 2 (E(sp1) hom |
| 5.99 | DLX1 | distal-less homeobox 1 |
| -5.98 | HPGD | hydroxyprostaglandin dehydrogenase 15-(NAD |
| -5.98 | HEPH | hephaestin |
| -5.98 | GATA6 | GATA binding protein 6 |
| -5.98 | — | — |
| -5.97 | FGFR4 | fibroblast growth factor receptor 4 |
| -5.97 | LOC440338 | hypothetical gene supported by AJ002784 |
| -5.97 | HIST1H2BD | Histone cluster 1, H2bd |
| 5.96 | — | — |
| 5.96 | ZNF287 | zinc finger protein 287 |
| -5.95 | BCL11B | B-cell CLL/lymphoma 11B (zinc finger protein) |
| -5.95 | — | CDNA FLJ12624 fis, clone NT2RM4001754 |
| -5.94 | — | — |
| -5.94 | FOXH1 | forkhead box H1 |
| -5.94 | FLJ20273 | RNA-binding protein |
| -5.93 | HBA1 /// HBA2 | hemoglobin, alpha 1 /// hemoglobin, alpha 2 |
| -5.93 | DEPDC6 | DEP domain containing 6 |
| -5.93 | PDGFA | platelet-derived growth factor alpha polypeptide |
| 5.93 | PRDM13 | PR domain containing 13 |
| -5.93 | MUC3B | mucin 3B, cell surface associated |
| 5.92 | HOXA1 | homeobox A1 |
| -5.92 | PRDM14 | PR domain containing 14 |
| 5.91 | — | — |
| -5.91 | ABCG2 | ATP-binding cassette, sub-family G (WHITE), |
| 5.90 | FLJ37440 | hypothetical protein FLJ3744C |
| 5.90 | — | — |
| -5.89 | APOE | apolipoprotein E |
| -5.89 | — | — |
| -5.88 | C1S | complement component 1, s subcomponent |
| 5.88 | — | — |
| 5.87 | — | Clone 24626 mRNA sequence |
| 5.87 | RGS4 | regulator of G-protein signalling 4 |
| -5.86 | — | — |
| -5.85 | SRY | sex determining region Y |
| 5.85 | SYNE1 | spectrin repeat containing, nuclear envelope 1 |
| -5.84 | PPP1R1B | protein phosphatase 1, regulatory (inhibitor) su |
| 5.84 | DLX2 | distal-less homeobox 2 |
| 5.84 | PKNOX2 | PBX/knotted 1 homeobox 2 |
| 5.84 | TNFRSF19 | tumor necrosis factor receptor superfamily, me |
| 5.83 | NR2F1 | nuclear receptor subfamily 2, group F, member |
| -5.83 | FUT1 | fucosyltransferase 1 (galactoside 2-alpha-L-fuc |
| -5.80 | LOC130951 | hypothetical protein BC014602 |
| 5.79 | FAM70A | family with sequence similarity 70, member A |
| -5.78 | FLJ40125 | hypothetical protein FLJ40125 |
| -5.78 | SH2D3A | SH2 domain containing 3A |
| -5.78 | PROCR | protein C receptor, endothelial (EPCR) |
| 5.78 | HOXB9 | homeobox B9 |
| -5.77 | — | Homo sapiens, clone IMAGE:3454042, mRNA |
| 5.75 | PAX3 | paired box gene 3 (Waardenburg syndrome 1) |
| -5.75 | STYK1 | serine/threonine/tyrosine kinase 1 |
| -5.75 | PIK3R5 | phosphoinositide-3-kinase, regulatory subunit 5 |
| -5.75 | COBL | cordon-bleu homolog (mouse) |
| -5.74 | RBM35B | RNA binding motif protein 35B |
| 5.74 | HOXD12 | homeobox D12 |
| -5.74 | MYL9 | myosin, light chain 9, regulatory |
| 5.74 | LIX1 | Lix1 homolog (mouse) |
| -5.73 | — | — |
| 5.73 | SORBS2 | sorbin and SH3 domain containing 2 |
| 5.73 | MEGF11 | multiple EGF-like-domains 11 |
| 5.72 | LOC284244 | hypothetical protein LOC284244 |
| -5.71 | PRKCDBP | protein kinase C, delta binding protein |
| -5.70 | IFITM3 | interferon induced transmembrane protein 3 (1 |
| 5.70 | BAALC | brain and acute leukemia, cytoplasmic |
| 5.70 | SPAG6 | sperm associated antigen 6 |
| -5.69 | IFITM2 | interferon induced transmembrane protein 2 (1 |
| -5.68 | LOC202451 | hypothetical protein LOC202451 |
| -5.67 | — | — |
| -5.67 | CHST9 | carbohydrate (N-acetylgalactosamine 4-0) sulfo |
| 5.67 | ASCL1 | achaete-scute complex homolog 1 (Drosophila) |
| -5.66 | LOC202451 | hypothetical protein LOC202451 |
| 5.66 | C11orf70 | chromosome 11 open reading frame 70 /// chro |
| 5.65 | SPARCL1 | SPARC-like 1 (mast9, hevin) |
| -5.65 | GAL | galanin |
| 5.64 | HOXA10 | homeobox A10 |
| -5.64 | — | — |
| 5.64 | PAX6 | paired box gene 6 (aniridia, keratitis) |
| 6.04 | C8orf4 | chromosome 8 open reading frame 4 |
| -6.03 | CAV1 | caveolin 1, caveolae protein, 22kDa |
| 6.02 | — | CDNA clone IMAGE:5273964 |
| -6.00 | GLS2 | glutaminase 2 (liver, mitochondrial) |
| -6.00 | HBA2 | hemoglobin, alpha 2 /// hemoglobin, alpha 2 |
| 6.00 | CXorf1 | chromosome X open reading frame 1 |
| -5.99 | HLA-DPB2 | major histocompatibility complex, class II, DP |
| -5.99 | EFEMP1 | EGF-containing fibulin-like extracellular matrix |
| 5.99 | — | — |
| -5.98 | LOC202451 | hypothetical protein LOC202451 |
| 5.98 | — | — |
| 5.98 | LOC286411 | hypothetical protein LOC286411 |
| -5.98 | — | MRNA; cDNA DKFZp686L0310 (from clone DK |
| 5.97 | HOXA10 | homeobox A10 |
| -5.97 | HBA1 /// HBA2 | hemoglobin, alpha 1 /// hemoglobin, alpha 1 /// |
| -5.97 | SLFN5 | schlafen family member 5 |
| -5.95 | MUC3B | mucin 3B, cell surface associated |
| -5.94 | — | — |
| -5.94 | LCK | lymphocyte-specific protein tyrosine kinase |
| 5.93 | LHFP | lipoma HMGIC fusion partner |
| -5.92 | NR5A2 | nuclear receptor subfamily 5, group A, member |
| -5.90 | — | — |
| 5.90 | — | — |
| 5.89 | FLJ25694 | hypothetical protein FLJ25694 |
| -5.88 | LOC136306 | hypothetical protein LOC136306 |
| 5.88 | LOC143381 | hypothetical protein LOC143381 |
| 5.88 | GLIS3 | GLIS family zinc finger 3 |
| -5.88 | LOC130951 | hypothetical protein BC014602 |
| -5.88 | ZNF141 | Zinc finger protein 141 |
| -5.87 | FXYD5 | FXYD domain containing ion transport regulato |
| 5.87 | TCF8 | transcription factor 8 (represses interleukin 2 e |
| -5.87 | HLA-DPB1 | major histocompatibility complex, class II, DP |
| -5.85 | ATP2A3 | ATPase, Ca++ transporting, ubiquitous |
| -5.85 | — | — |
| 5.85 | DDC | dopa decarboxylase (aromatic L-amino acid de |
| 5.85 | FHOD3 | formin homology 2 domain containing 3 |
| 5.84 | FLJ37440 | hypothetical protein FLJ3744C |
| -5.84 | IL28RA | interleukin 28 receptor, alpha (interferon, lambo |
| 5.84 | BCHE | butyrylcholinesterase |
| -5.84 | TRPC6 | transient receptor potential cation channel, sub |
| -5.83 | NFIA | nuclear factor I/A |
| -5.83 | PROCR | protein C receptor, endothelial (EPCR) |
| -5.83 | TFAP2C | transcription factor AP-2 gamma (activating en |
| -5.82 | DPPA3 | developmental pluripotency associated 3 |
| 5.82 | DACH1 | dachshund homolog 1 (Drosophila) |
| -5.82 | AP1M2 | adaptor-related protein complex 1, mu 2 subun |
| 5.82 | HOXC10 | homeobox C10 |
| -5.82 | OR2A20P /// OR2A | olfactory receptor, family 2, subfamily A, memb |
| -5.80 | TNC | tenascin C (hexabrachion) |
| -5.80 | LASS4 | LAG1 homolog, ceramide synthase 4 (S. cerev |
| 5.80 | MBNL2 | muscleblind-like 2 (Drosophila) |
| 5.80 | EMP1 | epithelial membrane protein 1 |
| -5.80 | MT1M | metallothionein 1M |
| 5.79 | — | — |
| 5.79 | — | Transcribed locus |
| 5.78 | ZBTB16 | zinc finger and BTB domain containing 16 |
| -5.77 | PRKCDBP | protein kinase C, delta binding protein |
| -5.77 | ZNF206 | zinc finger protein 206 |
| 5.77 | LHFP | Lipoma HMGIC fusion partner |
| -5.77 | SMPDL3B | sphingomyelin phosphodiesterase, acid-like 3B |
| -5.76 | GUCA1A | guanylate cyclase activator 1A (retina) |
| 5.76 | MTTP | microsomal triglyceride transfer protein |
| -5.76 | IFITM3 | interferon induced transmembrane protein 3 (1 |
| 5.76 | NR2F1 | nuclear receptor subfamily 2, group F, member |
| -5.75 | C1orf85 | chromosome 1 open reading frame 85 |
| 5.74 | SCRG1 | scrapie responsive protein 1 |
| -5.73 | NR5A2 | nuclear receptor subfamily 5, group A, member |
| -5.73 | APOE | apolipoprotein E |
| -5.73 | EFEMP1 | EGF-containing fibulin-like extracellular matrix |
| 5.73 | MMRN1 | multimerin 1 |
| 5.73 | — | Transcribed locus |
| 5.71 | — | — |
| -5.70 | KIAA1244 | KIAA1244 |
| -5.70 | COBL | cordon-bleu homolog (mouse) |
| -5.69 | TCEAL2 | transcription elongation factor A (SII)-like 2 |
| 5.69 | SORBS2 | sorbin and SH3 domain containing 2 |
| 5.68 | ZNF536 | zinc finger protein 536 |
| -5.68 | RAB3B | RAB3B, member RAS oncogene family |
| 5.68 | MAP6 | microtubule-associated protein 6 |

Appendix 1

| Value | Gene | Description |
|---|---|---|
| -5.63 | — | MRNA; cDNA DKFZp686L0310 (from clone DK |
| -5.63 | GSTT2 | glutathione S-transferase theta 2 |
| -5.62 | HPGD | hydroxyprostaglandin dehydrogenase 15-(NAD |
| 5.61 | ITGB8 | integrin, beta 8 |
| 5.61 | KCNJ6 | potassium inwardly-rectifying channel, subfami |
| -5.60 | — | — |
| -5.59 | SCNN1G | sodium channel, nonvoltage-gated 1, gamma |
| 5.59 | PLEKHG1 | pleckstrin homology domain containing, family |
| 5.58 | MEIS1 | Meis1, myeloid ecotropic viral integration site 1 |
| -5.58 | COBL | cordon-bleu homolog (mouse) |
| -5.58 | ATP2A3 | ATPase, Ca++ transporting, ubiquitous |
| -5.57 | — | — |
| 5.57 | COL3A1 | collagen, type III, alpha 1 (Ehlers-Danlos syndr |
| 5.56 | — | CDNA FLJ11723 fis, clone HEMBA1005314 |
| -5.56 | — | Similar to AI661453 protein |
| 5.56 | ABCB1 | ATP-binding cassette, sub-family B (MDR/TAP |
| -5.55 | TFAP2C | transcription factor AP-2 gamma (activating en |
| -5.55 | FZD5 | frizzled homolog 5 (Drosophila) |
| 5.55 | SEMA6A | sema domain, transmembrane domain (TM), a |
| -5.55 | — | — |
| 5.54 | MMRN1 | multimerin 1 |
| 5.54 | IFIT5 | interferon-induced protein with tetratricopeptide |
| 5.53 | ST18 | suppression of tumorigenicity 18 (breast carcin |
| 5.53 | SLITRK2 | SLIT and NTRK-like family, member 2 |
| 5.53 | — | — |
| 5.52 | — | — |
| 5.52 | CRYBA1 | crystallin, beta A1 |
| 5.52 | NR2F2 | nuclear receptor subfamily 2, group F, member |
| 5.51 | ST8SIA2 | ST8 alpha-N-acetyl-neuraminide alpha-2,8-sial |
| 5.51 | — | — |
| -5.51 | IRF6 | interferon regulatory factor 6 |
| -5.51 | GPR64 | G protein-coupled receptor 64 |
| -5.51 | IRF6 | interferon regulatory factor 6 |
| 5.50 | KIAA1546 | KIAA1546 |
| 5.50 | ELAVL3 | ELAV (embryonic lethal, abnormal vision, Dros |
| -5.50 | VSNL1 | visinin-like 1 |
| 5.49 | — | Transcribed locus |
| 5.49 | FAM125B | family with sequence similarity 125, member B |
| 5.48 | ZFHX1B | zinc finger homeobox 1b |
| -5.48 | — | — |
| 5.48 | KIF1A | Kinesin family member 1A |
| -5.48 | NRK | Nik related kinase |
| -5.47 | — | Transcribed locus |
| 5.47 | LRIG1 | leucine-rich repeats and immunoglobulin-like d |
| 5.47 | CSPG5 | chondroitin sulfate proteoglycan 5 (neuroglycan |
| -5.46 | ASS1 | argininosuccinate synthetase 1 |
| 5.45 | — | — |
| 5.45 | DACH1 | dachshund homolog 1 (Drosophila) |
| -5.44 | CCDC69 | coiled-coil domain containing 69 |
| -5.44 | — | — |
| 5.44 | LRRC17 | leucine rich repeat containing 17 |
| -5.43 | WFDC2 | WAP four-disulfide core domain 2 |
| 5.43 | NXPH2 | neurexophilin 2 |
| 5.42 | MBNL2 | muscleblind-like 2 (Drosophila) |
| -5.42 | FAM46B | family with sequence similarity 46, member B |
| -5.41 | — | — |
| 5.41 | KIAA0895 | KIAA0895 protein |
| -5.41 | MAGEA4 | melanoma antigen family A, 4 |
| -5.41 | IFI30 | interferon, gamma-inducible protein 30 |
| 5.40 | — | — |
| 5.39 | — | — |
| -5.39 | IGSF21 | immunoglobin superfamily, member 21 |
| -5.39 | KDR | kinase insert domain receptor (a type III recept |
| -5.39 | INHBE | inhibin, beta E |
| -5.38 | C1orf172 | chromosome 1 open reading frame 172 |
| 5.38 | — | — |
| 5.38 | CXorf1 | chromosome X open reading frame 1 |
| 5.38 | LOC145786 | hypothetical protein LOC145786 |
| -5.38 | — | — |
| -5.37 | — | — |
| 5.37 | — | CDNA FLJ37333 fis, clone BRAMY2020106 |
| 5.36 | CRB1 | crumbs homolog 1 (Drosophila) |
| 5.36 | — | Transcribed locus |
| 5.36 | SORBS2 | sorbin and SH3 domain containing 2 |
| -5.35 | EPAS1 | endothelial PAS domain protein 1 |
| -5.35 | IL28RA | interleukin 28 receptor, alpha (interferon, lambd |
| 5.35 | GPR177 | G protein-coupled receptor 177 |
| 5.34 | FABP7 | fatty acid binding protein 7, brain |
| 5.34 | LOC388419 | similar to Galectin-3 binding protein precursor ( |

| Value | Gene | Description |
|---|---|---|
| 5.68 | TEX10 | Testis expressed sequence 10 |
| -5.68 | — | — |
| -5.68 | MICB | MHC class I polypeptide-related sequence E |
| -5.67 | C20orf42 | chromosome 20 open reading frame 42 |
| 5.67 | — | CDNA FLJ11723 fis, clone HEMBA1005314 |
| 5.67 | PTPRN2 | protein tyrosine phosphatase, receptor type, N |
| -5.67 | PDGFA | platelet-derived growth factor alpha polypeptide |
| -5.67 | CXCL12 | chemokine (C-X-C motif) ligand 12 (stromal ce |
| -5.66 | BAMBI | BMP and activin membrane-bound inhibitor ho |
| 5.66 | CDKN2B | cyclin-dependent kinase inhibitor 2B (p15, inhi |
| 5.66 | SPARCL1 | SPARC-like 1 (mast9, hevin) |
| -5.65 | — | — |
| -5.65 | MYCT1 | myc target 1 |
| -5.65 | PTGIS | prostaglandin I2 (prostacyclin) synthase /// pros |
| -5.64 | HSPA2 | heat shock 70kDa protein 2 |
| 5.64 | — | Transcribed locus, moderately similar to XP_4 |
| -5.64 | HTR2C | 5-hydroxytryptamine (serotonin) receptor 2C |
| -5.63 | CYP2S1 | cytochrome P450, family 2, subfamily S, polype |
| 5.63 | MYBPC1 | myosin binding protein C, slow type |
| 5.63 | COL2A1 | collagen, type II, alpha 1 (primary osteoarthritis |
| -5.62 | ATP2A3 | ATPase, Ca++ transporting, ubiquitous |
| 5.61 | CST3 | Cystatin C (amyloid angiopathy and cerebral h |
| 5.61 | — | CDNA FLJ42405 fis, clone ASTRO3000474 |
| 5.61 | — | — |
| 5.60 | PRDM16 | PR domain containing 16 |
| -5.60 | MT1X | metallothionein 1X |
| -5.59 | HBA1 /// HBA2 | hemoglobin, alpha 1 /// hemoglobin, alpha 1 /// |
| -5.59 | CER1 | cerberus 1, cysteine knot superfamily, homolog |
| 5.59 | ABCC9 | ATP-binding cassette, sub-family C (CFTR/MR |
| -5.59 | GUCA1A | guanylate cyclase activator 1A (retina) |
| 5.59 | RNF165 | ring finger protein 165 |
| -5.59 | DPPA5 | developmental pluripotency associated 5 |
| -5.59 | — | — |
| 5.58 | CP | ceruloplasmin (ferroxidase) |
| -5.58 | — | Transcribed locus |
| -5.58 | VSNL1 | visinin-like 1 |
| -5.58 | FGF4 | fibroblast growth factor 4 (heparin secretory tra |
| -5.57 | LOC202451 | hypothetical protein LOC202451 |
| 5.57 | PLAGL1 | pleiomorphic adenoma gene-like 1 |
| 5.57 | IFIT5 | interferon-induced protein with tetratricopeptide |
| 5.57 | — | Transcribed locus |
| -5.56 | OLFM1 | olfactomedin 1 |
| -5.56 | CST1 | cystatin SN |
| 5.56 | PCDH17 | protocadherin 17 |
| -5.56 | LAMA2 | laminin, alpha 2 (merosin, congenital muscular |
| -5.56 | — | Transcribed locus |
| -5.56 | — | Transcribed locus, weakly similar to NP_00101 |
| -5.55 | OLFML3 | olfactomedin-like 3 |
| 5.55 | CHN2 | chimerin (chimaerin) 2 |
| -5.55 | — | — |
| -5.54 | TFPI | tissue factor pathway inhibitor (lipoprotein-assc |
| -5.54 | — | — |
| 5.54 | — | — |
| -5.54 | WDR72 | WD repeat domain 72 |
| -5.52 | — | Full length insert cDNA clone ZD51F08 |
| -5.52 | FBN3 | fibrillin 3 |
| -5.52 | FOXC1 | forkhead box C1 |
| -5.51 | HTATIP2 | HIV-1 Tat interactive protein 2, 30kDa |
| 5.51 | RGS4 | regulator of G-protein signalling 4 |
| 5.51 | FLJ10748 | Hypothetical protein FLJ10748 |
| 5.51 | PLAGL1 | Pleiomorphic adenoma gene-like 1 |
| -5.50 | IL4R | interleukin 4 receptor |
| 5.50 | LIX1 | Lix1 homolog (mouse) |
| -5.50 | HBA1 /// HBA2 | hemoglobin, alpha 1 /// hemoglobin, alpha 1 /// |
| -5.49 | KDR | kinase insert domain receptor (a type III recept |
| -5.49 | LRFN5 | leucine rich repeat and fibronectin type III doma |
| 5.49 | BAALC | brain and acute leukemia, cytoplasmic |
| -5.48 | — | — |
| -5.48 | LOC112703 | hypothetical protein BC004941 |
| 5.48 | HOXA2 | homeobox A2 |
| -5.47 | NFE2L3 | nuclear factor (erythroid-derived 2)-like 3 |
| -5.47 | FGFR4 | fibroblast growth factor receptor 4 |
| 5.46 | PDE1A | phosphodiesterase 1A, calmodulin-dependent |
| -5.46 | SH2D3A | SH2 domain containing 3A |
| -5.45 | QPCT | glutaminyl-peptide cyclotransferase (glutaminyl |
| -5.45 | FLJ25801 | hypothetical protein FLJ25801 |
| -5.44 | EBF2 | Early B-cell factor 2 |
| 5.44 | ARL4C | ADP-ribosylation factor-like 4C |
| 5.44 | A2M | alpha-2-macroglobulin |

Appendix 1

| | | | |
|---|---|---|---|
| -5.34 TBX5 | T-box 5 | -5.43 SLC7A8 | solute carrier family 7 (cationic amino acid tran |
| -5.34 KCNJ16 | potassium inwardly-rectifying channel, subfami | -5.43 PAK6 | p21(CDKN1A)-activated kinase 6 |
| -5.33 FGF4 | fibroblast growth factor 4 (heparin secretory tra | 5.43 GPM6A | glycoprotein M6A |
| -5.33 GUCA1A | guanylate cyclase activator 1A (retina) | 5.42 MEIS1 | Meis1, myeloid ecotropic viral integration site 1 |
| -5.33 SOX15 | SRY (sex determining region Y)-box 15 | -5.41 LOC440132 | LOC440132 |
| -5.32 — | — | 5.41 KIAA0895 | KIAA0895 protein |
| 5.32 ARL4C | ADP-ribosylation factor-like 4C | 5.40 GRIK2 | glutamate receptor, ionotropic, kainate 2 |
| -5.31 MAP4K1 | mitogen-activated protein kinase kinase kinase | -5.40 GDF3 | growth differentiation factor 3 |
| 5.30 — | — | -5.39 HCG11 | HLA complex group 11 |
| -5.30 APOC1 | apolipoprotein C-I | -5.39 BCL11B | B-cell CLL/lymphoma 11B (zinc finger protein) |
| -5.29 CRIP1 /// GALK2 | cysteine-rich protein 1 (intestinal) /// galactokin | -5.39 EDIL3 | EGF-like repeats and discoidin I-like domains 3 |
| 5.29 LRRC4B | leucine rich repeat containing 4B | 5.38 C20orf91 /// LOC40 | chromosome 20 open reading frame 91 /// simi |
| 5.29 — | — | -5.38 ITM2A | integral membrane protein 2A |
| -5.28 ITPR3 | inositol 1,4,5-triphosphate receptor, type 3 | -5.37 HPGD | hydroxyprostaglandin dehydrogenase 15-(NAD |
| 5.28 TMEM47 | transmembrane protein 47 | -5.37 PCDH10 | Protocadherin 10 |
| -5.27 YBX2 | Y box binding protein 2 | 5.37 SCN3B | sodium channel, voltage-gated, type III, beta |
| -5.27 — | — | -5.37 TNMD | tenomodulin |
| 5.27 PSMAL | growth-inhibiting protein 26 | 5.37 — | CDNA FLJ33585 fis, clone BRAMY2012163 |
| 5.27 FAM49A | family with sequence similarity 49, member A | -5.36 — | — |
| -5.27 LECT1 | leukocyte cell derived chemotaxin 1 | -5.36 SCNN1B | sodium channel, nonvoltage-gated 1, beta (Lid |
| -5.27 IL4R | interleukin 4 receptor | -5.36 — | — |
| 5.27 DPYSL5 | dihydropyrimidinase-like 5 | -5.36 IFITM2 | interferon induced transmembrane protein 2 (1 |
| -5.26 CTSL2 | cathepsin L2 | 5.36 ARL4C | ADP-ribosylation factor-like 4C |
| -5.26 OLFML3 | olfactomedin-like 3 | -5.36 PRDM14 | PR domain containing 14 |
| 5.26 SOX5 | SRY (sex determining region Y)-box 5 | 5.36 KIAA1546 | KIAA1546 |
| -5.26 CCL4 | chemokine (C-C motif) ligand 4 | 5.36 FABP7 | fatty acid binding protein 7, brain |
| -5.25 NFE2 | nuclear factor (erythroid-derived 2), 45kDa | -5.35 — | — |
| 5.25 ARNT2 | aryl-hydrocarbon receptor nuclear translocator | -5.35 LOC286044 | hypothetical protein LOC286044 |
| 5.25 — | — | -5.35 ITPR3 | inositol 1,4,5-triphosphate receptor, type 3 |
| -5.25 VAMP8 | vesicle-associated membrane protein 8 (endob | -5.35 — | — |
| -5.25 SEMA6A | sema domain, transmembrane domain (TM), a | 5.35 MSX1 | msh homeobox 1 |
| -5.25 HAS2 | hyaluronan synthase 2 | 5.34 — | — |
| -5.25 — | — | -5.34 EPB41L5 | Erythrocyte membrane protein band 4.1 like 5 |
| 5.24 DIRAS2 | DIRAS family, GTP-binding RAS-like 2 | -5.34 C1QTNF3 | C1q and tumor necrosis factor related protein 3 |
| -5.24 — | — | -5.34 CYP4X1 | cytochrome P450, family 4, subfamily X, polype |
| 5.24 — | Tetraspanin 11 | 5.34 SOX5 | SRY (sex determining region Y)-box 5 |
| -5.24 F11R | F11 receptor | -5.34 FOXA2 | forkhead box A2 |
| 5.23 NR2F2 | nuclear receptor subfamily 2, group F, member | -5.33 MAP4K1 | mitogen-activated protein kinase kinase kinase |
| -5.23 NUDT16P | nudix (nucleoside diphosphate linked moiety X) | -5.33 PRSS16 | protease, serine, 16 (thymus) |
| 5.23 PRSS23 | Protease, serine, 23 | -5.33 TANC | TPR domain, ankyrin-repeat and coiled-coil-co |
| 5.22 — | CDNA FLJ37216 fis, clone BRALZ2008696 | 5.32 CAMK1G | calcium/calmodulin-dependent protein kinase I |
| 5.21 DCN | decorin | -5.32 — | — |
| -5.21 EPS8L2 | EPS8-like 2 | -5.32 LAMA2 | laminin, alpha 2 (merosin, congenital muscular |
| 5.21 — | Transcribed locus, moderately similar to XP_4 | -5.32 FLJ12684 | hypothetical protein FLJ12684 |
| 5.21 SOX2OT | SOX2 overlapping transcript (non-coding RNA) | 5.32 DKFZP686A01247 | hypothetical protein |
| -5.21 CPZ | carboxypeptidase Z /// carboxypeptidase Z | 5.32 FRZB | frizzled-related protein |
| 5.21 NCAM1 | neural cell adhesion molecule 1 | 5.31 — | — |
| -5.20 NRK | Nik related kinase | -5.31 — | — |
| 5.20 — | — | -5.31 FLJ36748 | hypothetical protein FLJ36748 |
| 5.20 HOXA7 | homeobox A7 | -5.31 PLAU | plasminogen activator, urokinase /// plasminog |
| 5.20 NCAM1 | neural cell adhesion molecule 1 | -5.30 C6orf148 | chromosome 6 open reading frame 148 |
| 5.20 TEX10 | Testis expressed sequence 10 | 5.30 — | — |
| 5.20 ASCL1 | achaete-scute complex homolog 1 (Drosophila | -5.30 FZD5 | frizzled homolog 5 (Drosophila) |
| -5.20 — | — | 5.30 — | — |
| -5.19 — | — | 5.29 — | — |
| -5.19 APOE | apolipoprotein E | -5.28 — | — |
| -5.19 PDZD2 | PDZ domain containing 2 | -5.28 ALDH1A3 | aldehyde dehydrogenase 1 family, member A3 |
| 5.18 RNF165 | ring finger protein 165 | 5.27 PDE1A | phosphodiesterase 1A, calmodulin-dependent |
| -5.17 — | Transcribed locus, weakly similar to NP_00101 | 5.27 — | — |
| 5.17 — | CDNA FLJ42405 fis, clone ASTRO3000474 | -5.27 RAB3B | RAB3B, member RAS oncogene family |
| 5.17 CGI-38 | brain specific protein /// brain specific protein | -5.26 IGSF21 | immunoglobin superfamily, member 21 |
| -5.16 MT1H | metallothionein 1H | 5.25 — | CDNA FLJ37216 fis, clone BRALZ2008696 |
| 5.16 — | Transcribed locus | -5.25 GDA | guanine deaminase |
| -5.16 HAPLN1 | hyaluronan and proteoglycan link protein 1 | -5.25 ETS1 | v-ets erythroblastosis virus E26 oncogene hom |
| 5.16 GAS1 | growth arrest-specific 1 | -5.25 FLJ14712 | hypothetical protein FLJ14712 |
| 5.16 ABAT | 4-aminobutyrate aminotransferase | 5.25 CDKN2A | cyclin-dependent kinase inhibitor 2A (melanom |
| -5.16 LOC728377 | similar to rho guanine nucleotide exchange fac | -5.25 CECR1 | cat eye syndrome chromosome region, candid |
| 5.15 KLHDC8A | kelch domain containing 8A | 5.25 — | — |
| -5.14 ESPN | espin | 5.25 LOC284244 | hypothetical protein LOC284244 |
| -5.14 — | — | -5.24 MARVELD2 | MARVEL domain containing 2 |
| -5.14 PDGFA | platelet-derived growth factor alpha polypeptide | -5.23 KLF4 | Kruppel-like factor 4 (gut) |
| 5.14 — | CDNA: FLJ23131 fis, clone LNG08502 | -5.23 HAS2 | hyaluronan synthase 2 |
| 5.14 CLRN1 | clarin 1 | -5.23 LAMA2 | laminin, alpha 2 (merosin, congenital muscular |
| -5.14 WDR72 | WD repeat domain 72 | -5.23 ARHGAP8 /// LOC5 | Rho GTPase activating protein 8 /// PRR5-ARH |
| -5.13 TFAP2C | transcription factor AP-2 gamma (activating en | -5.22 CTSL2 | cathepsin L2 |
| -5.13 EFEMP1 | EGF-containing fibulin-like extracellular matrix | -5.22 LOC389129 | similar to CG9996-PA |
| 5.12 NAV2 | neuron navigator 2 | 5.22 SPAG6 | sperm associated antigen 6 |
| -5.12 COL1A2 | Collagen, type I, alpha 2 | -5.22 ZNF630 | zinc finger protein 630 |
| -5.12 CLIC6 | chloride intracellular channel 6 | 5.22 ABAT | 4-aminobutyrate aminotransferase |

Appendix 1

| | | | | |
|---|---|---|---|---|
| -5.12 | CALB1 | calbindin 1, 28kDa | -5.21 FGF4 | fibroblast growth factor 4 (heparin secretory tra |
| -5.11 | TFPI | tissue factor pathway inhibitor (lipoprotein-asso | 5.21 PAX6 | paired box gene 6 (aniridia, keratitis) |
| 5.11 | FOLH1 | folate hydrolase (prostate-specific membrane a | -5.21 MPP1 | membrane protein, palmitoylated 1, 55kDa |
| -5.11 | MATK | megakaryocyte-associated tyrosine kinase | -5.20 TAGLN | transgelin |
| 5.11 | FLJ32447 | hypothetical protein LOC151278 | -5.20 HIST1H2BD | Histone cluster 1, H2bd |
| 5.11 | GPR56 | G protein-coupled receptor 56 | 5.20 KCNJ16 | potassium inwardly-rectifying channel, subfami |
| 5.11 | PLAGL1 | pleiomorphic adenoma gene-like 1 | -5.20 YBX2 | Y box binding protein 2 |
| -5.10 | ST14 | suppression of tumorigenicity 14 (colon carcino | -5.19 HPGD | hydroxyprostaglandin dehydrogenase 15-(NAD |
| 5.10 | — | Transcribed locus | 5.19 KIAA1713 | KIAA1713 |
| -5.10 | IL15 | interleukin 15 | -5.19 — | — |
| -5.10 | MT1M | metallothionein 1M | 5.19 ZFHX1B | zinc finger homeobox 1b |
| -5.09 | DUSP23 | dual specificity phosphatase 23 | -5.19 — | — |
| 5.09 | PCSK2 | proprotein convertase subtilisin/kexin type 2 | -5.19 HIST1H2BD | Histone cluster 1, H2bd |
| -5.08 | CLDN3 | claudin 3 | 5.19 NDST4 | N-deacetylase/N-sulfotransferase (heparan glu |
| 5.08 | GPR85 | G protein-coupled receptor 85 | -5.18 — | . |
| 5.08 | COL2A1 | collagen, type II, alpha 1 (primary osteoarthritis | -5.17 FLJ22662 | hypothetical protein FLJ22662 |
| 5.07 | LOC143381 | hypothetical protein LOC143381 | -5.17 SIX3 | sine oculis homeobox homolog 3 (Drosophila) |
| -5.06 | GDF3 | growth differentiation factor 3 | 5.17 ST8SIA2 | ST8 alpha-N-acetyl-neuraminide alpha-2,8-sial |
| -5.06 | ARTN | artemin | 5.17 PLEKHG1 | pleckstrin homology domain containing, family |
| -5.05 | TBX3 | T-box 3 (ulnar mammary syndrome) | -5.16 DEPDC6 | DEP domain containing 6 |
| -5.05 | DHRS2 | dehydrogenase/reductase (SDR family) memb | 5.16 FAM125B | family with sequence similarity 125, member B |
| 5.04 | — | — | 5.16 ITGB8 | integrin, beta 8 |
| 5.04 | RP5-875H10.1 | SAM domain containing 1 | -5.16 BNC2 | basonuclin 2 |
| 5.04 | — | — | 5.15 FOLH1 | folate hydrolase (prostate-specific membrane a |
| 5.04 | FABP7 | fatty acid binding protein 7, brain | -5.15 EFCBP1 | EF-hand calcium binding protein 1 |
| -5.03 | LRFN5 | leucine rich repeat and fibronectin type III dom | -5.14 HAPLN1 | hyaluronan and proteoglycan link protein 1 |
| 5.03 | FLJ10748 | Hypothetical protein FLJ10748 | 5.14 PDE1A | phosphodiesterase 1A, calmodulin-dependent |
| -5.03 | MPP1 | membrane protein, palmitoylated 1, 55kDa | 5.14 — | |
| -5.03 | LRRC2 | leucine rich repeat containing 2 | -5.13 LOC643194 | Hypothetical LOC643194 |
| 5.02 | — | — | 5.13 TMEM47 | transmembrane protein 47 |
| 5.02 | — . | — | -5.13 RHOD | ras homolog gene family, member D |
| -5.02 | FGF4 | fibroblast growth factor 4 (heparin secretory tra | 5.13 IRX5 | iroquois homeobox protein 5 |
| -5.01 | TSLP | thymic stromal lymphopoietin | 5.13 — | |
| -5.01 | BCL11B | B-cell CLL/lymphoma 11B (zinc finger protein) | -5.12 RBP7 | retinol binding protein 7, cellular |
| -5.01 | HTR3A | 5-hydroxytryptamine (serotonin) receptor 3A | -5.11 ATP8B3 | ATPase, Class I, type 8B, member 3 |
| 5.01 | NDP | Norrie disease (pseudoglioma) | -5.11 MT1X | metallothionein 1X |
| 5.01 | MTTP | microsomal triglyceride transfer protein | -5.11 TEX14 | testis expressed sequence 14 /// testis express |
| -5.01 | — | — | -5.11 SFN | stratifin |
| -5.00 | EDIL3 | EGF-like repeats and discoidin I-like domains 3 | -5.11 — | — |
| 5.00 | PTPRO | protein tyrosine phosphatase, receptor type, O | -5.10 LOC388494 | hypothetical gene supported by AL365406; BC |
| -5.00 | TCIRG1 | T-cell, immune regulator 1, ATPase, H+ transp | 5.10 LOC387856 | similar to expressed sequence AI836003 |
| -5.00 | LOC136306 | hypothetical protein LOC136306 | -5.09 MT1F | metallothionein 1F (functional) |
| -5.00 | F11R | F11 receptor | -5.09 IL23A | interleukin 23, alpha subunit p19 |
| 4.99 | C8orf4 | chromosome 8 open reading frame 4 | -5.09 CLDN10 | claudin 10 |
| 4.99 | CDH20 | cadherin 20, type 2 | 5.09 LOC401648 | Similar to heat shock 70kD protein binding prot |
| 4.99 | KIAA1713 | KIAA1713 | 5.09 FABP7 | fatty acid binding protein 7, brain |
| 4.99 | C3orf15 | chromosome 3 open reading frame 15 | 5.08 GPM6A | glycoprotein M6A |
| -4.98 | CKMT1B /// CKMT1 | creatine kinase, mitochondrial 1B /// creatine ki | -5.08 ERBB3 | v-erb-b2 erythroblastic leukemia viral oncogene |
| 4.98 | HOXD13 | homeobox D13 | -5.07 KLK10 | kallikrein-related peptidase 10 |
| 4.97 | SCRG1 | scrapie responsive protein 1 | 5.07 TFAP2B | transcription factor AP-2 beta (activating enhan |
| -4.97 | EPPK1 | epiplakin 1 | 5.07 — | Transcribed locus |
| 4.97 | PALM2 | paralemmin 2 | -5.06 AIM1 | absent in melanoma 1 |
| -4.96 | TMPRSS11E /// LO | transmembrane protease, serine 11E /// similar | -5.06 LOC202451 | hypothetical protein LOC202451 |
| 4.96 | GPM6A | glycoprotein M6A | 5.06 — | — |
| -4.96 | MAFB | v-maf musculoaponeurotic fibrosarcoma oncog | -5.06 — | — |
| 4.95 | NDST4 | N-deacetylase/N-sulfotransferase (heparan glu | -5.06 C9orf61 | chromosome 9 open reading frame 61 |
| -4.95 | MT1F | metallothionein 1F (functional) | -5.05 HAS2 | Hyaluronan synthase 2 |
| -4.95 | AURKC | aurora kinase C | 5.05 — | — |
| 4.95 | — | — | 5.05 NCAM1 | neural cell adhesion molecule 1 |
| 4.95 | NLRP1 | NLR family, pyrin domain containing 1 | -5.05 LOC729659 /// LOC | similar to Putative S100 calcium-binding protei |
| 4.94 | — | CDNA FLJ35396 fis, clone SKNSH2003483 | 5.04 KCNJ6 | potassium inwardly-rectifying channel, subfami |
| 4.94 | ABAT | 4-aminobutyrate aminotransferase | -5.04 GPR160 | G protein-coupled receptor 160 |
| -4.94 | — | — | -5.03 — | MRNA full length insert cDNA clone EUROIMA |
| 4.94 | HOXA11 | homeobox A11 | -5.03 NPW | neuropeptide W |
| -4.93 | ATP8B3 | ATPase, Class I, type 8B, member 3 | -5.03 COBL | cordon-bleu homolog (mouse) |
| -4.93 | TMC5 | Transmembrane channel-like 5 | 5.02 HOXA7 | homeobox A7 |
| 4.93 | — | — | 5.02 PSMAL | growth-inhibiting protein 26 |
| -4.93 | RET | Ret proto-oncogene (multiple endocrine neopla | -5.01 NFIA | nuclear factor I/A |
| 4.93 | TAGLN3 | transgelin 3 | -5.01 C10orf96 | chromosome 10 open reading frame 96 |
| -4.93 | — | — | 5.01 GUCY1A3 | guanylate cyclase 1, soluble, alpha 3 |
| 4.93 | LGI2 | leucine-rich repeat LGI family, member 2 | -5.00 PERP | PERP, TP53 apoptosis effector |
| -4.92 | C1orf210 | chromosome 1 open reading frame 210 | 5.00 COL14A1 | collagen, type XIV, alpha 1 (undulin) |
| 4.92 | WDR52 | WD repeat domain 52 | -5.00 AXL | AXL receptor tyrosine kinase |
| 4.92 | — | CDNA clone IMAGE:5273964 | -5.00 FXYD5 | FXYD domain containing ion transport regulato |
| -4.92 | D21S2088E | D21S2088E | -4.99 — | — |
| 4.92 | — | — | -4.99 DENND1C | DENN/MADD domain containing 1C |
| 4.92 | CST3 | Cystatin C (amyloid angiopathy and cerebral h | -4.99 — | — |
| 4.92 | — | Clone 23786 mRNA sequence | -4.99 CPZ | carboxypeptidase Z /// carboxypeptidase Z |
| 4.91 | SLC18A1 | solute carrier family 18 (vesicular monoamine) | 4.99 C4orf18 | chromosome 4 open reading frame 18 |

Appendix 1

| Value | Gene | Description |
|---|---|---|
| -4.91 | HAS2 | Hyaluronan synthase 2 |
| 4.91 | PLAGL1 | Pleiomorphic adenoma gene-like 1 |
| 4.91 | CDKN2A | cyclin-dependent kinase inhibitor 2A (melanom |
| -4.91 | KLK10 | kallikrein-related peptidase 10 |
| -4.90 | MYCT1 | myc target 1 |
| 4.90 | — | — |
| -4.89 | CALB1 | calbindin 1, 28kDa |
| 4.89 | PCDH17 | protocadherin 17 |
| -4.89 | FLJ22662 | hypothetical protein FLJ22662 |
| -4.89 | — | — |
| -4.89 | KLF4 | Kruppel-like factor 4 (gut) |
| -4.89 | ST14 | suppression of tumorigenicity 14 (colon carcino |
| 4.88 | ARL4C | ADP-ribosylation factor-like 4C |
| 4.88 | DNAH9 | dynein, axonemal, heavy chain 9 |
| 4.88 | — | — |
| -4.87 | FZD5 | frizzled homolog 5 (Drosophila) /// frizzled hom |
| -4.87 | MET | met proto-oncogene (hepatocyte growth factor |
| -4.86 | ETS1 | v-ets erythroblastosis virus E26 oncogene hom |
| -4.85 | GATA5 | GATA binding protein 5 |
| 4.85 | NKX6-1 | NK6 transcription factor related, locus 1 (Droso |
| 4.85 | CDH7 | cadherin 7, type 2 |
| 4.85 | RHOBTB2 | Rho-related BTB domain containing 2 |
| 4.85 | LRRC4 | leucine rich repeat containing 4 |
| 4.84 | CSPG5 | chondroitin sulfate proteoglycan 5 (neuroglycan |
| 4.84 | TTBK2 | Tau tubulin kinase 2 |
| -4.84 | MT1M | metallothionein 1M |
| 4.84 | — | — |
| -4.83 | EPB41L5 | erythrocyte membrane protein band 4.1 like 5 |
| -4.83 | STC2 | stanniocalcin 2 |
| -4.83 | SCNN1B | sodium channel, nonvoltage-gated 1, beta (Lid |
| -4.82 | BAMBI | BMP and activin membrane-bound inhibitor ho |
| -4.82 | TG | Thyroglobulin |
| 4.82 | — | — |
| -4.81 | — | MRNA; cDNA DKFZp564N1116 (from clone D |
| -4.81 | SEMA6A | sema domain, transmembrane domain (TM), a |
| 4.80 | NEUROG2 | neurogenin 2 |
| -4.80 | — | — |
| -4.80 | — | CDNA FLJ30478 fis, clone BRAWH1000167 |
| -4.80 | TRIM38 | tripartite motif-containing 38 |
| -4.78 | LOC285401 | hypothetical protein LOC285401 |
| -4.78 | CYBA | cytochrome b-245, alpha polypeptide |
| -4.78 | ZNF560 | zinc finger protein 560 |
| -4.78 | — | Transcribed locus |
| -4.78 | — | C33.6 unnamed HERV-H protein |
| -4.77 | GRHL2 | grainyhead-like 2 (Drosophila) |
| -4.77 | — | — |
| -4.77 | — | MRNA; cDNA DKFZp667L064 (from clone DK |
| -4.77 | LOC112703 | hypothetical protein BC004941 |
| -4.77 | MAL2 | mal, T-cell differentiation protein 2 |
| 4.76 | — | — |
| -4.76 | UTS2 | urotensin 2 |
| -4.76 | GLS2 | glutaminase 2 (liver, mitochondrial) |
| -4.76 | CCL5 | chemokine (C-C motif) ligand 5 |
| -4.76 | C20orf42 | chromosome 20 open reading frame 42 |
| -4.75 | — | — |
| -4.75 | SOX17 | SRY (sex determining region Y)-box 17 |
| 4.75 | EMP1 | epithelial membrane protein 1 |
| -4.75 | LRRK1 | Leucine-rich repeat kinase 1 |
| 4.75 | C21orf34 | chromosome 21 open reading frame 34 |
| -4.74 | PTCHD1 | patched domain containing 1 |
| -4.73 | ZNF429 | Zinc finger protein 429 |
| 4.73 | GPM6A | glycoprotein M6A |
| 4.73 | GUCY1A3 | guanylate cyclase 1, soluble, alpha 3 |
| 4.72 | — | — |
| 4.72 | THSD7A | Thrombospondin, type I, domain containing 7A |
| -4.72 | — | — |
| 4.72 | SRGAP3 | SLIT-ROBO Rho GTPase activating protein 3 |
| -4.71 | — | — |
| -4.71 | GRB7 | growth factor receptor-bound protein 7 |
| -4.70 | ITM2A | integral membrane protein 2A |
| -4.70 | CD55 | CD55 molecule, decay accelerating factor for c |
| 4.70 | KCNK10 | potassium channel, subfamily K, member 10 |
| 4.70 | TPM2 | tropomyosin 2 (beta) |
| 4.69 | HOXD4 | homeobox D4 |
| -4.68 | MAP4K1 | mitogen-activated protein kinase kinase kinase |
| -4.68 | SLCO3A1 | solute carrier organic anion transporter family, |
| -4.68 | CYP2B7P1 | cytochrome P450, family 2, subfamily B, polyp |
| 4.68 | — | — |
| -4.67 | — | Transcribed locus, moderately similar to XP_00 |
| -4.99 | MYC | v-myc myelocytomatosis viral oncogene homol |
| 4.99 | — | — |
| -4.99 | — | — |
| -4.97 | TFAP2C | transcription factor AP-2 gamma (activating en |
| -4.97 | MT1G | metallothionein 1G |
| -4.97 | BAIAP2L1 | BAI1-associated protein 2-like 1 |
| 4.97 | DNAH9 | dynein, axonemal, heavy chain 9 |
| 4.97 | ARNT2 | aryl-hydrocarbon receptor nuclear translocator |
| 4.97 | ELAVL3 | ELAV (embryonic lethal, abnormal vision, Dros |
| -4.95 | SOX15 | SRY (sex determining region Y)-box 15 |
| -4.95 | MAL2 | mal, T-cell differentiation protein 2 |
| -4.95 | HSPA1A /// HSPA1 | heat shock 70kDa protein 1A /// heat shock 70 |
| -4.95 | SPIB | Spi-B transcription factor (Spi-1/PU.1 related) / |
| 4.95 | — | — |
| 4.95 | COL2A1 | collagen, type II, alpha 1 (primary osteoarthritis |
| 4.94 | SCN3B | sodium channel, voltage-gated, type III, beta |
| -4.94 | HLA-C | major histocompatibility complex, class I, C |
| 4.94 | CGI-38 | brain specific protein /// brain specific protein |
| 4.93 | COL14A1 | collagen, type XIV, alpha 1 (undulin) |
| -4.92 | OSBPL10 | oxysterol binding protein-like 10 |
| -4.92 | — | MRNA; cDNA DKFZp667L064 (from clone DKF |
| -4.92 | APOC1 | apolipoprotein C-I |
| 4.92 | PRSS23 | protease, serine, 23 |
| -4.92 | WFDC2 | WAP four-disulfide core domain 2 |
| -4.91 | IL8 | interleukin 8 |
| 4.91 | — | — |
| 4.91 | ASCL1 | achaete-scute complex homolog 1 (Drosophila |
| 4.91 | — | Transcribed locus |
| 4.91 | NLRP1 | NLR family, pyrin domain containing 1 |
| -4.90 | ABCG2 | ATP-binding cassette, sub-family G (WHITE), |
| -4.90 | HPGD | hydroxyprostaglandin dehydrogenase 15-(NAD |
| 4.90 | — | — |
| 4.89 | NR2F2 | nuclear receptor subfamily 2, group F, member |
| -4.88 | TOMM40 | Translocase of outer mitochondrial membrane |
| 4.88 | PCSK2 | proprotein convertase subtilisin/kexin type 2 |
| -4.88 | NFE2 | nuclear factor (erythroid-derived 2), 45kDa |
| -4.88 | ITM2A | integral membrane protein 2A |
| -4.87 | GSTT2 | glutathione S-transferase theta 2 |
| -4.87 | CKMT1B /// CKMT1 | creatine kinase, mitochondrial 1B /// creatine ki |
| -4.86 | FAM20C | family with sequence similarity 20, member C |
| 4.86 | KCND2 | potassium voltage-gated channel, Shal-related |
| -4.86 | FIBCD1 | fibrinogen C domain containing 1 |
| 4.86 | SOX2OT | SOX2 overlapping transcript (non-coding RNA) |
| -4.85 | HTATIP2 | HIV-1 Tat interactive protein 2, 30kDa |
| -4.84 | — | — |
| -4.84 | LOC729890 /// LOC | hypothetical protein LOC729890 /// hypothetica |
| 4.84 | DNAH9 | dynein, axonemal, heavy chain 9 |
| -4.83 | RRAS | related RAS viral (r-ras) oncogene homolog |
| 4.83 | CTNND2 | catenin (cadherin-associated protein), delta 2 ( |
| 4.83 | ABAT | 4-aminobutyrate aminotransferase |
| 4.83 | ZNF287 | zinc finger protein 287 |
| -4.83 | FLT1 | fms-related tyrosine kinase 1 (vascular endothe |
| -4.83 | — | — |
| 4.83 | C11orf70 | chromosome 11 open reading frame 70 /// chro |
| -4.83 | BCL11B | B-cell CLL/lymphoma 11B (zinc finger protein) |
| 4.82 | CSPG5 | chondroitin sulfate proteoglycan 5 (neuroglycan |
| -4.82 | CGNL1 | cingulin-like 1 |
| -4.82 | MARVELD3 | MARVEL domain containing 3 |
| -4.82 | DSCR1L2 | Down syndrome critical region gene 1-like 2 |
| 4.82 | HOXB9 | homeobox B9 |
| -4.81 | DSP | Desmoplakin |
| -4.81 | ESPN | espin |
| -4.81 | TCIRG1 | T-cell, immune regulator 1, ATPase, H+ transp |
| 4.81 | TFAP2A | transcription factor AP-2 alpha (activating enha |
| -4.81 | HTR3A | 5-hydroxytryptamine (serotonin) receptor 3A |
| 4.81 | NR2F2 | nuclear receptor subfamily 2, group F, member |
| -4.81 | LOC728377 | similar to rho guanine nucleotide exchange fac |
| -4.80 | C1orf211 | chromosome 1 open reading frame 211 |
| -4.80 | SLC27A6 | solute carrier family 27 (fatty acid transporter), |
| -4.80 | HSPA1A | heat shock 70kDa protein 1A |
| -4.80 | SLC16A5 | solute carrier family 16, member 5 (monocarbo |
| -4.80 | ANXA3 | annexin A3 |
| 4.80 | — | Transcribed locus |
| 4.79 | — | — |
| -4.79 | CXCL5 | chemokine (C-X-C motif) ligand 5 |
| -4.79 | — | — |
| -4.79 | CAPG | capping protein (actin filament), gelsolin-like |
| -4.79 | — | — |
| 4.79 | — | — |

Appendix 1

| Value | Gene | Description |
|---|---|---|
| -4.67 | TCEAL2 | transcription elongation factor A (SII)-like 2 |
| -4.67 | CDKN2B | cyclin-dependent kinase inhibitor 2B (p15, inhib |
| -4.66 | — | — |
| -4.66 | LOC136288 | hypothetical protein LOC136288 |
| -4.65 | — | — |
| -4.65 | DDC | dopa decarboxylase (aromatic L-amino acid de |
| -4.65 | — | — |
| -4.65 | — | — |
| -4.65 | — | — |
| -4.64 | HBA1 /// HBA2 | hemoglobin, alpha 1 /// hemoglobin, alpha 1 /// |
| -4.64 | KCNG3 | potassium voltage-gated channel, subfamily G, |
| -4.64 | — | — |
| -4.64 | TTYH1 | tweety homolog 1 (Drosophila) |
| -4.64 | MSX1 | msh homeobox 1 |
| -4.64 | PRSS16 | protease, serine, 16 (thymus) |
| -4.64 | OR2A20P /// OR2A | olfactory receptor, family 2, subfamily A, memb |
| -4.64 | — | Transcribed locus |
| -4.64 | LEF1 | lymphoid enhancer-binding factor 1 |
| -4.63 | SOX3 | SRY (sex determining region Y)-box 3 |
| -4.63 | NRCAM | neuronal cell adhesion molecule |
| -4.63 | SOX21 | SRY (sex determining region Y)-box 21 |
| -4.63 | KIAA0319 | KIAA0319 |
| -4.62 | MSRB3 | methionine sulfoxide reductase B3 |
| -4.62 | CCL5 | chemokine (C-C motif) ligand 5 /// chemokine ( |
| -4.62 | FLJ14213 | hypothetical protein FLJ14213 |
| -4.61 | — | Transcribed locus |
| -4.61 | — | Transcribed locus |
| -4.60 | GPR37 | G protein-coupled receptor 37 (endothelin rece |
| -4.60 | — | — |
| -4.60 | GPR37 | G protein-coupled receptor 37 (endothelin rece |
| -4.60 | TFAP2B | transcription factor AP-2 beta (activating enhan |
| -4.60 | NRCAM | neuronal cell adhesion molecule |
| -4.60 | LY75 | lymphocyte antigen 75 |
| -4.59 | — | — |
| -4.59 | FGF14 | fibroblast growth factor 14 |
| -4.59 | SERPINB9 | serpin peptidase inhibitor, clade B (ovalbumin), |
| -4.59 | BCHE | butyrylcholinesterase |
| -4.59 | CYP4X1 | cytochrome P450, family 4, subfamily X, polype |
| -4.58 | FLI1 | Friend leukemia virus integration 1 |
| -4.58 | LOC286044 | hypothetical protein LOC286044 |
| -4.58 | ADCY2 | adenylate cyclase 2 (brain) |
| -4.58 | FLJ12057 | Hypothetical protein FLJ12057 |
| -4.58 | MYOZ3 | myozenin 3 |
| -4.57 | ERBB3 | v-erb-b2 erythroblastic leukemia viral oncogene |
| -4.57 | WDR78 | WD repeat domain 78 |
| -4.57 | HBA1 /// HBA2 | hemoglobin, alpha 1 /// hemoglobin, alpha 1 /// |
| -4.57 | LOC729659 /// LOC | similar to Putative S100 calcium-binding protein |
| -4.57 | CHST8 | carbohydrate (N-acetylgalactosamine 4-0) sulfo |
| -4.57 | LOC645323 | Hypothetical LOC645323 |
| -4.57 | MEIS2 | Meis1, myeloid ecotropic viral integration site 1 |
| -4.56 | HOXD3 | homeobox D3 |
| -4.56 | — | — |
| -4.56 | CCL3 /// CCL3L1 | chemokine (C-C motif) ligand 3 /// chemokine ( |
| -4.56 | HOXA11 | homeobox A11 |
| -4.55 | TRA@ /// TRD@ /// | T cell receptor alpha locus /// T cell receptor de |
| -4.55 | GLRB | glycine receptor, beta |
| -4.55 | TMEM171 | transmembrane protein 171 |
| -4.54 | DNAH9 | dynein, axonemal, heavy chain 9 |
| -4.54 | IL21R | interleukin 21 receptor |
| -4.53 | EDG7 | endothelial differentiation, lysophosphatidic aci |
| -4.53 | HBA1 /// HBA2 | hemoglobin, alpha 1 /// hemoglobin, alpha 1 /// |
| -4.53 | — | — |
| -4.52 | CORO2A | coronin, actin binding protein, 2A |
| -4.52 | MCOLN3 | mucolipin 3 |
| -4.52 | — | — |
| -4.52 | LOC255480 | hypothetical protein LOC255480 |
| -4.51 | LRRC55 | Leucine rich repeat containing 55 |
| -4.51 | — | — |
| -4.51 | LOC439949 | hypothetical gene supported by AY007155 |
| -4.50 | PRRX1 | paired related homeobox 1 |
| -4.50 | TRDN | triadin |
| -4.50 | MOXD1 | monooxygenase, DBH-like 1 |
| -4.50 | MT1F | metallothionein 1F (functional) |
| -4.49 | C10orf41 | chromosome 10 open reading frame 41 |
| -4.49 | COL1A2 | collagen, type I, alpha 2 |
| -4.49 | NFE2L3 | nuclear factor (erythroid-derived 2)-like 3 |
| -4.49 | LOC440160 | hypothetical gene supported by AK022914; AK |
| -4.49 | DENND1C | DENN/MADD domain containing 1C |
| -4.49 | — | — |
| -4.78 | ASCL1 | achaete-scute complex homolog 1 (Drosophila) |
| -4.78 | PDE4B | phosphodiesterase 4B, cAMP-specific (phosph |
| -4.78 | C1orf210 | chromosome 1 open reading frame 210 |
| -4.78 | — | — |
| -4.78 | — | — |
| -4.78 | — | — |
| -4.77 | CRB2 | crumbs homolog 2 (Drosophila) |
| -4.77 | BAIAP2L1 | BAI1-associated protein 2-like 1 |
| -4.77 | OVOL2 | ovo-like 2 (Drosophila) /// ovo-like 2 (Drosophila |
| -4.77 | HOXA10 | homeobox A10 |
| -4.77 | ARMCX1 | armadillo repeat containing, X-linked 1 |
| -4.77 | EGR1 | early growth response 1 |
| -4.77 | COL1A1 | collagen, type I, alpha 1 |
| -4.76 | — | — |
| -4.76 | — | — |
| -4.76 | PDZD2 | PDZ domain containing 2 |
| -4.76 | C1orf186 | chromosome 1 open reading frame 186 |
| -4.75 | PIM2 | pim-2 oncogene |
| -4.75 | — | — |
| -4.75 | MBP | myelin basic protein |
| -4.74 | CROT | carnitine O-octanoyltransferase |
| -4.74 | ELAVL3 | ELAV (embryonic lethal, abnormal vision, Dros |
| -4.74 | CLIC6 | chloride intracellular channel 6 |
| -4.74 | LOC285401 | hypothetical protein LOC285401 |
| -4.73 | — | — |
| -4.73 | MEIS2 | Meis1, myeloid ecotropic viral integration site 1 |
| -4.73 | TAGLN3 | transgelin 3 |
| -4.73 | ABCD2 | ATP-binding cassette, sub-family D (ALD), mer |
| -4.73 | HAS3 | hyaluronan synthase 3 |
| -4.72 | CDH20 | cadherin 20, type 2 |
| -4.72 | — | CDNA FLJ36653 fis, clone UTERU2001176 |
| -4.72 | — | — |
| -4.72 | — | — |
| -4.72 | — | Transcribed locus |
| -4.72 | LOC202181 | hypothetical protein LOC202181 |
| -4.71 | TBX5 | T-box 5 |
| -4.71 | GAL | galanin |
| -4.71 | ACSM3 | acyl-CoA synthetase medium-chain family men |
| -4.71 | NR5A2 | nuclear receptor subfamily 5, group A, member |
| -4.71 | VAX2 | ventral anterior homeobox 2 |
| -4.71 | HPGD | hydroxyprostaglandin dehydrogenase 15-(NAD |
| -4.71 | TKTL1 | transketolase-like 1 |
| -4.70 | CAPN6 | calpain 6 |
| -4.70 | LOC144997 | hypothetical protein LOC144997 |
| -4.70 | — | — |
| -4.70 | CD9 | CD9 molecule |
| -4.70 | NRCAM | neuronal cell adhesion molecule |
| -4.69 | — | — |
| -4.69 | EDG7 | endothelial differentiation, lysophosphatidic aci |
| -4.69 | — | CDNA FLJ39164 fis, clone OCBBF2002656 |
| -4.69 | LRAT | lecithin retinol acyltransferase (phosphatidylcho |
| -4.69 | MYLIP | myosin regulatory light chain interacting protein |
| -4.68 | APC2 | adenomatosis polyposis coli 2 |
| -4.68 | — | — |
| -4.68 | OLFML2A | olfactomedin-like 2A |
| -4.68 | SLC6A6 | solute carrier family 6 (neurotransmitter transpo |
| -4.67 | — | — |
| -4.66 | — | CDNA FLJ37333 fis, clone BRAMY2020106 |
| -4.66 | — | Homo sapiens, clone IMAGE:4732650, mRNA |
| -4.65 | DPYSL5 | dihydropyrimidinase-like 5 |
| -4.64 | GLT25D2 | glycosyltransferase 25 domain containing 2 |
| -4.64 | CDH10 | cadherin 10, type 2 (T2-cadherin) |
| -4.64 | CORO2A | coronin, actin binding protein, 2A |
| -4.64 | — | — |
| -4.64 | — | CDNA FLJ35259 fis, clone PROST2004251 |
| -4.64 | ENPP2 | ectonucleotide pyrophosphatase/phosphodiest |
| -4.63 | SPINK2 | serine peptidase inhibitor, Kazal type 2 (acrosin |
| -4.63 | — | — |
| -4.63 | IRF6 | interferon regulatory factor 6 |
| -4.63 | PRKCD | protein kinase C, delta |
| -4.63 | TAGLN2 | transgelin 2 |
| -4.63 | — | — |
| -4.63 | GPR177 | G protein-coupled receptor 177 |
| -4.62 | — | — |
| -4.62 | — | — |
| -4.62 | SYT6 | Synaptotagmin VI |
| -4.62 | GCNT1 | glucosaminyl (N-acetyl) transferase 1, core 2 (I |
| -4.62 | — | — |
| -4.61 | GRB7 | growth factor receptor-bound protein 7 |

Appendix 1

| Value | Gene | Description |
|---|---|---|
| 4.49 | — | — |
| -4.49 | OVOL2 | ovo-like 2 (Drosophila) /// ovo-like 2 (Drosophila) |
| 4.48 | ZFHX4 | Zinc finger homeodomain 4 |
| 4.48 | AUTS2 | autism susceptibility candidate 2 |
| -4.48 | — | — |
| -4.48 | BMP2 | bone morphogenetic protein 2 |
| 4.48 | PKNOX2 | PBX/knotted 1 homeobox 2 |
| 4.48 | ZHX1 | zinc fingers and homeoboxes 1 |
| 4.47 | RARRES1 | retinoic acid receptor responder (tazarotene ind |
| -4.47 | CD52 | CD52 molecule |
| 4.47 | — | — |
| -4.47 | TRPC6 | transient receptor potential cation channel, sub |
| -4.47 | MARVELD2 | MARVEL domain containing 2 |
| -4.46 | FLI1 | Friend leukemia virus integration 1 |
| -4.46 | MT1E | metallothionein 1E (functional) |
| 4.46 | TRIM36 | tripartite motif-containing 36 |
| -4.46 | CER1 | cerberus 1, cysteine knot superfamily, homolog |
| 4.45 | ABCD2 | ATP-binding cassette, sub-family D (ALD), mer |
| -4.45 | SFN | stratifin |
| 4.45 | TBC1D9 | TBC1 domain family, member 9 (with GRAM d |
| -4.44 | HOOK1 | hook homolog 1 (Drosophila) |
| 4.44 | C20orf91 /// LOC40 | chromosome 20 open reading frame 91 /// simi |
| 4.44 | LOC144997 | hypothetical protein LOC144997 |
| 4.44 | HOXB5 | homeobox B5 |
| 4.43 | ST8SIA2 | ST8 alpha-N-acetyl-neuraminide alpha-2,8-sial |
| -4.43 | CRISPLD2 | cysteine-rich secretory protein LCCL domain co |
| -4.43 | CARD10 | caspase recruitment domain family, member 10 |
| -4.43 | MARVELD3 | MARVEL domain containing 3 |
| -4.42 | SLC16A5 | solute carrier family 16, member 5 (monocarbo |
| 4.42 | SCN3B | sodium channel, voltage-gated, type III, beta |
| -4.42 | KLK8 | kallikrein-related peptidase 8 |
| 4.42 | — | CDNA FLJ30948 fis, clone FEBRA2007900 |
| -4.42 | HEY2 | hairy/enhancer-of-split related with YRPW motif |
| 4.42 | ATP9B | ATPase, Class II, type 9B |
| -4.41 | — | — |
| -4.41 | RYR1 | ryanodine receptor 1 (skeletal) |
| 4.41 | LGR5 | leucine-rich repeat-containing G protein-couple |
| -4.41 | AIM1 | absent in melanoma 1 |
| -4.41 | RIT2 | Ras-like without CAAX 2 |
| -4.40 | ITM2A | integral membrane protein 2A |
| 4.40 | CDKN2A | cyclin-dependent kinase inhibitor 2A (melanom |
| 4.40 | LSAMP | limbic system-associated membrane protein |
| -4.39 | MMP9 | matrix metallopeptidase 9 (gelatinase B, 92kDa |
| -4.39 | NR5A2 | nuclear receptor subfamily 5, group A, membe |
| -4.39 | KLF4 | Kruppel-like factor 4 (gut) |
| -4.38 | EDN1 | endothelin 1 |
| -4.38 | ATP2A3 | ATPase, Ca++ transporting, ubiquitous |
| 4.38 | — | — |
| 4.38 | — | — |
| 4.38 | PGM5P1 | phosphoglucomutase 5 pseudogene 1 |
| -4.38 | GPR74 | G protein-coupled receptor 74 |
| -4.38 | ETS1 | v-ets erythroblastosis virus E26 oncogene hom |
| -4.38 | UNC5D | Unc-5 homolog D (C. elegans) |
| 4.38 | FLJ36166 | Hypothetical protein FLJ36166 |
| -4.37 | OTX2 | orthodenticle homolog 2 (Drosophila) |
| -4.37 | TOMM40 | Translocase of outer mitochondrial membrane |
| 4.36 | — | — |
| 4.36 | AFF3 | AF4/FMR2 family, member 3 |
| -4.36 | CRYM | crystallin, mu |
| -4.35 | IL23A | interleukin 23, alpha subunit p19 |
| 4.35 | — | — |
| -4.35 | — | — |
| 4.35 | EPHB2 | EPH receptor B2 |
| 4.35 | — | — |
| -4.34 | — | — |
| -4.34 | — | — |
| 4.34 | — | — |
| 4.34 | LHFP | Lipoma HMGIC fusion partner |
| 4.34 | — | — |
| -4.34 | PPP1R1A | protein phosphatase 1, regulatory (inhibitor) su |
| 4.33 | BMI1 | B lymphoma Mo-MLV insertion region (mouse) |
| -4.33 | RBP7 | retinol binding protein 7, cellular |
| -4.33 | PAK6 | p21(CDKN1A)-activated kinase 6 |
| 4.33 | PDE1A | phosphodiesterase 1A, calmodulin-dependent |
| -4.33 | — | — |
| -4.33 | C10orf95 | Chromosome 10 open reading frame 95 |
| -4.32 | COMT | catechol-O-methyltransferase |
| -4.32 | HAPLN1 | hyaluronan and proteoglycan link protein 1 |
| 4.32 | — | — |
| -4.61 | SOCS1 | suppressor of cytokine signaling 1 |
| -4.61 | SLFN13 | schlafen family member 13 |
| -4.61 | ZMAT4 | zinc finger, matrin type 4 |
| 4.61 | CDH7 | cadherin 7, type 2 |
| -4.60 | KLF5 | Kruppel-like factor 5 (intestinal) |
| -4.60 | CAV1 | caveolin 1, caveolae protein, 22kDa |
| -4.60 | — | — |
| 4.60 | LOC613266 | hypothetical LOC613266 |
| 4.60 | CROT | carnitine O-octanoyltransferase |
| -4.60 | — | Similar to AI661453 protein |
| 4.60 | WDR78 | WD repeat domain 78 |
| 4.59 | TNFRSF19 | tumor necrosis factor receptor superfamily, me |
| -4.59 | EPAS1 | endothelial PAS domain protein 1 |
| 4.59 | FLJ22184 | hypothetical protein FLJ22184 |
| -4.59 | LRRK1 | Leucine-rich repeat kinase 1 |
| -4.59 | EDG7 | Endothelial differentiation, lysophosphatidic aci |
| -4.59 | MAFB | v-maf musculoaponeurotic fibrosarcoma oncog |
| -4.58 | LDHD | lactate dehydrogenase D |
| -4.58 | SCN5A | sodium channel, voltage-gated, type V, alpha ( |
| 4.58 | NRIP3 | Nuclear receptor interacting protein 3 |
| 4.57 | — | — |
| -4.57 | MMP9 | matrix metallopeptidase 9 (gelatinase B, 92kDa |
| -4.57 | — | — |
| 4.56 | FAM49A | family with sequence similarity 49, member A |
| 4.56 | TBC1D9 | TBC1 domain family, member 9 (with GRAM d |
| 4.56 | KLHL13 | kelch-like 13 (Drosophila) |
| -4.56 | PERP | PERP, TP53 apoptosis effector |
| -4.56 | RRP22 | RAS-related on chromosome 22 |
| -4.56 | MAGEA4 | melanoma antigen family A, 4 |
| -4.56 | GPR74 | G protein-coupled receptor 74 |
| 4.55 | C10orf39 | chromosome 10 open reading frame 39 |
| 4.55 | — | — |
| -4.55 | — | — |
| -4.55 | CYP2C8 | cytochrome P450, family 2, subfamily C, polype |
| -4.54 | ACAD8 | Acyl-Coenzyme A dehydrogenase family, mem |
| 4:54 | — | MRNA; cDNA DKFZp564N1116 (from clone DI |
| 4.54 | GLRB | glycine receptor, beta |
| 4.54 | PCDH17 | protocadherin 17 |
| -4.54 | CCBE1 | collagen and calcium binding EGF domains 1 |
| -4.54 | PYY | peptide YY |
| -4.53 | SERPINB9 | serpin peptidase inhibitor, clade B (ovalbumin) |
| 4.53 | CLRN1 | clarin 1 |
| -4.53 | GABRA5 /// LOC72 | gamma-aminobutyric acid (GABA) A receptor, |
| -4.53 | GABRP | gamma-aminobutyric acid (GABA) A receptor, |
| -4.53 | — | — |
| -4.53 | HHEX | homeobox, hematopoietically expressed |
| 4.53 | PTRF | polymerase I and transcript release factor |
| -4.52 | SLC7A8 | solute carrier family 7 (cationic amino acid tran |
| -4.52 | CYP2B7P1 | cytochrome P450, family 2, subfamily B, polype |
| 4.52 | WDR49 | WD repeat domain 49 |
| 4.51 | DIRAS2 | DIRAS family, GTP-binding RAS-like 2 |
| -4.51 | UGT3A1 | UDP glycosyltransferase 3 family, polypeptide |
| 4.51 | — | CDNA FLJ35396 fis, clone SKNSH2003483 |
| -4.51 | SLC16A5 | solute carrier family 16, member 5 (monocarbo |
| -4.51 | FAM83H | family with sequence similarity 83, member H |
| -4.51 | TLE2 | transducin-like enhancer of split 2 (E(sp1) hom |
| 4.51 | KLHDC8A | kelch domain containing 8A |
| -4.50 | FBLIM1 | filamin binding LIM protein 1 |
| -4.50 | — | Transcribed locus |
| -4.50 | PDE5A | phosphodiesterase 5A, cGMP-specific |
| 4.49 | LRRC4B | leucine rich repeat containing 4B |
| -4.49 | BCL11A | B-cell CLL/lymphoma 11A (zinc finger protein) |
| -4.49 | DUSP23 | dual specificity phosphatase 23 |
| -4.49 | — | — |
| 4.49 | KCNK10 | potassium channel, subfamily K, member 10 |
| 4.48 | — | — |
| -4.48 | — | Transcribed locus |
| 4.48 | — | — |
| 4.48 | — | CDNA FLJ35396 fis, clone SKNSH2003483 |
| -4.48 | ROR1 | receptor tyrosine kinase-like orphan receptor 1 |
| 4.47 | PAK7 | p21(CDKN1A)-activated kinase 7 |
| -4.47 | MT1M | metallothionein 1M |
| -4.46 | ROR1 | Receptor tyrosine kinase-like orphan receptor |
| 4.46 | RGS20 | regulator of G-protein signalling 20 |
| 4.46 | — | — |
| -4.46 | TBX3 | T-box 3 (ulnar mammary syndrome) |
| 4.46 | — | — |
| -4.46 | C21orf56 | chromosome 21 open reading frame 56 |

Appendix 1

| Value | Symbol | Description |
|---|---|---|
| -4.32 | CCKBR | cholecystokinin B receptor |
| 4.32 | PLXNC1 | plexin C1 |
| -4.31 | SEPP1 | selenoprotein P, plasma, 1 |
| -4.31 | — | — |
| -4.31 | KYNU | kynureninase (L-kynurenine hydrolase) |
| -4.31 | C10orf39 | chromosome 10 open reading frame 39 |
| -4.31 | — | — |
| -4.31 | TRHDE | thyrotropin-releasing hormone degrading enzym |
| 4.31 | ASTN1 | astrotactin 1 |
| 4.31 | ST8SIA4 | ST8 alpha-N-acetyl-neuraminide alpha-2,8-sial |
| -4.30 | AKR1C3 | aldo-keto reductase family 1, member C3 (3-al |
| -4.30 | — | Transcribed locus |
| 4.30 | ZIC1 | Zic family member 1 (odd-paired homolog, Dro |
| -4.29 | — | — |
| -4.29 | MIXL1 | Mix1 homeobox-like 1 (Xenopus laevis) |
| -4.29 | C1orf116 | chromosome 1 open reading frame 116 |
| 4.29 | KCNC1 | potassium voltage-gated channel, Shaw-relate |
| 4.29 | ABCA5 | ATP-binding cassette, sub-family A (ABC1), m |
| -4.28 | TNFAIP6 | tumor necrosis factor, alpha-induced protein 6 |
| -4.28 | DSP | desmoplakin |
| 4.28 | MYBPC1 | myosin binding protein C, slow type |
| -4.28 | C1orf211 | chromosome 1 open reading frame 211 |
| -4.28 | LOC643224 | similar to tubulin, beta 8 |
| 4.28 | — | — |
| -4.27 | TDH | L-threonine dehydrogenase |
| -4.27 | PRKCB1 | Protein kinase C, beta 1 |
| -4.27 | — | MRNA full length insert cDNA clone EUROIMA |
| -4.27 | POLR3G | polymerase (RNA) III (DNA directed) polypepti |
| -4.27 | — | — |
| -4.27 | — | — |
| -4.27 | BSPRY | B-box and SPRY domain containing |
| 4.27 | — | Full length insert cDNA clone YT94E02 |
| 4.27 | ALDH5A1 | aldehyde dehydrogenase 5 family, member A1 |
| -4.26 | SLFN5 | schlafen family member 5 |
| 4.26 | LOC129881 | hypothetical LOC129881 |
| 4.26 | — | — |
| 4.26 | MGC33846 | hypothetical protein MGC33846 |
| -4.26 | — | — |
| 4.26 | — | — |
| 4.25 | PRTG | protogenin homolog (Gallus gallus) |
| 4.25 | APC2 | adenomatosis polyposis coli 2 |
| -4.25 | GALNT6 | UDP-N-acetyl-alpha-D-galactosamine:polypep |
| -4.25 | LOC202451 | hypothetical protein LOC202451 |
| -4.24 | DDX43 | DEAD (Asp-Glu-Ala-Asp) box polypeptide 43 |
| 4.24 | — | Transcribed locus |
| 4.24 | — | — |
| -4.24 | NLRP12 | NLR family, pyrin domain containing 12 |
| 4.24 | AFF3 /// MLL | AF4/FMR2 family, member 3 /// myeloid/lymph |
| -4.23 | — | — |
| 4.23 | SYT11 | synaptotagmin XI |
| -4.22 | PTGS2 | prostaglandin-endoperoxide synthase 2 (prost |
| 4.22 | — | CDNA FLJ33585 fis, clone BRAMY2012163 |
| 4.22 | TANC2 | tetratricopeptide repeat, ankyrin repeat and coi |
| -4.22 | — | — |
| -4.22 | RDH12 | retinol dehydrogenase 12 (all-trans and 9-cis) |
| -4.22 | LOC642587 | NPC-A-5 |
| 4.21 | — | — |
| 4.21 | FBN1 | fibrillin 1 |
| 4.21 | DUSP4 | dual specificity phosphatase 4 |
| -4.21 | — | — |
| 4.21 | CNPY1 | canopy 1 homolog (zebrafish) |
| 4.21 | SOX3 | SRY (sex determining region Y)-box 3 |
| -4.21 | IL1B | interleukin 1, beta |
| -4.21 | PYCARD | PYD and CARD domain containing |
| -4.20 | ROR1 | Receptor tyrosine kinase-like orphan receptor |
| 4.20 | FRZB | frizzled-related protein |
| -4.20 | MT1G | metallothionein 1G |
| -4.20 | — | Hypothetical protein LOC285679 |
| 4.20 | MAPK11 | mitogen-activated protein kinase 11 |
| 4.20 | — | — |
| 4.20 | KIAA1644 | KIAA1644 protein |
| -4.19 | COL1A2 | collagen, type I, alpha 2 |
| -4.19 | SLFN13 | schlafen family member 13 |
| 4.19 | — | — |
| -4.19 | FOXE1 | forkhead box E1 (thyroid transcription factor 2) |
| 4.19 | — | Transcribed locus |
| -4.19 | MYC | v-myc myelocytomatosis viral oncogene homol |
| -4.18 | SAMSN1 | SAM domain, SH3 domain and nuclear localiza |
| 4.18 | — | — |

| Value | Symbol | Description |
|---|---|---|
| -4.46 | SLC7A8 | solute carrier family 7 (cationic amino acid tran |
| 4.46 | TUBB2B | Tubulin, beta 2B |
| -4.45 | ST14 | suppression of tumorigenicity 14 (colon carcino |
| -4.45 | — | — |
| 4.45 | CRISPLD2 | cysteine-rich secretory protein LCCL domain c |
| 4.45 | LGR5 | leucine-rich repeat-containing G protein-couple |
| -4.44 | CRIP1 /// GALK2 | cysteine-rich protein 1 (intestinal) /// galactokin |
| -4.44 | CACNA2D3 | calcium channel, voltage-dependent, alpha 2/d |
| 4.44 | GNGT1 | guanine nucleotide binding protein (G protein), |
| -4.44 | MYLIP | myosin regulatory light chain interacting protei |
| -4.44 | — | — |
| -4.44 | PTCHD1 | patched domain containing 1 |
| -4.44 | MIXL1 | Mix1 homeobox-like 1 (Xenopus laevis) |
| 4.44 | DUSP4 | dual specificity phosphatase 4 |
| -4.43 | IRF6 | interferon regulatory factor 6 |
| -4.43 | — | Transcribed locus |
| 4.43 | SLC7A8 | solute carrier family 7 (cationic amino acid tran |
| 4.43 | FLJ14213 | hypothetical protein FLJ14213 |
| -4.43 | C20orf54 | chromosome 20 open reading frame 54 |
| -4.43 | GPD2 | glycerol-3-phosphate dehydrogenase 2 (mitoch |
| -4.43 | TNFSF11 | tumor necrosis factor (ligand) superfamily, mer |
| 4.43 | — | Transcribed locus |
| 4.43 | ERBB4 | v-erb-a erythroblastic leukemia viral oncogene |
| -4.42 | PDE4A | phosphodiesterase 4A, cAMP-specific (phosph |
| 4.42 | LEF1 | lymphoid enhancer-binding factor 1 |
| -4.42 | HOOK1 | hook homolog 1 (Drosophila) |
| -4.42 | LOC729678 | hypothetical protein LOC729678 |
| 4.42 | — | — |
| -4.41 | ARRB1 | arrestin, beta 1 |
| -4.41 | — | — |
| -4.41 | STAT6 | signal transducer and activator of transcription |
| 4.40 | SORBS2 | sorbin and SH3 domain containing 2 |
| -4.40 | PDLIM1 | PDZ and LIM domain 1 (elfin) |
| 4.40 | ZSWIM5 | zinc finger, SWIM-type containing 5 |
| -4.40 | ID1 | inhibitor of DNA binding 1, dominant negative h |
| 4.40 | ABCA5 | ATP-binding cassette, sub-family A (ABC1), m |
| 4.40 | ATP1A2 | ATPase, Na+/K+ transporting, alpha 2 (+) poly |
| -4.40 | — | — |
| -4.40 | KLK8 | kallikrein-related peptidase 8 |
| 4.40 | SLC1A4 | solute carrier family 1 (glutamate/neutral amino |
| -4.39 | LOC286044 | hypothetical protein LOC286044 |
| 4.39 | ABCB1 /// ABCB4 | ATP-binding cassette, sub-family B (MDR/TAP |
| 4.38 | — | — |
| 4.38 | PKNOX2 | PBX/knotted 1 homeobox 2 |
| 4.38 | — | Transcribed locus |
| -4.38 | ACOT2 /// ACOT1 | acyl-CoA thioesterase 2 /// acyl-CoA thioestera |
| 4.37 | ODZ2 | odz, odd Oz/ten-m homolog 2 (Drosophila) |
| -4.37 | AP1G2 | adaptor-related protein complex 1, gamma 2 su |
| 4.37 | CTNND2 | catenin (cadherin-associated protein), delta 2 ( |
| -4.37 | UST | uronyl-2-sulfotransferase |
| 4.37 | PHF11 | PHD finger protein 11 |
| 4.37 | GTF2IRD2 | GTF2I repeat domain containing 2 |
| -4.37 | BCL11A | B-cell CLL/lymphoma 11A (zinc finger protein) |
| -4.36 | CXCL12 | chemokine (C-X-C motif) ligand 12 (stromal ce |
| 4.36 | C21orf34 | chromosome 21 open reading frame 34 |
| -4.36 | APOBEC3G | apolipoprotein B mRNA editing enzyme, cataly |
| -4.36 | HCG11 | HLA complex group 11 |
| 4.36 | AUTS2 | autism susceptibility candidate 2 |
| -4.36 | SOX17 | SRY (sex determining region Y)-box 17 |
| -4.36 | CALCR | calcitonin receptor |
| -4.35 | PCDHAC2 | protocadherin alpha subfamily C, 2 |
| -4.35 | POLD4 | polymerase (DNA-directed), delta 4 |
| -4.34 | GNB5 | guanine nucleotide binding protein (G protein), |
| 4.34 | SNAP25 | synaptosomal-associated protein, 25kDa |
| 4.34 | FEZ1 | fasciculation and elongation protein zeta 1 (zyg |
| -4.34 | BTBD4 | BTB (POZ) domain containing 4 |
| 4.34 | CCDC73 | Coiled-coil domain containing 73 |
| -4.34 | LHX6 | LIM homeobox 6 |
| -4.33 | OSBPL10 | oxysterol binding protein-like 10 |
| -4.33 | DYSF | dysferlin, limb girdle muscular dystrophy 2B (au |
| -4.33 | TMEPAI | Transmembrane, prostate androgen induced R |
| -4.33 | MUC4 | mucin 4, cell surface associated |
| 4.33 | LSAMP | limbic system-associated membrane protein |
| -4.33 | — | — |
| 4.33 | WDR52 | WD repeat domain 52 |
| -4.32 | TMC5 | Transmembrane channel-like 5 |
| -4.32 | — | — |
| -4.32 | IL15 | interleukin 15 |
| -4.32 | TPM2 | tropomyosin 2 (beta) |

Appendix 1

| Value | Gene | Description |
|---|---|---|
| -4.18 | RRAS | related RAS viral (r-ras) oncogene homolog |
| -4.18 | ACPP | acid phosphatase, prostate |
| 4.18 | PAX6 | paired box gene 6 (aniridia, keratitis) |
| -4.18 | CGNL1 | cingulin-like 1 |
| 4.17 | FRMD4B | FERM domain containing 4B |
| -4.17 | — | — |
| 4.17 | SCN3B | sodium channel, voltage-gated, type III, beta |
| 4.17 | — | — |
| 4.17 | CLRN1 | clarin 1 |
| 4.17 | — | — |
| 4.17 | B4GALNT1 | beta-1,4-N-acetyl-galactosaminyl transferase 1 |
| 4.17 | — | — |
| 4.17 | CROT | carnitine O-octanoyltransferase |
| -4.17 | — | — |
| -4.17 | UGT3A1 | UDP glycosyltransferase 3 family, polypeptide |
| 4.17 | — | Homo sapiens, clone IMAGE:3881549, mRNA |
| 4.16 | EGR1 | early growth response 1 |
| -4.16 | GCNT1 | glucosaminyl (N-acetyl) transferase 1, core 2 |
| 4.16 | CNGA3 | cyclic nucleotide gated channel alpha 3 |
| 4.16 | ZSWIM5 | zinc finger, SWIM-type containing 5 |
| -4.16 | SGK3 | serum/glucocorticoid regulated kinase family, |
| 4.16 | — | — |
| 4.16 | MSRB3 | methionine sulfoxide reductase B3 |
| -4.16 | C20orf160 | chromosome 20 open reading frame 160 |
| -4.15 | NR3C2 | nuclear receptor subfamily 3, group C, member |
| 4.15 | — | — |
| -4.15 | MT1X | metallothionein 1X |
| -4.15 | PIM2 | pim-2 oncogene |
| -4.15 | — | — |
| -4.15 | — | — |
| 4.15 | RTN1 | reticulon 1 |
| -4.14 | — | — |
| 4.14 | — | CDNA FLJ35396 fis, clone SKNSH2003483 |
| -4.14 | MUC4 | mucin 4, cell surface associated |
| -4.14 | FIBCD1 | fibrinogen C domain containing 1 |
| 4.14 | — | — |
| 4.13 | PAX3 | paired box gene 3 (Waardenburg syndrome 1) |
| 4.13 | A2M | alpha-2-macroglobulin |
| 4.13 | SNAP25 | synaptosomal-associated protein, 25kDa |
| -4.13 | CAPG | capping protein (actin filament), gelsolin-like |
| -4.13 | FOXC1 | forkhead box C1 |
| 4.13 | RGS4 | regulator of G-protein signalling 4 |
| 4.13 | — | — |
| -4.12 | SOCS1 | suppressor of cytokine signaling 1 |
| 4.12 | AFF3 | AF4/FMR2 family, member 3 |
| -4.12 | CAV1 | caveolin 1, caveolae protein, 22kDa |
| -4.12 | — | — |
| -4.12 | — | — |
| 4.12 | MLLT3 | myeloid/lymphoid or mixed-lineage leukemia (t |
| 4.12 | — | — |
| -4.11 | FAM20A | Family with sequence similarity 20, member A |
| -4.11 | LOC728377 | Similar to rho guanine nucleotide exchange fac |
| -4.11 | — | — |
| 4.11 | PACRG | PARK2 co-regulated |
| -4.10 | CD55 | CD55 molecule, decay accelerating factor for c |
| -4.10 | C19orf4 | chromosome 19 open reading frame 4 |
| 4.10 | — | — |
| -4.10 | TNNI3 | troponin I type 3 (cardiac) |
| 4.09 | KLHL13 | kelch-like 13 (Drosophila) |
| -4.09 | PLAU | plasminogen activator, urokinase /// plasminog |
| 4.09 | — | Transcribed locus |
| 4.09 | NF1 | neurofibromin 1 (neurofibromatosis, von Reckli |
| -4.09 | PPP2R2C | protein phosphatase 2 (formerly 2A), regulator |
| -4.09 | LOC155036 | hypothetical protein LOC155036 |
| 4.09 | — | — |
| 4.08 | — | — |
| 4.08 | HOXD8 | Homeobox D8 |
| -4.08 | POLD4 | polymerase (DNA-directed), delta 4 |
| 4.08 | NHLH1 | nescient helix loop helix 1 |
| 4.08 | ID4 | inhibitor of DNA binding 4, dominant negative |
| -4.08 | MYLIP | myosin regulatory light chain interacting protein |
| 4.07 | — | — |
| 4.07 | NOTCH1 | Notch homolog 1, translocation-associated (Dr |
| 4.07 | PRRX1 | Paired related homeobox 1 |
| -4.07 | ITGA3 | integrin, alpha 3 (antigen CD49C, alpha 3 subu |
| 4.06 | PHYHIPL | phytanoyl-CoA 2-hydroxylase interacting prote |
| -4.06 | — | — |
| -4.06 | RYR2 | ryanodine receptor 2 (cardiac) |
| 4.06 | CNIH2 | cornichon homolog 2 (Drosophila) |
| -4.32 | ARHGAP4 | Rho GTPase activating protein 4 |
| -4.32 | TRDN | triadin |
| -4.32 | DAPK1 | death-associated protein kinase 1 |
| -4.31 | RNF43 | ring finger protein 43 |
| 4.31 | LIX1L | Lix1 homolog (mouse)-like |
| 4.31 | — | Full length insert cDNA clone YT94E02 |
| 4.31 | CDKN2A | cyclin-dependent kinase inhibitor 2A (melanom |
| -4.31 | EPB41L5 | erythrocyte membrane protein band 4.1 like 5 |
| -4.30 | LOC255480 | hypothetical protein LOC255480 |
| 4.30 | RTN1 | reticulon 1 |
| 4.30 | — | CDNA FLJ37366 fis, clone BRAMY2024416 |
| -4.30 | DST | dystonin |
| -4.30 | SLC16A5 | solute carrier family 16, member 5 (monocarbo |
| 4.29 | BMI1 | B lymphoma Mo-MLV insertion region (mouse) |
| -4.29 | FLJ21963 | FLJ21963 protein |
| -4.29 | SLC9A7 | solute carrier family 9 (sodium/hydrogen excha |
| -4.28 | LOC255104 | Transmembrane and coiled-coil domains 4 |
| -4.28 | — | — |
| 4.28 | YAF2 | YY1 associated factor 2 |
| -4.28 | STYK1 | serine/threonine/tyrosine kinase 1 |
| -4.27 | IFI30 | interferon, gamma-inducible protein 30 |
| -4.27 | VAMP8 | vesicle-associated membrane protein 8 (endob |
| 4.26 | SLC1A4 | solute carrier family 1 (glutamate/neutral amino |
| -4.26 | TMC4 | transmembrane channel-like 4 |
| -4.26 | C8orf47 | chromosome 8 open reading frame 47 |
| 4.26 | RBMS3 | RNA binding motif, single stranded interacting |
| -4.26 | TFCP2L1 | Transcription factor CP2-like 1 |
| -4.26 | COL5A3 | collagen, type V, alpha 3 |
| 4.25 | — | — |
| -4.25 | KLKB1 | kallikrein B, plasma (Fletcher factor) 1 |
| 4.25 | ALDH5A1 | aldehyde dehydrogenase 5 family, member A1 |
| -4.25 | FBLIM1 | filamin binding LIM protein 1 |
| -4.24 | CRYM | crystallin, mu |
| 4.24 | LRRC4 | leucine rich repeat containing 4 |
| 4.24 | — | — |
| -4.24 | DDB2 | damage-specific DNA binding protein 2, 48kDa |
| -4.24 | — | — |
| -4.24 | FZD5 | frizzled homolog 5 (Drosophila) /// frizzled hom |
| -4.24 | THRB | thyroid hormone receptor, beta (erythroblastic |
| -4.23 | ZNF165 | zinc finger protein 165 |
| 4.23 | CSPG5 | chondroitin sulfate proteoglycan 5 (neuroglycan |
| -4.23 | LAMC2 | laminin, gamma 2 |
| 4.23 | LOC399959 | Hypothetical gene supported by BX647606 |
| 4.23 | GUCY1A3 | Guanylate cyclase 1, soluble, alpha 3 |
| -4.23 | — | — |
| -4.23 | C20orf42 | chromosome 20 open reading frame 42 |
| -4.22 | UTS2 | urotensin 2 |
| 4.22 | — | — |
| -4.22 | FXYD7 | FXYD domain containing ion transport regulato |
| -4.22 | — | Transcribed locus |
| -4.22 | — | Homo sapiens, clone IMAGE:3454042, mRNA |
| 4.21 | SCN3A | sodium channel, voltage-gated, type III, alpha |
| -4.21 | — | CDNA clone IMAGE:5263207 |
| -4.21 | — | CDNA clone IMAGE:5262438 |
| 4.20 | — | CDNA: FLJ23070 fis, clone LNG05629 |
| -4.20 | MET | met proto-oncogene (hepatocyte growth factor |
| -4.20 | SLC7A7 | solute carrier family 7 (cationic amino acid tran |
| -4.20 | HYAL1 | hyaluronoglucosaminidase 1 |
| 4.20 | — | — |
| 4.20 | — | — |
| -4.19 | CCL2 | chemokine (C-C motif) ligand 2 |
| 4.19 | — | CDNA FLJ30128 fis, clone BRACE1000124 |
| -4.19 | RIT2 | Ras-like without CAAX 2 |
| 4.19 | SYT11 | synaptotagmin XI |
| 4.19 | BMPR1B | Bone morphogenetic protein receptor, type IB |
| 4.19 | — | — |
| 4.19 | ZFHX4 | Zinc finger homeodomain 4 |
| -4.18 | — | Transcribed locus |
| -4.18 | IRF6 | interferon regulatory factor 6 |
| 4.18 | PHYHIPL | phytanoyl-CoA 2-hydroxylase interacting prote |
| -4.18 | — | — |
| 4.17 | NRG1 | neuregulin 1 |
| -4.17 | FRAT2 | frequently rearranged in advanced T-cell lymph |
| 4.17 | — | — |
| -4.16 | — | — |
| 4.16 | BCL11A | B-cell CLL/lymphoma 11A (zinc finger protein) |
| 4.16 | — | — |
| 4.16 | — | Transcribed locus |
| 4.16 | GLULD1 | glutamate-ammonia ligase (glutamine synthetas |

Appendix 1

| Value | Symbol | Description |
|---|---|---|
| -4.06 | ASPHD1 | aspartate beta-hydroxylase domain containing |
| -4.06 | WDR49 | WD repeat domain 49 |
| -4.05 | FEZ1 | fasciculation and elongation protein zeta 1 (zyg |
| -4.05 | VPS35 | Vacuolar protein sorting 35 (yeast) |
| -4.05 | RGS20 | regulator of G-protein signalling 20 |
| -4.05 | WBSCR17 | Williams-Beuren syndrome chromosome region |
| -4.05 | MOG | myelin oligodendrocyte glycoprotein |
| -4.04 | CROT | carnitine O-octanoyltransferase |
| -4.04 | FLJ22184 | hypothetical protein FLJ22184 |
| -4.04 | DGKA | diacylglycerol kinase, alpha 80kDa |
| -4.04 | — | — |
| -4.04 | OR2A9P | Olfactory receptor, family 2, subfamily A, memb |
| -4.03 | — | — |
| -4.03 | SDHALP2 | succinate dehydrogenase complex, subunit A, |
| -4.03 | ARHGEF17 | Rho guanine nucleotide exchange factor (GEF) |
| -4.02 | IL15 | interleukin 15 |
| -4.02 | SYTL4 | synaptotagmin-like 4 (granuphilin-a) |
| -4.02 | — | CDNA FLJ30810 fis, clone FEBRA2001440 |
| -4.02 | COMMD3 | COMM domain containing 3 |
| -4.02 | COL14A1 | collagen, type XIV, alpha 1 (undulin) |
| -4.02 | CXCL12 | chemokine (C-X-C motif) ligand 12 (stromal cel |
| -4.02 | LOC645745 | metallothionein 1H-like protein |
| -4.01 | TNC | tenascin C (hexabrachion) |
| -4.01 | — | — |
| -4.01 | C1orf62 | chromosome 1 open reading frame 62 |
| -4.01 | FLJ35934 | FLJ35934 protein |
| -4.01 | — | — |
| -4.01 | CHN2 | chimerin (chimaerin) 2 |
| -4.01 | ZNF165 | zinc finger protein 165 |
| -4.00 | — | CDNA FLJ36653 fis, clone UTERU2001176 |
| -4.00 | PKNOX2 | PBX/knotted 1 homeobox 2 |
| -4.00 | FLJ31485 | hypothetical gene supported by AK056047; AK |
| -4.00 | B3GALT2 | UDP-Gal:betaGlcNAc beta 1,3-galactosyltransf |
| -4.00 | SPDYA | speedy homolog A (Drosophila) |
| -4.00 | REEP1 | receptor accessory protein 1 |
| -4.00 | RPS4Y1 | ribosomal protein S4, Y-linked 1 |
| -4.00 | FXYD6 | FXYD domain containing ion transport regulato |
| -3.99 | — | — |
| -3.99 | GRM3 | glutamate receptor, metabotropic 3 |
| -3.99 | SYT11 | synaptotagmin XI |
| -3.99 | TMEM47 | transmembrane protein 47 |
| -3.98 | LOC401321 | hypothetical LOC401321 |
| -3.98 | — | — |
| -3.98 | FGFR4 | fibroblast growth factor receptor 4 |
| -3.98 | POU3F3 | POU domain, class 3, transcription factor 3 |
| -3.98 | FXYD7 | FXYD domain containing ion transport regulato |
| -3.98 | RTP1 | receptor (chemosensory) transporter protein 1 |
| -3.98 | LOC202181 | hypothetical protein LOC202181 |
| -3.98 | RERG | RAS-like, estrogen-regulated, growth inhibitor |
| -3.97 | TMBIM1 | transmembrane BAX inhibitor motif containing |
| -3.97 | PCDHAC2 | protocadherin alpha subfamily C, 2 |
| -3.97 | CTNND2 | catenin (cadherin-associated protein), delta 2 ( |
| -3.96 | FGF21 | fibroblast growth factor 21 |
| -3.96 | — | Transcribed locus |
| -3.96 | ST8SIA2 | ST8 alpha-N-acetyl-neuraminide alpha-2,8-sial |
| -3.96 | HOXD13 | homeobox D13 |
| -3.96 | KIAA1679 | KIAA1679 protein |
| -3.96 | SH3GL3 | SH3-domain GRB2-like 3 |
| -3.96 | DPYSL4 | dihydropyrimidinase-like 4 |
| -3.96 | APOA2 | apolipoprotein A-II |
| -3.96 | OCIAD2 | OCIA domain containing 2 |
| -3.96 | — | — |
| -3.95 | LGALS1 | lectin, galactoside-binding, soluble, 1 (galectin |
| -3.95 | SYN2 | synapsin II |
| -3.95 | RGS12 | regulator of G-protein signalling 12 |
| -3.95 | SLC19A3 | solute carrier family 19, member 3 |
| -3.95 | LAMC2 | laminin, gamma 2 |
| -3.95 | ZNF436 | zinc finger protein 436 |
| -3.94 | SFRS12 | Splicing factor, arginine/serine-rich 12 |
| -3.94 | TFEC | transcription factor EC |
| -3.94 | SKIL | SKI-like |
| -3.94 | NPAS3 | Neuronal PAS domain protein 3 |
| -3.93 | — | CDNA clone IMAGE:5263207 |
| -3.93 | RORA | RAR-related orphan receptor A |
| -3.93 | EDA | ectodysplasin A |
| -3.93 | — | — |
| -3.93 | LIX1L | Lix1 homolog (mouse)-like |
| -3.93 | TMEM125 | transmembrane protein 125 |
| -3.93 | ACSM3 | acyl-CoA synthetase medium-chain family mem |
| -4.16 | — | — |
| -4.15 | SPATA9 | spermatogenesis associated 9 |
| -4.15 | JAZF1 | JAZF zinc finger 1 |
| -4.15 | — | Transcribed locus |
| -4.15 | C19orf4 | chromosome 19 open reading frame 4 |
| -4.15 | RARG | retinoic acid receptor, gamma |
| -4.15 | IL1B | interleukin 1, beta |
| -4.15 | CXCL5 | chemokine (C-X-C motif) ligand 5 |
| -4.14 | LEMD1 | LEM domain containing 1 |
| -4.14 | EGR1 | early growth response 1 |
| -4.14 | — | Full length insert cDNA clone YY86C01 |
| -4.14 | CST4 | cystatin S |
| -4.14 | — | — |
| -4.13 | PKNOX2 | PBX/knotted 1 homeobox 2 |
| -4.13 | — | — |
| -4.13 | CADPS | Ca2+-dependent secretion activator |
| -4.13 | GH2 | growth hormone 2 |
| -4.13 | EBF2 | early B-cell factor 2 |
| -4.12 | HOXC4 | homeobox C4 |
| -4.12 | C20orf160 | chromosome 20 open reading frame 160 |
| -4.12 | — | — |
| -4.12 | NFE2L3 | nuclear factor (erythroid-derived 2)-like 3 |
| -4.12 | CDH11 | Cadherin 11, type 2, OB-cadherin (osteoblast) |
| -4.11 | MLSTD1 | male sterility domain containing 1 |
| -4.11 | PAPSS2 | 3'-phosphoadenosine 5'-phosphosulfate syntha |
| -4.11 | — | — |
| -4.11 | SOX3 | SRY (sex determining region Y)-box 3 |
| -4.11 | — | — |
| -4.11 | HOXC5 | homeobox C5 |
| -4.10 | LOC284361 | Hematopoietic signal peptide-containing |
| -4.10 | HDAC9 | histone deacetylase 9 |
| -4.10 | SRGAP3 | SLIT-ROBO Rho GTPase activating protein 3 |
| -4.10 | — | — |
| -4.10 | COL4A4 | collagen, type IV, alpha 4 |
| -4.10 | — | — |
| -4.09 | — | Transcribed locus, strongly similar to XP_5296 |
| -4.09 | KIAA1853 | KIAA1853 |
| -4.09 | LOC388630 | similar to C05G5.5 |
| -4.09 | ZIC1 | Zic family member 1 (odd-paired homolog, Dro |
| -4.09 | NRG1 | neuregulin 1 |
| -4.09 | SMAD7 | SMAD family member 7 |
| -4.09 | IL8 | interleukin 8 |
| -4.08 | SLC7A8 | solute carrier family 7 (cationic amino acid tran |
| -4.08 | CHN2 | chimerin (chimaerin) 2 |
| -4.08 | — | — |
| -4.08 | KCNE3 | potassium voltage-gated channel, Isk-related fa |
| -4.08 | PPP1R1B | protein phosphatase 1, regulatory (inhibitor) su |
| -4.08 | LMO3 | LIM domain only 3 (rhombotin-like 2) |
| -4.07 | TMEM125 | transmembrane protein 125 |
| -4.07 | AURKC | aurora kinase C |
| -4.07 | NRIP3 | nuclear receptor interacting protein 3 |
| -4.07 | ERBB3 | v-erb-b2 erythroblastic leukemia viral oncogene |
| -4.07 | MYLIP | myosin regulatory light chain interacting protein |
| -4.06 | PGM5P1 | phosphoglucomutase 5 pseudogene 1 |
| -4.06 | HOXA11 | homeobox A11 |
| -4.06 | PAPSS2 | 3'-phosphoadenosine 5'-phosphosulfate syntha |
| -4.06 | GRAMD3 | GRAM domain containing 3 |
| -4.06 | SNAP91 | synaptosomal-associated protein, 91kDa homo |
| -4.06 | HCN1 | hyperpolarization activated cyclic nucleotide-ga |
| -4.05 | PACRG | PARK2 co-regulated |
| -4.05 | DACH1 | dachshund homolog 1 (Drosophila) |
| -4.05 | BAI3 | brain-specific angiogenesis inhibitor 3 |
| -4.05 | FRMD4B | FERM domain containing 4B |
| -4.05 | — | Transcribed locus |
| -4.05 | DKFZP586H2123 | regeneration associated muscle protease |
| -4.05 | — | — |
| -4.05 | COMMD3 | COMM domain containing 3 |
| -4.05 | — | — |
| -4.04 | FUT1 | fucosyltransferase 1 (galactoside 2-alpha-L-fuc |
| -4.04 | RUNX1T1 | runt-related transcription factor 1; translocated |
| -4.04 | CYBA | cytochrome b-245, alpha polypeptide |
| -4.04 | UNC93B1 | unc-93 homolog B1 (C. elegans) |
| -4.04 | PALLD | palladin, cytoskeletal associated protein |
| -4.04 | PDE4B | phosphodiesterase 4B, cAMP-specific (phosph |
| -4.04 | SERPINH1 | serpin peptidase inhibitor, clade H (heat shock |
| -4.04 | GRHL2 | grainyhead-like 2 (Drosophila) |
| -4.03 | LXN | latexin |
| -4.03 | — | — |
| -4.03 | — | — |

Appendix 1

| | | | |
|---|---|---|---|
| -3.92 MST1 | macrophage stimulating 1 (hepatocyte growth | 4.03 C13orf21 | Chromosome 13 open reading frame 21 |
| -3.92 CD19 | CD19 molecule | -4.02 MAP3K1 | mitogen-activated protein kinase kinase kinase |
| 3.92 GSTM3 | glutathione S-transferase M3 (brain) | -4.02 — | — |
| 3.92 APBA2 | amyloid beta (A4) precursor protein-binding, fa | -4.02 — | CDNA clone IMAGE:4793048 |
| -3.92 PLAU | plasminogen activator, urokinase | -4.02 GAL3ST1 | galactose-3-O-sulfotransferase 1 |
| -3.92 — | CDNA clone IMAGE:4811759 | 4.01 LOC285771 | hypothetical protein LOC285771 |
| 3.92 PDE4B | phosphodiesterase 4B, cAMP-specific (phosph | 4.01 SYTL4 | synaptotagmin-like 4 (granuphilin-a) |
| -3.92 — | — | 4.01 SLITRK2 | SLIT and NTRK-like family, member 2 |
| -3.92 TFCP2L1 | Transcription factor CP2-like 1 | -4.01 NRK | Nik related kinase |
| -3.91 STC2 | stanniocalcin 2 | 4.01 MARCH-I | Membrane-associated ring finger (C3HC4) 1 |
| 3.91 KIAA1462 | KIAA1462 | 4.01 — | — |
| -3.91 — | — | -4.00 MYLIP | myosin regulatory light chain interacting protein |
| 3.91 HDAC9 | histone deacetylase 9 | -4.00 — | — |
| 3.91 DACH1 | dachshund homolog 1 (Drosophila) | 4.00 — | Tetraspanin 11 |
| 3.90 GPRIN1 | G protein regulated inducer of neurite outgrowt | 4.00 SMOC1 | SPARC related modular calcium binding 1 |
| 3.90 TFAP2B | transcription factor AP-2 beta (activating enhan | -4.00 HRLP5 | H-rev107-like protein 5 |
| -3.90 CCL5 | chemokine (C-C motif) ligand 5 | -4.00 PDGFA | platelet-derived growth factor alpha polypeptide |
| 3.90 ST3GAL4 | ST3 beta-galactoside alpha-2,3-sialyltransferas | 3.99 ST8SIA2 | ST8 alpha-N-acetyl-neuraminide alpha-2,8-sial |
| -3.90 RARG | retinoic acid receptor, gamma | 3.99 SLC2A1 | solute carrier family 2 (facilitated glucose trans |
| -3.89 LASS4 | LAG1 homolog, ceramide synthase 4 (S. cerev | -3.99 SLC2A3 | solute carrier family 2 (facilitated glucose trans |
| 3.89 FZD10 | frizzled homolog 10 (Drosophila) | -3.99 SAV1 | Salvador homolog 1 (Drosophila) |
| -3.89 EPB41L5 | Erythrocyte membrane protein band 4.1 like 5 | 3.99 — | Homo sapiens, clone IMAGE:3881549, mRNA |
| -3.89 LAMA2 | laminin, alpha 2 (merosin, congenital muscular | -3.98 LOXL2 | lysyl oxidase-like 2 |
| 3.89 ANKRD38 | ankyrin repeat domain 38 | -3.98 — | — |
| -3.89 SLC7A8 | solute carrier family 7 (cationic amino acid tran | 3.98 TMEM47 | transmembrane protein 47 |
| -3.89 ATP8B3 | ATPase, Class I, type 8B, member 3 | -3.98 GRID2 | glutamate receptor, ionotropic, delta 2 |
| -3.89 — | — | 3.98 LOC147670 | hypothetical protein LOC147670 |
| -3.88 GALNT14 | UDP-N-acetyl-alpha-D-galactosamine:polypept | 3.98 IQCH | IQ motif containing H |
| -3.88 LOC401312 | LOC401318 | -3.98 — | — |
| -3.88 FLJ20449 | hypothetical protein FLJ20449 | -3.98 — | — |
| 3.87 COL3A1 | collagen, type III, alpha 1 (Ehlers-Danlos syndr | 3.97 — | — |
| -3.87 MS4A7 | membrane-spanning 4-domains, subfamily A, | 3.97 CHRDL1 | chordin-like 1 |
| -3.87 MYLIP | myosin regulatory light chain interacting protein | 3.97 — | CDNA clone IMAGE:5266257 |
| -3.86 CD55 | CD55 molecule, decay accelerating factor for c | -3.97 TPM2 /// PPIL5 | tropomyosin 2 (beta) /// peptidylprolyl isomeras |
| -3.86 ARHGAP9 | Rho GTPase activating protein 9 | -3.96 CHST4 | carbohydrate (N-acetylglucosamine 6-O) sulfot |
| -3.86 PRSS1 /// PRSS2 | // protease, serine, 1 (trypsin 1) /// protease, seri | -3.96 OCLN /// NAIP | occludin /// similar to Occludin |
| -3.86 FLJ31204 | hypothetical protein FLJ31204 | 3.96 — | — |
| 3.85 THSD7A | thrombospondin, type I, domain containing 7A | -3.96 GATA4 | GATA binding protein 4 |
| -3.85 MT1X | metallothionein 1X | 3.96 KIAA1644 | KIAA1644 protein |
| 3.85 LOC780776 | hypothetical LOC780776 | -3.96 — | — |
| 3.85 GPR162 | G protein-coupled receptor 162 | 3.95 TTYH1 | tweety homolog 1 (Drosophila) |
| 3.85 — | Full length insert cDNA clone ZA88B06 | 3.95 MSRB3 | methionine sulfoxide reductase B3 |
| 3.84 HOXC4 | homeobox C4 | -3.95 CACNA2D1 | calcium channel, voltage-dependent, alpha 2/d |
| 3.84 — | CDNA: FLJ23070 fis, clone LNG05629 | -3.95 SNAI1 | snail homolog 1 (Drosophila) |
| 3.84 FRZB | frizzled-related protein | 3.95 SLCO6A1 | solute carrier organic anion transporter family, |
| -3.83 GH2 | growth hormone 2 | -3.94 FLJ21963 | FLJ21963 protein |
| 3.83 ENPP2 | ectonucleotide pyrophosphatase/phosphodiest | 3.94 — | — |
| 3.83 LOC389895 | similar to CG4768-PA | -3.94 KCNG3 | potassium voltage-gated channel, subfamily G |
| 3.83 ARL4C | ADP-ribosylation factor-like 4C | 3.94 — | — |
| -3.83 LYPD3 | LY6/PLAUR domain containing 3 | 3.94 — | — |
| 3.82 CCDC92 | coiled-coil domain containing 92 | 3.94 SLC2A1 | solute carrier family 2 (facilitated glucose trans |
| -3.82 SLC2A3 | solute carrier family 2 (facilitated glucose trans | -3.94 LAMC3 | laminin, gamma 3 |
| 3.82 C1orf114 | chromosome 1 open reading frame 114 | -3.94 TAGLN2 | transgelin 2 |
| -3.82 HBA1 | hemoglobin, alpha 1 /// hemoglobin, alpha 1 | -3.93 TRIM14 | tripartite motif-containing 14 |
| -3.82 GATA4 | GATA binding protein 4 | -3.93 FLJ16287 | FLJ16287 protein |
| 3.82 RP5-875H10.1 | SAM domain containing 1 | 3.93 FLJ10159 | Hypothetical protein FLJ10159 |
| 3.82 ZHX1 | zinc fingers and homeoboxes 1 | 3.93 PALLD | palladin, cytoskeletal associated protein |
| -3.81 PRKCH | protein kinase C, eta | -3.93 RYR1 | ryanodine receptor 1 (skeletal) |
| 3.81 LRRN3 | leucine rich repeat neuronal 3 | -3.93 APOA2 | apolipoprotein A-II |
| -3.81 MMP25 | matrix metallopeptidase 25 | 3.92 HOXB4 | homeobox B4 |
| 3.81 KIF5A | kinesin family member 5A | 3.92 — | — |
| 3.81 — | — | -3.92 IL15 | interleukin 15 |
| -3.80 — | — | -3.92 PAK6 | p21(CDKN1A)-activated kinase 6 |
| 3.80 PRRX2 | paired related homeobox 2 | 3.92 WFDC1 | WAP four-disulfide core domain 1 |
| 3.80 SYDE1 | synapse defective 1, Rho GTPase, homolog 1 | -3.92 — | — |
| 3.80 — | — | 3.92 — | Transcribed locus |
| -3.80 IL6 | interleukin 6 (interferon, beta 2) | -3.92 LGALS1 | lectin, galactoside-binding, soluble, 1 (galectin |
| 3.80 — | — | 3.92 MLLT3 | myeloid/lymphoid or mixed-lineage leukemia (t |
| -3.80 FLJ30707 | hypothetical protein FLJ30707 | -3.91 PODXL | podocalyxin-like |
| -3.80 LOC388630 | similar to C05G5.5 | 3.91 — | — |
| 3.80 NOL4 | nucleolar protein 4 | 3.91 TMED4 | transmembrane emp24 protein transport doma |
| 3.80 MAPK8IP2 | mitogen-activated protein kinase 8 interacting | -3.91 STXBP2 | syntaxin binding protein 2 |
| 3.80 FGF9 | fibroblast growth factor 9 (glia-activating factor) | 3.91 GPR56 | G protein-coupled receptor 56 |
| -3.80 — | — | -3.91 LOC642587 | NPC-A-5 |
| -3.79 CAPN6 | calpain 6 | 3.90 APBA2 | amyloid beta (A4) precursor protein-binding, fa |
| 3.79 — | — | -3.90 ARTN | artemin |
| 3.79 PDE4B | phosphodiesterase 4B, cAMP-specific (phosph | 3.90 CLGN | calmegin |
| -3.79 RGL3 | ral guanine nucleotide dissociation stimulator-li | 3.90 LOC728052 /// LOC | Hypothetical protein LOC728052 /// Hematopoi |
| -3.79 C14orf115 | chromosome 14 open reading frame 115 | 3.90 RPIB9 | Rap2-binding protein 9 |

Appendix 1

| | | | | |
|---|---|---|---|---|
| -3.79 | KLHDC7A | kelch domain containing 7A | 3.90 AFF3 | AF4/FMR2 family, member 3 |
| -3.79 | PPP2R5C | protein phosphatase 2, regulatory subunit B (B | -3.89 PDGFRA | platelet-derived growth factor receptor, alpha p |
| 3.79 | B4GALNT1 | beta-1,4-N-acetyl-galactosaminyl transferase 1 | 3.89 KIAA0408 | KIAA0408 |
| 3.79 | — | — | -3.89 NLRP12 | NLR family, pyrin domain containing 12 |
| 3.79 | C1orf114 | chromosome 1 open reading frame 114 | 3.89 DEDD | Death effector domain containing |
| -3.79 | F2RL1 | coagulation factor II (thrombin) receptor-like 1 | 3.89 KIAA1644 | KIAA1644 protein |
| 3.79 | C20orf58 | chromosome 20 open reading frame 58 | 3.89 CNPY1 | canopy 1 homolog (zebrafish) |
| -3.78 | STOM | stomatin | 3.89 PALM2 | paralemmin 2 |
| -3.78 | TFPI | tissue factor pathway inhibitor (lipoprotein-asso | -3.89 C21orf63 | chromosome 21 open reading frame 63 |
| 3.78 | ABCB1 /// ABCB4 | ATP-binding cassette, sub-family B (MDR/TAP | 3.89 — | Transcribed locus |
| -3.78 | — | — | -3.88 C18orf4 | chromosome 18 open reading frame 4 |
| 3.78 | MEGF9 | multiple EGF-like-domains 9 | -3.88 HMMR | Hyaluronan-mediated motility receptor (RHAM |
| 3.78 | — | Transcribed locus | -3.88 MLSTD1 | Male sterility domain containing 1 |
| -3.78 | PRODH | proline dehydrogenase (oxidase) 1 | 3.88 — | — |
| 3.78 | PYGO1 | pygopus homolog 1 (Drosophila) | 3.88 KIAA1772 | KIAA1772 |
| -3.78 | — | Transcribed locus | 3.88 HOXD4 | homeobox D4 |
| 3.78 | — | CDNA FLJ37333 fis, clone BRAMY2020106 | 3.88 FBN1 | fibrillin 1 |
| 3.78 | TBC1D16 | TBC1 domain family, member 16 | -3.88 MT2A | metallothionein 2A |
| -3.78 | SPINK1 | serine peptidase inhibitor, Kazal type 1 | -3.88 — | — |
| 3.78 | — | — | -3.88 TMEPAI | transmembrane, prostate androgen induced R |
| -3.77 | HSPA1A | heat shock 70kDa protein 1A | 3.87 SLC1A4 | solute carrier family 1 (glutamate/neutral amino |
| -3.77 | AP1G2 | adaptor-related protein complex 1, gamma 2 s | -3.87 — | — |
| -3.77 | — | — | 3.87 — | — |
| 3.77 | RARRES1 | retinoic acid receptor responder (tazarotene in | -3.86 MAP4K1 | mitogen-activated protein kinase kinase kinase |
| 3.77 | CLIPR-59 | CLIP-170-related protein | -3.86 GPRC5C | G protein-coupled receptor, family C, group 5, |
| 3.77 | VAX2 | ventral anterior homeobox 2 | -3.86 MET | met proto-oncogene (hepatocyte growth factor |
| 3.77 | WDR17 | WD repeat domain 17 | 3.86 HOXB5 | homeobox B5 |
| -3.76 | MMP23B /// MMP2? | matrix metallopeptidase 23B /// matrix metallop | -3.86 TBC1D1 | TBC1 (tre-2/USP6, BUB2, cdc16) domain fami |
| 3.76 | C11orf70 | chromosome 11 open reading frame 70 | -3.86 KLF4 | Kruppel-like factor 4 (gut) |
| 3.76 | MAP1A | microtubule-associated protein 1A | -3.86 C18orf4 | chromosome 18 open reading frame 4 |
| -3.76 | — | — | 3.85 CHN2 | chimerin (chimaerin) 2 |
| -3.76 | SULT1C1 | sulfotransferase family, cytosolic, 1C, member | 3.85 MOV10L1 | Mov10l1, Moloney leukemia virus 10-like 1, ho |
| 3.76 | — | CDNA clone IMAGE:5287047 | -3.85 MCOLN3 | mucolipin 3 |
| -3.76 | — | — | -3.85 ZSCAN2 | zinc finger and SCAN domain containing 2 |
| 3.76 | — | Transcribed locus | -3.85 — | — |
| 3.76 | MAPRE3 | microtubule-associated protein, RP/EB family, | -3.85 MYOZ3 | myozenin 3 |
| -3.75 | NR5A2 | nuclear receptor subfamily 5, group A, member | -3.85 CCDC69 | coiled-coil domain containing 69 |
| -3.75 | — | — | 3.85 PRTG | protogenin homolog (Gallus gallus) |
| -3.75 | LOC153469 | hypothetical protein LOC153469 | 3.85 HOXD8 | Homeobox D8 |
| 3.75 | PCDH17 | protocadherin 17 | -3.84 DLC1 | deleted in liver cancer 1 |
| -3.75 | LOC130951 | hypothetical protein BC014602 | -3.84 SOX17 | SRY (sex determining region Y)-box 17 |
| -3.74 | — | — | -3.84 PYCARD | PYD and CARD domain containing |
| 3.74 | — | — | 3.84 C1orf114 | chromosome 1 open reading frame 114 |
| 3.74 | SV2C | synaptic vesicle glycoprotein 2C | 3.84 KCNAB1 | potassium voltage-gated channel, shaker-relat |
| 3.74 | PKNOX2 | PBX/knotted 1 homeobox 2 | 3.84 — | — |
| 3.74 | APCDD1 | adenomatosis polyposis coli down-regulated 1 | -3.83 — | — |
| 3.74 | — | — | 3.83 — | CDNA FLJ11554 fis, clone HEMBA1003037 |
| 3.74 | — | MRNA; cDNA DKFZp686I18116 (from clone D | -3.83 AQP4 | aquaporin 4 |
| 3.73 | EME2 | Essential meiotic endonuclease 1 homolog 2 (S | -3.83 PTGIS | prostaglandin I2 (prostacyclin) synthase |
| 3.73 | — | — | -3.83 HBA1 | hemoglobin, alpha 1 /// hemoglobin, alpha 1 |
| -3.73 | MYLIP | myosin regulatory light chain interacting protei | -3.83 PPP1R1A | protein phosphatase 1, regulatory (inhibitor) su |
| -3.73 | SERPINB9 | serpin peptidase inhibitor, clade B (ovalbumin), | -3.82 SIX2 | sine oculis homeobox homolog 2 (Drosophila) |
| -3.73 | C15orf27 | chromosome 15 open reading frame 27 | 3.82 LOC150568 | hypothetical protein LOC150568 |
| 3.73 | MLLT3 | myeloid/lymphoid or mixed-lineage leukemia (t | 3.82 — | — |
| 3.73 | CUBN | cubilin (intrinsic factor-cobalamin receptor) | 3.82 HHAT | hedgehog acyltransferase |
| 3.73 | — | — | -3.82 MB | myoglobin |
| 3.72 | KIAA1644 | KIAA1644 protein | -3.82 — | — |
| -3.72 | LCP1 | lymphocyte cytosolic protein 1 (L-plastin) | -3.82 AIM1L /// FLJ38020 | absent in melanoma 1-like /// similar to absent |
| 3.72 | — | — | 3.81 C1orf114 | chromosome 1 open reading frame 114 |
| -3.72 | FRAT2 | frequently rearranged in advanced T-cell lymph | -3.81 JPH3 | junctophilin 3 |
| -3.72 | JPH3 | junctophilin 3 | 3.81 GPATC2 | G patch domain containing 2 |
| 3.72 | SARM1 | sterile alpha and TIR motif containing 1 | 3.81 NF1 | neurofibromin 1 (neurofibromatosis, von Reckli |
| -3.72 | PODXL | podocalyxin-like | -3.80 KIAA1305 | KIAA1305 |
| -3.72 | HHLA1 | HERV-H LTR-associating 1 | 3.80 GRK4 | G protein-coupled receptor kinase 4 |
| -3.71 | SOCS1 | suppressor of cytokine signaling 1 | 3.80 TANC2 | tetratricopeptide repeat, ankyrin repeat and coi |
| 3.71 | HOXB6 | Homeo box B6 | -3.80 — | — |
| 3.71 | — | CDNA FLJ10151 fis, clone HEMBA1003402 | -3.80 MMP25 | matrix metallopeptidase 25 |
| -3.71 | FAM83H | family with sequence similarity 83, member H | -3.80 — | — |
| 3.71 | — | CDNA FLJ38345 fis, clone FCBBF3028671 | 3.79 LRRN3 | leucine rich repeat neuronal 3 |
| -3.71 | SERINC5 | Serine incorporator 5 | 3.79 LOC387755 | hypothetical protein |
| -3.71 | GATA2 | GATA binding protein 2 | -3.79 STAT6 | signal transducer and activator of transcription |
| -3.71 | AMIGO2 | adhesion molecule with Ig-like domain 2 | -3.79 GPD2 | glycerol-3-phosphate dehydrogenase 2 (mitoch |
| -3.71 | KIAA1305 | KIAA1305 | -3.79 PAPSS2 | 3'-phosphoadenosine 5'-phosphosulfate synth |
| -3.71 | — | — | -3.79 C20orf59 | chromosome 20 open reading frame 59 |
| 3.71 | — | — | 3.79 NEFM | neurofilament, medium polypeptide 150kDa |
| 3.71 | APBA2 | amyloid beta (A4) precursor protein-binding, fa | -3.79 — | Transcribed locus, weakly similar to NP_00101 |
| 3.70 | HCN1 | hyperpolarization activated cyclic nucleotide-ga | -3.79 NINJ2 | Ninjurin 2 |
| -3.70 | — | — | -3.78 FAM124B | family with sequence similarity 124B |
| 3.70 | MSRB3 | methionine sulfoxide reductase B3 | -3.78 SCG5 | secretogranin V (7B2 protein) |

Appendix 1

| Value | Symbol | Description |
|---|---|---|
| 3.70 | LOC283400 | hypothetical protein LOC283400 |
| -3.70 | HTATIP2 | HIV-1 Tat interactive protein 2, 30kDa |
| -3.70 | MUC4 | mucin 4, cell surface associated |
| 3.70 | — | Homo sapiens, clone IMAGE:5245882, mRNA |
| 3.70 | — | — |
| -3.69 | PLAC1 | placenta-specific 1 |
| -3.69 | FLJ20449 | hypothetical protein FLJ20449 |
| 3.69 | — | Full-length cDNA clone CS0DC002YJ17 of Neu |
| -3.68 | KCND2 | potassium voltage-gated channel, Shal-related |
| -3.68 | — | Transcribed locus |
| -3.68 | CACNA2D1 | calcium channel, voltage-dependent, alpha 2/d |
| -3.68 | — | — |
| 3.68 | KIAA0408 | KIAA0408 |
| -3.67 | THRB | thyroid hormone receptor, beta (erythroblastic |
| -3.67 | — | CDNA clone IMAGE:5285271 |
| 3.67 | IKZF1 | IKAROS family zinc finger 1 (Ikaros) |
| 3.67 | LOC284361 | Hematopoietic signal peptide-containing |
| -3.67 | PERP | PERP, TP53 apoptosis effector |
| -3.67 | PIK3CD | phosphoinositide-3-kinase, catalytic, delta poly |
| -3.67 | PTPRC | Protein tyrosine phosphatase, receptor type, C |
| -3.67 | PTGIS | prostaglandin I2 (prostacyclin) synthase |
| 3.67 | SLC26A10 | solute carrier family 26, member 10 |
| -3.67 | — | — |
| -3.67 | — | Transcribed locus |
| 3.66 | LYPD1 | LY6/PLAUR domain containing 1 |
| -3.66 | DBC1 | deleted in bladder cancer 1 |
| -3.66 | SAMD4A | sterile alpha motif domain containing 4A |
| -3.66 | NR5A2 | nuclear receptor subfamily 5, group A, member |
| -3.66 | TJP3 | tight junction protein 3 (zona occludens 3) |
| 3.66 | LGR5 | leucine-rich repeat-containing G protein-couple |
| 3.65 | LOC283658 | hypothetical protein LOC283658 |
| 3.65 | LHFP | Lipoma HMGIC fusion partner |
| 3.65 | C14orf162 | chromosome 14 open reading frame 162 |
| 3.65 | TFDP2 | Transcription factor Dp-2 (E2F dimerization pa |
| -3.65 | SGK3 | serum/glucocorticoid regulated kinase family, |
| -3.65 | CALCR | calcitonin receptor |
| -3.65 | SLC7A7 | solute carrier family 7 (cationic amino acid tran |
| -3.65 | PLA2G2A | phospholipase A2, group IIA (platelets, synovia |
| 3.65 | PRDM16 | PR domain containing 16 |
| 3.65 | CRYGC | crystallin, gamma C |
| 3.65 | SARM1 | sterile alpha and TIR motif containing 1 |
| -3.64 | CCDC69 | coiled-coil domain containing 69 |
| 3.64 | — | Transcribed locus |
| -3.64 | — | Transcribed locus, moderately similar to XP_5 |
| -3.64 | — | — |
| 3.64 | TUBB2B | Tubulin, beta 2B |
| 3.64 | — | CDNA FLJ34815 fis, clone NT2NE2007786 |
| -3.64 | ZNF204 | zinc finger protein 204 |
| 3.64 | HADHA | Hydroxyacyl-Coenzyme A dehydrogenase/3-ke |
| 3.64 | GLT25D2 | glycosyltransferase 25 domain containing 2 |
| 3.64 | CTNND2 | catenin (cadherin-associated protein), delta 2 ( |
| 3.63 | PRKXP1 | protein kinase, X-linked, pseudogene 1 |
| 3.63 | — | Hypothetical gene supported by BC008046 |
| 3.63 | FJX1 | four jointed box 1 (Drosophila) |
| 3.63 | IGSF4C | immunoglobulin superfamily, member 4C |
| -3.63 | LOC644242 | Hypothetical protein LOC644242 |
| 3.62 | PHF11 | PHD finger protein 11 |
| 3.62 | CREBBP | CREB binding protein (Rubinstein-Taybi syndro |
| -3.62 | HSPB8 | heat shock 22kDa protein 8 |
| 3.62 | BAALC | brain and acute leukemia, cytoplasmic |
| -3.62 | LOC729890 /// LOC | hypothetical protein LOC729890 /// hypothetica |
| -3.62 | — | CDNA clone IMAGE:5532261 |
| 3.61 | LRRN3 | leucine rich repeat neuronal 3 |
| -3.61 | GSDMDC1 | gasdermin domain containing 1 |
| 3.61 | C1orf186 | chromosome 1 open reading frame 186 |
| -3.61 | PYY | peptide YY |
| 3.60 | LOC654342 | Similar to lymphocyte-specific protein 1 |
| 3.60 | REEP1 | receptor accessory protein 1 |
| 3.60 | NRXN3 | neurexin 3 |
| 3.60 | MCF2L | MCF.2 cell line derived transforming sequence |
| 3.60 | — | CDNA FLJ34826 fis, clone NT2NE2008803 |
| 3.60 | — | CDNA FLJ30897 fis, clone FEBRA2005476 |
| -3.60 | C21orf88 | chromosome 21 open reading frame 88 |
| -3.59 | ABCC13 | ATP-binding cassette, sub-family C (CFTR/MR |
| 3.59 | TMED4 | transmembrane emp24 protein transport doma |
| -3.59 | PRSS2 | protease, serine, 2 (trypsin 2) |
| 3.59 | — | — |
| 3.59 | B3GNT5 | UDP-GlcNAc:betaGal beta-1,3-N-acetylglucos |
| -3.59 | — | CDNA FLJ32963 fis, clone TESTI2008405 |
| -3.78 | BIC | BIC transcript |
| -3.78 | C18orf1 | chromosome 18 open reading frame 1 |
| -3.78 | FAM46D | family with sequence similarity 46, member D |
| -3.78 | LOC728377 | Similar to rho guanine nucleotide exchange fac |
| 3.78 | ASTN1 | astrotactin 1 |
| -3.78 | PHLDA2 | pleckstrin homology-like domain, family A, mer |
| -3.78 | F2RL1 | coagulation factor II (thrombin) receptor-like 1 |
| -3.78 | — | — |
| 3.77 | PRSS23 | protease, serine, 23 |
| 3.77 | — | CDNA FLJ36413 fis, clone THYMU2010816 |
| -3.77 | EDIL3 | EGF-like repeats and discoidin I-like domains |
| 3.77 | FLJ12057 | Hypothetical protein FLJ12057 |
| -3.76 | — | Transcribed locus |
| 3.76 | CLIPR-59 | CLIP-170-related protein |
| -3.76 | ESPN | espin |
| -3.76 | BNC1 | basonuclin 1 |
| 3.76 | REEP1 | receptor accessory protein 1 |
| -3.76 | PDE4A | phosphodiesterase 4A, cAMP-specific (phosph |
| -3.75 | AFMID | Arylformamidase |
| -3.75 | PTPLAD2 | protein tyrosine phosphatase-like A domain co |
| -3.75 | LRRC2 | leucine rich repeat containing 2 |
| -3.75 | DHDH | dihydrodiol dehydrogenase (dimeric) |
| -3.75 | MOG | myelin oligodendrocyte glycoprotein |
| 3.75 | — | — |
| -3.75 | SLC39A4 | solute carrier family 39 (zinc transporter), mem |
| 3.75 | LRRN3 | leucine rich repeat neuronal 3 |
| -3.75 | STYX /// LOC73043 | serine/threonine/tyrosine interacting protein /// |
| -3.75 | DIAPH2 | diaphanous homolog 2 (Drosophila) |
| 3.75 | — | — |
| -3.75 | ZNF395 | zinc finger protein 395 |
| -3.75 | FAM20A | Family with sequence similarity 20, member A |
| 3.74 | DMRTC1 /// LOC72 | DMRT-like family C1 /// similar to doublesex an |
| 3.74 | ARL4C | ADP-ribosylation factor-like 4C |
| -3.74 | UNC5D | Unc-5 homolog D (C. elegans) |
| -3.74 | TRY6 | trypsinogen C |
| 3.74 | SARM1 | sterile alpha and TIR motif containing 1 |
| 3.74 | SYT11 | synaptotagmin XI |
| -3.74 | BCL11A | B-cell CLL/lymphoma 11A (zinc finger protein) |
| -3.74 | FLJ11286 | hypothetical protein FLJ11286 |
| 3.74 | LOC388419 | similar to Galectin-3 binding protein precursor |
| 3.74 | SLC26A10 | solute carrier family 26, member 10 |
| 3.74 | TAGLN | transgelin |
| -3.73 | — | — |
| 3.73 | — | — |
| 3.73 | ST8SIA4 | ST8 alpha-N-acetyl-neuraminide alpha-2,8-sial |
| -3.73 | — | CDNA clone IMAGE:4819775 |
| 3.73 | — | — |
| 3.73 | PALLD | palladin, cytoskeletal associated protein |
| -3.73 | — | — |
| -3.73 | C1S | complement component 1, s subcomponent |
| -3.73 | RAB3B | RAB3B, member RAS oncogene family |
| -3.73 | HTATIP2 | HIV-1 Tat interactive protein 2, 30kDa |
| -3.72 | — | — |
| 3.72 | — | — |
| -3.72 | AP4E1 | adaptor-related protein complex 4, epsilon 1 su |
| 3.72 | — | Transcribed locus |
| 3.72 | C10orf32 | chromosome 10 open reading frame 32 |
| -3.72 | RUNX1T1 | runt-related transcription factor 1; translocated |
| -3.72 | C21orf30 | chromosome 21 open reading frame 30 |
| -3.72 | — | — |
| 3.72 | LOC130951 | hypothetical protein BC014602 |
| -3.72 | TMEPAI | transmembrane, prostate androgen induced RI |
| -3.72 | CLCN5 /// PCYT1B | chloride channel 5 (nephrolithiasis 2, X-linked, |
| 3.72 | SNCA | synuclein, alpha (non A4 component of amyloi |
| -3.71 | OTX2 | orthodenticle homolog 2 (Drosophila) |
| -3.71 | AKR1C3 | aldo-keto reductase family 1, member C3 (3-al |
| -3.71 | C1orf183 | chromosome 1 open reading frame 183 |
| -3.71 | SLFN13 | schlafen family member 13 |
| 3.71 | PLA2G4A | phospholipase A2, group IVA (cytosolic, calciu |
| -3.71 | CAV2 | caveolin 2 |
| -3.71 | — | — |
| -3.71 | HHLA1 | HERV-H LTR-associating 1 |
| -3.71 | HLA-C /// LOC7320 | major histocompatibility complex, class I, C /// |
| -3.71 | APOBEC3C | apolipoprotein B mRNA editing enzyme, cataly |
| -3.71 | — | CDNA clone IMAGE:5262752 |
| 3.71 | TADA1L | Transcriptional adaptor 1 (HFI1 homolog, yeas |
| 3.71 | SCML1 | Sex comb on midleg-like 1 (Drosophila) |
| 3.71 | FZD10 | frizzled homolog 10 (Drosophila) |
| -3.71 | TAF4B | TAF4b RNA polymerase II, TATA box binding |

Appendix 1

| | | | | |
|---|---|---|---|---|
| -3.59 CD9 | CD9 molecule | | -3.71 — | — |
| -3.59 — | — | | -3.71 — | Transcribed locus |
| -3.59 — | — | | 3.71 HOXA11 | homeobox A11 |
| -3.58 SLC9A7 | solute carrier family 9 (sodium/hydrogen excha | | -3.70 KLHDC7A | kelch domain containing 7A |
| 3.58 LOC387790 | hypothetical LOC387790 | | 3.70 — | Full-length cDNA clone CS0DI042YD07 of Pla |
| 3.58 9-Mar | membrane-associated ring finger (C3HC4) 9 | | 3.70 DPYSL4 | dihydropyrimidinase-like 4 |
| 3.58 — | CDNA FLJ36413 fis, clone THYMU2010816 | | 3.70 — | — |
| -3.58 HYAL1 | hyaluronoglucosaminidase 1 | | -3.69 BSPRY | B-box and SPRY domain containing |
| -3.58 CTH | cystathionase (cystathionine gamma-lyase) | | 3.69 — | Homo sapiens, clone IMAGE:5245882, mRNA |
| -3.58 — | — | | -3.69 PDE5A | phosphodiesterase 5A, cGMP-specific |
| 3.58 MEGF9 | multiple EGF-like-domains 9 | | 3.69 WDR17 | WD repeat domain 17 |
| 3.58 — | — | | -3.69 THY1 | Thy-1 cell surface antigen |
| 3.58 C20orf102 | chromosome 20 open reading frame 102 | | 3.69 — | — |
| -3.57 GCNT2 | glucosaminyl (N-acetyl) transferase 2, I-branch | | -3.68 SGK3 | serum/glucocorticoid regulated kinase family, n |
| -3.57 BARX1 | BarH-like homeobox 1 | | -3.68 — | — |
| -3.57 SLC39A14 | solute carrier family 39 (zinc transporter), mem | | 3.68 AGTR1 | angiotensin II receptor, type 1 |
| -3.57 OSBPL10 | oxysterol binding protein-like 10 | | -3.68 MARVELD3 | MARVEL domain containing 3 |
| 3.57 DPYSL4 | dihydropyrimidinase-like 4 | | 3.67 SDHALP2 | succinate dehydrogenase complex, subunit A, |
| -3.57 RRP22 | RAS-related on chromosome 22 | | -3.67 ARSJ | arylsulfatase family, member J |
| 3.57 FLJ10159 | Hypothetical protein FLJ10159 | | -3.67 C21orf88 | chromosome 21 open reading frame 88 |
| 3.57 COL9A1 | collagen, type IX, alpha 1 | | 3.67 — | Homo sapiens, clone IMAGE:3922927, mRNA |
| -3.57 LOC152195 | hypothetical protein LOC152195 | | -3.66 RPP25 | ribonuclease P 25kDa subunit |
| 3.57 KIAA0644 | KIAA0644 gene product | | 3.66 PYGO1 | pygopus homolog 1 (Drosophila) |
| 3.57 QKI | quaking homolog, KH domain RNA binding (m | | -3.66 SGK | serum/glucocorticoid regulated kinase |
| 3.56 ING3 | inhibitor of growth family, member 3 | | 3.66 — | Homo sapiens, Similar to neuronal thread prot |
| -3.56 CAV1 | caveolin 1, caveolae protein, 22kDa | | -3.66 — | — |
| 3.56 IQCH | IQ motif containing H | | -3.66 — | — |
| 3.56 — | — | | -3.66 ASAM | adipocyte-specific adhesion molecule |
| -3.56 TRY6 | trypsinogen C | | -3.65 LDHC | lactate dehydrogenase C |
| 3.56 TUBB1 | Tubulin, beta 1 | | 3.65 GBP3 | guanylate binding protein 3 |
| 3.56 — | — | | 3.65 PCSK6 | proprotein convertase subtilisin/kexin type 6 |
| -3.56 — | — | | -3.65 COL5A1 | collagen, type V, alpha 1 |
| -3.55 DYSF | dysferlin, limb girdle muscular dystrophy 2B (a | | 3.65 ST8SIA4 | ST8 alpha-N-acetyl-neuraminide alpha-2,8-sia |
| 3.55 FAM5C | family with sequence similarity 5, member C | | 3.65 C4orf31 | Chromosome 4 open reading frame 31 |
| 3.55 CDKN2C | cyclin-dependent kinase inhibitor 2C (p18, inhi | | 3.65 — | CDNA FLJ25677 fis, clone TST04054 |
| 3.55 — | CDNA FLJ25677 fis, clone TST04054 | | -3.65 — | — |
| 3.55 WNT7B /// LOC647 | wingless-type MMTV integration site family, me | | 3.65 SLC16A14 | solute carrier family 16, member 14 (monocarb |
| 3.55 C7orf16 | chromosome 7 open reading frame 16 | | -3.65 FLJ44894 | similar to zinc finger protein 91 |
| -3.54 OCLN /// NAIP | occludin /// similar to Occludin | | -3.65 TJP2 | Tight junction protein 2 (zona occludens 2) |
| 3.54 AUTS2 | Autism susceptibility candidate 2 | | -3.64 MGAT4C | mannosyl (alpha-1,3-)-glycoprotein beta-1,4-N- |
| 3.54 — | — | | -3.64 RASL12 | RAS-like, family 12 |
| -3.54 CDCP1 | CUB domain containing protein 1 | | -3.64 — | — |
| 3.54 CHRNA7 | Cholinergic receptor, nicotinic, alpha polypepti | | 3.64 — | CDNA FLJ34826 fis, clone NT2NE2008803 |
| 3.54 — | — | | 3.64 MAPK11 | mitogen-activated protein kinase 11 |
| -3.54 — | — | | -3.64 TMPRSS11E /// LO | transmembrane protease, serine 11E /// simila |
| -3.54 — | CDNA clone IMAGE:5284367 | | 3.64 — | — |
| 3.53 SIX4 | sine oculis homeobox homolog 4 (Drosophila) | | 3.64 FSIP1 | fibrous sheath interacting protein 1 |
| -3.53 — | — | | 3.64 — | — |
| -3.53 SYN2 | synapsin II | | 3.64 — | MRNA; cDNA DKFZp566F0224 (from clone Dk |
| -3.53 ACVR1C | activin A receptor, type IC | | 3.64 FLJ42117 | FLJ42117 protein |
| 3.53 DLX1 | distal-less homeobox 1 | | -3.63 CRIP3 | cysteine-rich protein 3 |
| 3.53 D2HGDH | D-2-hydroxyglutarate dehydrogenase | | -3.63 — | — |
| 3.53 NEK4 | NIMA (never in mitosis gene a)-related kinase | | 3.63 LOC219688 | hypothetical protein LOC219688 |
| 3.53 — | — | | -3.63 ADCY2 | adenylate cyclase 2 (brain) |
| 3.53 ENPP2 | ectonucleotide pyrophosphatase/phosphodiest | | 3.63 — | — |
| 3.53 LOC400954 | similar to echinoderm microtubule associated p | | 3.63 — | — |
| 3.52 CNNM3 | Cyclin M3 | | -3.63 LOC730399 /// LOC | hypothetical protein LOC730399 /// hypothetica |
| 3.52 FAM13C1 | family with sequence similarity 13, member C1 | | 3.63 WHSC2 | Wolf-Hirschhorn syndrome candidate 2 |
| -3.52 — | MRNA; cDNA DKFZp564C203 (from clone DK | | -3.62 — | Full length insert cDNA YN57B01 |
| 3.52 — | Transcribed locus | | 3.62 FLJ31485 | hypothetical gene supported by AK056047; AK |
| 3.52 FOXP4 | forkhead box P4 | | -3.62 MYOZ3 | myozenin 3 |
| -3.52 SLC7A8 | solute carrier family 7 (cationic amino acid tran | | -3.62 — | Surfactant associated protein F mRNA, partial |
| -3.52 DPPA4 | developmental pluripotency associated 4 | | -3.62 TIMP4 | TIMP metallopeptidase inhibitor 4 |
| -3.52 — | Transcribed locus | | -3.62 LOC285547 | hypothetical protein LOC285547 |
| 3.52 ZNF3 | zinc finger protein 3 | | -3.62 — | — |
| -3.52 — | — | | 3.62 GPR54 | G protein-coupled receptor 54 |
| 3.52 CP | ceruloplasmin (ferroxidase) | | -3.62 — | — |
| 3.52 POU3F4 | POU domain, class 3, transcription factor 4 | | -3.62 — | — |
| 3.52 ID4 | inhibitor of DNA binding 4, dominant negative | | -3.62 CAPN6 | calpain 6 |
| -3.52 HSPA2 | heat shock 70kDa protein 2 | | 3.62 GSTM3 | glutathione S-transferase M3 (brain) |
| -3.52 RPL21 | Ribosomal protein L21 | | 3.62 — | — |
| 3.52 C13orf21 | Chromosome 13 open reading frame 21 | | -3.61 TRAF3IP2 | TRAF3 interacting protein 2 |
| -3.51 MYLIP | myosin regulatory light chain interacting protei | | 3.61 — | — |
| 3.51 EP400 | E1A binding protein p400 | | -3.61 UGT8 | UDP glycosyltransferase 8 (UDP-galactose cer |
| -3.51 PERP | PERP, TP53 apoptosis effector | | -3.61 P2RX5 | purinergic receptor P2X, ligand-gated ion chan |
| -3.51 SVEP1 | sushi, von Willebrand factor type A, EGF and p | | -3.61 LOC115749 | hypothetical protein LOC115749 |
| -3.51 — | — | | 3.61 SULF1 | sulfatase 1 |
| 3.51 — | — | | 3.61 NMNAT2 | nicotinamide nucleotide adenylyltransferase 2 |
| 3.51 — | — | | 3.61 — | — |

Appendix 1

| Value | Symbol | Description |
|---|---|---|
| -3.51 | LOC255104 | Transmembrane and coiled-coil domains 4 |
| -3.51 | — | — |
| 3.51 | LOC339742 /// LOC | hypothetical protein LOC339742 /// hypothetica |
| 3.51 | MBD2 | methyl-CpG binding domain protein 2 |
| 3.51 | — | CDNA FLJ30128 fis, clone BRACE1000124 |
| 3.51 | — | — |
| 3.50 | LOC254559 | hypothetical protein LOC254559 |
| -3.50 | SH3GL3 | SH3-domain GRB2-like 3 |
| 3.50 | — | CDNA clone IMAGE:5303499 |
| 3.50 | — | Homo sapiens, Similar to neuronal thread prote |
| 3.50 | ZFHX4 | zinc finger homeodomain 4 |
| 3.50 | — | — |
| -3.50 | LHX8 | LIM homeobox 8 |
| -3.50 | CTH | cystathionase (cystathionine gamma-lyase) |
| -3.50 | FLJ36848 | hypothetical LOC647115 |
| 3.50 | FLJ23322 | hypothetical protein FLJ23322 |
| 3.50 | MBNL2 | muscleblind-like 2 (Drosophila) |
| -3.50 | BAIAP2L1 | BAI1-associated protein 2-like 1 |
| 3.50 | HOXB4 | homeobox B4 |
| 3.50 | FLJ90757 | hypothetical protein LOC440465 |
| -3.50 | PTRF | polymerase I and transcript release factor |
| 3.49 | — | — |
| 3.49 | FLJ39198 | Hypothetical protein LOC643763 |
| -3.49 | TTC9 | tetratricopeptide repeat domain 9 |
| -3.49 | KLF8 | Kruppel-like factor 8 |
| -3.49 | DDB2 | damage-specific DNA binding protein 2, 48kDa |
| 3.49 | BSN | bassoon (presynaptic cytomatrix protein) |
| -3.49 | PRKCQ | protein kinase C, theta |
| -3.49 | HPN | hepsin (transmembrane protease, serine 1) |
| 3.48 | TMEM178 | transmembrane protein 178 |
| -3.48 | TPD52L1 | tumor protein D52-like 1 |
| 3.48 | BTBD9 | BTB (POZ) domain containing 9 |
| -3.48 | — | — |
| -3.48 | SLC16A5 | solute carrier family 16, member 5 (monocarbo |
| 3.48 | WFDC1 | WAP four-disulfide core domain 1 |
| 3.48 | ACACA | Acetyl-Coenzyme A carboxylase alpha |
| -3.48 | olfactory receptor, f | CDNA FLJ11504 fis, clone HEMBA1002119 |
| 3.47 | C8orf46 | chromosome 8 open reading frame 46 |
| 3.47 | SETBP1 | SET binding protein 1 |
| 3.47 | LOC389362 | hypothetical LOC389362 |
| 3.47 | — | CDNA FLJ38252 fis, clone FCBBF3000269 |
| 3.47 | — | Transcribed locus |
| 3.47 | NRG1 | neuregulin 1 |
| 3.47 | PRKCE | protein kinase C, epsilon |
| -3.46 | UTS2 | urotensin 2 |
| -3.46 | BLVRB | biliverdin reductase B (flavin reductase (NADP |
| -3.46 | — | — |
| 3.46 | — | — |
| 3.46 | — | CDNA FLJ11723 fis, clone HEMBA1005314 |
| 3.46 | CDH10 | cadherin 10, type 2 (T2-cadherin) |
| -3.46 | FLT1 | fms-related tyrosine kinase 1 (vascular endothe |
| 3.46 | ODC1 | ornithine decarboxylase 1 |
| 3.45 | — | Transcribed locus |
| 3.45 | ID4 | Inhibitor of DNA binding 4, dominant negative |
| 3.45 | TNRC4 | trinucleotide repeat containing 4 |
| -3.45 | SLC7A8 | solute carrier family 7 (cationic amino acid tran |
| 3.45 | — | Transcribed locus |
| 3.45 | — | MRNA; cDNA DKFZp686E22185 (from clone D |
| -3.45 | — | — |
| -3.45 | HOOK1 | hook homolog 1 (Drosophila) |
| -3.45 | TMEM37 | transmembrane protein 37 |
| -3.44 | EFCBP1 | EF-hand calcium binding protein 1 |
| -3.44 | F2RL1 | coagulation factor II (thrombin) receptor-like 1 |
| 3.44 | — | CDNA clone IMAGE:4811567 |
| -3.44 | NFATC3 | Nuclear factor of activated T-cells, cytoplasmic |
| 3.44 | PRSS23 | protease, serine, 23 |
| -3.44 | KLF8 | Kruppel-like factor 8 |
| -3.44 | — | Homo sapiens, clone IMAGE:5742196, mRNA |
| 3.44 | GNGT1 | guanine nucleotide binding protein (G protein), |
| -3.44 | COL4A4 | collagen, type IV, alpha 4 |
| 3.44 | NMNAT2 | nicotinamide nucleotide adenylyltransferase 2 |
| 3.44 | — | — |
| -3.44 | MME | membrane metallo-endopeptidase (neutral end |
| -3.44 | RORA | RAR-related orphan receptor A |
| 3.44 | — | — |
| -3.43 | CACNA2D3 | calcium channel, voltage-dependent, alpha 2/d |
| 3.43 | DPF1 | D4, zinc and double PHD fingers family 1 |
| 3.43 | PLA2G4A | phospholipase A2, group IVA (cytosolic, calciu |
| 3.43 | ZNF771 | zinc finger protein 771 |
| 3.61 | ID4 | inhibitor of DNA binding 4, dominant negative |
| -3.61 | MTMR11 | myotubularin related protein 11 |
| -3.61 | CD44 | CD44 molecule (Indian blood group) |
| 3.61 | NEFL | neurofilament, light polypeptide 68kDa |
| -3.60 | — | — |
| -3.60 | BOK | BCL2-related ovarian killer |
| 3.60 | OGFOD1 | 2-oxoglutarate and iron-dependent oxygenase |
| 3.60 | — | — |
| 3.60 | RHOBTB2 | Rho-related BTB domain containing 2 |
| -3.60 | EPB41L4B | erythrocyte membrane protein band 4.1 like 4B |
| -3.60 | ST14 | suppression of tumorigenicity 14 (colon carcino |
| 3.60 | — | Transcribed locus |
| -3.59 | ATP1A2 | ATPase, Na+/K+ transporting, alpha 2 (+) poly |
| -3.59 | CTSL2 | Cathepsin L2 |
| 3.59 | NEFL | neurofilament, light polypeptide 68kDa |
| -3.59 | — | — |
| -3.59 | ZNF204 | zinc finger protein 204 |
| -3.59 | TG | Thyroglobulin |
| 3.59 | GALNTL1 | UDP-N-acetyl-alpha-D-galactosamine:polypept |
| -3.59 | CASP8 | caspase 8, apoptosis-related cysteine peptidas |
| -3.58 | GM2A | GM2 ganglioside activator |
| -3.58 | ALDH1A1 | aldehyde dehydrogenase 1 family, member A1 |
| 3.58 | FGF9 | fibroblast growth factor 9 (glia-activating factor) |
| 3.58 | WDR17 | WD repeat domain 17 |
| 3.58 | — | — |
| 3.58 | — | Transcribed locus |
| -3.58 | OLFM2 | olfactomedin 2 |
| 3.57 | — | — |
| 3.57 | CHRNA7 | Cholinergic receptor, nicotinic, alpha polypeptid |
| 3.57 | MBOAT5 | Membrane bound O-acyltransferase domain co |
| 3.57 | PON2 | paraoxonase 2 |
| -3.57 | KIAA0513 | KIAA0513 |
| -3.57 | — | — |
| 3.57 | — | MRNA; cDNA DKFZp686I18116 (from clone D |
| 3.57 | — | — |
| -3.57 | SLC2A3 | solute carrier family 2 (facilitated glucose trans |
| 3.56 | HOXA4 | homeobox A4 |
| -3.56 | LOC155036 | hypothetical protein LOC155036 |
| -3.56 | NFIA | Nuclear factor I/A |
| 3.55 | FLJ23577 | KPL2 protein |
| 3.55 | HS3ST3B1 | heparan sulfate (glucosamine) 3-O-sulfotransfe |
| 3.55 | EPHB2 | EPH receptor B2 |
| -3.55 | CACNB2 | calcium channel, voltage-dependent, beta 2 su |
| -3.55 | CDCP1 | CUB domain containing protein 1 |
| -3.55 | — | — |
| 3.55 | — | — |
| -3.55 | — | — |
| -3.55 | FLJ30707 | hypothetical protein FLJ30707 |
| 3.55 | — | Full length insert cDNA clone ZA88B06 |
| -3.55 | POLR3G | polymerase (RNA) III (DNA directed) polypepti |
| -3.55 | — | — |
| -3.54 | — | C33,6 unnamed HERV-H protein |
| 3.54 | — | — |
| 3.54 | CAMK2D | Calcium/calmodulin-dependent protein kinase |
| 3.54 | KCNJ4 | potassium inwardly-rectifying channel, subfami |
| -3.54 | B3GNT2 | UDP-GlcNAc:betaGal beta-1,3-N-acetylglucos |
| -3.54 | — | — |
| -3.54 | MMP23B /// MMP23 | matrix metallopeptidase 23B /// matrix metallop |
| -3.54 | CLDN3 | claudin 3 |
| -3.54 | SSTR2 | somatostatin receptor 2 |
| 3.53 | FOXJ1 | Forkhead box J1 |
| -3.53 | AMIGO2 | adhesion molecule with Ig-like domain 2 |
| -3.53 | EDN1 | endothelin 1 |
| -3.53 | — | — |
| -3.53 | LDHA | lactate dehydrogenase A |
| -3.53 | ZNF436 | zinc finger protein 436 |
| -3.53 | ANTXR1 | anthrax toxin receptor 1 |
| -3.52 | CCL3 /// CCL3L1 /// | chemokine (C-C motif) ligand 3 /// chemokine ( |
| -3.52 | C1QL1 | complement component 1, q subcomponent-lik |
| -3.52 | SLC24A3 | solute carrier family 24 (sodium/potassium/calc |
| 3.52 | AMPH | amphiphysin (Stiff-Man syndrome with breast c |
| -3.52 | IGFBP7 | insulin-like growth factor binding protein 7 |
| 3.51 | PEX5L | peroxisomal biogenesis factor 5-like |
| 3.51 | — | Transcribed locus |
| 3.51 | PRKCE | protein kinase C, epsilon |
| -3.51 | RBM15 | RNA binding motif protein 15 |
| 3.51 | — | — |
| 3.51 | — | — |

Appendix 1

| | | | |
|---|---|---|---|
| 3.43 RASGRP1 | RAS guanyl releasing protein 1 (calcium and D | -3.51 GCNT2 | glucosaminyl (N-acetyl) transferase 2, I-branch |
| 3.43 — | — | -3.51 CCL4 | chemokine (C-C motif) ligand 4 |
| 3.43 — | MRNA; cDNA DKFZp564E143 (from clone DK | -3.51 TWIST2 | twist homolog 2 (Drosophila) |
| 3.43 MCART6 | mitochondrial carrier triple repeat 6 | -3.51 ESRRB | Estrogen-related receptor beta |
| -3.43 TRAF3IP2 | TRAF3 interacting protein 2 | -3.50 ZDHHC23 | zinc finger, DHHC-type containing 23 |
| -3.42 TWIST2 | twist homolog 2 (Drosophila) | 3.50 FLJ90757 | hypothetical protein LOC440465 |
| 3.42 — | — | -3.50 SKIL | SKI-like |
| 3.42 — | — | -3.50 PLEKHG6 | pleckstrin homology domain containing, family |
| 3.42 TADA1L | Transcriptional adaptor 1 (HFI1 homolog, yeas | -3.50 TRIM38 | tripartite motif-containing 38 |
| 3.42 — | — | 3.50 ABCA8 | ATP-binding cassette, sub-family A (ABC1), m |
| -3.42 HAS3 | hyaluronan synthase 3 | -3.49 SGK3 | serum/glucocorticoid regulated kinase family, r |
| 3.42 MPPED2 | metallophosphoesterase domain containing 2 | -3.49 SLFN5 | schlafen family member 5 |
| 3.42 NEFM | neurofilament, medium polypeptide 150kDa | -3.49 ST6GAL1 | ST6 beta-galactosamide alpha-2,6-sialyltranfer |
| 3.41 — | — | 3.49 NAV2 | neuron navigator 2 |
| -3.41 — | — | -3.49 PLAU | plasminogen activator, urokinase |
| -3.41 EPB41L4B | erythrocyte membrane protein band 4.1 like 4B | -3.49 ADAMTS19 | ADAM metallopeptidase with thrombospondin |
| -3.41 SLC2A3 | solute carrier family 2 (facilitated glucose trans | 3.49 FAM13C1 | family with sequence similarity 13, member C1 |
| 3.41 — | Transcribed locus, weakly similar to XP_52063 | -3.49 POLR3G | polymerase (RNA) III (DNA directed) polypepti |
| -3.41 — | — | -3.49 GALNT14 | UDP-N-acetyl-alpha-D-galactosamine:polypep |
| 3.41 — | — | -3.49 — | — |
| 3.41 — | CDNA FLJ11554 fis, clone HEMBA1003037 | -3.48 C9orf64 | chromosome 9 open reading frame 64 |
| -3.41 IL1B | interleukin 1, beta | 3.48 — | — |
| 3.41 LRRTM2 | leucine rich repeat transmembrane neuronal 2 | -3.48 NFIB | nuclear factor I/B |
| 3.41 — | CDNA clone IMAGE:5271897 | -3.48 — | — |
| -3.41 GPRC5C | G protein-coupled receptor, family C, group 5, | -3.48 BIK | BCL2-interacting killer (apoptosis-inducing) |
| 3.41 HYMAI | hydatidiform mole associated and imprinted | -3.48 C9orf24 | chromosome 9 open reading frame 24 |
| 3.41 — | CDNA FLJ32491 fis, clone SKNSH1000308 | 3.48 NHLH1 | nescient helix loop helix 1 |
| 3.41 HS6ST2 | heparan sulfate 6-O-sulfotransferase 2 | 3.48 PROS1 | protein S (alpha) |
| -3.40 GNA14 | guanine nucleotide binding protein (G protein), | 3.48 WNT7A | wingless-type MMTV integration site family, me |
| 3.40 NCOA1 | Nuclear receptor coactivator 1 | -3.48 NMI | N-myc (and STAT) interactor |
| -3.40 TMC4 | transmembrane channel-like 4 | -3.48 ZHX2 | Zinc fingers and homeoboxes 2 |
| 3.40 — | — | -3.48 — | Transcribed locus |
| 3.40 — | Transcribed locus, strongly similar to XP_5294 | -3.47 — | Transcribed locus |
| -3.40 MFAP3L | microfibrillar-associated protein 3-like | 3.47 COL14A1 | collagen, type XIV, alpha 1 (undulin) |
| 3.40 — | CDNA: FLJ20929 fis, clone ADSE01218 | -3.47 LHX8 | LIM homeobox 8 |
| -3.40 GABRA5 | gamma-aminobutyric acid (GABA) A receptor, | 3.47 WDR78 /// SLC35D | WD repeat domain 78 /// Solute carrier family 3 |
| 3.40 CCNE2 | cyclin E2 | 3.47 D2HGDH | D-2-hydroxyglutarate dehydrogenase |
| -3.40 PPAP2C | phosphatidic acid phosphatase type 2C | 3.47 SV2C | synaptic vesicle glycoprotein 2C |
| -3.40 SMAD7 | SMAD family member 7 | -3.47 SFN | stratifin |
| -3.40 SLCO4C1 | solute carrier organic anion transporter family, | 3.47 ZNF37B | Zinc finger protein 37b (KOX 21) |
| 3.39 MLLT3 | myeloid/lymphoid or mixed-lineage leukemia (t | 3.47 LOC144363 | Hypothetical protein LOC144363 |
| 3.39 — | — | -3.46 LOC439949 | hypothetical gene supported by AY007155 |
| 3.39 — | — | -3.46 SLC5A12 | solute carrier family 5 (sodium/glucose cotrans |
| -3.39 — | — | -3.46 SOCS1 | suppressor of cytokine signaling 1 |
| -3.39 — | — | -3.46 GAS7 | growth arrest-specific 7 |
| 3.39 — | — | -3.46 FLI1 | Friend leukemia virus integration 1 |
| 3.39 GUCY1A3 | Guanylate cyclase 1, soluble, alpha 3 | 3.46 ENPP2 | ectonucleotide pyrophosphatase/phosphodiest |
| 3.39 SUHW4 | suppressor of hairy wing homolog 4 (Drosophil | 3.46 PRO1073 | PRO1073 protein |
| 3.39 LOC728052 /// LOC | Hypothetical protein LOC728052 /// Hematopoi | -3.46 FLT1 | Fms-related tyrosine kinase 1 (vascular endoth |
| 3.39 BOC | brother of CDO | 3.46 SOX3 | SRY (sex determining region Y)-box 3 |
| 3.38 PABPC5 | poly(A) binding protein, cytoplasmic 5 | 3.46 SARM1 | sterile alpha and TIR motif containing 1 |
| 3.38 RP13-401N8.2 | Hypothetical gene supported by BC042812 | -3.45 KLC3 | kinesin light chain 3 |
| 3.38 CLGN | calmegin | 3.45 — | — |
| 3.38 WDR17 | WD repeat domain 17 | 3.45 MLLT3 | myeloid/lymphoid or mixed-lineage leukemia (t |
| -3.38 PDLIM1 | PDZ and LIM domain 1 (elfin) | -3.45 PHACS | 1-aminocyclopropane-1-carboxylate synthase |
| -3.38 RAB37 | RAB37, member RAS oncogene family | -3.45 FLJ35934 | FLJ35934 protein |
| 3.38 SIDT1 | SID1 transmembrane family, member 1 | 3.45 — | — |
| 3.38 RERG | RAS-like, estrogen-regulated, growth inhibitor | -3.45 — | CDNA clone IMAGE:4792693 |
| 3.38 MCART6 | mitochondrial carrier triple repeat 6 | -3.45 ZNF788 | zinc finger family member 788 |
| -3.37 LNX1 | ligand of numb-protein X 1 | -3.45 DLC1 | deleted in liver cancer 1 |
| -3.37 TERF1 | telomeric repeat binding factor (NIMA-interactir | -3.44 VAMP5 | vesicle-associated membrane protein 5 (myobr |
| -3.37 FLT1 | Fms-related tyrosine kinase 1 (vascular endoth | 3.44 SNAP25 | Synaptosomal-associated protein, 25kDa |
| 3.37 FLJ33790 | hypothetical protein FLJ33790 | 3.44 ZNF276 | zinc finger protein 276 |
| 3.37 C1QTNF3 | C1q and tumor necrosis factor related protein 3 | -3.44 TMBIM1 | transmembrane BAX inhibitor motif containing |
| 3.37 KALRN | kalirin, RhoGEF kinase | -3.44 — | — |
| -3.37 — | — | -3.44 STOM | stomatin |
| -3.37 NR0B1 | nuclear receptor subfamily 0, group B, member | 3.44 ODC1 | ornithine decarboxylase 1 |
| -3.37 — | Full-length cDNA clone CS0DJ013YE21 of T c | -3.44 STEAP3 | STEAP family member 3 |
| 3.37 LOC133308 | hypothetical protein BC009732 | 3.44 | 9-Mar membrane-associated ring finger (C3HC4) 9 |
| 3.37 NEUROG3 | neurogenin 3 | -3.44 — | — |
| 3.37 LOC643911 /// LOC | hypothetical LOC643911 /// hypothetical protei | -3.43 PHF15 | PHD finger protein 15 |
| -3.37 GUCY2C | guanylate cyclase 2C (heat stable enterotoxin r | -3.43 — | — |
| 3.37 NRIP3 | Nuclear receptor interacting protein 3 | -3.43 ADAMTS19 | ADAM metallopeptidase with thrombospondin |
| 3.36 — | CDNA: FLJ23194 fis, clone REC00490 | 3.43 ASIP | Agouti signaling protein, nonagouti homolog (m |
| 3.36 — | CDNA FLJ35508 fis, clone SMINT2011958 | 3.43 — | MRNA; cDNA DKFZp686E22185 (from clone D |
| 3.36 — | — | 3.43 — | Transcribed locus |
| 3.36 — | — | 3.43 LOC133308 | hypothetical protein BC009732 |
| 3.36 RAB36 | RAB36, member RAS oncogene family | 3.43 GALP | galanin-like peptide precursor |
| -3.36 QPCT | glutaminyl-peptide cyclotransferase (glutaminyl | -3.43 MUC3B | mucin 3B, cell surface associated |

Appendix 1

| Value | Gene | Description |
|---|---|---|
| -3.36 | — | — |
| -3.36 | APOC1 | apolipoprotein C-I |
| -3.36 | — | CDNA FLJ33993 fis, clone DFNES2007757 |
| -3.36 | FBN3 | fibrillin 3 |
| 3.35 | YAF2 | YY1 associated factor 2 |
| -3.35 | FBXO2 | F-box protein 2 |
| -3.35 | SLC2A3 | solute carrier family 2 (facilitated glucose trans |
| 3.35 | C10orf32 | chromosome 10 open reading frame 32 |
| 3.35 | FLJ90757 | hypothetical protein LOC440465 |
| -3.35 | MICB | MHC class I polypeptide-related sequence E |
| 3.35 | FMN2 | formin 2 |
| 3.35 | PREX1 | phosphatidylinositol 3,4,5-trisphosphate-depen |
| -3.35 | — | — |
| 3.35 | ST8SIA4 | ST8 alpha-N-acetyl-neuraminide alpha-2,8-sial |
| -3.35 | ARHGAP4 | Rho GTPase activating protein 4 |
| 3.35 | NRXN3 | neurexin 3 |
| -3.35 | — | — |
| 3.35 | DCN | decorin |
| 3.35 | FSIP1 | fibrous sheath interacting protein 1 |
| 3.34 | SNCA | synuclein, alpha (non A4 component of amyloid |
| 3.34 | BGN /// TSHZ1 | biglycan /// teashirt family zinc finger 1 |
| 3.34 | SBF1 | SET binding factor 1 |
| -3.34 | ESPN | espin |
| -3.34 | STXBP2 | syntaxin binding protein 2 |
| -3.34 | GPX2 | glutathione peroxidase 2 (gastrointestinal) |
| -3.34 | PTPRU | protein tyrosine phosphatase, receptor type, U |
| 3.34 | — | Transcribed locus |
| 3.34 | TMEM106C | transmembrane protein 106C |
| -3.34 | — | Transcribed locus |
| 3.34 | — | — |
| -3.34 | GLS2 | glutaminase 2 (liver, mitochondrial) |
| -3.33 | — | — |
| 3.33 | PALLD | palladin, cytoskeletal associated protein |
| -3.33 | SLC27A6 | solute carrier family 27 (fatty acid transporter), |
| 3.33 | — | Full-length cDNA clone CS0DD005YM12 of Ne |
| 3.33 | ZNF276 | zinc finger protein 276 |
| -3.33 | PDE5A | phosphodiesterase 5A, cGMP-specific |
| 3.33 | NTRK2 | neurotrophic tyrosine kinase, receptor, type 2 |
| 3.33 | HOXB3 | homeobox B3 |
| -3.33 | — | CDNA: FLJ22478 fis, clone HRC10816 |
| 3.33 | LOC284262 | hypothetical protein LOC284262 |
| 3.33 | FRMD4A | FERM domain containing 4A |
| -3.32 | LOC285500 | hypothetical protein LOC285500 |
| 3.32 | EVI5 | ecotropic viral integration site 5 |
| -3.32 | — | — |
| 3.32 | METTL6 | methyltransferase like 6 |
| 3.32 | SOX6 | SRY (sex determining region Y)-box 6 |
| 3.32 | — | — |
| 3.32 | — | — |
| -3.32 | CASQ1 | calsequestrin 1 (fast-twitch, skeletal muscle) |
| -3.31 | — | — |
| 3.31 | SCD5 | stearoyl-CoA desaturase 5 |
| -3.31 | C1orf183 | chromosome 1 open reading frame 183 |
| -3.31 | IGSF1 | immunoglobulin superfamily, member 1 |
| -3.31 | SLC16A5 | solute carrier family 16, member 5 (monocarbo |
| 3.31 | ANKRD20A1 /// AN | ankyrin repeat domain 20 family, member A1 // |
| 3.31 | — | — |
| 3.30 | PSTPIP2 | proline-serine-threonine phosphatase interactir |
| -3.30 | MB | myoglobin |
| 3.30 | VAPB | VAMP (vesicle-associated membrane protein)- |
| 3.30 | PALLD | palladin, cytoskeletal associated protein |
| -3.30 | PPAP2A | phosphatidic acid phosphatase type 2A |
| -3.30 | SFN | stratifin |
| 3.30 | MAPK1 | Mitogen-activated protein kinase 1 |
| -3.30 | SERPINH1 | serpin peptidase inhibitor, clade H (heat shock |
| -3.30 | MGC45491 | Hypothetical protein MGC45491 |
| -3.30 | TRIM38 | tripartite motif-containing 38 |
| -3.30 | LPPR4 | plasticity related gene 1 |
| 3.29 | GAS1 | growth arrest-specific 1 |
| -3.29 | APOBEC3C | apolipoprotein B mRNA editing enzyme, cataly |
| 3.29 | NUP98 | nucleoporin 98kDa |
| -3.29 | HHEX | homeobox, hematopoietically expressed |
| -3.29 | MAF | v-maf musculoaponeurotic fibrosarcoma oncog |
| -3.29 | PPP2R2C | protein phosphatase 2 (formerly 2A), regulatory |
| -3.29 | KCNE3 | potassium voltage-gated channel, Isk-related fa |
| 3.29 | — | CDNA FLJ33441 fis, clone BRACE2021932 |
| 3.28 | PAX3 | paired box gene 3 (Waardenburg syndrome 1) |
| -3.28 | — | — |
| -3.28 | PHF15 | PHD finger protein 15 |
| -3.42 | ZNF429 | Zinc finger protein 429 |
| 3.42 | CD58 | CD58 molecule |
| -3.42 | NMRAL1 | NmrA-like family domain containing 1 |
| -3.42 | D4S234E | DNA segment on chromosome 4 (unique) 234 |
| -3.42 | MUC4 | mucin 4, cell surface associated |
| 3.42 | RBMS3 | RNA binding motif, single stranded interacting |
| -3.42 | CLDN3 | claudin 3 |
| 3.42 | ST18 | suppression of tumorigenicity 18 (breast carcin |
| -3.42 | — | — |
| -3.42 | FGF12 | fibroblast growth factor 12 |
| -3.41 | HLA-DPA1 | major histocompatibility complex, class II, DP a |
| -3.41 | KCNK1 | potassium channel, subfamily K, member 1 |
| -3.41 | CD97 | CD97 molecule |
| -3.41 | ATP6V0A4 | ATPase, H+ transporting, lysosomal V0 subuni |
| -3.41 | — | Homo sapiens, Similar to otoconin 90, clone IM |
| -3.41 | TJP3 | tight junction protein 3 (zona occludens 3) |
| -3.41 | — | — |
| 3.41 | FLJ39198 | Hypothetical protein LOC643762 |
| -3.41 | CADPS | Ca2+-dependent secretion activator |
| 3.41 | GAB2 | GRB2-associated binding protein 2 |
| 3.41 | — | — |
| -3.40 | MMP14 | matrix metallopeptidase 14 (membrane-inserte |
| 3.40 | — | CDNA FLJ11723 fis, clone HEMBA1005314 |
| 3.40 | — | — |
| 3.40 | PUNC | putative neuronal cell adhesion molecule |
| -3.40 | — | — |
| -3.40 | VAV1 | vav 1 oncogene |
| 3.40 | — | — |
| -3.40 | RYR2 | ryanodine receptor 2 (cardiac) |
| 3.40 | RASGRP1 | RAS guanyl releasing protein 1 (calcium and D |
| -3.40 | — | Transcribed locus, moderately similar to NP_8 |
| 3.40 | — | — |
| 3.40 | — | — |
| -3.40 | BARX1 | BarH-like homeobox 1 |
| 3.40 | — | — |
| 3.40 | — | — |
| -3.39 | ABCC13 | ATP-binding cassette, sub-family C (CFTR/MR |
| -3.39 | SLC43A3 | solute carrier family 43, member 3 |
| -3.39 | ATP1A4 | ATPase, Na+/K+ transporting, alpha 4 polypep |
| -3.39 | — | MRNA; cDNA DKFZp761H1023 (from clone DI |
| -3.39 | — | — |
| 3.39 | — | Transcribed locus, moderately similar to NP_0 |
| -3.39 | CABP1 | calcium binding protein 1 (calbrain) |
| -3.39 | — | — |
| -3.39 | — | CDNA FLJ32963 fis, clone TEST12008405 |
| -3.38 | HOOK1 | hook homolog 1 (Drosophila) |
| -3.38 | LOC730124 /// LOC | hypothetical protein LOC730124 /// hypothetica |
| -3.38 | SP110 | SP110 nuclear body protein |
| -3.38 | — | — |
| -3.38 | TA-NFKBH | T-cell activation NFKB-like protein |
| 3.38 | KRTAP21-1 | keratin associated protein 21-1 |
| 3.38 | — | CDNA FLJ30740 fis, clone FEBRA2000319 |
| 3.38 | — | — |
| 3.38 | DLX1 | distal-less homeobox 1 |
| 3.38 | SLC44A5 | solute carrier family 44, member 5 |
| -3.38 | IGFBP7 | insulin-like growth factor binding protein 7 |
| -3.38 | HLA-C | major histocompatibility complex, class I, C |
| 3.38 | MEGF9 | multiple EGF-like-domains 9 |
| -3.37 | — | CDNA clone IMAGE:5296510 |
| -3.37 | C14orf115 | chromosome 14 open reading frame 115 |
| 3.37 | PRKXP1 | protein kinase, X-linked, pseudogene 1 |
| 3.37 | — | CDNA clone IMAGE:4300887 |
| 3.37 | RBM24 | RNA binding motif protein 24 |
| 3.37 | GLRA2 | glycine receptor, alpha 2 |
| 3.37 | LOC645513 | Similar to septin 7 |
| -3.37 | EPPK1 | epiplakin 1 /// epiplakin 1 |
| 3.37 | — | — |
| 3.36 | — | — |
| 3.36 | ZHX1 | zinc fingers and homeoboxes 1 |
| -3.36 | FAM100A | family with sequence similarity 100, member A |
| 3.36 | LOC389895 | similar to CG4768-PA |
| 3.36 | SCOC | Short coiled-coil protein |
| 3.36 | AMDHD1 | amidohydrolase domain containing 1 |
| 3.36 | — | CDNA FLJ39389 fis, clone PLACE6003621 |
| -3.36 | TRPC6 | transient receptor potential cation channel, sub |
| -3.36 | MOBP | myelin-associated oligodendrocyte basic prote |
| -3.36 | HLA-C | major histocompatibility complex, class I, C |
| 3.36 | LOC284033 | hypothetical protein LOC284033 |
| 3.36 | NFE2L3 | Nuclear factor (erythroid-derived 2)-like 3 |

Appendix 1

| Value | Symbol | Description |
|---|---|---|
| -3.28 | SPINK2 | serine peptidase inhibitor, Kazal type 2 (acrosi |
| -3.28 | PAPSS2 | 3'-phosphoadenosine 5'-phosphosulfate synth |
| -3.28 | — | — |
| 3.27 | FKBP7 | FK506 binding protein 7 |
| 3.27 | PROX1 | Prospero-related homeobox 1 |
| 3.27 | FGFRL1 | fibroblast growth factor receptor-like 1 |
| 3.27 | APLP1 | amyloid beta (A4) precursor-like protein 1 |
| -3.27 | BIK | BCL2-interacting killer (apoptosis-inducing) |
| -3.27 | CD40 | CD40 molecule, TNF receptor superfamily mer |
| -3.27 | CACNA1A | Calcium channel, voltage-dependent, P/Q type |
| 3.26 | — | CDNA FLJ26539 fis, clone KDN09310 |
| -3.26 | SYTL1 | synaptotagmin-like 1 |
| -3.26 | PCTK3 | PCTAIRE protein kinase 3 |
| 3.26 | ZDHHC14 | zinc finger, DHHC-type containing 14 |
| 3.26 | COL14A1 | collagen, type XIV, alpha 1 (undulin) |
| 3.26 | — | — |
| -3.26 | HERC6 | hect domain and RLD 6 |
| 3.26 | C14orf152 | chromosome 14 open reading frame 152 |
| -3.26 | ADAMTS19 | ADAM metallopeptidase with thrombospondin |
| -3.26 | HTATIP2 | HIV-1 Tat interactive protein 2, 30kDa |
| -3.26 | LRRC2 | leucine rich repeat containing 2 |
| -3.25 | CADPS | Ca2+-dependent secretion activator |
| 3.25 | — | CDNA FLJ37366 fis, clone BRAMY2024416 |
| 3.25 | ATP9A | ATPase, Class II, type 9A |
| -3.25 | POLR3G | polymerase (RNA) III (DNA directed) polypepti |
| 3.25 | HOXA3 | Homeo box A3 |
| -3.25 | C20orf54 | chromosome 20 open reading frame 54 |
| 3.25 | CDH4 | cadherin 4, type 1, R-cadherin (retinal) |
| -3.25 | NS3TP2 | HCV NS3-transactivated protein 2 |
| 3.25 | — | — |
| -3.25 | KCNE3 | potassium voltage-gated channel, Isk-related f |
| -3.25 | GSTO2 | glutathione S-transferase omega 2 |
| 3.25 | — | Transcribed locus |
| -3.25 | ABCC13 | ATP-binding cassette, sub-family C (CFTR/MR |
| 3.25 | — | — |
| -3.24 | — | — |
| 3.24 | AMPH | amphiphysin (Stiff-Man syndrome with breast |
| 3.24 | CCDC73 | Coiled-coil domain containing 73 |
| -3.24 | MT2A | metallothionein 2A |
| -3.24 | — | — |
| -3.24 | C21orf88 | chromosome 21 open reading frame 88 |
| 3.24 | IAPP | islet amyloid polypeptide |
| 3.24 | — | — |
| -3.24 | IGSF4D | immunoglobulin superfamily, member 4D |
| 3.24 | GRIA3 | glutamate receptor, ionotrophic, AMPA 3 |
| -3.24 | — | — |
| -3.24 | LY6E | lymphocyte antigen 6 complex, locus E |
| -3.24 | FBLN5 | fibulin 5 |
| 3.24 | ATBF1 | AT-binding transcription factor 1 |
| 3.24 | FLJ14213 | hypothetical protein FLJ14213 |
| -3.24 | — | CDNA clone IMAGE:4733238 |
| -3.24 | — | CDNA clone IMAGE:5262438 |
| 3.23 | CCDC73 | Coiled-coil domain containing 73 |
| -3.23 | — | Transcribed locus, moderately similar to XP_4 |
| 3.23 | LIX1L | Lix1 homolog (mouse)-like |
| -3.23 | DIAPH2 | diaphanous homolog 2 (Drosophila) |
| 3.23 | — | Transcribed locus |
| 3.23 | HHAT | hedgehog acyltransferase |
| -3.23 | — | CDNA FLJ45450 fis, clone BRSTN2002691 |
| 3.23 | PSCD1 | Pleckstrin homology, Sec7 and coiled-coil dom |
| 3.23 | — | Transcribed locus |
| 3.22 | — | Full length insert cDNA clone ZD53C10 |
| -3.22 | ATP6V0A4 | ATPase, H+ transporting, lysosomal V0 subuni |
| 3.22 | — | — |
| -3.22 | DUSP13 | dual specificity phosphatase 13 |
| 3.22 | ANGPTL2 | angiopoietin-like 2 |
| 3.22 | RRAGD | Ras-related GTP binding D |
| -3.22 | HERC5 | hect domain and RLD 5 |
| -3.22 | — | CDNA FLJ32963 fis, clone TESTI2008405 |
| 3.22 | RNF175 | ring finger protein 175 |
| 3.22 | GRM1 | glutamate receptor, metabotropic 1 |
| 3.22 | STMN4 | stathmin-like 4 /// stathmin-like 4 |
| -3.21 | — | — |
| -3.21 | STOM | stomatin |
| -3.21 | GRID2 | glutamate receptor, ionotropic, delta 2 |
| 3.21 | NRG1 | neuregulin 1 |
| 3.21 | 3-Sep | septin 3 |
| 3.21 | — | — |
| -3.21 | TAGLN | transgelin |

| Value | Symbol | Description |
|---|---|---|
| -3.36 | C2orf12 | chromosome 2 open reading frame 12 |
| 3.36 | — | CDNA FLJ30897 fis, clone FEBRA2005476 |
| -3.35 | RAB15 | RAB15, member RAS oncogene family |
| -3.35 | CCDC69 | coiled-coil domain containing 69 |
| 3.35 | DNAJC18 | DnaJ (Hsp40) homolog, subfamily C, member |
| 3.35 | ID4 | Inhibitor of DNA binding 4, dominant negative |
| -3.35 | — | — |
| -3.35 | SYT17 | synaptotagmin XVII |
| -3.35 | DUSP5 | dual specificity phosphatase 5 |
| 3.35 | ZNF124 | zinc finger protein 124 |
| -3.35 | GAS7 | growth arrest-specific 7 |
| 3.34 | SDK2 | sidekick homolog 2 (chicken) |
| 3.34 | GPR39 | G protein-coupled receptor 39 |
| -3.34 | RIPK4 | receptor-interacting serine-threonine kinase 4 |
| -3.34 | SSH3 | slingshot homolog 3 (Drosophila) |
| -3.34 | — | — |
| -3.33 | FLRT2 | fibronectin leucine rich transmembrane protein |
| -3.33 | MMP15 | matrix metallopeptidase 15 (membrane-inserte |
| 3.33 | RHOBTB3 | Rho-related BTB domain containing 3 |
| 3.33 | PKNOX2 | PBX/knotted 1 homeobox 2 |
| -3.33 | FAM124A | family with sequence similarity 124A |
| -3.33 | KIAA1529 | KIAA1529 |
| 3.33 | PUNC | Putative neuronal cell adhesion molecule |
| -3.33 | GCNT1 | glucosaminyl (N-acetyl) transferase 1, core 2 ( |
| -3.32 | TPD52L1 | tumor protein D52-like 1 |
| -3.32 | DGKA | diacylglycerol kinase, alpha 80kDa |
| 3.32 | — | — |
| 3.32 | SSPN | sarcospan (Kras oncogene-associated gene) |
| 3.32 | DLX2 | distal-less homeobox 2 |
| 3.32 | — | — |
| 3.32 | HOXD9 | Homeobox D9 |
| 3.32 | — | — |
| -3.32 | LOC136288 | hypothetical protein LOC136288 |
| 3.32 | KIAA1257 | KIAA1257 |
| 3.32 | — | MRNA; cDNA DKFZp564E143 (from clone DK |
| 3.32 | OSBPL10 | oxysterol binding protein-like 1C |
| -3.32 | SLC2A3 | solute carrier family 2 (facilitated glucose trans |
| 3.32 | LOC400954 | similar to echinoderm microtubule associated |
| 3.31 | SOX6 | SRY (sex determining region Y)-box 6 |
| 3.31 | — | Transcribed locus |
| -3.31 | — | — |
| 3.31 | HYMAI | hydatidiform mole associated and imprinted |
| 3.31 | — | CDNA: FLJ23194 fis, clone REC00490 |
| -3.31 | CPT1A | carnitine palmitoyltransferase 1A (liver) |
| 3.31 | CCDC92 | coiled-coil domain containing 92 |
| 3.30 | GPR155 | G protein-coupled receptor 155 |
| 3.30 | TAIP-2 | TGF-beta induced apoptosis protein 2 |
| 3.30 | HS3ST3B1 | Heparan sulfate (glucosamine) 3-O-sulfotransf |
| 3.30 | MAPK1 | Mitogen-activated protein kinase 1 |
| 3.30 | AFF3 /// MLL | AF4/FMR2 family, member 3 /// myeloid/lymph |
| -3.30 | ETV6 | Ets variant gene 6 (TEL oncogene) |
| 3.30 | DOK6 | docking protein 6 |
| -3.29 | HLA-DPA1 | major histocompatibility complex, class II, DP |
| 3.29 | — | — |
| 3.29 | CASKIN1 | CASK interacting protein 1 |
| 3.29 | — | — |
| 3.29 | — | — |
| -3.29 | TPD52 | tumor protein D52 |
| -3.29 | — | — |
| -3.29 | CHRNA9 | cholinergic receptor, nicotinic, alpha 9 |
| 3.29 | NPAS3 | Neuronal PAS domain protein 3 |
| -3.28 | TMEM92 | transmembrane protein 92 |
| 3.28 | EVI5 | ecotropic viral integration site 5 |
| 3.28 | FGFR2 | fibroblast growth factor receptor 2 (bacteria-exp |
| -3.28 | — | — |
| -3.28 | LOC440338 | hypothetical gene supported by AJ002784 |
| 3.28 | — | Full length insert cDNA clone YZ38E04 |
| -3.28 | TMEPAI | transmembrane, prostate androgen induced RN |
| 3.28 | C9orf72 | chromosome 9 open reading frame 72 |
| -3.28 | — | — |
| -3.28 | C6orf150 | chromosome 6 open reading frame 150 |
| -3.28 | MST1 | macrophage stimulating 1 (hepatocyte growth |
| 3.28 | PON2 | Paraoxonase 2 |
| 3.28 | KIF5A | Kinesin family member 5A |
| 3.27 | — | Transcribed locus |
| -3.27 | HERC6 | hect domain and RLD 6 |
| -3.27 | SLC2A3 | solute carrier family 2 (facilitated glucose trans |
| -3.27 | ZNF747 | zinc finger protein 747 |
| 3.27 | SUHW4 | suppressor of hairy wing homolog 4 (Drosophil |

Appendix 1

| | | | | |
|---|---|---|---|---|
| 3.21 | TFAP2A | transcription factor AP-2 alpha (activating enha | -3.27 KIAA0040 | KIAA0040 |
| -3.21 | LOC286044 | hypothetical protein LOC286044 | 3.26 — | Hypothetical gene supported by BC008048 |
| -3.21 | DKFZP586H2123 | regeneration associated muscle protease | 3.26 — | — |
| -3.21 | KIAA0040 | KIAA0040 | 3.26 — | Transcribed locus, weakly similar to XP_52063 |
| 3.20 | — | — | 3.26 ZHX1 | zinc fingers and homeoboxes 1 |
| -3.20 | HLA-C /// LOC7320 | major histocompatibility complex, class I, C /// | 3.26 TP53AP1 | TP53 activated protein 1 |
| 3.20 | TAF7L | TAF7-like RNA polymerase II, TATA box bindin | -3.26 PIK3CD | phosphoinositide-3-kinase, catalytic, delta poly |
| 3.20 | CUEDC1 | CUE domain containing 1 | -3.26 NID2 | nidogen 2 (osteonidogen) |
| 3.20 | — | — | -3.26 — | — |
| 3.20 | — | — | -3.26 SLCO1B1 | solute carrier organic anion transporter family, |
| 3.19 | WNT7A | wingless-type MMTV integration site family, me | -3.26 — | cDNA clone IMAGE:5532261 |
| 3.19 | BTN3A2 | butyrophilin, subfamily 3, member A2 | 3.26 KIAA0141 | KIAA0141 |
| -3.19 | CD1D | CD1d molecule /// CD1d molecule | 3.25 — | Full-length cDNA clone CS0DC002YJ17 of Ne |
| 3.19 | — | — | 3.25 — | Transcribed locus |
| 3.19 | TMSL8 | thymosin-like 8 | -3.25 RAB37 | RAB37, member RAS oncogene family |
| -3.19 | — | — | -3.25 F11R | F11 receptor |
| 3.18 | — | — | 3.25 — | — |
| 3.18 | — | — | 3.25 PAK3 | p21 (CDKN1A)-activated kinase 3 |
| 3.18 | RARB | retinoic acid receptor, beta | 3.25 FRY | furry homolog (Drosophila) |
| 3.18 | LOC285771 | hypothetical protein LOC285771 | -3.25 SH3GL3 | SH3-domain GRB2-like 3 |
| 3.18 | — | — | 3.25 RIN2 | Ras and Rab interactor 2 |
| 3.18 | C5orf24 | chromosome 5 open reading frame 24 | -3.25 — | — |
| 3.18 | KCNJ4 | potassium inwardly-rectifying channel, subfami | 3.25 — | — |
| -3.18 | — | — | 3.25 — | — |
| -3.18 | PRKCQ | protein kinase C, theta | 3.24 PRRT1 | proline-rich transmembrane protein 1 |
| -3.18 | — | — | -3.24 — | — |
| 3.18 | FLJ30594 | hypothetical locus FLJ30594 | -3.24 TRHDE | thyrotropin-releasing hormone degrading enzyr |
| -3.17 | — | cDNA clone IMAGE:4799094 | -3.24 CD52 | CD52 molecule |
| 3.17 | FLJ39005 | hypothetical protein FLJ39005 | 3.24 RHD | Rh blood group, D antigen |
| 3.17 | C4orf31 | chromosome 4 open reading frame 31 | 3.24 — | — |
| 3.17 | DGKH | Diacylglycerol kinase, eta | -3.24 EDG8 | endothelial differentiation, sphingolipid G-prote |
| 3.17 | PTDSR | phosphatidylserine receptor | -3.24 — | — |
| 3.17 | — | — | -3.24 — | — |
| -3.17 | HSPB1 /// MEIS3 | heat shock 27kDa protein 1 /// Meis1, myeloid | 3.24 FXYD6 | FXYD domain containing ion transport regulato |
| 3.17 | KIAA1462 | KIAA1462 | -3.24 TULP2 | tubby like protein 2 |
| 3.17 | — | — | -3.24 NYD-SP18 | testes development-related NYD-SP18 |
| 3.17 | — | — | 3.24 RP11-301I17.1 | proliferation-inducing protein 38 |
| -3.17 | NMI | N-myc (and STAT) interactor | -3.23 LPHN1 | latrophilin 1 |
| 3.17 | TTC3 | tetratricopeptide repeat domain 3 | -3.23 SPAG11 /// LOC65: | sperm associated antigen 11 /// similar to sperr |
| -3.16 | DIAPH2 | diaphanous homolog 2 (Drosophila) | 3.23 CXCR7 | chemokine (C-X-C motif) receptor 7 |
| 3.16 | — | — | 3.23 GPR1 | G protein-coupled receptor 1 |
| 3.16 | C6orf174 | chromosome 6 open reading frame 174 | 3.23 NFKBIZ | Nuclear factor of kappa light polypeptide gene |
| -3.16 | LOC643194 | Hypothetical LOC643194 | 3.23 — | — |
| 3.16 | — | — | 3.23 — | — |
| -3.16 | MGAT4C | mannosyl (alpha-1,3-)-glycoprotein beta-1,4-N- | -3.23 RPS4Y1 | ribosomal protein S4, Y-linked 1 |
| 3.16 | EDG1 | endothelial differentiation, sphingolipid G-prote | -3.23 EHD2 | EH-domain containing 2 |
| 3.16 | NHLH2 | nescient helix loop helix 2 | -3.23 ASPHD1 | aspartate beta-hydroxylase domain containing |
| -3.16 | PPAP2A | phosphatidic acid phosphatase type 2A | -3.23 SYTL1 | synaptotagmin-like 1 |
| -3.16 | MAFB | v-maf musculoaponeurotic fibrosarcoma oncog | -3.22 HSPB8 | heat shock 22kDa protein 8 |
| -3.16 | GRAMD3 | GRAM domain containing 3 | 3.22 ERCC5 | Excision repair cross-complementing rodent re |
| 3.16 | IFNAR1 | interferon (alpha, beta and omega) receptor 1 | 3.22 RPS6KA2 | ribosomal protein S6 kinase, 90kDa, polypeptid |
| -3.15 | — | — | -3.22 SERINC5 | Serine incorporator 5 |
| 3.15 | FOXJ1 | Forkhead box J1 | 3.22 C5orf24 | chromosome 5 open reading frame 24 |
| 3.15 | RP11-301I17.1 | proliferation-inducing protein 38 | -3.22 JAKMIP2 | janus kinase and microtubule interacting protei |
| 3.15 | KIAA0523 | KIAA0523 protein | -3.22 TAF4B | TAF4b RNA polymerase II, TATA box binding |
| -3.15 | C18orf4 | chromosome 18 open reading frame 4 | 3.22 NRCAM | neuronal cell adhesion molecule |
| -3.15 | FAM125A | Family with sequence similarity 125, member A | 3.22 FOXP4 | forkhead box P4 |
| 3.15 | GALNTL1 | UDP-N-acetyl-alpha-D-galactosamine:polypept | -3.22 — | — |
| 3.15 | PODXL2 | podocalyxin-like 2 | 3.21 — | — |
| -3.15 | — | cDNA clone IMAGE:4792693 | 3.21 RHOBTB3 | Rho-related BTB domain containing 3 |
| 3.15 | CHN2 | chimerin (chimaerin) 2 | -3.21 PTPRU | protein tyrosine phosphatase, receptor type, L |
| -3.14 | — | cDNA FLJ11796 fis, clone HEMBA1006158, h | 3.21 — | — |
| -3.14 | SLC2A14 | Solute carrier family 2 (facilitated glucose trans | 3.21 RSN | Restin (Reed-Steinberg cell-expressed interm |
| 3.14 | RABL5 | RAB, member RAS oncogene family-like 5 | -3.21 STOM | stomatin |
| -3.14 | — | Mesenchymal stem cell protein DSC96 | -3.21 FGFR4 | fibroblast growth factor receptor 4 |
| -3.14 | NAP1L2 | nucleosome assembly protein 1-like 2 | -3.21 FLJ11286 | hypothetical protein FLJ11286 |
| 3.14 | C6orf174 | chromosome 6 open reading frame 174 | -3.21 — | — |
| 3.14 | GPR1 | G protein-coupled receptor 1 | -3.21 TMEM37 | transmembrane protein 37 |
| -3.14 | RABGAP1L | RAB GTPase activating protein 1-like | 3.21 — | — |
| 3.14 | KCNJ8 | potassium inwardly-rectifying channel, subfami | 3.20 CCDC73 | Coiled-coil domain containing 73 |
| 3.14 | KIAA1772 | KIAA1772 | 3.20 C7orf38 | chromosome 7 open reading frame 38 |
| 3.14 | TOR1AIP2 | torsin A interacting protein 2 | -3.20 — | — |
| 3.14 | RRAGD | Ras-related GTP binding D | -3.20 CD2AP | CD2-associated protein |
| -3.14 | CD2AP | CD2-associated protein | 3.20 HOXA3 | Homeo box A3 |
| 3.14 | DLL3 | delta-like 3 (Drosophila) | 3.20 DNAI1 | dynein, axonemal, intermediate chain 1 |
| 3.14 | TMEM158 | transmembrane protein 158 | -3.20 EDNRB | endothelin receptor type B |
| 3.14 | ERBB4 | v-erb-a erythroblastic leukemia viral oncogene | -3.20 — | cDNA clone IMAGE:5275948 |
| -3.13 | — | — | -3.20 PAK1 | p21/Cdc42/Rac1-activated kinase 1 (STE20 ho |
| -3.13 | TRIM14 | tripartite motif-containing 14 | 3.19 LOC401134 | hypothetical gene supported by BC040544 |

Appendix 1

| Value | Gene | Description |
|---|---|---|
| 3.13 | — | — |
| 3.13 | TTC3 | tetratricopeptide repeat domain 3 |
| -3.13 | HLA-C | major histocompatibility complex, class I, C |
| 3.13 | ODZ2 | odz, odd Oz/ten-m homolog 2 (Drosophila) |
| 3.13 | KIAA1257 | KIAA1257 |
| 3.13 | SLC2A1 | solute carrier family 2 (facilitated glucose trans |
| 3.13 | ABCC9 | ATP-binding cassette, sub-family C (CFTR/MR |
| -3.12 | — | — |
| 3.12 | BACE1 | beta-site APP-cleaving enzyme 1 |
| 3.12 | PAK7 | p21(CDKN1A)-activated kinase 7 |
| 3.12 | — | cDNA FLJ37023 fis, clone BRACE2010828 |
| 3.12 | DMRTC1 /// LOC72 | DMRT-like family C1 /// similar to doublesex an |
| -3.12 | SLC2A3 | solute carrier family 2 (facilitated glucose trans |
| -3.12 | TACSTD2 | tumor-associated calcium signal transducer 2 |
| -3.12 | — | — |
| -3.11 | HMCN1 | hemicentin 1 |
| 3.11 | PRRT1 | proline-rich transmembrane protein 1 |
| -3.11 | LDHD | lactate dehydrogenase D |
| -3.11 | SLC1A1 | solute carrier family 1 (neuronal/epithelial high |
| -3.11 | ROR1 | receptor tyrosine kinase-like orphan receptor 1 |
| -3.11 | LRAT | lecithin retinol acyltransferase (phosphatidylch |
| 3.11 | CX3CL1 | chemokine (C-X3-C motif) ligand 1 |
| 3.11 | — | cDNA clone IMAGE:4300887 |
| 3.11 | SLITRK1 | SLIT and NTRK-like family, member 1 |
| 3.11 | — | Transcribed locus |
| -3.10 | — | — |
| -3.10 | CDCP1 | CUB domain containing protein 1 |
| -3.10 | — | — |
| 3.10 | RUFY3 | RUN and FYVE domain containing 3 |
| -3.10 | — | — |
| 3.10 | GPR161 | G protein-coupled receptor 161 |
| -3.10 | CD44 /// MAPK10 | CD44 molecule (Indian blood group) /// mitoger |
| 3.10 | — | — |
| 3.10 | — | — |
| 3.10 | STXBP4 | syntaxin binding protein 4 |
| -3.10 | ADAMTSL1 | ADAMTS-like 1 |
| 3.10 | CCNE2 | cyclin E2 |
| 3.10 | — | cDNA FLJ30740 fis, clone FEBRA2000319 |
| 3.10 | — | — |
| 3.10 | KIAA1546 | KIAA1546 |
| 3.10 | C6orf118 | chromosome 6 open reading frame 118 |
| -3.09 | HNMT | histamine N-methyltransferase /// histamine N- |
| -3.09 | DAZ1 /// DAZ3 /// D | deleted in azoospermia 1 /// deleted in azoospe |
| 3.09 | HOXB6 | homeobox B6 |
| 3.09 | CACNG4 | calcium channel, voltage-dependent, gamma s |
| 3.09 | PHYHIP | phytanoyl-CoA 2-hydroxylase interacting prote |
| -3.09 | SLC7A8 | solute carrier family 7 (cationic amino acid tran |
| 3.09 | PLCL1 | phospholipase C-like 1 |
| 3.09 | — | — |
| -3.09 | LIN28 | lin-28 homolog (C. elegans) |
| 3.09 | GRK5 | G protein-coupled receptor kinase 5 |
| 3.09 | — | — |
| -3.09 | ID1 | inhibitor of DNA binding 1, dominant negative h |
| 3.09 | DPYD | dihydropyrimidine dehydrogenase |
| -3.09 | RYR2 | ryanodine receptor 2 (cardiac) |
| -3.08 | MBP | myelin basic protein |
| -3.08 | NF2 | neurofibromin 2 (bilateral acoustic neuroma) |
| -3.08 | TNFAIP6 | tumor necrosis factor, alpha-induced protein 6 |
| 3.08 | RHOBTB3 | Rho-related BTB domain containing 3 |
| -3.08 | CTSL2 | Cathepsin L2 |
| -3.08 | — | — |
| -3.08 | CG018 | hypothetical gene CG018 |
| 3.08 | — | — |
| -3.08 | MAN2A1 | mannosidase, alpha, class 2A, member 1 |
| -3.08 | MST1 | macrophage stimulating 1 (hepatocyte growth f |
| 3.08 | — | — |
| 3.08 | GPSM2 | G-protein signalling modulator 2 (AGS3-like, C |
| -3.08 | SLC39A4 | solute carrier family 39 (zinc transporter), mem |
| -3.08 | ANKS6 | ankyrin repeat and sterile alpha motif domain c |
| 3.08 | DCHS1 | dachsous 1 (Drosophila) |
| -3.08 | FLJ16287 | FLJ16287 protein |
| -3.08 | RAB3B | RAB3B, member RAS oncogene family |
| 3.08 | RNF182 | ring finger protein 182 |
| -3.07 | LAMA2 | laminin, alpha 2 (merosin, congenital muscular |
| 3.07 | PCSK6 | proprotein convertase subtilisin/kexin type 6 |
| -3.07 | SILV | silver homolog (mouse) |
| 3.07 | ABAT | 4-aminobutyrate aminotransferase |
| -3.07 | RASIP1 | Ras interacting protein 1 |
| -3.07 | — | — |
| -3.07 | RASGRP2 | RAS guanyl releasing protein 2 (calcium and D |
| -3.19 | WDR72 | WD repeat domain 72 |
| -3.19 | CRH | corticotropin releasing hormone |
| 3.19 | GPR85 | G protein-coupled receptor 85 |
| -3.19 | C1Borf1 | chromosome 18 open reading frame 1 |
| 3.19 | — | — |
| -3.19 | CASP8 | caspase 8, apoptosis-related cysteine peptidas |
| -3.19 | HLA-A | major histocompatibility complex, class I, A |
| 3.19 | ALDH5A1 | aldehyde dehydrogenase 5 family, member A1 |
| -3.18 | C10orf90 | chromosome 10 open reading frame 90 |
| 3.18 | ZNF529 | Zinc finger protein 529 |
| -3.18 | — | Transcribed locus |
| 3.18 | IGSF4C | immunoglobulin superfamily, member 4C |
| 3.18 | LOC138046 | hypothetical protein LOC138046 |
| 3.18 | — | — |
| -3.18 | CD19 | CD19 molecule |
| 3.17 | — | — |
| -3.17 | — | Transcribed locus |
| -3.17 | — | — |
| -3.17 | HTR3A | 5-hydroxytryptamine (serotonin) receptor 3A |
| 3.17 | EMP1 | epithelial membrane protein 1 |
| -3.17 | EPB41L4B | erythrocyte membrane protein band 4.1 like 4E |
| 3.17 | CTGF | connective tissue growth factor |
| 3.17 | ACSL3 | Acyl-CoA synthetase long-chain family membe |
| 3.17 | — | — |
| 3.17 | AKR1C2 | aldo-keto reductase family 1, member C2 (dihy |
| -3.17 | — | — |
| -3.17 | SAV1 | salvador homolog 1 (Drosophila) |
| -3.17 | CDS1 | CDP-diacylglycerol synthase (phosphatidate cy |
| 3.17 | — | — |
| 3.17 | FLJ21986 | hypothetical protein FLJ21986 |
| 3.17 | QKI | quaking homolog, KH domain RNA binding (mc |
| -3.16 | ZNF185 | zinc finger protein 185 (LIM domain) |
| 3.16 | LOC643911 /// LOC | hypothetical LOC643911 /// hypothetical protei |
| 3.16 | — | Full-length cDNA clone CS0DD001YA12 of Ne |
| -3.16 | — | — |
| -3.16 | MBP | myelin basic protein |
| 3.16 | — | cDNA clone IMAGE:3950788 |
| 3.16 | COL11A1 | collagen, type XI, alpha 1 |
| -3.16 | LPHN1 | latrophilin 1 |
| 3.16 | MAP2K5 | mitogen-activated protein kinase kinase 5 |
| 3.16 | — | MRNA; cDNA DKFZp564E143 (from clone DKl |
| 3.16 | C4orf31 | chromosome 4 open reading frame 31 |
| 3.16 | — | cDNA FLJ40252 fis, clone TESTI2024299 |
| 3.16 | LOC283658 | hypothetical protein LOC283658 |
| 3.16 | CDKN2C | cyclin-dependent kinase inhibitor 2C (p18, inhil |
| 3.15 | FAM125B | family with sequence similarity 125, member B |
| 3.15 | LMO3 | LIM domain only 3 (rhombotin-like 2) |
| -3.15 | RBMS1 | RNA binding motif, single stranded interacting |
| 3.15 | MLLT3 | myeloid/lymphoid or mixed-lineage leukemia (tr |
| 3.15 | BTN3A2 | butyrophilin, subfamily 3, member A2 |
| -3.15 | RHOF | ras homolog gene family, member F (in filopod |
| -3.15 | TRIM6 | tripartite motif-containing 6 |
| -3.14 | HTR2C | 5-hydroxytryptamine (serotonin) receptor 2C |
| 3.14 | DGKH | Diacylglycerol kinase, eta |
| -3.14 | KCNMB4 | potassium large conductance calcium-activated |
| -3.14 | — | — |
| 3.14 | ARHGEF17 | Rho guanine nucleotide exchange factor (GEF) |
| 3.14 | FST | follistatin |
| -3.14 | LHFPL2 | lipoma HMGIC fusion partner-like 2 |
| 3.14 | TREX1 | three prime repair exonuclease 1 |
| 3.14 | APBA2 | amyloid beta (A4) precursor protein-binding, fa |
| 3.13 | — | Transcribed locus |
| -3.13 | — | — |
| 3.13 | LOC643911 /// LOC | hypothetical LOC643911 /// hypothetical protei |
| -3.13 | DDT | D-dopachrome tautomerase |
| -3.13 | LOC643224 | similar to tubulin, beta 8 |
| -3.13 | CHURC1 | churchill domain containing 1 |
| -3.12 | — | — |
| -3.12 | SAV1 | salvador homolog 1 (Drosophila) |
| -3.12 | GFPT2 | glutamine-fructose-6-phosphate transaminase |
| 3.12 | ABCC4 | ATP-binding cassette, sub-family C (CFTR/MR |
| 3.12 | — | — |
| 3.12 | FBXL13 | F-box and leucine-rich repeat protein 13 |
| 3.12 | RHOBTB3 | Rho-related BTB domain containing 3 |
| 3.11 | C20orf58 | chromosome 20 open reading frame 58 |
| 3.11 | FKBP7 | FK506 binding protein 7 |
| 3.11 | COL11A1 | collagen, type XI, alpha 1 |
| 3.11 | — | Homo sapiens, clone IMAGE:4214654, mRNA |
| -3.11 | MBP | myelin basic protein |

Appendix 1

| | | | |
|---|---|---|---|
| -3.07 PRLR | prolactin receptor | 3.11 NMNAT2 | nicotinamide nucleotide adenylyltransferase 2 |
| 3.07 LOC127003 | similar to CG5435-PA | -3.10 — | — |
| 3.07 HSPA12A | heat shock 70kDa protein 12A | -3.10 CA4 | carbonic anhydrase IV |
| 3.07 PRR3 | proline rich 3 | -3.10 FGF17 | fibroblast growth factor 17 |
| 3.07 LONRF2 | LON peptidase N-terminal domain and ring fing | -3.10 FBXO2 | F-box protein 2 |
| -3.07 NPR1 | natriuretic peptide receptor A/guanylate cyclase | -3.10 ROR1 | receptor tyrosine kinase-like orphan receptor 1 |
| -3.06 — | — | 3.10 ANKRD20A1 /// C2 | ankyrin repeat domain 20 family, member A1 // |
| -3.06 TAGLN | transgelin | 3.10 — | — |
| 3.06 FBXW8 | F-box and WD-40 domain protein 8 | -3.09 LY6E | lymphocyte antigen 6 complex, locus E |
| -3.06 — | Transcribed locus | -3.09 ACTN3 | actinin, alpha 3 |
| 3.06 RNF8 | ring finger protein 8 | 3.09 — | — |
| 3.06 STON1 | Stonin 1 | -3.09 GPR37 | G protein-coupled receptor 37 (endothelin rece |
| -3.06 — | Clone 23555 mRNA sequence | 3.09 MGC33846 | hypothetical protein MGC33846 |
| 3.06 HS6ST2 | heparan sulfate 6-O-sulfotransferase 2 | 3.09 PTPRO | protein tyrosine phosphatase, receptor type, C |
| 3.06 FYN | FYN oncogene related to SRC, FGR, YES | -3.09 CBR1 | carbonyl reductase 1 |
| -3.06 SGK | serum/glucocorticoid regulated kinase | -3.09 SH2D2A | SH2 domain protein 2A |
| -3.06 — | MRNA; cDNA DKFZp313A1040 (from clone DI | 3.09 FLJ90757 | hypothetical protein LOC440465 |
| 3.06 HOXB8 | homeobox B8 | 3.09 HS6ST2 | heparan sulfate 6-O-sulfotransferase 2 |
| 3.06 — | Homo sapiens, clone IMAGE:4214654, mRNA | -3.09 — | Transcribed locus |
| -3.05 SOX17 | SRY (sex determining region Y)-box 17 | 3.09 ZIC1 | Zic family member 1 (odd-paired homolog, Dro |
| -3.05 MBP | myelin basic protein | 3.09 ANGPTL2 | angiopoietin-like 2 |
| -3.05 IL7R | interleukin 7 receptor | -3.09 REC8L1 | REC8-like 1 (yeast) |
| 3.05 — | Similar to leucine rich repeat containing 10 | -3.09 CCKBR | cholecystokinin B receptor |
| -3.05 KYNU | kynureninase (L-kynurenine hydrolase) | 3.09 PABPC5 | poly(A) binding protein, cytoplasmic 5 |
| -3.05 STEAP3 | STEAP family member 3 | 3.09 ARTS-1 | Type 1 tumor necrosis factor receptor shedding |
| 3.05 FLJ90757 | hypothetical protein LOC440465 | 3.09 MTCH2 | mitochondrial carrier homolog 2 (C. elegans) |
| -3.05 BANK1 | B-cell scaffold protein with ankyrin repeats 1 | -3.09 — | — |
| 3.05 LRP2 | low density lipoprotein-related protein 2 | -3.09 BMP2 | bone morphogenetic protein 2 |
| 3.05 LOC92017 | similar to RIKEN cDNA 4933437K13 | 3.09 TNRC4 | trinucleotide repeat containing 4 |
| 3.05 DNER | delta/notch-like EGF repeat containing | -3.08 CPS1 | carbamoyl-phosphate synthetase 1, mitochond |
| -3.04 CCNA1 | cyclin A1 | -3.08 TGFB1 | transforming growth factor, beta 1 (Camurati-E |
| -3.04 MYO1E | Myosin IE | -3.08 TBX5 | T-box 5 |
| 3.04 PON2 | paraoxonase 2 | -3.08 BNC2 | Basonuclin 2 |
| -3.04 — | — | -3.08 — | — |
| -3.04 CNN1 | calponin 1, basic, smooth muscle | 3.08 PROX1 | Prospero-related homeobox 1 |
| 3.04 PHC2 | polyhomeotic homolog 2 (Drosophila) | 3.08 FLJ25967 | Hypothetical gene supported by AK098833 |
| 3.04 HS6ST2 | heparan sulfate 6-O-sulfotransferase 2 | -3.08 CHST8 | carbohydrate (N-acetylgalactosamine 4-0) sulf |
| 3.04 — | Homo sapiens, clone IMAGE:4732650, mRNA | -3.08 ARHGAP10 | Rho GTPase activating protein 10 |
| -3.04 LOC133491 | hypothetical protein LOC133491 | -3.08 — | — |
| 3.04 SLC16A14 | solute carrier family 16, member 14 (monocarb | 3.08 XTP2 | BAT2 domain containing 1 |
| -3.04 PAK6 | p21(CDKN1A)-activated kinase 6 | 3.08 CALCB | calcitonin-related polypeptide, beta |
| 3.04 CELSR2 | cadherin, EGF LAG seven-pass G-type recept | 3.08 VEGFC | vascular endothelial growth factor C |
| -3.04 BEST2 | bestrophin 2 | -3.08 ARHGAP23 | Rho GTPase activating protein 23 |
| 3.04 BMP6 | bone morphogenetic protein 6 | 3.07 — | Transcribed locus |
| 3.03 psiTPTE22 | TPTE pseudogene | -3.07 LCP1 | lymphocyte cytosolic protein 1 (L-plastin) |
| 3.03 RTN1 | reticulon 1 | -3.07 PLP2 | proteolipid protein 2 (colonic epithelium-enrich |
| -3.03 FLJ11286 | hypothetical protein FLJ11286 | 3.07 — | — |
| 3.03 CD47 | CD47 molecule | 3.07 — | — |
| 3.03 SDK2 | sidekick homolog 2 (chicken) | 3.07 ANGPTL2 | angiopoietin-like 2 |
| -3.03 ZNF630 | zinc finger protein 630 | -3.07 PRRX2 | paired related homeobox 2 |
| -3.03 FGF17 | fibroblast growth factor 17 | 3.07 — | CDNA clone IMAGE:4811557 |
| 3.03 GDPD2 | glycerophosphodiester phosphodiesterase don | -3.07 GALK1 | galactokinase 1 |
| 3.03 — | — | -3.06 — | Full-length cDNA clone CS0DH005Y118 of T ce |
| -3.03 HRASLS3 | HRAS-like suppressor 3 | -3.06 PCTK3 | PCTAIRE protein kinase 3 |
| -3.03 ASPHD1 | aspartate beta-hydroxylase domain containing | -3.06 RBPMS | RNA binding protein with multiple splicing |
| 3.03 LRRC17 | leucine rich repeat containing 17 | -3.06 — | — |
| 3.03 RBM24 | RNA binding motif protein 24 | -3.06 PRODH | proline dehydrogenase (oxidase) 1 |
| 3.03 MGC14289 | similar to RIKEN cDNA 1200014N16 gene | 3.06 — | CDNA clone IMAGE:5288757 |
| 3.03 — | — | -3.06 KCTD14 | potassium channel tetramerisation domain con |
| 3.03 ANKRD6 | ankyrin repeat domain 6 | 3.06 — | CDNA clone IMAGE:5303499 |
| 3.03 — | — | 3.06 RNF175 | ring finger protein 175 |
| 3.03 — | Transcribed locus | -3.05 F11R | F11 receptor |
| -3.03 TERF1 | telomeric repeat binding factor (NIMA-interactir | -3.05 FAM38A | family with sequence similarity 38, member A |
| 3.03 DKFZp313A2432 | hypothetical protein DKFZp313A2432 | -3.05 LOC730432 | similar to serine/threonine/tyrosine interacting p |
| -3.02 CECR1 | cat eye syndrome chromosome region, candida | 3.05 C9orf93 | Chromosome 9 open reading frame 93 |
| 3.02 NEFL | neurofilament, light polypeptide 68kDa | -3.05 UTX | ubiquitously transcribed tetratricopeptide repea |
| 3.02 — | — | -3.05 CRABP2 | cellular retinoic acid binding protein 2 |
| 3.02 SLC16A9 | solute carrier family 16, member 9 (monocarbo | 3.05 — | Transcribed locus |
| 3.02 PALLD | palladin, cytoskeletal associated protein | -3.05 DBC1 | deleted in bladder cancer 1 |
| 3.02 GPR85 | G protein-coupled receptor 85 | 3.05 — | Full length insert cDNA clone YZ38E04 |
| -3.02 C1orf61 | chromosome 1 open reading frame 61 | 3.05 ABCB4 | ATP-binding cassette, sub-family B (MDR/TAP |
| 3.02 SLC6A8 | solute carrier family 6 (neurotransmitter transpo | -3.04 LAD1 | ladinin 1 |
| -3.02 HRLP5 | H-rev107-like protein 5 | 3.04 SLC4A4 | solute carrier family 4, sodium bicarbonate cotr |
| -3.01 HSD11B1 | Hydroxysteroid (11-beta) dehydrogenase 1 | -3.04 DHRS2 | dehydrogenase/reductase (SDR family) membe |
| -3.01 — | — | -3.04 TFPI | tissue factor pathway inhibitor (lipoprotein-asso |
| 3.01 PURG | purine-rich element binding protein G | -3.04 FBLN5 | fibulin 5 |
| 3.01 — | CDNA FLJ40252 fis, clone TESTI2024299 | -3.04 HLA-B | major histocompatibility complex, class I, B |
| -3.01 SLC1A4 | solute carrier family 1 (glutamate/neutral amino | 3.04 — | — |
| -3.01 PDE4A | phosphodiesterase 4A, cAMP-specific (phosph | 3.04 RABL5 | RAB, member RAS oncogene family-like 5 |

Appendix 1

| | | | | |
|---|---|---|---|---|
| -3.01 | PVALB | parvalbumin | 3.04 | — | — |
| 3.01 | MLLT4 | Myeloid/lymphoid or mixed-lineage leukemia (t| 3.04 | ARL5B | ADP-ribosylation factor-like 5B |
| 3.01 | PPP1R14C | protein phosphatase 1, regulatory (inhibitor) su | -3.04 | — | — |
| 3.01 | BMPR1B | Bone morphogenetic protein receptor, type IE | -3.04 | CYB5R2 | cytochrome b5 reductase 2 |
| -3.01 | TIMP4 | TIMP metallopeptidase inhibitor 4 | -3.04 | LPHN1 | latrophilin 1 |
| -3.00 | TPM2 /// PPIL5 | tropomyosin 2 (beta) /// peptidylprolyl isomeras | 3.04 | GNG2 | guanine nucleotide binding protein (G protein), |
| -3.00 | — | Full length insert cDNA YN57B01 | -3.04 | — | Full-length cDNA clone CS0DJ013YE21 of T c |
| -3.00 | TAF4B | TAF4b RNA polymerase II, TATA box binding | -3.03 | SYN2 | synapsin II |
| 3.00 | PHC2 | Polyhomeotic homolog 2 (Drosophila) | -3.03 | RBMS1 | RNA binding motif, single stranded interacting |
| -3.00 | LAMC3 | laminin, gamma 3 | 3.03 | HSPA4L | heat shock 70kDa protein 4-like |
| 3.00 | LOC220686 | Hypothetical protein LOC220686 | 3.03 | SOSTDC1 | sclerostin domain containing 1 |
| -3.00 | CDS1 | CDP-diacylglycerol synthase (phosphatidate c | 3.03 | TMSL8 | thymosin-like 8 |
| -3.00 | HPGD | hydroxyprostaglandin dehydrogenase 15-(NAD | -3.03 | HIST1H1A | histone cluster 1, H1a |
| 3.00 | NEUROD1 | neurogenic differentiation 1 | 3.03 | STXBP6 | syntaxin binding protein 6 (amisyn) |
| -3.00 | SPP1 | secreted phosphoprotein 1 (osteopontin, bone | 3.03 | SNCA | synuclein, alpha (non A4 component of amyloi |
| 2.99 | BTG3 | BTG family, member 3 | -3.03 | — | — |
| 2.99 | — | — | 3.03 | ATBF1 | AT-binding transcription factor 1 |
| 2.99 | FZD1 | frizzled homolog 1 (Drosophila) | -3.02 | MCTP2 | multiple C2 domains, transmembrane 2 |
| -2.99 | HIST1H1A | histone cluster 1, H1a | 3.02 | C11orf63 | chromosome 11 open reading frame 63 |
| 2.99 | NPTX1 | neuronal pentraxin I | -3.02 | ENO3 | enolase 3 (beta, muscle) |
| -2.99 | ROR2 | receptor tyrosine kinase-like orphan receptor 2 | -3.02 | MAFB | v-maf musculoaponeurotic fibrosarcoma oncog |
| -2.99 | SMURF2 | SMAD specific E3 ubiquitin protein ligase 2 | -3.02 | MYBBP1A | MYB binding protein (P160) 1a |
| -2.99 | TES | testis derived transcript (3 LIM domains) | 3.02 | — | Transcribed locus |
| 2.99 | SAV1 | salvador homolog 1 (Drosophila) | -3.02 | HSPB1 /// MEIS3 | heat shock 27kDa protein 1 /// Meis1, myeloid |
| -2.99 | TNFRSF8 | tumor necrosis factor receptor superfamily, me | -3.02 | GUCY2C | guanylate cyclase 2C (heat stable enterotoxin |
| -2.99 | LOC133874 | Hypothetical gene LOC133874 | -3.02 | KLK13 | kallikrein-related peptidase 13 |
| -2.98 | EPHA7 | EPH receptor A7 | -3.02 | TERF1 | telomeric repeat binding factor (NIMA-interacti |
| -2.98 | — | — | -3.02 | AIG1 | Androgen-induced 1 |
| 2.98 | — | Hypothetical LOC388934 | 3.02 | FLJ30594 | hypothetical locus FLJ30594 |
| 2.98 | MGC26718 | Similar to ankyrin repeat domain 20A | 3.02 | APOLD1 | apolipoprotein L domain containing 1 /// apolipo |
| 2.98 | TAIP-2 | TGF-beta induced apoptosis protein 2 | 3.01 | PDE4D | phosphodiesterase 4D, cAMP-specific (phosph |
| -2.98 | — | — | 3.01 | PDE4D | phosphodiesterase 4D, cAMP-specific (phosph |
| 2.98 | MSRB3 | Methionine sulfoxide reductase B3 | 3.01 | LYPD1 | LY6/PLAUR domain containing 1 |
| 2.98 | NEFL | neurofilament, light polypeptide 68kDa | -3.01 | CTNND1 | catenin (cadherin-associated protein), delta 1 |
| -2.98 | PLSCR1 | phospholipid scramblase 1 | 3.01 | PAPPA | pregnancy-associated plasma protein A, pappa |
| 2.98 | — | — | -3.01 | RBMS1 | RNA binding motif, single stranded interacting |
| -2.98 | CPS1 | carbamoyl-phosphate synthetase 1, mitochond | -3.01 | LRRC2 | leucine rich repeat containing 2 |
| 2.98 | FAM125B | family with sequence similarity 125, member B | 3.01 | SMURF2 | SMAD specific E3 ubiquitin protein ligase 2 |
| -2.97 | RBPMS | RNA binding protein with multiple splicing | -3.01 | — | — |
| -2.97 | CD44 | CD44 molecule (Indian blood group) | 3.01 | KIAA1217 | KIAA1217 |
| 2.97 | SERHL2 | Serine hydrolase-like 2 | 3.00 | PKN2 | protein kinase N2 |
| 2.97 | LOC200169 | hypothetical protein LOC200169 | 3.00 | LONRF2 | LON peptidase N-terminal domain and ring fing |
| 2.97 | SGCB | sarcoglycan, beta (43kDa dystrophin-associate | 3.00 | TTC3 | tetratricopeptide repeat domain 3 |
| -2.97 | LHX6 | LIM homeobox 6 | -3.00 | THY1 | Thy-1 cell surface antigen |
| 2.97 | LOC222070 | hypothetical protein LOC222070 | 3.00 | KIAA1546 | KIAA1546 |
| 2.97 | HOXB5 | homeobox B5 | -3.00 | KCTD4 | potassium channel tetramerisation domain con |
| 2.97 | SMEK2 | SMEK homolog 2, suppressor of mek1 (Dictyo | 3.00 | — | cDNA FLJ35508 fis, clone SMINT2011958 |
| 2.97 | SLC44A5 | solute carrier family 44, member 5 | -3.00 | ZNF217 | zinc finger protein 217 |
| -2.97 | SLC7A8 | solute carrier family 7 (cationic amino acid tran | -3.00 | FGF12 | fibroblast growth factor 12 |
| -2.97 | C2orf12 | chromosome 2 open reading frame 12 | 3.00 | CREBBP | CREB binding protein (Rubinstein-Taybi syndro |
| -2.97 | — | — | -2.99 | ABHD11 | abhydrolase domain containing 11 |
| 2.97 | — | — | 2.99 | LOC222070 | hypothetical protein LOC222070 |
| -2.97 | SORL1 | sortilin-related receptor, L(DLR class) A repeat | 2.99 | DKFZP564D166 | putative ankyrin-repeat containing protein |
| 2.97 | — | — | 2.99 | FGFRL1 | fibroblast growth factor receptor-like 1 |
| -2.96 | CRIP3 | cysteine-rich protein 3 | -2.99 | C21orf88 | chromosome 21 open reading frame 88 |
| 2.96 | LEF1 | lymphoid enhancer-binding factor 1 | -2.99 | GABARAPL1 | GABA(A) receptor-associated protein like 1 |
| 2.96 | C6orf134 | chromosome 6 open reading frame 134 | -2.99 | KLF5 | Kruppel-like factor 5 (intestinal) |
| 2.96 | SMOC1 | SPARC related modular calcium binding 1 | -2.98 | F2RL1 | coagulation factor II (thrombin) receptor-like 1 |
| 2.96 | — | cDNA FLJ31660 fis, clone NT2RI2004410 | 2.98 | DNER | delta/notch-like EGF repeat containing |
| -2.96 | SLC2A3 | Solute carrier family 2 (facilitated glucose trans | 2.98 | RAB7 | RAB7, member RAS oncogene family |
| 2.96 | FGFRL1 | fibroblast growth factor receptor-like 1 | 2.98 | HSPA12A | heat shock 70kDa protein 12A |
| 2.96 | — | Transcribed locus, moderately similar to NP_0 | -2.98 | MDFI | MyoD family inhibitor |
| -2.96 | MTMR11 | myotubularin related protein 11 | -2.98 | HLA-DRB1 /// LOC7 | major histocompatibility complex, class II, DR |
| 2.96 | HS3ST3B1 | heparan sulfate (glucosamine) 3-O-sulfotransf | 2.98 | BOC | brother of CDO |
| 2.96 | RHOBTB3 | Rho-related BTB domain containing 3 | 2.98 | — | — |
| 2.95 | ANKS1B | ankyrin repeat and sterile alpha motif domain c | -2.98 | MSL3L1 | male-specific lethal 3-like 1 (Drosophila) |
| 2.95 | ITGB8 | integrin, beta 8 | 2.98 | ALK | anaplastic lymphoma kinase (Ki-1) |
| 2.95 | — | — | 2.98 | ATP9A | ATPase, Class II, type 9A |
| 2.95 | SNAP25 | Synaptosomal-associated protein, 25kDa | -2.97 | ATP2A3 | ATPase, Ca++ transporting, ubiquitous |
| 2.95 | — | — | 2.97 | TTC3 | tetratricopeptide repeat domain 3 |
| -2.95 | IGFBP7 | insulin-like growth factor binding protein 7 | 2.97 | TTC3 | tetratricopeptide repeat domain 3 |
| 2.95 | KITLG | KIT ligand | -2.97 | UTX | ubiquitously transcribed tetratricopeptide repea |
| -2.95 | PDE4A | phosphodiesterase 4A, cAMP-specific (phosph | -2.97 | — | cDNA FLJ37143 fis, clone BRACE2024222 |
| 2.95 | IGFBPL1 | Insulin-like growth factor binding protein-like 1 | 2.97 | C5orf13 | Chromosome 5 open reading frame 13 |
| -2.94 | — | Homo sapiens, clone IMAGE:4047715, mRNA | -2.97 | LOC133491 | hypothetical protein LOC133491 |
| -2.94 | GATA3 | GATA binding protein 3 | 2.97 | — | Transcribed locus |
| -2.94 | GYLTL1B | glycosyltransferase-like 1B | -2.96 | PRSS2 | protease, serine, 2 (trypsin 2) |
| -2.94 | KCNQ1 | potassium voltage-gated channel, KQT-like sub | -2.96 | ECHDC2 | enoyl Coenzyme A hydratase domain containi |
| 2.94 | CHL1 | cell adhesion molecule with homology to L1CA | -2.96 | FBP1 | fructose-1,6-bisphosphatase 1 |

Appendix 1

| Value | Symbol | Description |
|---|---|---|
| 2.94 | TTC3 | tetratricopeptide repeat domain 3 |
| 2.94 | RGS12 | regulator of G-protein signalling 12 |
| 2.94 | IQCE | IQ motif containing E |
| 2.93 | KCNJ8 | potassium inwardly-rectifying channel, subfami |
| 2.93 | CD47 | CD47 molecule |
| 2.93 | FKBP7 | FK506 binding protein 7 |
| 2.93 | — | Transcribed locus |
| 2.93 | TTLL9 | tubulin tyrosine ligase-like family, member 9 |
| -2.93 | CHST4 | carbohydrate (N-acetylglucosamine 6-O) sulfot |
| 2.93 | SPAG9 | sperm associated antigen 9 |
| 2.93 | — | — |
| 2.93 | PROX1 | prospero-related homeobox 1 |
| 2.93 | — | Full-length cDNA clone CS0DD001YA12 of Ne |
| 2.93 | PROS1 | protein S (alpha) |
| 2.93 | SLC2A1 | solute carrier family 2 (facilitated glucose trans |
| 2.93 | — | — |
| -2.93 | — | — |
| 2.93 | SLC44A5 | solute carrier family 44, member 5 |
| 2.93 | TTLL11 | tubulin tyrosine ligase-like family, member 11 |
| 2.93 | FLJ13391 | hypothetical protein FLJ13391 |
| -2.93 | AQP4 | aquaporin 4 |
| -2.92 | PTGIS | prostaglandin I2 (prostacyclin) synthase /// pros |
| -2.92 | SLC2A3 | solute carrier family 2 (facilitated glucose trans |
| 2.92 | FAM59B | family with sequence similarity 59, member B |
| 2.92 | — | Transcribed locus |
| 2.92 | BAI3 | brain-specific angiogenesis inhibitor 3 |
| -2.92 | FLJ21963 | FLJ21963 protein |
| -2.92 | CA4 | carbonic anhydrase IV |
| 2.92 | GNAZ | guanine nucleotide binding protein (G protein), |
| -2.92 | MMP24 | matrix metallopeptidase 24 (membrane-inserte |
| -2.92 | PDE5A | phosphodiesterase 5A, cGMP-specific |
| -2.92 | — | Nucleoporin (GYLZ-RCC18) mRNA, GYLZ-RC |
| 2.92 | — | — |
| 2.92 | — | — |
| -2.91 | GDA | guanine deaminase |
| -2.91 | KCTD14 | potassium channel tetramerisation domain con |
| -2.91 | — | — |
| 2.91 | — | Transcribed locus |
| -2.91 | TBX5 | T-box 5 |
| -2.91 | GABARAPL1 | GABA(A) receptor-associated protein like 1 |
| -2.91 | — | — |
| -2.91 | NLGN4Y | neuroligin 4, Y-linked |
| 2.91 | — | — |
| -2.91 | PHLDA2 | pleckstrin homology-like domain, family A, mer |
| -2.91 | PHF11 /// RP13-36( | PHD finger protein 11 /// cancer/testis antigen ( |
| -2.90 | MBP | myelin basic protein |
| 2.90 | — | Full length insert cDNA clone YZ38E04 |
| 2.90 | — | — |
| -2.90 | KLK8 | kallikrein-related peptidase 8 |
| 2.90 | — | — |
| -2.90 | RASGRF2 | Ras protein-specific guanine nucleotide-releasi |
| -2.90 | FGF18 | fibroblast growth factor 18 /// fibroblast growth |
| -2.90 | SYT6 | Synaptotagmin VI |
| -2.89 | HLA-C | major histocompatibility complex, class I, C |
| -2.89 | — | — |
| 2.89 | HDLBP | High density lipoprotein binding protein (vigilin) |
| 2.89 | LOC283075 | Hypothetical protein LOC283075 |
| 2.89 | FCHSD2 | FCH and double SH3 domains 2 |
| 2.89 | — | — |
| 2.89 | SEC22C | SEC22 vesicle trafficking protein homolog C (S |
| -2.89 | — | — |
| -2.89 | TBX5 | T-box 5 |
| 2.89 | D2HGDH | D-2-hydroxyglutarate dehydrogenase |
| -2.89 | SEZ6L2 | seizure related 6 homolog (mouse)-like 2 |
| 2.89 | RFX2 | regulatory factor X, 2 (influences HLA class II e |
| 2.89 | PTX3 | pentraxin-related gene, rapidly induced by IL-1 |
| -2.88 | — | Transcribed locus, strongly similar to XP_5296 |
| 2.88 | ZNF25 | zinc finger protein 25 (KOX 19) |
| 2.88 | PIK3R3 | phosphoinositide-3-kinase, regulatory subunit 3 |
| 2.88 | FLRT3 | fibronectin leucine rich transmembrane protein |
| -2.88 | HTR3A | 5-hydroxytryptamine (serotonin) receptor 3A |
| -2.88 | — | CDNA clone IMAGE:4793048 |
| 2.88 | GNG11 | guanine nucleotide binding protein (G protein), |
| -2.88 | PLSCR1 | phospholipid scramblase 1 |
| -2.88 | SIX2 | sine oculis homeobox homolog 2 (Drosophila) |
| 2.88 | — | Full-length cDNA clone CS0DI042YD07 of Pla |
| 2.88 | — | — |
| -2.88 | LOC390940 | similar to R28379_1 |
| 2.88 | SLIT1 | slit homolog 1 (Drosophila) |
| 2.96 | — | — |
| -2.96 | SFN | stratifin |
| -2.96 | FLJ31204 | hypothetical protein FLJ31204 |
| 2.96 | LOC654342 | Similar to lymphocyte-specific protein 1 |
| -2.96 | STYK1 | serine/threonine/tyrosine kinase 1 /// serine/thr |
| -2.96 | VASH2 | vasohibin 2 |
| -2.96 | TMOD1 | tropomodulin 1 |
| 2.96 | RPL31 /// LOC2852 | ribosomal protein L31 /// similar to ribosomal pr |
| -2.96 | — | — |
| -2.96 | — | MRNA; cDNA DKFZp564B213 (from clone DKI |
| 2.96 | — | — |
| -2.96 | CNN1 | calponin 1, basic, smooth muscle |
| -2.96 | GRIK5 | glutamate receptor, ionotropic, kainate 5 |
| -2.95 | PHLDA1 | pleckstrin homology-like domain, family A, mer |
| -2.95 | — | CDNA clone IMAGE:4811759 |
| 2.95 | NOL4 | nucleolar protein 4 |
| 2.95 | — | — |
| 2.95 | TTC3 | tetratricopeptide repeat domain 3 |
| -2.95 | TMEM63A | transmembrane protein 63A |
| -2.95 | NLRP1 | NLR family, pyrin domain containing 1 |
| -2.95 | — | — |
| -2.95 | LOC400120 | hypothetical LOC400120 |
| -2.95 | RPS24 | Ribosomal protein S24 |
| 2.95 | TTLL9 | tubulin tyrosine ligase-like family, member 9 |
| -2.95 | LOC400680 | hypothetical gene supported by AK097381; BC |
| -2.95 | JPH3 | junctophilin 3 |
| 2.95 | ASE-1 | CD3E antigen, epsilon polypeptide associated |
| -2.94 | — | — |
| 2.94 | SECP43 | tRNA selenocysteine associated protein |
| 2.94 | EPS8 | epidermal growth factor receptor pathway subs |
| -2.94 | BSPRY | B-box and SPRY domain containing |
| 2.94 | GDPD1 | glycerophosphodiester phosphodiesterase dor |
| 2.94 | FABP7 | Fatty acid binding protein 7, brain |
| -2.94 | H2AFJ | H2A histone family, member J |
| -2.94 | — | — |
| 2.94 | HERPUD1 | Homocysteine-inducible, endoplasmic reticulur |
| -2.94 | ZNF649 | zinc finger protein 649 |
| -2.94 | — | — |
| 2.94 | — | CDNA FLJ37023 fis, clone BRACE2010828 |
| -2.94 | — | — |
| 2.94 | RAB9B | RAB9B, member RAS oncogene family |
| 2.94 | FKBP7 | FK506 binding protein 7 |
| 2.94 | NAV3 | neuron navigator 3 |
| -2.94 | — | — |
| 2.94 | PLXNA2 | plexin A2 |
| 2.93 | — | — |
| 2.93 | LHFP | Lipoma HMGIC fusion partner |
| -2.93 | DNMT3B | DNA (cytosine-5-)-methyltransferase 3 beta |
| -2.93 | — | — |
| 2.93 | CEP290 | centrosomal protein 290kDa |
| 2.93 | MAP1A | microtubule-associated protein 1A |
| -2.93 | STC2 | stanniocalcin 2 |
| -2.93 | — | — |
| -2.93 | TRAF3IP2 | TRAF3 interacting protein 2 |
| -2.93 | SAT1 | spermidine/spermine N1-acetyltransferase 1 |
| -2.93 | HLA-G | HLA-G histocompatibility antigen, class I, G |
| -2.93 | — | — |
| -2.92 | — | — |
| 2.92 | LOC651466 | Similar to retinoic acid receptor responder (taz |
| 2.92 | CHST3 | carbohydrate (chondroitin 6) sulfotransferase 3 |
| 2.92 | KALRN | kalirin, RhoGEF kinase |
| -2.92 | TERF1 | telomeric repeat binding factor (NIMA-interacti |
| 2.92 | LGR5 | leucine-rich repeat-containing G protein-couple |
| 2.92 | MCTP1 | Multiple C2-domains with two transmembrane |
| -2.92 | PRICKLE1 | prickle homolog 1 (Drosophila) |
| -2.92 | FLJ13195 | Stromal antigen 3-like |
| 2.92 | EFCBP2 | EF-hand calcium binding protein 2 |
| -2.92 | MME | membrane metallo-endopeptidase (neutral end |
| 2.92 | — | — |
| 2.92 | DST | Dystonin |
| 2.92 | RRAGD | Ras-related GTP binding D |
| 2.92 | FAT3 | FAT tumor suppressor homolog 3 (Drosophila) |
| -2.92 | GPC4 | glypican 4 |
| -2.92 | — | — |
| -2.91 | — | CDNA clone IMAGE:5311608 |
| 2.91 | FYN | FYN oncogene related to SRC, FGR, YES |
| -2.91 | SILV | silver homolog (mouse) |
| -2.91 | — | — |
| -2.91 | TMEM132D | transmembrane protein 132D |

Appendix 1

| Value | Gene | Description |
|---|---|---|
| 2.88 | DCHS1 | dachsous 1 (Drosophila) |
| 2.88 | MTCH2 | mitochondrial carrier homolog 2 (C. elegans) |
| 2.88 | LOC389073 | similar to RIKEN cDNA D630023F18 |
| 2.88 | ELOVL2 | elongation of very long chain fatty acids (FEN1 |
| 2.87 | — | CDNA: FLJ22546 fis, clone HSI00290 |
| -2.87 | ADAMTS19 | ADAM metallopeptidase with thrombospondin |
| -2.87 | DOCK2 | dedicator of cytokinesis 2 |
| 2.87 | NFKBIZ | Nuclear factor of kappa light polypeptide gene |
| 2.87 | MECP2 | methyl CpG binding protein 2 (Rett syndrome) |
| 2.87 | — | — |
| -2.87 | RBMS1 | RNA binding motif, single stranded interacting |
| 2.87 | — | EST from clone 27306, 5' end |
| -2.87 | DIAPH2 | diaphanous homolog 2 (Drosophila) |
| 2.87 | — | — |
| 2.87 | ASXL1 | additional sex combs like 1 (Drosophila) |
| 2.86 | IL17RB | interleukin 17 receptor B |
| 2.86 | — | — |
| -2.86 | ANXA4 | annexin A4 |
| 2.86 | ABCC4 | ATP-binding cassette, sub-family C (CFTR/MR |
| 2.86 | FLJ22965 | hypothetical protein FLJ22965 |
| -2.86 | 6-Sep | septin 6 |
| 2.86 | MEIS1 | Meis1, myeloid ecotropic viral integration site 1 |
| 2.86 | NTRK2 | neurotrophic tyrosine kinase, receptor, type 2 |
| 2.86 | PACS1 | phosphofurin acidic cluster sorting protein 1 |
| 2.86 | ERBB4 | v-erb-a erythroblastic leukemia viral oncogene |
| -2.86 | PLEK | pleckstrin |
| 2.85 | SEMA6D | sema domain, transmembrane domain (TM), a |
| -2.85 | TMEM92 | transmembrane protein 92 |
| -2.85 | — | Mesenchymal stem cell protein DSC96 |
| -2.85 | VASH2 | vasohibin 2 |
| -2.85 | IQGAP2 | IQ motif containing GTPase activating protein |
| 2.85 | — | MRNA; cDNA DKFZp564E143 (from clone DK |
| 2.85 | NPAS3 | neuronal PAS domain protein 3 |
| 2.85 | FST | follistatin |
| -2.85 | — | — |
| 2.85 | KCNH7 | Potassium voltage-gated channel, subfamily H |
| 2.85 | FNDC5 | fibronectin type III domain containing 5 |
| -2.85 | IGFBP7 | insulin-like growth factor binding protein 7 |
| -2.85 | RLN2 | relaxin 2 |
| 2.85 | PON2 | paraoxonase 2 |
| -2.84 | — | — |
| -2.84 | LDHA | lactate dehydrogenase A |
| 2.84 | WDR52 | WD repeat domain 52 |
| -2.84 | — | — |
| 2.84 | EPS8 | epidermal growth factor receptor pathway subs |
| 2.84 | — | Transcribed locus |
| -2.83 | LOC285547 | hypothetical protein LOC285547 |
| 2.83 | — | CDNA clone IMAGE:5303499 |
| -2.83 | GABRA5 /// LOC72 | gamma-aminobutyric acid (GABA) A receptor, |
| 2.83 | TMEM142B | transmembrane protein 142B |
| -2.83 | MARVELD3 | MARVEL domain containing 3 |
| 2.83 | FLJ25967 | Hypothetical gene supported by AK098833 |
| -2.83 | RARRES2 | retinoic acid receptor responder (tazarotene in |
| -2.83 | INDO | indoleamine-pyrrole 2,3 dioxygenase |
| -2.83 | — | — |
| 2.83 | FLJ23577 | KPL2 protein |
| 2.83 | KIAA0523 | KIAA0523 protein |
| 2.83 | NRIP3 | nuclear receptor interacting protein 3 |
| -2.83 | KLF5 | Kruppel-like factor 5 (intestinal) |
| -2.83 | TMOD1 | tropomodulin 1 |
| -2.83 | MOG | myelin oligodendrocyte glycoprotein |
| -2.82 | TMEPAI | transmembrane, prostate androgen induced R |
| 2.82 | PANX1 | Pannexin 1 |
| -2.82 | — | — |
| 2.82 | — | — |
| -2.82 | CLEC7A | C-type lectin domain family 7, member A /// C- |
| -2.82 | SKIL | SKI-like oncogene |
| 2.82 | SLC45A1 | solute carrier family 45, member 1 |
| 2.82 | TFDP2 | Transcription factor Dp-2 (E2F dimerization pa |
| -2.82 | KCNN2 | potassium intermediate/small conductance cal |
| 2.82 | — | — |
| -2.82 | DUSP10 | dual specificity phosphatase 10 |
| 2.81 | RSNL2 | restin-like 2 |
| -2.81 | FAM20C | family with sequence similarity 20, member C |
| -2.81 | TMEPAI | Transmembrane, prostate androgen induced R |
| -2.81 | CD44 | CD44 molecule (Indian blood group) |
| -2.81 | ADCY2 | adenylate cyclase 2 (brain) |
| -2.81 | SHOX2 | short stature homeobox 2 |
| -2.81 | KAZALD1 | Kazal-type serine peptidase inhibitor domain 1 |
| 2.91 | VEPH1 | ventricular zone expressed PH domain homolo |
| -2.91 | CADPS | Ca2+-dependent secretion activator |
| -2.91 | TIMP1 | TIMP metallopeptidase inhibitor 1 |
| 2.91 | U2AF2 | U2 small nuclear RNA auxiliary factor 2 |
| 2.91 | KCNAB1 | potassium voltage-gated channel, shaker-relat |
| -2.91 | — | PTR2 mRNA for repetitive sequence |
| -2.91 | — | — |
| -2.91 | PRKCQ | protein kinase C, theta |
| 2.91 | TTC3 | tetratricopeptide repeat domain 3 |
| 2.91 | CELSR2 | cadherin, EGF LAG seven-pass G-type recept |
| 2.91 | — | CDNA FLJ37333 fis, clone BRAMY2020106 |
| 2.91 | — | — |
| 2.90 | — | — |
| -2.90 | RDH12 | retinol dehydrogenase 12 (all-trans and 9-cis) |
| 2.90 | LOC347475 | hypothetical gene supported by BC017958 |
| 2.90 | LOC389073 | similar to RIKEN cDNA D630023F18 |
| -2.90 | — | — |
| 2.90 | — | CDNA FLJ37302 fis, clone BRAMY2016009 |
| 2.90 | SIM2 | single-minded homolog 2 (Drosophila) |
| 2.90 | — | CDNA clone IMAGE:5288757 |
| -2.90 | HLA-A | major histocompatibility complex, class I, A |
| -2.90 | HSCARG | HSCARG protein |
| 2.90 | — | CDNA clone IMAGE:4823793 |
| -2.89 | MOCOS | Molybdenum cofactor sulfurase |
| 2.89 | — | Transcribed locus |
| 2.89 | CDH6 | cadherin 6, type 2, K-cadherin (fetal kidney) |
| -2.89 | RBPMS | RNA binding protein with multiple splicing |
| -2.89 | NFIB | nuclear factor I/B |
| -2.89 | PBX1 | Pre-B-cell leukemia transcription factor 1 |
| 2.89 | DKK3 | dickkopf homolog 3 (Xenopus laevis) |
| 2.89 | GPRIN1 | G protein regulated inducer of neurite outgrowt |
| 2.89 | FMN2 | formin 2 |
| 2.89 | DKFZp666G057 | hypothetical protein DKFZp666G057 |
| -2.89 | — | — |
| 2.89 | — | — |
| -2.89 | CYP2E1 | cytochrome P450, family 2, subfamily E, polyp |
| 2.88 | — | — |
| 2.88 | GRIA2 | glutamate receptor, ionotropic, AMPA 2 |
| -2.88 | ACP5 | acid phosphatase 5, tartrate resistant |
| -2.88 | RPL23 | ribosomal protein L23 |
| 2.88 | PTDSR | phosphatidylserine receptor |
| -2.87 | ST8SIA3 | ST8 alpha-N-acetyl-neuraminide alpha-2,8-sial |
| 2.87 | — | — |
| 2.87 | — | — |
| -2.87 | ARRB1 | Arrestin, beta 1 |
| -2.87 | SERPINB12 | serpin peptidase inhibitor, clade B (ovalbumin) |
| 2.87 | — | — |
| 2.87 | TP53AP1 | TP53 activated protein 1 |
| -2.87 | IGFBP4 | insulin-like growth factor binding protein 4 |
| -2.87 | RAB20 | RAB20, member RAS oncogene family |
| 2.87 | SFXN3 | Sideroflexin 3 |
| 2.87 | FLJ14213 | hypothetical protein FLJ14213 |
| 2.87 | C14orf152 | chromosome 14 open reading frame 152 |
| -2.87 | ZIC3 | Zic family member 3 heterotaxy 1 (odd-paired |
| -2.87 | ADCY2 | adenylate cyclase 2 (brain) |
| 2.87 | — | — |
| -2.87 | GCNT2 /// SPTLC3 | glucosaminyl (N-acetyl) transferase 2, I-branch |
| -2.87 | HLA-B | major histocompatibility complex, class I, B /// |
| -2.87 | — | Transcribed locus |
| 2.87 | CAPZA1 | Capping protein (actin filament) muscle Z-line, |
| 2.86 | BCL2 | B-cell CLL/lymphoma 2 |
| -2.86 | — | CDNA FLJ32963 fis, clone TESTI2008405 |
| 2.86 | SERAC1 | serine active site containing 1 |
| -2.86 | HMGA1 | high mobility group AT-hook 1 |
| -2.86 | olfactory receptor, f | CDNA FLJ11504 fis, clone HEMBA1002119 |
| -2.86 | — | — |
| -2.86 | MUC3A | mucin 3A, cell surface associated |
| 2.86 | REEP1 | receptor accessory protein 1 |
| -2.86 | — | — |
| -2.86 | GRPR | gastrin-releasing peptide receptor |
| -2.86 | — | Transcribed locus |
| 2.85 | — | — |
| 2.85 | FBXL16 | F-box and leucine-rich repeat protein 16 |
| 2.85 | MCTP1 | multiple C2 domains, transmembrane 1 |
| -2.85 | THY1 | Thy-1 cell surface antigen |
| -2.85 | NFIB | nuclear factor I/B |
| 2.85 | ZNF25 | zinc finger protein 25 (KOX 19) |
| 2.85 | RPS11 | Ribosomal protein S11 |
| -2.85 | — | — |

Appendix 1

| | | |
|---|---|---|
| -2.81 | RUTBC2 | RUN and TBC1 domain containing 2 |
| -2.81 | GFPT2 | glutamine-fructose-6-phosphate transaminase |
| -2.81 | C20orf19 | chromosome 20 open reading frame 19 |
| -2.81 | ZNF671 | zinc finger protein 671 |
| 2.81 | INSM1 | insulinoma-associated 1 |
| 2.81 | — | CDNA clone IMAGE:5263177 |
| 2.81 | SECP43 | tRNA selenocysteine associated protein |
| 2.81 | ANKRD20A1 /// C2 | ankyrin repeat domain 20 family, member A1 /// |
| -2.81 | RAB3B | RAB3B, member RAS oncogene family |
| -2.81 | D21S2088E | D21S2088E |
| -2.81 | HLA-DQA1 | major histocompatibility complex, class II, DQ |
| 2.81 | CORO2B | coronin, actin binding protein, 2B |
| -2.80 | RBMS1 | RNA binding motif, single stranded interacting |
| -2.80 | — | — |
| -2.80 | — | Transcribed locus |
| 2.80 | IGSF4 | immunoglobulin superfamily, member 4 |
| 2.80 | TIMP2 | TIMP metallopeptidase inhibitor 2 |
| -2.80 | ZDHHC23 | zinc finger, DHHC-type containing 23 |
| 2.80 | GLULD1 | glutamate-ammonia ligase (glutamine synthetase |
| -2.80 | CCL2 | chemokine (C-C motif) ligand 2 |
| 2.80 | — | — |
| -2.80 | CABP1 | calcium binding protein 1 (calbrain) |
| -2.80 | — | — |
| 2.80 | ZNF343 | zinc finger protein 343 |
| 2.80 | CXorf6 | chromosome X open reading frame 6 |
| -2.80 | ZNF788 | zinc finger family member 788 |
| 2.80 | TMEM65 | transmembrane protein 65 |
| -2.80 | RBMS1 | RNA binding motif, single stranded interacting |
| 2.80 | SCRN3 | secernin 3 |
| -2.79 | ZBTB3 | zinc finger and BTB domain containing 3 |
| 2.79 | HOXC5 | homeobox C5 |
| 2.79 | IFIT5 | interferon-induced protein with tetratricopeptide |
| -2.79 | SPIB | Spi-B transcription factor (Spi-1/PU.1 related) /// |
| 2.79 | LRP11 | Low density lipoprotein receptor-related protein |
| -2.79 | TPD52L1 | tumor protein D52-like 1 |
| -2.79 | — | — |
| 2.79 | LOC643911 /// LOC | hypothetical LOC643911 /// hypothetical protein |
| -2.79 | KCNK1 | potassium channel, subfamily K, member 1 |
| 2.79 | GNG2 | guanine nucleotide binding protein (G protein), |
| -2.79 | XDH | xanthine dehydrogenase |
| 2.79 | KIAA1102 | KIAA1102 protein |
| 2.79 | YPEL4 | Yippee-like 4 (Drosophila) |
| -2.79 | — | — |
| 2.79 | HPCAL4 | hippocalcin like 4 |
| 2.79 | CEECAM1 | cerebral endothelial cell adhesion molecule 1 |
| -2.78 | — | — |
| -2.78 | C9orf61 | chromosome 9 open reading frame 61 |
| 2.78 | SCML1 | Sex comb on midleg-like 1 (Drosophila) |
| 2.78 | DIXDC1 | DIX domain containing 1 |
| -2.77 | MFAP3L | microfibrillar-associated protein 3-like |
| -2.77 | OVOL1 | ovo-like 1(Drosophila) |
| 2.77 | — | CDNA FLJ26260 fis, clone DMC05193 |
| 2.77 | MAPK8IP1 | mitogen-activated protein kinase 8 interacting |
| 2.77 | DKFZp313A2432 | hypothetical protein DKFZp313A2432 |
| 2.77 | — | — |
| 2.77 | LMO3 | LIM domain only 3 (rhombotin-like 2) |
| -2.77 | — | — |
| -2.77 | DNAJA4 | DnaJ (Hsp40) homolog, subfamily A, member 4 |
| -2.77 | — | Homo sapiens, Similar to LOC169932, clone IM |
| -2.77 | PTTG1IP | Pituitary tumor-transforming 1 interacting prote |
| 2.77 | SUV39H2 | suppressor of variegation 3-9 homolog 2 (Dros |
| -2.77 | — | — |
| 2.77 | KIAA0101 | KIAA0101 /// KIAA0101 |
| -2.77 | PRICKLE1 | prickle homolog 1 (Drosophila) |
| 2.77 | SLC6A16 | solute carrier family 6, member 16 |
| 2.77 | ANKRD6 | ankyrin repeat domain 6 |
| -2.76 | BTBD4 | BTB (POZ) domain containing 4 |
| 2.76 | — | — |
| -2.76 | RORA | RAR-related orphan receptor A |
| 2.76 | — | — |
| 2.76 | ASE-1 | CD3E antigen, epsilon polypeptide associated |
| 2.76 | MARCKS | myristoylated alanine-rich protein kinase C sub |
| -2.76 | LOC201895 | hypothetical protein LOC201895 |
| -2.76 | KLF10 | Kruppel-like factor 10 |
| 2.76 | CSDC2 | cold shock domain containing C2, RNA binding |
| -2.76 | CCND2 | cyclin D2 |
| -2.76 | PRICKLE1 | Prickle-like 1 (Drosophila) |
| -2.76 | — | — |
| 2.76 | VIM | vimentin |
| 2.85 | — | — |
| 2.85 | KCNJ8 | potassium inwardly-rectifying channel, subfami |
| 2.85 | CBX8 | chromobox homolog 8 (Pc class homolog, Dros |
| -2.85 | LYPD3 | LY6/PLAUR domain containing 3 |
| 2.85 | — | — |
| -2.85 | IFI16 | interferon, gamma-inducible protein 16 |
| 2.85 | GRM3 | glutamate receptor, metabotropic 3 |
| 2.84 | GNAZ | guanine nucleotide binding protein (G protein), |
| 2.84 | — | — |
| -2.84 | COL13A1 | collagen, type XIII, alpha 1 |
| -2.84 | RASGRP2 | RAS guanyl releasing protein 2 (calcium and D |
| 2.84 | — | Transcribed locus |
| -2.84 | NEB | Nebulin |
| 2.84 | — | — |
| 2.84 | PTX3 | pentraxin-related gene, rapidly induced by IL-1 |
| -2.83 | GPD2 | glycerol-3-phosphate dehydrogenase 2 (mitoch |
| -2.83 | MGC24665 | hypothetical protein MGC24665 |
| 2.83 | FAM55C | family with sequence similarity 55, member C |
| 2.83 | SHANK3 | SH3 and multiple ankyrin repeat domains 3 |
| -2.83 | WBSCR17 | Williams-Beuren syndrome chromosome region |
| -2.83 | HLA-B | major histocompatibility complex, class I, B |
| 2.83 | — | CDNA FLJ38252 fis, clone FCBBF3000269 |
| 2.83 | — | — |
| 2.83 | AKR1C1 | aldo-keto reductase family 1, member C1 (dihy |
| -2.83 | TRIP6 | thyroid hormone receptor interactor 6 |
| 2.83 | PLEKHB1 | pleckstrin homology domain containing, family |
| -2.83 | — | Homo sapiens, Similar to LOC169932, clone IM |
| 2.83 | ALPK2 | alpha-kinase 2 |
| 2.83 | — | — |
| 2.83 | — | — |
| 2.83 | PROX1 | prospero-related homeobox 1 |
| -2.83 | 6-Sep | septin 6 |
| 2.83 | LOC284262 | hypothetical protein LOC284262 |
| 2.83 | TIGA1 | TIGA1 |
| -2.82 | GADD45B | growth arrest and DNA-damage-inducible, beta |
| 2.82 | — | — |
| -2.82 | GPR37 | G protein-coupled receptor 37 (endothelin rece |
| 2.82 | MCPH1 | Microcephaly, primary autosomal recessive 1 |
| -2.82 | TDH | L-threonine dehydrogenase |
| 2.82 | — | CDNA FLJ26260 fis, clone DMC05193 |
| -2.82 | MFAP3L | microfibrillar-associated protein 3-like |
| 2.82 | LRP2 | low density lipoprotein-related protein 2 |
| 2.82 | LOC643187 | Similar to ankyrin repeat domain 20A |
| -2.82 | ARHGAP29 | Rho GTPase activating protein 29 |
| -2.82 | RP13-36C9.1 /// RP | cancer/testis antigen CT45-2 /// cancer/testis a |
| 2.82 | CXCL14 | chemokine (C-X-C motif) ligand 14 |
| -2.82 | — | — |
| 2.82 | CENTD1 | centaurin, delta 1 |
| -2.81 | — | Hypothetical protein LOC285679 |
| 2.81 | — | MRNA; cDNA DKFZp686D0673 (from clone DK |
| -2.81 | TBX5 | T-box 5 |
| -2.81 | CTSL2 | Cathepsin L2 |
| 2.81 | — | — |
| -2.81 | ATP8B3 | ATPase, Class I, type 8B, member 3 |
| -2.81 | USP28 | ubiquitin specific peptidase 28 |
| -2.81 | GABRA5 | gamma-aminobutyric acid (GABA) A receptor, |
| 2.81 | PCDHB10 | protocadherin beta 10 |
| -2.80 | ANXA4 | annexin A4 |
| -2.80 | KLK8 | kallikrein-related peptidase 8 |
| -2.80 | PTRF | polymerase I and transcript release factor |
| 2.80 | FLJ90757 | hypothetical protein LOC440465 |
| 2.80 | MEIS1 | Meis1, myeloid ecotropic viral integration site 1 |
| 2.80 | FGFRL1 | fibroblast growth factor receptor-like 1 |
| -2.80 | CHES1 | checkpoint suppressor 1 |
| -2.80 | ZNF452 | zinc finger protein 452 |
| 2.80 | ERBB4 | v-erb-a erythroblastic leukemia viral oncogene |
| 2.80 | FLJ10159 | Hypothetical protein FLJ10159 |
| 2.80 | MAPK10 | mitogen-activated protein kinase 10 |
| -2.80 | SEPP1 | selenoprotein P, plasma, 1 |
| -2.79 | PPP2R5C | protein phosphatase 2, regulatory subunit B (B |
| 2.79 | B4GALNT1 | beta-1,4-N-acetyl-galactosaminyl transferase 1 |
| 2.79 | ZFHX4 | zinc finger homeodomain 4 |
| 2.79 | TTC3 | tetratricopeptide repeat domain 3 |
| -2.79 | F12 | coagulation factor XII (Hageman factor) |
| -2.79 | CYP2E1 | cytochrome P450, family 2, subfamily E, polype |
| 2.79 | — | Transcribed locus |
| 2.79 | QKI | Quaking homolog, KH domain RNA binding (m |
| -2.79 | USP44 | ubiquitin specific peptidase 44 |
| 2.79 | ING3 | inhibitor of growth family, member 3 |

Appendix 1

| Value | Gene | Description |
|---|---|---|
| 2.76 | ACCN2 | amiloride-sensitive cation channel 2, neuronal |
| 2.76 | GPR54 | G protein-coupled receptor 54 |
| 2.76 | — | — |
| 2.76 | NMNAT2 | nicotinamide nucleotide adenylyltransferase 2 |
| -2.76 | SULT1C1 | sulfotransferase family, cytosolic, 1C, member |
| -2.76 | IRF6 | interferon regulatory factor 6 |
| 2.76 | — | — |
| -2.76 | — | — |
| 2.76 | PLXNA2 | plexin A2 |
| -2.76 | FLJ14001 | hypothetical protein FLJ14001 |
| -2.75 | C20orf59 | chromosome 20 open reading frame 59 |
| 2.75 | — | — |
| -2.75 | HLA-B | major histocompatibility complex, class I, B |
| -2.75 | TLR3 | toll-like receptor 3 |
| 2.75 | — | — |
| -2.75 | ATP2A3 | ATPase, Ca++ transporting, ubiquitous |
| -2.75 | G0S2 | G0/G1switch 2 |
| -2.75 | — | — |
| -2.75 | JAZF1 | JAZF zinc finger 1 |
| -2.75 | — | — |
| -2.75 | BTD | biotinidase |
| -2.75 | SPAG16 | Sperm associated antigen 16 |
| 2.75 | KIAA1648 | KIAA1648 protein |
| 2.75 | DKFZp547D2210 | hypothetical protein DKFZp547D2210 |
| 2.74 | NRIP1 | nuclear receptor interacting protein 1 |
| 2.74 | FOSL1 | FOS-like antigen 1 |
| 2.74 | DKK3 | dickkopf homolog 3 (Xenopus laevis) |
| -2.74 | HCLS1 | hematopoietic cell-specific Lyn substrate 1 |
| 2.74 | — | — |
| -2.74 | EDA | ectodysplasin A |
| 2.74 | RASSF2 | Ras association (RalGDS/AF-6) domain family |
| -2.74 | RBPMS | RNA binding protein with multiple splicing |
| 2.74 | PUNC | Putative neuronal cell adhesion molecule |
| 2.74 | GBX2 | gastrulation brain homeobox 2 |
| 2.73 | TBX1 | T-box 1 |
| -2.73 | FLJ11286 | hypothetical protein FLJ11286 |
| 2.73 | PPM1L | Protein phosphatase 1 (formerly 2C)-like |
| 2.73 | — | — |
| -2.73 | MMP14 | matrix metallopeptidase 14 (membrane-inserte |
| -2.73 | PPP2R5C | Protein phosphatase 2, regulatory subunit B (B |
| 2.73 | — | MRNA; cDNA DKFZp762l0915 (from clone DK |
| 2.73 | ARIH2 | Ariadne homolog 2 (Drosophila) |
| 2.73 | SLC4A4 | solute carrier family 4, sodium bicarbonate cotr |
| 2.73 | SSPN | sarcospan (Kras oncogene-associated gene) |
| 2.73 | FZD1 | frizzled homolog 1 (Drosophila) |
| 2.73 | — | — |
| 2.73 | HSPA4L | heat shock 70kDa protein 4-like |
| 2.73 | LOX | lysyl oxidase |
| 2.73 | — | — |
| 2.73 | FST | follistatin |
| -2.72 | CLDN10 | claudin 10 |
| -2.72 | TRIM6 | tripartite motif-containing 6 |
| 2.72 | — | — |
| 2.72 | — | CDNA FLJ30383 fis, clone BRACE2008102 |
| 2.72 | AYTL1 | acyltransferase like 1 |
| 2.72 | — | CDNA clone IMAGE:4826097 |
| -2.72 | — | — |
| 2.72 | HOXA6 | homeobox A6 |
| 2.72 | ALDH5A1 | aldehyde dehydrogenase 5 family, member A1 |
| -2.72 | MSTP9 | macrophage stimulating, pseudogene 9 |
| 2.72 | ZFP3 | zinc finger protein 3 homolog (mouse) |
| 2.71 | CACNG4 | calcium channel, voltage-dependent, gamma s |
| 2.71 | HS3ST3B1 | Heparan sulfate (glucosamine) 3-O-sulfotransfe |
| -2.71 | CPO | carboxypeptidase O |
| 2.71 | F10 | coagulation factor X |
| -2.71 | BAIAP2L1 | BAI1-associated protein 2-like 1 |
| -2.71 | — | — |
| -2.71 | ARHGAP28 | Rho GTPase activating protein 28 |
| -2.71 | GAL | galanin |
| -2.71 | BMP2 | bone morphogenetic protein 2 |
| 2.71 | — | Transcribed locus |
| -2.71 | ORM1 /// ORM2 | orosomucoid 1 /// orosomucoid 2 |
| 2.71 | SLC8A3 | Solute carrier family 8 (sodium-calcium exchan |
| -2.70 | SERPINB9 | serpin peptidase inhibitor, clade B (ovalbumin), |
| 2.70 | RALGDS | ral guanine nucleotide dissociation stimulator |
| 2.70 | SLC1A4 | solute carrier family 1 (glutamate/neutral aminc |
| -2.70 | LAPTM5 | lysosomal associated multispanning membrane |
| -2.70 | H2AFJ | H2A histone family, member J |
| 2.70 | RPIB9 | Rap2-binding protein 9 |
| 2.79 | TFAP2A | Transcription factor AP-2 alpha (activating enh |
| -2.78 | DNAJA4 | DnaJ (Hsp40) homolog, subfamily A, member |
| 2.78 | — | CDNA FLJ36584 fis, clone TRACH2013450 |
| 2.78 | AYTL1 | acyltransferase like 1 |
| 2.78 | PRDM16 | PR domain containing 16 |
| 2.78 | APLP1 | amyloid beta (A4) precursor-like protein 1 |
| -2.78 | TMEM171 | transmembrane protein 171 |
| -2.78 | RTP1 | receptor (chemosensory) transporter protein 1 |
| -2.78 | TRIM38 | tripartite motif-containing 38 |
| -2.78 | OVOL1 | ovo-like 1(Drosophila) |
| -2.78 | AKT2 | v-akt murine thymoma viral oncogene homolog |
| 2.78 | — | — |
| -2.78 | PPAP2A | phosphatidic acid phosphatase type 2A |
| -2.77 | C1orf61 | chromosome 1 open reading frame 61 |
| 2.77 | ENPEP | glutamyl aminopeptidase (aminopeptidase A) |
| -2.77 | CHES1 | checkpoint suppressor 1 |
| -2.77 | APOBEC3G /// APC | apolipoprotein B mRNA editing enzyme, cataly |
| 2.77 | — | — |
| 2.77 | PDE1A | phosphodiesterase 1A, calmodulin-dependent |
| -2.77 | RBMS1 | RNA binding motif, single stranded interacting |
| 2.77 | — | — |
| -2.77 | KCNS3 | potassium voltage-gated channel, delayed-rect |
| -2.77 | LOC342892 | Hypothetical protein LOC342892 |
| 2.77 | DKFZp313A2432 | hypothetical protein DKFZp313A2432 |
| -2.76 | C1RL | complement component 1, r subcomponent-lik |
| -2.76 | PLEKHC1 | pleckstrin homology domain containing, family |
| -2.76 | RBP1 | retinol binding protein 1, cellular |
| -2.76 | ENPP1 | ectonucleotide pyrophosphatase/phosphodiest |
| 2.76 | SCD5 | stearoyl-CoA desaturase 5 |
| -2.76 | GCHFR | GTP cyclohydrolase I feedback regulator |
| 2.76 | C6orf174 | chromosome 6 open reading frame 174 |
| 2.76 | TMEM106C | transmembrane protein 106C |
| -2.76 | MYO5C | myosin VC |
| 2.76 | TOX | thymus high mobility group box protein TOX |
| 2.76 | FAT3 | FAT tumor suppressor homolog 3 (Drosophila) |
| 2.76 | MKRN3 | makorin, ring finger protein, 3 |
| 2.76 | WNT5A | Wingless-type MMTV integration site family, m |
| 2.76 | — | CDNA FLJ11796 fis, clone HEMBA1006158, h |
| 2.76 | HS6ST2 | heparan sulfate 6-O-sulfotransferase 2 |
| 2.75 | FLJ42709 | Hypothetical gene supported by AK124699 |
| 2.75 | CAMK2N1 | calcium/calmodulin-dependent protein kinase I |
| -2.75 | SLC35F2 | solute carrier family 35, member F2 |
| 2.75 | MCART6 | mitochondrial carrier triple repeat 6 |
| 2.75 | — | — |
| -2.75 | — | — |
| 2.75 | — | — |
| 2.75 | LOC51145 | erythrocyte transmembrane protein |
| -2.75 | SMPDL3B | sphingomyelin phosphodiesterase, acid-like 3B |
| -2.75 | FER1L3 | fer-1-like 3, myoferlin (C. elegans) |
| 2.75 | RAB36 | RAB36, member RAS oncogene family |
| -2.75 | P2RX1 | purinergic receptor P2X, ligand-gated ion chan |
| 2.75 | NPAS3 | neuronal PAS domain protein 3 |
| 2.75 | — | — |
| -2.75 | — | — |
| -2.75 | — | — |
| 2.75 | TPPP | brain-specific protein p25 alpha |
| 2.74 | ZNF396 | zinc finger protein 396 |
| -2.74 | TBC1D8 | TBC1 domain family, member 8 (with GRAM d |
| -2.74 | IL1B | interleukin 1, beta |
| -2.74 | LOC728473 | hypothetical protein LOC728473 |
| -2.74 | ITGA3 | integrin, alpha 3 (antigen CD49C, alpha 3 subu |
| 2.74 | TXNDC4 | thioredoxin domain containing 4 (endoplasmic |
| 2.74 | EDG1 | endothelial differentiation, sphingolipid G-prote |
| -2.74 | PIPOX | pipecolic acid oxidase |
| -2.74 | — | — |
| -2.74 | TPM1 | tropomyosin 1 (alpha) |
| -2.74 | DNAJB6 | DnaJ (Hsp40) homolog, subfamily B, member |
| 2.74 | BAALC | brain and acute leukemia, cytoplasmic |
| 2.74 | — | Full-length cDNA clone CS0DF032YA11 of Fet |
| -2.73 | GABRB3 | Gamma-aminobutyric acid (GABA) A receptor, |
| 2.73 | WDR42A | WD repeat domain 42A |
| -2.73 | PRKCH | protein kinase C, eta |
| 2.73 | RTN1 | reticulon 1 |
| -2.73 | CD55 | CD55 molecule, decay accelerating factor for c |
| 2.73 | — | — |
| 2.73 | — | CDNA FLJ31660 fis, clone NT2RI2004410 |
| 2.73 | MYLK | myosin, light polypeptide kinase |
| 2.73 | RRAGD | Ras-related GTP binding D |
| -2.73 | LOC123688 | similar to RIKEN cDNA C630028N24 gene |

Appendix 1

| | | | | |
|---|---|---|---|---|
| -2.70 | FAM124B | family with sequence similarity 124B | 2.73 EP400 | E1A binding protein p400 |
| -2.70 | GCHFR | GTP cyclohydrolase I feedback regulator | -2.73 MSTP9 | macrophage stimulating, pseudogene 9 |
| -2.70 | — | — | 2.73 ATP10D | ATPase, Class V, type 10D |
| 2.70 | TIFA | TRAF-interacting protein with a forkhead-assoc | -2.73 ASS1 | argininosuccinate synthetase 1 |
| -2.70 | ART3 | ADP-ribosyltransferase 3 | -2.73 HMCN1 | hemicentin 1 |
| 2.70 | CDH4 | cadherin 4, type 1, R-cadherin (retinal) | -2.73 LLGL2 | lethal giant larvae homolog 2 (Drosophila) |
| 2.70 | DKK3 | dickkopf homolog 3 (Xenopus laevis) | 2.73 NCAM1 | Neural cell adhesion molecule 1 |
| -2.70 | ARRB1 | arrestin, beta 1 | -2.72 CNGA1 | cyclic nucleotide gated channel alpha 1 |
| -2.70 | SLC1A3 | solute carrier family 1 (glial high affinity glutama | -2.72 SLC25A43 | solute carrier family 25, member 43 |
| 2.70 | — | — | 2.72 LASS3 | LAG1 homolog, ceramide synthase 3 (S. cerev |
| -2.69 | VSIG1 | V-set and immunoglobulin domain containing 1 | 2.72 TMEM5 | transmembrane protein 5 |
| 2.69 | MDH1B | malate dehydrogenase 1B, NAD (soluble) | -2.72 — | CDNA: FLJ21735 fis, clone COLF3350 |
| 2.69 | DCX | doublecortex; lissencephaly, X-linked (doublec | -2.72 GSDMDC1 | gasdermin domain containing 1 |
| 2.69 | GPR161 | G protein-coupled receptor 161 | -2.72 LMO6 | LIM domain only 6 |
| 2.69 | NEFL | neurofilament, light polypeptide 68kDa | 2.72 FLJ14503 | hypothetical protein FLJ14503 |
| -2.69 | — | — | -2.71 ICAM4 | intercellular adhesion molecule 4 (Landsteiner- |
| -2.69 | REPS2 | RALBP1 associated Eps domain containing 2 | 2.71 3-Sep | septin 3 |
| 2.69 | — | Full length insert cDNA clone YZ38E04 | 2.71 FYN | FYN oncogene related to SRC, FGR, YES |
| 2.69 | CXXC4 | CXXC finger 4 | 2.71 KLHL8 | kelch-like 8 (Drosophila) |
| 2.69 | TTMA | two transmembrane domain family member A | -2.71 JAZF1 | JAZF zinc finger 1 |
| -2.69 | BCL6B | B-cell CLL/lymphoma 6, member B (zinc finger | 2.71 CDO1 | cysteine dioxygenase, type |
| 2.69 | — | — | -2.71 AP1S3 | adaptor-related protein complex 1, sigma 3 sub |
| 2.69 | C11orf41 | chromosome 11 open reading frame 41 | -2.71 SERPINB9 | serpin peptidase inhibitor, clade B (ovalbumin), |
| -2.69 | ICAM4 | intercellular adhesion molecule 4 (Landsteiner- | 2.71 — | — |
| 2.69 | — | — | 2.71 — | CDNA clone IMAGE:5303499 |
| -2.69 | HSPB6 | heat shock protein, alpha-crystallin-related, B6 | 2.71 PCDH19 | protocadherin 19 |
| 2.69 | TMEM2 | Transmembrane protein 2 | -2.71 ARFGEF1 | ADP-ribosylation factor guanine nucleotide-exc |
| 2.68 | — | — | 2.71 CHST3 | carbohydrate (chondroitin 6) sulfotransferase 3 |
| 2.68 | — | — | -2.71 NME3 | non-metastatic cells 3, protein expressed in |
| 2.68 | FZD9 | frizzled homolog 9 (Drosophila) | -2.71 WDHD1 | WD repeat and HMG-box DNA binding protein |
| -2.68 | RASL12 | RAS-like, family 12 | 2.71 THSD7A | thrombospondin, type I, domain containing 7A |
| 2.68 | — | — | 2.71 DFNA5 | deafness, autosomal dominant 5 |
| 2.68 | — | — | -2.70 ATP2A3 | ATPase, Ca++ transporting, ubiquitous |
| 2.68 | — | — | 2.70 — | — |
| 2.68 | STXBP4 | syntaxin binding protein 4 | 2.70 GAS1 | growth arrest-specific 1 |
| 2.68 | NCAM1 | Neural cell adhesion molecule 1 | -2.70 UPK1A | uroplakin 1A |
| 2.68 | TTC3 | tetratricopeptide repeat domain 3 | 2.70 RFX2 | regulatory factor X, 2 (influences HLA class II e |
| -2.68 | CNGA1 | cyclic nucleotide gated channel alpha 1 | 2.70 PTD004 | GTP-binding protein PTD004 /// GTP-binding p |
| 2.68 | NFE2L3 | Nuclear factor (erythroid-derived 2)-like 3 | 2.70 CUL3 | cullin 3 |
| -2.68 | ZNF141 | Zinc finger protein 141 | 2.70 ZNF710 /// DOCK4 | Zinc finger protein 710 /// MRNA full length inse |
| 2.68 | CXCR4 | chemokine (C-X-C motif) receptor 4 | -2.70 SYT6 | synaptotagmin VI |
| -2.68 | GPR157 | G protein-coupled receptor 157 | -2.70 B3GNT1 | UDP-GlcNAc:betaGal beta-1,3-N-acetylglucosa |
| 2.68 | CXCR7 | chemokine (C-X-C motif) receptor 7 | -2.70 PLSCR1 | phospholipid scramblase 1 |
| -2.68 | SFN | stratifin | 2.70 RIT1 | Ras-like without CAAX 1 |
| -2.68 | YPEL3 | yippee-like 3 (Drosophila) | 2.70 FLJ25477 | Hypothetical protein FLJ25477 |
| -2.67 | USP32 | ubiquitin specific peptidase 32 /// ubiquitin spec | 2.70 LOC345630 | similar to fibrillarin |
| -2.67 | PCDHA2 | protocadherin alpha 2 | -2.69 CDS1 | CDP-diacylglycerol synthase (phosphatidate cy |
| -2.67 | TNFRSF12A | tumor necrosis factor receptor superfamily, me | -2.69 GPR176 | G protein-coupled receptor 176 |
| -2.67 | RUNX1T1 | runt-related transcription factor 1; translocated | -2.69 TNFSF13 /// TNFSF | tumor necrosis factor (ligand) superfamily, mer |
| 2.67 | PUNC | putative neuronal cell adhesion molecule | -2.69 — | — |
| -2.67 | — | — | -2.69 ID2 | inhibitor of DNA binding 2, dominant negative h |
| -2.67 | RAB3B | RAB3B, member RAS oncogene family | 2.69 STAMBPL1 | STAM binding protein-like 1 |
| -2.67 | KCNK1 | potassium channel, subfamily K, member 1 | 2.69 — | — |
| -2.67 | SLC25A21 | solute carrier family 25 (mitochondrial oxodicar | -2.69 HRASLS3 | HRAS-like suppressor 3 |
| 2.67 | RAB9B | RAB9B, member RAS oncogene family | -2.69 DNAJB6 /// LOC387 | DnaJ (Hsp40) homolog, subfamily B, member |
| 2.67 | ZNF238 | zinc finger protein 238 | -2.69 PRKCQ | protein kinase C, theta |
| -2.67 | C11orf32 | chromosome 11 open reading frame 32 | -2.69 — | — |
| 2.67 | — | — | 2.69 NRIP1 | nuclear receptor interacting protein 1 |
| -2.67 | BCL2A1 | BCL2-related protein A1 | 2.69 — | Full length insert cDNA YH77E09 |
| 2.67 | — | — | -2.68 EPHA7 | EPH receptor A7 |
| 2.66 | LOC347475 | hypothetical gene supported by BC017958 | 2.68 CLASP1 | Cytoplasmic linker associated protein 1 |
| -2.66 | SYN2 | synapsin II | -2.68 OR2A9P | Olfactory receptor, family 2, subfamily A, memb |
| -2.66 | PDE5A | phosphodiesterase 5A, cGMP-specific | 2.68 GM2A | GM2 ganglioside activator |
| 2.66 | — | — | 2.68 DCLRE1C | DNA cross-link repair 1C (PSO2 homolog, S. c |
| 2.66 | EMID1 | EMI domain containing 1 | -2.68 SYNPR | synaptoporin |
| 2.66 | NCAM1 | Neural cell adhesion molecule 1 | 2.68 TFDP2 | Transcription factor Dp-2 (E2F dimerization pa |
| 2.66 | ADCYAP1R1 | Adenylate cyclase activating polypeptide 1 (pitu | 2.68 FRZB | Frizzled-related protein |
| 2.66 | SLC44A5 | solute carrier family 44, member 5 | 2.68 LOC92154 | hypothetical protein BC002770 |
| -2.66 | RILP | Rab interacting lysosomal protein | 2.68 — | CDNA FLJ32491 fis, clone SKNSH1000308 |
| -2.66 | CYB5R2 | cytochrome b5 reductase 2 | -2.67 ERBB2 | v-erb-b2 erythroblastic leukemia viral oncogene |
| -2.66 | FLRT2 | fibronectin leucine rich transmembrane protein | 2.67 — | — |
| -2.66 | CHES1 | checkpoint suppressor 1 | 2.67 FBXW8 | F-box and WD-40 domain protein 8 |
| -2.66 | BSPRY | B-box and SPRY domain containing | 2.67 RUFY3 | RUN and FYVE domain containing 3 |
| 2.66 | C9orf3 | Chromosome 9 open reading frame 3 | -2.67 GATA2 | GATA binding protein 2 |
| 2.65 | RBBP9 | retinoblastoma binding protein 9 | 2.67 ST7 | suppression of tumorigenicity 7 |
| 2.65 | SLC1A4 | solute carrier family 1 (glutamate/neutral amino | -2.67 ADAM28 | ADAM metallopeptidase domain 28 |
| -2.65 | TES | testis derived transcript (3 LIM domains) | -2.67 LOC646561 | similar to WW45 protein |
| 2.65 | — | Transcribed locus | -2.67 EDNRB | endothelin receptor type B |
| 2.65 | C8orf48 | chromosome 8 open reading frame 48 | -2.67 LOC255458 | Hypothetical protein LOC255458 |

Appendix 1

| Value | Gene | Description |
|---|---|---|
| -2.65 | — | — |
| -2.65 | — | — |
| -2.65 | LOC653147 | Similar to 60S ribosomal protein L26-like 1 |
| -2.65 | — | — |
| -2.65 | ADRB1 | adrenergic, beta-1-, receptor |
| 2.65 | — | — |
| 2.65 | CNTFR | ciliary neurotrophic factor receptor |
| 2.65 | CELSR1 | cadherin, EGF LAG seven-pass G-type recepto |
| -2.64 | MCTP2 | multiple C2 domains, transmembrane 2 |
| 2.64 | — | CDNA FLJ36584 fis, clone TRACH2013450 |
| 2.64 | PPP1R3D | protein phosphatase 1, regulatory subunit 3D |
| -2.64 | — | — |
| 2.64 | HCN1 | hyperpolarization activated cyclic nucleotide-ga |
| -2.64 | EHD2 | EH-domain containing 2 |
| 2.64 | — | — |
| 2.64 | KIAA0644 | KIAA0644 gene product |
| -2.64 | CDS1 | CDP-diacylglycerol synthase (phosphatidate c |
| 2.64 | PRSS23 | protease, serine, 23 |
| 2.64 | DLL1 | delta-like 1 (Drosophila) |
| -2.64 | — | — |
| -2.64 | UPK1A | uroplakin 1A |
| -2.64 | DHDH | dihydrodiol dehydrogenase (dimeric) |
| -2.64 | RBMS1 | RNA binding motif, single stranded interacting |
| 2.64 | SAMD14 | sterile alpha motif domain containing 14 |
| 2.64 | — | Transcribed locus |
| 2.64 | ZNF710 /// DOCK4 | Zinc finger protein 710 /// MRNA full length inse |
| 2.64 | — | — |
| 2.64 | TGFB1I4 | TSC22 domain family, member 1 |
| 2.64 | RGL1 | ral guanine nucleotide dissociation stimulator-li |
| 2.64 | FLJ42117 | FLJ42117 protein |
| 2.64 | — | Homo sapiens, clone IMAGE:5787583, mRNA |
| -2.63 | PLEKHC1 | pleckstrin homology domain containing, family |
| -2.63 | CDX4 | caudal type homeobox transcription factor 4 |
| -2.63 | — | — |
| -2.63 | LPIN1 | Lipin 1 |
| 2.63 | AGTR1 | angiotensin II receptor, type 1 |
| -2.63 | C10orf75 | Chromosome 10 open reading frame 75 |
| -2.63 | PIPOX | pipecolic acid oxidase |
| -2.63 | DNMT3B | DNA (cytosine-5-)-methyltransferase 3 beta |
| -2.63 | PYGL | phosphorylase, glycogen; liver (Hers disease, |
| 2.63 | PHF20L1 | PHD finger protein 20-like 1 |
| 2.63 | — | — |
| -2.62 | — | Transcribed locus |
| -2.62 | LOC728473 | hypothetical protein LOC728473 |
| 2.62 | — | Transcribed locus |
| 2.62 | JAKMIP2 | janus kinase and microtubule interacting protei |
| 2.62 | GTF2IRD2 | GTF2I repeat domain containing 2 |
| -2.62 | — | Transcribed locus |
| -2.62 | — | Full length insert cDNA YH97G12 |
| 2.62 | PCBP4 | poly(rC) binding protein 4 |
| 2.62 | H2AFY2 | H2A histone family, member Y2 |
| -2.62 | RGS10 | regulator of G-protein signalling 10 |
| -2.62 | EPHA7 | EPH receptor A7 |
| -2.62 | CES1 | carboxylesterase 1 (monocyte/macrophage ser |
| 2.62 | EFCBP2 | EF-hand calcium binding protein 2 |
| 2.62 | LOC163131 | hypothetical BC331191_1 |
| 2.62 | — | Homo sapiens, clone IMAGE:4214654, mRNA |
| -2.62 | MYO5C | myosin VC |
| 2.62 | — | — |
| 2.62 | — | — |
| -2.62 | — | CDNA clone IMAGE:4819775 |
| 2.62 | ABCC4 | ATP-binding cassette, sub-family C (CFTR/MR |
| 2.62 | C9orf72 | chromosome 9 open reading frame 72 |
| -2.61 | RBPMS | RNA binding protein with multiple splicing |
| 2.61 | ZNF529 | Zinc finger protein 529 |
| 2.61 | EBF2 | Early B-cell factor 2 |
| -2.61 | — | — |
| -2.61 | CLDN3 | claudin 3 |
| 2.61 | PTPRO | protein tyrosine phosphatase, receptor type, O |
| 2.61 | ANGPTL2 | angiopoietin-like 2 |
| -2.61 | KIAA1529 | KIAA1529 |
| -2.61 | EPO | erythropoietin |
| 2.61 | THSD7A | thrombospondin, type I, domain containing 7A |
| 2.61 | — | Transcribed locus |
| 2.61 | RHOBTB2 | Rho-related BTB domain containing 2 |
| 2.61 | SLITRK5 | SLIT and NTRK-like family, member 5 |
| 2.61 | NFIB | nuclear factor I/B |
| 2.61 | GPR155 | G protein-coupled receptor 155 |
| -2.60 | — | — |
| -2.67 | — | Transcribed locus |
| -2.67 | FLNB | filamin B, beta (actin binding protein 278) |
| -2.67 | — | — |
| -2.67 | — | — |
| -2.67 | DDIT4L | DNA-damage-inducible transcript 4-like |
| 2.66 | NAV3 | neuron navigator 3 |
| 2.66 | NOG | Noggin |
| 2.66 | SLC25A30 | Solute carrier family 25, member 30 |
| 2.66 | SOX11 | SRY (sex determining region Y)-box 11 |
| 2.66 | MAP2K5 | mitogen-activated protein kinase kinase 5 |
| -2.66 | SNRPN /// SNURF | small nuclear ribonucleoprotein polypeptide N / |
| 2.66 | SEMA6D | sema domain, transmembrane domain (TM), a |
| -2.66 | — | — |
| 2.66 | IGFBPL1 | Insulin-like growth factor binding protein-like 1 |
| 2.66 | AK1 | adenylate kinase 1 |
| 2.66 | — | Transcribed locus, weakly similar to XP_52559 |
| -2.66 | SOCS2 | suppressor of cytokine signaling 2 |
| -2.66 | ADRB2 | adrenergic, beta-2-, receptor, surface |
| 2.66 | TAS2R10 | taste receptor, type 2, member 10 |
| 2.66 | DNAH14 /// LOC12 | dynein, axonemal, heavy chain 14 /// hypotheti |
| 2.66 | C20orf58 | chromosome 20 open reading frame 58 |
| 2.66 | — | Transcribed locus |
| -2.65 | ARSK | Arylsulfatase family, member K |
| 2.65 | LOC441440 | hypothetical LOC441440 |
| 2.65 | DKFZp313A2432 | hypothetical protein DKFZp313A2432 |
| 2.65 | MPPED2 | metallophosphoesterase domain containing 2 |
| -2.65 | TPM1 | tropomyosin 1 (alpha) |
| -2.65 | ULK4 | Unc-51-like kinase 4 (C. elegans) |
| -2.65 | SLC16A1 | solute carrier family 16, member 1 (monocarbo |
| 2.65 | MARCKS | Myristoylated alanine-rich protein kinase C sub |
| 2.65 | — | — |
| -2.65 | BLVRB | biliverdin reductase B (flavin reductase (NADP |
| -2.65 | — | — |
| -2.65 | PI15 | peptidase inhibitor 15 |
| 2.65 | — | CDNA FLJ38345 fis, clone FCBBF3028671 |
| -2.64 | — | — |
| 2.64 | STMN4 | stathmin-like 4 /// stathmin-like 4 |
| -2.64 | — | — |
| 2.64 | — | — |
| 2.64 | SIAT7E | ST6 (alpha-N-acetyl-neuraminyl-2,3-beta-galac |
| -2.64 | PCNXL2 | pecanex-like 2 (Drosophila) |
| -2.64 | — | Similar to hypothetical protein LOC284701 |
| 2.64 | — | — |
| 2.64 | — | — |
| 2.64 | — | — |
| -2.64 | AP1S3 | adaptor-related protein complex 1, sigma 3 sub |
| 2.64 | TBC1D16 | TBC1 domain family, member 16 |
| 2.64 | TTMA | two transmembrane domain family member A |
| -2.64 | TNS3 | tensin 3 |
| -2.64 | HLA-G | HLA-G histocompatibility antigen, class I, G |
| -2.64 | STAT5A | signal transducer and activator of transcription |
| 2.64 | — | CDNA FLJ33441 fis, clone BRACE2021932 |
| 2.64 | RSNL2 | restin-like 2 |
| 2.63 | AP3M1 | adaptor-related protein complex 3, mu 1 subun |
| 2.63 | C6orf118 | chromosome 6 open reading frame 118 |
| -2.63 | IL2RB | interleukin 2 receptor, beta /// interleukin 2 rece |
| 2.63 | LSM11 | LSM11, U7 small nuclear RNA associated |
| 2.63 | GRK5 | G protein-coupled receptor kinase 5 |
| -2.63 | CDS1 | CDP-diacylglycerol synthase (phosphatidate c |
| 2.63 | — | — |
| -2.63 | C10orf75 | Chromosome 10 open reading frame 75 |
| -2.63 | SIPA1 | signal-induced proliferation-associated gene 1 |
| 2.63 | COPB2 | Coatomer protein complex, subunit beta 2 (bet |
| 2.63 | KHSRP | KH-type splicing regulatory protein (FUSE bind |
| 2.63 | VPREB1 | pre-B lymphocyte gene 1 |
| 2.63 | C6orf65 | chromosome 6 open reading frame 65 |
| -2.63 | ID2 /// ID2B | inhibitor of DNA binding 2, dominant negative h |
| 2.63 | TP73L | tumor protein p73-like |
| 2.63 | CX3CL1 | chemokine (C-X3-C motif) ligand 1 |
| -2.63 | — | Transcribed locus |
| 2.62 | — | — |
| 2.62 | C5orf28 | chromosome 5 open reading frame 28 |
| 2.62 | SMARCA4 | SWI/SNF related, matrix associated, actin dep |
| -2.62 | RRAS2 | related RAS viral (r-ras) oncogene homolog 2 |
| -2.62 | — | — |
| 2.62 | — | — |
| 2.62 | — | — |
| 2.62 | — | — |
| -2.62 | ZNF311 | zinc finger protein 311 |

Appendix 1

| Value | Symbol | Description |
|---|---|---|
| 2.60 | RHBDL4 | rhomboid, veinlet-like 4 (Drosophila) |
| 2.60 | EPB41L5 | erythrocyte membrane protein band 4.1 like 5 |
| -2.60 | PAPSS2 | 3'-phosphoadenosine 5'-phosphosulfate syntha |
| 2.60 | SRGAP3 | SLIT-ROBO Rho GTPase activating protein 3 |
| 2.60 | — | — |
| 2.60 | PIK3R3 | phosphoinositide-3-kinase, regulatory subunit 3 |
| 2.60 | FAM59B | family with sequence similarity 59, member B |
| -2.60 | LOC123688 | similar to RIKEN cDNA C630028N24 gene |
| -2.60 | MATN2 | matrilin 2 |
| 2.60 | — | CDNA FLJ30386 fis, clone BRACE2008216 |
| 2.60 | MKRN3 | makorin, ring finger protein, 3 |
| 2.60 | GPR153 | G protein-coupled receptor 153 |
| -2.60 | COL21A1 | collagen, type XXI, alpha 1 /// collagen, type X |
| 2.60 | FAM55C | family with sequence similarity 55, member C |
| -2.60 | — | — |
| 2.60 | PRMT8 | protein arginine methyltransferase 8 |
| 2.60 | ABCC4 | ATP-binding cassette, sub-family C (CFTR/MR |
| -2.60 | JAK3 | Janus kinase 3 (a protein tyrosine kinase, leuk |
| 2.60 | GP1BB /// SEPT5 | glycoprotein Ib (platelet), beta polypeptide /// s |
| 2.60 | — | CDNA clone IMAGE:4842353 |
| 2.60 | SDC1 | syndecan 1 |
| 2.60 | — | — |
| 2.59 | — | Transcribed locus |
| 2.59 | LOC283874 | hypothetical protein LOC283874 |
| 2.59 | MGC24039 | hypothetical protein MGC24039 |
| -2.59 | PCK2 | phosphoenolpyruvate carboxykinase 2 (mitoch |
| 2.59 | — | — |
| 2.59 | TMEM2 | transmembrane protein 2 |
| 2.59 | COL12A1 | collagen, type XII, alpha 1 |
| 2.59 | CDC42 | cell division cycle 42 (GTP binding protein, 25k |
| -2.59 | — | — |
| -2.59 | NME3 | non-metastatic cells 3, protein expressed in |
| -2.59 | — | — |
| -2.59 | FLJ35024 | hypothetical LOC401491 |
| 2.59 | CBX8 | chromobox homolog 8 (Pc class homolog, Dros |
| -2.59 | PAK1 | p21/Cdc42/Rac1-activated kinase 1 (STE20 h |
| -2.59 | FLJ21963 | FLJ21963 protein |
| 2.59 | LOC283859 | hypothetical protein LOC283859 |
| -2.58 | SLC24A3 | solute carrier family 24 (sodium/potassium/calc |
| 2.58 | — | — |
| -2.58 | PITX2 | paired-like homeodomain transcription factor 2 |
| 2.58 | RSN | Restin (Reed-Steinberg cell-expressed interme |
| 2.58 | FABP7 | Fatty acid binding protein 7, brain |
| 2.58 | YAF2 | YY1 associated factor 2 |
| 2.58 | WBSCR16 | Williams-Beuren syndrome chromosome region |
| -2.58 | CRABP2 | cellular retinoic acid binding protein 2 |
| -2.58 | PCNXL2 | pecanex-like 2 (Drosophila) |
| -2.58 | B3GNT2 | UDP-GlcNAc:betaGal beta-1,3-N-acetylglucosa |
| 2.58 | CTXN1 | cortexin 1 |
| 2.58 | NPTX2 | neuronal pentraxin II |
| -2.57 | STYK1 | serine/threonine/tyrosine kinase 1 /// serine/thr |
| -2.57 | PAPSS2 | 3'-phosphoadenosine 5'-phosphosulfate syntha |
| 2.57 | — | Transcribed locus |
| -2.57 | KCNE1L | KCNE1-like |
| -2.57 | KLC3 | kinesin light chain 3 |
| 2.57 | MTSS1 | metastasis suppressor 1 |
| -2.57 | — | — |
| 2.57 | SLCO3A1 | Solute carrier organic anion transporter family, |
| 2.57 | TTC3 | tetratricopeptide repeat domain 3 |
| -2.57 | VAV1 | vav 1 oncogene |
| -2.57 | GAD1 /// LASS6 | glutamate decarboxylase 1 (brain, 67kDa) /// L |
| 2.57 | QKI | Quaking homolog, KH domain RNA binding (m |
| 2.57 | NRGN | neurogranin (protein kinase C substrate, RC3) |
| 2.57 | TTC3 | tetratricopeptide repeat domain 3 |
| -2.56 | COL4A3 | collagen, type IV, alpha 3 (Goodpasture antige |
| -2.56 | EPPK1 | epiplakin 1 /// epiplakin 1 |
| -2.56 | — | — |
| -2.56 | TGFBR2 | transforming growth factor, beta receptor II (70 |
| 2.56 | PDE10A | phosphodiesterase 10A |
| -2.56 | USP53 | Ubiquitin specific peptidase 53 |
| 2.56 | — | CDNA clone IMAGE:3919515 /// CDNA clone |
| 2.56 | ACSS1 | acyl-CoA synthetase short-chain family membe |
| 2.56 | CSNK2A1 | Casein kinase 2, alpha 1 polypeptide |
| 2.56 | MYO1D | myosin ID |
| -2.56 | — | — |
| -2.56 | SEZ6L2 | seizure related 6 homolog (mouse)-like 2 |
| 2.55 | MAP1B | microtubule-associated protein 1B |
| 2.55 | LOC283012 | hypothetical protein LOC283012 |
| 2.55 | GRK5 | G protein-coupled receptor kinase 5 |
| -2.62 | CCL5 | chemokine (C-C motif) ligand 5 |
| 2.62 | KIAA1545 | KIAA1545 protein |
| -2.61 | PRKCI | protein kinase C, iota |
| -2.61 | MATK | megakaryocyte-associated tyrosine kinase |
| 2.61 | — | — |
| -2.61 | SLC6A6 | solute carrier family 6 (neurotransmitter transpo |
| 2.61 | — | — |
| 2.61 | — | CDNA FLJ26539 fis, clone KDN09310 |
| 2.61 | — | — |
| 2.61 | SLC30A7 | Solute carrier family 30 (zinc transporter), mem |
| -2.61 | — | — |
| -2.61 | GPR | putative G protein coupled receptor |
| 2.61 | — | — |
| 2.61 | — | — |
| 2.61 | LYRM5 | LYR motif containing 5 |
| -2.61 | — | — |
| 2.61 | DCHS1 | dachsous 1 (Drosophila) |
| -2.61 | LOC284242 | hypothetical protein LOC284242 |
| 2.61 | STON1 | Stonin 1 |
| 2.61 | RHOBTB3 | Rho-related BTB domain containing 3 |
| 2.61 | FRMD4A | FERM domain containing 4A |
| 2.60 | C14orf162 | chromosome 14 open reading frame 162 |
| 2.60 | BVES | blood vessel epicardial substance |
| -2.60 | DIAPH2 | diaphanous homolog 2 (Drosophila) |
| -2.60 | LOC283012 | hypothetical protein LOC283012 |
| -2.60 | SHANK2 | SH3 and multiple ankyrin repeat domains 2 |
| -2.60 | — | — |
| 2.60 | PHTF1 | Putative homeodomain transcription factor 1 |
| -2.60 | CYP2E1 | cytochrome P450, family 2, subfamily E, polyp |
| 2.60 | FAS | Fas (TNF receptor superfamily, member 6) |
| 2.60 | — | — |
| -2.60 | OPCML | opioid binding protein/cell adhesion molecule-li |
| -2.60 | SCNN1G | sodium channel, nonvoltage-gated 1, gamma |
| -2.60 | NUDT7 | nudix (nucleoside diphosphate linked moiety X |
| 2.60 | ANKRD6 | ankyrin repeat domain 6 |
| -2.60 | RPL21 | Ribosomal protein L21 |
| -2.60 | IQGAP2 | IQ motif containing GTPase activating protein 2 |
| -2.60 | SULT1C1 | sulfotransferase family, cytosolic, 1C, member |
| 2.60 | TTLL11 | tubulin tyrosine ligase-like family, member 11 |
| -2.59 | MYSM1 | myb-like, SWIRM and MPN domains 1 |
| -2.59 | SKIL | SKI-like oncogene |
| -2.59 | LOC285500 | hypothetical protein LOC285500 |
| 2.59 | SYDE2 | synapse defective 1, Rho GTPase, homolog 2 |
| 2.59 | — | — |
| 2.59 | KIF21A | kinesin family member 21A |
| 2.59 | SLC1A3 | solute carrier family 1 (glial high affinity glutama |
| -2.59 | KAZALD1 | Kazal-type serine peptidase inhibitor domain 1 |
| 2.59 | PSTPIP2 | proline-serine-threonine phosphatase interactin |
| -2.59 | WDHD1 | WD repeat and HMG-box DNA binding protein |
| 2.59 | NCAM1 | Neural cell adhesion molecule 1 |
| 2.59 | PHC2 | polyhomeotic homolog 2 (Drosophila) |
| -2.58 | HMG4L | high-mobility group (nonhistone chromosomal) |
| -2.58 | IQSEC2 | IQ motif and Sec7 domain 2 |
| 2.58 | CBX4 | chromobox homolog 4 (Pc class homolog, Dros |
| -2.58 | — | — |
| -2.58 | CHST7 | carbohydrate (N-acetylglucosamine 6-O) sulfot |
| 2.58 | PREX1 | phosphatidylinositol 3,4,5-trisphosphate-depen |
| -2.58 | TMEM46 | transmembrane protein 46 |
| 2.58 | C6orf134 | chromosome 6 open reading frame 134 |
| 2.58 | SEC22C | SEC22 vesicle trafficking protein homolog C (S |
| -2.57 | — | — |
| -2.57 | GAD1 /// LASS6 | glutamate decarboxylase 1 (brain, 67kDa) /// L |
| 2.57 | — | CDNA FLJ30383 fis, clone BRACE2008102 |
| -2.57 | MUC4 | mucin 4, cell surface associated |
| 2.57 | KLHL20 | Kelch-like 20 (Drosophila) |
| -2.57 | IPW | imprinted in Prader-Willi syndrome |
| -2.57 | DLK1 | delta-like 1 homolog (Drosophila) |
| 2.57 | PON2 | paraoxonase 2 |
| -2.57 | — | — |
| -2.57 | CPT1A | carnitine palmitoyltransferase 1A (liver) |
| -2.57 | — | — |
| -2.57 | OR2H1 | Olfactory receptor, family 2, subfamily H, mem |
| 2.57 | C5orf15 | Chromosome 5 open reading frame 15 |
| 2.57 | — | CDNA FLJ45995 fis, clone SKNMC2003639 |
| -2.57 | DPYSL3 | dihydropyrimidinase-like 3 |
| -2.57 | IL1F7 | interleukin 1 family, member 7 (zeta) |
| 2.57 | SLC6A8 | solute carrier family 6 (neurotransmitter transpo |
| -2.57 | — | Transcribed locus |
| 2.57 | ZNF710 /// DOCK4 | Zinc finger protein 710 /// MRNA full length ins |

Appendix 1

| Value | Gene | Description |
|---|---|---|
| -2.55 | HNF4G | hepatocyte nuclear factor 4, gamma |
| 2.55 | IFIH1 | interferon induced with helicase C domain 1 |
| 2.55 | EME2 | Essential meiotic endonuclease 1 homolog 2 ( |
| 2.55 | AMH | anti-Mullerian hormone |
| -2.55 | PLEKHC1 | pleckstrin homology domain containing, family |
| -2.55 | CHST7 | carbohydrate (N-acetylglucosamine 6-O) sulfot |
| 2.55 | RUFY3 | RUN and FYVE domain containing 3 |
| -2.55 | PHC1 | polyhomeotic homolog 1 (Drosophila) |
| -2.55 | RP11-298P3.3 | CG016 |
| -2.55 | LAMA2 | laminin, alpha 2 (merosin, congenital muscular |
| -2.54 | PDGFRA | platelet-derived growth factor receptor, alpha p |
| 2.54 | — | CDNA FLJ42688 fis, clone BRAMY3002120 |
| 2.54 | CRIP2 | cysteine-rich protein 2 |
| 2.54 | RHOBTB3 | Rho-related BTB domain containing 3 |
| -2.54 | PRKCB1 | protein kinase C, beta 1 |
| 2.54 | CDH6 | cadherin 6, type 2, K-cadherin (fetal kidney) |
| -2.54 | KCNS3 | potassium voltage-gated channel, delayed-rect |
| 2.54 | ID4 | Inhibitor of DNA binding 4, dominant negative h |
| 2.54 | — | — |
| -2.54 | — | — |
| 2.54 | — | — |
| 2.54 | ZNF710 /// DOCK4 | Zinc finger protein 710 /// MRNA full length inse |
| -2.54 | — | — |
| 2.54 | FOXRED2 | FAD-dependent oxidoreductase domain contai |
| 2.54 | DCTN4 | dynactin 4 (p62) |
| 2.54 | FARSLB | phenylalanine-tRNA synthetase-like, beta subu |
| 2.54 | IPO9 | Importin 9 |
| 2.54 | FAM89B | family with sequence similarity 89, member B |
| -2.54 | ST6GAL1 | ST6 beta-galactosamide alpha-2,6-sialyltranfer |
| -2.54 | LDB2 | LIM domain binding 2 |
| -2.54 | LAD1 | ladinin 1 |
| -2.54 | DEF6 | differentially expressed in FDCP 6 homolog (m |
| -2.53 | WIPI1 | WD repeat domain, phosphoinositide interactin |
| -2.53 | HLA-E | major histocompatibility complex, class I, E |
| -2.53 | — | — |
| 2.53 | KLF12 | Kruppel-like factor 12 |
| 2.53 | VEPH1 | ventricular zone expressed PH domain homolo |
| 2.53 | FYN | FYN oncogene related to SRC, FGR, YES |
| 2.53 | — | CDNA clone IMAGE:3950788 |
| 2.53 | — | — |
| 2.53 | C16orf45 | chromosome 16 open reading frame 45 |
| -2.53 | SLC19A3 | solute carrier family 19, member 3 |
| 2.53 | GREM2 | gremlin 2, cysteine knot superfamily, homolog |
| 2.53 | STAT5B | signal transducer and activator of transcription |
| -2.53 | FA2H | fatty acid 2-hydroxylase |
| 2.53 | — | Homo sapiens, clone IMAGE:4480133, mRNA |
| 2.53 | ZNF710 | Zinc finger protein 710 |
| -2.52 | IL1RN | interleukin 1 receptor antagonist |
| -2.52 | TESK2 | testis-specific kinase 2 |
| 2.52 | UTX | ubiquitously transcribed tetratricopeptide repea |
| 2.52 | OXR1 | oxidation resistance 1 |
| 2.52 | — | — |
| -2.52 | CCDC28A | coiled-coil domain containing 28A |
| -2.52 | — | Transcribed locus |
| 2.52 | DDR1 | discoidin domain receptor family, member 1 |
| -2.52 | SAV1 | salvador homolog 1 (Drosophila) |
| -2.52 | CARTPT | CART prepropeptide |
| 2.52 | — | — |
| -2.52 | TBC1D8 | TBC1 domain family, member 8 (with GRAM d |
| -2.52 | GABARAPL1 /// GA | GABA(A) receptor-associated protein like 1 /// |
| -2.51 | LOC389634 | hypothetical LOC389634 |
| -2.51 | CUL4A | Cullin 4A |
| 2.51 | — | — |
| -2.51 | PCSK1 | proprotein convertase subtilisin/kexin type 1 |
| 2.51 | — | — |
| 2.51 | — | — |
| -2.51 | MGC13017 | similar to RIKEN cDNA A430101B06 gene |
| 2.51 | DCX | doublecortex; lissencephaly, X-linked (doublec |
| 2.51 | — | — |
| 2.51 | SRrp35 | Serine-arginine repressor protein (35 kDa) |
| 2.50 | MGC45564 | GTPase activating Rap/RanGAP domain-like 1 |
| -2.50 | UGP2 | UDP-glucose pyrophosphorylase 2 |
| 2.50 | PPM1E | protein phosphatase 1E (PP2C domain contain |
| 2.50 | — | — |
| -2.50 | TMEM46 | transmembrane protein 46 |
| -2.50 | — | Full length insert cDNA clone ZD51F08 |
| 2.50 | TP53AP1 | TP53 activated protein 1 |
| -2.50 | — | — |
| -2.50 | RENBP | renin binding protein |
| -2.56 | PYGL | phosphorylase, glycogen; liver (Hers disease, |
| -2.56 | CD55 | CD55 molecule, decay accelerating factor for c |
| -2.56 | PLSCR1 | Phospholipid scramblase 1 |
| 2.56 | POU3F3 | POU domain, class 3, transcription factor 3 |
| -2.56 | — | — |
| -2.56 | — | — |
| -2.56 | ITGA5 | integrin, alpha 5 (fibronectin receptor, alpha po |
| 2.56 | SLC6A16 | solute carrier family 6, member 16 |
| 2.56 | FST | follistatin |
| 2.56 | — | Transcribed locus |
| 2.56 | SETBP1 | SET binding protein 1 |
| -2.56 | — | — |
| -2.56 | — | — |
| 2.56 | — | EST from clone 27306, 5' end |
| 2.56 | KBTBD11 | kelch repeat and BTB (POZ) domain containin |
| -2.56 | ZNF589 | zinc finger protein 589 |
| -2.56 | HHEX | homeobox, hematopoietically expressed |
| -2.56 | — | CDNA: FLJ22478 fis, clone HRC10816 |
| 2.56 | ARID5B | AT rich interactive domain 5B (MRF1-like) |
| -2.55 | SIVA1 | SIVA1, apoptosis-inducing factor |
| -2.55 | — | — |
| -2.55 | SLC16A1 | solute carrier family 16, member 1 (monocarbo |
| 2.55 | — | — |
| -2.55 | TREML1 | triggering receptor expressed on myeloid cells- |
| -2.55 | DKFZP564J0863 | DKFZP564J0863 protein |
| -2.55 | POSTN | periostin, osteoblast specific factor |
| -2.55 | MYST3 | MYST histone acetyltransferase (monocytic leu |
| -2.55 | NUMB | numb homolog (Drosophila) |
| 2.55 | — | — |
| -2.55 | BTD | biotinidase |
| -2.55 | ARF6 | ADP-ribosylation factor 6 |
| -2.55 | LPIN1 | Lipin 1 |
| 2.55 | — | — |
| -2.55 | ST6GAL1 | ST6 beta-galactosamide alpha-2,6-sialyltranfer |
| 2.55 | — | — |
| 2.55 | — | — |
| -2.54 | C6orf189 | chromosome 6 open reading frame 189 |
| 2.54 | WDR52 | WD repeat domain 52 |
| -2.54 | — | — |
| -2.54 | ANXA4 | annexin A4 |
| 2.54 | KRAS | v-Ki-ras2 Kirsten rat sarcoma viral oncogene h |
| 2.54 | RUFY3 | RUN and FYVE domain containing 3 |
| -2.54 | HESX1 | homeobox, ES cell expressed 1 |
| 2.54 | KIAA0101 /// KIAA0101 | KIAA0101 /// KIAA0101 |
| -2.54 | SLC7A10 | solute carrier family 7, (neutral amino acid tran |
| 2.54 | FLJ22965 | hypothetical protein FLJ22965 |
| 2.54 | — | — |
| -2.54 | CHST2 | carbohydrate (N-acetylglucosamine-6-O) sulfot |
| 2.54 | — | — |
| 2.54 | CPEB1 | cytoplasmic polyadenylation element binding p |
| 2.54 | MXRA7 | matrix-remodelling associated 7 |
| -2.54 | SNAP23 | synaptosomal-associated protein, 23kDa |
| 2.54 | BICD1 | bicaudal D homolog 1 (Drosophila) |
| -2.54 | ARRB1 | arrestin, beta 1 |
| -2.54 | — | — |
| -2.53 | DRD1IP | dopamine receptor D1 interacting protein |
| -2.53 | ARFGEF1 | ADP-ribosylation factor guanine nucleotide-exc |
| -2.53 | FZD8 | frizzled homolog 8 (Drosophila) /// frizzled hom |
| 2.53 | SPAG9 | sperm associated antigen 9 |
| 2.53 | NME5 | non-metastatic cells 5, protein expressed in (n |
| 2.53 | — | — |
| -2.53 | PVALB | parvalbumin |
| -2.53 | RPS6KA5 | ribosomal protein S6 kinase, 90kDa, polypeptid |
| 2.53 | POLR3GL | polymerase (RNA) III (DNA directed) polypepti |
| -2.53 | MET | met proto-oncogene (hepatocyte growth factor |
| 2.53 | — | — |
| -2.53 | CTH | cystathionase (cystathionine gamma-lyase) |
| 2.53 | CARD12 | Caspase recruitment domain family, member 1 |
| 2.53 | LOC283859 | hypothetical protein LOC283859 |
| 2.53 | C11orf70 | chromosome 11 open reading frame 70 |
| -2.53 | VASH2 | vasohibin 2 |
| 2.53 | — | — |
| 2.53 | ZNF436 | zinc finger protein 436 |
| 2.53 | CD47 | CD47 molecule |
| -2.52 | ITPR2 | Inositol 1,4,5-triphosphate receptor, type 2 |
| 2.52 | SLC8A3 | Solute carrier family 8 (sodium-calcium exchan |
| -2.52 | ATF3 | activating transcription factor 3 |
| 2.52 | KIAA0984 | KIAA0984 protein |
| 2.52 | COPB2 | Coatomer protein complex, subunit beta 2 (bet |

Appendix 1

| Value | Gene | Description |
|---|---|---|
| 2.50 | RPS6KA2 | ribosomal protein S6 kinase, 90kDa, polypeptid |
| 2.50 | NCOA5 | nuclear receptor coactivator 5 |
| -2.50 | UTX | ubiquitously transcribed tetratricopeptide repea |
| 2.50 | ATBF1 | AT-binding transcription factor 1 |
| -2.50 | LOC692247 | hypothetical locus LOC692247 |
| -2.49 | MTBP | Mdm2, transformed 3T3 cell double minute 2, |
| -2.49 | VAMP5 | vesicle-associated membrane protein 5 (myobr |
| -2.49 | DCP2 | DCP2 decapping enzyme homolog (S. cerevisi |
| -2.49 | TJP2 | tight junction protein 2 (zona occludens 2) |
| 2.49 | FLJ25694 | hypothetical protein FLJ25694 |
| 2.49 | ZNF124 | zinc finger protein 124 |
| 2.49 | — | MRNA; cDNA DKFZp686F1844 (from clone DH |
| -2.49 | IPW | imprinted in Prader-Willi syndrome |
| 2.49 | SYDE1 | synapse defective 1, Rho GTPase, homolog 1 |
| -2.49 | FZD8 | frizzled homolog 8 (Drosophila) /// frizzled hom |
| -2.48 | — | Transcribed locus |
| 2.48 | SCOC | Short coiled-coil protein |
| 2.48 | — | — |
| 2.48 | HIPK2 | Homeodomain interacting protein kinase 2 |
| -2.48 | — | — |
| -2.48 | ENO3 | enolase 3 (beta, muscle) |
| 2.48 | SEMA5B | sema domain, seven thrombospondin repeats |
| -2.48 | RUNX1T1 | runt-related transcription factor 1; translocated |
| 2.48 | PON2 | Paraoxonase 2 |
| 2.48 | — | — |
| -2.48 | — | — |
| -2.48 | PTGER4 | prostaglandin E receptor 4 (subtype EP4) |
| 2.48 | — | — |
| -2.48 | — | CDNA FLJ29007 fis, clone STM04662, highly |
| 2.48 | DNAI1 | dynein, axonemal, intermediate chain 1 |
| 2.48 | — | — |
| -2.47 | C10orf118 | chromosome 10 open reading frame 118 |
| -2.47 | PLP2 | proteolipid protein 2 (colonic epithelium-enriche |
| -2.47 | PODN | podocan |
| -2.47 | — | — |
| 2.47 | MTX1 | Metaxin 1 |
| 2.47 | CUEDC1 | CUE domain containing 1 |
| 2.47 | PRR14 | proline rich 14 |
| 2.47 | NCOA6 | nuclear receptor coactivator 6 |
| -2.47 | COMT | catechol-O-methyltransferase |
| 2.47 | DKFZp313A2432 | hypothetical protein DKFZp313A2432 |
| 2.47 | ATP8A2 | ATPase, aminophospholipid transporter-like, C |
| -2.47 | NUDT7 | nudix (nucleoside diphosphate linked moiety X |
| 2.47 | E2F2 | E2F transcription factor 2 |
| -2.47 | USP28 | ubiquitin specific peptidase 28 |
| -2.46 | TNS3 | tensin 3 |
| -2.46 | GCNT1 | glucosaminyl (N-acetyl) transferase 1, core 2 ( |
| 2.46 | TXNDC4 | thioredoxin domain containing 4 (endoplasmic |
| 2.46 | — | — |
| 2.46 | GDF1 /// LASS1 | growth differentiation factor 1 /// LAG1 homolog |
| 2.46 | — | — |
| 2.46 | — | — |
| -2.46 | — | — |
| -2.46 | — | — |
| -2.46 | TEX14 | testis expressed sequence 14 /// testis express |
| -2.46 | LOC400680 | hypothetical gene supported by AK097381; BC |
| -2.46 | ARRB1 | arrestin, beta 1 |
| 2.46 | NME5 | non-metastatic cells 5, protein expressed in (n |
| 2.46 | CENPI | centromere protein I |
| 2.46 | PNMA2 | paraneoplastic antigen MA2 |
| 2.46 | APOLD1 | apolipoprotein L domain containing 1 /// apolipo |
| -2.46 | BIC | BIC transcript |
| -2.46 | BICD1 | bicaudal D homolog 1 (Drosophila) |
| -2.46 | HLA-C | major histocompatibility complex, class I, C |
| 2.45 | EPHB2 | EPH receptor B2 |
| -2.45 | RNF43 | ring finger protein 43 |
| -2.45 | CD44 | CD44 molecule (Indian blood group) |
| 2.45 | DKFZp762A217 | hypothetical protein DKFZp762A217 |
| -2.45 | DDT | D-dopachrome tautomerase |
| 2.45 | CHST3 | carbohydrate (chondroitin 6) sulfotransferase |
| 2.45 | GNG2 | guanine nucleotide binding protein (G protein), |
| -2.45 | — | — |
| 2.45 | PLCL2 | phospholipase C-like 2 |
| -2.45 | HHEX | homeobox, hematopoietically expressed |
| 2.45 | — | — |
| 2.45 | C6orf89 | chromosome 6 open reading frame 89 |
| -2.45 | NID2 | nidogen 2 (osteonidogen) |
| -2.45 | ANXA4 | annexin A4 |
| 2.52 | NEFL | neurofilament, light polypeptide 68kDa |
| -2.52 | ZNF589 | zinc finger protein 589 |
| -2.52 | — | — |
| -2.52 | MGC29814 | hypothetical protein MGC29814 |
| 2.52 | LOC283400 | hypothetical protein LOC283400 |
| 2.51 | CNTN6 | contactin 6 |
| 2.51 | MDH1B | malate dehydrogenase 1B, NAD (soluble) |
| 2.51 | TTC3 | tetratricopeptide repeat domain 3 |
| 2.51 | SH3BP5 | SH3-domain binding protein 5 (BTK-associated |
| 2.51 | SLFNL1 | schlafen-like 1 |
| 2.51 | HHIP | hedgehog interacting protein |
| -2.51 | SPRY1 | sprouty homolog 1, antagonist of FGF signaling |
| -2.51 | USP28 | ubiquitin specific peptidase 28 |
| 2.51 | — | Full-length cDNA clone CS0DJ013YP06 of T c |
| 2.51 | DOCK11 | dedicator of cytokinesis 11 |
| -2.51 | HLA-F | major histocompatibility complex, class I, F |
| 2.51 | NF2 | neurofibromin 2 (bilateral acoustic neuroma) |
| -2.51 | DSC2 | desmocollin 2 |
| -2.51 | ROD1 | ROD1 regulator of differentiation 1 (S. pombe) |
| -2.51 | KLF8 | Kruppel-like factor 8 |
| -2.51 | EMR2 | egf-like module containing, mucin-like, hormon |
| -2.51 | HIVEP2 | human immunodeficiency virus type I enhance |
| -2.51 | GATM | glycine amidinotransferase (L-arginine:glycine |
| 2.51 | PLXNA1 | plexin A1 |
| -2.50 | SSH3 | slingshot homolog 3 (Drosophila) |
| -2.50 | NFIB | nuclear factor I/B |
| -2.50 | PTPN6 | protein tyrosine phosphatase, non-receptor typ |
| -2.50 | C11orf67 | chromosome 11 open reading frame 67 |
| -2.50 | PTHR1 | parathyroid hormone receptor 1 |
| -2.50 | RAB5A | RAB5A, member RAS oncogene family |
| 2.50 | ATP8A2 | ATPase, aminophospholipid transporter-like, C |
| -2.50 | ITGB1 | integrin, beta 1 (fibronectin receptor, beta poly |
| 2.50 | RALGDS | ral guanine nucleotide dissociation stimulator |
| -2.50 | SLC2A3 | solute carrier family 2 (facilitated glucose trans |
| 2.50 | SLC44A5 | solute carrier family 44, member 5 |
| -2.50 | WDR59 | WD repeat domain 59 |
| -2.50 | JARID2 | Jumonji, AT rich interactive domain 2 |
| -2.50 | PPAP2A | phosphatidic acid phosphatase type 2A |
| -2.49 | — | — |
| 2.49 | — | Homo sapiens, clone IMAGE:4940467, mRNA |
| -2.49 | RANBP1 | RAN binding protein 1 |
| -2.49 | — | — |
| 2.49 | DPP4 | dipeptidyl-peptidase 4 (CD26, adenosine dear |
| -2.49 | ARHGAP28 | Rho GTPase activating protein 28 |
| -2.49 | SKIL | SKI-like oncogene |
| -2.49 | DENND2C | DENN/MADD domain containing 2C |
| 2.49 | — | CDNA FLJ30810 fis, clone FEBRA2001440 |
| 2.49 | — | — |
| 2.49 | SEC31B | SEC31 homolog B (S. cerevisiae) |
| 2.49 | HOXB5 | homeobox B5 |
| 2.49 | — | CDNA clone IMAGE:5263177 |
| -2.49 | ASB9 | ankyrin repeat and SOCS box-containing 9 |
| -2.49 | PRICKLE1 | prickle homolog 1 (Drosophila) |
| 2.49 | — | — |
| 2.49 | — | — |
| -2.49 | CTHRC1 | collagen triple helix repeat containing 1 |
| -2.49 | DKFZP56400823 | DKFZp564O0823 protein |
| 2.49 | EMID1 | EMI domain containing 1 |
| 2.49 | SKAP2 | src kinase associated phosphoprotein 2 |
| -2.49 | FLJ14001 | hypothetical protein FLJ14001 |
| -2.49 | PRICKLE1 | Prickle-like 1 (Drosophila) |
| 2.48 | KIAA0523 | KIAA0523 protein |
| -2.48 | — | — |
| 2.48 | PPM1E | protein phosphatase 1E (PP2C domain contain |
| -2.48 | ITGB1 | integrin, beta 1 (fibronectin receptor, beta poly |
| 2.48 | GPR153 | G protein-coupled receptor 153 |
| 2.48 | SLC1A6 | solute carrier family 1 (high affinity aspartate/gl |
| -2.48 | DSG2 | desmoglein 2 |
| -2.48 | BCL2A1 | BCL2-related protein A1 |
| -2.48 | CPO | carboxypeptidase O |
| 2.48 | COL11A1 | collagen, type XI, alpha 1 |
| 2.47 | ZDHHC14 | zinc finger, DHHC-type containing 14 |
| 2.47 | — | CDNA FLJ40174 fis, clone TESTI2016996 |
| 2.47 | LOC387895 | Hypothetical gene supported by BC040060 |
| 2.47 | — | — |
| -2.47 | H1F0 | H1 histone family, member 0 |
| 2.47 | LOC650392 | Full-length cDNA clone CS0DF015YK23 of Fet |
| 2.47 | LOC127003 | similar to CG5435-PA |
| -2.47 | RASL11B | RAS-like, family 11, member B |

Appendix 1

| Value | Symbol | Description |
|---|---|---|
| -2.45 | DENND2C | DENN/MADD domain containing 2C |
| 2.45 | KLHL22 | kelch-like 22 (Drosophila) |
| 2.44 | ZNF436 | zinc finger protein 436 |
| 2.44 | CABP7 | calcium binding protein 7 |
| 2.44 | FHL1 | four and a half LIM domains 1 |
| 2.44 | — | — |
| -2.44 | STX6 /// RHEBL1 | syntaxin 6 /// Ras homolog enriched in brain lik |
| 2.44 | SLC35F5 | solute carrier family 35, member F5 |
| 2.44 | DKFZp547K054 | hypothetical protein DKFZp547K054 |
| -2.44 | SULT1C1 | sulfotransferase family, cytosolic, 1C, member |
| 2.44 | — | — |
| 2.44 | TTC23 | tetratricopeptide repeat domain 23 |
| 2.44 | FNBP1 | Formin binding protein 1 |
| -2.44 | ICAM3 | intercellular adhesion molecule 3 |
| 2.44 | BVES | blood vessel epicardial substance |
| 2.44 | ASXL1 | additional sex combs like 1 (Drosophila) |
| -2.44 | KLF5 | Kruppel-like factor 5 (intestinal) |
| -2.43 | CHES1 | checkpoint suppressor 1 |
| -2.43 | EML2 | echinoderm microtubule associated protein like |
| 2.43 | CD99L2 | CD99 molecule-like 2 |
| 2.43 | IKZF1 | IKAROS family zinc finger 1 (Ikaros) |
| 2.43 | DENND2A | DENN/MADD domain containing 2A |
| 2.43 | SH3-domain GRB2- | SH3-domain GRB2-like pseudogene 3 |
| 2.43 | MGC40405 | Zinc finger, SWIM-type containing 6 |
| -2.43 | SKIL | SKI-like oncogene |
| 2.43 | — | — |
| -2.43 | MAN1C1 | mannosidase, alpha, class 1C, member 1 |
| -2.43 | PWCR1 | Prader-Willi syndrome chromosome region 1 |
| -2.43 | TBC1D8B | TBC1 domain family, member 8B (with GRAM |
| 2.43 | MXRA7 | matrix-remodelling associated 7 |
| -2.43 | HBP1 | HMG-box transcription factor 1 |
| -2.43 | OLFM1 | olfactomedin 1 |
| 2.43 | RAB40B | RAB40B, member RAS oncogene family |
| 2.42 | — | Clone FLB8310 PRO2225 |
| 2.42 | PTCH1 | patched homolog 1 (Drosophila) |
| 2.42 | SPA17 | Sperm autoantigenic protein 17 |
| -2.42 | — | — |
| -2.42 | IFI44 | Interferon-induced protein 44 |
| -2.42 | — | — |
| 2.42 | DKFZP564D166 | putative ankyrin-repeat containing protein |
| -2.42 | — | — |
| -2.42 | C1RL | complement component 1, r subcomponent-lik |
| -2.42 | PHACS | 1-aminocyclopropane-1-carboxylate synthase |
| -2.42 | — | — |
| 2.42 | MSI1 | musashi homolog 1 (Drosophila) |
| 2.42 | MAP2K5 | mitogen-activated protein kinase kinase 5 |
| -2.42 | FLNB | filamin B, beta (actin binding protein 278) |
| -2.42 | — | CDNA FLJ39361 fis, clone PEBLM2004733 |
| -2.42 | TMEM63A | transmembrane protein 63A |
| -2.42 | — | — |
| 2.42 | MUC6 | mucin 6, oligomeric mucus/gel-forming |
| 2.42 | CRLS1 | cardiolipin synthase 1 |
| -2.42 | CABP1 | calcium binding protein 1 (calbrain) |
| 2.42 | — | MRNA; cDNA DKFZp686G08203 (from clone |
| 2.41 | MLLT1 | myeloid/lymphoid or mixed-lineage leukemia (t |
| 2.41 | HIST1H2BD | Histone 1, H2bd |
| 2.41 | CCND1 | cyclin D1 |
| 2.41 | ELOVL2 | elongation of very long chain fatty acids (FEN1 |
| 2.41 | TTC3 | tetratricopeptide repeat domain 3 |
| -2.41 | KCNMB4 | potassium large conductance calcium-activated |
| 2.41 | ABCB4 | ATP-binding cassette, sub-family B (MDR/TAP |
| -2.41 | GALK1 | galactokinase 1 |
| 2.41 | PLCL2 | phospholipase C-like 2 |
| -2.41 | GPSM3 | G-protein signalling modulator 3 (AGS3-like, C |
| 2.41 | VEGFC | vascular endothelial growth factor C |
| 2.41 | — | — |
| -2.41 | — | — |
| 2.41 | — | — |
| 2.41 | FHL1 | four and a half LIM domains 1 |
| 2.41 | SOAT1 | sterol O-acyltransferase (acyl-Coenzyme A: ch |
| -2.41 | GNPTAB | N-acetylglucosamine-1-phosphate transferase, |
| -2.41 | EVA1 | epithelial V-like antigen 1 |
| 2.41 | PDLIM3 | PDZ and LIM domain 3 |
| 2.41 | TULP4 | Tubby like protein 4 |
| -2.40 | LOC389129 | similar to CG9996-PA |
| 2.40 | PIGM | phosphatidylinositol glycan anchor biosynthesis |
| 2.40 | DIXDC1 | DIX domain containing 1 |
| -2.40 | FGD5 | FYVE, RhoGEF and PH domain containing 5 |
| -2.40 | — | — |
| 2.47 | — | — |
| -2.47 | ZNF785 | zinc finger protein 785 |
| 2.47 | — | Homo sapiens, clone IMAGE:4346533, mRNA |
| -2.47 | DENND3 | DENN/MADD domain containing 3 |
| -2.47 | LNX1 | ligand of numb-protein X 1 |
| 2.47 | — | — |
| 2.47 | MLR1 | transcription factor MLR1 |
| 2.47 | NEBL | nebulette |
| -2.47 | TES | testis derived transcript (3 LIM domains) |
| 2.47 | — | — |
| 2.47 | — | — |
| 2.46 | — | — |
| 2.46 | PIK3R3 | phosphoinositide-3-kinase, regulatory subunit 3 |
| 2.46 | SCCPDH | saccharopine dehydrogenase (putative) |
| -2.46 | — | — |
| -2.46 | FGD6 | FYVE, RhoGEF and PH domain containing 6 |
| 2.46 | PAPPA | pregnancy-associated plasma protein A, pappa |
| 2.46 | EXOSC6 | Exosome component 6 |
| -2.46 | IL6 | interleukin 6 (interferon, beta 2) |
| -2.46 | CA4 | carbonic anhydrase IV |
| -2.46 | TPD52 | tumor protein D52 |
| -2.46 | CALCA | calcitonin/calcitonin-related polypeptide, alpha |
| 2.46 | PPOX | protoporphyrinogen oxidase |
| 2.46 | CUEDC1 | CUE domain containing 1 |
| 2.46 | GNG11 | guanine nucleotide binding protein (G protein), |
| -2.45 | LOC390940 | similar to R28379_1 |
| 2.45 | RUFY3 | RUN and FYVE domain containing 3 |
| -2.45 | CTSC | cathepsin C |
| -2.45 | FGF2 | fibroblast growth factor 2 (basic) |
| 2.45 | HDLBP | High density lipoprotein binding protein (vigilin) |
| -2.45 | CNFN | cornifelin /// cornifelin |
| 2.45 | RIG | regulated in glioma |
| 2.45 | — | — |
| 2.45 | — | LOC440309 |
| -2.44 | ZSCAN2 | zinc finger and SCAN domain containing 2 |
| -2.44 | RGL3 | ral guanine nucleotide dissociation stimulator-li |
| -2.44 | SLC12A6 | solute carrier family 12 (potassium/chloride trar |
| 2.44 | LSDP5 | lipid storage droplet protein 5 |
| -2.44 | MAF | v-maf musculoaponeurotic fibrosarcoma oncog |
| 2.44 | — | Homo sapiens, clone IMAGE:5242623 |
| -2.44 | SH2D4A | SH2 domain containing 4A |
| 2.44 | MGC40405 | Zinc finger, SWIM-type containing 6 |
| -2.44 | AMT | aminomethyltransferase |
| -2.44 | HLA-G | HLA-G histocompatibility antigen, class I, G |
| 2.44 | KCNJ8 | potassium inwardly-rectifying channel, subfami |
| -2.44 | KCNMB4 | potassium large conductance calcium-activated |
| -2.44 | RPP25 | ribonuclease P 25kDa subunit |
| -2.44 | ZNF560 | zinc finger protein 560 |
| -2.44 | ZNF747 | zinc finger protein 747 |
| -2.44 | PHC1 | polyhomeotic homolog 1 (Drosophila) |
| -2.44 | CD164 | CD164 molecule, sialomucin |
| -2.43 | CASP10 | caspase 10, apoptosis-related cysteine peptida |
| 2.43 | RBMS3 | RNA binding motif, single stranded interacting |
| -2.43 | STX6 | syntaxin 6 |
| 2.43 | — | — |
| -2.43 | ZNF589 | zinc finger protein 589 |
| 2.43 | ENTPD4 | ectonucleoside triphosphate diphosphohydrola |
| 2.43 | IFNAR1 | interferon (alpha, beta and omega) receptor 1 |
| -2.43 | KIAA1333 | KIAA1333 |
| 2.43 | C18orf8 | Chromosome 18 open reading frame 8 |
| 2.43 | UGCGL2 | UDP-glucose ceramide glucosyltransferase-like |
| 2.43 | — | — |
| 2.43 | — | — |
| -2.43 | MGC17624 | MGC17624 protein |
| -2.42 | MET | met proto-oncogene (hepatocyte growth factor |
| 2.42 | — | Transcribed locus |
| -2.42 | LOC283731 | hypothetical protein LOC283731 |
| -2.42 | SIVA1 | SIVA1, apoptosis-inducing factor |
| -2.42 | COL21A1 | collagen, type XXI, alpha 1 /// collagen, type X |
| -2.42 | PCSK1 | proprotein convertase subtilisin/kexin type 1 |
| 2.42 | — | — |
| -2.42 | FGD5 | FYVE, RhoGEF and PH domain containing 5 |
| 2.42 | — | Transcribed locus |
| -2.42 | CHES1 | checkpoint suppressor 1 |
| -2.42 | TNRC6A | trinucleotide repeat containing 6A |
| 2.42 | FAS | Fas (TNF receptor superfamily, member 6) |
| -2.42 | ARHGAP28 | Rho GTPase activating protein 28 |
| -2.42 | ASPHD1 | aspartate beta-hydroxylase domain containing |
| 2.41 | BAIAP2 | BAI1-associated protein 2 |

Appendix 1

| Value | Gene | Description |
|---|---|---|
| -2.40 | PLEKHC1 | pleckstrin homology domain containing, family |
| -2.40 | LOC730069 /// LOC | similar to nuclear receptor binding factor 2 /// si |
| -2.40 | C14orf151 | chromosome 14 open reading frame 151 /// ch |
| -2.40 | CPLX1 | complexin 1 |
| -2.40 | — | — |
| -2.40 | — | — |
| -2.40 | PCK2 | Phosphoenolpyruvate carboxykinase 2 (mitoch |
| -2.40 | MLSTD1 | male sterility domain containing 1 |
| -2.40 | CDS1 | CDP-diacylglycerol synthase (phosphatidate c |
| -2.40 | GLYATL1 | glycine-N-acyltransferase-like 1 |
| -2.40 | COMMD10 | CDNA clone IMAGE:5277380 /// COMM domai |
| 2.40 | — | — |
| -2.40 | — | — |
| -2.39 | — | — |
| 2.39 | PB1 | polybromo 1 |
| -2.39 | CHES1 | checkpoint suppressor 1 |
| -2.39 | — | — |
| 2.39 | ZNF584 | zinc finger protein 584 |
| 2.39 | — | — |
| -2.39 | TSPO | translocator protein (18kDa) |
| 2.39 | C8orf55 | chromosome 8 open reading frame 55 |
| 2.39 | SOX11 | SRY (sex determining region Y)-box 11 |
| -2.39 | — | MRNA; cDNA DKFZp761H1023 (from clone D |
| -2.39 | SLC43A1 | solute carrier family 43, member 1 |
| -2.39 | PIM1 | pim-1 oncogene /// pim-1 oncogene |
| -2.39 | FURIN | furin (paired basic amino acid cleaving enzyme |
| -2.38 | TDH | L-threonine dehydrogenase |
| 2.38 | POLR2J2 | DNA directed RNA polymerase II polypeptide J |
| -2.38 | GNB5 | guanine nucleotide binding protein (G protein), |
| 2.38 | RAB32 | RAB32, member RAS oncogene family |
| 2.38 | — | — |
| 2.38 | — | — |
| 2.38 | DMPK | dystrophia myotonica-protein kinase |
| 2.38 | BCL2 | B-cell CLL/lymphoma 2 |
| -2.38 | ALOX12 | arachidonate 12-lipoxygenase |
| 2.38 | SEMA6D | sema domain, transmembrane domain (TM), a |
| 2.38 | SMARCA4 | SWI/SNF related, matrix associated, actin depe |
| 2.38 | — | — |
| -2.38 | PPM1B | protein phosphatase 1B (formerly 2C), magnes |
| -2.38 | RPP25 | ribonuclease P 25kDa subunit |
| 2.38 | — | Transcribed locus, weakly similar to XP_51193 |
| 2.38 | — | — |
| 2.38 | — | — |
| 2.37 | TMEM5 | transmembrane protein 5 |
| -2.37 | DKFZP564I1171 | DKFZP564I1171 protein |
| -2.37 | FLJ44894 | similar to zinc finger protein 91 |
| -2.37 | — | — |
| -2.37 | — | — |
| -2.37 | PRG1 | proteoglycan 1, secretory granule |
| -2.37 | CYP2C8 | cytochrome P450, family 2, subfamily C, polyp |
| -2.37 | C1QL1 | complement component 1, q subcomponent-lik |
| -2.37 | LEPR | leptin receptor |
| -2.37 | EMR2 | egf-like module containing, mucin-like, hormon |
| 2.37 | SH3BP5 | SH3-domain binding protein 5 (BTK-associated |
| 2.37 | MAGEA11 | melanoma antigen family A, 11 |
| 2.37 | ACCN2 | amiloride-sensitive cation channel 2, neuronal |
| 2.37 | — | — |
| -2.37 | SLC16A3 | solute carrier family 16, member 3 (monocarbo |
| 2.37 | LPL | lipoprotein lipase |
| 2.37 | ST7 | suppression of tumorigenicity 7 |
| 2.37 | PLEKHO1 | pleckstrin homology domain containing, family |
| -2.37 | CD177 | CD177 molecule |
| 2.37 | ARL3 | ADP-ribosylation factor-like 3 |
| -2.36 | SDC4 | syndecan 4 (amphiglycan, ryudocan) |
| -2.36 | ATHL1 | ATH1, acid trehalase-like 1 (yeast) |
| 2.36 | LOC283012 | hypothetical protein LOC283012 |
| 2.36 | CTGF | connective tissue growth factor |
| 2.36 | SHANK3 | SH3 and multiple ankyrin repeat domains 3 |
| -2.36 | DUSP10 | dual specificity phosphatase 10 |
| -2.36 | — | — |
| 2.36 | FLJ10292 | mago-nashi homolog |
| 2.36 | ANAPC7 | anaphase promoting complex subunit 7 |
| 2.36 | C6orf153 | Chromosome 6 open reading frame 153 |
| 2.36 | LOC550631 | Hypothetical LOC550631 |
| 2.36 | — | — |
| 2.36 | ABCA2 | ATP-binding cassette, sub-family A (ABC1), m |
| 2.36 | MCF2L | MCF.2 cell line derived transforming sequence |
| 2.36 | C19orf20 | chromosome 19 open reading frame 20 |
| 2.36 | — | — |

| Value | Gene | Description |
|---|---|---|
| -2.41 | GABRB3 | gamma-aminobutyric acid (GABA) A receptor, |
| 2.41 | DLL3 | delta-like 3 (Drosophila) |
| 2.41 | — | — |
| -2.41 | — | CDNA clone IMAGE:4819775 |
| -2.41 | SLC2A3 | Solute carrier family 2 (facilitated glucose trans |
| -2.41 | DSG2 | Desmoglein 2 |
| 2.41 | MBD2 | methyl-CpG binding domain protein 2 |
| 2.41 | — | Similar to hypothetical protein |
| -2.41 | MMP24 | matrix metallopeptidase 24 (membrane-inserte |
| 2.41 | NEBL | Nebulette |
| -2.41 | CDCP1 | CUB domain containing protein 1 |
| 2.41 | — | CDNA FLJ11655 fis, clone HEMBA1004554 |
| 2.41 | MAGED4 | melanoma antigen family D, 4 /// melanoma an |
| -2.40 | VAMP1 | vesicle-associated membrane protein 1 (synap |
| 2.40 | — | — |
| -2.40 | — | — |
| 2.40 | ZNF3 | zinc finger protein 3 |
| -2.40 | SEPHS1 | selenophosphate synthetase 1 |
| -2.40 | STX6 | syntaxin 6 |
| -2.40 | PXN | paxillin |
| -2.40 | GSTO2 | glutathione S-transferase omega 2 |
| -2.40 | — | — |
| 2.40 | DCLRE1C | DNA cross-link repair 1C (PSO2 homolog, S. c |
| 2.40 | — | Transcribed locus |
| 2.40 | C7orf16 | chromosome 7 open reading frame 16 |
| 2.40 | C1orf102 | chromosome 1 open reading frame 102 |
| 2.40 | YAF2 | YY1 associated factor 2 |
| 2.40 | SLITRK5 | SLIT and NTRK-like family, member 5 |
| -2.40 | MLLT4 | myeloid/lymphoid or mixed-lineage leukemia (t |
| 2.40 | SLC16A9 | solute carrier family 16, member 9 (monocarbo |
| 2.39 | UBE2J1 | ubiquitin-conjugating enzyme E2, J1 (UBC6 ho |
| 2.39 | DKFZp762A217 | hypothetical protein DKFZp762A217 |
| -2.39 | MYCBP | c-myc binding protein |
| 2.39 | — | CDNA clone IMAGE:3910094 |
| -2.39 | — | CDNA FLJ33993 fis, clone DFNES2007757 |
| 2.39 | PACS1 | phosphofurin acidic cluster sorting protein 1 |
| 2.39 | NUCB2 | nucleobindin 2 |
| -2.39 | — | — |
| 2.39 | — | — |
| 2.39 | — | Transcribed locus |
| -2.39 | — | — |
| -2.39 | COMT | catechol-O-methyltransferase |
| 2.39 | ZC3H14 | Zinc finger CCCH-type containing 14 |
| 2.39 | TOX | thymus high mobility group box protein TOX |
| 2.39 | MAPKBP1 /// KLHL | mitogen activated protein kinase binding protei |
| 2.39 | — | — |
| 2.39 | CALML4 | calmodulin-like 4 |
| -2.39 | ROD1 | ROD1 regulator of differentiation 1 (S. pombe) |
| -2.39 | LOC730432 | similar to serine/threonine/tyrosine interacting |
| 2.39 | CYP4V2 | cytochrome P450, family 4, subfamily V, polyp |
| 2.39 | ZNF346 | Zinc finger protein 346 |
| -2.39 | KIAA1815 | KIAA1815 |
| 2.39 | VASH1 | vasohibin 1 |
| 2.39 | — | — |
| -2.39 | COCH | coagulation factor C homolog, cochlin (Limulus |
| 2.39 | GPSM2 | G-protein signalling modulator 2 (AGS3-like, C |
| 2.39 | EME2 | Essential meiotic endonuclease 1 homolog 2 ( |
| 2.39 | KIF1B | Kinesin family member 1B |
| -2.38 | C14orf1 | chromosome 14 open reading frame 1 |
| -2.38 | CHGA | chromogranin A (parathyroid secretory protein |
| 2.38 | KIAA0523 | KIAA0523 protein |
| 2.38 | SEMA6D | sema domain, transmembrane domain (TM), a |
| 2.38 | FLJ37562 | hypothetical protein FLJ37562 |
| -2.38 | ZBTB44 | zinc finger and BTB domain containing 44 |
| 2.38 | — | — |
| 2.38 | PIGX | Phosphatidylinositol glycan, class X |
| 2.38 | TTC28 | tetratricopeptide repeat domain 28 |
| -2.38 | CDC14B | CDC14 cell division cycle 14 homolog B (S. ce |
| -2.38 | CNTNAP2 | contactin associated protein-like 2 |
| -2.38 | FAM124A | family with sequence similarity 124A |
| 2.38 | MAN2A1 | mannosidase, alpha, class 2A, member 1 |
| -2.38 | CXCL1 | chemokine (C-X-C motif) ligand 1 (melanoma g |
| 2.38 | — | — |
| -2.38 | KCNE3 | potassium voltage-gated channel, Isk-related f |
| 2.38 | TMEM2 | Transmembrane protein 2 |
| 2.38 | — | — |
| 2.38 | HGSNAT | heparan-alpha-glucosaminide N-acetyltransfer |
| -2.38 | TNFRSF21 | tumor necrosis factor receptor superfamily, me |
| -2.38 | SYN2 | synapsin II |

Appendix 1

| | | | | |
|---|---|---|---|---|
| -2.35 | TAGLN2 | transgelin 2 | -2.38 | CPT1A | carnitine palmitoyltransferase 1A (liver) |
| -2.35 | GLS | glutaminase | -2.38 | — | — |
| -2.35 | IFI16 | interferon, gamma-inducible protein 16 | 2.37 | CRYL1 | Crystallin, lambda 1 |
| 2.35 | ZDHHC21 | zinc finger, DHHC-type containing 21 | -2.37 | FLJ22659 | hypothetical protein FLJ22659 |
| 2.35 | — | — | -2.37 | CD44 | CD44 molecule (Indian blood group) |
| 2.35 | PSMB2 | proteasome (prosome, macropain) subunit, bet | 2.37 | MAN2A2 | mannosidase, alpha, class 2A, member 2 |
| -2.35 | CPS1 | carbamoyl-phosphate synthetase 1, mitochond | 2.37 | VEPH1 | ventricular zone expressed PH domain homolo |
| -2.35 | MNAT1 | menage a trois homolog 1, cyclin H assembly f | -2.37 | FOXO1A | forkhead box O1A (rhabdomyosarcoma) |
| -2.35 | LXN | latexin | 2.37 | — | — |
| 2.35 | AGPAT3 | 1-acylglycerol-3-phosphate O-acyltransferase 3 | 2.37 | RIT1 | Ras-like without CAAX 1 |
| 2.35 | — | CDNA FLJ39389 fis, clone PLACE6003621 | -2.37 | TKT | transketolase (Wernicke-Korsakoff syndrome) |
| 2.35 | MSI2 | musashi homolog 2 (Drosophila) | -2.37 | TNFAIP6 | tumor necrosis factor, alpha-induced protein 6 |
| -2.35 | TPD52 | tumor protein D52 | -2.37 | — | MRNA; cDNA DKFZp313A1040 (from clone DI |
| -2.35 | — | CDNA FLJ26242 fis, clone DMC00770 | 2.37 | — | — |
| 2.35 | SFRS11 | splicing factor, arginine/serine-rich 11 | 2.37 | — | — |
| -2.35 | BMPR1A | Bone morphogenetic protein receptor, type IA | -2.37 | RAB15 | RAB15, member RAS oncogene family |
| -2.35 | SLC13A3 | Solute carrier family 13 (sodium-dependent dic | -2.37 | SIRT1 | sirtuin (silent mating type information regulation |
| 2.35 | EPB41L1 | erythrocyte membrane protein band 4.1-like 1 | -2.37 | RBPMS | RNA binding protein with multiple splicing |
| -2.35 | IL27RA | interleukin 27 receptor, alpha | -2.37 | — | — |
| -2.35 | FOXQ1 | forkhead box Q1 | -2.37 | SDC4 | syndecan 4 (amphiglycan, ryudocan) |
| -2.35 | C9orf64 | chromosome 9 open reading frame 64 | -2.36 | BTD | biotinidase |
| 2.35 | CASKIN1 | CASK interacting protein 1 | -2.36 | ETV4 | ets variant gene 4 (E1A enhancer binding prote |
| -2.35 | C8orf47 | chromosome 8 open reading frame 47 | -2.36 | TMEM63A | transmembrane protein 63A |
| -2.35 | NAIP | similar to Occludin | -2.36 | KCNK6 | potassium channel, subfamily K, member 6 |
| 2.35 | VASH1 | vasohibin 1 | 2.36 | ZNF496 | Zinc finger protein 496 |
| 2.35 | MAPK10 | mitogen-activated protein kinase 10 | 2.36 | ACCN2 | amiloride-sensitive cation channel 2, neuronal |
| -2.34 | KIAA0485 | KIAA0485 protein | 2.36 | RGMB | RGM domain family, member B |
| 2.34 | C6orf60 | Chromosome 6 open reading frame 60 | -2.36 | FKBP4 | FK506 binding protein 4, 59kDa |
| -2.34 | FLJ32810 | hypothetical protein FLJ32810 | -2.36 | DOCK2 | dedicator of cytokinesis 2 |
| 2.34 | RGS12 | regulator of G-protein signalling 12 | 2.36 | LOC388588 | hypothetical gene supported by BC035379; BC |
| -2.34 | NMRAL1 | NmrA-like family domain containing 1 | -2.36 | HMGB3 | high-mobility group box 3 |
| -2.34 | — | — | 2.36 | POLH | Polymerase (DNA directed), eta |
| 2.34 | CEP290 | centrosomal protein 290kDa | 2.36 | C5orf24 | chromosome 5 open reading frame 24 |
| -2.34 | CCRN4L | CCR4 carbon catabolite repression 4-like (S. c | 2.36 | — | — |
| 2.34 | — | — | 2.36 | TULP4 | Tubby like protein 4 |
| -2.34 | TRIM37 | tripartite motif-containing 37 | 2.36 | LOC92482 | hypothetical protein LOC92482 |
| -2.34 | — | — | -2.36 | ETV4 | ets variant gene 4 (E1A enhancer binding prote |
| 2.34 | TMEM17 | transmembrane protein 17 | -2.36 | METTL7A | methyltransferase like 7A |
| 2.34 | EP400 | E1A binding protein p400 | -2.36 | — | MRNA; cDNA DKFZp686H1629 (from clone DI |
| -2.34 | NPAL3 | NIPA-like domain containing 3 | -2.36 | UBE3C | ubiquitin protein ligase E3C |
| -2.34 | GRIK5 | glutamate receptor, ionotropic, kainate 5 | -2.36 | UTX | ubiquitously transcribed tetratricopeptide repea |
| -2.34 | PCDHA9 /// PCDHA | protocadherin alpha 9 /// protocadherin alpha s | 2.36 | WDR31 | WD repeat domain 31 |
| 2.34 | — | — | 2.36 | D2HGDH | D-2-hydroxyglutarate dehydrogenase |
| 2.34 | FLJ25477 | Hypothetical protein FLJ25477 | 2.36 | FJX1 | four jointed box 1 (Drosophila) |
| -2.33 | B3GNT1 | UDP-GlcNAc:betaGal beta-1,3-N-acetylglucosa | 2.35 | VAPA | VAMP (vesicle-associated membrane protein)- |
| 2.33 | LOC219688 | hypothetical protein LOC219688 | 2.35 | POLR2J2 | DNA directed RNA polymerase II polypeptide J |
| 2.33 | ELAC1 | elaC homolog 1 (E. coli) | 2.35 | — | CDNA clone IMAGE:5263177 |
| 2.33 | CHST3 | carbohydrate (chondroitin 6) sulfotransferase 3 | 2.35 | FLJ31951 | Hypothetical protein FLJ31951 |
| 2.33 | — | — | 2.35 | — | — |
| -2.33 | — | — | 2.35 | MSI2 | Musashi homolog 2 (Drosophila) |
| -2.33 | LOC492311 | similar to bovine IgA regulatory protein | -2.35 | FKBP1A | FK506 binding protein 1A, 12kDa |
| 2.33 | MGC39900 | hypothetical protein MGC39900 | -2.35 | RILP | Rab interacting lysosomal protein |
| -2.33 | F12 | coagulation factor XII (Hageman factor) | 2.35 | — | Transcribed locus |
| -2.33 | — | — | -2.35 | IQGAP1 | IQ motif containing GTPase activating protein |
| 2.33 | PRO2964 | hypothetical protein PRO2964 | -2.35 | C10orf6 | Chromosome 10 open reading frame 6 |
| 2.33 | — | CDNA FLJ41303 fis, clone BRAMY2042131 | 2.35 | DYNC2LI1 | dynein, cytoplasmic 2, light intermediate chain |
| 2.33 | — | — | -2.35 | CPS1 | carbamoyl-phosphate synthetase 1, mitochond |
| 2.33 | B3GALNT1 | beta-1,3-N-acetylgalactosaminyltransferase 1 ( | 2.35 | CPLX1 | complexin 1 |
| -2.33 | MSTP9 | macrophage stimulating, pseudogene 9 | -2.34 | SERPINB9 | serpin peptidase inhibitor, clade B (ovalbumin) |
| -2.33 | — | CDNA clone IMAGE:5311619 | -2.34 | HLA-F | major histocompatibility complex, class I, F |
| 2.33 | LOC441204 | hypothetical locus LOC441204 | -2.34 | MMP14 | matrix metallopeptidase 14 (membrane-inserte |
| 2.33 | ZNF496 | Zinc finger protein 496 | -2.34 | KIAA0746 | KIAA0746 protein |
| -2.33 | RAC2 | ras-related C3 botulinum toxin substrate 2 (rho | 2.34 | MTHFD2L | methylenetetrahydrofolate dehydrogenase (NA |
| 2.33 | GALNTL1 | UDP-N-acetyl-alpha-D-galactosamine:polypept | -2.34 | — | Homo sapiens, Similar to LOC169932, clone IM |
| 2.33 | — | — | 2.34 | SPA17 | Sperm autoantigenic protein 17 |
| -2.32 | IL20RB | interleukin 20 receptor beta | 2.34 | DEF6 | differentially expressed in FDCP 6 homolog (m |
| 2.32 | LOC92154 | hypothetical protein BC002770 | 2.34 | PHF20L1 | PHD finger protein 20-like 1 |
| -2.32 | PMAIP1 | phorbol-12-myristate-13-acetate-induced prote | 2.34 | DPYD | dihydropyrimidine dehydrogenase |
| -2.32 | — | — | -2.34 | — | — |
| 2.32 | LOC200169 | hypothetical protein LOC200169 | -2.34 | PRRG2 | proline rich Gla (G-carboxyglutamic acid) 2 |
| -2.32 | SAT1 | spermidine/spermine N1-acetyltransferase 1 | -2.34 | — | — |
| -2.32 | PBX1 | Pre-B-cell leukemia transcription factor 1 | 2.34 | — | Transcribed locus |
| 2.32 | — | MRNA; cDNA DKFZp564E143 (from clone DKF | -2.34 | GSTZ1 | glutathione transferase zeta 1 (maleylacetoace |
| 2.32 | — | — | -2.34 | C10orf118 | chromosome 10 open reading frame 118 |
| -2.32 | CADPS | Ca2+-dependent secretion activator | -2.34 | PLA2G12A | phospholipase A2, group XIIA |
| 2.32 | — | — | 2.34 | BTN3A3 /// BTN3A2 | butyrophilin, subfamily 3, member A3 /// butyro |
| 2.32 | — | — | 2.34 | LOC642732 /// LOC | similar to CG10721-PA /// similar to CG10721-I |
| -2.32 | — | — | 2.34 | ARTS-1 | type 1 tumor necrosis factor receptor shedding |
| -2.32 | CAV2 | caveolin 2 | 2.34 | PPIL6 | peptidylprolyl isomerase (cyclophilin)-like 6 |

Appendix 1

| Value | Gene | Description |
|---|---|---|
| -2.32 | SMPDL3B | sphingomyelin phosphodiesterase, acid-like 3B |
| 2.32 | LATS1 | LATS, large tumor suppressor, homolog 1 (Dro |
| 2.32 | FBXL16 | F-box and leucine-rich repeat protein 16 |
| 2.32 | CHRDL1 | chordin-like 1 |
| 2.32 | NHS | Nance-Horan syndrome (congenital cataracts a |
| -2.31 | SLC11A1 | solute carrier family 11 (proton-coupled divalen |
| 2.31 | ABHD12 | abhydrolase domain containing 12 |
| -2.31 | RPS24 | Ribosomal protein S24 |
| -2.31 | RPUSD3 | RNA pseudouridylate synthase domain contain |
| -2.31 | TDRD7 | tudor domain containing 7 |
| 2.31 | C20orf58 | chromosome 20 open reading frame 58 |
| 2.31 | ABHD3 | abhydrolase domain containing 3 |
| 2.31 | — | — |
| 2.31 | — | — |
| 2.31 | TOX | thymus high mobility group box protein TOX |
| 2.31 | FBN1 | fibrillin 1 |
| 2.31 | WDR31 | WD repeat domain 31 |
| 2.31 | ZNF638 | Zinc finger protein 638 |
| -2.31 | ANXA1 | annexin A1 |
| 2.31 | FAS | Fas (TNF receptor superfamily, member 6) |
| 2.31 | KBTBD11 | kelch repeat and BTB (POZ) domain containing |
| -2.31 | L2HGDH | L-2-hydroxyglutarate dehydrogenase |
| 2.31 | SHC4 | SHC (Src homology 2 domain containing) fami |
| 2.31 | FAM49A | family with sequence similarity 49, member A |
| -2.30 | ZADH1 | zinc binding alcohol dehydrogenase, domain c |
| 2.30 | FHL1 | four and a half LIM domains 1 |
| 2.30 | — | — |
| 2.30 | PDZRN3 | PDZ domain containing RING finger 3 |
| 2.30 | — | — |
| -2.30 | SAMD3 | sterile alpha motif domain containing 3 |
| -2.30 | TRIM38 | tripartite motif-containing 38 |
| 2.30 | GPR161 | G protein-coupled receptor 161 |
| -2.30 | CBX7 | chromobox homolog 7 |
| -2.30 | — | — |
| 2.30 | KLHDC4 | Kelch domain containing 4 |
| 2.30 | — | Transcribed locus |
| -2.30 | ATXN3 | ataxin 3 |
| -2.30 | C1orf88 | chromosome 1 open reading frame 88 |
| 2.30 | ODF2 | outer dense fiber of sperm tails 2 |
| 2.30 | BCL7A | B-cell CLL/lymphoma 7A |
| -2.30 | MGC29814 | hypothetical protein MGC29814 |
| 2.30 | CELSR2 | cadherin, EGF LAG seven-pass G-type recept |
| -2.30 | — | — |
| -2.30 | WIPI1 | WD repeat domain, phosphoinositide interactin |
| -2.30 | — | — |
| 2.30 | FLJ21986 | hypothetical protein FLJ21986 |
| 2.30 | CALML4 | calmodulin-like 4 |
| 2.29 | DDR1 | discoidin domain receptor family, member 1 |
| -2.29 | CASP8 | caspase 8, apoptosis-related cysteine peptidas |
| -2.29 | AMT | aminomethyltransferase |
| 2.29 | IGSF4C | immunoglobulin superfamily, member 4C |
| -2.29 | KIAA0143 | KIAA0143 protein |
| 2.29 | LANCL2 | LanC lantibiotic synthetase component C-like 2 |
| 2.29 | FHL1 | four and a half LIM domains 1 |
| -2.29 | — | — |
| -2.29 | ARRDC2 | arrestin domain containing 2 |
| 2.29 | C20orf58 | chromosome 20 open reading frame 58 |
| 2.29 | — | — |
| 2.29 | — | — |
| 2.29 | — | — |
| 2.29 | AP1GBP1 | AP1 gamma subunit binding protein 1 |
| -2.29 | PPM1J | protein phosphatase 1J (PP2C domain contain |
| 2.29 | — | CDNA clone IMAGE:5288594 |
| 2.29 | — | Full-length cDNA clone CS0DC015YK09 of Ne |
| 2.29 | LRRN1 | leucine rich repeat neuronal 1 |
| 2.29 | ATP10A | ATPase, Class V, type 10A |
| 2.29 | — | Transcribed locus, moderately similar to NP_0 |
| -2.29 | GABRB3 | Gamma-aminobutyric acid (GABA) A receptor, |
| -2.29 | CTSS | cathepsin S |
| -2.28 | HMMR | Hyaluronan-mediated motility receptor (RHAM |
| -2.28 | FAM124A | family with sequence similarity 124A |
| 2.28 | POLH | Polymerase (DNA directed), eta |
| 2.28 | RIMBP2 | RIMS binding protein 2 |
| 2.28 | BACE1 | beta-site APP-cleaving enzyme 1 |
| -2.28 | RABGAP1L | RAB GTPase activating protein 1-like |
| -2.28 | CREB3L4 | cAMP responsive element binding protein 3-lik |
| -2.28 | — | Transcribed locus |
| -2.28 | GABARAPL1 | GABA(A) receptor-associated protein like 1 |
| 2.28 | — | — |
| -2.34 | C6orf89 | chromosome 6 open reading frame 89 |
| -2.34 | CD109 | CD109 molecule |
| -2.34 | LMTK3 | lemur tyrosine kinase 3 |
| -2.33 | SORL1 | sortilin-related receptor, L(DLR class) A repeat |
| -2.33 | SNAP23 | synaptosomal-associated protein, 23kDa |
| 2.33 | — | Transcribed locus |
| 2.33 | — | CDNA FLJ36544 fis, clone TRACH2006378 |
| 2.33 | ZNF710 | Zinc finger protein 710 |
| 2.33 | SLC16A6 /// LOC44 | solute carrier family 16 (monocarboxylic acid tr |
| -2.33 | GAS7 | growth arrest-specific 7 /// growth arrest-specifi |
| 2.33 | TAF1B | TATA box binding protein (TBP)-associated fa |
| 2.33 | SPOP | speckle-type POZ protein |
| -2.33 | GATM | glycine amidinotransferase (L-arginine:glycine |
| -2.33 | LGALS3 | lectin, galactoside-binding, soluble, 3 (galectin |
| 2.33 | SH3-domain GRB2- | SH3-domain GRB2-like pseudogene 3 |
| 2.33 | SOX11 | SRY (sex determining region Y)-box 11 |
| -2.33 | FLJ36848 | hypothetical LOC647115 |
| -2.33 | ABCC13 | ATP-binding cassette, sub-family C (CFTR/MR |
| 2.33 | — | CDNA clone IMAGE:5311370 |
| 2.33 | — | — |
| 2.33 | AKR1C1 | aldo-keto reductase family 1, member C1 (dihy |
| 2.33 | VPS24 | vacuolar protein sorting 24 (yeast) |
| 2.32 | IFIT5 | interferon-induced protein with tetratricopeptide |
| 2.32 | C9orf72 | chromosome 9 open reading frame 72 |
| 2.32 | — | Homo sapiens, clone IMAGE:4214654, mRNA |
| 2.32 | TRIM73 | tripartite motif-containing 73 |
| -2.32 | — | — |
| 2.32 | SOAT1 | sterol O-acyltransferase (acyl-Coenzyme A: ch |
| -2.32 | TJP2 | tight junction protein 2 (zona occludens 2) |
| -2.32 | GYLTL1B | glycosyltransferase-like 1B |
| 2.32 | — | Similar to leucine rich repeat containing 10 |
| 2.32 | LOC283713 | hypothetical protein LOC283713 |
| 2.32 | DENND2A | DENN/MADD domain containing 2A |
| 2.32 | NEDD9 | neural precursor cell expressed, developmenta |
| -2.32 | — | — |
| -2.32 | — | — |
| -2.32 | CDKN3 | cyclin-dependent kinase inhibitor 3 (CDK2-asso |
| 2.32 | TP53AP1 | TP53 activated protein 1 |
| -2.31 | SPP1 | secreted phosphoprotein 1 (osteopontin, bone |
| -2.31 | TPM1 | tropomyosin 1 (alpha) |
| -2.31 | CAV2 | caveolin 2 |
| 2.31 | TBX1 | T-box 1 |
| 2.31 | — | — |
| 2.31 | SLC1A4 | solute carrier family 1 (glutamate/neutral amino |
| 2.31 | LOC283075 | Hypothetical protein LOC283075 |
| 2.31 | — | — |
| 2.31 | C11orf17 /// NUAK2 | chromosome 11 open reading frame 17 /// chro |
| 2.31 | DMXL2 | Dmx-like 1 |
| -2.31 | PLSCR4 | phospholipid scramblase 4 |
| 2.31 | TXNL2 | Thioredoxin-like 2 |
| 2.31 | — | — |
| -2.31 | GMPR2 | guanosine monophosphate reductase 2 |
| -2.31 | PLSCR1 | phospholipid scramblase 1 |
| -2.31 | PYGM | phosphorylase, glycogen; muscle (McArdle syn |
| 2.31 | C13orf18 | chromosome 13 open reading frame 18 |
| 2.31 | — | — |
| -2.30 | D21S2088E | D21S2088E |
| -2.30 | RAPGEF2 | Rap guanine nucleotide exchange factor (GEF |
| -2.30 | EPHX1 | epoxide hydrolase 1, microsomal (xenobiotic) |
| -2.30 | MNS1 | meiosis-specific nuclear structural 1 |
| 2.30 | — | — |
| -2.30 | CNTNAP2 | contactin associated protein-like 2 |
| 2.30 | VAPB | VAMP (vesicle-associated membrane protein)- |
| -2.30 | RASIP1 | Ras interacting protein 1 |
| -2.30 | USP28 | ubiquitin specific peptidase 28 |
| -2.30 | — | — |
| 2.30 | OXR1 | oxidation resistance 1 |
| 2.30 | KLF3 | Kruppel-like factor 3 (basic) |
| 2.30 | EFNB3 | ephrin-B3 |
| -2.30 | UTS2 | urotensin 2 |
| -2.30 | CGN | cingulin |
| 2.30 | BEX1 | brain expressed, X-linked 1 |
| 2.29 | PAK3 | P21 (CDKN1A)-activated kinase 3 |
| -2.29 | — | — |
| -2.29 | HIST1H4K /// HIST1 | histone cluster 1, H4k /// histone cluster 1, H4j |
| 2.29 | TTC28 | tetratricopeptide repeat domain 28 |
| -2.29 | LBH | limb bud and heart development homolog (mou |
| 2.29 | DCX | doublecortex; lissencephaly, X-linked (doublec |
| 2.29 | DDHD2 | DDHD domain containing 2 |

Appendix 1

| | | | |
|---|---|---|---|
| 2.28 ZNF439 | zinc finger protein 439 | -2.29 MCAM | melanoma cell adhesion molecule |
| -2.28 — | — | -2.29 KCNQ1 | potassium voltage-gated channel, KQT-like sub |
| 2.28 — | — | -2.29 TTC9 | tetratricopeptide repeat domain 9 |
| 2.28 LOC442367 | Hypothetical LOC442367 | 2.29 C10orf58 | chromosome 10 open reading frame 58 |
| 2.28 — | — | 2.29 MGC21644 | Hypothetical protein MGC21644 |
| 2.28 SMO | smoothened homolog (Drosophila) | 2.29 DKFZp313A2432 | hypothetical protein DKFZp313A2432 |
| 2.28 — | — | 2.29 RAB7L1 | RAB7, member RAS oncogene family-like 1 |
| 2.28 MLR1 | transcription factor MLR1 | 2.28 SYTL2 | synaptotagmin-like 2 |
| 2.28 MGC39900 | hypothetical protein MGC39900 | 2.28 — | — |
| 2.28 RALGDS | ral guanine nucleotide dissociation stimulator | -2.28 UGP2 | UDP-glucose pyrophosphorylase 2 |
| 2.28 COPB2 | Coatomer protein complex, subunit beta 2 (bet | -2.28 — | Mesenchymal stem cell protein DSC96 |
| 2.28 — | — | -2.28 — | Transcribed locus, moderately similar to XP_5 |
| 2.28 FAM89B | family with sequence similarity 89, member B | 2.28 TTC23 | tetratricopeptide repeat domain 23 |
| 2.27 CLCN4 | chloride channel 4 | -2.28 LOC147650 | hypothetical protein LOC147650 |
| 2.27 LATS2 | LATS, large tumor suppressor, homolog 2 (Dro | -2.28 SEMA6B | sema domain, transmembrane domain (TM), a |
| -2.27 LOC728215 /// LOC | similar to transmembrane protein 28 /// similar | 2.28 — | — |
| -2.27 PIK3CB | phosphoinositide-3-kinase, catalytic, beta poly | 2.28 MTX1 | Metaxin 1 |
| 2.27 HOXA4 | homeobox A4 | 2.28 SC65 | synaptonemal complex protein SC65 |
| -2.27 METTL7A | methyltransferase like 7A | -2.28 — | — |
| -2.27 WARS | tryptophanyl-tRNA synthetase | 2.28 MSRB2 | methionine sulfoxide reductase B2 |
| -2.27 CA4 | carbonic anhydrase IV | -2.28 APLP2 | amyloid beta (A4) precursor-like protein 2 |
| 2.27 RNASEL | ribonuclease L (2',5'-oligoisoadenylate synthet | -2.28 — | — |
| 2.27 MGC39900 | hypothetical protein MGC39900 | -2.28 NR2F6 | nuclear receptor subfamily 2, group F, member |
| -2.27 LHFPL2 | lipoma HMGIC fusion partner-like 2 | -2.28 DCP2 | DCP2 decapping enzyme homolog (S. cerevisi |
| -2.27 OLFM1 | olfactomedin 1 | 2.28 — | — |
| 2.27 PAX3 | Paired box gene 3 (Waardenburg syndrome 1) | 2.27 PDE4D | phosphodiesterase 4D, cAMP-specific (phosph |
| -2.27 FAM91A2 | family with sequence similarity 91, member A2 | 2.27 — | CDNA FLJ31066 fis, clone HSYRA2001153 |
| -2.27 GCNT2 /// SPTLC3 | glucosaminyl (N-acetyl) transferase 2, I-branch | 2.27 — | — |
| 2.27 CENTD1 | centaurin, delta 1 | 2.27 GPR161 | G protein-coupled receptor 161 |
| -2.27 SH3KBP1 | SH3-domain kinase binding protein 1 | -2.27 MDN1 | MDN1, midasin homolog (yeast) |
| -2.27 LOC283454 | hypothetical protein LOC283454 | 2.27 — | — |
| 2.26 SNCA | synuclein, alpha (non A4 component of amyloi | 2.27 KIAA1377 | KIAA1377 |
| -2.26 — | Clone IMAGE:121687 mRNA sequence | 2.27 — | — |
| 2.26 PHF10 | PHD finger protein 10 | 2.27 PAM | peptidylglycine alpha-amidating monooxygena |
| 2.26 SYT13 | synaptotagmin XIII | -2.27 — | — |
| 2.26 CYP2U1 | cytochrome P450, family 2, subfamily U, polyp | 2.27 XPA | xeroderma pigmentosum, complementation gr |
| 2.26 RHOBTB3 | Rho-related BTB domain containing 3 | -2.27 PRIM2A | primase, polypeptide 2A, 58kDa |
| -2.26 ARRB1 | arrestin, beta 1 | -2.27 GAS7 | growth arrest-specific 7 |
| 2.26 TTC28 | tetratricopeptide repeat domain 28 | 2.27 — | — |
| 2.26 HHIP | hedgehog interacting protein | 2.27 — | CDNA FLJ36544 fis, clone TRACH2006378 |
| -2.26 — | — | -2.27 MRPL52 | mitochondrial ribosomal protein L52 |
| -2.26 EGLN3 | egl nine homolog 3 (C. elegans) | -2.27 NDUFA1 | NADH dehydrogenase (ubiquinone) 1 alpha su |
| -2.26 ERBB3 | v-erb-b2 erythroblastic leukemia viral oncogen | -2.27 ZNF347 | zinc finger protein 347 |
| 2.26 DDR1 | discoidin domain receptor family, member 1 | 2.27 — | CDNA clone IMAGE:4791887 /// MRNA; cDNA |
| -2.26 SNRPN /// SNURF | small nuclear ribonucleoprotein polypeptide N | -2.27 WDR1 | WD repeat domain 1 |
| -2.26 CXCL1 | chemokine (C-X-C motif) ligand 1 (melanoma g | -2.27 ETS1 | v-ets erythroblastosis virus E26 oncogene hom |
| 2.26 — | | 2.27 CDC42 | cell division cycle 42 (GTP binding protein, 25K |
| 2.26 CYP4V2 | cytochrome P450, family 4, subfamily V, polyp | 2.27 ZNF584 | zinc finger protein 584 |
| 2.26 DHFRL1 | dihydrofolate reductase-like 1 | 2.27 — | — |
| -2.26 SAV1 | salvador homolog 1 (Drosophila) | 2.27 C11orf41 | chromosome 11 open reading frame 41 |
| 2.26 LIG4 | ligase IV, DNA, ATP-dependent | 2.27 DCLRE1C | DNA cross-link repair 1C (PSO2 homolog, S. c |
| 2.26 FYN | FYN oncogene related to SRC, FGR, YES | -2.26 ATXN1 | ataxin 1 |
| 2.26 SPAG9 | sperm associated antigen 9 | -2.26 SPAG4 | sperm associated antigen 4 |
| -2.25 SPRY4 | sprouty homolog 4 (Drosophila) | 2.26 — | — |
| -2.25 PINK1 | PTEN induced putative kinase 1 | -2.26 ITM2C | integral membrane protein 2C /// integral memb |
| 2.25 FARP1 | FERM, RhoGEF (ARHGEF) and pleckstrin dor | -2.26 — | — |
| 2.25 — | | 2.26 PB1 | polybromo 1 |
| 2.25 FOXB1 | forkhead box B1 | 2.26 — | — |
| -2.25 CTNND1 | catenin (cadherin-associated protein), delta 1 | 2.26 TSGA14 | testis specific, 14 |
| -2.25 XAGE1 /// LOC727 | X antigen family, member 1 /// similar to G anti | -2.26 CDYL | chromodomain protein, Y-like |
| 2.25 SEC31B | SEC31 homolog B (S. cerevisiae) | -2.26 ROD1 | ROD1 regulator of differentiation 1 (S. pombe) |
| 2.25 FLJ31485 | hypothetical gene supported by AK056047; AK | -2.26 ZNF609 | zinc finger protein 609 |
| 2.25 ASIP | Agouti signaling protein, nonagouti homolog (m | -2.26 FAM124A | family with sequence similarity 124A |
| -2.25 ZNF217 | zinc finger protein 217 | 2.26 ZNF336 | zinc finger protein 336 |
| -2.25 OLFML2A | olfactomedin-like 2A | 2.26 FARSLB | phenylalanine-tRNA synthetase-like, beta subu |
| 2.25 PLEKHB1 | pleckstrin homology domain containing, family | -2.26 LOC201895 | hypothetical protein LOC201895 |
| -2.25 RAB26 | RAB26, member RAS oncogene family | 2.26 TSGA10 | Testis specific, 10 |
| 2.25 ELAC1 | elaC homolog 1 (E. coli) | 2.26 LIPG | lipase, endothelial |
| 2.25 — | — | -2.26 — | — |
| -2.25 ALDH1A1 | aldehyde dehydrogenase 1 family, member A1 | -2.26 — | — |
| 2.25 — | Transcribed locus | 2.26 KIAA1715 | KIAA1715 |
| 2.25 — | — | 2.26 DUSP16 | Dual specificity phosphatase 16 |
| 2.25 IKZF1 | IKAROS family zinc finger 1 (Ikaros) | -2.26 SOX4 | SRY (sex determining region Y)-box 4 |
| 2.25 FRY | furry homolog (Drosophila) | -2.26 FGFR4 | fibroblast growth factor receptor 4 |
| 2.25 GLI2 | GLI-Kruppel family member GLI2 | -2.26 PINK1 | PTEN induced putative kinase 1 |
| 2.25 RHOBTB1 | Rho-related BTB domain containing 1 | 2.26 MAP1B | microtubule-associated protein 1B |
| 2.24 FILIP1L | filamin A interacting protein 1-like | -2.26 NEDD8 | neural precursor cell expressed, developmenta |
| 2.24 FZD3 | frizzled homolog 3 (Drosophila) | | |
| -2.24 COL4A3BP | Collagen, type IV, alpha 3 (Goodpasture antige | | |

Appendix 1

| | | | | |
|---|---|---|---|---|
| -2.24 | — | — | -2.25 | FOXO1A | forkhead box O1A (rhabdomyosarcoma) |
| -2.24 | RUNX1 | Runt-related transcription factor 1 (acute myelo | -2.25 | CBX7 | chromobox homolog 7 |
| -2.24 | SERPINF1 | serpin peptidase inhibitor, clade F (alpha-2 anti | 2.25 | KLHDC1 | kelch domain containing 1 |
| 2.24 | GPR153 | G protein-coupled receptor 153 | 2.25 | — | — |
| -2.24 | FGF12 | fibroblast growth factor 12 | 2.25 | — | — |
| 2.24 | — | — | 2.25 | RUFY3 | RUN and FYVE domain containing 3 |
| 2.24 | PTN | pleiotrophin (heparin binding growth factor 8, n | -2.25 | — | — |
| -2.24 | RBPMS | RNA binding protein with multiple splicing | 2.25 | SMYD2 | SET and MYND domain containing 2 |
| 2.24 | BAIAP2 | BAI1-associated protein 2 | 2.25 | FYN | FYN oncogene related to SRC, FGR, YES |
| -2.24 | TMEM63A | transmembrane protein 63A | -2.25 | PWCR1 | Prader-Willi syndrome chromosome region 1 |
| -2.24 | TRAPPC6A | trafficking protein particle complex 6A | 2.25 | RNF182 | ring finger protein 182 |
| -2.24 | FLJ20449 | hypothetical protein FLJ20449 | 2.25 | ST6GALNAC5 | ST6 (alpha-N-acetyl-neuraminyl-2,3-beta-galac |
| 2.24 | — | CDNA FLJ11489 fis, clone HEMBA1001915 | 2.25 | MGC45564 | GTPase activating Rap/RanGAP domain-like 1 |
| -2.24 | HSPA1A /// HSPA1 | heat shock 70kDa protein 1A /// heat shock 70 | 2.25 | — | — |
| -2.24 | CREM | cAMP responsive element modulator | -2.24 | — | Transcribed locus |
| 2.24 | PARD6G | par-6 partitioning defective 6 homolog gamma | 2.24 | MGC26733 | hypothetical protein MGC26733 |
| 2.24 | SLC6A8 /// SLC6A1 | solute carrier family 6 (neurotransmitter transpo | 2.24 | — | — |
| -2.24 | SMARCD3 | SWI/SNF related, matrix associated, actin dep | 2.24 | — | — |
| -2.23 | BNC2 | Basonuclin 2 | 2.24 | — | CDNA FLJ11653 fis, clone HEMBA1004538 |
| 2.23 | — | — | 2.24 | — | — |
| -2.23 | LOC730432 | similar to serine/threonine/tyrosine interacting | -2.24 | EPHA7 | EPH receptor A7 |
| -2.23 | DENND1C | DENN/MADD domain containing 1C | -2.24 | TMEM63A | transmembrane protein 63A |
| 2.23 | SLC44A5 | solute carrier family 44, member 5 | 2.24 | CDH2 | cadherin 2, type 1, N-cadherin (neuronal) |
| 2.23 | — | — | -2.24 | LHPP | phospholysine phosphohistidine inorganic pyro |
| 2.23 | SMYD2 | SET and MYND domain containing 2 | -2.24 | ETS2 | v-ets erythroblastosis virus E26 oncogene hom |
| -2.23 | CHES1 | checkpoint suppressor 1 | 2.24 | PTHB1 | parathyroid hormone-responsive B1 |
| 2.23 | MAPRE3 | microtubule-associated protein, RP/EB family, | 2.24 | CXXC4 | CXXC finger 4 |
| 2.23 | HIPK2 | Homeodomain interacting protein kinase 2 | -2.24 | WIPI1 | WD repeat domain, phosphoinositide interactin |
| 2.23 | — | MRNA; cDNA DKFZp686D0673 (from clone D | 2.24 | VASH1 | Vasohibin 1 |
| 2.23 | TMEM107 | transmembrane protein 107 /// transmembrane | -2.24 | NQO1 | NAD(P)H dehydrogenase, quinone 1 |
| -2.23 | PRB3 | proline-rich protein BstNI subfamily 3 | -2.24 | — | — |
| 2.23 | FLJ14503 | hypothetical protein FLJ14503 | 2.24 | DKFZp451J0118 | Taxilin alpha |
| 2.23 | IGSF9 | immunoglobulin superfamily, member 9 | -2.24 | AASS | aminoadipate-semialdehyde synthase |
| -2.23 | UTX | ubiquitously transcribed tetratricopeptide repea | -2.24 | — | Transcribed locus |
| 2.23 | — | CDNA FLJ37494 fis, clone BRAWH2015385 | 2.24 | EYA1 | eyes absent homolog 1 (Drosophila) |
| 2.23 | C18orf8 | Chromosome 18 open reading frame 8 | 2.24 | — | — |
| 2.23 | — | — | -2.23 | RTKN | rhotekin |
| 2.23 | HOXB2 | homeobox B2 | -2.23 | GADD45B | growth arrest and DNA-damage-inducible, beta |
| -2.22 | FOXO1A | forkhead box O1A (rhabdomyosarcoma) | -2.23 | APOC4 | apolipoprotein C-IV |
| 2.22 | B3GALNT1 | beta-1,3-N-acetylgalactosaminyltransferase 1 | -2.23 | CYB561 | cytochrome b-561 |
| 2.22 | TUB | tubby homolog (mouse) | -2.23 | — | — |
| 2.22 | MAPK11 | mitogen-activated protein kinase 11 | 2.23 | — | — |
| -2.22 | LOC153222 | adult retina protein | 2.23 | RBM14 | RNA binding motif protein 14 |
| -2.22 | UST | uronyl-2-sulfotransferase | 2.23 | EXOC3 | exocyst complex component 3 |
| -2.22 | MYO5B | myosin VB | 2.23 | DBNDD2 | Dysbindin (dystrobrevin binding protein 1) dom |
| -2.22 | — | — | -2.23 | WDHD1 | WD repeat and HMG-box DNA binding protein |
| -2.22 | ANG /// RNASE4 | angiogenin, ribonuclease, RNase A family, 5 /// | -2.23 | — | — |
| 2.22 | KIAA1545 | KIAA1545 protein | 2.23 | PHC2 | Polyhomeotic homolog 2 (Drosophila) |
| 2.22 | SCHIP1 | schwannomin interacting protein 1 | 2.23 | MBNL2 | Muscleblind-like 2 (Drosophila) |
| -2.22 | VANGL1 | vang-like 1 (van gogh, Drosophila) | 2.23 | SERHL2 | Serine hydrolase-like 2 |
| -2.22 | LOC284242 | hypothetical protein LOC284242 | 2.23 | PAOX | polyamine oxidase (exo-N4-amino) |
| 2.22 | TBC1D8 | TBC1 domain family, member 8 (with GRAM d | -2.23 | LLGL2 | lethal giant larvae homolog 2 (Drosophila) |
| 2.22 | — | — | 2.23 | — | CDNA FLJ30026 fis, clone 3NB692001123 |
| 2.22 | PAOX | polyamine oxidase (exo-N4-amino) | -2.23 | SNX5 | Sorting nexin 5 |
| 2.22 | POLH | polymerase (DNA directed), eta | 2.23 | IKZF1 | IKAROS family zinc finger 1 (Ikaros) |
| 2.22 | — | — | -2.23 | EPS8L1 | EPS8-like 1 |
| 2.21 | FARP1 | FERM, RhoGEF (ARHGEF) and pleckstrin dom | -2.23 | CHES1 | checkpoint suppressor 1 |
| 2.21 | — | Similar to lymphocyte-specific protein 1 | 2.23 | CREM | cAMP responsive element modulator |
| 2.21 | PTN | pleiotrophin (heparin binding growth factor 8, n | -2.22 | ZBTB3 | zinc finger and BTB domain containing 3 |
| 2.21 | BBS5 | Bardet-Biedl syndrome 5 | 2.22 | — | — |
| 2.21 | — | — | -2.22 | ICAM3 | intercellular adhesion molecule 3 |
| -2.21 | GSTZ1 | glutathione transferase zeta 1 (maleylacetoace | 2.22 | LRIG1 | leucine-rich repeats and immunoglobulin-like d |
| 2.21 | MEGF10 | multiple EGF-like-domains 10 | 2.22 | C6orf48 | chromosome 6 open reading frame 48 |
| 2.21 | — | Transcribed locus, weakly similar to XP_49845 | 2.22 | CDW92 | Solute carrier family 44, member 1 |
| -2.21 | NPM3 | nucleophosmin/nucleoplasmin, 3 | -2.22 | BCL11A | B-cell CLL/lymphoma 11A (zinc finger protein) |
| 2.21 | IGSF4 | Immunoglobulin superfamily, member 4 | -2.22 | NEDD4L | neural precursor cell expressed, developmenta |
| 2.21 | AP3M1 | adaptor-related protein complex 3, mu 1 subun | -2.22 | ACMSD | Aminocarboxymuconate semialdehyde decarb |
| -2.21 | IGFBP4 | insulin-like growth factor binding protein 4 | -2.22 | SH3D19 | SH3 domain protein D19 |
| 2.21 | — | Transcribed locus | -2.22 | C1orf85 | Chromosome 1 open reading frame 85 |
| 2.21 | — | — | -2.22 | C12orf28 | chromosome 12 open reading frame 28 |
| 2.21 | — | MRNA; cDNA DKFZp667B0924 (from clone D | 2.22 | ALS2CR16 | amyotrophic lateral sclerosis 2 (juvenile) chrom |
| -2.21 | FLJ32942 | hypothetical protein FLJ32942 | 2.22 | APCDD1 | adenomatosis polyposis coli down-regulated 1 |
| 2.21 | — | — | 2.22 | FLJ42709 | hypothetical gene supported by AK124699 |
| 2.21 | CD47 | CD47 molecule /// CD47 molecule | -2.22 | — | — |
| -2.21 | GLS | glutaminase | 2.22 | — | — |
| 2.21 | HGSNAT | heparan-alpha-glucosaminide N-acetyltransfer | 2.22 | FHL1 | four and a half LIM domains 1 |
| -2.21 | TUBA1 | tubulin, alpha 1 | 2.22 | FRY | furry homolog (Drosophila) |
| -2.21 | SIRT4 | sirtuin (silent mating type information regulatio | 2.22 | RGL1 | ral guanine nucleotide dissociation stimulator-li |
| 2.21 | — | — | -2.21 | RRAS2 | related RAS viral (r-ras) oncogene homolog 2 |

Appendix 1

| Value | Gene | Description |
|---|---|---|
| -2.20 | CSMD2 | CUB and Sushi multiple domains 2 |
| 2.20 | DNAH14 /// LOC121 | dynein, axonemal, heavy chain 14 /// hypotheti |
| 2.20 | IRAK1BP1 | Interleukin-1 receptor-associated kinase 1 bind |
| 2.20 | DBNDD2 | Dysbindin (dystrobrevin binding protein 1) dom |
| -2.20 | C5orf4 | chromosome 5 open reading frame 4 |
| 2.20 | FLJ31951 | Hypothetical protein FLJ31951 |
| -2.20 | ENPP1 | ectonucleotide pyrophosphatase/phosphodiest |
| -2.20 | SIRT1 | sirtuin (silent mating type information regulatio |
| 2.20 | — | — |
| 2.20 | — | — |
| 2.20 | — | Transcribed locus |
| -2.20 | — | — |
| -2.20 | — | — |
| -2.20 | OLFM2 | olfactomedin 2 |
| -2.20 | NFIA | nuclear factor I/A |
| -2.20 | FER1L3 | fer-1-like 3, myoferlin (C. elegans) |
| 2.20 | QTRTD1 | Queuine tRNA-ribosyltransferase domain conta |
| 2.20 | PHF14 | PHD finger protein 14 |
| 2.20 | FLRT3 | fibronectin leucine rich transmembrane protein |
| -2.20 | — | — |
| -2.20 | BNC2 | basonuclin 2 |
| -2.20 | ZSCAN2 | zinc finger and SCAN domain containing 2 |
| 2.20 | PAK3 | p21 (CDKN1A)-activated kinase 3 |
| -2.20 | ZNF483 | Zinc finger protein 483 |
| 2.20 | — | — |
| 2.20 | — | — |
| -2.19 | C9orf52 | Chromosome 9 open reading frame 52 |
| 2.19 | STS | steroid sulfatase (microsomal), arylsulfatase C |
| -2.19 | KCNK6 | potassium channel, subfamily K, member 6 |
| 2.19 | — | — |
| 2.19 | C11orf31 | chromosome 11 open reading frame 31 |
| -2.19 | ANPEP | alanyl (membrane) aminopeptidase (aminopep |
| 2.19 | — | — |
| 2.19 | — | — |
| -2.19 | MGC24665 | hypothetical protein MGC24665 |
| 2.19 | — | — |
| 2.19 | HP1BP3 | heterochromatin protein 1, binding protein 3 |
| 2.19 | GPM6B | glycoprotein M6B |
| 2.19 | C15orf38 | Chromosome 15 open reading frame 38 |
| -2.19 | — | — |
| -2.19 | NBL1 | neuroblastoma, suppression of tumorigenicity |
| -2.19 | AMY1A /// SSBP1 | amylase, alpha 1A; salivary /// single-stranded |
| 2.19 | GLRB | glycine receptor, beta |
| 2.19 | — | — |
| 2.19 | MSRB2 | methionine sulfoxide reductase B2 |
| 2.19 | WDR78 /// SLC35D | WD repeat domain 78 /// Solute carrier family 3 |
| 2.19 | CALML3 | calmodulin-like 3 |
| 2.19 | DST | Dystonin |
| 2.19 | CRLS1 | Cardiolipin synthase 1 |
| 2.19 | PCAF | p300/CBP-associated factor |
| 2.19 | ELAVL2 | ELAV (embryonic lethal, abnormal vision, Dros |
| -2.18 | PCOLCE | procollagen C-endopeptidase enhancer |
| 2.18 | — | — |
| -2.18 | SLC7A3 | solute carrier family 7 (cationic amino acid tran |
| 2.18 | FUS | fusion (involved in t(12;16) in malignant liposar |
| 2.18 | NEUROG1 | neurogenin 1 |
| 2.18 | OPA3 | optic atrophy 3 (autosomal recessive, with chor |
| 2.18 | NEDD9 | neural precursor cell expressed, developmenta |
| -2.18 | PTRF | polymerase I and transcript release factor |
| -2.18 | STARD8 | START domain containing 8 |
| -2.18 | RASGRF2 | Ras protein-specific guanine nucleotide-releasi |
| 2.18 | CCDC99 | Coiled-coil domain containing 99 |
| 2.18 | — | — |
| 2.18 | PKIA | protein kinase (cAMP-dependent, catalytic) inh |
| -2.18 | SEPHS1 | selenophosphate synthetase 1 |
| -2.18 | MBP | myelin basic protein |
| -2.18 | HLA-B | major histocompatibility complex, class I, B /// |
| -2.18 | SH2B3 | SH2B adaptor protein 3 |
| 2.18 | HIPK2 | Homeodomain interacting protein kinase 2 |
| -2.18 | — | PTR2 mRNA for repetitive sequence |
| 2.18 | — | Transcribed locus |
| 2.18 | BRSK2 | BR serine/threonine kinase 2 |
| 2.18 | DTX4 | deltex 4 homolog (Drosophila) |
| 2.18 | CNKSR2 | connector enhancer of kinase suppressor of Ra |
| -2.17 | FAM121A | family with sequence similarity 121A |
| 2.17 | FLJ42709 | Hypothetical gene supported by AK124699 |
| 2.17 | TFDP2 | transcription factor Dp-2 (E2F dimerization par |
| -2.17 | C7orf34 | chromosome 7 open reading frame 34 |
| 2.17 | AUTS2 | Autism susceptibility candidate 2 |
| -2.21 | — | — |
| -2.21 | FA2H | fatty acid 2-hydroxylase |
| 2.21 | ARSB | arylsulfatase B |
| 2.21 | — | CDNA clone IMAGE:5288594 |
| -2.21 | WEE1 | WEE1 homolog (S. pombe) |
| -2.21 | — | — |
| 2.21 | TLR4 | toll-like receptor 4 /// toll-like receptor 4 |
| 2.21 | DLL1 | delta-like 1 (Drosophila) |
| 2.21 | ZNF585A | zinc finger protein 585A |
| 2.21 | — | — |
| 2.21 | C11orf57 | Chromosome 11 open reading frame 57 |
| 2.21 | — | — |
| 2.21 | EFCAB2 | EF-hand calcium binding domain 2 |
| -2.20 | ARFGEF1 | ADP-ribosylation factor guanine nucleotide-exc |
| 2.20 | KIF7 | kinesin family member 7 |
| 2.20 | MDSRP | myelodysplastic syndromes relative |
| -2.20 | — | CDNA FLJ29007 fis, clone STM04662, highly s |
| 2.20 | CELSR2 | cadherin, EGF LAG seven-pass G-type recepto |
| -2.20 | KCNK5 | Potassium channel, subfamily K, member 5 |
| 2.20 | — | — |
| 2.20 | — | — |
| -2.20 | SAV1 | salvador homolog 1 (Drosophila) |
| 2.20 | MAP2K5 | mitogen-activated protein kinase kinase 5 |
| 2.20 | DDR1 | discoidin domain receptor family, member 1 |
| 2.20 | LOC92312 | Hypothetical protein LOC92312 |
| 2.20 | RAB32 | RAB32, member RAS oncogene family |
| 2.20 | — | Transcribed locus |
| 2.20 | PCGF5 | polycomb group ring finger 5 |
| 2.20 | — | — |
| 2.20 | — | — |
| 2.20 | HERPUD1 | homocysteine-inducible, endoplasmic reticulum |
| 2.20 | NHSL1 | NHS-like 1 |
| 2.19 | DCX | doublecortex; lissencephaly, X-linked (doublec |
| -2.19 | NFATC3 | Nuclear factor of activated T-cells, cytoplasmic |
| 2.19 | — | MRNA; cDNA DKFZp667E0114 (from clone D |
| 2.19 | — | — |
| 2.19 | RPS23 | ribosomal protein S23 |
| 2.19 | FARP1 | FERM, RhoGEF (ARHGEF) and pleckstrin dor |
| 2.19 | SLCO3A1 | Solute carrier organic anion transporter family, |
| -2.19 | NBL1 | neuroblastoma, suppression of tumorigenicity |
| 2.19 | — | Transcribed locus |
| 2.19 | — | Clone FLB8310 PRO2225 |
| 2.19 | PITPNC1 | phosphatidylinositol transfer protein, cytoplasm |
| -2.19 | TLE1 | transducin-like enhancer of split 1 (E(sp1) hom |
| -2.19 | MYD88 | myeloid differentiation primary response gene |
| -2.18 | SLC43A1 | solute carrier family 43, member 1 |
| 2.18 | — | — |
| -2.18 | C14orf112 | chromosome 14 open reading frame 112 |
| -2.18 | — | MRNA; cDNA DKFZp686H1629 (from clone D |
| -2.18 | CAPN1 | calpain 1, (mu/I) large subunit |
| 2.18 | — | — |
| 2.18 | CELSR1 | cadherin, EGF LAG seven-pass G-type recepto |
| 2.18 | KPNB1 | Karyopherin (importin) beta 1 |
| 2.18 | RASA4 | RAS p21 protein activator 4 |
| 2.18 | — | — |
| -2.18 | CD44 | CD44 molecule (Indian blood group) |
| 2.18 | KIAA0562 | KIAA0562 |
| 2.18 | COTL1 | coactosin-like 1 (Dictyostelium) |
| -2.18 | ERO1L | ERO1-like (S. cerevisiae) |
| 2.18 | MYLK | myosin, light chain kinase /// myosin, light chai |
| -2.18 | CD164 | CD164 molecule, sialomucin |
| -2.18 | TRAF1 | TNF receptor-associated factor 1 |
| 2.18 | GRIA3 | glutamate receptor, ionotrophic, AMPA 3 |
| 2.18 | SHC3 | SHC (Src homology 2 domain containing) trans |
| 2.18 | FLJ32745 | hypothetical protein FLJ32745 |
| -2.18 | SLC9A3R2 | solute carrier family 9 (sodium/hydrogen excha |
| 2.18 | — | Transcribed locus |
| 2.17 | GKAP1 | G kinase anchoring protein 1 |
| -2.17 | LOC400713 | zinc finger-like |
| -2.17 | HSPA1B | heat shock 70kDa protein 1B |
| 2.17 | PDLIM4 | PDZ and LIM domain 4 |
| 2.17 | — | CDNA clone IMAGE:4797645 |
| 2.17 | IQCE | IQ motif containing E |
| -2.17 | PAWR | PRKC, apoptosis, WT1, regulator |
| -2.17 | — | Transcribed locus |
| 2.17 | TTL | tubulin tyrosine ligase |
| 2.17 | CCDC52 | coiled-coil domain containing 52 |
| 2.17 | SNRPE | small nuclear ribonucleoprotein polypeptide E |
| -2.17 | ZNF483 | Zinc finger protein 483 |

Appendix 1

| | | | |
|---|---|---|---|
| 2.17 | SMYD2 | SET and MYND domain containing 2 | |
| 2.17 | CDO1 | cysteine dioxygenase, type | |
| -2.17 | MGC20983 | hypothetical protein MGC20983 | |
| 2.17 | ZNF346 | Zinc finger protein 346 | |
| -2.17 | CD40 | CD40 molecule, TNF receptor superfamily mer | |
| -2.17 | FGFR4 | fibroblast growth factor receptor 4 | |
| -2.17 | ULK4 | Unc-51-like kinase 4 (C. elegans) | |
| 2.17 | — | — | |
| 2.17 | — | — | |
| 2.17 | PPIL6 | peptidylprolyl isomerase (cyclophilin)-like 6 | |
| 2.17 | — | — | |
| -2.17 | APOBEC3G | apolipoprotein B mRNA editing enzyme, cataly | |
| 2.17 | EPHB2 | EPH receptor B2 | |
| 2.17 | WIPF1 | WAS/WASL interacting protein family, member | |
| 2.17 | PLXNA3 | plexin A3 | |
| 2.17 | AOF1 | amine oxidase (flavin containing) domain 1 | |
| -2.17 | LOC201895 | Hypothetical protein LOC201895 | |
| 2.17 | — | Transcribed locus | |
| 2.16 | THSD7A | thrombospondin, type I, domain containing 7A | |
| 2.16 | LOC113386 | similar to envelope protein | |
| 2.16 | BAIAP2 | BAI1-associated protein 2 | |
| 2.16 | — | — | |
| 2.16 | — | — | |
| 2.16 | — | — | |
| 2.16 | MOXD1 | monooxygenase, DBH-like 1 | |
| -2.16 | ZIC2 | Zic family member 2 (odd-paired homolog, Dro | |
| -2.16 | WDHD1 | WD repeat and HMG-box DNA binding protein | |
| -2.16 | CXCL5 | chemokine (C-X-C motif) ligand 5 | |
| 2.16 | — | CDNA clone IMAGE:5263177 | |
| -2.16 | SPRY1 | sprouty homolog 1, antagonist of FGF signaling | |
| -2.16 | USP28 | ubiquitin specific peptidase 28 | |
| 2.16 | — | MRNA; cDNA DKFZp761L1121 (from clone DK | |
| 2.16 | LDOC1L | leucine zipper, down-regulated in cancer 1-like | |
| 2.16 | PPP1R3C | protein phosphatase 1, regulatory (inhibitor) su | |
| 2.16 | FYN | FYN oncogene related to SRC, FGR, YES | |
| 2.15 | DOK6 | docking protein 6 | |
| 2.15 | DDR1 | discoidin domain receptor family, member 1 | |
| 2.15 | CAB39L | Calcium binding protein 39-like | |
| 2.15 | WASF3 | WAS protein family, member 3 | |
| 2.15 | SGEF | Src homology 3 domain-containing guanine nu | |
| -2.15 | FAM100A | family with sequence similarity 100, member A | |
| -2.15 | HLA-DRB1 /// HLA-I | major histocompatibility complex, class II, DR b | |
| 2.15 | PAG1 | phosphoprotein associated with glycosphingoli | |
| 2.15 | ENDOGL1 | endonuclease G-like 1 | |
| 2.15 | — | CDNA FLJ34585 fis, clone KIDNE2008758 | |
| 2.15 | GNG2 | guanine nucleotide binding protein (G protein), | |
| 2.15 | ST3GAL5 | ST3 beta-galactoside alpha-2,3-sialyltransferas | |
| -2.15 | SETD3 | SET domain containing 3 | |
| -2.15 | ROR1 | Receptor tyrosine kinase-like orphan receptor | |
| 2.15 | DLL3 | delta-like 3 (Drosophila) | |
| 2.15 | PITPNC1 | phosphatidylinositol transfer protein, cytoplasm | |
| 2.15 | CDH2 | cadherin 2, type 1, N-cadherin (neuronal) | |
| 2.15 | TEX261 | testis expressed sequence 261 | |
| -2.15 | EDG8 | endothelial differentiation, sphingolipid G-prote | |
| 2.15 | NRIP1 | nuclear receptor interacting protein 1 | |
| -2.15 | FER1L3 | fer-1-like 3, myoferlin (C. elegans) | |
| 2.15 | NRCAM | Neuronal cell adhesion molecule | |
| -2.15 | JAZF1 | JAZF zinc finger 1 | |
| -2.15 | KLHL24 | kelch-like 24 (Drosophila) | |
| 2.15 | ZNRF3 | zinc and ring finger 3 | |
| 2.14 | — | Transcribed locus | |
| -2.14 | CHURC1 | churchill domain containing 1 | |
| 2.14 | CA3 | carbonic anhydrase III, muscle specific | |
| 2.14 | — | Transcribed locus, moderately similar to NP_00 | |
| 2.14 | ANKRD13B | ankyrin repeat domain 13B | |
| 2.14 | — | Transcribed locus | |
| -2.14 | HLA-B | major histocompatibility complex, class I, B | |
| 2.14 | — | — | |
| 2.14 | — | Transcribed locus | |
| 2.14 | SHC3 | SHC (Src homology 2 domain containing) trans | |
| 2.14 | MYST3 | MYST histone acetyltransferase (monocytic leu | |
| -2.14 | PINK1 | PTEN induced putative kinase 1 | |
| 2.14 | RUFY3 | RUN and FYVE domain containing 3 | |
| 2.14 | — | CDNA clone IMAGE:4842353 | |
| 2.13 | UBE2J1 | ubiquitin-conjugating enzyme E2, J1 (UBC6 ho | |
| -2.13 | — | — | |
| 2.13 | — | — | |
| 2.13 | — | — | |
| 2.13 | — | — | |
| 2.17 | CD47 | CD47 molecule | |
| 2.17 | TBC1D8 | TBC1 domain family, member 8 (with GRAM d | |
| -2.17 | ELF3 | E74-like factor 3 (ets domain transcription facto | |
| -2.17 | LOC389440 | hypothetical LOC389440 | |
| 2.17 | FLJ31818 | hypothetical protein FLJ31818 | |
| 2.17 | TMEM178 | transmembrane protein 178 | |
| -2.17 | — | — | |
| 2.17 | — | CDNA clone IMAGE:4831311 | |
| 2.17 | — | — | |
| 2.17 | LOC730069 /// LOC | similar to nuclear receptor binding factor 2 /// si | |
| -2.17 | RABGAP1L | RAB GTPase activating protein 1-like | |
| 2.17 | DZIP1 | DAZ interacting protein 1 | |
| -2.17 | ATCAY | ataxia, cerebellar, Cayman type (caytaxin) | |
| -2.17 | CTTN | cortactin | |
| 2.17 | TFDP2 | transcription factor Dp-2 (E2F dimerization par | |
| 2.17 | CXXC4 | CXXC finger 4 | |
| -2.17 | ESRRG | estrogen-related receptor gamma | |
| -2.17 | GAD1 /// LASS6 | glutamate decarboxylase 1 (brain, 67kDa) /// L | |
| 2.17 | SLC44A5 | solute carrier family 44, member 5 | |
| -2.17 | DUSP10 | dual specificity phosphatase 10 | |
| 2.17 | FILIP1L | filamin A interacting protein 1-like | |
| -2.16 | VIL2 | villin 2 (ezrin) | |
| -2.16 | — | — | |
| 2.16 | MGC26690 | Hypothetical protein MGC26690 | |
| -2.16 | NUDT21 | nudix (nucleoside diphosphate linked moiety X) | |
| 2.16 | — | Clone IMAGE:26186, mRNA sequence | |
| 2.16 | IKZF4 | IKAROS family zinc finger 4 (Eos) | |
| 2.16 | — | — | |
| -2.16 | C14orf156 | chromosome 14 open reading frame 156 /// chr | |
| -2.16 | FAM124A | Family with sequence similarity 124A | |
| -2.16 | FOS | v-fos FBJ murine osteosarcoma viral oncogene | |
| -2.16 | MATN2 | matrilin 2 | |
| 2.16 | — | — | |
| -2.16 | CDKN3 | cyclin-dependent kinase inhibitor 3 (CDK2-asso | |
| -2.16 | — | — | |
| -2.16 | HERC5 | hect domain and RLD 5 | |
| -2.16 | C1orf88 | chromosome 1 open reading frame 88 | |
| 2.16 | — | — | |
| -2.16 | RASEF | RAS and EF-hand domain containing | |
| -2.16 | LOC727918 | Hypothetical protein LOC727918 | |
| 2.16 | MAPK11 | mitogen-activated protein kinase 11 | |
| 2.16 | CYP7B1 | cytochrome P450, family 7, subfamily B, polype | |
| 2.16 | VIM | vimentin | |
| -2.16 | USP32 | ubiquitin specific peptidase 32 /// ubiquitin spec | |
| -2.16 | PMS2L11 | postmeiotic segregation increased 2-like 11 | |
| -2.16 | — | — | |
| -2.16 | MYCBP | c-myc binding protein | |
| 2.16 | LRRC49 | leucine rich repeat containing 49 | |
| -2.15 | CUL4A | Cullin 4A | |
| 2.15 | TMEM65 | transmembrane protein 65 | |
| 2.15 | PSMC2 | Proteasome (prosome, macropain) 26S subuni | |
| -2.15 | TRIB1 | tribbles homolog 1 (Drosophila) | |
| 2.15 | INSM1 | insulinoma-associated 1 | |
| 2.15 | DKK3 | dickkopf homolog 3 (Xenopus laevis) | |
| -2.15 | NDUFB7 | NADH dehydrogenase (ubiquinone) 1 beta sub | |
| -2.15 | PELI2 | pellino homolog 2 (Drosophila) | |
| -2.15 | SIX4 | sine oculis homeobox homolog 4 (Drosophila) | |
| 2.15 | — | — | |
| 2.15 | — | — | |
| 2.15 | TMEM17 | transmembrane protein 17 | |
| 2.15 | GNE | glucosamine (UDP-N-acetyl)-2-epimerase/N-ac | |
| -2.15 | TRAPPC6A | trafficking protein particle complex 6A | |
| 2.15 | ABHD12 | abhydrolase domain containing 12 | |
| -2.15 | SYN2 | synapsin II | |
| -2.15 | PLEKHC1 | pleckstrin homology domain containing, family | |
| -2.15 | CREB3L4 | cAMP responsive element binding protein 3-lik | |
| -2.15 | TRIM38 | tripartite motif-containing 38 | |
| 2.15 | BTN3A3 | butyrophilin, subfamily 3, member A3 | |
| 2.15 | ST8SIA1 | ST8 alpha-N-acetyl-neuraminide alpha-2,8-sial | |
| 2.15 | FLJ22028 | hypothetical protein FLJ22028 | |
| 2.15 | TRIM2 | tripartite motif-containing 2 | |
| -2.15 | DGKA /// BCDO2 | diacylglycerol kinase, alpha 80kDa /// beta-caro | |
| -2.15 | IGSF1 | immunoglobulin superfamily, member 1 | |
| 2.15 | KIAA1641 | KIAA1641 | |
| 2.15 | — | Full length insert cDNA clone ZD78G02 | |
| 2.15 | DDR1 | discoidin domain receptor family, member 1 | |
| -2.14 | HHLA3 | HERV-H LTR-associating 3 | |
| -2.14 | TBC1D14 | TBC1 domain family, member 14 | |
| 2.14 | JAG1 | Jagged 1 (Alagille syndrome) | |

Appendix 1

| | | | | |
|---|---|---|---|---|
| 2.13 NUCB2 | nucleobindin 2 | | 2.14 TMEM2 | transmembrane protein 2 |
| -2.13 — | — | | 2.14 PTER | phosphotriesterase related |
| 2.13 — | — | | -2.14 TMED10 | transmembrane emp24-like trafficking protein |
| -2.13 SAT1 | spermidine/spermine N1-acetyltransferase 1 | | -2.14 — | — |
| 2.13 MARCKS | myristoylated alanine-rich protein kinase C sub | | 2.14 — | — |
| -2.13 RNASE1 | ribonuclease, RNase A family, 1 (pancreatic) | | 2.14 ZNF333 | Zinc finger protein 333 |
| 2.13 RGMB | RGM domain family, member B | | 2.14 — | CDNA clone IMAGE:4817255 |
| 2.13 SDC1 | syndecan 1 | | 2.14 EGF | epidermal growth factor (beta-urogastrone) |
| 2.13 KIAA1702 | KIAA1702 protein | | -2.14 KCNK5 | potassium channel, subfamily K, member 5 |
| -2.12 LRRC16 | Leucine rich repeat containing 16 | | -2.14 TNFRSF8 | tumor necrosis factor receptor superfamily, me |
| 2.12 MAGED4 | melanoma antigen family D, 4 /// melanoma an | | -2.14 DMC1 | DMC1 dosage suppressor of mck1 homolog, m |
| 2.12 — | — | | 2.14 FLJ30851 | hypothetical LOC653140 |
| -2.12 — | — | | -2.14 MYO5B | myosin VB |
| 2.12 ST8SIA1 | ST8 alpha-N-acetyl-neuraminide alpha-2,8-sial | | -2.14 TBC1D22B | TBC1 domain family, member 22B |
| -2.12 HMHA1 | histocompatibility (minor) HA-1 | | 2.14 — | — |
| -2.12 — | — | | 2.14 — | — |
| 2.12 — | — | | 2.14 C10orf58 | Chromosome 10 open reading frame 58 |
| 2.12 STK17A | Serine/threonine kinase 17a (apoptosis-inducin | | -2.14 CCNA1 | cyclin A1 |
| -2.12 — | Homo sapiens, clone IMAGE:4179986 | | 2.14 — | — |
| 2.12 — | — | | -2.14 ZFYVE21 | zinc finger, FYVE domain containing 21 |
| 2.12 CKLFSF3 | chemokine-like factor superfamily 3 | | 2.14 ARHGAP6 | Rho GTPase activating protein 6 |
| 2.12 — | Full length insert cDNA YH77E09 | | 2.14 — | Transcribed locus |
| -2.12 SYNGR1 | synaptogyrin 1 | | 2.14 SLC1A6 | solute carrier family 1 (high affinity aspartate/gl |
| -2.12 — | Similar to hypothetical protein LOC284701 | | 2.14 NIN | ninein (GSK3B interacting protein) |
| -2.12 CASP10 | caspase 10, apoptosis-related cysteine peptida | | 2.14 — | — |
| 2.12 NBPF1 /// NBPF10 | neuroblastoma breakpoint family, member 1 /// | | 2.14 KIAA0644 | KIAA0644 gene product |
| 2.12 — | — | | 2.13 GNPDA2 | glucosamine-6-phosphate deaminase 2 |
| 2.12 — | — | | -2.13 TOMM22 | translocase of outer mitochondrial membrane 2 |
| 2.12 — | — | | -2.13 AFP | alpha-fetoprotein |
| 2.12 — | — | | 2.13 EIF5A2 | eukaryotic translation initiation factor 5A2 |
| 2.12 CDKN2C | cyclin-dependent kinase inhibitor 2C (p18, inhib | | 2.13 — | — |
| 2.12 TBRG4 | transforming growth factor beta regulator 4 /// t | | -2.13 — | Full-length cDNA clone CL0BB018ZE07 of Neu |
| 2.12 TP53AP1 | TP53 activated protein 1 | | -2.13 NPR1 | natriuretic peptide receptor A/guanylate cyclase |
| -2.11 RUNX1T1 | runt-related transcription factor 1; translocated | | 2.13 TBL2 | transducin (beta)-like 2 |
| -2.11 DSP | Desmoplakin | | 2.13 ZBTB38 | zinc finger and BTB domain containing 38 |
| 2.11 TPPP | brain-specific protein p25 alpha | | 2.13 TRPS1 | trichorhinophalangeal syndrome I |
| 2.11 TIMP2 | TIMP metallopeptidase inhibitor 2 | | 2.13 BAT1 | HLA-B associated transcript 1 |
| 2.11 CHD3 | chromodomain helicase DNA binding protein 3 | | 2.13 — | CDNA FLJ40823 fis, clone TRACH2011093 |
| 2.11 TBX1 | T-box 1 | | 2.13 NPAS3 | Neuronal PAS domain protein 3 |
| 2.11 CYFIP2 | cytoplasmic FMR1 interacting protein 2 /// cytop | | 2.13 TM4SF11 | Plasma membrane proteolipid (plasmolipin) |
| -2.11 — | — | | -2.13 CDX4 | caudal type homeobox transcription factor 4 |
| 2.11 C1orf165 | chromosome 1 open reading frame 165 | | -2.12 NDUFS8 | NADH dehydrogenase (ubiquinone) Fe-S prote |
| -2.11 CHES1 | checkpoint suppressor 1 | | -2.12 — | — |
| 2.11 MBD3 | Methyl-CpG binding domain protein 3 | | -2.12 — | — |
| 2.11 — | — | | 2.12 SMYD2 | SET and MYND domain containing 2 |
| 2.11 — | — | | 2.12 SLC35F1 | solute carrier family 35, member F1 |
| 2.11 VPS37B | vacuolar protein sorting 37 homolog B (S. cere | | -2.12 — | Transcribed locus |
| -2.11 TAGLN2 | transgelin 2 | | -2.12 RASEF | RAS and EF-hand domain containing |
| -2.11 JARID2 | jumonji, AT rich interactive domain 2 | | 2.12 CDK5R1 | cyclin-dependent kinase 5, regulatory subunit 1 |
| 2.11 — | Similar to hypothetical protein | | 2.12 HABP4 | hyaluronan binding protein 4 |
| 2.11 LRRC49 | leucine rich repeat containing 49 | | -2.12 TDRD7 | tudor domain containing 7 |
| 2.11 TTC7B | Tetratricopeptide repeat domain 7B | | 2.12 — | — |
| 2.11 VAPA | VAMP (vesicle-associated membrane protein)- | | 2.12 — | CDNA: FLJ22256 fis, clone HRC02860 |
| 2.10 FAM55C | Family with sequence similarity 55, member C | | -2.12 — | — |
| -2.10 — | — | | 2.12 — | — |
| 2.10 CXCR4 | chemokine (C-X-C motif) receptor 4 | | -2.12 PPP2R2B | protein phosphatase 2 (formerly 2A), regulatory |
| 2.10 MYLK | myosin, light polypeptide kinase | | -2.12 TEAD4 | TEA domain family member 4 |
| -2.10 PFKP | phosphofructokinase, platelet | | -2.12 PLS1 | plastin 1 (I isoform) |
| -2.10 LAPTM4A | lysosomal-associated protein transmembrane 4 | | 2.12 C10orf110 | chromosome 10 open reading frame 110 |
| -2.10 HDAC8 | histone deacetylase 8 | | -2.12 SLCO4A1 | solute carrier organic anion transporter family, |
| 2.10 ZBTB20 | zinc finger and BTB domain containing 20 | | 2.12 SLC6A16 | Solute carrier family 6, member 16 |
| 2.10 — | — | | 2.12 RHOBTB1 | Rho-related BTB domain containing 1 |
| 2.10 CREM | cAMP responsive element modulator | | 2.12 FAM59B | family with sequence similarity 59, member B |
| -2.10 — | CDNA FLJ31650 fis, clone NT2RI2004079 | | 2.12 NAALAD2 | N-acetylated alpha-linked acidic dipeptidase 2 |
| 2.10 DERA | 2-deoxyribose-5-phosphate aldolase homolog | | 2.12 FZD1 | frizzled homolog 1 (Drosophila) |
| 2.10 TCF12 | Transcription factor 12 (HTF4, helix-loop-helix t | | 2.12 REV3L | REV3-like, catalytic subunit of DNA polymerase |
| -2.10 KIAA1815 | KIAA1815 | | -2.11 UNC5B | unc-5 homolog B (C. elegans) |
| 2.10 — | Transcribed locus | | 2.11 NBR2 | neighbor of BRCA1 gene 2 |
| -2.10 CDC14B | CDC14 cell division cycle 14 homolog B (S. cer | | 2.11 GPR153 | G protein-coupled receptor 153 |
| -2.10 C9orf95 | chromosome 9 open reading frame 95 | | -2.11 — | — |
| 2.10 SBNO1 | Strawberry notch homolog 1 (Drosophila) | | -2.11 GNPTAB | N-acetylglucosamine-1-phosphate transferase, |
| 2.10 — | CDNA FLJ42310 fis, clone TRACH2007733 | | 2.11 — | Transcribed locus |
| 2.10 ZMYM6 | zinc finger, MYM-type 6 | | 2.11 ABCC4 | ATP-binding cassette, sub-family C (CFTR/MR |
| 2.10 ARID5B | AT rich interactive domain 5B (MRF1-like) | | -2.11 FGF21 | fibroblast growth factor 21 |
| 2.10 MSL-1 | male-specific lethal-1 homolog | | 2.11 LOC401317 | hypothetical LOC401317 |
| -2.09 DUSP5 | dual specificity phosphatase 5 | | -2.11 TMC5 | transmembrane channel-like 5 |
| 2.09 ADCY6 | adenylate cyclase 6 | | 2.11 TAF1B | TATA box binding protein (TBP)-associated fac |
| 2.09 SAMD14 | sterile alpha motif domain containing 14 | | 2.11 TMEM112 | transmembrane protein 112 |
| 2.09 — | Homo sapiens, clone IMAGE:4346533, mRNA | | -2.11 VANGL1 | vang-like 1 (van gogh, Drosophila) |

Appendix 1

| Value | Gene | Description |
|---|---|---|
| -2.09 | TTMB | cDNA DKFZp434C184 gene |
| 2.09 | LOC92482 | hypothetical protein LOC92482 |
| -2.09 | ATCAY | ataxia, cerebellar, Cayman type (caytaxin) |
| 2.09 | PDCD8 | Programmed cell death 8 (apoptosis-inducing f |
| 2.09 | EFNB3 | ephrin-B3 |
| 2.09 | RNF130 | Ring finger protein 130 |
| 2.09 | HD | huntingtin (Huntington disease) |
| 2.09 | PDE3B | Phosphodiesterase 3B, cGMP-inhibited |
| -2.09 | FAM124A | Family with sequence similarity 124A |
| -2.09 | CD74 | CD74 molecule, major histocompatibility compl |
| 2.09 | KIAA0427 | KIAA0427 |
| 2.09 | DOCK11 | dedicator of cytokinesis 11 |
| 2.09 | — | cDNA FLJ34425 fis, clone HHDPC2008297 |
| 2.09 | SLC35F1 | solute carrier family 35, member F1 |
| -2.09 | — | Transcribed locus, weakly similar to XP_51765 |
| 2.09 | — | — |
| 2.09 | IGFBP5 | insulin-like growth factor binding protein 5 |
| -2.09 | CGN | cingulin |
| -2.09 | ZBTB25 | zinc finger and BTB domain containing 25 |
| 2.09 | LOC728424 | Similar to hyperpolarization activated cyclic nu |
| 2.09 | WIZ | WIZ zinc finger |
| 2.09 | PALM | paralemmin |
| -2.08 | — | — |
| 2.08 | NRTN | neurturin |
| 2.08 | EIF2AK1 | eukaryotic translation initiation factor 2-alpha k |
| 2.08 | — | — |
| -2.08 | COL4A3BP | collagen, type IV, alpha 3 (Goodpasture antige |
| 2.08 | MCF2L | MCF.2 cell line derived transforming sequence |
| -2.08 | ZNF589 | zinc finger protein 589 |
| 2.08 | YPEL1 | yippee-like 1 (Drosophila) |
| -2.08 | ZNF785 | zinc finger protein 785 |
| -2.08 | MAP7 | microtubule-associated protein 7 |
| -2.08 | LLGL2 | lethal giant larvae homolog 2 (Drosophila) |
| -2.08 | ACP5 | acid phosphatase 5, tartrate resistant |
| 2.08 | UBE2J1 | ubiquitin-conjugating enzyme E2, J1 (UBC6 ho |
| 2.08 | — | — |
| -2.08 | FRAT1 | frequently rearranged in advanced T-cell lymph |
| -2.08 | TMEPAI | transmembrane, prostate androgen induced R |
| 2.08 | TXNL2 | Thioredoxin-like 2 |
| 2.07 | MAST1 | microtubule associated serine/threonine kinase |
| -2.07 | FOXO1A | forkhead box O1A (rhabdomyosarcoma) |
| 2.07 | APOM | apolipoprotein M |
| 2.07 | CHST1 | carbohydrate (keratan sulfate Gal-6) sulfotrans |
| -2.07 | SLC35F2 | solute carrier family 35, member F2 |
| -2.07 | HESX1 | homeobox, ES cell expressed 1 |
| 2.07 | DFNA5 | deafness, autosomal dominant 5 |
| 2.07 | — | — |
| 2.07 | MCPH1 | Microcephaly, primary autosomal recessive 1 |
| 2.07 | CYP46A1 | cytochrome P450, family 46, subfamily A, poly |
| 2.07 | RABL2B /// RABL2/ | RAB, member of RAS oncogene family-like 2B |
| 2.07 | — | — |
| -2.07 | NUMB | numb homolog (Drosophila) |
| 2.07 | ZNF345 | zinc finger protein 345 |
| 2.07 | LPIN2 | lipin 2 |
| 2.07 | VPS24 | vacuolar protein sorting 24 (yeast) |
| -2.07 | — | — |
| -2.07 | UGCGL2 | UDP-glucose ceramide glucosyltransferase-lik |
| -2.07 | DKFZP564O0823 | DKFZP564O0823 protein |
| 2.07 | DGCR5 | DiGeorge syndrome critical region gene 5 (non |
| 2.07 | WFIKKN1 | WAP, follistatin/kazal, immunoglobulin, kunitz a |
| 2.07 | — | Transcribed locus |
| -2.07 | JARID1B | jumonji, AT rich interactive domain 1B |
| -2.07 | FAM124A | family with sequence similarity 124A |
| -2.07 | OSBPL10 | oxysterol binding protein-like 10 |
| -2.07 | — | — |
| -2.07 | — | — |
| -2.07 | ROR1 | receptor tyrosine kinase-like orphan receptor 1 |
| -2.07 | — | — |
| 2.07 | AP1M1 | adaptor-related protein complex 1, mu 1 subun |
| -2.07 | CBR1 | carbonyl reductase 1 |
| -2.07 | OCEL1 | occludin/ELL domain containing 1 |
| -2.06 | LZTR2 | leucine zipper transcription regulator 2 |
| 2.06 | NRXN3 | neurexin 3 |
| 2.06 | ENC1 | ectodermal-neural cortex (with BTB-like domai |
| -2.06 | MAP7 | microtubule-associated protein 7 |
| -2.06 | LOC138255 | OTTHUMP00000021439 |
| -2.06 | GADD45B | growth arrest and DNA-damage-inducible, beta |
| 2.06 | — | — |
| 2.06 | TPD52 | tumor protein D52 |
| 2.11 | C1orf56 | chromosome 1 open reading frame 56 |
| -2.11 | — | — |
| 2.11 | SYT13 | synaptotagmin XIII |
| 2.11 | — | — |
| 2.11 | LOC387790 | hypothetical LOC387790 |
| -2.11 | — | — |
| -2.11 | COLEC12 | collectin sub-family member 12 /// collectin sub |
| 2.11 | — | — |
| -2.10 | C11orf32 | chromosome 11 open reading frame 32 |
| 2.10 | ABCC9 | ATP-binding cassette, sub-family C (CFTR/MR |
| 2.10 | — | Clone 23555 mRNA sequence |
| -2.10 | — | — |
| -2.10 | KIF6 | Kinesin family member 6 |
| 2.10 | — | Transcribed locus, strongly similar to XP_5310 |
| -2.10 | — | — |
| -2.10 | CCL5 | chemokine (C-C motif) ligand 5 |
| -2.10 | JAK3 | Janus kinase 3 (a protein tyrosine kinase, leuk |
| 2.10 | NEBL | nebulette |
| 2.10 | KLHDC4 | Kelch domain containing 4 |
| -2.10 | FOXQ1 | forkhead box Q1 |
| -2.10 | SLCO4C1 | solute carrier organic anion transporter family, |
| -2.10 | TESC | tescalcin |
| 2.10 | EIF1B | Eukaryotic translation initiation factor 1B |
| 2.10 | FLJ30851 | FLJ30851 protein |
| 2.10 | GREB1 | GREB1 protein |
| -2.09 | ZADH1 | zinc binding alcohol dehydrogenase, domain c |
| -2.09 | C1orf38 | chromosome 1 open reading frame 38 |
| -2.09 | BANK1 | B-cell scaffold protein with ankyrin repeats 1 |
| 2.09 | — | — |
| -2.09 | SVEP1 | sushi, von Willebrand factor type A, EGF and p |
| 2.09 | SLTM | SAFB-like, transcription modulator |
| -2.09 | ARL4D | ADP-ribosylation factor-like 4D |
| -2.09 | DUSP10 | dual specificity phosphatase 10 |
| -2.09 | FRAT1 | frequently rearranged in advanced T-cell lymph |
| 2.09 | INPP1 | inositol polyphosphate-1-phosphatase |
| -2.09 | LY75 | lymphocyte antigen 75 |
| 2.09 | PRR6 | Proline rich 6 |
| 2.09 | FLJ10292 | mago-nashi homolog |
| 2.09 | KPNB1 | Karyopherin (importin) beta 1 |
| 2.09 | — | — |
| 2.09 | — | Transcribed locus, strongly similar to XP_5132 |
| 2.09 | — | Transcribed locus |
| -2.09 | SYNGR1 | synaptogyrin 1 |
| -2.09 | TEAD2 | TEA domain family member 2 |
| 2.09 | SESN2 | sestrin 2 |
| 2.09 | IQCK | IQ motif containing K |
| -2.09 | TUBA1 | tubulin, alpha 1 |
| 2.09 | PTPRS | Protein tyrosine phosphatase, receptor type, S |
| 2.09 | — | — |
| -2.09 | NAP1L2 | nucleosome assembly protein 1-like 2 |
| -2.09 | CYP1B1 | cytochrome P450, family 1, subfamily B, polyp |
| 2.09 | — | — |
| 2.09 | NAP1L5 | nucleosome assembly protein 1-like 5 |
| -2.08 | — | Transcribed locus |
| 2.08 | — | — |
| 2.08 | DDR1 | discoidin domain receptor family, member 1 |
| 2.08 | C16orf45 | chromosome 16 open reading frame 45 |
| 2.08 | NUDT4 /// NUDT4P | nudix (nucleoside diphosphate linked moiety X |
| 2.08 | PSMB4 | Proteasome (prosome, macropain) subunit, be |
| -2.08 | — | — |
| -2.08 | LOC644242 | Hypothetical protein LOC644242 |
| 2.08 | KIAA1908 | KIAA1908 protein |
| 2.08 | AKR1C2 | Aldo-keto reductase family 1, member C2 (dihy |
| 2.08 | PCAF | p300/CBP-associated factor |
| -2.08 | ETS2 | v-ets erythroblastosis virus E26 oncogene hom |
| 2.08 | TMEM107 | transmembrane protein 107 /// transmembrane |
| 2.08 | DYNC2LI1 | dynein, cytoplasmic 2, light intermediate chain |
| 2.08 | TEX261 | testis expressed sequence 261 |
| 2.08 | TTLL3 | tubulin tyrosine ligase-like family, member 3 |
| -2.08 | GALC | galactosylceramidase |
| -2.08 | CLDN11 | claudin 11 (oligodendrocyte transmembrane pr |
| -2.08 | ZNF114 | zinc finger protein 114 |
| -2.08 | — | CDNA clone IMAGE:5296106 |
| 2.08 | — | — |
| 2.08 | SLC35D1 | solute carrier family 35 (UDP-glucuronic acid/U |
| 2.08 | — | — |
| 2.08 | ZKSCAN1 | zinc finger with KRAB and SCAN domains 1 |
| -2.08 | KIAA1618 | KIAA1618 |
| -2.08 | MST1 | macrophage stimulating 1 (hepatocyte growth |

Appendix 1

| Value | Symbol | Description |
|---|---|---|
| 2.06 | DLEU2 /// DLEU2L | deleted in lymphocytic leukemia, 2 /// deleted in |
| -2.06 | KLHL24 | kelch-like 24 (Drosophila) |
| 2.06 | MGC16703 | alpha tubulin-like |
| 2.06 | CXorf57 | chromosome X open reading frame 57 |
| -2.06 | ZNF311 | zinc finger protein 311 |
| -2.06 | FLJ35848 | hypothetical protein FLJ35848 |
| 2.06 | NDRG4 | NDRG family member 4 |
| 2.06 | SCCPDH | saccharopine dehydrogenase (putative) |
| -2.06 | — | — |
| -2.06 | FTH1 | ferritin, heavy polypeptide 1 |
| -2.06 | LOC221442 | hypothetical protein LOC221442 |
| 2.06 | KIF1B | Kinesin family member 1B |
| 2.06 | — | Transcribed locus |
| 2.06 | ATBF1 | AT-binding transcription factor 1 |
| -2.06 | — | — |
| -2.06 | FLJ20152 | hypothetical protein FLJ20152 |
| 2.06 | FLJ31818 | hypothetical protein FLJ31818 |
| -2.05 | GCH1 | GTP cyclohydrolase 1 (dopa-responsive dyston |
| 2.05 | CBX6 | chromobox homolog 6 |
| 2.05 | — | — |
| -2.05 | PRG1 | proteoglycan 1, secretory granule |
| -2.05 | EIF2AK4 | eukaryotic translation initiation factor 2 alpha ki |
| 2.05 | DCLRE1C | DNA cross-link repair 1C (PSO2 homolog, S. c |
| 2.05 | LEF1 | lymphoid enhancer-binding factor 1 |
| 2.05 | DCN | decorin |
| -2.05 | LOC342918 | hypothetical LOC342918 |
| 2.05 | — | CDNA clone IMAGE:5288757 |
| 2.05 | PRR14 | proline rich 14 |
| 2.05 | COPB2 | Coatomer protein complex, subunit beta 2 (beta |
| 2.05 | CXXC4 | CXXC finger 4 |
| -2.05 | MUC3A | mucin 3A, cell surface associated |
| 2.05 | KIAA1641 | KIAA1641 |
| 2.05 | ULK2 | unc-51-like kinase 2 (C. elegans) |
| 2.05 | SIAT7E | ST6 (alpha-N-acetyl-neuraminyl-2,3-beta-galac |
| -2.05 | — | CDNA FLJ34677 fis, clone LIVER2002660 |
| -2.05 | CD97 | CD97 molecule |
| 2.05 | — | Similar to onecut 3 |
| 2.05 | — | — |
| 2.05 | RHBDL7 | rhomboid, veinlet-like 7 (Drosophila) |
| -2.05 | PPM1H | protein phosphatase 1H (PP2C domain contain |
| -2.05 | — | — |
| -2.05 | SLC16A3 | solute carrier family 16, member 3 (monocarbo |
| -2.05 | CD44 | CD44 molecule (Indian blood group) |
| 2.05 | — | — |
| 2.05 | SYDE2 | synapse defective 1, Rho GTPase, homolog 2 |
| 2.05 | DYNC2H1 | dynein, cytoplasmic 2, heavy chain 1 |
| 2.05 | LRIG1 | leucine-rich repeats and immunoglobulin-like d |
| -2.04 | EML2 | echinoderm microtubule associated protein like |
| -2.04 | PLAC8 | placenta-specific 8 |
| 2.04 | — | CDNA FLJ38419 fis, clone FEBRA2009846 |
| -2.04 | CD200 | CD200 molecule |
| -2.04 | KCNK5 | potassium channel, subfamily K, member 5 |
| -2.04 | GATM | glycine amidinotransferase (L-arginine:glycine |
| -2.04 | FILIP1 | filamin A interacting protein 1 |
| -2.04 | — | — |
| 2.04 | PDPN | podoplanin |
| 2.04 | — | — |
| -2.04 | BCL11A | B-cell CLL/lymphoma 11A (zinc finger protein) |
| 2.04 | FZD2 | frizzled homolog 2 (Drosophila) |
| -2.04 | FNTB | Farnesyltransferase, CAAX box, beta |
| 2.04 | ABCG1 | ATP-binding cassette, sub-family G (WHITE), r |
| 2.04 | — | Transcribed locus |
| 2.04 | TNRC9 | trinucleotide repeat containing 9 |
| -2.04 | PPFIBP2 | PTPRF interacting protein, binding protein 2 (li |
| -2.04 | ZNF747 | zinc finger protein 747 |
| 2.04 | ELAVL3 | ELAV (embryonic lethal, abnormal vision, Dros |
| -2.04 | — | — |
| -2.04 | — | — |
| 2.04 | — | — |
| -2.03 | RASGRP2 | RAS guanyl releasing protein 2 (calcium and D |
| -2.03 | — | — |
| 2.03 | EPB41L4A | erythrocyte membrane protein band 4.1 like 4A |
| -2.03 | PACSIN3 | protein kinase C and casein kinase substrate in |
| 2.03 | ATP10D | ATPase, Class V, type 10D |
| -2.03 | TPM1 | tropomyosin 1 (alpha) |
| -2.03 | — | — |
| 2.03 | METRN | meteorin, glial cell differentiation regulator |
| 2.03 | CTNS | cystinosis, nephropathic |
| 2.08 | — | Transcribed locus |
| 2.08 | — | — |
| 2.08 | AKR1C2 | aldo-keto reductase family 1, member C2 (dihy |
| 2.08 | CREM | cAMP responsive element modulator |
| -2.07 | ANXA1 | annexin A1 |
| -2.07 | TLE1 | transducin-like enhancer of split 1 (E(sp1) hom |
| -2.07 | MGC20983 | hypothetical protein MGC20983 |
| -2.07 | GADD45B | growth arrest and DNA-damage-inducible, beta |
| 2.07 | FAM49A | family with sequence similarity 49, member A / |
| 2.07 | AP1M1 | adaptor-related protein complex 1, mu 1 subun |
| -2.07 | MCM5 | MCM5 minichromosome maintenance deficien |
| 2.07 | NRTN | neurturin |
| 2.07 | MAP9 | microtubule-associated protein 9 |
| 2.07 | FOXP1 | forkhead box P1 |
| -2.07 | DAGLBETA | diacylglycerol lipase beta |
| 2.07 | NHLH2 | nescient helix loop helix 2 |
| -2.07 | PHB | prohibitin |
| -2.07 | MAN1C1 | mannosidase, alpha, class 1C, member 1 |
| 2.07 | TCF12 | Transcription factor 12 (HTF4, helix-loop-helix |
| -2.07 | — | — |
| -2.07 | XDH | xanthine dehydrogenase |
| 2.07 | — | Transcribed locus |
| 2.07 | — | Transcribed locus |
| -2.07 | COMT | catechol-O-methyltransferase |
| 2.07 | YPEL4 | Yippee-like 4 (Drosophila) |
| -2.06 | — | MRNA, clone: TH072F08 |
| -2.06 | — | Transcribed locus |
| 2.06 | — | — |
| 2.06 | PIP5K1B | phosphatidylinositol-4-phosphate 5-kinase, typ |
| 2.06 | LIX1L | Lix1 homolog (mouse)-like |
| 2.06 | TBX1 | T-box 1 |
| 2.06 | CSAD | cysteine sulfinic acid decarboxylase |
| -2.06 | ZNF75 | zinc finger protein 75 (D8C6) |
| 2.06 | — | Transcribed locus, weakly similar to NP_06255 |
| -2.06 | TOMM7 /// LOC201 | translocase of outer mitochondrial membrane 7 |
| -2.06 | ACOX1 | acyl-Coenzyme A oxidase 1, palmitoy |
| -2.06 | PXN | paxillin |
| 2.06 | — | Full length insert cDNA clone ZB81B12 |
| 2.06 | — | — |
| -2.06 | COL6A1 | collagen, type VI, alpha 1 |
| -2.06 | RORA | RAR-related orphan receptor A |
| 2.06 | C5orf33 | chromosome 5 open reading frame 33 |
| -2.06 | — | — |
| 2.06 | — | CDNA FLJ34425 fis, clone HHDPC2008297 |
| -2.06 | TRIB1 | tribbles homolog 1 (Drosophila) |
| 2.06 | GLDN | gliomedin |
| -2.05 | LOC390861 | similar to cytoplasmic beta-actin |
| 2.05 | — | — |
| -2.05 | MGC18216 | hypothetical protein MGC18216 |
| -2.05 | LOC57228 | small trans-membrane and glycosylated protein |
| -2.05 | SORBS1 | sorbin and SH3 domain containing 1 |
| 2.05 | UBE2J1 | ubiquitin-conjugating enzyme E2, J1 (UBC6 ho |
| -2.05 | ALDH7A1 | aldehyde dehydrogenase 7 family, member A1 |
| 2.05 | SFXN1 /// LOC7322 | sideroflexin 1 /// hypothetical protein LOC7322 |
| -2.05 | LOC497257 | Hypothetical LOC497257 |
| 2.05 | — | — |
| -2.05 | FLJ32810 | hypothetical protein FLJ32810 |
| 2.05 | C9orf127 | chromosome 9 open reading frame 127 |
| -2.05 | — | — |
| 2.05 | CCDC123 | coiled-coil domain containing 123 |
| 2.05 | — | — |
| 2.05 | SMARCD3 | SWI/SNF related, matrix associated, actin depe |
| -2.05 | VANGL1 | vang-like 1 (van gogh, Drosophila) |
| -2.05 | JARID2 | jumonji, AT rich interactive domain 2 |
| 2.05 | — | Full-length cDNA clone CS0DC015YK09 of Ne |
| -2.05 | — | — |
| 2.05 | TRIM9 | tripartite motif-containing 9 |
| 2.05 | DNAJC12 | DnaJ (Hsp40) homolog, subfamily C, member |
| 2.05 | — | — |
| -2.04 | — | — |
| 2.04 | FREM1 | FRAS1 related extracellular matrix 1 |
| 2.04 | — | — |
| 2.04 | LOC440993 | hypothetical gene supported by AK128346 |
| 2.04 | C13orf18 | chromosome 13 open reading frame 18 |
| -2.04 | RPRM | reprimo, TP53 dependent G2 arrest mediator c |
| 2.04 | — | Transcribed locus, weakly similar to XP_51193 |
| 2.04 | — | — |
| 2.04 | FAM92A1 | family with sequence similarity 92, member A1 |
| -2.04 | — | — |

Appendix 1

| Value | Gene | Description |
|---|---|---|
| 2.03 | ASXL1 | additional sex combs like 1 (Drosophila) |
| 2.03 | MGC26690 | Hypothetical protein MGC26690 |
| 2.03 | MTMR4 | myotubularin related protein 4 |
| -2.03 | MMP14 | matrix metallopeptidase 14 (membrane-inserte |
| 2.03 | SOCS6 | suppressor of cytokine signaling 6 |
| 2.03 | — | — |
| 2.03 | HOMER3 | homer homolog 3 (Drosophila) |
| -2.03 | USP28 | ubiquitin specific peptidase 28 |
| -2.03 | — | Transcribed locus |
| -2.03 | HHLA3 | HERV-H LTR-associating 3 |
| -2.03 | HLA-DRB1 /// LOC7 | major histocompatibility complex, class II, DR |
| 2.03 | TBX1 | T-box 1 |
| -2.03 | EPHX1 | epoxide hydrolase 1, microsomal (xenobiotic) |
| -2.03 | ARFGEF1 | ADP-ribosylation factor guanine nucleotide-exc |
| 2.03 | CERK | ceramide kinase |
| -2.03 | HSCARG | HSCARG protein |
| 2.03 | — | Transcribed locus |
| -2.02 | GM2A | GM2 ganglioside activator |
| -2.02 | ZNF649 | zinc finger protein 649 |
| -2.02 | NPY1R | neuropeptide Y receptor Y1 |
| 2.02 | LOC90557 /// DKFZ | hypothetical protein BC016861 /// hypothetical |
| -2.02 | DOCK9 | dedicator of cytokinesis 9 |
| 2.02 | PHTF1 | Putative homeodomain transcription factor 1 |
| -2.02 | SERPINI1 | serpin peptidase inhibitor, clade I (neuroserpin) |
| -2.02 | SLC6A15 | solute carrier family 6, member 15 |
| -2.02 | S100A4 | S100 calcium binding protein A4 |
| -2.02 | GLB1L3 | galactosidase, beta 1 like 3 |
| 2.02 | LPL | lipoprotein lipase |
| 2.02 | — | — |
| 2.02 | NCOA5 | nuclear receptor coactivator 5 |
| -2.02 | JARID1B | jumonji, AT rich interactive domain 1B |
| -2.02 | ZFYVE21 | zinc finger, FYVE domain containing 21 |
| 2.02 | — | — |
| -2.02 | DCP2 | DCP2 decapping enzyme homolog (S. cerevisi |
| 2.02 | — | Clone TESTIS-814 mRNA sequence |
| 2.02 | DYRK2 | dual-specificity tyrosine-(Y)-phosphorylation re |
| 2.02 | LOC283874 | hypothetical protein LOC283874 |
| 2.02 | TOX | thymus high mobility group box protein TOX |
| 2.02 | WWC1 | WW and C2 domain containing 1 |
| 2.02 | CUL3 | cullin 3 |
| 2.02 | IGSF4C | immunoglobulin superfamily, member 4C |
| 2.02 | — | — |
| 2.02 | ARL2BP | ADP-ribosylation factor-like 2 binding protein |
| 2.02 | ZIC1 | Zic family member 1 (odd-paired homolog, Dro |
| 2.02 | CXCR4 | chemokine (C-X-C motif) receptor 4 /// chemok |
| -2.02 | — | — |
| -2.02 | RHBDF2 | rhomboid 5 homolog 2 (Drosophila) |
| 2.02 | HIPK2 | Homeodomain interacting protein kinase 2 |
| -2.01 | P2RX5 | purinergic receptor P2X, ligand-gated ion chan |
| -2.01 | NFIA | nuclear factor I/A |
| -2.01 | ZNF185 | zinc finger protein 185 (LIM domain) |
| -2.01 | ARSE | arylsulfatase E (chondrodysplasia punctata 1) |
| -2.01 | — | — |
| -2.01 | — | Clone N1 NTera2D1 teratocarcinoma mRNA |
| -2.01 | FAM38A | family with sequence similarity 38, member A |
| -2.01 | TPM1 | tropomyosin 1 (alpha) |
| -2.01 | RPS6KA5 | ribosomal protein S6 kinase, 90kDa, polypepti |
| -2.01 | — | Transcribed locus |
| 2.01 | CYP2U1 | cytochrome P450, family 2, subfamily U, polyp |
| 2.01 | BEX1 | brain expressed, X-linked 1 |
| 2.01 | KIAA1450 | KIAA1450 protein |
| -2.01 | SEMA6A | Sema domain, transmembrane domain (TM), a |
| -2.01 | — | — |
| -2.01 | — | — |
| -2.01 | SNAI1 | snail homolog 1 (Drosophila) |
| 2.01 | — | — |
| 2.01 | — | — |
| 2.01 | CCDC32 | coiled-coil domain containing 32 |
| 2.01 | TP53AP1 | TP53 activated protein 1 |
| 2.01 | DUSP4 | dual specificity phosphatase 4 |
| 2.01 | ENPEP | glutamyl aminopeptidase (aminopeptidase A) |
| 2.01 | CAMK1 | calcium/calmodulin-dependent protein kinase I |
| 2.01 | FLJ16008 | FLJ16008 protein |
| 2.01 | — | CDNA clone IMAGE:5288757 |
| 2.01 | ZC3H12C | zinc finger CCCH-type containing 12C |
| 2.01 | NMT2 | N-myristoyltransferase 2 |
| 2.01 | MGC24039 | hypothetical protein MGC24039 |
| 2.01 | COTL1 | Coactosin-like 1 (Dictyostelium) |
| -2.00 | TRIB1 | tribbles homolog 1 (Drosophila) |
| -2.04 | YPEL3 | yippee-like 3 (Drosophila) |
| -2.04 | — | — |
| 2.04 | — | — |
| 2.04 | PRR3 | proline rich 3 |
| 2.04 | RAB33A | RAB33A, member RAS oncogene family |
| 2.04 | FLJ10781 | hypothetical protein FLJ10781 |
| -2.04 | KCNK1 | potassium channel, subfamily K, member 1 |
| 2.04 | SLC45A1 | solute carrier family 45, member 1 |
| 2.04 | MGC16703 | alpha tubulin-like |
| 2.04 | NCOA6 | nuclear receptor coactivator 6 |
| 2.04 | FSD1L | FSD1-like |
| 2.04 | DKFZP434B0335 | DKFZP434B0335 protein |
| -2.04 | PBX1 | pre-B-cell leukemia transcription factor 1 |
| 2.04 | HS6ST2 | heparan sulfate 6-O-sulfotransferase 2 |
| 2.04 | LONRF1 | LON peptidase N-terminal domain and ring fing |
| -2.04 | PARVB | parvin, beta |
| 2.04 | PAM | peptidylglycine alpha-amidating monooxygenas |
| 2.04 | 6-Mar | membrane-associated ring finger (C3HC4) 6 |
| -2.04 | ITPR2 | Inositol 1,4,5-triphosphate receptor, type 2 |
| 2.04 | FLJ20481 | hypothetical protein FLJ20481 |
| 2.04 | IGSF4 | immunoglobulin superfamily, member 4 |
| 2.04 | FBN1 | fibrillin 1 |
| 2.03 | SEMA5B | sema domain, seven thrombospondin repeats ( |
| 2.03 | TNFRSF10B | tumor necrosis factor receptor superfamily, mer |
| -2.03 | CABYR | calcium binding tyrosine-(Y)-phosphorylation re |
| -2.03 | SLCO2A1 | solute carrier organic anion transporter family, |
| 2.03 | CORO2B | coronin, actin binding protein, 2B |
| 2.03 | — | — |
| 2.03 | SCFD2 | sec1 family domain containing 2 |
| 2.03 | IGSF9 | immunoglobulin superfamily, member 9 |
| 2.03 | ITGB8 | integrin, beta 8 |
| 2.03 | EPB41L5 | erythrocyte membrane protein band 4.1 like 5 |
| 2.03 | LOC144363 | hypothetical protein LOC144363 |
| 2.03 | — | — |
| -2.03 | FGD6 | FYVE, RhoGEF and PH domain containing 6 |
| -2.03 | PTBP2 | polypyrimidine tract binding protein 2 |
| 2.03 | FLJ37562 | hypothetical protein FLJ37562 |
| 2.03 | — | — |
| 2.03 | DDR1 | discoidin domain receptor family, member 1 |
| -2.03 | CD44 /// MAPK10 | CD44 molecule (Indian blood group) /// mitoger |
| 2.03 | ANAPC13 | anaphase promoting complex subunit 13 |
| -2.03 | — | — |
| -2.03 | GLIPR1L1 | GLI pathogenesis-related 1 like 1 |
| -2.03 | PITPNM2 | phosphatidylinositol transfer protein, membrane |
| 2.03 | CD47 | CD47 molecule /// CD47 molecule |
| 2.03 | VPS24 | vacuolar protein sorting 24 homolog (S. cerevis |
| -2.03 | GPSM3 | G-protein signalling modulator 3 (AGS3-like, C. |
| 2.03 | POU3F4 | POU domain, class 3, transcription factor 4 |
| 2.03 | PCGF5 | polycomb group ring finger 5 |
| 2.03 | CDC14B | CDC14 cell division cycle 14 homolog B (S. cer |
| -2.02 | SLC43A3 | solute carrier family 43, member 3 |
| -2.02 | — | — |
| 2.02 | — | — |
| -2.02 | KCNN2 | potassium intermediate/small conductance cal |
| 2.02 | TERF2IP | telomeric repeat binding factor 2, interacting pr |
| -2.02 | — | — |
| -2.02 | POLR2L | polymerase (RNA) II (DNA directed) polypeptid |
| 2.02 | VPS37B | vacuolar protein sorting 37 homolog B (S. cere |
| -2.02 | ATXN3 | ataxin 3 |
| -2.02 | — | — |
| -2.02 | OIT3 | Oncoprotein induced transcript 3 |
| 2.02 | EPM2A | epilepsy, progressive myoclonus type 2A, Lafo |
| 2.02 | CXorf57 | chromosome X open reading frame 57 |
| -2.02 | — | MRNA; cDNA DKFZp564C203 (from clone DKF |
| -2.02 | MAF | v-maf musculoaponeurotic fibrosarcoma oncog |
| -2.02 | SORBS1 | sorbin and SH3 domain containing 1 |
| 2.02 | — | — |
| -2.01 | EHD4 | EH-domain containing 4 |
| -2.01 | LMO7 | LIM domain 7 |
| -2.01 | STX6 | syntaxin 6 |
| 2.01 | ABCA2 | ATP-binding cassette, sub-family A (ABC1), me |
| 2.01 | SEPT6 /// N-PAC | septin 6 /// cytokine-like nuclear factor n-pac |
| 2.01 | PCDHB14 | protocadherin beta 14 |
| 2.01 | COTL1 | Coactosin-like 1 (Dictyostelium) |
| -2.01 | GAS7 | growth arrest-specific 7 |
| -2.01 | DTWD2 | DTW domain containing 2 |
| -2.01 | SNAI2 | snail homolog 2 (Drosophila) |
| -2.01 | — | Full-length cDNA clone CL0BB018ZE07 of Neu |
| -2.01 | PCDHA9 /// PCDHA | protocadherin alpha 9 /// protocadherin alpha s |

Appendix 1

| Value | Symbol | Description |
|---|---|---|
| 2.00 | C6orf89 | chromosome 6 open reading frame 89 |
| 2.00 | EFHC1 | EF-hand domain (C-terminal) containing 1 |
| 2.00 | RBM12 | RNA binding motif protein 12 |
| 2.00 | — | — |
| 2.00 | PPOX | protoporphyrinogen oxidase |
| 2.00 | — | Transcribed locus |
| -2.00 | MYCBP | c-myc binding protein |
| -2.00 | ACY1 | aminoacylase 1 |
| 2.00 | STAMBPL1 | STAM binding protein-like 1 |
| -2.00 | GMDS | GDP-mannose 4,6-dehydratase |
| 2.00 | KIAA0363 | KIAA0363 protein |
| 2.00 | C13orf12 | chromosome 13 open reading frame 12 |
| -2.00 | C14orf143 | chromosome 14 open reading frame 143 |
| -2.00 | CSTA | cystatin A (stefin A) |
| -2.00 | MGLL | monoglyceride lipase /// monoglyceride lipase |
| 2.00 | KIF5A | Kinesin family member 5A |
| 2.00 | — | — |
| -2.00 | CR1 | complement component (3b/4b) receptor 1 (Kn |
| 2.00 | SNW1 | CDNA FLJ35189 fis, clone PLACE6016210 /// |
| 2.00 | WDR73 | WD repeat domain 73 |
| 2.00 | SH3-domain GRB2- | SH3-domain GRB2-like pseudogene 3 |
| 2.00 | LOC387882 | hypothetical protein |
| -2.00 | TPD52 | tumor protein D52 |
| -2.00 | IL6R | interleukin 6 receptor /// interleukin 6 receptor |
| 2.00 | — | Transcribed locus |
| 2.00 | RIN2 | Ras and Rab interactor 2 |
| 2.00 | HUNK | hormonally upregulated Neu-associated kinase |
| 2.00 | PAFAH1B1 | platelet-activating factor acetylhydrolase, isofor |
| -2.00 | — | — |
| 2.00 | ZNF655 | zinc finger protein 655 |
| 2.00 | FKBP9 | FK506 binding protein 9, 63 kDa |
| -2.01 | LOC388237 /// LOC | similar to kidney-specific protein (KS) /// similar |
| -2.01 | PGLYRP4 | peptidoglycan recognition protein 4 |
| 2.01 | FLJ22167 | hypothetical protein FLJ22167 |
| 2.01 | CAP2 | CAP, adenylate cyclase-associated protein, 2 ( |
| -2.01 | PPP2R5C | Protein phosphatase 2, regulatory subunit B (B |
| -2.01 | SLC13A3 | Solute carrier family 13 (sodium-dependent dic |
| 2.01 | OXR1 | oxidation resistance 1 |
| 2.01 | KLHDC5 | kelch domain containing 5 |
| -2.01 | PFN1 | profilin 1 |
| -2.01 | FN1 | fibronectin 1 |
| -2.01 | HIST1H2BH | histone cluster 1, H2bh |
| 2.01 | MCF2L | MCF.2 cell line derived transforming sequence- |
| 2.01 | — | Similar to implantation-associated protein |
| -2.01 | — | CDNA FLJ34677 fis, clone LIVER2002660 |
| -2.01 | NEFH | neurofilament, heavy polypeptide 200kDa |
| -2.00 | BCL9L | B-cell CLL/lymphoma 9-like |
| -2.00 | HBP1 | HMG-box transcription factor 1 |
| -2.00 | MOSPD1 | motile sperm domain containing 1 |
| -2.00 | UNC13A | unc-13 homolog A (C. elegans) |
| 2.00 | — | — |
| -2.00 | — | — |
| 2.00 | — | — |
| -2.00 | MFAP3L | microfibrillar-associated protein 3-like |
| -2.00 | ZNF439 | zinc finger protein 439 |
| -2.00 | DIO3 | deiodinase, iodothyronine, type II |
| 2.00 | ABHD14A | abhydrolase domain containing 14A |
| 2.00 | AMH | anti-Mullerian hormone |
| 2.00 | CNN3 | Calponin 3, acidic |
| 2.00 | — | (clone B3B3E13) Huntington's disease candida |
| -2.00 | PNRC1 | proline-rich nuclear receptor coactivator 1 |
| -2.00 | CABYR | calcium binding tyrosine-(Y)-phosphorylation re |
| -2.00 | TNFRSF12A | tumor necrosis factor receptor superfamily, mer |
| -2.00 | RNF26 | ring finger protein 26 /// ring finger protein 26 |
| 2.00 | ING3 | Inhibitor of growth family, member 3 |
| -2.00 | PINK1 | PTEN induced putative kinase 1 |

Appendix 1

| MMC CXCR4 sorted | | | MMC P4 | | |
|---|---|---|---|---|---|
| Est Log Ratio | Gene Symbol | Gene Descriptor | Est Log Ratio | Gene Symbol | Gene Descriptor |
| -13.99 | HESRG | embryonic stem cell related protein | 12.91 | LUM | lumican |
| -11.18 | NANOG | Nanog homeobox | 10.70 | NR2F1 | Nuclear receptor subfamily 2, group F, membe |
| -10.85 | CDH1 | cadherin 1, type 1, E-cadherin (epithelial) | 10.56 | COL3A1 | collagen, type III, alpha 1 (Ehlers-Danlos syndr |
| -10.75 | LOC645682 | POU domain, class 5, transcription factor 1 pse | 10.23 | COL3A1 | collagen, type III, alpha 1 (Ehlers-Danlos syndr |
| -10.74 | F11R | F11 receptor | 10.18 | PRRX1 | paired related homeobox 1 |
| 10.74 | IL13RA2 | interleukin 13 receptor, alpha 2 | 9.94 | — | — |
| -10.69 | DSP | desmoplakin | 9.84 | PRRX1 | Paired related homeobox 1 |
| -10.66 | CLDN6 | claudin 6 | -9.84 | — | — |
| -10.32 | — | Transcribed locus | 9.62 | TFAP2B | transcription factor AP-2 beta (activating enhan |
| -10.27 | SCNN1A | sodium channel, nonvoltage-gated 1 alpha | 9.60 | — | — |
| -10.15 | DPPA4 | developmental pluripotency associated 4 | 9.50 | DCN | decorin |
| -10.03 | DPPA4 | developmental pluripotency associated 4 | -9.40 | ZFP42 | zinc finger protein 42 homolog (mouse) |
| -10.01 | IFITM1 | interferon induced transmembrane protein 1 (9 | 9.27 | A2M | alpha-2-macroglobulin |
| -9.98 | RBM35A | RNA binding motif protein 35A | -9.24 | SCNN1A | sodium channel, nonvoltage-gated 1 alpha |
| -9.91 | — | Transcribed locus | 9.06 | ZIC1 | Zic family member 1 (odd-paired homolog, Dro |
| -9.82 | — | Homo sapiens, Similar to otoconin 90, clone IM | 9.02 | KIAA0644 | KIAA0644 gene product |
| 9.67 | HOXA9 | homeobox A9 | -8.88 | — | Homo sapiens, Similar to otoconin 90, clone IM |
| -9.66 | KRT19 | keratin 19 | 8.81 | RHOJ | ras homolog gene family, member J |
| -9.52 | ZFP42 | zinc finger protein 42 | -8.80 | — | — |
| 9.52 | NR2F1 | Nuclear receptor subfamily 2, group F, membe | 8.68 | FLJ41747 | hypothetical gene supported by AK123741 |
| -9.51 | TDGF1 /// TDGF3 | teratocarcinoma-derived growth factor 1 /// tera | -8.68 | — | — |
| -9.36 | RBM35A | RNA binding motif protein 35A | -8.67 | CDA | cytidine deaminase |
| 9.36 | PTPRN2 | protein tyrosine phosphatase, receptor type, N | -8.60 | KRT19 | keratin 19 |
| 9.30 | FOLH1 | folate hydrolase (prostate-specific membrane a | -8.53 | LEFTY1 | left-right determination factor 1 |
| 9.27 | EN2 | engrailed homolog 2 | 8.46 | HOXA9 | homeobox A9 |
| -9.26 | — | — | -8.45 | LEFTY2 | left-right determination factor 2 |
| 9.25 | TRIM48 | tripartite motif-containing 48 | 8.41 | — | Transcribed locus |
| -9.23 | CR1L | complement component (3b/4b) receptor 1-like | 8.38 | HOXA5 | homeobox A5 |
| 9.21 | PTPRN2 | protein tyrosine phosphatase, receptor type, N | 8.37 | HOXC6 | homeobox C6 |
| -9.21 | ZFP42 | zinc finger protein 42 homolog (mouse) | 8.29 | DLX1 | distal-less homeobox 1 |
| -9.20 | KRT18 | keratin 18 | 8.28 | DNM3 | Dynamin 3 |
| -9.18 | L1TD1 | LINE-1 type transposase domain containing 1 | -8.24 | RAB25 | RAB25, member RAS oncogene family |
| 9.09 | SOX1 | SRY (sex determining region Y)-box 1 | 8.22 | — | — |
| 9.09 | FLJ20366 | hypothetical protein FLJ20366 | -8.16 | ZNF206 | zinc finger protein 206 |
| -9.00 | IFITM1 | interferon induced transmembrane protein 1 (9 | 8.14 | DLX2 | distal-less homeobox 2 |
| -9.00 | TACSTD1 | tumor-associated calcium signal transducer 1 | 8.08 | COL3A1 | collagen, type III, alpha 1 (Ehlers-Danlos syndr |
| 9.00 | — | — | -8.03 | — | Transcribed locus |
| -8.98 | CDA | cytidine deaminase | -8.02 | CDH1 | cadherin 1, type 1, E-cadherin (epithelial) |
| -8.96 | SEMA6A | sema domain, transmembrane domain (TM), a | 8.02 | — | — |
| 8.93 | HES5 | hairy and enhancer of split 5 (Drosophila) | -8.02 | RBM35A | RNA binding motif protein 35A |
| -8.91 | POU5F1 /// POU5F | POU domain, class 5, transcription factor 1 /// F | -7.99 | — | Transcribed locus |
| 8.91 | ZIC1 | Zic family member 1 (odd-paired homolog, Dro | 7.98 | BGN /// TSHZ1 | biglycan /// teashirt family zinc finger 1 |
| 8.78 | NCALD | neurocalcin delta /// neurocalcin delta | 7.93 | MOXD1 | monooxygenase, DBH-like 1 |
| -8.77 | DPPA2 | developmental pluripotency associated 2 | -7.92 | GARNL4 | GTPase activating Rap/RanGAP domain-like 4 |
| 8.77 | EPHA3 | EPH receptor A3 | -7.91 | — | — |
| -8.77 | — | — | 7.89 | SCRG1 | scrapie responsive protein 1 |
| -8.62 | RAB25 | RAB25, member RAS oncogene family | 7.87 | ANKRD38 | ankyrin repeat domain 38 |
| 8.61 | — | — | -7.84 | ZFP42 | zinc finger protein 42 homolog (mouse) |
| -8.58 | — | — | 7.79 | — | CDNA clone IMAGE:4811567 |
| -8.57 | — | — | 7.78 | KIAA0644 | KIAA0644 gene product |
| 8.57 | — | — | 7.77 | — | CDNA FLJ11723 fis, clone HEMBA1005314 |
| -8.54 | LOC642559 | POU domain, class 5, transcription factor 1 pse | -7.74 | TACSTD1 | tumor-associated calcium signal transducer 1 |
| 8.48 | FOLH1 | folate hydrolase (prostate-specific membrane a | 7.73 | HOXD4 | homeobox D4 |
| -8.48 | VSNL1 | visinin-like 1 | 7.73 | EN2 | engrailed homolog 2 |
| -8.47 | CLDN6 | claudin 6 | -7.69 | — | — |
| 8.45 | TMEM16C | transmembrane protein 16C | 7.68 | — | — |
| -8.42 | POU5F1 /// POU5F | POU domain, class 5, transcription factor 1 /// F | 7.62 | TNFRSF19 | tumor necrosis factor receptor superfamily, me |
| -8.41 | — | — | 7.61 | — | — |
| -8.38 | — | — | -7.58 | HIST1H2BD | Histone cluster 1, H2bd |
| -8.38 | HPGD | hydroxyprostaglandin dehydrogenase 15-(NAD | -7.56 | CLDN7 | claudin 7 |
| -8.36 | HAS2 | hyaluronan synthase 2 | -7.56 | RBM35A | RNA binding motif protein 35A |
| -8.34 | ERBB3 | v-erb-b2 erythroblastic leukemia viral oncogene | 7.54 | GDF10 | growth differentiation factor 10 |
| -8.32 | SPINT2 | serine peptidase inhibitor, Kunitz type, 2 | 7.52 | NCALD | neurocalcin delta /// neurocalcin delta |
| -8.26 | S100A11 | S100 calcium binding protein A11 | -7.50 | LOC728342 | Hypothetical protein LOC728342 |
| -8.25 | GARNL4 | GTPase activating Rap/RanGAP domain-like 4 | 7.48 | — | — |
| -8.25 | LOC388638 | hypothetical LOC388638 | -7.48 | — | — |
| -8.23 | TFPI | tissue factor pathway inhibitor (lipoprotein-asso | 7.46 | TWIST1 | twist homolog 1 (acrocephalosyndactyly 3; Sae |
| -8.23 | — | Transcribed locus | 7.46 | — | MRNA; cDNA DKFZp564N1116 (from clone DK |
| -8.22 | KIAA1244 | KIAA1244 | -7.43 | C14orf29 | chromosome 14 open reading frame 29 |

Appendix 1

| Value | Symbol | Description |
|---|---|---|
| -8.21 | — | — |
| -8.16 | CYP26A1 | cytochrome P450, family 26, subfamily A, polyp |
| -8.16 | HEY2 | hairy/enhancer-of-split related with YRPW moti |
| -8.16 | GALNT3 | UDP-N-acetyl-alpha-D-galactosamine:polypept |
| -8.15 | CDH1 | cadherin 1, type 1, E-cadherin (epithelial) |
| -8.10 | TMEM30B | transmembrane protein 30B |
| -8.09 | — | Homo sapiens, Similar to otoconin 90, clone IM |
| 8.07 | PCDH8 | protocadherin 8 |
| -8.05 | CHST9 | carbohydrate (N-acetylgalactosamine 4-0) sulf |
| -8.05 | ZFP42 | zinc finger protein 42 homolog (mouse) |
| -8.04 | SPINT1 | serine peptidase inhibitor, Kunitz type 1 |
| 8.02 | — | — |
| -7.99 | — | Transcribed locus |
| 7.99 | HOXC6 | homeobox C6 |
| -7.96 | CLDN7 | claudin 7 |
| -7.96 | LEFTY1 | left-right determination factor 1 |
| -7.95 | — | CDNA FLJ30478 fis, clone BRAWH1000167 |
| -7.90 | PRAC | small nuclear protein PRAC |
| -7.89 | B3GNT7 | UDP-GlcNAc:betaGal beta-1,3-N-acetylglucosa |
| -7.88 | ITPR3 | inositol 1,4,5-triphosphate receptor, type 3 |
| -7.86 | CCDC4 | coiled-coil domain containing 4 |
| 7.84 | PDE1A | phosphodiesterase 1A, calmodulin-dependent |
| -7.84 | C14orf29 | chromosome 14 open reading frame 29 |
| -7.82 | — | CDNA FLJ12624 fis, clone NT2RM4001754 |
| -7.82 | NTS | neurotensin |
| -7.81 | HIST1H2BD | Histone cluster 1, H2bd |
| -7.80 | LSR | lipolysis stimulated lipoprotein receptor |
| -7.79 | COL1A1 | collagen, type I, alpha 1 |
| -7.76 | EPHA1 | EPH receptor A1 |
| 7.75 | EN1 | engrailed homolog 1 |
| -7.75 | HEPH | hephaestin |
| 7.74 | — | — |
| 7.74 | — | — |
| -7.72 | LCK | lymphocyte-specific protein tyrosine kinase |
| -7.69 | COL9A3 | collagen, type IX, alpha 3 |
| -7.69 | CALB1 | calbindin 1, 28kDa |
| -7.69 | ZYG11A | zyg-11 homolog A (C. elegans) |
| 7.67 | RFX4 | regulatory factor X, 4 (influences HLA class II e |
| -7.66 | — | — |
| 7.65 | SOX1 | SRY (sex determining region Y)-box 1 |
| -7.61 | — | — |
| -7.59 | EFEMP1 | EGF-containing fibulin-like extracellular matrix |
| 7.56 | HOXB8 | homeobox B8 |
| -7.55 | FOXH1 | forkhead box H1 |
| -7.54 | FOXH1 | forkhead box H1 |
| -7.54 | LEFTY2 | left-right determination factor 2 |
| -7.51 | GLOXD1 | glyoxalase domain containing 1 |
| -7.51 | RPL39L | ribosomal protein L39-like |
| -7.51 | GNA14 | guanine nucleotide binding protein (G protein), |
| -7.48 | TNNT1 | troponin T type 1 (skeletal, slow) |
| 7.46 | NR2F2 | nuclear receptor subfamily 2, group F, member |
| -7.44 | RAB17 | RAB17, member RAS oncogene family |
| -7.44 | FLJ20273 | RNA-binding protein |
| 7.41 | GPR56 | G protein-coupled receptor 56 |
| 7.41 | — | — |
| 7.39 | — | — |
| -7.37 | PITX2 | paired-like homeodomain transcription factor 2 |
| -7.36 | CRLF1 | cytokine receptor-like factor 1 |
| -7.36 | — | — |
| -7.36 | AP1M2 | adaptor-related protein complex 1, mu 2 subun |
| -7.35 | COL1A2 | collagen, type I, alpha 2 |
| -7.32 | — | Transcribed locus |
| 7.31 | EPHA3 | EPH receptor A3 |
| 7.31 | — | CDNA clone IMAGE:4811567 |
| -7.31 | GLB1L3 | galactosidase, beta 1 like 3 |
| 7.31 | NR2F2 | nuclear receptor subfamily 2, group F, member |
| 7.28 | HOXD4 | homeobox D4 |
| -7.27 | ZNF206 | zinc finger protein 206 |
| 7.26 | — | — |
| -7.24 | CDH3 | cadherin 3, type 1, P-cadherin (placental) |
| -7.22 | MTAC2D1 | membrane targeting (tandem) C2 domain cont |
| 7.21 | SCUBE2 | signal peptide, CUB domain, EGF-like 2 |
| -7.20 | EFEMP1 | EGF-containing fibulin-like extracellular matrix |
| -7.17 | S100A10 | S100 calcium binding protein A10 |
| -7.16 | NFIA | nuclear factor I/A |
| 7.16 | — | — |
| -7.16 | ERBB3 | v-erb-b2 erythroblastic leukemia viral oncogene |
| 7.14 | FAM70A | family with sequence similarity 70, member A |
| -7.14 | PPL | periplakin |
| 7.39 | SOX1 | SRY (sex determining region Y)-box 1 |
| -7.38 | ZFP42 | zinc finger protein 42 |
| 7.37 | MAB21L2 | mab-21-like 2 (C. elegans) |
| 7.37 | HOXA10 | homeobox A10 |
| 7.37 | COL2A1 | collagen, type II, alpha 1 (primary osteoarthritis |
| 7.32 | RERG | RAS-like, estrogen-regulated, growth inhibitor |
| -7.32 | ARHGAP8 /// LOC5 | Rho GTPase activating protein 8 /// PRR5-ARH |
| -7.31 | LCK | lymphocyte-specific protein tyrosine kinase |
| 7.30 | — | — |
| 7.30 | NR2F2 | nuclear receptor subfamily 2, group F, member |
| -7.29 | — | — |
| -7.27 | SPINT1 | serine peptidase inhibitor, Kunitz type 1 |
| -7.26 | CHST9 | carbohydrate (N-acetylgalactosamine 4-0) sulf |
| 7.25 | — | — |
| 7.23 | HOXC10 | homeobox C10 |
| 7.22 | HOXD3 | homeobox D3 |
| -7.22 | — | — |
| 7.21 | BGN | biglycan |
| 7.21 | FAM70A | family with sequence similarity 70, member A |
| -7.17 | CCDC4 | coiled-coil domain containing 4 |
| -7.16 | AP1M2 | adaptor-related protein complex 1, mu 2 subun |
| 7.16 | HOXD10 | homeobox D10 |
| 7.15 | FLJ21986 | hypothetical protein FLJ21986 |
| 7.14 | — | CDNA FLJ12425 fis, clone MAMMA1003104 |
| -7.13 | GAL | galanin |
| -7.13 | FLJ14712 | hypothetical protein FLJ14712 |
| 7.12 | — | — |
| -7.11 | HIST1H2BD | Histone cluster 1, H2bd |
| -7.09 | — | CDNA FLJ12557 fis, clone NT2RM4000783 |
| 7.07 | DCN | decorin |
| -7.06 | TMEM30B | transmembrane protein 30B |
| -7.05 | HESRG | embryonic stem cell related protein |
| 7.04 | LIX1 | Lix1 homolog (mouse) |
| 7.02 | C8orf4 | chromosome 8 open reading frame 4 |
| -7.01 | DPPA5 | developmental pluripotency associated 5 |
| 6.99 | WFDC1 | WAP four-disulfide core domain 1 |
| -6.95 | MTAC2D1 | membrane targeting (tandem) C2 domain cont |
| 6.93 | NR2F2 | nuclear receptor subfamily 2, group F, member |
| 6.92 | — | Transcribed locus |
| 6.91 | HOXD11 | homeobox D11 |
| 6.89 | — | — |
| 6.88 | HOXC9 | homeobox C9 |
| -6.87 | HLA-DPB2 | major histocompatibility complex, class II, DP b |
| -6.85 | NTS | neurotensin |
| -6.85 | IL8 | interleukin 8 |
| 6.84 | TCF8 | transcription factor 8 (represses interleukin 2 e |
| 6.82 | KBTBD10 | kelch repeat and BTB (POZ) domain containing |
| 6.80 | HOXA1 | homeobox A1 |
| -6.80 | MYCT1 | myc target 1 |
| 6.79 | — | — |
| 6.79 | HOXA11 | homeobox A11 |
| -6.78 | LOC645682 | POU domain, class 5, transcription factor 1 pse |
| 6.78 | RERG | RAS-like, estrogen-regulated, growth inhibitor |
| 6.78 | NR2F1 | nuclear receptor subfamily 2, group F, member |
| -6.76 | CALB1 | calbindin 1, 28kDa |
| -6.75 | AP1M2 | adaptor-related protein complex 1, mu 2 subun |
| -6.72 | FLJ25801 | hypothetical protein FLJ25801 |
| 6.71 | — | Transcribed locus |
| -6.70 | IL15 | interleukin 15 |
| 6.68 | MSX1 | msh homeobox 1 |
| 6.68 | COL12A1 | collagen, type XII, alpha 1 |
| -6.67 | NANOG | Nanog homeobox |
| 6.65 | — | — |
| 6.64 | FBN1 | fibrillin 1 |
| -6.63 | — | — |
| 6.63 | HOXB8 | homeobox B8 |
| 6.61 | HOXB6 | Homeo box B6 |
| -6.59 | ZYG11A | zyg-11 homolog A (C. elegans) |
| 6.58 | HOXB3 | homeobox B3 |
| 6.58 | COL12A1 | collagen, type XII, alpha 1 |
| -6.57 | — | — |
| 6.56 | ITGA4 | integrin, alpha 4 (antigen CD49D, alpha 4 subu |
| -6.56 | KIAA1244 | KIAA1244 |
| 6.55 | C4orf19 | Chromosome 4 open reading frame 19 |
| -6.54 | ATP2A3 | ATPase, Ca++ transporting, ubiquitous |
| 6.53 | HOXD10 | homeobox D10 |
| -6.51 | UTF1 | undifferentiated embryonic cell transcription fac |
| 6.50 | HOXA10 | homeobox A10 |
| 6.50 | MEOX2 | mesenchyme homeobox 2 |

Appendix 1

| | | | |
|---|---|---|---|
| -7.14 HLA-DPB2 | major histocompatibility complex, class II, DP b | -6.46 TDGF1 /// TDGF3 | teratocarcinoma-derived growth factor 1 /// tera |
| -7.13 DPPA5 | developmental pluripotency associated 5 | -6.46 — | — |
| -7.12 — | — | -6.45 CST1 | cystatin SN |
| -7.11 EPPK1 | epiplakin 1 | -6.44 FLJ44186 | FLJ44186 protein |
| -7.11 — | — | -6.44 EPPK1 | epiplakin 1 |
| -7.10 — | — | -6.44 SLITRK6 | SLIT and NTRK-like family, member 6 |
| -7.10 FLJ25801 | hypothetical protein FLJ25801 | -6.43 KIAA1713 | KIAA1713 |
| -7.10 PLAGL1 | pleiomorphic adenoma gene-like 1 | -6.43 CALB1 | calbindin 1, 28kDa |
| -7.08 FLJ20273 | RNA-binding protein | -6.42 — | — |
| -7.06 KRT8 | keratin 8 /// keratin 8 | -6.41 — | — |
| -7.06 HOXA9 | homeobox A9 | -6.41 DOCK10 | dedicator of cytokinesis 10 |
| -7.05 ZNF206 | zinc finger protein 206 | -6.40 IGSF21 | immunoglobin superfamily, member 21 |
| -7.05 SEMA6A | sema domain, transmembrane domain (TM), a | -6.40 SLITRK6 | SLIT and NTRK-like family, member 6 |
| -7.05 TKTL1 | transketolase-like 1 | -6.40 LOC642559 | POU domain, class 5, transcription factor 1 pse |
| -7.04 GPR64 | G protein-coupled receptor 64 | -6.40 EPHA3 | EPH receptor A3 |
| -7.02 LONRF2 | LON peptidase N-terminal domain and ring fing | -6.36 TFAP2B | transcription factor AP-2 beta (activating enhan |
| -7.01 — | — | -6.34 GPR177 | G protein-coupled receptor 177 |
| -7.00 — | — | -6.34 HPGD | hydroxyprostaglandin dehydrogenase 15-(NAD |
| -6.99 — | — | -6.33 DDR2 | discoidin domain receptor family, member 2 |
| -6.98 — | — | -6.33 FGF4 | fibroblast growth factor 4 (heparin secretory tra |
| -6.97 — | — | -6.33 C5orf23 | chromosome 5 open reading frame 23 |
| -6.97 HOXD3 | homeobox D3 | -6.32 HOXB6 | homeobox B6 |
| -6.96 — | — | -6.32 POU5F1 /// POU5F | POU domain, class 5, transcription factor 1 /// |
| -6.96 HOXB7 | homeobox B7 | -6.32 LOC729890 /// LOC | hypothetical protein LOC729890 /// hypothetica |
| -6.96 APOC1 | apolipoprotein C-I | -6.31 MT1M | metallothionein 1M |
| -6.95 PROCR | protein C receptor, endothelial (EPCR) | -6.31 — | — |
| -6.95 CR1 /// CR1L | complement component (3b/4b) receptor 1, inc | -6.29 RHOJ | ras homolog gene family, member J |
| -6.94 C21orf105 | chromosome 21 open reading frame 105 | -6.29 EMILIN1 | elastin microfibril interfacer 1 |
| -6.93 DKFZP686A01247 | hypothetical protein | -6.29 COL2A1 | collagen, type II, alpha 1 (primary osteoarthritis |
| -6.93 CAV1 | caveolin 1, caveolae protein, 22kDa | -6.27 — | — |
| -6.91 APOE | apolipoprotein E | -6.26 PRDM14 | PR domain containing 14 |
| -6.91 CCL4 | chemokine (C-C motif) ligand 4 | -6.26 LOC202451 | hypothetical protein LOC202451 |
| -6.89 HDCMA18P | HDCMA18P protein | -6.26 DPPA2 | developmental pluripotency associated 2 |
| -6.88 AP1M2 | adaptor-related protein complex 1, mu 2 subun | -6.24 JPH3 | junctophilin 3 |
| -6.85 — | CDNA FLJ39179 fis, clone OCBBF2004147 | -6.23 ZNF287 | zinc finger protein 287 |
| -6.84 HOXB7 | homeobox B7 | -6.21 TFAP2B | transcription factor AP-2 beta (activating enhan |
| -6.84 PCSK9 | proprotein convertase subtilisin/kexin type 9 | -6.20 SERPINB9 | serpin peptidase inhibitor, clade B (ovalbumin), |
| -6.84 COL1A2 | collagen, type I, alpha 2 | -6.20 NODAL | nodal homolog (mouse) |
| -6.83 TFAP2C | transcription factor AP-2 gamma (activating en | -6.20 C21orf105 | chromosome 21 open reading frame 105 |
| -6.83 FLJ14712 | hypothetical protein FLJ14712 | 6.19 HOXA9 | homeobox A9 |
| -6.82 — | — | -6.19 HRASLS3 | HRAS-like suppressor 3 |
| -6.81 TPD52L1 | tumor protein D52-like 1 | -6.19 VENTX | VENT homeobox homolog (Xenopus laevis) |
| -6.80 GSTT2 | glutathione S-transferase theta 2 | 6.19 DKFZP686A01247 | hypothetical protein |
| -6.80 MME | membrane metallo-endopeptidase (neutral end | 6.18 HOXA11 | homeobox A11 |
| -6.79 — | — | -6.18 — | — |
| -6.79 ATP2A3 | ATPase, Ca++ transporting, ubiquitous | 6.16 — | — |
| -6.78 HOXA5 | homeobox A5 | -6.16 LCK | lymphocyte-specific protein tyrosine kinase |
| -6.77 HTATIP2 | HIV-1 Tat interactive protein 2, 30kDa | 6.15 — | CDNA FLJ37216 fis, clone BRALZ2008696 |
| -6.76 GNAS | GNAS complex locus | 6.15 MBNL2 | muscleblind-like 2 (Drosophila) |
| -6.76 HSPA2 | heat shock 70kDa protein 2 | 6.14 TFAP2A | transcription factor AP-2 alpha (activating enha |
| -6.74 CALB1 | calbindin 1, 28kDa | -6.13 — | — |
| -6.74 IL8 | interleukin 8 | -6.12 COBL | cordon-bleu homolog (mouse) |
| -6.73 LOC153469 | hypothetical protein LOC153469 | -6.12 F2RL1 | coagulation factor II (thrombin) receptor-like 1 |
| 6.73 HOXB7 | homeobox B7 | -6.11 — | — |
| -6.72 — | MRNA; cDNA DKFZp686L0310 (from clone DK | 6.11 — | — |
| -6.72 FLJ21963 | FLJ21963 protein | 6.10 PRRX1 | paired related homeobox 1 |
| 6.72 PLAGL1 | pleiomorphic adenoma gene-like 1 | 6.09 FHOD3 | formin homology 2 domain containing 3 |
| -6.71 — | CDNA FLJ12557 fis, clone NT2RM4000783 | 6.08 DKFZP686A01247 | hypothetical protein |
| -6.70 PRKCDBP | protein kinase C, delta binding protein | -6.08 — | CDNA FLJ12624 fis, clone NT2RM4001754 |
| -6.70 MT1H | metallothionein 1H | -6.07 — | Homo sapiens, Similar to otoconin 90, clone IM |
| -6.69 DDB2 | damage-specific DNA binding protein 2, 48kDa | -6.07 TNMD | tenomodulin |
| -6.68 IL8 | interleukin 8 | -6.07 GDF3 | growth differentiation factor 3 |
| -6.68 HTR2C | 5-hydroxytryptamine (serotonin) receptor 2C | -6.07 HPGD | hydroxyprostaglandin dehydrogenase 15-(NAD |
| -6.68 CECR1 | cat eye syndrome chromosome region, candida | -6.05 SMPDL3B | sphingomyelin phosphodiesterase, acid-like 3B |
| 6.67 — | Homo sapiens, clone IMAGE:5019307, mRNA | 6.03 MAB21L2 | mab-21-like 2 (C. elegans) |
| 6.67 HOXB3 | homeobox B3 | -6.02 CDH1 | cadherin 1, type 1, E-cadherin (epithelial) |
| 6.67 — | Transcribed locus | -6.02 — | — |
| 6.66 MEGF11 | multiple EGF-like-domains 11 | -6.02 EFCBP1 | EF-hand calcium binding protein 1 |
| 6.64 MEIS1 | Meis1, myeloid ecotropic viral integration site 1 | 6.02 LRRC32 | leucine rich repeat containing 32 |
| -6.63 VENTX | VENT homeobox homolog (Xenopus laevis) | 6.01 — | — |
| -6.63 PDGFA | platelet-derived growth factor alpha polypeptide | 6.01 — | CDNA clone IMAGE:5294528 |
| 6.62 — | Transcribed locus, moderately similar to XP_41 | -6.00 — | Transcribed locus |
| -6.61 C1orf85 | chromosome 1 open reading frame 85 | 5.99 RGS4 | regulator of G-protein signalling 4 |
| -6.61 BST2 | bone marrow stromal cell antigen 2 | -5.99 ABHD9 | abhydrolase domain containing 9 |
| 6.60 TCF8 | transcription factor 8 (represses interleukin 2 ex | -5.98 GALNT3 | UDP-N-acetyl-alpha-D-galactosamine:polypep |
| 6.60 ASCL1 | achaete-scute complex homolog 1 (Drosophila) | 5.97 — | Homo sapiens, clone IMAGE:5019307, mRNA |
| -6.60 LOC136288 | hypothetical protein LOC136288 | -5.96 PPL | periplakin |
| 6.59 LOC145786 | hypothetical protein LOC145786 | -5.96 SIX3 | sine oculis homeobox homolog 3 (Drosophila) |
| -6.59 MYL9 | myosin, light chain 9, regulatory | 5.96 — | — |

Appendix 1

| | | | |
|---|---|---|---|
| -6.58 | LOC391020 | similar to Interferon-induced transmembrane p[rotein] | |
| -6.57 | TFPI | tissue factor pathway inhibitor (lipoprotein-asso[c]) | |
| -6.57 | NODAL | nodal homolog (mouse) | |
| -6.56 | ARHGAP8 /// LOC5 | Rho GTPase activating protein 8 /// PRR5-ARH[GAP8] | |
| -6.56 | NRK | Nik related kinase | |
| -6.55 | RARRES2 | retinoic acid receptor responder (tazarotene in[d]) | |
| -6.55 | PRSS8 | protease, serine, 8 (prostasin) | |
| -6.54 | PAX6 | paired box gene 6 (aniridia, keratitis) | |
| -6.54 | HOXC9 | homeobox C9 | |
| -6.52 | LOC286411 | hypothetical protein LOC286411 | |
| -6.52 | FAM46B | family with sequence similarity 46, member B | |
| -6.51 | — | MRNA full length insert cDNA clone EUROIMA[GE] | |
| -6.48 | PRDM13 | PR domain containing 13 | |
| -6.48 | HOXB6 | homeobox B6 | |
| -6.47 | APOC1 | apolipoprotein C-I | |
| -6.47 | IRF6 | interferon regulatory factor 6 | |
| -6.47 | ST8SIA1 | ST8 alpha-N-acetyl-neuraminide alpha-2,8-sial[yltransferase] | |
| -6.46 | — | — | |
| -6.46 | SLC7A8 | solute carrier family 7 (cationic amino acid tran[sporter]) | |
| -6.45 | SLFN5 | schlafen family member 5 | |
| -6.45 | SMPDL3B | sphingomyelin phosphodiesterase, acid-like 3B | |
| -6.45 | ABCB1 | ATP-binding cassette, sub-family B (MDR/TAP) | |
| -6.44 | — | — | |
| -6.44 | POU3F2 | POU domain, class 3, transcription factor 2 | |
| -6.43 | C1orf172 | chromosome 1 open reading frame 172 | |
| -6.41 | FGFR4 | fibroblast growth factor receptor 4 | |
| -6.41 | — | — | |
| -6.41 | CSPG3 | chondroitin sulfate proteoglycan 3 (neurocan) | |
| -6.40 | CXCL5 | chemokine (C-X-C motif) ligand 5 | |
| -6.39 | TRPC6 | transient receptor potential cation channel, sub[family] | |
| 6.39 | — | — | |
| -6.38 | NAP5 | Nck-associated protein 5 | |
| -6.38 | PDE1A | phosphodiesterase 1A, calmodulin-dependent | |
| -6.38 | HEY2 | hairy/enhancer-of-split related with YRPW moti[f] | |
| 6.37 | — | — | |
| -6.37 | EBF2 | Early B-cell factor 2 | |
| -6.36 | LOC202451 | hypothetical protein LOC202451 | |
| 6.35 | DKFZP686A01247 | hypothetical protein | |
| -6.33 | PPAP2C | phosphatidic acid phosphatase type 2C | |
| -6.33 | C10orf96 | chromosome 10 open reading frame 96 | |
| -6.32 | MARVELD2 | MARVEL domain containing 2 | |
| 6.32 | — | — | |
| -6.31 | ALDH1A3 | aldehyde dehydrogenase 1 family, member A3 | |
| -6.31 | GAL | galanin | |
| -6.30 | LCK | lymphocyte-specific protein tyrosine kinase | |
| -6.30 | CORO2A | coronin, actin binding protein, 2A | |
| 6.29 | — | Transcribed locus | |
| -6.28 | IL28RA | interleukin 28 receptor, alpha (interferon, lamb[da]) | |
| -6.28 | B3GNT7 | UDP-GlcNAc:betaGal beta-1,3-N-acetylglucos[aminyltransferase] | |
| -6.27 | — | — | |
| -6.27 | RAB3B | RAB3B, member RAS oncogene family | |
| 6.27 | — | Homo sapiens, clone IMAGE:5019307, mRNA | |
| -6.26 | RUNX1T1 | runt-related transcription factor 1; translocated | |
| -6.26 | MT1F | metallothionein 1F (functional) | |
| -6.25 | — | — | |
| 6.24 | — | — | |
| 6.22 | KIAA1713 | KIAA1713 | |
| 6.22 | PTPRN2 | protein tyrosine phosphatase, receptor type, N | |
| -6.21 | — | — | |
| -6.21 | IFITM3 | interferon induced transmembrane protein 3 (1[-8U]) | |
| -6.21 | CRISPLD2 | cysteine-rich secretory protein LCCL domain c[ontaining] | |
| 6.20 | — | — | |
| 6.20 | SMYD2 | SET and MYND domain containing 2 | |
| -6.19 | YBX2 | Y box binding protein 2 | |
| 6.19 | FRZB | frizzled-related protein | |
| -6.19 | ARHGEF5 | Rho guanine nucleotide exchange factor (GEF) | |
| 6.18 | HOXA1 | homeobox A1 | |
| 6.18 | MAP2 | microtubule-associated protein 2 | |
| -6.18 | GAL3ST1 | galactose-3-O-sulfotransferase 1 | |
| -6.17 | — | — | |
| 6.17 | CRYBA1 | crystallin, beta A1 | |
| -6.16 | PRDM14 | PR domain containing 14 | |
| 6.16 | SYNE1 | spectrin repeat containing, nuclear envelope 1 | |
| -6.16 | — | — | |
| -6.15 | LOC440132 | LOC440132 | |
| -6.15 | NPW | neuropeptide W | |
| 6.14 | — | Clone 24626 mRNA sequence | |
| -6.13 | GUCA1A | guanylate cyclase activator 1A (retina) | |
| -6.13 | NUDT16P | nudix (nucleoside diphosphate linked moiety X) | |

| | | |
|---|---|---|
| 5.95 | CYP1B1 | cytochrome P450, family 1, subfamily B, polyp[eptide] |
| 5.95 | — | — |
| 5.95 | CDH11 | cadherin 11, type 2, OB-cadherin (osteoblast) |
| 5.94 | APCDD1 | adenomatosis polyposis coli down-regulated 1 |
| -5.94 | CXCL5 | chemokine (C-X-C motif) ligand 5 |
| 5.93 | — | — |
| 5.93 | — | — |
| -5.92 | FLJ20273 | RNA-binding protein |
| 5.92 | PALM2 | paralemmin 2 |
| -5.92 | HBA1 /// HBA2 | hemoglobin, alpha 1 /// hemoglobin, alpha 2 |
| -5.92 | — | MRNA; cDNA DKFZp667L064 (from clone DKF[Zp667L064]) |
| 5.91 | FRZB | frizzled-related protein |
| 5.91 | — | CDNA FLJ35396 fis, clone SKNSH2003483 |
| -5.91 | MAL2 | mal, T-cell differentiation protein 2 |
| 5.90 | MAB21L1 | mab-21-like 1 (C. elegans) |
| -5.90 | MARVELD2 | MARVEL domain containing 2 |
| -5.89 | PRSS8 | protease, serine, 8 (prostasin) |
| 5.89 | — | — |
| -5.89 | FLJ40125 | hypothetical protein FLJ40125 |
| 5.89 | TCF8 | transcription factor 8 (represses interleukin 2 e[nhancer]) |
| 5.88 | PKNOX2 | PBX/knotted 1 homeobox 2 |
| 5.88 | — | — |
| -5.88 | KDR | kinase insert domain receptor (a type III recept[or]) |
| 5.88 | PRELP | proline/arginine-rich end leucine-rich repeat pr[otein] |
| -5.87 | NR5A2 | nuclear receptor subfamily 5, group A, member |
| -5.86 | NR5A2 | nuclear receptor subfamily 5, group A, member |
| 5.86 | MGP | matrix Gla protein |
| 5.85 | MEF2C | MADS box transcription enhancer factor 2, pol[ypeptide] |
| 5.85 | THSD7A | Thrombospondin, type I, domain containing 7A |
| 5.84 | LOC284244 | hypothetical protein LOC284244 |
| 5.84 | BGN | biglycan |
| 5.83 | VCAM1 | vascular cell adhesion molecule 1 |
| 5.82 | IFIT5 | interferon-induced protein with tetratricopeptide |
| -5.82 | COBL | cordon-bleu homolog (mouse) |
| -5.81 | RAB17 | RAB17, member RAS oncogene family |
| 5.80 | FRZB | frizzled-related protein |
| -5.80 | HPGD | hydroxyprostaglandin dehydrogenase 15-(NAD) |
| -5.79 | FOXH1 | forkhead box H1 |
| -5.79 | EPHA1 | EPH receptor A1 |
| 5.79 | DKFZP686A01247 | hypothetical protein |
| -5.79 | TDH | L-threonine dehydrogenase |
| 5.78 | SNAI2 | snail homolog 2 (Drosophila) |
| -5.78 | EPB41L5 | Erythrocyte membrane protein band 4.1 like 5 |
| 5.78 | LRRC17 | leucine rich repeat containing 17 |
| 5.78 | DLX1 | distal-less homeobox 1 |
| 5.77 | EYA4 | Eyes absent homolog 4 (Drosophila) |
| 5.77 | HOXB7 | homeobox B7 |
| -5.77 | POU5F1 /// POU5F | POU domain, class 5, transcription factor 1 /// |
| 5.77 | LEF1 | lymphoid enhancer-binding factor 1 |
| -5.76 | EPS8L2 | EPS8-like 2 |
| 5.76 | — | — |
| -5.75 | — | — |
| 5.74 | HOXD13 | homeobox D13 |
| -5.73 | DPPA3 | developmental pluripotency associated 3 |
| -5.73 | GSTT2 | glutathione S-transferase theta 2 |
| -5.72 | — | Homo sapiens, clone IMAGE:3454042, mRNA |
| 5.72 | PAX3 | paired box gene 3 (Waardenburg syndrome 1) |
| 5.72 | — | — |
| 5.71 | RFX4 | regulatory factor X, 4 (influences HLA class II e[xpression]) |
| -5.71 | C1orf172 | chromosome 1 open reading frame 172 |
| -5.69 | RIT2 | Ras-like without CAAX 2 |
| -5.69 | LOC255480 | hypothetical protein LOC255480 |
| 5.69 | TGFBI | transforming growth factor, beta-induced, 68kD[a] |
| -5.68 | CYP2S1 | cytochrome P450, family 2, subfamily S, polyp[eptide] |
| 5.68 | — | — |
| -5.68 | EPB41L5 | erythrocyte membrane protein band 4.1 like 5 |
| -5.67 | EPPK1 | epiplakin 1 |
| 5.66 | — | — |
| -5.66 | ACSM3 | acyl-CoA synthetase medium-chain family mer |
| 5.65 | — | Homo sapiens, clone IMAGE:5019307, mRNA |
| -5.65 | GPR74 | G protein-coupled receptor 74 |
| 5.65 | — | — |
| 5.64 | FLJ20366 | hypothetical protein FLJ20366 |
| -5.64 | VSNL1 | visinin-like 1 |
| 5.63 | SOX5 | SRY (sex determining region Y)-box 5 |
| 5.63 | BMP5 | bone morphogenetic protein 5 |
| -5.62 | KLK8 | kallikrein-related peptidase 8 |
| 5.62 | RHOJ | ras homolog gene family, member J |
| -5.62 | FGF4 | fibroblast growth factor 4 (heparin secretory tra[nsforming]) |

Appendix 1

| Value | Gene | Description |
|---|---|---|
| -6.13 | ZNF141 | Zinc finger protein 141 |
| 6.13 | PRSS23 | Protease, serine, 23 |
| 6.12 | HOXA10 | homeobox A10 |
| -6.12 | HTATIP2 | HIV-1 Tat interactive protein 2, 30kDa |
| -6.12 | OCIAD2 | OCIA domain containing 2 |
| -6.12 | — | — |
| 6.12 | ELAVL3 | ELAV (embryonic lethal, abnormal vision, Dros |
| -6.12 | ACSM3 | acyl-CoA synthetase medium-chain family mer |
| 6.12 | LRRC17 | leucine rich repeat containing 17 |
| -6.11 | IL4R | interleukin 4 receptor |
| -6.11 | — | — |
| 6.11 | — | — |
| 6.11 | PDE1A | phosphodiesterase 1A, calmodulin-dependent |
| 6.10 | ABCC9 | ATP-binding cassette, sub-family C (CFTR/MR |
| -6.09 | C9orf64 | chromosome 9 open reading frame 64 |
| -6.08 | RBM35B | RNA binding motif protein 35B |
| 6.07 | HOXC10 | homeobox C10 |
| -6.07 | PHF11 /// RP13-36C | PHD finger protein 11 /// cancer/testis antigen |
| -6.07 | — | — |
| -6.08 | TANC | TPR domain, ankyrin-repeat and coiled-coil-co |
| -6.06 | EBF2 | early B-cell factor 2 |
| 6.04 | — | — |
| -6.04 | IFITM2 | interferon induced transmembrane protein 2 (1 |
| -6.04 | COBL | cordon-bleu homolog (mouse) |
| -6.03 | C1orf211 | chromosome 1 open reading frame 211 |
| -6.03 | ETS1 | v-ets erythroblastosis virus E26 oncogene hom |
| 6.02 | — | — |
| 6.02 | ZNF536 | zinc finger protein 536 |
| -6.02 | LECT1 | leukocyte cell derived chemotaxin 1 |
| -6.02 | FXYD5 | FXYD domain containing ion transport regulato |
| 6.01 | GPR85 | G protein-coupled receptor 85 |
| -6.00 | ATP2A3 | ATPase, Ca++ transporting, ubiquitous |
| -6.00 | CLDN10 | claudin 10 |
| -6.00 | SEMA6A | sema domain, transmembrane domain (TM), a |
| 5.99 | UGT2B4 | UDP glucuronosyltransferase 2 family, polypep |
| 5.99 | CRB1 | crumbs homolog 1 (Drosophila) |
| -5.99 | HSPA1A /// HSPA1 | heat shock 70kDa protein 1A /// heat shock 70 |
| 5.99 | FLJ21986 | hypothetical protein FLJ21986 |
| 5.98 | NDP | Norrie disease (pseudoglioma) |
| -5.97 | FLJ44186 | FLJ44186 protein |
| 5.97 | — | — |
| 5.96 | LOC143381 | hypothetical protein LOC143381 |
| 5.95 | — | CDNA clone IMAGE:5273964 |
| -5.95 | AXL | AXL receptor tyrosine kinase |
| 5.94 | MMRN1 | multimerin 1 |
| 5.94 | EMP1 | epithelial membrane protein 1 |
| -5.94 | — | — |
| 5.94 | ZBTB16 | zinc finger and BTB domain containing 16 |
| -5.94 | TFPI | tissue factor pathway inhibitor (lipoprotein-asso |
| 5.93 | ITGB8 | integrin, beta 8 |
| 5.92 | C4orf18 | chromosome 4 open reading frame 18 |
| -5.92 | ZD52F10 | dermokine |
| -5.91 | GALNT6 | UDP-N-acetyl-alpha-D-galactosamine:polypept |
| -5.91 | — | Transcribed locus |
| -5.90 | — | — |
| -5.90 | — | — |
| 5.90 | JAM2 | junctional adhesion molecule 2 |
| -5.90 | HAPLN1 | hyaluronan and proteoglycan link protein 1 |
| 5.90 | CXorf1 | chromosome X open reading frame 1 |
| -5.90 | NFIA | nuclear factor I/A |
| -5.89 | TAGLN | transgelin |
| 5.88 | — | — |
| 5.88 | MBNL2 | muscleblind-like 2 (Drosophila) |
| 5.88 | LHFP | lipoma HMGIC fusion partner |
| -5.88 | UTF1 | undifferentiated embryonic cell transcription fac |
| 5.88 | — | — |
| -5.87 | LOC728342 | Hypothetical protein LOC728342 |
| -5.86 | TNMD | tenomodulin |
| -5.86 | — | — |
| -5.86 | NR5A2 | nuclear receptor subfamily 5, group A, member |
| -5.85 | — | — |
| -5.85 | — | — |
| -5.84 | CYP2S1 | cytochrome P450, family 2, subfamily S, polype |
| -5.84 | DSP | Desmoplakin |
| -5.83 | ITGB1BP3 | integrin beta 1 binding protein 3 |
| 5.82 | DKFZP686A01247 | hypothetical protein |
| 5.82 | — | CDNA FLJ42405 fis, clone ASTRO3000474 |
| -5.81 | CBR3 | carbonyl reductase 3 |
| -5.81 | VSNL1 | visinin-like 1 |

| Value | Gene | Description |
|---|---|---|
| 5.59 | SLC8A3 | solute carrier family 8 (sodium-calcium exchan |
| -5.59 | SOX17 | SRY (sex determining region Y)-box 17 |
| 5.59 | LOC338773 | hypothetical protein LOC338773 |
| -5.57 | TPD52 | tumor protein D52 |
| -5.57 | CXCL3 | chemokine (C-X-C motif) ligand 3 |
| -5.56 | HBA2 | hemoglobin, alpha 2 /// hemoglobin, alpha 2 |
| -5.55 | — | — |
| 5.55 | MOXD1 | monooxygenase, DBH-like 1 |
| 5.55 | DKK2 | dickkopf homolog 2 (Xenopus laevis) |
| 5.55 | — | — |
| -5.55 | HDCMA18P | HDCMA18P protein |
| 5.54 | — | — |
| 5.54 | WIF1 | WNT inhibitory factor 1 |
| -5.52 | GLS2 | glutaminase 2 (liver, mitochondrial) |
| -5.51 | NR5A2 | nuclear receptor subfamily 5, group A, membe |
| 5.51 | BAALC | brain and acute leukemia, cytoplasmic |
| -5.51 | LOC157627 | hypothetical protein LOC157627 |
| -5.51 | — | — |
| 5.50 | WNT11 | wingless-type MMTV integration site family, me |
| -5.50 | FZD5 | frizzled homolog 5 (Drosophila) /// frizzled hom |
| -5.48 | — | MRNA full length insert cDNA clone EUROIMA |
| 5.48 | LSAMP | limbic system-associated membrane protein |
| 5.46 | C4orf18 | chromosome 4 open reading frame 18 |
| -5.45 | — | — |
| -5.45 | — | — |
| 5.45 | LOC145786 | hypothetical protein LOC145786 |
| 5.45 | HOXA2 | homeobox A2 |
| -5.44 | LECT1 | leukocyte cell derived chemotaxin 1 |
| -5.43 | TNFSF11 | tumor necrosis factor (ligand) superfamily, men |
| 5.42 | DCN | decorin |
| -5.42 | PPP1R16B | protein phosphatase 1, regulatory (inhibitor) su |
| -5.41 | CR1 /// CR1L | complement component (3b/4b) receptor 1, inc |
| -5.41 | FLJ20449 | hypothetical protein FLJ20449 |
| 5.41 | — | — |
| -5.40 | KLK10 | kallikrein-related peptidase 10 |
| 5.40 | TMEM16C | transmembrane protein 16C |
| 5.40 | — | — |
| 5.40 | FAP | fibroblast activation protein, alpha |
| -5.39 | — | — |
| 5.39 | — | CDNA FLJ34815 fis, clone NT2NE2007786 |
| 5.39 | — | — |
| -5.39 | PIK3R5 | phosphoinositide-3-kinase, regulatory subunit 5 |
| -5.38 | GNA14 | guanine nucleotide binding protein (G protein), |
| 5.38 | HOXA11S | Homeo box A11, antisense |
| 5.37 | SOX6 | SRY (sex determining region Y)-box 6 |
| 5.37 | — | — |
| 5.37 | LHFP | lipoma HMGIC fusion partner |
| -5.36 | FOXA2 | forkhead box A2 |
| -5.36 | — | Homo sapiens, Similar to otoconin 90, clone IM |
| 5.36 | HOXB7 | homeobox B7 |
| -5.35 | ZD52F10 | dermokine |
| -5.35 | GNAS | GNAS complex locus |
| -5.34 | F11R | F11 receptor |
| 5.34 | — | CDNA clone IMAGE:5287047 |
| -5.33 | FGFR4 | fibroblast growth factor receptor 4 |
| 5.33 | — | — |
| -5.33 | MUC3B | mucin 3B, cell surface associated |
| 5.32 | S100B | S100 calcium binding protein B |
| -5.31 | LOC112703 | hypothetical protein BC004941 |
| -5.30 | ARHGAP8 /// LOC5 | Rho GTPase activating protein 8 /// PRR5-ARH |
| 5.30 | — | CDNA FLJ35396 fis, clone SKNSH2003483 |
| -5.30 | CLDN6 | claudin 6 |
| -5.30 | MGC16044 | hypothetical protein MGC16044 |
| 5.29 | NDST4 | N-deacetylase/N-sulfotransferase (heparan glu |
| -5.28 | SPINT2 | serine peptidase inhibitor, Kunitz type, 2 |
| 5.28 | PDGFRB | platelet-derived growth factor receptor, beta po |
| 5.27 | — | — |
| -5.26 | FZD5 | frizzled homolog 5 (Drosophila) |
| -5.26 | — | — |
| 5.24 | — | — |
| 5.24 | HOXB7 | homeobox B7 |
| 5.24 | CACNA1C | calcium channel, voltage-dependent, L type, al |
| 5.23 | — | — |
| -5.23 | — | — |
| 5.23 | HOXD4 | homeobox D4 |
| 5.23 | — | — |
| -5.22 | PRSS16 | protease, serine, 16 (thymus) |
| -5.22 | MUC4 | mucin 4, cell surface associated |
| 5.22 | ANGPTL1 | angiopoietin-like 1 /// angiopoietin-like 1 |

Appendix 1

| Value | Symbol | Description |
|---|---|---|
| -5.81 | SLC7A7 | solute carrier family 7 (cationic amino acid tran |
| -5.80 | GLS2 | glutaminase 2 (liver, mitochondrial) |
| -5.80 | HIST1H2BD | Histone cluster 1, H2bd |
| -5.80 | — | — |
| 5.79 | — | — |
| -5.77 | TFPI | tissue factor pathway inhibitor (lipoprotein-assc |
| 5.77 | LIX1 | Lix1 homolog (mouse) |
| -5.77 | ARHGAP8 /// LOC5 | Rho GTPase activating protein 8 /// PRR5-ARH |
| 5.77 | RGS4 | regulator of G-protein signalling 4 |
| 5.76 | PKNOX2 | PBX/knotted 1 homeobox 2 |
| -5.76 | FOXA2 | forkhead box A2 |
| 5.75 | DDC | dopa decarboxylase (aromatic L-amino acid de |
| -5.74 | MCOLN3 | mucolipin 3 |
| -5.74 | LOC645745 | metallothionein 1H-like protein |
| -5.74 | GUCA1A | guanylate cyclase activator 1A (retina) |
| 5.73 | GLIS3 | GLIS family zinc finger 3 |
| -5.73 | — | — |
| -5.73 | OLFML3 | olfactomedin-like 3 |
| -5.73 | GLS2 | glutaminase 2 (liver, mitochondrial) |
| -5.73 | — | Transcribed locus, weakly similar to NP_00101 |
| -5.72 | MUC3B | mucin 3B, cell surface associated |
| -5.72 | — | — |
| 5.72 | BAALC | brain and acute leukemia, cytoplasmic |
| 5.68 | TCF8 | transcription factor 8 (represses interleukin 2 e |
| 5.68 | C8orf4 | chromosome 8 open reading frame 4 |
| 5.68 | HOXB9 | homeobox B9 |
| 5.68 | MTTP | microsomal triglyceride transfer protein |
| 5.67 | BCHE | butyrylcholinesterase |
| 5.67 | FHOD3 | formin homology 2 domain containing 3 |
| -5.67 | EDG8 | endothelial differentiation, sphingolipid G-prote |
| -5.67 | FGD5 | FYVE, RhoGEF and PH domain containing 5 |
| -5.66 | HBA2 | hemoglobin, alpha 2 /// hemoglobin, alpha 2 |
| 5.66 | COL2A1 | collagen, type II, alpha 1 (primary osteoarthritis |
| -5.66 | — | — |
| -5.66 | KLK8 | kallikrein-related peptidase 8 |
| 5.66 | — | — |
| 5.66 | FRZB | frizzled-related protein |
| -5.65 | QPCT | glutaminyl-peptide cyclotransferase (glutaminy |
| 5.64 | PLAGL1 | Pleiomorphic adenoma gene-like 1 |
| -5.64 | APOE | apolipoprotein E |
| 5.64 | — | CDNA FLJ11723 fis, clone HEMBA1005314 |
| 5.64 | FLJ25694 | hypothetical protein FLJ25694 |
| -5.64 | SCNN1B | sodium channel, nonvoltage-gated 1, beta (Lid |
| -5.64 | IRF6 | interferon regulatory factor 6 |
| -5.63 | — | — |
| -5.63 | — | — |
| -5.63 | C20orf160 | chromosome 20 open reading frame 160 |
| -5.63 | ABCG2 | ATP-binding cassette, sub-family G (WHITE), |
| 5.63 | KIF1A | Kinesin family member 1A |
| 5.63 | LOC284244 | hypothetical protein LOC284244 |
| 5.62 | SCN3B | sodium channel, voltage-gated, type III, beta |
| -5.62 | IGSF21 | immunoglobin superfamily, member 21 |
| 5.62 | FOLH1 | folate hydrolase (prostate-specific membrane a |
| -5.62 | LOC728377 | similar to rho guanine nucleotide exchange fac |
| -5.61 | SRY | sex determining region Y |
| -5.61 | ACSM3 | acyl-CoA synthetase medium-chain family mer |
| -5.61 | FLT1 | Fms-related tyrosine kinase 1 (vascular endoth |
| -5.61 | PPP1R1A | protein phosphatase 1, regulatory (inhibitor) su |
| 5.61 | PLEKHG1 | pleckstrin homology domain containing, family |
| -5.60 | — | Transcribed locus, strongly similar to XP_5296 |
| -5.60 | KDR | kinase insert domain receptor (a type III recept |
| -5.59 | MAFB | v-maf musculoaponeurotic fibrosarcoma oncog |
| -5.59 | — | — |
| 5.58 | IFIT5 | interferon-induced protein with tetratricopeptid |
| -5.58 | LRRC2 | leucine rich repeat containing 2 |
| 5.58 | — | — |
| 5.57 | SCN3A | sodium channel, voltage-gated, type III, alpha |
| 5.57 | HOXA2 | homeobox A2 |
| 5.56 | PRDM16 | PR domain containing 16 |
| 5.56 | FABP7 | fatty acid binding protein 7, brain |
| 5.55 | NR2F1 | nuclear receptor subfamily 2, group F, member |
| 5.55 | LUM | lumican |
| -5.55 | CXCL12 | chemokine (C-X-C motif) ligand 12 (stromal ce |
| -5.54 | EPS8L2 | EPS8-like 2 |
| 5.54 | TEX10 | Testis expressed sequence 10 |
| 5.53 | PCDH17 | protocadherin 17 |
| -5.53 | SPIB | Spi-B transcription factor (Spi-1/PU.1 related) / |
| -5.52 | DPPA3 | developmental pluripotency associated 3 |
| 5.52 | SOX1 | SRY (sex determining region Y)-box 1 |
| 5.21 | FLJ32447 | hypothetical protein LOC151278 |
| -5.21 | FLJ20273 | RNA-binding protein |
| -5.21 | TLE2 | transducin-like enhancer of split 2 (E(sp1) hom |
| -5.19 | SH2D3A | SH2 domain containing 3A |
| 5.19 | RUNX2 | runt-related transcription factor 2 |
| -5.19 | ATP2A3 | ATPase, Ca++ transporting, ubiquitous |
| 5.19 | CDH11 | cadherin 11, type 2, OB-cadherin (osteoblast) |
| 5.18 | GREM1 | gremlin 1, cysteine knot superfamily, homolog |
| -5.18 | — | — |
| 5.18 | EPHA3 | EPH receptor A3 |
| -5.18 | IL8 | interleukin 8 |
| 5.18 | ST8SIA2 | ST8 alpha-N-acetyl-neuraminide alpha-2,8-sial |
| 5.17 | — | — |
| 5.17 | WDR52 | WD repeat domain 52 |
| -5.17 | LOC285547 | hypothetical protein LOC285547 |
| -5.17 | FAM124A | family with sequence similarity 124A |
| 5.16 | C16orf30 | chromosome 16 open reading frame 30 |
| -5.16 | SHANK2 | SH3 and multiple ankyrin repeat domains 2 |
| -5.15 | — | — |
| -5.15 | HBA1 /// HBA2 | hemoglobin, alpha 1 /// hemoglobin, alpha 1 /// |
| -5.15 | LOC136306 | hypothetical protein LOC136306 |
| -5.14 | MARVELD3 | MARVEL domain containing 3 |
| 5.14 | FBXL21 | F-box and leucine-rich repeat protein 21 |
| 5.14 | EMP1 | epithelial membrane protein 1 |
| -5.14 | GATA6 | GATA binding protein 6 |
| -5.14 | — | Transcribed locus |
| -5.13 | C10orf96 | chromosome 10 open reading frame 96 |
| 5.12 | MMRN1 | multimerin 1 |
| -5.11 | — | — |
| 5.11 | MSRB3 | methionine sulfoxide reductase B3 |
| -5.11 | ZNF206 | zinc finger protein 206 |
| 5.11 | — | — |
| -5.11 | LOC645619 /// LOC | similar to Adenylate kinase isoenzyme 4, mitoc |
| -5.10 | CACNA1A | Calcium channel, voltage-dependent, P/Q type |
| 5.10 | KIAA1713 | KIAA1713 |
| 5.09 | MEF2C | MADS box transcription enhancer factor 2, pol |
| -5.09 | — | — |
| 5.09 | ST8SIA4 | ST8 alpha-N-acetyl-neuraminide alpha-2,8-sial |
| -5.08 | ANTXR1 | anthrax toxin receptor 1 |
| 5.07 | EMX2 | empty spiracles homolog 2 (Drosophila) |
| 5.07 | HOXA11S | homeo box A11, antisense |
| 5.07 | GPR56 | G protein-coupled receptor 56 |
| 5.06 | TNFRSF11B | tumor necrosis factor receptor superfamily, me |
| -5.06 | CD1D | CD1d molecule /// CD1d molecule |
| -5.05 | F11R | F11 receptor |
| 5.05 | TIMP3 | TIMP metallopeptidase inhibitor 3 (Sorsby fund |
| 5.04 | ZFPM2 | zinc finger protein, multitype 2 |
| 5.04 | LEF1 | lymphoid enhancer-binding factor 1 |
| 5.03 | ITGA4 | integrin, alpha 4 (antigen CD49D, alpha 4 subu |
| 5.03 | NPR3 | natriuretic peptide receptor C/guanylate cyclas |
| 5.03 | EDNRA | endothelin receptor type A |
| -5.03 | GLDC | glycine dehydrogenase (decarboxylating) |
| -5.03 | CLDN6 | claudin 6 |
| 5.02 | DDR2 | Discoidin domain receptor family, member 2 |
| 5.02 | DUSP7 | dual specificity phosphatase 7 |
| -5.02 | LOC440132 | LOC440132 |
| -5.01 | — | — |
| -5.01 | CPZ | carboxypeptidase Z /// carboxypeptidase Z |
| 5.01 | WDR78 | WD repeat domain 78 |
| -4.99 | C9orf135 | chromosome 9 open reading frame 135 |
| -4.99 | CR1L | complement component (3b/4b) receptor 1-like |
| -4.99 | GCNT2 | glucosaminyl (N-acetyl) transferase 2, I-branch |
| 4.99 | PDGFRA | platelet-derived growth factor receptor, alpha p |
| -4.99 | CER1 | cerberus 1, cysteine knot superfamily, homolog |
| -4.99 | — | — |
| 4.99 | BNC1 | basonuclin 1 |
| 4.99 | SLITRK6 | SLIT and NTRK-like family, member 6 |
| 4.98 | NR2F2 | nuclear receptor subfamily 2, group F, member |
| 4.98 | GAS1 | growth arrest-specific 1 |
| 4.97 | — | — |
| -4.97 | RBM35B | RNA binding motif protein 35B |
| -4.96 | KLKB1 | kallikrein B, plasma (Fletcher factor) 1 |
| -4.96 | KLF4 | Kruppel-like factor 4 (gut) |
| 4.96 | PTPRN2 | protein tyrosine phosphatase, receptor type, N |
| 4.96 | F2RL1 | coagulation factor II (thrombin) receptor-like 1 |
| 4.96 | BNC1 | basonuclin 1 |
| -4.96 | ASPHD1 | aspartate beta-hydroxylase domain containing |
| 4.95 | ELTD1 | EGF, latrophilin and seven transmembrane dor |
| -4.95 | KRT8 | keratin 8 /// keratin 8 |

Appendix 1

| Value | Gene | Description |
|---|---|---|
| 5.51 | ASCL1 | achaete-scute complex homolog 1 (Drosophila) |
| -5.51 | FZD5 | frizzled homolog 5 (Drosophila) |
| 5.51 | FLJ37440 | hypothetical protein FLJ37440 |
| -5.50 | — | — |
| 5.50 | MAP6 | microtubule-associated protein 6 |
| -5.50 | FLJ22662 | hypothetical protein FLJ22662 |
| -5.50 | ABCC13 | ATP-binding cassette, sub-family C (CFTR/MR |
| -5.50 | LOC643224 | similar to tubulin, beta 8 |
| -5.49 | MT1X | metallothionein 1X |
| -5.49 | SH2D3A | SH2 domain containing 3A |
| -5.49 | LOC286044 | hypothetical protein LOC286044 |
| 5.49 | DCC | deleted in colorectal carcinoma |
| -5.49 | CARD10 | caspase recruitment domain family, member 10 |
| -5.49 | C1orf85 | chromosome 1 open reading frame 85 |
| -5.49 | C19orf4 | chromosome 19 open reading frame 4 |
| -5.47 | TFAP2C | transcription factor AP-2 gamma (activating en |
| 5.47 | PLAGL1 | pleiomorphic adenoma gene-like 1 |
| 5.46 | PDE1A | phosphodiesterase 1A, calmodulin-dependent |
| -5.45 | TFCP2L1 | Transcription factor CP2-like 1 |
| 5.45 | TKTL1 | transketolase-like 1 |
| -5.45 | SLC16A5 | solute carrier family 16, member 5 (monocarbo |
| 5.44 | — | — |
| 5.44 | — | — |
| -5.44 | PERP | PERP, TP53 apoptosis effector |
| 5.44 | — | Transcribed locus |
| -5.43 | MICB | MHC class I polypeptide-related sequence E |
| -5.43 | — | CDNA FLJ35259 fis, clone PROST2004251 |
| 5.43 | MEIS1 | Meis1, myeloid ecotropic viral integration site 1 |
| -5.43 | MARVELD3 | MARVEL domain containing 3 |
| 5.43 | CYBA | cytochrome b-245, alpha polypeptide |
| 5.43 | KCNJ6 | potassium inwardly-rectifying channel, subfami |
| 5.41 | ARL4C | ADP-ribosylation factor-like 4C |
| -5.41 | — | — |
| -5.40 | IL1B | interleukin 1, beta |
| 5.40 | CDKN2B | cyclin-dependent kinase inhibitor 2B (p15, inhib |
| 5.40 | CHN2 | chimerin (chimaerin) 2 |
| -5.40 | — | — |
| -5.40 | FBN3 | fibrillin 3 |
| 5.39 | FLJ10748 | Hypothetical protein FLJ10748 |
| 5.39 | ZFHX1B | zinc finger homeobox 1b |
| -5.39 | HBA1 /// HBA2 | hemoglobin, alpha 1 /// hemoglobin, alpha 2 |
| -5.38 | FLJ21963 | FLJ21963 protein |
| -5.38 | C20orf42 | chromosome 20 open reading frame 42 |
| 5.38 | KIAA0895 | KIAA0895 protein |
| 5.37 | SCRG1 | scrapie responsive protein 1 |
| 5.37 | IRX5 | iroquois homeobox protein 5 |
| 5.37 | TNFRSF19 | tumor necrosis factor receptor superfamily, me |
| 5.37 | MYBPC1 | myosin binding protein C, slow type |
| 5.37 | SORBS2 | sorbin and SH3 domain containing 2 |
| -5.36 | — | — |
| -5.36 | LOC112703 | hypothetical protein BC004941 |
| 5.36 | SOX5 | SRY (sex determining region Y)-box 5 |
| -5.35 | TLE2 | transducin-like enhancer of split 2 (E(sp1) hom |
| 5.35 | IL23A | interleukin 23, alpha subunit p19 |
| -5.35 | CYP2B7P1 | cytochrome P450, family 2, subfamily B, polype |
| -5.35 | HHEX | homeobox, hematopoietically expressed |
| 5.35 | ARL4C | ADP-ribosylation factor-like 4C |
| 5.34 | DACH1 | dachshund homolog 1 (Drosophila) |
| -5.34 | SOX15 | SRY (sex determining region Y)-box 15 |
| 5.34 | MGC16044 | hypothetical protein MGC16044 |
| -5.34 | SEMG1 | semenogelin I |
| 5.34 | LRIG1 | leucine-rich repeats and immunoglobulin-like d |
| 5.33 | GPM6A | glycoprotein M6A |
| 5.33 | FABP7 | fatty acid binding protein 7, brain |
| -5.33 | WDR72 | WD repeat domain 72 |
| -5.32 | — | — |
| -5.31 | — | — |
| -5.31 | MT1E | metallothionein 1E (functional) |
| -5.31 | LASS4 | LAG1 homolog, ceramide synthase 4 (S. cerev |
| -5.30 | FLI1 | Friend leukemia virus integration 1 |
| 5.29 | KCNJ16 | potassium inwardly-rectifying channel, subfami |
| -5.29 | ETS1 | v-ets erythroblastosis virus E26 oncogene hom |
| -5.29 | MARVELD3 | MARVEL domain containing 3 |
| -5.29 | COL1A1 | collagen, type I, alpha 1 |
| -5.29 | MUC4 | mucin 4, cell surface associated |
| -5.28 | TMEM125 | transmembrane protein 125 |
| 5.28 | PDE1A | phosphodiesterase 1A, calmodulin-dependent |
| 5.28 | TFAP2B | transcription factor AP-2 beta (activating enhan |
| -5.28 | NFIA | nuclear factor I/A |
| 4.95 | — | CDNA FLJ11723 fis, clone HEMBA1005314 |
| -4.95 | — | — |
| 4.94 | RP5-875H10.1 | SAM domain containing 1 |
| 4.94 | ASTN1 | astrotactin 1 |
| 4.94 | — | Transcribed locus |
| 4.94 | ITGA4 | integrin, alpha 4 (antigen CD49D, alpha 4 subu |
| 4.93 | SCN3A | sodium channel, voltage-gated, type III, alpha |
| 4.92 | F2RL2 | coagulation factor II (thrombin) receptor-like 2 |
| -4.92 | IFITM1 | interferon induced transmembrane protein 1 (9 |
| 4.92 | PLAGL1 | pleiomorphic adenoma gene-like 1 |
| 4.91 | — | CDNA FLJ38181 fis, clone FCBBF1000125 |
| 4.91 | — | — |
| 4.91 | LUM | Lumican |
| 4.90 | DACH1 | dachshund homolog 1 (Drosophila) |
| 4.90 | MAP2 | microtubule-associated protein 2 |
| 4.90 | THSD7A | thrombospondin, type I, domain containing 7A |
| -4.89 | ESPN | espin |
| 4.88 | LONP2 | Lon peptidase 2, peroxisomal |
| -4.88 | FOXH1 | forkhead box H1 |
| 4.88 | NT5E | 5'-nucleotidase, ecto (CD73) |
| -4.88 | LOC202451 | hypothetical protein LOC202451 |
| -4.86 | — | — |
| -4.86 | — | — |
| -4.85 | — | — |
| 4.85 | HOXB9 | homeobox B9 |
| -4.85 | — | MRNA; cDNA DKFZp686L0310 (from clone DK |
| -4.85 | TPD52 | tumor protein D52 |
| 4.84 | FAM125B | family with sequence similarity 125, member B |
| 4.84 | — | Transcribed locus |
| 4.83 | — | — |
| -4.83 | FLJ20449 | hypothetical protein FLJ20449 |
| 4.82 | — | — |
| 4.82 | — | Transcribed locus |
| -4.82 | — | — |
| -4.81 | HBA1 /// HBA2 | hemoglobin, alpha 1 /// hemoglobin, alpha 1 /// |
| -4.81 | EDG7 | Endothelial differentiation, lysophosphatidic aci |
| -4.81 | CLDN3 | claudin 3 |
| -4.80 | TMPRSS11E /// LO | transmembrane protease, serine 11E /// similar |
| 4.80 | C5 | complement component 5 |
| -4.80 | ANK3 | Ankyrin 3, node of Ranvier (ankyrin G) |
| 4.80 | — | Transcribed locus |
| 4.80 | FKBP7 | FK506 binding protein 7 |
| 4.80 | MBD2 | methyl-CpG binding domain protein 2 |
| -4.79 | PODXL | podocalyxin-like |
| 4.79 | FLJ39155 | hypothetical protein FLJ39155 |
| -4.78 | — | — |
| -4.78 | SLC27A6 | solute carrier family 27 (fatty acid transporter), |
| 4.78 | TEX10 | Testis expressed sequence 10 |
| 4.78 | BCHE | butyrylcholinesterase |
| -4.78 | — | — |
| 4.78 | FBN1 | fibrillin 1 |
| 4.77 | — | — |
| -4.77 | SOX15 | SRY (sex determining region Y)-box 15 |
| 4.77 | ROPN1 | ropporin, rhophilin associated protein 1 |
| 4.76 | IGFBP5 | insulin-like growth factor binding protein 5 |
| -4.75 | — | — |
| 4.74 | BMP5 | bone morphogenetic protein 5 |
| -4.74 | — | — |
| -4.74 | — | — |
| 4.74 | IGFBP5 | insulin-like growth factor binding protein 5 |
| -4.74 | — | — |
| 4.73 | — | CDNA clone IMAGE:4792693 |
| 4.72 | HOXD13 | homeobox D13 |
| -4.72 | ABCG2 | ATP-binding cassette, sub-family G (WHITE), m |
| 4.71 | EDNRA | endothelin receptor type A |
| 4.70 | — | Tetraspanin 11 |
| -4.70 | — | — |
| 4.70 | WNT5A | Wingless-type MMTV integration site family, me |
| 4.69 | PRDM16 | PR domain containing 16 |
| -4.69 | — | — |
| 4.69 | DGKH | Diacylglycerol kinase, eta |
| 4.68 | — | — |
| 4.68 | ZFHX1B | zinc finger homeobox 1b |
| 4.68 | — | — |
| 4.68 | LONRF2 | LON peptidase N-terminal domain and ring fing |
| -4.67 | CRLF1 | cytokine receptor-like factor 1 |
| 4.67 | GUCY1A3 | guanylate cyclase 1, soluble, alpha 3 |
| 4.66 | CYP1B1 | cytochrome P450, family 1, subfamily B, polype |

Appendix 1

| | | | |
|---|---|---|---|
| -5.27 | EPPK1 | epiplakin 1 | |
| 5.27 | GPM6A | glycoprotein M6A | |
| 5.26 | ZNF287 | zinc finger protein 287 | |
| -5.26 | FXYD5 | FXYD domain containing ion transport regulat[or] | |
| -5.25 | MATK | megakaryocyte-associated tyrosine kinase | |
| -5.25 | SLFN5 | schlafen family member 5 | |
| -5.25 | ZNF560 | zinc finger protein 560 | |
| -5.24 | ANXA3 | annexin A3 | |
| 5.24 | CDKN2A | cyclin-dependent kinase inhibitor 2A (melanoma[) | |
| -5.24 | TRDN | triadin | |
| -5.24 | TLE2 | transducin-like enhancer of split 2 (E(sp1) hom[olog] | |
| -5.23 | FLJ31204 | hypothetical protein FLJ31204 | |
| -5.23 | CER1 | cerberus 1, cysteine knot superfamily, homolog | |
| -5.22 | GPR160 | G protein-coupled receptor 160 | |
| -5.22 | BAMBI | BMP and activin membrane-bound inhibitor ho[molog] | |
| -5.22 | MAGEA4 | melanoma antigen family A, 4 | |
| -5.22 | — | MRNA; cDNA DKFZp667L064 (from clone DKF[Z...] | |
| 5.22 | — | — | |
| 5.21 | — | — | |
| -5.21 | — | MRNA full length insert cDNA clone EUROIMA[GE...] | |
| -5.21 | — | — | |
| 5.21 | FOLH1 | folate hydrolase (prostate-specific membrane a[ntigen] | |
| 5.20 | GRIK2 | glutamate receptor, ionotropic, kainate 2 | |
| -5.20 | WFDC2 | WAP four-disulfide core domain 2 | |
| 5.20 | PAX6 | paired box gene 6 (aniridia, keratitis) | |
| -5.20 | IL15 | interleukin 15 | |
| -5.20 | ITM2A | integral membrane protein 2A | |
| 5.19 | C21orf34 | chromosome 21 open reading frame 34 | |
| -5.19 | DSCR1L2 | Down syndrome critical region gene 1-like 2 | |
| 5.19 | — | MRNA; cDNA DKFZp564N1116 (from clone D[K...] | |
| 5.19 | SLITRK2 | SLIT and NTRK-like family, member 2 | |
| 5.18 | SPARCL1 | SPARC-like 1 (mast9, hevin) | |
| -5.18 | ESPN | espin | |
| 5.18 | — | — | |
| -5.18 | HAS2 | Hyaluronan synthase 2 | |
| 5.18 | A2M | alpha-2-macroglobulin | |
| 5.18 | C1QTNF3 | C1q and tumor necrosis factor related protein 3 | |
| 5.18 | COL14A1 | collagen, type XIV, alpha 1 (undulin) | |
| -5.17 | LAMA2 | laminin, alpha 2 (merosin, congenital muscular | |
| -5.16 | — | — | |
| -5.16 | — | — | |
| -5.16 | EDG7 | Endothelial differentiation, lysophosphatidic aci[d] | |
| -5.16 | PDGFA | platelet-derived growth factor alpha polypeptide | |
| 5.16 | — | — | |
| 5.16 | ASCL1 | achaete-scute complex homolog 1 (Drosophila) | |
| -5.16 | — | — | |
| 5.16 | — | CDNA FLJ33585 fis, clone BRAMY2012163 | |
| 5.15 | LOC387856 | similar to expressed sequence AI836003 | |
| -5.15 | CHST8 | carbohydrate (N-acetylgalactosamine 4-0) sulf[o] | |
| 5.15 | CAMK1G | calcium/calmodulin-dependent protein kinase I[G] | |
| 5.14 | NCAM1 | neural cell adhesion molecule 1 | |
| 5.14 | GDF3 | growth differentiation factor 3 | |
| -5.14 | TNNI3 | troponin I type 3 (cardiac) | |
| 5.14 | GALNT14 | UDP-N-acetyl-alpha-D-galactosamine:polypept[ide] | |
| -5.14 | GATA6 | GATA binding protein 6 | |
| 5.13 | NR2F2 | nuclear receptor subfamily 2, group F, membe[r] | |
| -5.13 | HPGD | hydroxyprostaglandin dehydrogenase 15-(NAD | |
| 5.13 | ABAT | 4-aminobutyrate aminotransferase | |
| 5.13 | PSMAL | growth-inhibiting protein 26 | |
| 5.13 | FAM49A | family with sequence similarity 49, member A | |
| -5.12 | — | — | |
| -5.12 | COBL | cordon-bleu homolog (mouse) | |
| -5.12 | CLDN3 | claudin 3 | |
| 5.11 | SPAG6 | sperm associated antigen 6 | |
| 5.11 | FAM125B | family with sequence similarity 125, member B | |
| -5.11 | APOBEC3G | apolipoprotein B mRNA editing enzyme, cataly[tic] | |
| 5.11 | — | Transcribed locus, moderately similar to XP_4[...] | |
| 5.10 | — | — | |
| -5.09 | NR5A2 | nuclear receptor subfamily 5, group A, membe[r] | |
| -5.09 | TBX5 | T-box 5 | |
| -5.09 | ST14 | suppression of tumorigenicity 14 (colon carcin[o] | |
| -5.09 | HCG11 | HLA complex group 11 | |
| 5.09 | LHFP | Lipoma HMGIC fusion partner | |
| -5.08 | SLC16A5 | solute carrier family 16, member 5 (monocarbo[xylate] | |
| 5.08 | ELAVL3 | ELAV (embryonic lethal, abnormal vision, Dros[ophila] | |
| 5.07 | — | CDNA FLJ37333 fis, clone BRAMY2020106 | |
| -5.07 | HBA1 /// HBA2 | hemoglobin, alpha 1 /// hemoglobin, alpha 1 /// | |
| -5.07 | LPPR4 | plasticity related gene 1 | |
| -5.06 | PTRF | polymerase I and transcript release factor | |

| | | | |
|---|---|---|---|
| -4.66 | SCNN1G | sodium channel, nonvoltage-gated 1, gamma | |
| -4.65 | KRT18 | keratin 18 | |
| -4.65 | KLF5 | Kruppel-like factor 5 (intestinal) | |
| 4.65 | STK32B | serine/threonine kinase 32B | |
| -4.65 | FAM124A | family with sequence similarity 124A | |
| -4.65 | C1orf210 | chromosome 1 open reading frame 210 | |
| 4.65 | TBC1D9 | TBC1 domain family, member 9 (with GRAM d[omain] | |
| 4.64 | VASH1 | vasohibin 1 | |
| 4.64 | HOXD9 | homeobox D9 | |
| 4.63 | OLFML1 | olfactomedin-like 1 | |
| 4.63 | PRELP | proline/arginine-rich end leucine-rich repeat pr[o] | |
| -4.63 | DENND1C | DENN/MADD domain containing 1C | |
| 4.62 | CST3 | Cystatin C (amyloid angiopathy and cerebral h[emorrhage] | |
| -4.62 | — | Transcribed locus | |
| 4.61 | GSTM3 | glutathione S-transferase M3 (brain) | |
| 4.61 | CX3CR1 | chemokine (C-X3-C motif) receptor 1 | |
| -4.60 | ANXA3 | annexin A3 | |
| 4.60 | — | — | |
| -4.60 | ARTN | artemin | |
| 4.60 | TNS1 | tensin 1 | |
| -4.60 | CD9 | CD9 molecule | |
| 4.59 | MEF2C | MADS box transcription enhancer factor 2, pol[y] | |
| -4.59 | — | — | |
| 4.59 | — | CDNA FLJ42405 fis, clone ASTRO3000474 | |
| 4.59 | — | — | |
| -4.58 | STC2 | stanniocalcin 2 | |
| -4.58 | IFITM1 | interferon induced transmembrane protein 1 (9[-27] | |
| -4.57 | HBA1 /// HBA2 | hemoglobin, alpha 1 /// hemoglobin, alpha 1 /// | |
| 4.56 | — | Clone 23786 mRNA sequence | |
| -4.56 | LRRC2 | leucine rich repeat containing 2 | |
| 4.56 | FLJ37440 | hypothetical protein FLJ37440 | |
| 4.56 | VASH1 | vasohibin 1 | |
| 4.56 | MEIS1 | Meis1, myeloid ecotropic viral integration site 1 | |
| -4.56 | IL23A | interleukin 23, alpha subunit p19 | |
| 4.56 | PLAGL1 | pleiomorphic adenoma gene-like 1 | |
| -4.55 | LRRC2 | leucine rich repeat containing 2 | |
| -4.55 | SERPINB9 | serpin peptidase inhibitor, clade B (ovalbumin), | |
| 4.55 | — | — | |
| -4.54 | — | MRNA full length insert cDNA clone EUROIMA[GE] | |
| -4.53 | LOC138255 | OTTHUMP00000021439 | |
| 4.53 | — | CDNA FLJ34826 fis, clone NT2NE2008803 | |
| -4.53 | PDLIM1 | PDZ and LIM domain 1 (elfin) | |
| -4.53 | — | Homo sapiens, clone IMAGE:4469683, mRNA | |
| 4.53 | LOC284033 | hypothetical protein LOC284033 | |
| 4.53 | LHX2 | LIM homeobox 2 | |
| -4.52 | TPD52 | tumor protein D52 | |
| 4.52 | PKNOX2 | PBX/knotted 1 homeobox 2 | |
| -4.52 | VSNL1 | visinin-like 1 | |
| -4.52 | DPPA4 | developmental pluripotency associated 4 | |
| 4.52 | — | Transcribed locus, weakly similar to XP_52063[...] | |
| -4.51 | GABRP | gamma-aminobutyric acid (GABA) A receptor, | |
| -4.51 | NETO1 | neuropilin (NRP) and tolloid (TLL)-like 1 | |
| -4.51 | HTR3A | 5-hydroxytryptamine (serotonin) receptor 3A | |
| 4.51 | LOC340061 | hypothetical protein LOC340061 | |
| -4.50 | HOOK1 | hook homolog 1 (Drosophila) | |
| 4.50 | PRELP | proline/arginine-rich end leucine-rich repeat pr[o] | |
| -4.50 | — | — | |
| 4.50 | GREM1 | gremlin 1, cysteine knot superfamily, homolog | |
| -4.49 | ITGB1BP3 | integrin beta 1 binding protein 3 | |
| 4.49 | MSRB3 | methionine sulfoxide reductase B3 | |
| 4.49 | NT5E | 5'-nucleotidase, ecto (CD73) | |
| 4.49 | RHOJ | ras homolog gene family, member J | |
| -4.49 | — | — | |
| 4.48 | — | CDNA clone IMAGE:5273964 | |
| 4.48 | ZBTB16 | zinc finger and BTB domain containing 16 | |
| -4.48 | CACNB2 | calcium channel, voltage-dependent, beta 2 su[bunit] | |
| 4.48 | NCAM1 | neural cell adhesion molecule 1 | |
| 4.48 | — | — | |
| -4.47 | — | Full-length cDNA clone CS0DC002YA18 of Ne[...] | |
| 4.47 | ADAM12 | ADAM metallopeptidase domain 12 (meltrin alp[ha] | |
| 4.47 | LRRC4B | leucine rich repeat containing 4B | |
| 4.46 | — | — | |
| -4.45 | F11R | F11 receptor | |
| 4.45 | GRM3 | glutamate receptor, metabotropic 3 | |
| 4.45 | SLC25A21 | Solute carrier family 25 (mitochondrial oxodica[rboxylate] | |
| -4.45 | — | — | |
| -4.44 | WFDC2 | WAP four-disulfide core domain 2 | |
| 4.44 | PCDH9 | protocadherin 9 | |
| 4.44 | — | CDNA FLJ33981 fis, clone DFNES2004608 | |

Appendix 1

| Value | Gene | Description |
|---|---|---|
| -5.06 | SFN | stratifin |
| -5.05 | ST8SIA2 | ST8 alpha-N-acetyl-neuraminide alpha-2,8-sial |
| -5.05 | PACSIN3 | protein kinase C and casein kinase substrate i |
| -5.05 | CST3 | Cystatin C (amyloid angiopathy and cerebral he |
| -5.05 | LOC729659 /// LOC | similar to Putative S100 calcium-binding protei |
| -5.05 | ACOT2 /// ACOT1 | acyl-CoA thioesterase 2 /// acyl-CoA thioestera |
| -5.04 | ARNT2 | aryl-hydrocarbon receptor nuclear translocator |
| -5.04 | SCNN1G | sodium channel, nonvoltage-gated 1, gamma |
| -5.03 | ITM2A | integral membrane protein 2A |
| -5.03 | MAP4K1 | mitogen-activated protein kinase kinase kinase |
| -5.03 | — | Transcribed locus |
| -5.03 | HOOK1 | hook homolog 1 (Drosophila) |
| -5.03 | LOC728377 | Similar to rho guanine nucleotide exchange fac |
| -5.02 | DUSP23 | dual specificity phosphatase 23 |
| -5.01 | LAMA2 | laminin, alpha 2 (merosin, congenital muscular |
| -5.01 | C1S | complement component 1, s subcomponent |
| -5.00 | — | — |
| -5.00 | — | — |
| 5.00 | MSX1 | msh homeobox 1 |
| 5.00 | SOX2OT | SOX2 overlapping transcript (non-coding RNA) |
| -4.99 | — | — |
| -4.99 | SLC7A8 | solute carrier family 7 (cationic amino acid tran |
| 4.99 | CP | ceruloplasmin (ferroxidase) |
| -4.99 | AURKC | aurora kinase C |
| -4.99 | — | — |
| 4.98 | — | — |
| 4.98 | — | — |
| -4.97 | GDA | guanine deaminase |
| -4.97 | LRFN5 | leucine rich repeat and fibronectin type III dom |
| -4.96 | CKMT1B /// CKMT1 | creatine kinase, mitochondrial 1B /// creatine ki |
| -4.96 | C9orf95 | chromosome 9 open reading frame 95 |
| -4.96 | SGK3 | serum/glucocorticoid regulated kinase family, |
| -4.96 | PRSS16 | protease, serine, 16 (thymus) |
| -4.95 | AP1G2 | adaptor-related protein complex 1, gamma 2 s |
| -4.94 | HSPA1A | heat shock 70kDa protein 1A |
| -4.94 | ABHD9 | abhydrolase domain containing 9 |
| -4.94 | FIBCD1 | fibrinogen C domain containing 1 |
| 4.92 | PRSS23 | protease, serine, 23 |
| 4.92 | KLHDC8A | kelch domain containing 8A |
| -4.92 | — | Transcribed locus |
| 4.91 | COL14A1 | collagen, type XIV, alpha 1 (undulin) |
| -4.91 | BCL11B | B-cell CLL/lymphoma 11B (zinc finger protein) |
| 4.91 | GPR177 | G protein-coupled receptor 177 |
| 4.91 | MEIS2 | Meis1, myeloid ecotropic viral integration site 1 |
| -4.91 | PHACS | 1-aminocyclopropane-1-carboxylate synthase |
| 4.91 | TFAP2A | transcription factor AP-2 alpha (activating enha |
| -4.90 | SOCS1 | suppressor of cytokine signaling 1 |
| -4.90 | — | — |
| -4.90 | BAIAP2L1 | BAI1-associated protein 2-like 1 |
| -4.90 | FGF4 | fibroblast growth factor 4 (heparin secretory tra |
| -4.90 | PERP | PERP, TP53 apoptosis effector |
| -4.90 | TNC | tenascin C (hexabrachion) |
| -4.90 | MAL2 | mal, T-cell differentiation protein 2 |
| -4.90 | SOCS1 | suppressor of cytokine signaling 1 |
| -4.89 | ESPN | espin |
| 4.89 | KIAA1713 | KIAA1713 |
| 4.89 | HOXA11 | homeobox A11 |
| -4.89 | — | — |
| 4.89 | HOXA10 | homeobox A10 |
| -4.88 | — | — |
| -4.88 | IFI30 | interferon, gamma-inducible protein 30 |
| -4.88 | GPR37 | G protein-coupled receptor 37 (endothelin rece |
| -4.87 | LOC130951 | hypothetical protein BC014602 |
| -4.87 | — | — |
| 4.87 | — | — |
| 4.87 | TAGLN3 | transgelin 3 |
| 4.87 | TMEM47 | transmembrane protein 47 |
| -4.86 | MT1F | metallothionein 1F (functional) |
| -4.86 | CST1 | cystatin SN |
| 4.85 | — | — |
| 4.85 | — | — |
| -4.85 | TPM2 | tropomyosin 2 (beta) |
| -4.84 | TRIM38 | tripartite motif-containing 38 |
| -4.84 | PIK3R5 | phosphoinositide-3-kinase, regulatory subunit 5 |
| -4.84 | LRRK1 | Leucine-rich repeat kinase 1 |
| 4.84 | C20orf91 /// LOC40 | chromosome 20 open reading frame 91 /// simi |
| 4.84 | TBC1D9 | TBC1 domain family, member 9 (with GRAM d |
| -4.84 | — | — |
| -4.83 | FLJ40125 | hypothetical protein FLJ40125 |
| -4.44 | AK3 | Adenylate kinase 3-like 1 |
| -4.44 | SEMG1 | semenogelin I |
| -4.43 | AURKC | aurora kinase C |
| 4.43 | FLJ23577 | KPL2 protein |
| 4.43 | RHOBTB2 | Rho-related BTB domain containing 2 |
| -4.43 | MUC3B | mucin 3B, cell surface associated |
| -4.42 | EDIL3 | EGF-like repeats and discoidin I-like domains 3 |
| 4.42 | CD36 | CD36 molecule (thrombospondin receptor) |
| 4.42 | SSPN | sarcospan (Kras oncogene-associated gene) |
| 4.42 | — | — |
| 4.42 | KIAA1210 | KIAA1210 protein |
| -4.42 | IRF6 | interferon regulatory factor 6 |
| 4.42 | NTRK2 | neurotrophic tyrosine kinase, receptor, type 2 |
| 4.42 | MPPED2 | metallophosphoesterase domain containing 2 |
| -4.41 | PRODH | proline dehydrogenase (oxidase) 1 |
| 4.41 | ZNF436 | zinc finger protein 436 |
| -4.41 | PCDH11Y | Protocadherin 11 Y-linked |
| -4.41 | — | Transcribed locus |
| 4.41 | YAF2 | YY1 associated factor 2 |
| 4.40 | LOC284530 | hypothetical protein LOC284530 |
| 4.40 | RIN3 | Ras and Rab interactor 3 |
| -4.39 | CXCL5 | chemokine (C-X-C motif) ligand 5 |
| 4.39 | — | — |
| 4.39 | NR2F2 | nuclear receptor subfamily 2, group F, member |
| -4.38 | ATPBD4 | ATP binding domain 4 |
| 4.37 | FBXL21 | F-box and leucine-rich repeat protein 21 |
| 4.37 | PCDH7 | BH-protocadherin (brain-heart) |
| -4.37 | OTX2 | orthodenticle homolog 2 (Drosophila) |
| 4.37 | LOC340061 | hypothetical protein LOC340061 |
| -4.37 | ATP8B3 | ATPase, Class I, type 8B, member 3 |
| -4.36 | C20orf42 | chromosome 20 open reading frame 42 |
| 4.36 | NTRK2 | neurotrophic tyrosine kinase, receptor, type 2 |
| 4.36 | EDNRA | endothelin receptor type A |
| -4.36 | CKMT1B /// CKMT1 | creatine kinase, mitochondrial 1B /// creatine ki |
| 4.36 | — | — |
| 4.36 | HOXA13 | homeobox A13 |
| -4.36 | — | Transcribed locus |
| -4.35 | — | — |
| 4.35 | RGS4 | regulator of G-protein signalling 4 |
| -4.35 | FLJ22662 | hypothetical protein FLJ22662 |
| -4.35 | ADCY2 | adenylate cyclase 2 (brain) |
| -4.35 | FAM124A | Family with sequence similarity 124A |
| 4.34 | TG | Thyroglobulin |
| -4.34 | PPP1R16B | protein phosphatase 1, regulatory (inhibitor) su |
| 4.34 | LOC143381 | hypothetical protein LOC143381 |
| 4.34 | IGFBP5 | insulin-like growth factor binding protein 5 |
| -4.34 | TPD52 | tumor protein D52 |
| -4.34 | — | — |
| -4.34 | TMEM125 | transmembrane protein 125 |
| -4.34 | C19orf4 | chromosome 19 open reading frame 4 |
| 4.34 | MSRB3 | methionine sulfoxide reductase B3 |
| 4.34 | — | — |
| 4.33 | AUTS2 | autism susceptibility candidate 2 |
| -4.33 | C20orf54 | chromosome 20 open reading frame 54 |
| -4.33 | — | Transcribed locus, moderately similar to NP_8 |
| -4.33 | — | — |
| 4.33 | CDX2 | caudal type homeobox transcription factor 2 |
| -4.32 | USP44 | ubiquitin specific peptidase 44 |
| -4.32 | KCNS3 | potassium voltage-gated channel, delayed-rec |
| 4.32 | — | CDNA FLJ10151 fis, clone HEMBA1003402 |
| -4.32 | — | — |
| 4.32 | — | — |
| 4.31 | LHX2 | LIM homeobox 2 |
| 4.31 | ST8SIA1 | ST8 alpha-N-acetyl-neuraminide alpha-2,8-sial |
| -4.31 | INDO | indoleamine-pyrrole 2,3 dioxygenase |
| -4.31 | NPW | neuropeptide W |
| -4.31 | — | — |
| 4.31 | SCN1A | sodium channel, voltage-gated, type I, alpha |
| 4.31 | — | — |
| -4.30 | — | — |
| -4.30 | — | — |
| -4.30 | DEPDC6 | DEP domain containing 6 |
| 4.29 | SPAG6 | sperm associated antigen 6 |
| 4.29 | IFI44L | interferon-induced protein 44-like |
| -4.29 | TNNT1 | troponin T type 1 (skeletal, slow) |
| 4.29 | FAM38B | family with sequence similarity 38, member B |
| -4.29 | — | CDNA clone IMAGE:5263207 |
| 4.29 | ASCL1 | achaete-scute complex homolog 1 (Drosophila) |
| -4.29 | — | — |

Appendix 1

| | | | |
|---|---|---|---|
| −4.83 | HBA1 /// HBA2 | hemoglobin, alpha 1 /// hemoglobin, alpha 1 /// |
| −4.83 | OR2A20P /// OR2A! | olfactory receptor, family 2, subfamily A, memb |
| −4.83 | LOC255480 | hypothetical protein LOC255480 |
| −4.83 | — | — |
| −4.82 | LOC144997 | hypothetical protein LOC144997 |
| −4.82 | COL2A1 | collagen, type II, alpha 1 (primary osteoarthritis |
| −4.82 | RNF165 | ring finger protein 165 |
| −4.82 | MT1X | metallothionein 1X |
| −4.82 | DNAJA4 | DnaJ (Hsp40) homolog, subfamily A, member |
| −4.82 | — | CDNA FLJ35396 fis, clone SKNSH2003483 |
| −4.81 | TBX5 | T-box 5 |
| −4.81 | — | — |
| −4.81 | NDST4 | N-deacetylase/N-sulfotransferase (heparan glu |
| −4.81 | CSPG5 | chondroitin sulfate proteoglycan 5 (neuroglycan |
| −4.80 | — | — |
| −4.80 | CGI-38 | brain specific protein /// brain specific protein |
| −4.80 | — | Homo sapiens, clone IMAGE:3454042, mRNA |
| −4.80 | — | — |
| −4.79 | ITPR3 | inositol 1,4,5-triphosphate receptor, type 3 |
| −4.79 | MYLIP | myosin regulatory light chain interacting protein |
| −4.78 | — | CDNA clone IMAGE:4792693 |
| −4.78 | PAK7 | p21(CDKN1A)-activated kinase 7 |
| −4.78 | — | — |
| −4.78 | DYSF | dysferlin, limb girdle muscular dystrophy 2B (au |
| −4.78 | PTGIS | prostaglandin I2 (prostacyclin) synthase /// pros |
| −4.77 | ZNF630 | zinc finger protein 630 |
| −4.77 | FOXC1 | forkhead box C1 |
| −4.77 | TG | Thyroglobulin |
| −4.76 | COL4A4 | collagen, type IV, alpha 4 |
| −4.76 | CDH20 | cadherin 20, type 2 |
| −4.76 | TCIRG1 | T-cell, immune regulator 1, ATPase, H+ transp |
| −4.76 | CTSL2 | cathepsin L2 |
| −4.76 | — | — |
| −4.76 | OLFM1 | olfactomedin 1 |
| −4.76 | — | — |
| −4.76 | ABAT | 4-aminobutyrate aminotransferase |
| −4.75 | ZNF204 | zinc finger protein 204 |
| −4.75 | TTBK2 | Tau tubulin kinase 2 |
| −4.75 | PCSK2 | proprotein convertase subtilisin/kexin type 2 |
| −4.75 | TOMM40 | Translocase of outer mitochondrial membrane |
| −4.74 | GRAMD3 | GRAM domain containing 3 |
| −4.74 | — | — |
| −4.74 | — | — |
| −4.74 | CRB2 | crumbs homolog 2 (Drosophila) |
| −4.73 | CPZ | carboxypeptidase Z /// carboxypeptidase Z |
| −4.73 | LOC389129 | similar to CG9996-PA |
| −4.73 | NLRP1 | NLR family, pyrin domain containing 1 |
| −4.73 | NR2F2 | nuclear receptor subfamily 2, group F, member |
| −4.73 | GUCY1A3 | guanylate cyclase 1, soluble, alpha 3 |
| −4.72 | — | CDNA FLJ37366 fis, clone BRAMY2024416 |
| −4.72 | — | — |
| −4.72 | GATA5 | GATA binding protein 5 |
| −4.71 | — | — |
| −4.71 | — | — |
| −4.71 | HLA-DPB1 | major histocompatibility complex, class II, DP b |
| −4.71 | TSLP | thymic stromal lymphopoietin |
| −4.70 | NRCAM | neuronal cell adhesion molecule |
| −4.70 | SCG5 | secretogranin V (7B2 protein) |
| −4.70 | PTGIS | prostaglandin I2 (prostacyclin) synthase |
| −4.69 | AKR1C3 | aldo-keto reductase family 1, member C3 (3-al |
| −4.69 | FLJ41747 | hypothetical gene supported by AK123741 |
| −4.69 | DNAH9 | dynein, axonemal, heavy chain 9 |
| −4.69 | PAX3 | paired box gene 3 (Waardenburg syndrome 1) |
| −4.68 | ARTN | artemin |
| −4.68 | ADAMTS19 | ADAM metallopeptidase with thrombospondin |
| −4.68 | — | — |
| −4.68 | VAMP8 | vesicle-associated membrane protein 8 (endob |
| −4.68 | SNAP25 | synaptosomal-associated protein, 25kDa |
| −4.67 | ATP8B3 | ATPase, Class I, type 8B, member 3 |
| −4.67 | GLRB | glycine receptor, beta |
| −4.66 | SERPINB9 | serpin peptidase inhibitor, clade B (ovalbumin), |
| −4.66 | — | — |
| −4.66 | WDR52 | WD repeat domain 52 |
| −4.66 | FXYD7 | FXYD domain containing ion transport regulato |
| −4.66 | — | CDNA FLJ37216 fis, clone BRALZ2008696 |
| −4.65 | C11orf52 | chromosome 11 open reading frame 52 |
| −4.64 | CAV1 | caveolin 1, caveolae protein, 22kDa |
| −4.64 | — | — |
| −4.64 | — | MRNA; cDNA DKFZp761H1023 (from clone D |
| −4.28 | FUT1 | fucosyltransferase 1 (galactoside 2-alpha-L-fuc |
| −4.28 | NAP5 | Nck-associated protein 5 |
| −4.28 | PTHLH | parathyroid hormone-like hormone |
| −4.27 | FGD5 | FYVE, RhoGEF and PH domain containing 5 |
| −4.27 | ZNF165 | zinc finger protein 165 |
| −4.27 | DIRAS3 | DIRAS family, GTP-binding RAS-like 3 |
| −4.26 | — | — |
| −4.26 | LOC729620 | Hypothetical protein LOC729620 |
| −4.26 | — | — |
| −4.26 | IGF1 | insulin-like growth factor 1 (somatomedin C) |
| −4.26 | — | — |
| −4.26 | CYP1B1 | cytochrome P450, family 1, subfamily B, polype |
| −4.25 | A2ML1 | alpha-2-macroglobulin-like 1 |
| −4.25 | ABCC13 | ATP-binding cassette, sub-family C (CFTR/MR |
| −4.25 | — | CDNA FLJ37333 fis, clone BRAMY2020106 |
| −4.25 | HOXA7 | homeobox A7 |
| −4.25 | GLS2 | glutaminase 2 (liver, mitochondrial) |
| −4.25 | — | — |
| −4.24 | BMI1 | B lymphoma Mo-MLV insertion region (mouse) |
| −4.24 | KCNK6 | potassium channel, subfamily K, member 6 |
| −4.24 | — | — |
| −4.24 | SPARCL1 | SPARC-like 1 (mast9, hevin) |
| −4.23 | OLFM3 | olfactomedin 3 |
| −4.23 | SLC6A15 | solute carrier family 6, member 15 |
| −4.23 | EDIL3 | EGF-like repeats and discoidin I-like domains 3 |
| −4.23 | SPP1 | Secreted phosphoprotein 1 (osteopontin, bone |
| −4.23 | KIAA1546 | KIAA1546 |
| −4.22 | SGCD | sarcoglycan, delta (35kDa dystrophin-associate |
| −4.22 | PTHLH | parathyroid hormone-like hormone /// parathyro |
| −4.22 | PAX2 | paired box gene 2 |
| −4.22 | — | Transcribed locus |
| −4.22 | NFATC3 | Nuclear factor of activated T-cells, cytoplasmic |
| −4.21 | SYNPO | synaptopodin |
| −4.21 | LRRC4 | leucine rich repeat containing 4 |
| −4.21 | FLJ20449 | hypothetical protein FLJ20449 |
| −4.20 | TPD52 | tumor protein D52 |
| −4.20 | NTF3 | neurotrophin 3 |
| −4.20 | — | CDNA clone IMAGE:5262438 |
| −4.20 | STC2 | stanniocalcin 2 |
| −4.20 | PAK6 | p21(CDKN1A)-activated kinase 6 |
| −4.19 | SCG3 | secretogranin III |
| −4.19 | SOX9 | SRY (sex determining region Y)-box 9 (campor |
| −4.19 | FKBP7 | FK506 binding protein 7 |
| −4.18 | — | — |
| −4.18 | SSPN | sarcospan (Kras oncogene-associated gene) |
| −4.18 | — | MRNA; cDNA DKFZp686G0585 (from clone D |
| −4.18 | PKNOX2 | PBX/knotted 1 homeobox 2 |
| −4.17 | HHAT | hedgehog acyltransferase |
| −4.17 | KIAA0562 | KIAA0562 |
| −4.17 | IL15 | interleukin 15 |
| −4.17 | TCBA1 | T-cell lymphoma breakpoint associated target |
| −4.17 | — | — |
| −4.17 | — | — |
| −4.16 | HOXD1 | homeobox D1 |
| −4.16 | CYP1B1 | cytochrome P450, family 1, subfamily B, polype |
| −4.16 | B3GNT7 | UDP-GlcNAc:betaGal beta-1,3-N-acetylglucosa |
| −4.16 | SCNN1B | sodium channel, nonvoltage-gated 1, beta (Lid |
| −4.15 | SMYD2 | SET and MYND domain containing 2 |
| −4.15 | — | — |
| −4.14 | C10orf72 | chromosome 10 open reading frame 72 |
| −4.13 | C20orf42 | chromosome 20 open reading frame 42 |
| −4.13 | — | — |
| −4.13 | NS5ATP13TP2 | NS5ATP13TP2 protein |
| −4.13 | KIAA0895 | KIAA0895 protein |
| −4.13 | APOA2 | apolipoprotein A-II |
| −4.13 | HDC | histidine decarboxylase |
| −4.12 | TMEM100 | transmembrane protein 100 |
| −4.12 | TMEM71 | transmembrane protein 71 |
| −4.11 | CDH6 | cadherin 6, type 2, K-cadherin (fetal kidney) |
| −4.11 | — | — |
| −4.11 | TNNI3 | troponin I type 3 (cardiac) |
| −4.11 | DDX43 | DEAD (Asp-Glu-Ala-Asp) box polypeptide 43 |
| −4.10 | RIN3 | Ras and Rab interactor 3 |
| −4.09 | FGF19 | fibroblast growth factor 19 |
| −4.09 | FIGF | c-fos induced growth factor (vascular endotheli |
| −4.09 | CREBBP | CREB binding protein (Rubinstein-Taybi syndro |
| −4.09 | — | — |
| −4.09 | — | Full-length cDNA clone CS0DD005YM12 of Ne |
| −4.08 | ALDH1A3 | aldehyde dehydrogenase 1 family, member A3 |

Appendix 1

| Value | Gene | Description |
|---|---|---|
| -4.63 | — | — |
| -4.63 | CXCL5 | chemokine (C-X-C motif) ligand 5 |
| -4.63 | LAMC3 | laminin, gamma 3 |
| -4.63 | KLK10 | kallikrein-related peptidase 10 |
| 4.62 | — | — |
| 4.62 | PKNOX2 | PBX/knotted 1 homeobox 2 |
| 4.62 | — | — |
| 4.62 | DPYSL5 | dihydropyrimidinase-like 5 |
| -4.62 | ZNF429 | Zinc finger protein 429 |
| -4.62 | — | — |
| -4.61 | LDHD | lactate dehydrogenase D |
| 4.61 | DIRAS2 | DIRAS family, GTP-binding RAS-like 2 |
| 4.61 | — | — |
| 4.61 | HOXA7 | homeobox A7 |
| -4.60 | RAB3B | RAB3B, member RAS oncogene family |
| -4.60 | — | — |
| 4.60 | — | — |
| 4.60 | CROT | carnitine O-octanoyltransferase |
| -4.59 | MAP4K1 | mitogen-activated protein kinase kinase kinase |
| -4.59 | TMPRSS11E /// LO | transmembrane protease, serine 11E /// similar |
| 4.59 | LEF1 | lymphoid enhancer-binding factor 1 |
| -4.59 | MT1M | metallothionein 1M |
| 4.59 | LOC401648 | Similar to heat shock 70kD protein binding prot |
| -4.58 | TRPC6 | transient receptor potential cation channel, sub |
| 4.58 | — | — |
| -4.58 | — | — |
| -4.57 | MYLIP | myosin regulatory light chain interacting protein |
| 4.57 | ABCB1 /// ABCB4 | ATP-binding cassette, sub-family B (MDR/TAP |
| 4.57 | DNAH9 | dynein, axonemal, heavy chain 9 |
| -4.56 | ARMCX1 | armadillo repeat containing, X-linked 1 |
| 4.56 | — | — |
| -4.55 | — | — |
| 4.55 | — | Tetraspanin 11 |
| -4.55 | — | — |
| -4.55 | CAPG | capping protein (actin filament), gelsolin-like |
| -4.55 | KLF4 | Kruppel-like factor 4 (gut) |
| -4.55 | EPB41L5 | Erythrocyte membrane protein band 4.1 like 5 |
| -4.55 | RRAS | related RAS viral (r-ras) oncogene homolog |
| -4.55 | LOC115749 | hypothetical protein LOC115749 |
| -4.54 | HLA-DPA1 | major histocompatibility complex, class II, DP a |
| 4.54 | VAX2 | ventral anterior homeobox 2 |
| 4.54 | CDKN2A | cyclin-dependent kinase inhibitor 2A (melanom |
| 4.54 | CROT | carnitine O-octanoyltransferase |
| -4.53 | ZNF165 | zinc finger protein 165 |
| -4.53 | — | — |
| 4.52 | FLJ22184 | hypothetical protein FLJ22184 |
| -4.52 | CRYM | crystallin, mu |
| 4.52 | EGR1 | early growth response 1 |
| 4.52 | — | Transcribed locus |
| 4.52 | SCN3B | sodium channel, voltage-gated, type III, beta |
| -4.52 | FAM20C | family with sequence similarity 20, member C |
| -4.52 | CCL3 /// CCL3L1 /// | chemokine (C-C motif) ligand 3 /// chemokine ( |
| 4.52 | ST8SIA4 | ST8 alpha-N-acetyl-neuraminide alpha-2,8-sial |
| 4.51 | SORBS2 | sorbin and SH3 domain containing 2 |
| -4.51 | LOC285401 | hypothetical protein LOC285401 |
| -4.51 | — | Full length insert cDNA clone ZD51F08 |
| 4.51 | — | — |
| -4.51 | MT1M | metallothionein 1M |
| -4.50 | PLA2G2A | phospholipase A2, group IIA (platelets, synovia |
| -4.50 | — | — |
| 4.50 | — | — |
| -4.49 | LOC202451 | hypothetical protein LOC202451 |
| -4.49 | HPGD | hydroxyprostaglandin dehydrogenase 15-(NAD |
| -4.49 | — | MRNA; cDNA DKFZp313A1040 (from clone Dk |
| 4.49 | — | — |
| 4.49 | APC2 | adenomatosis polyposis coli 2 |
| -4.49 | C8orf47 | chromosome 8 open reading frame 47 |
| -4.48 | TAGLN | transgelin |
| -4.48 | HPGD | hydroxyprostaglandin dehydrogenase 15-(NAD |
| 4.48 | NRIP3 | Nuclear receptor interacting protein 3 |
| 4.47 | LRRC4 | leucine rich repeat containing 4 |
| -4.47 | HYAL1 | hyaluronoglucosaminidase 1 |
| -4.47 | CTHRC1 | collagen triple helix repeat containing 1 |
| 4.47 | AUTS2 | autism susceptibility candidate 2 |
| 4.46 | PDE4B | phosphodiesterase 4B, cAMP-specific (phosph |
| -4.45 | — | — |
| -4.45 | MYC | v-myc myelocytomatosis viral oncogene homol |
| 4.45 | SRGAP3 | SLIT-ROBO Rho GTPase activating protein 3 |
| 4.45 | MMP14 | matrix metallopeptidase 14 (membrane-inserte |

| Value | Gene | Description |
|---|---|---|
| -4.08 | — | — |
| 4.08 | CDH6 | cadherin 6, type 2, K-cadherin (fetal kidney) |
| 4.08 | UNC13C | unc-13 homolog C (C. elegans) |
| -4.07 | MAP7 | microtubule-associated protein 7 |
| 4.07 | KCTD12 | potassium channel tetramerisation domain con |
| 4.07 | — | Transcribed locus |
| 4.07 | — | — |
| 4.06 | ZHX1 | zinc fingers and homeoboxes 1 |
| 4.06 | DDR2 | Discoidin domain receptor family, member 2 |
| -4.06 | — | — |
| -4.06 | PTRF | polymerase I and transcript release factor |
| 4.06 | ARNT2 | aryl-hydrocarbon receptor nuclear translocator |
| 4.05 | — | Transcribed locus |
| 4.05 | C21orf34 | chromosome 21 open reading frame 34 |
| 4.05 | HOXB5 | Homeobox B5 |
| -4.05 | — | — |
| -4.04 | TFCP2L1 | Transcription factor CP2-like 1 |
| -4.04 | — | — |
| -4.04 | — | CDNA clone IMAGE:4793048 |
| 4.03 | PLCD4 | phospholipase C, delta 4 /// phospholipase C, d |
| -4.03 | — | — |
| 4.03 | COMMD3 | COMM domain containing 3 |
| -4.03 | UPK1A | uroplakin 1A |
| -4.02 | AK3L1 | adenylate kinase 3-like 1 |
| -4.02 | NUDT16P | nudix (nucleoside diphosphate linked moiety X |
| -4.02 | — | — |
| -4.02 | MIXL1 | Mix1 homeobox-like 1 (Xenopus laevis) |
| 4.01 | WNT5A | wingless-type MMTV integration site family, me |
| 4.01 | ARHGAP6 | Rho GTPase activating protein 6 |
| -4.01 | CALN1 | calneuron 1 |
| 4.01 | — | — |
| 4.01 | ARHGEF17 | Rho guanine nucleotide exchange factor (GEF) |
| 4.01 | WNT5A | wingless-type MMTV integration site family, me |
| -4.00 | B3GNT7 | UDP-GlcNAc:betaGal beta-1,3-N-acetylglucosa |
| -4.00 | BSPRY | B-box and SPRY domain containing |
| 4.00 | POU3F2 | POU domain, class 3, transcription factor 2 |
| 4.00 | — | Homo sapiens, Similar to neuronal thread prote |
| 4.00 | — | CDNA FLJ30128 fis, clone BRACE1000124 |
| 4.00 | TFAP2A | transcription factor AP-2 alpha (activating enha |
| 4.00 | FLJ10159 | Hypothetical protein FLJ10159 |
| 4.00 | — | — |
| -4.00 | LOC401233 | similar to HIV TAT specific factor 1; cofactor re |
| -3.99 | CADPS | Ca2+-dependent secretion activator |
| 3.99 | THSD7A | thrombospondin, type I, domain containing 7A |
| -3.99 | LSR | lipolysis stimulated lipoprotein receptor |
| 3.99 | — | Transcribed locus |
| 3.98 | CCR2 /// LOC72923 | chemokine (C-C motif) receptor 2 /// chemokine |
| 3.98 | CCL2 | chemokine (C-C motif) ligand 2 |
| 3.98 | — | — |
| 3.98 | HOMER3 | homer homolog 3 (Drosophila) |
| -3.97 | MAP7 | microtubule-associated protein 7 |
| -3.97 | RAB37 | RAB37, member RAS oncogene family |
| 3.97 | C4orf19 | chromosome 4 open reading frame 19 |
| 3.97 | ANGPTL1 | angiopoietin-like 1 |
| -3.97 | — | — |
| -3.96 | — | Transcribed locus |
| -3.96 | CDS1 | CDP-diacylglycerol synthase (phosphatidate cy |
| -3.96 | — | C33.6 unnamed HERV-H protein |
| 3.95 | — | — |
| 3.95 | — | — |
| 3.95 | — | Transcribed locus |
| -3.95 | LOC221442 | hypothetical protein LOC221442 |
| 3.94 | SH2D3C | SH2 domain containing 3C |
| -3.94 | ESPN | espin |
| -3.94 | — | — |
| 3.94 | AFF3 | AF4/FMR2 family, member 3 |
| -3.94 | — | — |
| 3.94 | TRA@ /// TRD@ /// | T cell receptor alpha locus /// T cell receptor de |
| 3.93 | LOC283658 | hypothetical protein LOC283658 |
| -3.93 | LOC255104 | Transmembrane and coiled-coil domains 4 |
| -3.93 | GRB7 | growth factor receptor-bound protein 7 |
| 3.93 | TCTEX1D1 | Tctex1 domain containing 1 |
| -3.93 | GSTO2 | glutathione S-transferase omega 2 |
| 3.93 | C6orf32 | chromosome 6 open reading frame 32 |
| 3.93 | — | — |
| -3.92 | CCKBR | cholecystokinin B receptor |
| 3.92 | — | Transcribed locus |
| -3.92 | CLDN10 | claudin 10 |
| 3.91 | GLRB | glycine receptor, beta |

Appendix 1

| Value | Gene | Description |
|---|---|---|
| 4.45 | LOC613266 | hypothetical LOC613266 |
| -4.45 | LOC136306 | hypothetical protein LOC136306 |
| 4.45 | KLHL13 | kelch-like 13 (Drosophila) |
| -4.44 | — | — |
| -4.44 | ZMAT4 | zinc finger, matrin type 4 |
| 4.44 | PHF11 | PHD finger protein 11 |
| -4.44 | RIPK4 | receptor-interacting serine-threonine kinase 4 |
| -4.44 | CCKBR | cholecystokinin B receptor |
| 4.43 | CSPG5 | chondroitin sulfate proteoglycan 5 (neuroglycan) |
| 4.43 | LGR5 | leucine-rich repeat-containing G protein-coupled |
| 4.42 | PRTG | protogenin homolog (Gallus gallus) |
| -4.42 | — | — |
| -4.42 | — | — |
| 4.42 | HOXA11 | homeobox A11 |
| 4.41 | CLRN1 | clarin 1 |
| 4.41 | LOC129881 | hypothetical LOC129881 |
| -4.41 | IGFBP7 | insulin-like growth factor binding protein 7 |
| 4.41 | CDH10 | cadherin 10, type 2 (T2-cadherin) |
| -4.40 | HTR3A | 5-hydroxytryptamine (serotonin) receptor 3A |
| 4.40 | CHN2 | chimerin (chimaerin) 2 |
| 4.40 | SMOC1 | SPARC related modular calcium binding 1 |
| -4.40 | PCDHAC2 | protocadherin alpha subfamily C, 2 |
| -4.40 | GPR74 | G protein-coupled receptor 74 |
| -4.40 | UGT3A1 | UDP glycosyltransferase 3 family, polypeptide |
| -4.40 | CGNL1 | cingulin-like 1 |
| -4.39 | CYP2E1 | cytochrome P450, family 2, subfamily E, polype |
| -4.39 | — | CDNA clone IMAGE:4811759 |
| -4.39 | EPPK1 | epiplakin 1 /// epiplakin 1 |
| -4.38 | ANTXR1 | anthrax toxin receptor 1 |
| 4.38 | — | — |
| 4.38 | PALM2 | paralemmin 2 |
| 4.38 | SOX3 | SRY (sex determining region Y)-box 3 |
| -4.38 | NFE2L3 | nuclear factor (erythroid-derived 2)-like 3 |
| -4.38 | GRHL2 | grainyhead-like 2 (Drosophila) |
| 4.38 | ENPP2 | ectonucleotide pyrophosphatase/phosphodiest |
| -4.38 | CADPS | Ca2+-dependent secretion activator |
| -4.38 | — | — |
| 4.37 | SLC18A1 | solute carrier family 18 (vesicular monoamine) |
| 4.37 | BMI1 | B lymphoma Mo-MLV insertion region (mouse) |
| -4.37 | GPD2 | glycerol-3-phosphate dehydrogenase 2 (mitoch |
| -4.37 | ZSCAN2 | zinc finger and SCAN domain containing 2 |
| 4.37 | TUBB2B | Tubulin, beta 2B |
| -4.37 | CRIP1 /// GALK2 | cysteine-rich protein 1 (intestinal) /// galactokin |
| 4.37 | WDR49 | WD repeat domain 49 |
| -4.36 | OSBPL10 | oxysterol binding protein-like 1C |
| -4.36 | — | — |
| -4.36 | BCL11B | B-cell CLL/lymphoma 11B (zinc finger protein) |
| -4.36 | — | Transcribed locus, weakly similar to XP_51765 |
| 4.36 | — | — |
| 4.35 | KIAA1644 | KIAA1644 protein |
| -4.35 | — | — |
| -4.35 | RIT2 | Ras-like without CAAX 2 |
| 4.35 | C1orf186 | chromosome 1 open reading frame 186 |
| 4.35 | EPHA5 | EPH receptor A5 |
| 4.35 | RGS20 | regulator of G-protein signalling 20 |
| 4.35 | FLJ14213 | hypothetical protein FLJ14213 |
| -4.34 | RASEF | RAS and EF-hand domain containing |
| -4.34 | MIXL1 | Mix1 homeobox-like 1 (Xenopus laevis) |
| -4.34 | BAIAP2L1 | BAI1-associated protein 2-like 1 |
| 4.34 | C10orf39 | chromosome 10 open reading frame 39 |
| -4.34 | CHRNA9 | cholinergic receptor, nicotinic, alpha 9 |
| 4.34 | GPR56 | G protein-coupled receptor 56 |
| -4.33 | EPAS1 | endothelial PAS domain protein 1 |
| 4.33 | CTNND2 | catenin (cadherin-associated protein), delta 2 ( |
| -4.33 | LOC388494 | hypothetical gene supported by AL365406; BC |
| -4.33 | TMBIM1 | transmembrane BAX inhibitor motif containing |
| 4.33 | — | — |
| 4.33 | GLT25D2 | glycosyltransferase 25 domain containing 2 |
| -4.33 | RARG | retinoic acid receptor, gamma |
| -4.33 | OLFML2A | olfactomedin-like 2A |
| -4.32 | C20orf42 | chromosome 20 open reading frame 42 |
| -4.32 | LGALS1 | lectin, galactoside-binding, soluble, 1 (galectin |
| -4.32 | CYP4X1 | cytochrome P450, family 4, subfamily X, polype |
| 4.32 | — | — |
| -4.32 | — | — |
| -4.32 | MPP1 | membrane protein, palmitoylated 1, 55kDa |
| -4.31 | — | — |
| 4.31 | ITGB8 | integrin, beta 8 |
| -4.31 | PDLIM1 | PDZ and LIM domain 1 (elfin) |

| Value | Gene | Description |
|---|---|---|
| -3.91 | — | — |
| 3.91 | — | — |
| -3.91 | PKP2 | plakophilin 2 |
| -3.91 | KLF4 | Kruppel-like factor 4 (gut) |
| 3.90 | — | — |
| 3.90 | C8orf48 | chromosome 8 open reading frame 48 |
| -3.90 | — | — |
| 3.90 | FZD1 | frizzled homolog 1 (Drosophila) |
| -3.90 | TIMP4 | TIMP metallopeptidase inhibitor 4 |
| 3.89 | LOC283859 | hypothetical protein LOC283859 |
| 3.89 | RXFP1 | relaxin/insulin-like family peptide receptor 1 |
| 3.88 | LAMA4 | laminin, alpha 4 |
| 3.88 | LOX | lysyl oxidase |
| 3.88 | — | — |
| 3.87 | LHFP | Lipoma HMGIC fusion partner |
| -3.87 | MUC4 | mucin 4, cell surface associated |
| 3.87 | ASCL1 | achaete-scute complex homolog 1 (Drosophila) |
| 3.87 | — | Full length insert cDNA clone ZD53C10 |
| -3.87 | HERC5 | hect domain and RLD 5 |
| -3.87 | — | — |
| 3.87 | PRKXP1 | protein kinase, X-linked, pseudogene 1 |
| -3.87 | HHEX | homeobox, hematopoietically expressed |
| 3.87 | COL12A1 | Collagen, type XII, alpha 1 |
| -3.86 | — | — |
| 3.86 | HBE1 | hemoglobin, epsilon 1 /// hemoglobin, epsilon 1 |
| 3.86 | — | CDNA FLJ31066 fis, clone HSYRA2001153 |
| -3.85 | SFN | stratifin |
| 3.85 | — | — |
| -3.85 | — | — |
| -3.85 | — | Transcribed locus |
| 3.85 | — | Transcribed locus |
| 3.84 | SORBS2 | sorbin and SH3 domain containing 2 |
| -3.84 | IRF6 | interferon regulatory factor 6 |
| 3.84 | TIMP3 | TIMP metallopeptidase inhibitor 3 (Sorsby fund |
| 3.84 | PPEF1 | protein phosphatase, EF-hand calcium binding |
| -3.83 | GALNT14 | UDP-N-acetyl-alpha-D-galactosamine:polypept |
| 3.83 | PLEKHG1 | pleckstrin homology domain containing, family |
| -3.83 | MT1F | metallothionein 1F (functional) |
| -3.83 | MMP23B /// MMP23 | matrix metallopeptidase 23B /// matrix metallop |
| 3.83 | DCHS1 | dachsous 1 (Drosophila) |
| -3.83 | C1orf211 | chromosome 1 open reading frame 211 |
| -3.83 | SERPINB9 | serpin peptidase inhibitor, clade B (ovalbumin), |
| -3.82 | GH2 | growth hormone 2 |
| -3.82 | — | Transcribed locus |
| -3.82 | — | Homo sapiens, clone IMAGE:3344506 |
| 3.82 | — | — |
| -3.81 | RIPK4 | receptor-interacting serine-threonine kinase 4 |
| 3.81 | HOXC4 | homeobox C4 |
| 3.81 | FLJ21986 | hypothetical protein FLJ21986 |
| -3.81 | OSBPL10 | oxysterol binding protein-like 1C |
| 3.81 | UNC5C | unc-5 homolog C (C. elegans) |
| 3.81 | VASH1 | Vasohibin 1 |
| 3.81 | HOXD8 | Homeobox D8 |
| 3.81 | SDK2 | sidekick homolog 2 (chicken) |
| 3.80 | XYLB | xylulokinase homolog (H. influenzae) |
| -3.80 | LPPR4 | plasticity related gene 1 |
| 3.80 | RP5-875H10.1 | SAM domain containing 1 |
| 3.80 | ROPN1B | ropporin, rhophilin associated protein 1B |
| -3.80 | — | — |
| -3.80 | — | — |
| -3.80 | CRIP3 | cysteine-rich protein 3 |
| -3.79 | PIM2 | pim-2 oncogene |
| -3.79 | — | — |
| 3.79 | — | — |
| 3.79 | CCR2 /// LOC72923 | chemokine (C-C motif) receptor 2 /// chemokine |
| -3.79 | — | — |
| 3.79 | SH3MD4 | SH3 multiple domains 4 |
| 3.79 | REEP1 | receptor accessory protein 1 |
| -3.78 | FIBCD1 | fibrinogen C domain containing 1 |
| 3.78 | ZHX1 | zinc fingers and homeoboxes 1 |
| 3.78 | — | — |
| 3.78 | KCTD12 | potassium channel tetramerisation domain con |
| 3.78 | — | MRNA from chromosome 5q31-33 region |
| 3.78 | TNS1 | tensin 1 /// tensin 1 |
| -3.78 | OSBPL10 | oxysterol binding protein-like 1C |
| 3.78 | — | — |
| 3.77 | — | — |
| 3.77 | LOC284262 | hypothetical protein LOC284262 |
| 3.77 | RP11-301I17.1 | proliferation-inducing protein 38 |

Appendix 1

| | | | |
|---|---|---|---|
| -4.31 | EPB41L5 | erythrocyte membrane protein band 4.1 like 5 |
| -4.30 | UNC5D | Unc-5 homolog D (C. elegans) |
| -4.30 | BNC2 | basonuclin 2 |
| -4.30 | SULT1C1 | sulfotransferase family, cytosolic, 1C, member |
| -4.30 | PPM1J | protein phosphatase 1J (PP2C domain contain |
| -4.30 | LOC255480 | hypothetical protein LOC255480 |
| -4.30 | EDG7 | endothelial differentiation, lysophosphatidic aci |
| -4.30 | — | — |
| -4.30 | FAM20A | Family with sequence similarity 20, member A |
| -4.29 | MMP9 | matrix metallopeptidase 9 (gelatinase B, 92kDa |
| -4.29 | — | — |
| -4.29 | PKNOX2 | PBX/knotted 1 homeobox 2 |
| -4.29 | — | — |
| -4.29 | LIX1L | Lix1 homolog (mouse)-like |
| -4.29 | RHOD | ras homolog gene family, member D |
| -4.29 | — | — |
| -4.29 | KIAA1853 | KIAA1853 |
| -4.28 | TCEAL2 | transcription elongation factor A (SII)-like 2 |
| -4.28 | — | Full length insert cDNA clone YT94E02 |
| -4.28 | — | — |
| -4.28 | SLC7A8 | solute carrier family 7 (cationic amino acid tran |
| -4.28 | EDNRB | endothelin receptor type B |
| -4.28 | C21orf56 | chromosome 21 open reading frame 56 |
| -4.28 | BIK | BCL2-interacting killer (apoptosis-inducing) |
| -4.28 | ROR1 | Receptor tyrosine kinase-like orphan receptor |
| -4.27 | — | — |
| -4.26 | C18orf4 | chromosome 18 open reading frame 4 |
| -4.26 | — | Transcribed locus |
| -4.26 | — | Transcribed locus |
| -4.26 | — | — |
| -4.25 | C11orf70 | chromosome 11 open reading frame 70 /// chr |
| -4.25 | FZD5 | frizzled homolog 5 (Drosophila) /// frizzled hom |
| -4.25 | SGK3 | serum/glucocorticoid regulated kinase family, |
| -4.25 | GRID2 | glutamate receptor, ionotropic, delta 2 |
| -4.25 | — | CDNA FLJ39164 fis, clone OCBBF2002656 |
| -4.25 | — | — |
| -4.24 | MYCT1 | myc target 1 |
| -4.24 | — | — |
| -4.24 | — | — |
| -4.24 | — | — |
| -4.24 | KLHDC7A | kelch domain containing 7A |
| -4.24 | ASTN1 | astrotactin 1 |
| -4.24 | KIAA1546 | KIAA1546 |
| -4.24 | SGK | serum/glucocorticoid regulated kinase |
| -4.23 | MLSTD1 | male sterility domain containing 1 |
| -4.23 | PYCARD | PYD and CARD domain containing |
| -4.23 | PDE4B | phosphodiesterase 4B, cAMP-specific (phosph |
| -4.23 | GPR54 | G protein-coupled receptor 54 |
| -4.23 | — | Homo sapiens, clone IMAGE:5245882, mRNA |
| -4.23 | CNPY1 | canopy 1 homolog (zebrafish) |
| -4.23 | — | — |
| -4.23 | PHYHIPL | phytanoyl-CoA 2-hydroxylase interacting protei |
| -4.23 | UNC93B1 | unc-93 homolog B1 (C. elegans) |
| -4.23 | NRK | Nik related kinase |
| -4.23 | COL14A1 | collagen, type XIV, alpha 1 (undulin) |
| -4.22 | RUNX1T1 | runt-related transcription factor 1; translocated |
| -4.22 | UTS2 | urotensin 2 |
| -4.22 | — | Homo sapiens, clone IMAGE:3881549, mRNA |
| -4.22 | MAPK11 | mitogen-activated protein kinase 11 |
| -4.21 | — | — |
| -4.20 | — | CDNA: FLJ23070 fis, clone LNG05629 |
| -4.20 | FRMD4B | FERM domain containing 4B |
| -4.19 | MYLIP | myosin regulatory light chain interacting protei |
| -4.19 | HAS3 | hyaluronan synthase 3 |
| -4.19 | APOA2 | apolipoprotein A-II |
| -4.19 | SMAD7 | SMAD family member 7 |
| -4.18 | ZNF439 | zinc finger protein 439 |
| -4.18 | ATP1A2 | ATPase, Na+/K+ transporting, alpha 2 (+) poly |
| -4.18 | PDE4A | phosphodiesterase 4A, cAMP-specific (phosph |
| -4.18 | TMC5 | Transmembrane channel-like 5 |
| -4.18 | — | CDNA FLJ36653 fis, clone UTERU2001176 |
| -4.18 | — | — |
| -4.18 | ABCA5 | ATP-binding cassette, sub-family A (ABC1), m |
| -4.18 | DUSP4 | dual specificity phosphatase 4 |
| -4.17 | PHLDA2 | pleckstrin homology-like domain, family A, men |
| -4.17 | HLA-C | major histocompatibility complex, class I, C |
| -4.17 | FLJ36748 | hypothetical protein FLJ36748 |
| -4.17 | SOX3 | SRY (sex determining region Y)-box 3 |
| -4.17 | — | — |

| | | |
|---|---|---|
| -3.77 | PDGFA | platelet-derived growth factor alpha polypeptide |
| -3.77 | NKG7 | natural killer cell group 7 sequence |
| -3.77 | RAB3B | RAB3B, member RAS oncogene family |
| -3.76 | — | Transcribed locus |
| -3.76 | — | — |
| -3.76 | MCTP2 | multiple C2 domains, transmembrane 2 |
| -3.75 | — | Similar to AI661453 protein |
| -3.75 | PPP2R2C | protein phosphatase 2 (formerly 2A), regulatory |
| -3.75 | DPPA4 | developmental pluripotency associated 4 |
| -3.74 | — | — |
| -3.74 | — | — |
| -3.74 | — | — |
| 3.74 | PCDH9 | protocadherin 9 |
| -3.74 | LAMP3 | lysosomal-associated membrane protein 3 |
| 3.74 | SAMD9 | sterile alpha motif domain containing 9 |
| 3.73 | LYST | lysosomal trafficking regulator |
| -3.73 | LOC285401 | hypothetical protein LOC285401 |
| 3.73 | HOXA11S | homeo box A11, antisense |
| 3.73 | CRB2 | crumbs homolog 2 (Drosophila) |
| -3.73 | SOHLH2 | spermatogenesis and oogenesis specific basic |
| -3.73 | IFI30 | interferon, gamma-inducible protein 30 |
| -3.73 | CD55 | CD55 molecule, decay accelerating factor for c |
| -3.72 | GLB1L3 | galactosidase, beta 1 like 3 |
| 3.72 | OSR2 | odd-skipped related 2 (Drosophila) |
| -3.72 | EFEMP1 | EGF-containing fibulin-like extracellular matrix |
| 3.72 | — | — |
| 3.72 | SMOC1 | SPARC related modular calcium binding 1 |
| 3.72 | — | CDNA clone IMAGE:5266257 |
| 3.72 | FZD1 | frizzled homolog 1 (Drosophila) |
| -3.71 | SPAG16 | Sperm associated antigen 16 |
| 3.71 | — | Full length insert cDNA clone YT94E02 |
| 3.71 | ST6GALNAC3 | ST6 (alpha-N-acetyl-neuraminyl-2,3-beta-galac |
| -3.71 | TEX14 | testis expressed sequence 14 /// testis express |
| 3.71 | DIRAS2 | DIRAS family, GTP-binding RAS-like 2 |
| 3.71 | — | — |
| 3.70 | — | — |
| -3.70 | HMMR | Hyaluronan-mediated motility receptor (RHAMM |
| 3.70 | TLR4 | toll-like receptor 4 |
| 3.70 | SOX9 | SRY (sex determining region Y)-box 9 (campor |
| 3.70 | — | CDNA FLJ39179 fis, clone OCBBF2004147 |
| -3.70 | MAP4K1 | mitogen-activated protein kinase kinase kinase |
| -3.70 | LOC138046 | hypothetical protein LOC138046 |
| 3.69 | FOXP2 | forkhead box P2 |
| 3.69 | VAX2 | ventral anterior homeobox 2 |
| 3.69 | HOXA3 | Homeo box A3 |
| 3.69 | GPR161 | G protein-coupled receptor 161 |
| 3.69 | THSD7A | thrombospondin, type I, domain containing 7A |
| -3.69 | HOOK1 | hook homolog 1 (Drosophila) |
| -3.68 | HSD11B1 | Hydroxysteroid (11-beta) dehydrogenase |
| -3.68 | FRAT2 | frequently rearranged in advanced T-cell lymph |
| -3.68 | — | — |
| 3.68 | — | Transcribed locus |
| 3.68 | ROPN1 | ropporin, rhophilin associated protein 1 |
| 3.68 | APOLD1 | apolipoprotein L domain containing 1 /// apolipo |
| -3.68 | — | — |
| 3.68 | MBNL2 | muscleblind-like 2 (Drosophila) |
| 3.68 | MARVELD3 | MARVEL domain containing 3 |
| -3.67 | EFCAB4A | EF-hand calcium binding domain 4A |
| -3.67 | TFPI2 | tissue factor pathway inhibitor 2 |
| -3.67 | SOX17 | SRY (sex determining region Y)-box 17 |
| 3.67 | NOG | Noggin |
| 3.67 | OGFOD1 | 2-oxoglutarate and iron-dependent oxygenase |
| 3.67 | RHOC | Ras homolog gene family, member C |
| 3.67 | — | — |
| 3.67 | — | Homo sapiens, clone IMAGE:3881549, mRNA |
| 3.66 | FLJ13197 /// LOC7 | hypothetical protein FLJ13197 /// hypothetical p |
| 3.66 | TANC2 | tetratricopeptide repeat, ankyrin repeat and coil |
| 3.66 | CLIPR-59 | CLIP-170-related protein |
| -3.66 | INADL | InaD-like (Drosophila) |
| -3.66 | SOX14 | SRY (sex determining region Y)-box 14 |
| 3.66 | SETBP1 | SET binding protein 1 |
| 3.66 | ST8SIA4 | ST8 alpha-N-acetyl-neuraminide alpha-2,8-sial |
| -3.65 | — | — |
| 3.65 | — | — |
| 3.65 | PKNOX2 | PBX/knotted 1 homeobox 2 |
| 3.65 | EDG2 | endothelial differentiation, lysophosphatidic aci |
| 3.65 | TGFB1I1 | transforming growth factor beta 1 induced trans |
| 3.65 | LOC387856 | similar to expressed sequence AI836003 |
| 3.65 | LIX1L | Lix1 homolog (mouse)-like |

Appendix 1

| Value | Gene | Description |
|---|---|---|
| -4.16 | FBLIM1 | filamin binding LIM protein 1 |
| -4.16 | SLCO1A2 | solute carrier organic anion transporter family, |
| -4.16 | — | — |
| -4.16 | MAF | v-maf musculoaponeurotic fibrosarcoma oncog |
| -4.16 | NR5A2 | nuclear receptor subfamily 5, group A, member |
| -4.16 | LAMC2 | laminin, gamma 2 |
| 4.16 | HOXD11 | homeobox D11 |
| -4.16 | LDHC | lactate dehydrogenase C |
| 4.15 | — | — |
| -4.15 | FLT1 | fms-related tyrosine kinase 1 (vascular endothe |
| 4.15 | — | — |
| -4.14 | UPK1A | uroplakin 1A |
| -4.13 | CD44 /// MAPK10 | CD44 molecule (Indian blood group) /// mitoge |
| -4.13 | RAB37 | RAB37, member RAS oncogene family |
| 4.13 | FEZ1 | fasciculation and elongation protein zeta 1 (zyg |
| 4.13 | — | CDNA FLJ35396 fis, clone SKNSH2003483 |
| 4.12 | HOXD10 | homeobox D10 |
| 4.12 | HOXD8 | Homeobox D8 |
| -4.12 | DEPDC6 | DEP domain containing 6 |
| -4.12 | PAPSS2 | 3'-phosphoadenosine 5'-phosphosulfate syntha |
| -4.12 | PIK3CD | phosphoinositide-3-kinase, catalytic, delta poly |
| -4.12 | — | — |
| -4.11 | LEMD1 | LEM domain containing 1 |
| -4.11 | GRB7 | growth factor receptor-bound protein 7 |
| -4.11 | — | — |
| -4.11 | PDZD2 | PDZ domain containing 2 |
| 4.11 | FLJ39198 | Hypothetical protein LOC643763 |
| 4.11 | — | — |
| -4.11 | CAPN6 | calpain 6 |
| -4.10 | PRRX2 | paired related homeobox 2 |
| -4.10 | HCG11 | HLA complex group 11 |
| -4.10 | — | — |
| 4.10 | — | Full length insert cDNA clone YY86C01 |
| -4.10 | FLRT2 | fibronectin leucine rich transmembrane protein |
| -4.10 | — | Surfactant associated protein F mRNA, partial |
| -4.09 | ANXA4 | annexin A4 |
| 4.09 | CCDC73 | Coiled-coil domain containing 73 |
| -4.09 | ARHGAP4 | Rho GTPase activating protein 4 |
| 4.09 | — | — |
| 4.09 | ZSWIM5 | zinc finger, SWIM-type containing 5 |
| 4.09 | SLC1A4 | solute carrier family 1 (glutamate/neutral amino |
| -4.09 | SLC7A8 | solute carrier family 7 (cationic amino acid tran |
| -4.09 | C20orf54 | chromosome 20 open reading frame 54 |
| 4.08 | — | — |
| -4.08 | HPN | hepsin (transmembrane protease, serine 1) |
| 4.08 | TMEM47 | transmembrane protein 47 |
| 4.07 | KIAA0408 | KIAA0408 |
| -4.07 | PDE4A | phosphodiesterase 4A, cAMP-specific (phosph |
| 4.07 | — | — |
| -4.07 | HLA-A | major histocompatibility complex, class I, A |
| -4.06 | — | — |
| 4.06 | COMMD3 | COMM domain containing 3 |
| -4.06 | — | — |
| 4.06 | PACRG | PARK2 co-regulated |
| 4.06 | ERBB4 | v-erb-a erythroblastic leukemia viral oncogene |
| 4.06 | PCDH17 | protocadherin 17 |
| 4.05 | — | CDNA FLJ30128 fis, clone BRACE1000124 |
| 4.05 | — | — |
| -4.05 | C15orf27 | chromosome 15 open reading frame 27 |
| 4.05 | LOC202181 | hypothetical protein LOC202181 |
| -4.05 | ANK3 | Ankyrin 3, node of Ranvier (ankyrin G) |
| 4.05 | — | Transcribed locus |
| -4.05 | CYP2C8 | cytochrome P450, family 2, subfamily C, polyp |
| -4.05 | MLSTD1 | Male sterility domain containing 1 |
| -4.05 | — | — |
| -4.04 | — | — |
| -4.04 | — | — |
| -4.04 | TNFAIP6 | tumor necrosis factor, alpha-induced protein 6 |
| -4.04 | PIM2 | pim-2 oncogene |
| 4.04 | GAB2 | GRB2-associated binding protein 2 |
| -4.04 | ID1 | inhibitor of DNA binding 1, dominant negative h |
| -4.04 | — | — |
| -4.04 | LOC202451 | hypothetical protein LOC202451 |
| 4.03 | CREBBP | CREB binding protein (Rubinstein-Taybi syndr |
| -4.03 | — | — |
| 4.03 | SUHW4 | suppressor of hairy wing homolog 4 (Drosophil |
| -4.03 | JPH3 | junctophilin 3 |
| 4.03 | PRSS23 | protease, serine, 23 |
| -4.03 | PAPSS2 | 3'-phosphoadenosine 5'-phosphosulfate syntha |

| Value | Gene | Description |
|---|---|---|
| 3.64 | GPATC2 | G patch domain containing 2 |
| -3.64 | HLA-DQA1 | major histocompatibility complex, class II, DQ a |
| -3.64 | TMEM171 | transmembrane protein 171 |
| 3.64 | LOC401321 | hypothetical LOC401321 |
| 3.64 | HDAC9 | histone deacetylase 9 |
| -3.63 | — | — |
| 3.63 | — | — |
| 3.63 | — | — |
| 3.63 | EYA1 | eyes absent homolog 1 (Drosophila) |
| 3.63 | MEOX1 | mesenchyme homeobox 1 |
| -3.63 | NR3C2 | nuclear receptor subfamily 3, group C, member |
| 3.63 | — | Transcribed locus |
| -3.63 | KLF5 | Kruppel-like factor 5 (intestinal) |
| -3.63 | PLEKHG6 | pleckstrin homology domain containing, family |
| -3.63 | VSIG1 | V-set and immunoglobulin domain containing 1 |
| -3.63 | GLOXD1 | glyoxalase domain containing 1 |
| 3.63 | FMNL3 | formin-like 3 |
| 3.63 | MLLT3 | myeloid/lymphoid or mixed-lineage leukemia (tr |
| -3.62 | TSLP | thymic stromal lymphopoietin |
| 3.62 | WIPF1 | WAS/WASL interacting protein family, member |
| 3.62 | MLLT3 | myeloid/lymphoid or mixed-lineage leukemia (tr |
| 3.62 | — | Transcribed locus |
| 3.62 | HES5 | hairy and enhancer of split 5 (Drosophila) |
| -3.62 | BDNF | brain-derived neurotrophic factor |
| -3.62 | PLS1 | plastin 1 (I isoform) |
| 3.62 | SULF1 | sulfatase 1 |
| 3.62 | — | Transcribed locus |
| 3.62 | — | — |
| -3.62 | MAP7 | microtubule-associated protein 7 |
| 3.61 | — | — |
| -3.61 | CDX4 | caudal type homeobox transcription factor 4 |
| -3.61 | FXYD7 | FXYD domain containing ion transport regulato |
| -3.61 | C1S | complement component 1, s subcomponent |
| -3.61 | LLGL2 | lethal giant larvae homolog 2 (Drosophila) |
| -3.61 | POPDC3 | popeye domain containing 3 |
| -3.60 | GABRB3 | gamma-aminobutyric acid (GABA) A receptor, |
| -3.60 | LDHD | lactate dehydrogenase D |
| -3.60 | STX6 /// RHEBL1 | syntaxin 6 /// Ras homolog enriched in brain like |
| 3.60 | — | — |
| 3.60 | CLEC1A | C-type lectin domain family 1, member A |
| 3.60 | NLRP1 | NLR family, pyrin domain containing 1 |
| -3.60 | NFE2L3 | nuclear factor (erythroid-derived 2)-like 3 |
| -3.60 | — | Transcribed locus |
| -3.60 | — | — |
| 3.60 | — | — |
| 3.59 | — | — |
| 3.59 | FOSL2 | FOS-like antigen 2 |
| 3.59 | — | — |
| 3.59 | SLC26A10 | solute carrier family 26, member 10 |
| -3.59 | JAZF1 | JAZF zinc finger 1 |
| -3.59 | — | — |
| 3.59 | COL6A3 | collagen, type VI, alpha 3 |
| -3.59 | MMP9 | matrix metallopeptidase 9 (gelatinase B, 92kDa |
| -3.59 | — | — |
| -3.58 | FLJ14001 | hypothetical protein FLJ14001 |
| -3.58 | RYR2 | ryanodine receptor 2 (cardiac) |
| 3.58 | HOXC5 | homeobox C5 |
| -3.58 | RGL3 | ral guanine nucleotide dissociation stimulator-li |
| 3.58 | PYGO1 | pygopus homolog 1 (Drosophila) |
| -3.57 | HBA1 | hemoglobin, alpha 1 /// hemoglobin, alpha 1 |
| 3.57 | — | — |
| 3.57 | ARHGDIB | Rho GDP dissociation inhibitor (GDI) beta |
| -3.57 | HTATIP2 | HIV-1 Tat interactive protein 2, 30kDa |
| -3.57 | PTCHD1 | patched domain containing 1 |
| -3.57 | SFN | stratifin |
| -3.57 | PCSK9 | proprotein convertase subtilisin/kexin type 9 |
| -3.57 | ACSM3 | acyl-CoA synthetase medium-chain family men |
| 3.56 | PRTG | protogenin homolog (Gallus gallus) |
| -3.56 | — | CDNA FLJ26031 fis, clone PNC08078 |
| -3.56 | CDS1 | CDP-diacylglycerol synthase (phosphatidate cy |
| -3.56 | — | — |
| 3.56 | PPP3R1 | Protein phosphatase 3 (formerly 2B), regulator |
| 3.55 | — | — |
| 3.55 | DCN | decorin |
| 3.55 | CACNA1G | calcium channel, voltage-dependent, alpha 1G |
| 3.55 | RGL1 | ral guanine nucleotide dissociation stimulator-li |
| -3.55 | GNB5 | guanine nucleotide binding protein (G protein), |
| 3.55 | TDO2 | tryptophan 2,3-dioxygenase |
| -3.55 | RAB3B | RAB3B, member RAS oncogene family |

Appendix 1

| | | | | |
|---|---|---|---|---|
| 4.02 | — | — | -3.55 ATP2A3 | ATPase, Ca++ transporting, ubiquitous |
| 4.02 | MSRB3 | methionine sulfoxide reductase B3 | -3.55 BST2 | bone marrow stromal cell antigen 2 |
| 4.02 | LOC399959 | Hypothetical gene supported by BX647608 | -3.54 GABRB3 | Gamma-aminobutyric acid (GABA) A receptor, |
| -4.01 | TAGLN2 | transgelin 2 | 3.54 VWF | von Willebrand factor |
| -4.01 | MBP | myelin basic protein | 3.54 AGPAT3 | 1-acylglycerol-3-phosphate O-acyltransferase |
| 4.01 | MLLT3 | myeloid/lymphoid or mixed-lineage leukemia (t | -3.54 | — |
| -4.01 | LRRC2 | leucine rich repeat containing 2 | 3.54 DACH1 | dachshund homolog 1 (Drosophila) |
| -4.01 | — | — | 3.54 FRMD4A | FERM domain containing 4A |
| 4.01 | LRRC4B | leucine rich repeat containing 4B | 3.54 | — |
| -4.01 | — | — | 3.53 | — |
| -4.01 | RAB3B | RAB3B, member RAS oncogene family | 3.53 EPS8 | epidermal growth factor receptor pathway subs |
| 4.01 | — | Transcribed locus | -3.53 | — |
| -4.01 | — | Homo sapiens, Similar to otoconin 90, clone IM | 3.53 LHFP | Lipoma HMGIC fusion partner |
| 4.00 | RTN1 | reticulon 1 | 3.53 DUSP4 | dual specificity phosphatase 4 |
| 4.00 | RPIB9 | Rap2-binding protein 9 | 3.52 | — |
| -4.00 | LXN | latexin | 3.52 APBA2 | amyloid beta (A4) precursor protein-binding, fa |
| -4.00 | — | CDNA FLJ32963 fis, clone TESTI2008405 | 3.52 PAG1 | phosphoprotein associated with glycosphingoli |
| -4.00 | ATP2A3 | ATPase, Ca++ transporting, ubiquitous | -3.52 ADCY2 | adenylate cyclase 2 (brain) |
| -3.99 | — | — | -3.52 ICAM4 | intercellular adhesion molecule 4 (Landsteiner- |
| -3.99 | — | — | 3.51 PCDH12 | protocadherin 12 |
| 3.99 | PLD3 | Phospholipase D family, member 3 | 3.51 ZFHX4 | Zinc finger homeodomain 4 |
| -3.99 | FGF4 | fibroblast growth factor 4 (heparin secretory tra | -3.51 LOC133491 | hypothetical protein LOC133491 |
| 3.99 | HOXB4 | homeobox B4 | 3.51 ACTA2 | actin, alpha 2, smooth muscle, aorta |
| -3.99 | SH2D2A | SH2 domain protein 2A | 3.51 IFI44 | interferon-induced protein 44 |
| -3.99 | GCNT1 | glucosaminyl (N-acetyl) transferase 1, core 2 (I | 3.51 PALLD | palladin, cytoskeletal associated protein |
| 3.99 | NRCAM | neuronal cell adhesion molecule | -3.50 CYP26A1 | cytochrome P450, family 26, subfamily A, poly |
| 3.99 | CHN2 | chimerin (chimaerin) 2 | -3.50 SLC16A10 | solute carrier family 16 (monocarboxylic acid tr |
| -3.98 | — | CDNA FLJ36413 fis, clone THYMU2010815 | 3.50 PAX3 | paired box gene 3 (Waardenburg syndrome 1) |
| 3.98 | KIAA1644 | KIAA1644 protein | -3.50 LAD1 | ladinin 1 |
| -3.98 | DENND1C | DENN/MADD domain containing 1C | -3.49 TERF1 | telomeric repeat binding factor (NIMA-interactin |
| -3.98 | — | — | -3.49 GUCA1A | guanylate cyclase activator 1A (retina) |
| -3.98 | LOC93349 | hypothetical protein BC004921 | 3.49 GRHL2 | grainyhead-like 2 (Drosophila) |
| 3.98 | GUCY1A3 | Guanylate cyclase 1, soluble, alpha 3 | 3.49 FILIP1L | filamin A interacting protein 1-like |
| 3.98 | WDR78 | WD repeat domain 78 | -3.49 INHBE | inhibin, beta E |
| -3.97 | FGFR4 | fibroblast growth factor receptor 4 | -3.49 SOCS1 | suppressor of cytokine signaling 1 |
| -3.97 | PRKCD | protein kinase C, delta | -3.49 | CDNA clone IMAGE:5532261 |
| -3.97 | PRKCH | protein kinase C, eta | 3.49 COL5A1 | collagen, type V, alpha 1 |
| 3.97 | PLA2G4A | phospholipase A2, group IVA (cytosolic, calciu | 3.49 | — |
| -3.97 | — | CDNA: FLJ21389 fis, clone COL03455 | 3.49 ZNF3 | zinc finger protein 3 |
| 3.97 | NRG1 | neuregulin 1 | -3.48 | — |
| 3.97 | NEFM | neurofilament, medium polypeptide 150kDa | -3.48 | — |
| 3.96 | — | Homo sapiens, clone IMAGE:4732650, mRNA | -3.48 PCDH11Y /// LOC7 | protocadherin 11 Y-linked /// hypothetical protei |
| -3.96 | MT1G | metallothionein 1G | 3.48 DAAM2 | dishevelled associated activator of morphogen |
| -3.96 | NMRAL1 | NmrA-like family domain containing 1 | 3.48 | — |
| -3.96 | RNF43 | ring finger protein 43 | 3.48 | — |
| 3.96 | YAF2 | YY1 associated factor 2 | 3.47 SLC2A5 | solute carrier family 2 (facilitated glucose/fructo |
| -3.96 | RBP7 | retinol binding protein 7, cellular | 3.47 KBTBD10 | kelch repeat and BTB (POZ) domain containinc |
| -3.96 | TRIM6 | tripartite motif-containing 6 | -3.47 | — |
| -3.96 | — | — | 3.47 | — |
| -3.96 | MET | met proto-oncogene (hepatocyte growth factor | 3.47 FLJ23322 | hypothetical protein FLJ23322 |
| -3.96 | SULT1C1 | sulfotransferase family, cytosolic, 1C, member | 3.47 LRP11 | Low density lipoprotein receptor-related protein |
| -3.96 | AIM1 | absent in melanoma 1 | 3.47 NCF4 | neutrophil cytosolic factor 4, 40kDa /// neutroph |
| 3.95 | — | — | -3.47 | — |
| -3.95 | NR0B1 | nuclear receptor subfamily 0, group B, membe | 3.47 | — |
| -3.95 | BCL11A | B-cell CLL/lymphoma 11A (zinc finger protein) | -3.46 MICB | MHC class I polypeptide-related sequence E |
| 3.95 | HOXD4 | homeobox D4 | -3.46 SYT1 | synaptotagmin I |
| -3.95 | CD9 | CD9 molecule | 3.46 DLC1 | deleted in liver cancer 1 |
| 3.95 | TANC2 | tetratricopeptide repeat, ankyrin repeat and co | -3.46 | — |
| -3.94 | PODXL | podocalyxin-like | 3.46 DPYSL4 | dihydropyrimidinase-like 4 |
| -3.94 | CXCL12 | chemokine (C-X-C motif) ligand 12 (stromal ce | 3.45 GPR162 | G protein-coupled receptor 162 |
| 3.94 | NXPH2 | neurexophilin 2 | 3.45 | CDNA FLJ32121 fis, clone PEBLM1000083 |
| -3.94 | SLC19A3 | solute carrier family 19, member 3 | 3.45 LOC202181 | hypothetical protein LOC202181 |
| -3.94 | HLA-C | major histocompatibility complex, class I, C | 3.45 C10orf72 | Chromosome 10 open reading frame 72 |
| 3.94 | — | — | -3.45 TRPC6 | transient receptor potential cation channel, sub |
| -3.93 | COL5A1 | collagen, type V, alpha 1 | 3.45 HOXA13 | Homeo box A13 |
| 3.93 | SNAP91 | synaptosomal-associated protein, 91kDa homc | 3.45 DHRS9 | dehydrogenase/reductase (SDR family) memb |
| 3.93 | — | CDNA clone IMAGE:5266257 | 3.45 | — |
| 3.93 | ZFHX4 | Zinc finger homeodomain 4 | 3.45 | — |
| -3.93 | — | Transcribed locus | -3.45 | — |
| 3.93 | — | MRNA; cDNA DKFZp686E22185 (from clone D | -3.45 CNOT1 | CCR4-NOT transcription complex, subunit 1 |
| -3.93 | MMP23B /// MMP23 | matrix metallopeptidase 23B /// matrix metallop | 3.44 | — |
| -3.93 | TRAF3IP2 | TRAF3 interacting protein 2 | 3.44 | — |
| -3.92 | — | — | -3.44 CLDN3 | claudin 3 |
| 3.92 | GRM1 | glutamate receptor, metabotropic 1 | 3.44 SLC16A4 | solute carrier family 16, member 4 (monocarbo |
| 3.92 | CTNND2 | catenin (cadherin-associated protein), delta 2 ( | -3.44 | — |
| 3.92 | — | — | -3.44 C11orf32 | chromosome 11 open reading frame 32 |
| 3.92 | — | — | 3.44 | — |
| 3.91 | — | — | 3.44 ANGPTL2 | angiopoietin-like 2 |
| -3.91 | — | — | 3.43 SYDE1 | synapse defective 1, Rho GTPase, homolog 1 |

Appendix 1

| Value | Symbol | Description |
|---|---|---|
| 3.90 | FLJ10159 | Hypothetical protein FLJ10159 |
| -3.90 | YPEL3 | yippee-like 3 (Drosophila) |
| 3.90 | KCNK10 | potassium channel, subfamily K, member 10 |
| -3.90 | WDR72 | WD repeat domain 72 |
| -3.90 | TACSTD2 | tumor-associated calcium signal transducer 2 |
| -3.89 | KLC3 | kinesin light chain 3 |
| -3.89 | — | Transcribed locus, weakly similar to NP_00101 |
| 3.89 | DACH1 | dachshund homolog 1 (Drosophila) |
| 3.89 | — | — |
| 3.89 | LOC388419 | similar to Galectin-3 binding protein precursor |
| -3.89 | MOG | myelin oligodendrocyte glycoprotein |
| -3.89 | TMEM171 | transmembrane protein 171 |
| 3.89 | — | — |
| 3.89 | CLGN | calmegin |
| -3.89 | MT2A | metallothionein 2A |
| -3.89 | ROR1 | receptor tyrosine kinase-like orphan receptor 1 |
| -3.89 | FLJ16287 | FLJ16287 protein |
| 3.89 | LGI2 | leucine-rich repeat LGI family, member 2 |
| -3.89 | PYY | peptide YY |
| -3.88 | NMI | N-myc (and STAT) interactor |
| 3.88 | DPYSL4 | dihydropyrimidinase-like 4 |
| 3.88 | SLC1A4 | solute carrier family 1 (glutamate/neutral amino |
| 3.88 | — | Transcribed locus |
| 3.88 | — | CDNA FLJ30897 fis, clone FEBRA2005476 |
| -3.88 | POLD4 | polymerase (DNA-directed), delta 4 |
| 3.88 | ARL4C | ADP-ribosylation factor-like 4C |
| -3.88 | RYR1 | ryanodine receptor 1 (skeletal) |
| -3.88 | FAM124B | family with sequence similarity 124B |
| -3.87 | MOG | myelin oligodendrocyte glycoprotein |
| 3.87 | PALLD | palladin, cytoskeletal associated protein |
| 3.87 | ABCD2 | ATP-binding cassette, sub-family D (ALD), me |
| -3.87 | CD44 | CD44 molecule (Indian blood group) |
| -3.87 | SSH3 | slingshot homolog 3 (Drosophila) |
| -3.87 | — | — |
| -3.87 | — | Transcribed locus |
| -3.87 | KLF4 | Kruppel-like factor 4 (gut) |
| 3.87 | KIF5A | kinesin family member 5A |
| 3.87 | HOXC5 | homeobox C5 |
| 3.86 | — | Homo sapiens, clone IMAGE:4398657, mRNA |
| -3.86 | ADCY2 | adenylate cyclase 2 (brain) |
| -3.86 | OLFM1 | olfactomedin 1 |
| -3.86 | SERPINB9 | serpin peptidase inhibitor, clade B (ovalbumin) |
| 3.86 | NRG1 | neuregulin 1 |
| -3.86 | MYLIP | myosin regulatory light chain interacting protein |
| 3.86 | TTYH1 | tweety homolog 1 (Drosophila) |
| 3.86 | NF1 | neurofibromin 1 (neurofibromatosis, von Reckli |
| -3.86 | — | Hypothetical protein LOC285679 |
| 3.85 | KIAA1731 | KIAA1731 |
| -3.85 | PRRG2 | proline rich Gla (G-carboxyglutamic acid) 2 |
| -3.85 | HIST1H1A | histone cluster 1, H1a |
| -3.85 | HLA-C | major histocompatibility complex, class I, C |
| -3.85 | POLR3G | polymerase (RNA) III (DNA directed) polypepti |
| 3.85 | — | Transcribed locus |
| -3.85 | EHD2 | EH-domain containing 2 |
| -3.85 | PYGM | phosphorylase, glycogen; muscle (McArdle syn |
| -3.84 | LOC130951 | hypothetical protein BC014602 |
| -3.84 | — | Transcribed locus |
| -3.84 | — | — |
| 3.84 | WHSC2 | Wolf-Hirschhorn syndrome candidate 2 |
| -3.84 | — | — |
| 3.84 | SYT11 | synaptotagmin XI |
| -3.84 | OR2A9P | Olfactory receptor, family 2, subfamily A, memb |
| 3.84 | — | — |
| -3.84 | HLA-A | major histocompatibility complex, class I, A |
| -3.83 | C6orf148 | chromosome 6 open reading frame 148 |
| -3.83 | — | — |
| -3.83 | SLFN13 | schlafen family member 13 |
| 3.82 | — | Transcribed locus |
| 3.82 | BAI3 | brain-specific angiogenesis inhibitor 3 |
| -3.82 | NID2 | nidogen 2 (osteonidogen) |
| -3.82 | — | — |
| -3.82 | DHDH | dihydrodiol dehydrogenase (dimeric) |
| -3.82 | — | — |
| 3.82 | FSIP1 | fibrous sheath interacting protein 1 |
| 3.82 | — | — |
| -3.82 | VAMP5 | vesicle-associated membrane protein 5 (myobr |
| -3.82 | ECHDC2 | enoyl Coenzyme A hydratase domain containi |
| 3.82 | — | — |
| -3.81 | — | — |

| Value | Symbol | Description |
|---|---|---|
| -3.43 | CAV1 | caveolin 1, caveolae protein, 22kDa |
| -3.43 | GNAS | GNAS complex locus |
| 3.43 | IGSF4C | immunoglobulin superfamily, member 4C |
| 3.43 | — | — |
| -3.43 | TERT | telomerase reverse transcriptase |
| 3.43 | MCART6 | mitochondrial carrier triple repeat 6 |
| -3.43 | FLT1 | fms-related tyrosine kinase 1 (vascular endothe |
| -3.43 | MYC | v-myc myelocytomatosis viral oncogene homol |
| -3.43 | CTH | cystathionase (cystathionine gamma-lyase) |
| 3.43 | KLHDC1 | kelch domain containing 1 |
| -3.42 | C10orf95 | Chromosome 10 open reading frame 95 |
| 3.42 | MGC33556 | hypothetical LOC339541 |
| -3.42 | ATCAY | ataxia, cerebellar, Cayman type (caytaxin) |
| 3.42 | UNC5C | unc-5 homolog C (C. elegans) |
| 3.42 | PPFIBP2 | PTPRF interacting protein, binding protein 2 (li |
| -3.42 | IL6 | interleukin 6 (interferon, beta 2) |
| -3.42 | KLK8 | kallikrein-related peptidase 8 |
| 3.42 | — | — |
| 3.42 | NOD2 | nucleotide-binding oligomerization domain cont |
| 3.41 | — | — |
| 3.41 | PPP1R3C | protein phosphatase 1, regulatory (inhibitor) sul |
| 3.41 | — | — |
| 3.41 | MGC26963 | hypothetical protein MGC26963 |
| -3.41 | EDG7 | endothelial differentiation, lysophosphatidic acid |
| 3.41 | SFRS12 | Splicing factor, arginine/serine-rich 12 |
| 3.40 | RCSD1 | RCSD domain containing 1 |
| -3.40 | PITX2 | paired-like homeodomain transcription factor 2 |
| 3.40 | SORBS2 | sorbin and SH3 domain containing 2 |
| 3.40 | — | CDNA clone IMAGE:3347954 |
| -3.40 | FGFR4 | fibroblast growth factor receptor 4 |
| 3.40 | CASP1 | caspase 1, apoptosis-related cysteine peptidas |
| -3.40 | — | Full length insert cDNA YN57B01 |
| 3.39 | EDG3 | endothelial differentiation, sphingolipid G-protei |
| -3.39 | CTH | cystathionase (cystathionine gamma-lyase) |
| -3.39 | FGF2 | fibroblast growth factor 2 (basic) |
| 3.39 | — | — |
| 3.38 | LHX8 | LIM homeobox 8 |
| -3.38 | GAL | galanin |
| 3.38 | FAM49A | family with sequence similarity 49, member A |
| 3.38 | H2AFY | H2A histone family, member Y |
| -3.38 | — | — |
| -3.38 | NR5A2 | nuclear receptor subfamily 5, group A, member |
| -3.38 | — | — |
| -3.37 | HTATIP2 | HIV-1 Tat interactive protein 2, 30kDa |
| 3.37 | PCDH9 | Protocadherin 9 |
| -3.37 | CABP1 | calcium binding protein 1 (calbrain) |
| 3.37 | — | — |
| 3.37 | FXYD6 | FXYD domain containing ion transport regulato |
| 3.37 | SERTAD4 | SERTA domain containing 4 |
| 3.37 | GUCY1A3 | Guanylate cyclase 1, soluble, alpha 3 |
| 3.37 | — | — |
| 3.37 | C1orf86 | chromosome 1 open reading frame 86 |
| -3.37 | CRYGD | crystallin, gamma D |
| 3.37 | REEP1 | receptor accessory protein 1 |
| 3.36 | GP1BB /// SEPT5 | glycoprotein Ib (platelet), beta polypeptide /// se |
| -3.36 | — | — |
| 3.36 | — | Transcribed locus |
| 3.36 | MEGF9 | multiple EGF-like-domains 9 |
| 3.36 | OAF | OAF homolog (Drosophila) |
| -3.35 | CHST4 | carbohydrate (N-acetylglucosamine 6-O) sulfot |
| -3.35 | C10orf90 | chromosome 10 open reading frame 90 |
| -3.35 | PCDH21 | protocadherin 21 |
| 3.35 | GRK5 | G protein-coupled receptor kinase 5 |
| -3.35 | NDUFA9 | NADH dehydrogenase (ubiquinone) 1 alpha sul |
| -3.35 | — | — |
| -3.35 | — | — |
| 3.35 | TMEM16B | transmembrane protein 16B |
| 3.35 | TFAP2A | Transcription factor AP-2 alpha (activating enh |
| 3.34 | — | — |
| 3.34 | FNDC4 | fibronectin type III domain containing 4 |
| 3.34 | TLR4 | toll-like receptor 4 /// toll-like receptor 4 |
| -3.34 | ASPHD1 | aspartate beta-hydroxylase domain containing |
| -3.34 | LOC728473 | hypothetical protein LOC728473 |
| -3.34 | — | — |
| -3.34 | GRID2 | glutamate receptor, ionotropic, delta 2 |
| 3.34 | C9orf47 | chromosome 9 open reading frame 47 |
| 3.34 | — | — |
| -3.33 | TFPI2 | tissue factor pathway inhibitor 2 |
| -3.33 | OVOL2 | ovo-like 2 (Drosophila) /// ovo-like 2 (Drosophila |

Appendix 1

| Value | Gene | Description |
|---|---|---|
| -3.81 | — | — |
| -3.81 | GABRP | gamma-aminobutyric acid (GABA) A receptor, |
| 3.81 | HCN1 | hyperpolarization activated cyclic nucleotide-ga |
| 3.81 | HOXC4 | homeobox C4 |
| 3.80 | WDR17 | WD repeat domain 17 |
| -3.80 | IGFBP7 | insulin-like growth factor binding protein 7 |
| -3.80 | HLA-B | major histocompatibility complex, class I, B |
| -3.80 | ACAD8 | Acyl-Coenzyme A dehydrogenase family, mem |
| -3.80 | ARHGAP10 | Rho GTPase activating protein 10 |
| -3.79 | KCND2 | potassium voltage-gated channel, Shal-related |
| 3.79 | C10orf41 | chromosome 10 open reading frame 41 |
| 3.79 | — | — |
| 3.79 | C12orf62 | Chromosome 12 open reading frame 62 |
| -3.79 | TTC9 | tetratricopeptide repeat domain 9 |
| -3.79 | TIMP4 | TIMP metallopeptidase inhibitor 4 |
| -3.79 | CCDC69 | coiled-coil domain containing 69 |
| 3.79 | C13orf21 | Chromosome 13 open reading frame 21 |
| 3.78 | ZIC1 | Zic family member 1 (odd-paired homolog, Dro |
| 3.78 | KIAA1772 | KIAA1772 |
| -3.78 | FRAT2 | frequently rearranged in advanced T-cell lymph |
| 3.78 | LOC147670 | hypothetical protein LOC147670 |
| 3.78 | ST8SIA4 | ST8 alpha-N-acetyl-neuraminide alpha-2,8-sial |
| -3.78 | D21S2088E | D21S2088E |
| -3.78 | — | MRNA; cDNA DKFZp434H205 (from clone DK |
| 3.77 | ATBF1 | AT-binding transcription factor 1 |
| -3.77 | GATA4 | GATA binding protein 4 |
| 3.77 | IQCH | IQ motif containing H |
| -3.76 | PHF15 | PHD finger protein 15 |
| -3.76 | INDO | indoleamine-pyrrole 2,3 dioxygenase |
| -3.76 | IL15 | interleukin 15 |
| -3.76 | — | — |
| 3.76 | BMPR1B | Bone morphogenetic protein receptor, type IE |
| -3.76 | C14orf115 | chromosome 14 open reading frame 115 |
| 3.76 | SYT11 | synaptotagmin XI |
| -3.76 | — | — |
| -3.76 | — | — |
| 3.75 | LHFP | Lipoma HMGIC fusion partner |
| -3.75 | EDA | ectodysplasin A |
| 3.75 | CHRNA7 | Cholinergic receptor, nicotinic, alpha polypepti |
| -3.75 | TRIP6 | thyroid hormone receptor interactor 6 |
| -3.75 | MBP | myelin basic protein |
| -3.75 | CD44 | CD44 molecule (Indian blood group) |
| -3.75 | LOC642587 | NPC-A-5 |
| 3.75 | FBN1 | fibrillin 1 |
| -3.74 | MYOZ3 | myozenin 3 |
| -3.74 | KCNG3 | potassium voltage-gated channel, subfamily G, |
| 3.74 | FGF14 | fibroblast growth factor 14 |
| 3.74 | FZD10 | frizzled homolog 10 (Drosophila) |
| 3.74 | GLULD1 | glutamate-ammonia ligase (glutamine synthet |
| -3.74 | — | — |
| 3.74 | LRRN3 | leucine rich repeat neuronal 3 |
| 3.74 | PALLD | palladin, cytoskeletal associated protein |
| 3.74 | SLC2A1 | solute carrier family 2 (facilitated glucose trans |
| 3.74 | NAV2 | neuron navigator 2 |
| -3.74 | LOC439949 | hypothetical gene supported by AY007155 |
| -3.74 | FGF17 | fibroblast growth factor 17 |
| 3.73 | — | — |
| -3.73 | PCDH10 | Protocadherin 10 |
| 3.73 | ZNF436 | zinc finger protein 436 |
| 3.73 | HYMAI | hydatidiform mole associated and imprinted |
| -3.72 | TRIM14 | tripartite motif-containing 14 |
| -3.72 | — | — |
| -3.72 | STYK1 | serine/threonine/tyrosine kinase 1 |
| -3.71 | C6orf189 | chromosome 6 open reading frame 189 |
| -3.71 | PAK6 | p21(CDKN1A)-activated kinase 6 |
| 3.71 | — | — |
| -3.71 | — | Transcribed locus |
| -3.71 | SOX17 | SRY (sex determining region Y)-box 17 |
| 3.71 | SLC1A4 | solute carrier family 1 (glutamate/neutral amino |
| 3.70 | — | — |
| 3.70 | ENPP2 | ectonucleotide pyrophosphatase/phosphodiest |
| -3.70 | BCL11A | B-cell CLL/lymphoma 11A (zinc finger protein) |
| -3.70 | BCL11A | B-cell CLL/lymphoma 11A (zinc finger protein) |
| -3.70 | GAL | galanin |
| -3.70 | — | — |
| -3.70 | — | — |
| -3.69 | C1orf210 | chromosome 1 open reading frame 210 |
| -3.69 | LYPD3 | LY6/PLAUR domain containing 3 |
| 3.69 | — | Transcribed locus |

| Value | Gene | Description |
|---|---|---|
| 3.33 | PRKD1 | protein kinase D1 |
| 3.33 | — | CDNA FLJ26539 fis, clone KDN09310 |
| -3.33 | — | MRNA; cDNA DKFZp564C203 (from clone DKF |
| -3.33 | FLJ31204 | hypothetical protein FLJ31204 |
| -3.33 | FAM20A | Family with sequence similarity 20, member A |
| -3.33 | SLC4A11 | solute carrier family 4, sodium bicarbonate tran |
| -3.33 | CLU | clusterin |
| -3.32 | KCNJ2 | potassium inwardly-rectifying channel, subfamil |
| 3.32 | LRP1B | low density lipoprotein-related protein 1B (delet |
| -3.32 | LRAT | lecithin retinol acyltransferase (phosphatidylcho |
| 3.32 | SCML4 | sex comb on midleg-like 4 (Drosophila) |
| -3.32 | C6orf189 | chromosome 6 open reading frame 189 |
| 3.32 | — | — |
| 3.32 | SIX1 | sine oculis homeobox homolog 1 (Drosophila) |
| -3.32 | PPAP2C | phosphatidic acid phosphatase type 2C |
| 3.32 | CYTL1 | cytokine-like 1 |
| 3.31 | CCNE2 | cyclin E2 |
| -3.31 | HPGD | hydroxyprostaglandin dehydrogenase 15-(NAD |
| -3.31 | — | — |
| -3.31 | — | Transcribed locus, strongly similar to XP_5155 |
| 3.31 | SNCA | synuclein, alpha (non A4 component of amyloid |
| 3.31 | PLAGL1 | pleiomorphic adenoma gene-like 1 |
| -3.31 | TRPC6 | transient receptor potential cation channel, sub |
| 3.31 | — | — |
| 3.31 | — | — |
| 3.31 | TMEM121 | transmembrane protein 121 |
| -3.30 | MAP4K1 | mitogen-activated protein kinase kinase kinase |
| 3.30 | SEMA3E | sema domain, immunoglobulin domain (Ig), sho |
| -3.30 | SNHG4 | small nucleolar RNA host gene (non-protein co |
| 3.29 | C5orf24 | chromosome 5 open reading frame 24 |
| 3.29 | GAS1 | growth arrest-specific 1 |
| 3.29 | RNASEL | ribonuclease L (2',5'-oligoisoadenylate synthet |
| 3.29 | PDLIM4 | PDZ and LIM domain 4 |
| -3.29 | — | Transcribed locus, weakly similar to XP_51765 |
| -3.29 | SOHLH2 | spermatogenesis and oogenesis specific basic |
| 3.29 | SAMHD1 | SAM domain and HD domain 1 |
| 3.29 | — | MRNA; cDNA DKFZp779M2422 (from clone Dk |
| -3.29 | CXCL2 | chemokine (C-X-C motif) ligand 2 |
| -3.29 | CD55 | CD55 molecule, decay accelerating factor for c |
| 3.29 | — | — |
| -3.28 | LOC391020 | similar to Interferon-induced transmembrane pr |
| -3.28 | — | — |
| 3.28 | CCDC92 | coiled-coil domain containing 92 |
| -3.28 | CLU | clusterin |
| 3.28 | KALRN | kalirin, RhoGEF kinase |
| 3.27 | GPC5 | glypican 5 |
| 3.27 | — | Transcribed locus |
| -3.27 | ADAM28 | ADAM metallopeptidase domain 28 |
| -3.27 | NPR1 | natriuretic peptide receptor A/guanylate cyclase |
| 3.27 | HEY1 | hairy/enhancer-of-split related with YRPW motif |
| -3.27 | FRMD5 | FERM domain containing 5 |
| -3.27 | FLJ30707 | hypothetical protein FLJ30707 |
| 3.27 | TMSL8 | thymosin-like 8 |
| 3.26 | EDN3 | endothelin 3 |
| 3.26 | BAALC | brain and acute leukemia, cytoplasmic |
| 3.26 | CDKN2C | cyclin-dependent kinase inhibitor 2C (p18, inhib |
| -3.26 | HHLA1 | HERV-H LTR-associating 1 |
| 3.26 | — | — |
| 3.25 | MLLT3 | myeloid/lymphoid or mixed-lineage leukemia (tr |
| 3.25 | ABCB4 | ATP-binding cassette, sub-family B (MDR/TAP) |
| 3.25 | FILIP1L | filamin A interacting protein 1-like |
| -3.25 | GATA3 | GATA binding protein 3 |
| 3.25 | MEIS2 | Meis1, myeloid ecotropic viral integration site 1 |
| 3.25 | — | — |
| -3.25 | PBX1 | Pre-B-cell leukemia transcription factor 1 |
| 3.24 | VAPB | VAMP (vesicle-associated membrane protein)- |
| 3.24 | PCDH8 | protocadherin 8 |
| 3.24 | OLFM3 | olfactomedin 3 |
| 3.24 | ZIC1 | Zic family member 1 (odd-paired homolog, Dros |
| 3.24 | C9orf3 | Chromosome 9 open reading frame 3 |
| 3.23 | — | — |
| 3.23 | MPPED2 | metallophosphoesterase domain containing 2 |
| 3.23 | STXBP6 | syntaxin binding protein 6 (amisyn) |
| -3.23 | LOC388638 | hypothetical LOC388638 |
| 3.23 | CXCL10 | chemokine (C-X-C motif) ligand 10 |
| 3.23 | LRRC39 | leucine rich repeat containing 39 |
| -3.22 | — | — |
| 3.22 | ATP1A2 | ATPase, Na+/K+ transporting, alpha 2 (+) poly |
| -3.22 | PPP2R2C | protein phosphatase 2 (formerly 2A), regulatory |

Appendix 1

| | | | |
|---|---|---|---|
| -3.69 ARRDC2 | arrestin domain containing 2 | -3.22 — | cDNA clone IMAGE:4638753 |
| 3.69 LOC401321 | hypothetical LOC401321 | -3.22 MT1F | metallothionein 1F (functional) |
| -3.69 HLA-C /// LOC7320 | major histocompatibility complex, class I, C /// | 3.22 FLRT3 | fibronectin leucine rich transmembrane protein |
| -3.69 PAPSS2 | 3'-phosphoadenosine 5'-phosphosulfate syntha | 3.22 — | — |
| -3.69 EDNRB | endothelin receptor type B | 3.22 PALLD | palladin, cytoskeletal associated protein |
| -3.69 SPINK2 | serine peptidase inhibitor, Kazal type 2 (acrosir | -3.22 HTR3A | 5-hydroxytryptamine (serotonin) receptor 3A |
| 3.69 — | — | 3.22 MCART6 | mitochondrial carrier triple repeat 6 |
| -3.69 FAM83H | family with sequence similarity 83, member H | -3.22 HRLP5 | H-rev107-like protein 5 |
| -3.69 EDIL3 | EGF-like repeats and discoidin I-like domains 3 | 3.22 — | — |
| -3.68 RASL12 | RAS-like, family 12 | -3.21 AQP4 | aquaporin 4 |
| 3.68 ID4 | inhibitor of DNA binding 4, dominant negative H | 3.21 FAM38B | family with sequence similarity 38, member B |
| 3.68 HS3ST3B1 | heparan sulfate (glucosamine) 3-O-sulfotransfe | 3.21 PALLD | palladin, cytoskeletal associated protein |
| -3.68 VASH2 | vasohibin 2 | -3.21 — | — |
| 3.68 SNCA | synuclein, alpha (non A4 component of amyloid | 3.21 DLC1 | deleted in liver cancer 1 |
| 3.68 C3orf32 | chromosome 3 open reading frame 32 | 3.21 FAS | Fas (TNF receptor superfamily, member 6) |
| 3.68 — | — | 3.21 — | — |
| -3.67 PDGFRA | platelet-derived growth factor receptor, alpha p | -3.20 NLRP12 | NLR family, pyrin domain containing 12 |
| 3.67 FLJ39198 | Hypothetical protein LOC643763 | 3.20 AFF3 /// MLL | AF4/FMR2 family, member 3 /// myeloid/lymphc |
| -3.67 FAM100A | family with sequence similarity 100, member A | -3.20 LOC440338 | hypothetical gene supported by AJ002784 |
| -3.67 LOC123688 | similar to RIKEN cDNA C630028N24 gene | 3.20 PCDH7 | BH-protocadherin (brain-heart) |
| -3.67 HERC6 | hect domain and RLD 6 | -3.20 PMAIP1 | phorbol-12-myristate-13-acetate-induced protei |
| -3.67 COMT | catechol-O-methyltransferase | 3.20 GPR155 | G protein-coupled receptor 155 |
| -3.67 — | — | 3.20 DEDD | Death effector domain containing |
| -3.67 PLAU | plasminogen activator, urokinase /// plasminog | -3.20 ZHX2 | Zinc fingers and homeoboxes 2 |
| -3.67 — | — | 3.20 — | Transcribed locus |
| -3.67 — | — | 3.20 IFNAR1 | interferon (alpha, beta and omega) receptor 1 |
| -3.66 C1orf116 | chromosome 1 open reading frame 116 | 3.20 SCD5 | stearoyl-CoA desaturase 5 |
| 3.66 ST18 | suppression of tumorigenicity 18 (breast carcin | 3.20 SDHALP2 | succinate dehydrogenase complex, subunit A, |
| 3.66 — | cDNA FLJ33441 fis, clone BRACE2021932 | 3.20 AUTS2 | Autism susceptibility candidate 2 |
| 3.66 — | — | 3.19 ABAT | 4-aminobutyrate aminotransferase |
| 3.66 ST8SIA2 | ST8 alpha-N-acetyl-neuraminide alpha-2,8-sial | -3.19 POLR3G | polymerase (RNA) III (DNA directed) polypeptic |
| -3.66 — | — | -3.19 PCDH11X /// PCDH | protocadherin 11 X-linked /// protocadherin 11 |
| -3.66 PLAU | plasminogen activator, urokinase | 3.19 — | Transcribed locus |
| -3.66 NPR1 | natriuretic peptide receptor A/guanylate cyclase | -3.19 LOC642587 | NPC-A-5 |
| -3.66 — | — | -3.19 C2orf15 | chromosome 2 open reading frame 15 |
| -3.66 RYR2 | ryanodine receptor 2 (cardiac) | 3.19 CSPG4 | Chondroitin sulfate proteoglycan 4 (melanoma- |
| -3.65 EDIL3 | EGF-like repeats and discoidin I-like domains 3 | 3.19 FLRT3 | fibronectin leucine rich transmembrane protein |
| -3.65 — | — | -3.19 LOC157627 | hypothetical protein LOC157627 |
| -3.65 LY75 | lymphocyte antigen 75 | 3.19 LNPEP | leucyl/cystinyl aminopeptidase |
| -3.65 LOC155036 | hypothetical protein LOC155036 | 3.18 ATP1A2 | ATPase, Na+/K+ transporting, alpha 2 (+) polyp |
| 3.65 APBA2 | amyloid beta (A4) precursor protein-binding, fa | -3.18 KLC3 | kinesin light chain 3 |
| 3.65 ZHX1 | zinc fingers and homeoboxes 1 | -3.18 — | MRNA; cDNA DKFZp761N2217 (from clone DH |
| 3.65 PRSS2 | protease, serine, 2 (trypsin 2) | 3.18 — | — |
| -3.65 — | Transcribed locus | -3.17 ST14 | suppression of tumorigenicity 14 (colon carcino |
| 3.65 SLC2A1 | solute carrier family 2 (facilitated glucose trans | -3.17 — | — |
| 3.65 ODZ2 | odz, odd Oz/ten-m homolog 2 (Drosophila) | 3.17 FZD10 | frizzled homolog 10 (Drosophila) |
| -3.64 MFAP3L | microfibrillar-associated protein 3-like | -3.17 KIAA1155 | KIAA1155 protein |
| -3.64 — | — | 3.17 EDG3 | endothelial differentiation, sphingolipid G-protei |
| -3.64 RORA | RAR-related orphan receptor A | 3.17 PLD5 | phospholipase D family, member 5 |
| 3.64 DEDD | Death effector domain containing | 3.17 — | Transcribed locus |
| 3.64 SV2C | synaptic vesicle glycoprotein 2C | 3.17 ARL4C | ADP-ribosylation factor-like 4C |
| 3.64 CLRN1 | clarin 1 | 3.17 CALCRL | calcitonin receptor-like |
| -3.64 C9orf61 | chromosome 9 open reading frame 61 | 3.17 DLX5 | distal-less homeobox 5 |
| -3.64 NFIA | Nuclear factor I/A | -3.16 LDHC | lactate dehydrogenase C |
| -3.64 — | — | 3.16 RABL5 | RAB, member RAS oncogene family-like 5 |
| 3.64 — | — | -3.16 SORL1 | sortilin-related receptor, L(DLR class) A repeats |
| -3.64 ZNF788 | zinc finger family member 788 | 3.16 CCNE2 | cyclin E2 |
| 3.64 HOXB5 | homeobox B5 | 3.16 MSRA | Methionine sulfoxide reductase A |
| -3.63 LY6E | lymphocyte antigen 6 complex, locus E | -3.16 PROCR | protein C receptor, endothelial (EPCR) |
| -3.63 PDE5A | phosphodiesterase 5A, cGMP-specific | -3.16 DOCK9 | dedicator of cytokinesis 9 |
| -3.63 — | — | 3.16 HERPUD2 | HERPUD family member 2 |
| -3.63 MET | met proto-oncogene (hepatocyte growth factor | 3.16 RNF165 | ring finger protein 165 |
| -3.63 KCNE3 | potassium voltage-gated channel, Isk-related fa | 3.16 — | — |
| -3.63 C1S | complement component 1, s subcomponent | 3.16 MGC14289 | similar to RIKEN cDNA 1200014N16 gene |
| 3.63 REEP1 | receptor accessory protein 1 | -3.15 DNMT3B | DNA (cytosine-5-)-methyltransferase 3 beta |
| -3.62 FGF21 | fibroblast growth factor 21 | 3.15 CXCL14 | chemokine (C-X-C motif) ligand 14 |
| 3.62 — | — | 3.15 ISLR | immunoglobulin superfamily containing leucine- |
| 3.62 TMED4 | transmembrane emp24 protein transport doma | 3.15 PRKCE | protein kinase C, epsilon |
| -3.62 CCNA1 | cyclin A1 | 3.15 APOC2 | apolipoprotein C-II |
| 3.62 SNAP25 | Synaptosomal-associated protein, 25kDa | -3.15 TNFRSF12A | tumor necrosis factor receptor superfamily, mer |
| -3.62 ANKS6 | ankyrin repeat and sterile alpha motif domain c | -3.15 LPIN1 | Lipin 1 |
| 3.61 — | cDNA FLJ25677 fis, clone TST04054 | 3.15 FBLN2 | fibulin 2 |
| -3.61 TAF4B | TAF4b RNA polymerase II, TATA box binding p | 3.15 SFRS8 | splicing factor, arginine/serine-rich 8 (suppress |
| 3.61 LSAMP | limbic system-associated membrane protein | 3.15 THBD | thrombomodulin |
| -3.61 ASAM | adipocyte-specific adhesion molecule | -3.14 — | — |
| -3.61 ZDHHC23 | zinc finger, DHHC-type containing 23 | 3.14 — | cDNA clone IMAGE:4811567 |
| -3.61 F2RL1 | coagulation factor II (thrombin) receptor-like 1 | -3.14 CD55 | CD55 molecule, decay accelerating factor for c |
| 3.61 SARM1 | sterile alpha and TIR motif containing 1 | -3.14 — | — |
| 3.60 LOC645513 | Similar to septin 7 | 3.14 — | cDNA FLJ25677 fis, clone TST04054 |

Appendix 1

| | | | | |
|---|---|---|---|---|
| -3.60 | PTCHD1 | patched domain containing 1 | -3.13 | S100A14 | S100 calcium binding protein A14 |
| -3.60 | ITGA3 | integrin, alpha 3 (antigen CD49C, alpha 3 subu | 3.13 | NRP1 | neuropilin 1 |
| -3.60 | AMIGO2 | adhesion molecule with Ig-like domain 2 | 3.13 | HOXB5 | homeobox B5 |
| 3.60 | — | — | 3.13 | COL5A1 | collagen, type V, alpha 1 |
| -3.60 | FUT1 | fucosyltransferase 1 (galactoside 2-alpha-L-fuc | 3.13 | — | MRNA; cDNA DKFZp686I18116 (from clone DK |
| 3.60 | PRRX1 | Paired related homeobox 1 | 3.13 | — | Homo sapiens, clone IMAGE:3851018, mRNA |
| -3.59 | FBXO2 | F-box protein 2 | 3.13 | KIAA1772 | KIAA1772 |
| 3.59 | NRIP3 | nuclear receptor interacting protein 3 | -3.12 | EEF1A2 | eukaryotic translation elongation factor 1 alpha |
| -3.59 | JAZF1 | JAZF zinc finger 1 | -3.12 | CDCP1 | CUB domain containing protein 1 |
| -3.59 | ATP2A3 | ATPase, Ca++ transporting, ubiquitous | -3.12 | FBXO2 | F-box protein 2 |
| -3.59 | KIAA1305 | KIAA1305 | 3.12 | TTC3 | tetratricopeptide repeat domain 3 |
| 3.59 | AMPH | amphiphysin (Stiff-Man syndrome with breast c | -3.12 | DHRS2 | dehydrogenase/reductase (SDR family) membe |
| 3.58 | — | — | -3.12 | GCNT2 /// SPTLC3 | glucosaminyl (N-acetyl) transferase 2, I-branchi |
| -3.58 | STOM | stomatin | 3.12 | COL8A1 | collagen, type VIII, alpha 1 |
| 3.58 | — | — | -3.12 | KLF8 | Kruppel-like factor 8 |
| 3.58 | C4orf31 | Chromosome 4 open reading frame 31 | 3.11 | ACSL3 | Acyl-CoA synthetase long-chain family member |
| 3.58 | SLCO6A1 | solute carrier organic anion transporter family, | -3.11 | — | — |
| 3.58 | ZNF276 | zinc finger protein 276 | 3.11 | — | — |
| 3.58 | — | — | 3.11 | EFCBP2 | EF-hand calcium binding protein 2 |
| 3.57 | NMNAT2 | nicotinamide nucleotide adenylyltransferase 2 | -3.11 | — | — |
| -3.57 | — | — | 3.11 | JAM2 | junctional adhesion molecule 2 |
| 3.57 | — | — | 3.11 | LOC645513 | Similar to septin 7 |
| -3.57 | AOX1 | aldehyde oxidase 1 | 3.11 | — | CDNA clone IMAGE:5303499 |
| 3.57 | PROX1 | Prospero-related homeobox 1 | 3.10 | — | — |
| 3.57 | GPATC2 | G patch domain containing 2 | -3.10 | INADL | InaD-like (Drosophila) |
| -3.57 | STAT6 | signal transducer and activator of transcription | 3.10 | SULF2 | sulfatase 2 |
| -3.57 | LOC729678 | hypothetical protein LOC729678 | 3.10 | ATP9A | ATPase, Class II, type 9A |
| 3.57 | — | Homo sapiens, clone IMAGE:3851018, mRNA | -3.10 | EPAS1 | endothelial PAS domain protein 1 |
| 3.57 | PRKXP1 | protein kinase, X-linked, pseudogene 1 | -3.10 | TLE2 | transducin-like enhancer of split 2 (E(sp1) hom |
| 3.56 | LOC284033 | hypothetical protein LOC284033 | 3.10 | SULF2 | sulfatase 2 |
| 3.56 | PDE4D | phosphodiesterase 4D, cAMP-specific (phosph | 3.10 | CDH10 | cadherin 10, type 2 (T2-cadherin) |
| -3.56 | PCDH10 | Protocadherin 10 | 3.10 | ZDHHC14 | zinc finger, DHHC-type containing 14 |
| 3.56 | — | Transcribed locus | 3.10 | ARHGDIB | Rho GDP dissociation inhibitor (GDI) beta |
| 3.56 | MIER3 | Mesoderm induction early response 1, family m | 3.09 | — | — |
| -3.56 | — | — | 3.09 | ZAP70 | zeta-chain (TCR) associated protein kinase 70 |
| -3.56 | ARRB1 | arrestin, beta 1 | 3.09 | ARHGAP28 | Rho GTPase activating protein 28 |
| -3.56 | EPB41L4B | erythrocyte membrane protein band 4.1 like 4E | 3.09 | MAP1A | microtubule-associated protein 1A |
| -3.56 | OTX2 | orthodenticle homolog 2 (Drosophila) | 3.09 | KIAA1546 | KIAA1546 |
| 3.56 | — | Homo sapiens, Similar to neuronal thread prote | -3.09 | TERF1 | telomeric repeat binding factor (NIMA-interactin |
| -3.55 | MCTP2 | multiple C2 domains, transmembrane 2 | 3.09 | EDG2 | endothelial differentiation, lysophosphatidic acio |
| -3.55 | MUC3B | mucin 3B, cell surface associated | 3.09 | — | — |
| 3.55 | — | CDNA FLJ34815 fis, clone NT2NE2007786 | -3.09 | CHAC1 | ChaC, cation transport regulator homolog 1 (E. |
| 3.55 | — | — | 3.09 | — | — |
| 3.55 | — | — | -3.08 | NRK | Nik related kinase |
| -3.55 | — | CDNA: FLJ22478 fis, clone HRC10816 | 3.08 | — | — |
| -3.55 | SLC25A43 | solute carrier family 25, member 43 | 3.08 | — | — |
| 3.55 | — | CDNA clone IMAGE:5303499 | -3.08 | — | — |
| -3.54 | HLA-B | major histocompatibility complex, class I, B /// | -3.08 | ATP2A3 | ATPase, Ca++ transporting, ubiquitous |
| 3.54 | — | — | 3.08 | — | MRNA; cDNA DKFZp762I0915 (from clone DKI |
| -3.54 | KCTD14 | potassium channel tetramerisation domain con | 3.08 | MICAL2 | microtubule associated monoxygenase, calpon |
| -3.54 | — | — | 3.08 | ERG | v-ets erythroblastosis virus E26 oncogene hom |
| 3.54 | BTBD9 | BTB (POZ) domain containing 9 | 3.08 | — | — |
| 3.54 | CXCR7 | chemokine (C-X-C motif) receptor 7 | 3.08 | — | — |
| -3.54 | CGN | cingulin | -3.08 | — | Surfactant associated protein F mRNA, partial s |
| 3.54 | PPP1R7 | Protein phosphatase 1, regulatory subunit 7 | 3.08 | LOC387790 | hypothetical LOC387790 |
| -3.54 | UGT8 | UDP glycosyltransferase 8 (UDP-galactose cer | 3.08 | LOC153577 | hypothetical protein LOC153577 |
| 3.54 | — | — | 3.08 | — | — |
| 3.54 | SARM1 | sterile alpha and TIR motif containing 1 | 3.08 | YPEL4 | Yippee-like 4 (Drosophila) |
| -3.53 | LDHA | lactate dehydrogenase A | -3.07 | PPP1R1B | protein phosphatase 1, regulatory (inhibitor) sul |
| -3.53 | TNFRSF8 | tumor necrosis factor receptor superfamily, me | 3.07 | MS4A6A | membrane-spanning 4-domains, subfamily A, n |
| -3.53 | — | — | -3.07 | SPP1 | secreted phosphoprotein 1 (osteopontin, bone s |
| -3.53 | SERPINH1 | serpin peptidase inhibitor, clade H (heat shock | 3.07 | — | CDNA FLJ39389 fis, clone PLACE6003621 |
| -3.53 | C1RL | complement component 1, r subcomponent-like | -3.07 | LOC439949 | hypothetical gene supported by AY007155 |
| -3.53 | LOC255104 | Transmembrane and coiled-coil domains 4 | 3.07 | EDG2 | Endothelial differentiation, lysophosphatidic aci |
| -3.53 | FAM38A | family with sequence similarity 38, member A | 3.07 | UNC13C | unc-13 homolog C (C. elegans) |
| -3.53 | — | Similar to Al661453 protein | -3.07 | SPINK2 | serine peptidase inhibitor, Kazal type 2 (acrosir |
| -3.53 | PLAUR | plasminogen activator, urokinase receptor | 3.07 | — | — |
| -3.52 | CD44 /// MAPK10 | CD44 molecule (Indian blood group) /// mitoger | -3.07 | ENPP1 | ectonucleotide pyrophosphatase/phosphodieste |
| 3.52 | — | — | 3.07 | — | Transcribed locus |
| -3.52 | DKK4 | dickkopf homolog 4 (Xenopus laevis) | 3.06 | — | — |
| 3.52 | CHRDL1 | chordin-like 1 | 3.06 | — | — |
| -3.52 | — | — | -3.06 | — | — |
| -3.52 | RPS4Y1 | ribosomal protein S4, Y-linked 1 | 3.06 | NRIP1 | nuclear receptor interacting protein 1 |
| -3.52 | DLC1 | deleted in liver cancer 1 | 3.06 | COL8A1 | Collagen, type VIII, alpha 1 |
| -3.52 | SAV1 | Salvador homolog 1 (Drosophila) | 3.06 | TIMP3 | TIMP metallopeptidase inhibitor 3 (Sorsby fund |
| -3.51 | LRAT | lecithin retinol acyltransferase (phosphatidylcho | 3.06 | — | — |
| -3.51 | HBA1 | hemoglobin, alpha 1 /// hemoglobin, alpha 1 | -3.05 | BMPR1A | Bone morphogenetic protein receptor, type IA |
| 3.51 | GSTM3 | glutathione S-transferase M3 (brain) | 3.05 | — | — |
| -3.51 | GLS2 | glutaminase 2 (liver, mitochondrial) | 3.05 | HEY1 | hairy/enhancer-of-split related with YRPW motif |

Appendix 1

| | | | | |
|---|---|---|---|---|
| 3.51 | — | Full-length cDNA clone CS0DC002YJ17 of Net | -3.05 | BICD1 | bicaudal D homolog 1 (Drosophila) |
| -3.50 | C2orf12 | chromosome 2 open reading frame 12 | 3.05 | DHRS9 | dehydrogenase/reductase (SDR family) membe |
| -3.50 | SOX18 | SRY (sex determining region Y)-box 18 | -3.05 | EPPK1 | epiplakin 1 /// epiplakin 1 |
| 3.50 | — | MRNA; cDNA DKFZp686I18116 (from clone DI | -3.05 | ADM | adrenomedullin |
| 3.50 | — | — | -3.05 | — | — |
| -3.50 | CBR1 | carbonyl reductase 1 | 3.04 | — | — |
| -3.50 | JAK3 | Janus kinase 3 (a protein tyrosine kinase, leuke | 3.04 | PMP22 | peripheral myelin protein 22 |
| 3.50 | GPR85 | G protein-coupled receptor 85 | -3.04 | TAF4B | TAF4b RNA polymerase II, TATA box binding p |
| -3.50 | TEX14 | testis expressed sequence 14 /// testis express | 3.04 | — | Transcribed locus |
| -3.49 | FLJ11286 | hypothetical protein FLJ11286 | 3.04 | FREM1 | FRAS1 related extracellular matrix 1 |
| -3.49 | GNB5 | guanine nucleotide binding protein (G protein), | 3.04 | GRIA3 | glutamate receptor, ionotrophic, AMPA 3 |
| 3.49 | PCSK6 | proprotein convertase subtilisin/kexin type 6 | 3.04 | CPXM | carboxypeptidase X (M14 family) |
| 3.49 | — | CDNA FLJ37333 fis, clone BRAMY2020106 | 3.04 | C10orf72 | chromosome 10 open reading frame 72 |
| -3.49 | HLA-B | major histocompatibility complex, class I, B | 3.04 | SUHW4 | suppressor of hairy wing homolog 4 (Drosophila |
| 3.49 | RP11-125A7.3 | KIAA0564 protein | 3.04 | TTC28 | tetratricopeptide repeat domain 28 |
| -3.49 | UNC13A | unc-13 homolog A (C. elegans) | 3.03 | CROT | carnitine O-octanoyltransferase |
| -3.49 | ENO3 | enolase 3 (beta, muscle) | -3.03 | — | — |
| 3.49 | — | — | -3.03 | C10orf75 | Chromosome 10 open reading frame 75 |
| -3.49 | TNFAIP6 | tumor necrosis factor, alpha-induced protein 6 | 3.03 | ZNF276 | zinc finger protein 276 |
| -3.49 | — | — | 3.03 | NDP | Norrie disease (pseudoglioma) |
| -3.48 | — | — | -3.02 | — | — |
| -3.48 | LPHN1 | latrophilin 1 | -3.02 | — | Transcribed locus |
| -3.48 | OR2H1 | Olfactory receptor, family 2, subfamily H, memb | -3.02 | — | Transcribed locus |
| -3.48 | RAB20 | RAB20, member RAS oncogene family | -3.02 | GLRA1 | glycine receptor, alpha 1 (startle disease/hypere |
| -3.48 | TNFSF11 | tumor necrosis factor (ligand) superfamily, men | -3.02 | PDGFA | platelet-derived growth factor alpha polypeptide |
| 3.48 | MBNL2 | muscleblind-like 2 (Drosophila) | -3.02 | DNASE2 | deoxyribonuclease II, lysosoma |
| 3.48 | NEFL | neurofilament, light polypeptide 68kDa | -3.02 | — | — |
| 3.47 | BOC | brother of CDO | 3.02 | ZNF436 | zinc finger protein 436 |
| 3.47 | — | — | -3.02 | GABRA5 | gamma-aminobutyric acid (GABA) A receptor, a |
| 3.47 | — | Full length insert cDNA clone ZA88B05 | 3.02 | — | — |
| -3.47 | TMEPAI | Transmembrane, prostate androgen induced R | -3.02 | — | — |
| -3.47 | — | — | -3.01 | RTP1 | receptor (chemosensory) transporter protein 1 |
| 3.47 | C10orf32 | chromosome 10 open reading frame 32 | 3.01 | DPYD | dihydropyrimidine dehydrogenase |
| -3.47 | NLRP12 | NLR family, pyrin domain containing 12 | 3.01 | PTN | pleiotrophin (heparin binding growth factor 8, ne |
| -3.47 | ITGB3 | integrin, beta 3 (platelet glycoprotein IIIa, antige | -3.01 | — | — |
| -3.47 | ARHGAP29 | Rho GTPase activating protein 29 | -3.01 | NETO1 | neuropilin (NRP) and tolloid (TLL)-like 1 |
| 3.47 | — | — | -3.01 | KCND2 | potassium voltage-gated channel, Shal-related |
| -3.47 | ITGA5 | integrin, alpha 5 (fibronectin receptor, alpha po | -3.01 | PPAP2A | phosphatidic acid phosphatase type 2A |
| 3.47 | C1orf114 | chromosome 1 open reading frame 114 | -3.01 | PPAP2A | phosphatidic acid phosphatase type 2A |
| 3.47 | TACR1 | tachykinin receptor 1 | -3.01 | PCDH11Y | protocadherin 11 Y-linked |
| 3.46 | CLIPR-59 | CLIP-170-related protein | -3.00 | FILIP1 | filamin A interacting protein 1 |
| -3.46 | LPHN1 | latrophilin 1 | -3.00 | LRRK1 | Leucine-rich repeat kinase 1 |
| 3.46 | USP15 | ubiquitin specific peptidase 15 | 3.00 | NEK4 | NIMA (never in mitosis gene a)-related kinase 4 |
| -3.46 | — | — | 3.00 | BACE1 | beta-site APP-cleaving enzyme 1 |
| 3.46 | — | Transcribed locus | 3.00 | — | — |
| -3.46 | RILP | Rab interacting lysosomal protein | 3.00 | NKD1 | naked cuticle homolog 1 (Drosophila) |
| 3.46 | DLX1 | distal-less homeobox 1 | 2.99 | HECTD2 | HECT domain containing 2 |
| 3.46 | AFF3 | AF4/FMR2 family, member 3 | 2.99 | LOC221091 | similar to hypothetical protein |
| 3.46 | PALLD | palladin, cytoskeletal associated protein | 2.99 | PCDH7 | BH-protocadherin (brain-heart) |
| 3.46 | C20orf58 | chromosome 20 open reading frame 58 | -2.99 | PKP2 | plakophilin 2 |
| 3.45 | — | — | -2.99 | FXYD5 | FXYD domain containing ion transport regulato |
| 3.45 | ODC1 | ornithine decarboxylase 1 | 2.99 | SULF1 | sulfatase 1 |
| -3.45 | SPON1 | spondin 1, extracellular matrix protein | -2.99 | LOC643224 | similar to tubulin, beta 8 |
| -3.45 | — | — | -2.99 | — | Transcribed locus |
| 3.45 | — | CDNA: FLJ23194 fis, clone REC00490 | -2.99 | — | — |
| 3.45 | LOC138046 | hypothetical protein LOC138046 | -2.98 | GATA4 | GATA binding protein 4 |
| -3.45 | ARHGAP28 | Rho GTPase activating protein 28 | -2.98 | LOC152195 | hypothetical protein LOC152195 |
| -3.45 | HBA1 /// HBA2 | hemoglobin, alpha 1 /// hemoglobin, alpha 1 /// | 2.98 | — | — |
| -3.45 | CASP8 | caspase 8, apoptosis-related cysteine peptidas | 2.98 | ALDH5A1 | aldehyde dehydrogenase 5 family, member A1 |
| 3.45 | SPDYA | speedy homolog A (Drosophila) | 2.98 | — | — |
| -3.44 | EFCBP1 | EF-hand calcium binding protein 1 | 2.98 | CD58 | CD58 molecule |
| -3.44 | — | — | -2.98 | FLJ35024 | hypothetical LOC401491 |
| 3.44 | SMURF2 | SMAD specific E3 ubiquitin protein ligase 2 | -2.98 | — | — |
| -3.44 | CDS1 | CDP-diacylglycerol synthase (phosphatidate cy | 2.98 | ZSWIM5 | zinc finger, SWIM-type containing 5 |
| -3.44 | HHEX | homeobox, hematopoietically expressed | 2.98 | — | — |
| -3.44 | DPPA4 | developmental pluripotency associated 4 | 2.98 | TOR1AIP2 | torsin A interacting protein 2 |
| -3.44 | BTBD4 | BTB (POZ) domain containing 4 | 2.98 | GRK5 | G protein-coupled receptor kinase 5 |
| -3.44 | CRIP3 | cysteine-rich protein 3 | -2.98 | — | CDNA FLJ35259 fis, clone PROST2004251 |
| -3.44 | RUNX1T1 | runt-related transcription factor 1; translocated | 2.97 | SEMA3C | sema domain, immunoglobulin domain (Ig), sho |
| 3.44 | TREX1 | three prime repair exonuclease 1 | 2.97 | TTC3 | tetratricopeptide repeat domain 3 |
| 3.43 | SLC4A4 | solute carrier family 4, sodium bicarbonate cotr | 2.97 | LOC91526 | Ankyrin repeat domain 44 |
| -3.43 | FLJ14001 | hypothetical protein FLJ14001 | -2.97 | CDH3 | cadherin 3, type 1, P-cadherin (placental) |
| 3.43 | SYTL4 | synaptotagmin-like 4 (granuphilin-a) | 2.97 | ABAT | 4-aminobutyrate aminotransferase |
| 3.43 | LOC389895 | similar to CG4768-PA | -2.97 | — | Transcribed locus |
| 3.43 | — | — | 2.97 | RGS12 | regulator of G-protein signalling 12 |
| 3.42 | PYGO1 | pygopus homolog 1 (Drosophila) | -2.97 | CCNA1 | cyclin A1 |
| -3.42 | LOC54103 | hypothetical protein LOC54103 | -2.97 | FGFR3 | fibroblast growth factor receptor 3 (achondropla |
| 3.42 | DLX2 | distal-less homeobox 2 | 2.97 | — | — |
| 3.42 | FAM13C1 | family with sequence similarity 13, member C1 | -2.97 | WDR66 | WD repeat domain 66 |

Appendix 1

| Value | Gene | Description |
|---|---|---|
| 3.42 | ZHX1 | zinc fingers and homeoboxes 1 |
| -3.41 | F11R | F11 receptor |
| 3.41 | — | — |
| 3.41 | DMRTC1 /// LOC72 | DMRT-like family C1 /// similar to doublesex an |
| 3.41 | — | MRNA; cDNA DKFZp564E143 (from clone DKf |
| 3.41 | LOC283658 | hypothetical protein LOC283658 |
| 3.41 | LOC199800 | hypothetical protein LOC199800 |
| -3.41 | — | — |
| -3.41 | EDNRA | Endothelin receptor type A |
| 3.41 | CDKN2C | cyclin-dependent kinase inhibitor 2C (p18, inhit |
| 3.40 | SDK2 | sidekick homolog 2 (chicken) |
| 3.40 | PDE1A | phosphodiesterase 1A, calmodulin-dependent |
| 3.40 | LRRN3 | leucine rich repeat neuronal 3 |
| 3.40 | WDR17 | WD repeat domain 17 |
| -3.40 | RORA | RAR-related orphan receptor A |
| -3.40 | HSPA1B | heat shock 70kDa protein 1B |
| 3.40 | FLJ42117 | FLJ42117 protein |
| 3.40 | — | — |
| -3.40 | ICAM4 | intercellular adhesion molecule 4 (Landsteiner- |
| -3.39 | SLC7A8 | solute carrier family 7 (cationic amino acid tran |
| -3.39 | EPN3 | epsin 3 |
| -3.39 | DUSP5 | dual specificity phosphatase 5 |
| -3.39 | FLJ44894 | similar to zinc finger protein 91 |
| 3.39 | — | — |
| 3.39 | AGTR1 | angiotensin II receptor, type 1 |
| -3.39 | — | CDNA FLJ32963 fis, clone TESTI2008405 |
| 3.39 | ID4 | Inhibitor of DNA binding 4, dominant negative f |
| 3.38 | — | — |
| -3.38 | — | — |
| -3.38 | TWIST2 | twist homolog 2 (Drosophila) |
| -3.38 | BMP2 | bone morphogenetic protein 2 |
| 3.38 | HERPUD1 | Homocysteine-inducible, endoplasmic reticulun |
| -3.38 | RBMS1 | RNA binding motif, single stranded interacting |
| -3.38 | RBMS1 | RNA binding motif, single stranded interacting |
| 3.38 | KCNJ4 | potassium inwardly-rectifying channel, subfami |
| 3.38 | — | CDNA FLJ30810 fis, clone FEBRA2001440 |
| 3.37 | — | CDNA clone IMAGE:4300887 |
| -3.37 | GPD2 | glycerol-3-phosphate dehydrogenase 2 (mitocl |
| -3.37 | CRABP2 | cellular retinoic acid binding protein 2 |
| -3.37 | SLFN12 | schlafen family member 12 |
| -3.37 | BCL11B | B-cell CLL/lymphoma 11B (zinc finger protein) |
| -3.37 | SLC2A3 | Solute carrier family 2 (facilitated glucose trans |
| 3.37 | CCDC73 | Coiled-coil domain containing 73 |
| 3.37 | RHOBTB2 | Rho-related BTB domain containing 2 |
| 3.37 | ARHGEF17 | Rho guanine nucleotide exchange factor (GEF) |
| -3.37 | RRP22 | RAS-related on chromosome 22 |
| -3.37 | MATN2 | matrilin 2 |
| -3.36 | — | — |
| 3.36 | NAV3 /// LOC65272 | neuron navigator 3 /// similar to neuron navigat |
| -3.36 | — | — |
| -3.36 | IL1B | interleukin 1, beta |
| -3.36 | LOC730399 /// LOC | hypothetical protein LOC730399 /// hypothetica |
| -3.36 | RORA | RAR-related orphan receptor A |
| 3.36 | LOC133308 | hypothetical protein BC009732 |
| -3.36 | LOC255458 | Hypothetical protein LOC255458 |
| -3.36 | LOC388630 | similar to C05G5.5 |
| 3.36 | — | — |
| -3.35 | — | — |
| -3.35 | OVOL2 | ovo-like 2 (Drosophila) /// ovo-like 2 (Drosophila |
| 3.35 | PRKCE | protein kinase C, epsilon |
| 3.35 | FLJ31485 | hypothetical gene supported by AK056047; AK |
| -3.35 | CD2AP | CD2-associated protein |
| 3.34 | ZNF124 | zinc finger protein 124 |
| -3.34 | RHOF | ras homolog gene family, member F (in filopod |
| -3.34 | MLKL | mixed lineage kinase domain-like |
| -3.34 | SIX3 | sine oculis homeobox homolog 3 (Drosophila) |
| 3.34 | LOC729436 | Hypothetical protein LOC729436 |
| 3.34 | SLC44A5 | solute carrier family 44, member 5 |
| -3.34 | LAMA2 | laminin, alpha 2 (merosin, congenital muscular |
| 3.34 | — | — |
| -3.34 | KAZALD1 | Kazal-type serine peptidase inhibitor domain 1 |
| 3.33 | GNGT1 | guanine nucleotide binding protein (G protein), |
| -3.33 | LRRK1 | leucine-rich repeat kinase 1 |
| -3.33 | MET | met proto-oncogene (hepatocyte growth factor |
| -3.33 | ST14 | suppression of tumorigenicity 14 (colon carcino |
| 3.33 | MLLT3 | myeloid/lymphoid or mixed-lineage leukemia (t |
| -3.33 | SKIL | SKI-like |
| -3.33 | TIMP1 | TIMP metallopeptidase inhibitor 1 |
| -3.33 | BIC | BIC transcript |
| -2.96 | — | Transcribed locus |
| 2.96 | EVI1 | ecotropic viral integration site 1 |
| 2.96 | RFX4 | regulatory factor X, 4 (influences HLA class II e |
| -2.96 | GUCA1A | guanylate cyclase activator 1A (retina) |
| -2.96 | MGC17624 | MGC17624 protein |
| 2.96 | KCNK10 | potassium channel, subfamily K, member 10 |
| 2.96 | LOC728913 | Similar to Reticulocalbin-1 precursor |
| 2.96 | SDC1 | syndecan 1 |
| 2.96 | CDH11 | Cadherin 11, type 2, OB-cadherin (osteoblast) |
| -2.96 | MT1X | metallothionein 1X |
| -2.96 | NPAS1 | neuronal PAS domain protein 1 |
| -2.96 | PRSS2 | protease, serine, 2 (trypsin 2) |
| 2.95 | TMEM5 | transmembrane protein 5 |
| 2.95 | — | Full length insert cDNA clone YZ38E04 |
| 2.95 | PDE4B | phosphodiesterase 4B, cAMP-specific (phosph |
| -2.95 | DIAPH2 | diaphanous homolog 2 (Drosophila) |
| -2.95 | — | — |
| 2.95 | — | Similar to ribosomal protein S3a; 40S ribosoma |
| -2.95 | SYT4 | synaptotagmin IV |
| -2.95 | FLJ16287 | FLJ16287 protein |
| 2.95 | PACRG | PARK2 co-regulated |
| -2.95 | — | — |
| 2.95 | APBA2 | amyloid beta (A4) precursor protein-binding, fan |
| 2.95 | NDST3 | N-deacetylase/N-sulfotransferase (heparan glu |
| 2.94 | GSN | gelsolin (amyloidosis, Finnish type) |
| 2.94 | DCHS1 | dachsous 1 (Drosophila) |
| 2.94 | — | Transcribed locus |
| 2.94 | — | — |
| 2.94 | PTN | pleiotrophin (heparin binding growth factor 8, n |
| -2.94 | KREMEN2 | kringle containing transmembrane protein 2 |
| 2.94 | — | — |
| -2.94 | C6orf192 | Chromosome 6 open reading frame 192 |
| 2.94 | ING3 | inhibitor of growth family, member 3 |
| 2.94 | ULK2 | unc-51-like kinase 2 (C. elegans) |
| 2.94 | FLRT2 | fibronectin leucine rich transmembrane protein |
| -2.94 | EMR2 | egf-like module containing, mucin-like, hormone |
| -2.94 | TCEAL2 | transcription elongation factor A (SII)-like 2 |
| 2.94 | HOXB8 | homeobox B8 |
| 2.94 | C20orf142 | chromosome 20 open reading frame 142 |
| 2.94 | SRGAP3 | SLIT-ROBO Rho GTPase activating protein 3 |
| 2.93 | — | — |
| -2.93 | STMN2 | stathmin-like 2 |
| -2.93 | FLT1 | Fms-related tyrosine kinase 1 (vascular endoth |
| 2.93 | FBXL21 | F-box and leucine-rich repeat protein 21 |
| 2.93 | FRMD3 | FERM domain containing 3 |
| 2.93 | AFF2 | AF4/FMR2 family, member 2 |
| 2.93 | ZFHX4 | zinc finger homeodomain 4 |
| 2.93 | DMRTC1 /// LOC72 | DMRT-like family C1 /// similar to doublesex an |
| 2.93 | COL5A1 | collagen, type V, alpha 1 |
| -2.93 | — | CDNA FLJ37143 fis, clone BRACE2024222 |
| 2.93 | H2AFY2 | H2A histone family, member Y2 |
| 2.93 | — | — |
| 2.93 | — | — |
| 2.93 | PCDH17 | protocadherin 17 |
| 2.92 | GPR161 | G protein-coupled receptor 161 |
| -2.92 | — | — |
| -2.92 | CCDC11 | coiled-coil domain containing 11 |
| 2.92 | PLEKHA4 | pleckstrin homology domain containing, family |
| 2.92 | C1orf53 | chromosome 1 open reading frame 53 |
| 2.92 | GPM6A | glycoprotein M6A |
| -2.92 | CDS1 | CDP-diacylglycerol synthase (phosphatidate cy |
| 2.92 | FAM89B | family with sequence similarity 89, member B |
| 2.92 | — | — |
| 2.92 | SLITRK5 | SLIT and NTRK-like family, member 5 |
| -2.92 | TEAD4 | TEA domain family member 4 |
| 2.92 | CACNA1G | calcium channel, voltage-dependent, alpha 1G |
| 2.92 | FLJ25477 | Hypothetical protein FLJ25477 |
| 2.92 | — | — |
| 2.91 | PRAME | preferentially expressed antigen in melanoma |
| 2.91 | NRXN2 | neurexin 2 |
| -2.91 | PIPOX | pipecolic acid oxidase |
| -2.91 | APOC1 | apolipoprotein C-I |
| 2.91 | FLJ31132 | FLJ31132 protein |
| -2.91 | — | — |
| -2.91 | RYR2 | ryanodine receptor 2 (cardiac) |
| -2.91 | RDH12 | retinol dehydrogenase 12 (all-trans and 9-cis) |
| 2.90 | GALNTL1 | UDP-N-acetyl-alpha-D-galactosamine:polypept |
| 2.90 | PHF14 | PHD finger protein 14 |
| -2.90 | CYP2E1 | cytochrome P450, family 2, subfamily E, polype |

Appendix 1

| Value | Gene | Description |
|---|---|---|
| -3.33 | CD52 | CD52 molecule |
| -3.33 | THY1 | Thy-1 cell surface antigen |
| -3.33 | CACNA2D1 | calcium channel, voltage-dependent, alpha 2/d |
| 3.33 | — | — |
| 3.33 | — | Transcribed locus |
| -3.32 | TPD52L1 | tumor protein D52-like 1 |
| 3.32 | — | Transcribed locus |
| 3.32 | RP11-301I17.1 | proliferation-inducing protein 38 |
| -3.32 | KLF5 | Kruppel-like factor 5 (intestinal) |
| 3.32 | — | — |
| 3.32 | JAKMIP2 | janus kinase and microtubule interacting protei |
| 3.32 | MGC33846 | hypothetical protein MGC33846 |
| 3.32 | IGSF4C | immunoglobulin superfamily, member 4C |
| -3.32 | — | — |
| 3.32 | LOC144363 | Hypothetical protein LOC144363 |
| -3.32 | STAT6 | signal transducer and activator of transcription |
| -3.31 | SLC2A3 | solute carrier family 2 (facilitated glucose trans |
| -3.31 | CHST4 | carbohydrate (N-acetylglucosamine 6-O) sulfot |
| 3.31 | PON2 | Paraoxonase 2 |
| 3.31 | HSPA4L | heat shock 70kDa protein 4-like |
| 3.31 | — | — |
| 3.31 | LYPD1 | LY6/PLAUR domain containing 1 |
| -3.31 | REC8L1 | REC8-like 1 (yeast) |
| 3.31 | — | — |
| 3.31 | MEGF9 | multiple EGF-like-domains 9 |
| -3.30 | — | — |
| -3.30 | BNC2 | basonuclin 2 |
| 3.30 | — | — |
| 3.30 | — | — |
| 3.30 | — | Transcribed locus |
| -3.30 | F11R | F11 receptor |
| -3.30 | BSPRY | B-box and SPRY domain containing |
| 3.30 | PKNOX2 | PBX/knotted 1 homeobox 2 |
| -3.30 | SERPINE1 | serpin peptidase inhibitor, clade E (nexin, plas |
| -3.30 | SULT1C1 | sulfotransferase family, cytosolic, 1C, member |
| 3.30 | SYDE1 | synapse defective 1, Rho GTPase, homolog 1 |
| 3.30 | FST | follistatin |
| -3.30 | TRHDE | thyrotropin-releasing hormone degrading enzyr |
| 3.30 | LOC284361 | Hematopoietic signal peptide-containing |
| 3.30 | BSN | bassoon (presynaptic cytomatrix protein) |
| 3.29 | R3HDM1 | R3H domain containing 1 |
| -3.29 | GPRC5C | G protein-coupled receptor, family C, group 5, |
| -3.29 | TRIM38 | tripartite motif-containing 38 |
| -3.29 | COL21A1 | collagen, type XXI, alpha 1 /// collagen, type X |
| 3.29 | — | Full length insert cDNA clone YZ38E04 |
| 3.29 | CCDC92 | coiled-coil domain containing 92 |
| -3.29 | RBPMS | RNA binding protein with multiple splicing |
| -3.29 | FLJ36848 | hypothetical LOC647115 |
| -3.28 | LPHN1 | latrophilin 1 |
| 3.28 | — | — |
| -3.28 | GPR37 | G protein-coupled receptor 37 (endothelin rece |
| -3.28 | EPHA7 | EPH receptor A7 |
| 3.28 | MCART6 | mitochondrial carrier triple repeat 6 |
| -3.28 | LOC729890 /// LOC | hypothetical protein LOC729890 /// hypothetica |
| -3.27 | CPS1 | carbamoyl-phosphate synthetase 1, mitochond |
| 3.27 | — | — |
| -3.27 | FBLIM1 | filamin binding LIM protein 1 |
| 3.27 | EVI5 | ecotropic viral integration site 5 |
| -3.27 | — | — |
| 3.27 | — | Full length insert cDNA clone YZ38E04 |
| -3.26 | SLC16A5 | solute carrier family 16, member 5 (monocarbo |
| 3.26 | FGF9 | fibroblast growth factor 9 (glia-activating factor) |
| 3.26 | RBM24 | RNA binding motif protein 24 |
| -3.26 | ACP5 | acid phosphatase 5, tartrate resistant |
| -3.26 | — | — |
| 3.26 | — | — |
| 3.26 | HS3ST3B1 | Heparan sulfate (glucosamine) 3-O-sulfotransf |
| -3.26 | MBP | myelin basic protein |
| 3.26 | — | Transcribed locus |
| 3.26 | — | — |
| 3.26 | LONP2 | Lon peptidase 2, peroxisomal |
| 3.26 | — | — |
| 3.26 | — | — |
| 3.26 | HSPA12A | heat shock 70kDa protein 12A |
| -3.25 | LCP1 | lymphocyte cytosolic protein 1 (L-plastin) |
| 3.25 | ANKRD20A1 /// AN | ankyrin repeat domain 20 family, member A1 // |
| 3.25 | — | Hypothetical gene supported by BC008046 |
| -3.25 | CD1D | CD1d molecule /// CD1d molecule |
| 3.25 | HOXA3 | Homeo box A3 |

| Value | Gene | Description |
|---|---|---|
| 2.90 | STRA6 | stimulated by retinoic acid gene 6 homolog (mc |
| 2.90 | ADAMTS17 | ADAM metallopeptidase with thrombospondin t |
| 2.90 | MEGF6 | multiple EGF-like-domains 6 |
| -2.90 | PAWR | PRKC, apoptosis, WT1, regulator |
| 2.89 | PHC2 | polyhomeotic homolog 2 (Drosophila) |
| -2.89 | — | Transcribed locus |
| -2.89 | CADPS | Ca2+-dependent secretion activator |
| 2.89 | — | cDNA clone IMAGE:4402981 |
| 2.89 | SMARCD3 | SWI/SNF related, matrix associated, actin depe |
| 2.89 | ARL4C | ADP-ribosylation factor-like 4C |
| 2.89 | CPE | carboxypeptidase E |
| -2.89 | PTRF | polymerase I and transcript release factor |
| -2.89 | KIAA0746 | KIAA0746 protein |
| 2.89 | DOK2 | docking protein 2, 56kDa |
| 2.89 | EVC | Ellis van Creveld syndrome |
| 2.89 | C14orf132 | chromosome 14 open reading frame 132 |
| 2.88 | SECP43 | tRNA selenocysteine associated protein |
| 2.88 | — | cDNA FLJ26260 fis, clone DMC05193 |
| 2.88 | SLIT3 | slit homolog 3 (Drosophila) |
| 2.88 | — | Similar to leucine rich repeat containing 10 |
| 2.88 | SNCA | synuclein, alpha (non A4 component of amyloic |
| -2.88 | TFAP2C | transcription factor AP-2 gamma (activating enl |
| 2.88 | TAGLN3 | transgelin 3 |
| -2.88 | POLR3G | polymerase (RNA) III (DNA directed) polypeptic |
| 2.88 | MESDC1 | Mesoderm development candidate 1 |
| 2.88 | MGC15476 | thymus expressed gene 3-like |
| -2.88 | WBSCR17 | Williams-Beuren syndrome chromosome regior |
| 2.88 | — | — |
| -2.88 | — | cDNA: FLJ22478 fis, clone HRC10816 |
| 2.87 | RAB9B | RAB9B, member RAS oncogene family |
| 2.87 | MAPK1 | Mitogen-activated protein kinase 1 |
| -2.87 | PAWR | PRKC, apoptosis, WT1, regulator |
| 2.87 | SPON1 | spondin 1, extracellular matrix protein |
| -2.87 | — | Transcribed locus |
| -2.87 | CTTN | cortactin |
| 2.87 | NRCAM | neuronal cell adhesion molecule |
| 2.87 | NEFM | neurofilament, medium polypeptide 150kDa |
| 2.87 | — | — |
| -2.86 | PAK6 | p21(CDKN1A)-activated kinase 6 |
| -2.86 | UPP1 | uridine phosphorylase 1 |
| -2.86 | RASGRP2 | RAS guanyl releasing protein 2 (calcium and D, |
| -2.86 | YPEL3 | yippee-like 3 (Drosophila) |
| 2.86 | B3GALNT1 | beta-1,3-N-acetylgalactosaminyltransferase 1 ( |
| 2.86 | COL4A5 | collagen, type IV, alpha 5 (Alport syndrome) |
| 2.86 | ZNF771 | zinc finger protein 771 |
| 2.86 | MSX2 | msh homeobox 2 |
| 2.86 | FRMD4B | FERM domain containing 4B |
| -2.85 | TMEM132D | transmembrane protein 132D |
| 2.85 | PTGS2 | prostaglandin-endoperoxide synthase 2 (prosta |
| 2.85 | PPP1R7 | Protein phosphatase 1, regulatory subunit 7 |
| 2.85 | WIPF1 | WAS/WASL interacting protein family, member |
| -2.85 | CNTNAP2 | contactin associated protein-like 2 |
| 2.85 | ZNF618 | zinc finger protein 618 |
| 2.85 | C18orf30 | chromosome 18 open reading frame 30 |
| 2.85 | SOSTDC1 | sclerostin domain containing 1 |
| -2.84 | FXYD5 | FXYD domain containing ion transport regulato |
| 2.84 | — | — |
| 2.84 | RSNL2 | restin-like 2 |
| 2.84 | — | cDNA FLJ38345 fis, clone FCBBF3028671 |
| 2.84 | EVI1 | ecotropic viral integration site 1 |
| 2.84 | — | — |
| -2.84 | — | cDNA clone IMAGE:4811759 |
| -2.84 | C9orf24 | chromosome 9 open reading frame 24 |
| 2.84 | — | — |
| -2.84 | FOXO1A | forkhead box O1A (rhabdomyosarcoma) |
| -2.84 | P2RX5 | purinergic receptor P2X, ligand-gated ion chani |
| -2.84 | JAZF1 | JAZF zinc finger 1 |
| -2.84 | NRK | Nik related kinase |
| 2.84 | GPM6A | glycoprotein M6A |
| 2.84 | PDE4B | phosphodiesterase 4B, cAMP-specific (phosphi |
| -2.84 | SLC2A3 | solute carrier family 2 (facilitated glucose trans) |
| 2.83 | TNFRSF11B | tumor necrosis factor receptor superfamily, mei |
| -2.83 | GYLTL1B | glycosyltransferase-like 1B |
| -2.83 | RAB3B | RAB3B, member RAS oncogene family |
| -2.83 | FILIP1 | filamin A interacting protein 1 |
| 2.83 | COLEC12 | collectin sub-family member 12 /// collectin sub- |
| -2.83 | SOHLH2 | spermatogenesis and oogenesis specific basic |
| -2.83 | — | Homo sapiens, clone IMAGE:4047715, mRNA |
| -2.82 | PPP2R2B | protein phosphatase 2 (formerly 2A), regulatory |

Appendix 1

| Value | Gene | Description |
|---|---|---|
| 3.25 | CALCRL | calcitonin receptor-like |
| -3.24 | STOM | stomatin |
| -3.24 | NUPR1 | nuclear protein 1 |
| -3.24 | — | CDNA FLJ26242 fis, clone DMC00770 |
| -3.24 | — | — |
| -3.24 | RBPMS | RNA binding protein with multiple splicing |
| 3.24 | QKI | quaking homolog, KH domain RNA binding (m |
| -3.24 | — | PTR2 mRNA for repetitive sequence |
| -3.24 | SPINK1 | serine peptidase inhibitor, Kazal type 1 |
| 3.24 | LOC643911 /// LOC | hypothetical LOC643911 /// hypothetical protei |
| 3.24 | RBMS3 | RNA binding motif, single stranded interacting |
| -3.23 | TERF1 | telomeric repeat binding factor (NIMA-interacti |
| -3.23 | PLAC1 | placenta-specific 1 |
| 3.23 | — | CDNA FLJ40252 fis, clone TESTI2024299 |
| 3.23 | SLC26A10 | solute carrier family 26, member 10 |
| -3.23 | — | — |
| -3.23 | CD44 | CD44 molecule (Indian blood group) |
| 3.23 | FXYD6 | FXYD domain containing ion transport regulato |
| 3.23 | — | CDNA FLJ39389 fis, clone PLACE6003621 |
| -3.22 | — | CDNA FLJ29007 fis, clone STM04662, highly s |
| 3.22 | — | — |
| 3.22 | REEP1 | receptor accessory protein 1 |
| -3.22 | — | — |
| 3.22 | PROS1 | protein S (alpha) |
| -3.22 | ZNF185 | zinc finger protein 185 (LIM domain) |
| 3.22 | WNT7A | wingless-type MMTV integration site family, me |
| 3.22 | — | — |
| 3.22 | GPR1 | G protein-coupled receptor 1 |
| 3.22 | NEK4 | NIMA (never in mitosis gene a)-related kinase |
| 3.22 | GAS1 | growth arrest-specific 1 |
| -3.22 | — | — |
| 3.21 | — | — |
| -3.21 | CHST7 | carbohydrate (N-acetylglucosamine 6-O) sulfot |
| 3.21 | DNER | delta/notch-like EGF repeat containing |
| -3.21 | STC2 | stanniocalcin 2 |
| -3.21 | NFATC3 | Nuclear factor of activated T-cells, cytoplasmic |
| 3.21 | LOC728052 /// LOC | Hypothetical protein LOC728052 /// Hematopoi |
| 3.21 | C1orf114 | chromosome 1 open reading frame 114 |
| 3.21 | DCTN2 | Dynactin 2 (p50) |
| 3.21 | ABCC4 | ATP-binding cassette, sub-family C (CFTR/MR |
| -3.20 | — | — |
| -3.20 | — | Transcribed locus |
| 3.20 | — | — |
| -3.20 | KCNMB4 | potassium large conductance calcium-activated |
| -3.20 | LHX6 | LIM homeobox 6 |
| -3.20 | LOC727729 | similar to gamma-aminobutyric acid (GABA) A |
| -3.20 | OR52A1 | olfactory receptor, family 52, subfamily A, mem |
| -3.20 | PAK6 | p21(CDKN1A)-activated kinase 6 |
| -3.19 | NGB | neuroglobin |
| 3.19 | GALNTL1 | UDP-N-acetyl-alpha-D-galactosamine:polypep |
| -3.19 | LNX1 | ligand of numb-protein X 1 |
| -3.19 | C1orf61 | chromosome 1 open reading frame 61 |
| -3.19 | AKT2 | v-akt murine thymoma viral oncogene homolog |
| 3.19 | — | — |
| -3.19 | GYLTL1B | glycosyltransferase-like 1B |
| 3.18 | MEIS1 | Meis1, myeloid ecotropic viral integration site 1 |
| 3.18 | 9-Mar | membrane-associated ring finger (C3HC4) 9 |
| -3.18 | — | Transcribed locus |
| 3.18 | FOXJ1 | Forkhead box J1 |
| 3.18 | FAS | Fas (TNF receptor superfamily, member 6) |
| 3.18 | MTCH2 | mitochondrial carrier homolog 2 (C. elegans) |
| -3.18 | — | Homo sapiens, clone IMAGE:3616855, mRNA |
| 3.18 | RGS4 | regulator of G-protein signalling 4 |
| -3.18 | SOX14 | SRY (sex determining region Y)-box 14 |
| 3.18 | APBA2 | amyloid beta (A4) precursor protein-binding, fa |
| 3.17 | — | Transcribed locus, weakly similar to XP_52063 |
| -3.17 | ELF3 | E74-like factor 3 (ets domain transcription factc |
| -3.17 | STXBP2 | syntaxin binding protein 2 |
| -3.17 | ROR2 | receptor tyrosine kinase-like orphan receptor 2 |
| -3.17 | LOC390940 | similar to R28379_1 |
| -3.17 | MLXIP | MLX interacting protein |
| -3.17 | TMEM132D | transmembrane protein 132D |
| 3.16 | — | — |
| -3.16 | FLJ12684 | hypothetical protein FLJ12684 |
| -3.16 | PPP1R1B | protein phosphatase 1, regulatory (inhibitor) su |
| 3.16 | — | CDNA clone IMAGE:3950788 |
| 3.16 | KIAA1257 | KIAA1257 |
| 3.16 | MLLT3 | myeloid/lymphoid or mixed-lineage leukemia (t |
| -3.16 | KCNE3 | potassium voltage-gated channel, Isk-related fa |
| 2.82 | — | — |
| -2.82 | — | MRNA; cDNA DKFZp451E068 (from clone DKF |
| 2.82 | — | — |
| 2.82 | EGR1 | early growth response 1 |
| 2.82 | PCSK6 | proprotein convertase subtilisin/kexin type 6 |
| 2.81 | LOC144997 | hypothetical protein LOC144997 |
| 2.81 | — | — |
| 2.81 | ATP10A | ATPase, Class V, type 10A |
| 2.81 | — | — |
| -2.81 | ERBB4 | V-erb-a erythroblastic leukemia viral oncogene |
| -2.81 | NRP1 | Neuropilin 1 |
| 2.81 | DCTN4 | dynactin 4 (p62) |
| 2.81 | CDH6 | cadherin 6, type 2, K-cadherin (fetal kidney) |
| 2.81 | MMP2 | matrix metallopeptidase 2 (gelatinase A, 72kDa |
| -2.81 | FGF2 | fibroblast growth factor 2 (basic) |
| 2.81 | ABCA5 | ATP-binding cassette, sub-family A (ABC1), me |
| 2.80 | C10orf32 | chromosome 10 open reading frame 32 |
| -2.80 | HERC6 | hect domain and RLD 6 |
| 2.80 | — | — |
| -2.80 | EDN1 | endothelin 1 |
| -2.80 | PRSS1 /// PRSS2 | protease, serine, 1 (trypsin 1) /// protease, serir |
| 2.80 | FCGR2C | Fc fragment of IgG, low affinity IIc, receptor for |
| -2.80 | SERINC5 | Serine incorporator 5 |
| 2.80 | WDR52 | WD repeat domain 52 |
| 2.80 | PI15 | peptidase inhibitor 15 |
| -2.80 | RAP1GDS1 | RAP1, GTP-GDP dissociation stimulator 1 |
| -2.79 | KCNK1 | potassium channel, subfamily K, member 1 |
| 2.79 | PLA2G10 | phospholipase A2, group X |
| -2.79 | — | Transcribed locus, moderately similar to XP_00 |
| 2.79 | PURG | purine-rich element binding protein G |
| 2.79 | DPYSL5 | dihydropyrimidinase-like 5 |
| 2.79 | PLXNA4A | plexin A4, A |
| -2.79 | — | CDNA clone IMAGE:5296106 |
| 2.79 | — | Transcribed locus |
| 2.79 | C13orf21 | Chromosome 13 open reading frame 21 |
| -2.79 | — | — |
| 2.79 | LYPD1 | LY6/PLAUR domain containing 1 |
| 2.79 | CPE | carboxypeptidase E |
| 2.79 | SLC35D1 | solute carrier family 35 (UDP-glucuronic acid/U |
| -2.79 | TAF4B | TAF4b RNA polymerase II, TATA box binding p |
| -2.79 | LOC155036 | hypothetical protein LOC155036 |
| 2.79 | B3GNT5 | UDP-GlcNAc:betaGal beta-1,3-N-acetylglucosa |
| -2.78 | — | — |
| 2.78 | BTN3A2 | butyrophilin, subfamily 3, member A2 |
| 2.78 | — | — |
| -2.78 | IQSEC2 | IQ motif and Sec7 domain 2 |
| 2.78 | TBX2 | T-box 2 |
| -2.78 | CBR3 | carbonyl reductase 3 |
| -2.78 | LOC57228 | small trans-membrane and glycosylated protein |
| 2.78 | CDK5R1 | cyclin-dependent kinase 5, regulatory subunit 1 |
| -2.78 | — | CDNA: FLJ21041 fis, clone CAE10652 |
| 2.77 | — | — |
| -2.77 | BSPRY | B-box and SPRY domain containing |
| -2.77 | — | — |
| -2.77 | IFITM3 | interferon induced transmembrane protein 3 (1- |
| -2.77 | ATP6V0A4 | ATPase, H+ transporting, lysosomal V0 subuni |
| 2.77 | DISP1 | dispatched homolog 1 (Drosophila) |
| -2.76 | AFP | alpha-fetoprotein |
| 2.76 | — | — |
| 2.76 | PABPC5 | poly(A) binding protein, cytoplasmic 5 |
| 2.76 | CAMK2D | Calcium/calmodulin-dependent protein kinase ( |
| -2.76 | EBF2 | Early B-cell factor 2 |
| -2.76 | — | — |
| 2.76 | FLJ14213 | hypothetical protein FLJ14213 |
| 2.76 | C14orf139 | chromosome 14 open reading frame 139 |
| -2.76 | CECR1 | cat eye syndrome chromosome region, candid |
| -2.76 | — | — |
| 2.76 | HNT | neurotrimin |
| -2.76 | FAM46B | family with sequence similarity 46, member B |
| 2.75 | GTF2IRD2 | GTF2I repeat domain containing 2 |
| 2.75 | TIMP3 | TIMP metallopeptidase inhibitor 3 (Sorsby fund |
| -2.75 | GABRB3 | gamma-aminobutyric acid (GABA) A receptor, l |
| -2.75 | — | Full-length cDNA clone CS0DJ013YE21 of T ce |
| -2.75 | — | Full length insert cDNA YH97G12 |
| 2.75 | FLJ42709 | Hypothetical gene supported by AK124699 |
| 2.75 | RTN1 | reticulon 1 |
| -2.75 | TMEM38A | transmembrane protein 38A |
| 2.74 | — | CDNA clone IMAGE:4842353 |
| 2.74 | FKBP7 | FK506 binding protein 7 |

Appendix 1

| Value | Symbol | Description |
|---|---|---|
| 3.16 | — | — |
| 3.16 | LOC387755 | hypothetical protein |
| -3.16 | — | — |
| 3.16 | TMSL8 | thymosin-like 8 |
| 3.16 | NFE2L3 | Nuclear factor (erythroid-derived 2)-like 3 |
| -3.16 | — | — |
| 3.16 | C4orf31 | chromosome 4 open reading frame 31 |
| 3.16 | — | Transcribed locus, weakly similar to XP_50955 |
| 3.15 | — | — |
| -3.15 | CPT1A | carnitine palmitoyltransferase 1A (liver) |
| 3.15 | — | — |
| 3.15 | — | — |
| 3.15 | — | — |
| -3.15 | FLI1 | Friend leukemia virus integration 1 |
| 3.15 | TTC3 | tetratricopeptide repeat domain 3 |
| 3.15 | — | — |
| -3.15 | HLA-G | HLA-G histocompatibility antigen, class I, G |
| 3.15 | LOC387790 | hypothetical LOC387790 |
| 3.15 | RHOBTB3 | Rho-related BTB domain containing 3 |
| -3.15 | — | CDNA clone IMAGE:5532261 |
| -3.15 | MST1 | macrophage stimulating 1 (hepatocyte growth |
| -3.14 | MGC29814 | hypothetical protein MGC29814 |
| -3.14 | MTMR11 | myotubularin related protein 11 |
| 3.14 | MOV10L1 | Mov10l1, Moloney leukemia virus 10-like 1, ho |
| -3.14 | — | CDNA FLJ32411 fis, clone SKMUS2000515 |
| 3.14 | — | CDNA FLJ32491 fis, clone SKNSH1000308 |
| 3.14 | — | — |
| 3.14 | — | Full-length cDNA clone CS0DD001YA12 of Ne |
| -3.14 | IGFBP3 | insulin-like growth factor binding protein 3 |
| 3.14 | — | — |
| 3.14 | — | MRNA; cDNA DKFZp564E143 (from clone DKI |
| 3.13 | PON2 | paraoxonase 2 |
| 3.13 | RARB | retinoic acid receptor, beta |
| 3.13 | — | Transcribed locus |
| 3.13 | — | CDNA FLJ38252 fis, clone FCBBF3000269 |
| 3.13 | SLC16A14 | solute carrier family 16, member 14 (monocarb |
| -3.13 | ANXA4 | annexin A4 |
| -3.13 | DDX43 | DEAD (Asp-Glu-Ala-Asp) box polypeptide 43 |
| 3.13 | FGFRL1 | fibroblast growth factor receptor-like 1 |
| -3.13 | MUC4 | mucin 4, cell surface associated |
| -3.13 | HOOK1 | hook homolog 1 (Drosophila) |
| 3.12 | — | — |
| 3.12 | FLJ90757 | hypothetical protein LOC440465 |
| -3.12 | OCLN /// NAIP | occludin /// similar to Occludin |
| -3.12 | — | — |
| 3.12 | KIAA1546 | KIAA1546 |
| -3.12 | — | — |
| -3.12 | SYN2 | synapsin II |
| -3.12 | CD44 | CD44 molecule (Indian blood group) |
| -3.12 | ABCC13 | ATP-binding cassette, sub-family C (CFTR/MR |
| -3.12 | POLR3G | polymerase (RNA) III (DNA directed) polypepti |
| 3.12 | PUNC | Putative neuronal cell adhesion molecule |
| -3.12 | SSH3 | slingshot homolog 3 (Drosophila) |
| 3.12 | WDR78 /// SLC35D | WD repeat domain 78 /// Solute carrier family 3 |
| -3.12 | CADPS | Ca2+-dependent secretion activator |
| -3.11 | TPM2 /// PPIL5 | tropomyosin 2 (beta) /// peptidylprolyl isomeras |
| -3.11 | RPL21 | Ribosomal protein L21 |
| -3.11 | TGFB1 | transforming growth factor, beta 1 (Camurati-E |
| -3.11 | CYB5R2 | cytochrome b5 reductase 2 |
| -3.11 | — | — |
| 3.11 | PICALM | Phosphatidylinositol binding clathrin assembly |
| 3.11 | B4GALNT1 | beta-1,4-N-acetyl-galactosaminyl transferase 1 |
| 3.11 | — | — |
| 3.11 | LRP2 | low density lipoprotein-related protein 2 |
| -3.11 | SLC35F2 | solute carrier family 35, member F2 |
| 3.11 | SDHALP2 | succinate dehydrogenase complex, subunit A, |
| 3.11 | C5orf24 | chromosome 5 open reading frame 24 |
| -3.10 | MST1 | macrophage stimulating 1 (hepatocyte growth |
| -3.10 | HSCARG | HSCARG protein |
| 3.10 | — | — |
| -3.10 | GCSH | IQ motif and WD repeats 1 |
| -3.10 | FLJ30707 | hypothetical protein FLJ30707 |
| 3.10 | — | — |
| 3.10 | — | — |
| -3.10 | — | Transcribed locus, moderately similar to NP_8 |
| 3.10 | ANGPTL2 | angiopoietin-like 2 |
| 3.10 | — | — |
| 3.09 | FRMD4A | FERM domain containing 4A |
| -3.09 | GCNT2 | glucosaminyl (N-acetyl) transferase 2, I-branch |
| 2.74 | SULF1 | sulfatase 1 |
| -2.74 | — | — |
| 2.74 | — | — |
| 2.74 | SPON1 | spondin 1, extracellular matrix protein |
| 2.74 | YAF2 | YY1 associated factor 2 |
| -2.74 | TAGLN | transgelin |
| -2.74 | C6orf12 | chromosome 6 open reading frame 12 |
| 2.74 | DLX2 | distal-less homeobox 2 |
| -2.74 | PIM1 | pim-1 oncogene /// pim-1 oncogene |
| -2.74 | — | — |
| 2.74 | STS-1 | Cbl-interacting protein Sts-1 |
| 2.74 | C13orf18 | chromosome 13 open reading frame 18 |
| 2.74 | IGF2 /// INS-IGF2 | insulin-like growth factor 2 (somatomedin A) /// |
| -2.73 | EXPH5 | exophilin 5 |
| 2.73 | TBC1D16 | TBC1 domain family, member 16 |
| 2.73 | VIM | vimentin |
| 2.73 | SH3-domain GRB2- | SH3-domain GRB2-like pseudogene 3 |
| 2.73 | ATP10D | ATPase, Class V, type 10D |
| -2.73 | PRIMA1 | Proline rich membrane anchor 1 |
| -2.73 | CYP2B7P1 | cytochrome P450, family 2, subfamily B, polype |
| 2.73 | CD36 | CD36 molecule (thrombospondin receptor) |
| -2.73 | YBX2 | Y box binding protein 2 |
| 2.73 | NFKBIZ | Nuclear factor of kappa light polypeptide gene |
| 2.73 | FGF9 | fibroblast growth factor 9 (glia-activating factor) |
| -2.73 | CHST8 | carbohydrate (N-acetylgalactosamine 4-0) sulf |
| -2.73 | DENND3 | DENN/MADD domain containing 3 |
| -2.72 | MMP15 | matrix metallopeptidase 15 (membrane-inserte |
| -2.72 | MMP1 | matrix metallopeptidase 1 (interstitial collagena |
| 2.72 | SAMD14 | sterile alpha motif domain containing 14 |
| 2.72 | — | — |
| 2.72 | C13orf18 | chromosome 13 open reading frame 18 |
| -2.72 | PRAC | small nuclear protein PRAC |
| -2.72 | GPR37 | G protein-coupled receptor 37 (endothelin rece |
| -2.72 | SERTAD4 | SERTA domain containing 4 |
| -2.72 | MCAM | melanoma cell adhesion molecule |
| 2.72 | CSPG4 | chondroitin sulfate proteoglycan 4 (melanoma- |
| -2.72 | ONECUT1 | one cut domain, family member 1 |
| -2.72 | CR1 | complement component (3b/4b) receptor 1 (Kn |
| 2.72 | IFIT5 | interferon-induced protein with tetratricopeptide |
| -2.72 | LOC497257 | Hypothetical LOC497257 |
| 2.72 | RAB32 | RAB32, member RAS oncogene family |
| 2.72 | RHOBTB3 | Rho-related BTB domain containing 3 |
| -2.72 | — | — |
| -2.72 | SOCS1 | suppressor of cytokine signaling 1 |
| 2.71 | STXBP6 | syntaxin binding protein 6 (amisyn) |
| 2.71 | — | — |
| 2.71 | LEF1 | lymphoid enhancer-binding factor 1 |
| 2.71 | GNG11 | guanine nucleotide binding protein (G protein), |
| 2.71 | ALK | anaplastic lymphoma kinase (Ki-1) |
| 2.71 | FSIP1 | fibrous sheath interacting protein 1 |
| 2.71 | SPHK1 | sphingosine kinase 1 |
| 2.71 | C14orf128 | chromosome 14 open reading frame 128 |
| -2.71 | SLC2A3 | solute carrier family 2 (facilitated glucose trans |
| -2.71 | KIAA0746 | KIAA0746 protein |
| -2.71 | C14orf115 | chromosome 14 open reading frame 115 |
| 2.71 | — | — |
| -2.71 | ATP8B3 | ATPase, Class I, type 8B, member 3 |
| 2.71 | CLGN | calmegin |
| 2.71 | — | CDNA FLJ30762 fis, clone FEBRA2000575 |
| 2.71 | ASCL1 | achaete-scute complex homolog 1 (Drosophila) |
| 2.71 | — | CDNA FLJ38419 fis, clone FEBRA2009846 |
| -2.71 | ICA1 | islet cell autoantigen 1, 69kDa |
| 2.71 | PTN | pleiotrophin (heparin binding growth factor 8, n |
| -2.71 | LAMC2 | laminin, gamma 2 |
| -2.70 | MT1G | metallothionein 1G |
| -2.70 | — | — |
| 2.70 | ANGPTL2 | angiopoietin-like 2 |
| 2.70 | ODC1 | ornithine decarboxylase 1 |
| -2.70 | USP28 | ubiquitin specific peptidase 28 |
| -2.70 | CPT1A | carnitine palmitoyltransferase 1A (liver) |
| -2.70 | TJP2 | tight junction protein 2 (zona occludens 2) |
| -2.70 | — | — |
| 2.70 | — | — |
| 2.70 | HDLBP | High density lipoprotein binding protein (vigilin) |
| -2.70 | HEY2 | hairy/enhancer-of-split related with YRPW motif |
| 2.70 | PCOLCE | procollagen C-endopeptidase enhancer |
| -2.69 | C10orf47 | chromosome 10 open reading frame 47 |
| 2.69 | NOS3 | nitric oxide synthase 3 (endothelial cell) |
| 2.69 | — | Transcribed locus |

Appendix 1

| Value | Gene | Description |
|---|---|---|
| -3.09 | B3GNT2 | UDP-GlcNAc:betaGal beta-1,3-N-acetylglucos: |
| -3.09 | HAPLN1 | hyaluronan and proteoglycan link protein 1 |
| 3.09 | — | Transcribed locus |
| -3.08 | NME3 | non-metastatic cells 3, protein expressed in |
| -3.08 | — | — |
| -3.08 | — | Transcribed locus |
| 3.08 | SOX6 | SRY (sex determining region Y)-box 6 |
| 3.08 | TTLL9 | tubulin tyrosine ligase-like family, member 9 |
| 3.08 | ING3 | inhibitor of growth family, member 3 |
| -3.07 | GALK1 | galactokinase 1 |
| -3.07 | APOBEC3C | apolipoprotein B mRNA editing enzyme, cataly |
| -3.07 | GAS7 | growth arrest-specific 7 |
| 3.07 | LOC284262 | hypothetical protein LOC284262 |
| -3.07 | SAV1 | salvador homolog 1 (Drosophila) |
| 3.07 | — | Full-length cDNA clone CS0DI042YD07 of Pla |
| -3.07 | TMEPAI | transmembrane, prostate androgen induced R |
| 3.07 | EMP1 | epithelial membrane protein 1 |
| -3.06 | MMP25 | matrix metallopeptidase 25 |
| -3.06 | SAMD4A | sterile alpha motif domain containing 4A |
| 3.06 | FLJ21986 | hypothetical protein FLJ21986 |
| -3.06 | — | — |
| -3.06 | TMEM63A | transmembrane protein 63A |
| -3.06 | SLC27A6 | solute carrier family 27 (fatty acid transporter), |
| -3.06 | — | — |
| 3.06 | KRTAP21-1 | keratin associated protein 21-1 |
| -3.06 | — | — |
| -3.06 | HSPB1 /// MEIS3 | heat shock 27kDa protein 1 /// Meis1, myeloid |
| 3.06 | — | — |
| -3.05 | CYP2E1 | cytochrome P450, family 2, subfamily E, polyp |
| -3.05 | — | — |
| 3.05 | — | — |
| 3.05 | PDE4D | phosphodiesterase 4D, cAMP-specific (phosph |
| 3.05 | NEFL | neurofilament, light polypeptide 68kDa |
| -3.05 | — | — |
| -3.05 | PLEKHG6 | pleckstrin homology domain containing, family |
| 3.05 | — | — |
| 3.05 | KALRN | kalirin, RhoGEF kinase |
| -3.05 | — | — |
| 3.05 | CDH6 | cadherin 6, type 2, K-cadherin (fetal kidney) |
| -3.04 | DOCK5 | Dedicator of cytokinesis 5 |
| -3.04 | — | Transcribed locus |
| 3.04 | — | — |
| -3.04 | CABP1 | calcium binding protein 1 (calbrain) |
| -3.04 | JAZF1 | JAZF zinc finger 1 |
| -3.04 | ZXDA /// ZXDB | zinc finger, X-linked, duplicated A /// zinc finger |
| -3.04 | D4S234E | DNA segment on chromosome 4 (unique) 234 |
| 3.04 | FLJ30594 | hypothetical locus FLJ30594 |
| -3.04 | SAV1 | salvador homolog 1 (Drosophila) |
| -3.04 | — | — |
| 3.04 | RFX4 | regulatory factor X, 4 (influences HLA class II |
| 3.04 | PLXNA2 | plexin A2 |
| -3.04 | RBMS1 | RNA binding motif, single stranded interacting |
| -3.03 | DIAPH2 | diaphanous homolog 2 (Drosophila) |
| 3.03 | FKBP7 | FK506 binding protein 7 |
| -3.03 | SFN | stratifin |
| 3.03 | DGKH | Diacylglycerol kinase, eta |
| 3.03 | — | — |
| 3.03 | — | — |
| -3.03 | — | Transcribed locus |
| -3.02 | SERINC5 | Serine incorporator 5 |
| -3.02 | HDAC8 | histone deacetylase 8 |
| 3.02 | TBX1 | T-box 1 |
| -3.02 | CCL2 | chemokine (C-C motif) ligand 2 |
| -3.02 | GCNT1 | glucosaminyl (N-acetyl) transferase 1, core 2 ( |
| -3.02 | SLC2A3 | solute carrier family 2 (facilitated glucose trans |
| 3.02 | LOC347126 | hypothetical gene supported by BC017956 |
| -3.02 | XDH | xanthine dehydrogenase |
| 3.02 | RIN2 | Ras and Rab interactor 2 |
| -3.02 | DMC1 | DMC1 dosage suppressor of mck1 homolog, m |
| -3.02 | CDCP1 | CUB domain containing protein 1 |
| 3.02 | PABPC5 | poly(A) binding protein, cytoplasmic 5 |
| -3.02 | — | — |
| 3.02 | LOC643911 /// LOC | hypothetical LOC643911 /// hypothetical protei |
| -3.02 | HTR3A | 5-hydroxytryptamine (serotonin) receptor 3A |
| 3.02 | — | Transcribed locus |
| -3.02 | SEPP1 | selenoprotein P, plasma, 1 |
| -3.02 | — | Transcribed locus |
| 3.02 | ATP9A | ATPase, Class II, type 9A |
| 3.01 | — | — |

| Value | Gene | Description |
|---|---|---|
| -2.69 | ITGA3 | integrin, alpha 3 (antigen CD49C, alpha 3 subu |
| 2.69 | PLA2G4A | phospholipase A2, group IVA (cytosolic, calciur |
| 2.69 | RHOBTB3 | Rho-related BTB domain containing 3 |
| 2.69 | — | — |
| -2.69 | MOG | myelin oligodendrocyte glycoprotein |
| 2.69 | FCER1G | Fc fragment of IgE, high affinity I, receptor for; |
| 2.69 | DPYSL4 | dihydropyrimidinase-like 4 |
| 2.68 | FOXRED2 | FAD-dependent oxidoreductase domain contai |
| -2.68 | CHRNA9 | cholinergic receptor, nicotinic, alpha 9 |
| 2.68 | MGC39900 | hypothetical protein MGC39900 |
| 2.68 | KLF12 | Kruppel-like factor 12 |
| -2.68 | — | — |
| -2.68 | INMT | indolethylamine N-methyltransferase |
| 2.68 | — | — |
| -2.68 | MBD2 | methyl-CpG binding domain protein 2 |
| 2.68 | KIAA1545 | KIAA1545 protein |
| 2.68 | PIGM | phosphatidylinositol glycan anchor biosynthesi: |
| 2.67 | RHOBTB3 | Rho-related BTB domain containing 3 |
| 2.67 | PROS1 | protein S (alpha) |
| -2.67 | LLGL2 | lethal giant larvae homolog 2 (Drosophila) |
| -2.67 | LOC201895 | hypothetical protein LOC201895 |
| 2.67 | NUP98 | nucleoporin 98kDa |
| -2.67 | — | — |
| -2.67 | — | Transcribed locus |
| 2.67 | SLC6A15 | solute carrier family 6, member 15 |
| 2.67 | DENND2A | DENN/MADD domain containing 2A |
| 2.67 | SOAT1 | sterol O-acyltransferase (acyl-Coenzyme A: ch |
| 2.67 | PIGC | phosphatidylinositol glycan anchor biosynthesi: |
| 2.67 | CNPY1 | canopy 1 homolog (zebrafish) |
| 2.66 | PAX3 | paired box gene 3 (Waardenburg syndrome 1) |
| -2.66 | LYPD3 | LY6/PLAUR domain containing 3 |
| -2.66 | MB | myoglobin |
| 2.66 | LRRN3 | leucine rich repeat neuronal 3 |
| -2.66 | — | Homo sapiens, Similar to LOC169932, clone IM |
| 2.66 | KIAA0101 | KIAA0101 /// KIAA0101 |
| 2.66 | ARAF | v-raf murine sarcoma 3611 viral oncogene hom |
| 2.66 | PSCD4 | pleckstrin homology, Sec7 and coiled-coil dom: |
| 2.66 | LOC283400 | hypothetical protein LOC283400 |
| -2.66 | — | — |
| -2.66 | DIAPH2 | diaphanous homolog 2 (Drosophila) |
| 2.66 | — | Full-length cDNA clone CS0DC002YJ17 of Net |
| -2.66 | SEMA6A | sema domain, transmembrane domain (TM), a |
| 2.66 | — | cDNA: FLJ20929 fis, clone ADSE01218 |
| -2.65 | PRKCZ | protein kinase C, zeta |
| -2.65 | LHFPL3 | lipoma HMGIC fusion partner-like 3 |
| 2.65 | — | Transcribed locus, weakly similar to XP_51193 |
| -2.65 | NMU | neuromedin U |
| 2.65 | PRR3 | proline rich 3 |
| -2.65 | SYN2 | synapsin II |
| 2.65 | — | CDNA FLJ38472 fis, clone FEBRA2022148 |
| -2.65 | CPEB3 | cytoplasmic polyadenylation element binding pr |
| 2.65 | GLT8D2 | glycosyltransferase 8 domain containing 2 /// gl |
| -2.65 | SEMA6A | sema domain, transmembrane domain (TM), a |
| -2.65 | GPX2 | glutathione peroxidase 2 (gastrointestinal) |
| 2.65 | TTMA | two transmembrane domain family member A |
| -2.65 | ARHGEF5 | Rho guanine nucleotide exchange factor (GEF) |
| 2.65 | — | Transcribed locus, moderately similar to NP_06 |
| 2.65 | HGSNAT | heparan-alpha-glucosaminide N-acetyltransfera |
| -2.64 | LOC388494 | hypothetical gene supported by AL365406; BC( |
| -2.64 | MFAP3L | microfibrillar-associated protein 3-like |
| -2.64 | SCG5 | secretogranin V (7B2 protein) |
| -2.64 | RAB26 | RAB26, member RAS oncogene family |
| -2.64 | GPR37 | G protein-coupled receptor 37 (endothelin rece |
| 2.64 | FLJ10159 | Hypothetical protein FLJ10159 |
| -2.64 | HAS3 | hyaluronan synthase 3 |
| -2.64 | ZBTB3 | zinc finger and BTB domain containing 3 |
| 2.64 | — | — |
| 2.64 | CD93 | CD93 molecule |
| 2.64 | CRYBA1 | crystallin, beta A1 |
| 2.64 | LRRC8C | Leucine rich repeat containing 8 family, membe |
| -2.64 | IL1B | interleukin 1, beta |
| -2.64 | RBP7 | retinol binding protein 7, cellular |
| 2.64 | — | — |
| -2.63 | ENO2 | enolase 2 (gamma, neuronal) |
| -2.63 | THRB | thyroid hormone receptor, beta (erythroblastic l |
| 2.63 | PRKD3 | protein kinase D3 |
| -2.63 | SYNGR3 | synaptogyrin 3 |
| -2.63 | NFE2L3 | nuclear factor (erythroid-derived 2)-like 3 |
| -2.63 | PYGM | phosphorylase, glycogen; muscle (McArdle syn |

Appendix 1

| Value | Gene | Description |
|---|---|---|
| 3.01 | ZNF214 | zinc finger protein 214 |
| 3.01 | FABP7 | Fatty acid binding protein 7, brain |
| -3.01 | — | — |
| 3.01 | NOL4 | nucleolar protein 4 |
| -3.01 | — | CDNA clone IMAGE:4793048 |
| -3.00 | CHRM3 /// LOC730 | cholinergic receptor, muscarinic 3 /// similar to |
| 3.00 | SLITRK1 | SLIT and NTRK-like family, member 1 |
| -3.00 | — | — |
| 3.00 | LMO3 | LIM domain only 3 (rhombotin-like 2) |
| -3.00 | CASP8 | caspase 8, apoptosis-related cysteine peptidas |
| 3.00 | KIAA0141 | KIAA0141 |
| -3.00 | PBX1 | Pre-B-cell leukemia transcription factor 1 |
| 3.00 | B4GALNT1 | beta-1,4-N-acetyl-galactosaminyl transferase 1 |
| 3.00 | HS6ST2 | heparan sulfate 6-O-sulfotransferase 2 |
| 3.00 | — | — |
| 3.00 | — | — |
| -2.99 | GATM | glycine amidinotransferase (L-arginine:glycine |
| 2.99 | CALCB | calcitonin-related polypeptide, beta |
| 2.99 | RHOBTB3 | Rho-related BTB domain containing 3 |
| -2.99 | BCL11A | B-cell CLL/lymphoma 11A (zinc finger protein) |
| 2.99 | GNG2 | guanine nucleotide binding protein (G protein), |
| -2.99 | GPD2 | glycerol-3-phosphate dehydrogenase 2 (mitoch |
| 2.99 | NHLH1 | nescient helix loop helix 1 |
| 2.98 | PUNC | putative neuronal cell adhesion molecule |
| -2.98 | SCN5A | sodium channel, voltage-gated, type V, alpha ( |
| 2.98 | MAP2K5 | mitogen-activated protein kinase kinase 5 |
| 2.98 | — | — |
| 2.98 | RPS6KA2 | ribosomal protein S6 kinase, 90kDa, polypeptid |
| -2.98 | SLC2A3 | solute carrier family 2 (facilitated glucose trans |
| -2.98 | — | CDNA clone IMAGE:5262752 |
| -2.97 | GABRA5 | gamma-aminobutyric acid (GABA) A receptor, |
| -2.97 | SYTL1 | synaptotagmin-like 1 |
| 2.97 | SERHL2 | Serine hydrolase-like 2 |
| -2.97 | — | — |
| -2.97 | SIX2 | sine oculis homeobox homolog 2 (Drosophila) |
| 2.97 | FOXP4 | forkhead box P4 |
| -2.97 | PPAP2A | phosphatidic acid phosphatase type 2A |
| 2.97 | TOR1AIP2 | torsin A interacting protein 2 |
| -2.97 | PAK1 | p21/Cdc42/Rac1-activated kinase 1 (STE20 ho |
| 2.97 | STXBP6 | syntaxin binding protein 6 (amisyn) |
| 2.97 | FKBP7 | FK506 binding protein 7 |
| 2.96 | — | — |
| -2.96 | DKFZP564J0863 | DKFZP564J0863 protein |
| 2.96 | SCML1 | Sex comb on midleg-like 1 (Drosophila) |
| -2.96 | LHFPL2 | lipoma HMGIC fusion partner-like 2 |
| -2.96 | LOC400680 | hypothetical gene supported by AK097381; BC |
| -2.96 | — | — |
| 2.96 | ZNF25 | zinc finger protein 25 (KOX 19) |
| -2.96 | THY1 | Thy-1 cell surface antigen |
| 2.96 | C5orf28 | chromosome 5 open reading frame 28 |
| 2.96 | FGFRL1 | fibroblast growth factor receptor-like 1 |
| -2.95 | TPM1 | tropomyosin 1 (alpha) |
| -2.95 | — | — |
| 2.95 | — | CDNA FLJ11723 fis, clone HEMBA1005314 |
| -2.95 | GRIK5 | glutamate receptor, ionotropic, kainate 5 |
| 2.95 | LGR5 | leucine-rich repeat-containing G protein-couple |
| 2.95 | — | CDNA FLJ34826 fis, clone NT2NE2008803 |
| -2.95 | GFPT2 | glutamine-fructose-6-phosphate transaminase |
| -2.95 | ASS1 | argininosuccinate synthetase 1 |
| 2.95 | — | — |
| -2.95 | PPAP2A | phosphatidic acid phosphatase type 2A |
| -2.95 | KCNQ1 | potassium voltage-gated channel, KQT-like sub |
| 2.95 | AMDHD1 | amidohydrolase domain containing 1 |
| -2.95 | RBMS1 | RNA binding motif, single stranded interacting |
| -2.95 | FGFR4 | fibroblast growth factor receptor 4 |
| -2.95 | PTHLH /// MOCOS | parathyroid hormone-like hormone /// molybder |
| 2.95 | SETBP1 | SET binding protein 1 |
| 2.94 | ZIC1 | Zic family member 1 (odd-paired homolog, Dro |
| 2.94 | — | — |
| 2.94 | DKFZp666G057 | hypothetical protein DKFZp666G057 |
| 2.94 | NAV3 | neuron navigator 3 |
| -2.94 | TERF1 | telomeric repeat binding factor (NIMA-interactir |
| -2.94 | KCNK5 | Potassium channel, subfamily K, member 5 |
| 2.94 | RKHD2 | ring finger and KH domain containing 2 |
| -2.94 | PPP2R5C | Protein phosphatase 2, regulatory subunit B (B |
| 2.94 | CD58 | CD58 molecule |
| 2.94 | — | — |
| 2.94 | — | — |
| -2.94 | ENPP1 | ectonucleotide pyrophosphatase/phosphodiest |
| -2.63 | CTSL2 | cathepsin L2 |
| -2.63 | CNTNAP2 | contactin associated protein-like 2 |
| -2.63 | TRIM31 | tripartite motif-containing 31 |
| 2.63 | PRMT8 | protein arginine methyltransferase 8 |
| 2.63 | FMNL3 | formin-like 3 |
| 2.62 | MARCKS | myristoylated alanine-rich protein kinase C sub: |
| 2.62 | ASXL1 | additional sex combs like 1 (Drosophila) |
| 2.62 | TCEA3 | transcription elongation factor A (SII), 3 |
| 2.62 | ITGB8 | integrin, beta 8 |
| -2.62 | — | — |
| -2.62 | MYL9 | myosin, light chain 9, regulatory |
| -2.61 | — | — |
| -2.61 | LOC130951 | hypothetical protein BC014602 |
| 2.61 | — | — |
| 2.61 | HOXB4 | homeobox B4 |
| 2.61 | CYP2U1 | cytochrome P450, family 2, subfamily U, polype |
| -2.61 | CAV1 | caveolin 1, caveolae protein, 22kDa |
| -2.61 | MT1E | metallothionein 1E (functional) |
| 2.61 | SEMA6D | sema domain, transmembrane domain (TM), an |
| 2.61 | LOC144363 | Hypothetical protein LOC144363 |
| -2.61 | MAX | MYC associated factor X |
| 2.61 | TIFA | TRAF-interacting protein with a forkhead-assoc |
| 2.61 | ELAC1 | elaC homolog 1 (E. coli) |
| -2.61 | PFKP | phosphofructokinase, platelet |
| 2.61 | LIX1L | Lix1 homolog (mouse)-like |
| -2.60 | COL4A4 | collagen, type IV, alpha 4 |
| 2.60 | — | — |
| 2.60 | MEIS1 | Meis1, myeloid ecotropic viral integration site 1 |
| 2.60 | — | — |
| -2.60 | EPB41L4B | erythrocyte membrane protein band 4.1 like 4B |
| -2.60 | CPT1A | carnitine palmitoyltransferase 1A (liver) |
| -2.60 | MT1H | metallothionein 1H |
| -2.60 | GPR | putative G protein coupled receptor |
| -2.60 | CAPG | capping protein (actin filament), gelsolin-like |
| -2.60 | MBD2 | methyl-CpG binding domain protein 2 |
| 2.60 | — | — |
| -2.59 | CNN1 | calponin 1, basic, smooth muscle |
| -2.59 | — | — |
| 2.59 | SMOC1 | SPARC related modular calcium binding 1 |
| 2.59 | RHOBTB3 | Rho-related BTB domain containing 3 |
| 2.59 | ARHGAP30 | Rho GTPase activating protein 30 |
| -2.59 | STXBP2 | syntaxin binding protein 2 |
| -2.59 | ZADH1 | zinc binding alcohol dehydrogenase, domain co |
| 2.59 | — | — |
| 2.59 | AMPH | amphiphysin (Stiff-Man syndrome with breast c |
| -2.59 | SMAD7 | SMAD family member 7 |
| -2.59 | JARID2 | jumonji, AT rich interactive domain 2 |
| -2.59 | — | — |
| 2.59 | C20orf32 | chromosome 20 open reading frame 32 |
| 2.59 | TTC3 | tetratricopeptide repeat domain 3 |
| -2.59 | CPT1A | carnitine palmitoyltransferase 1A (liver) |
| 2.59 | — | — |
| 2.59 | — | Homo sapiens, clone IMAGE:4479080 |
| 2.59 | MYLK | myosin, light polypeptide kinase |
| -2.58 | CGNL1 | cingulin-like 1 |
| 2.58 | PDLIM4 | PDZ and LIM domain 4 |
| -2.58 | MAML2 | Mastermind-like 2 (Drosophila) |
| -2.58 | OCIAD2 | OCIA domain containing 2 |
| -2.58 | QPCT | glutaminyl-peptide cyclotransferase (glutaminyl |
| -2.58 | TRIM54 | tripartite motif-containing 54 |
| 2.58 | — | — |
| 2.58 | — | — |
| 2.58 | SNAP25 | synaptosomal-associated protein, 25kDa |
| -2.57 | CD2AP | CD2-associated protein |
| -2.57 | RAB38 | RAB38, member RAS oncogene family |
| 2.57 | DNASE1 | Deoxyribonuclease I |
| -2.57 | — | — |
| -2.57 | — | — |
| -2.57 | DNAJC6 | DnaJ (Hsp40) homolog, subfamily C, member 6 |
| 2.57 | RBMS3 | RNA binding motif, single stranded interacting |
| 2.57 | COL11A1 | collagen, type XI, alpha 1 |
| -2.57 | RUTBC2 | RUN and TBC1 domain containing 2 |
| 2.57 | LY6G6D | lymphocyte antigen 6 complex, locus G6C |
| 2.57 | TTC3 | tetratricopeptide repeat domain 3 |
| 2.57 | — | — |
| 2.57 | GLT25D2 | glycosyltransferase 25 domain containing 2 |
| 2.57 | COL13A1 | collagen, type XIII, alpha 1 |
| -2.57 | TKT | transketolase (Wernicke-Korsakoff syndrome) |
| 2.57 | — | Transcribed locus |

Appendix 1

| Value | Symbol | Description |
|---|---|---|
| -2.94 | OSBPL10 | oxysterol binding protein-like 1C |
| -2.94 | ASPHD1 | aspartate beta-hydroxylase domain containing |
| -2.94 | FGD5 | FYVE, RhoGEF and PH domain containing 5 |
| -2.94 | KLF5 | Kruppel-like factor 5 (intestinal) |
| -2.94 | PTPRU | protein tyrosine phosphatase, receptor type, U |
| -2.94 | — | Transcribed locus |
| 2.94 | RABL5 | RAB, member RAS oncogene family-like 5 |
| 2.94 | TTLL11 | tubulin tyrosine ligase-like family, member 11 |
| -2.94 | — | C33.6 unnamed HERV-H protein |
| -2.94 | PPP2R5C | protein phosphatase 2, regulatory subunit B (B |
| -2.93 | BLVRB | biliverdin reductase B (flavin reductase (NADP |
| -2.93 | SLC2A3 | solute carrier family 2 (facilitated glucose trans |
| -2.93 | SFN | stratifin |
| -2.93 | F2RL1 | coagulation factor II (thrombin) receptor-like 1 |
| 2.93 | BTN3A2 | butyrophilin, subfamily 3, member A2 |
| -2.93 | — | Full-length cDNA clone CS0DJ013YE21 of T c |
| -2.93 | PRODH | proline dehydrogenase (oxidase) 1 |
| 2.93 | — | — |
| -2.93 | HHLA3 | HERV-H LTR-associating 3 |
| 2.93 | FST | follistatin |
| -2.93 | TAGLN2 | transgelin 2 |
| 2.93 | DCTN4 | dynactin 4 (p62) |
| 2.92 | — | — |
| -2.92 | RDH12 | retinol dehydrogenase 12 (all-trans and 9-cis) |
| -2.92 | MSL3L1 | male-specific lethal 3-like 1 (Drosophila) |
| -2.92 | PRKCQ | protein kinase C, theta |
| -2.92 | BNC2 | Basonuclin 2 |
| 2.92 | — | — |
| -2.92 | OLFM2 | olfactomedin 2 |
| -2.92 | IL7R | interleukin 7 receptor |
| 2.92 | APOLD1 | apolipoprotein L domain containing 1 /// apolipo |
| -2.92 | — | — |
| 2.92 | — | CDNA FLJ30740 fis, clone FEBRA2000319 |
| -2.92 | HESX1 | homeobox, ES cell expressed 1 |
| -2.91 | D21S2088E | D21S2088E |
| -2.91 | HHLA1 | HERV-H LTR-associating 1 |
| -2.91 | COL13A1 | collagen, type XIII, alpha 1 |
| -2.91 | C18orf1 | chromosome 18 open reading frame 1 |
| 2.91 | — | CDNA FLJ26539 fis, clone KDN09310 |
| -2.91 | MYOZ3 | myozenin 3 |
| 2.91 | TBC1D16 | TBC1 domain family, member 16 |
| 2.91 | RASGRP1 | RAS guanyl releasing protein 1 (calcium and D |
| 2.91 | CAMK2N1 | calcium/calmodulin-dependent protein kinase I |
| -2.91 | TMEM37 | transmembrane protein 37 |
| 2.91 | — | — |
| 2.91 | — | — |
| -2.90 | LOC285500 | hypothetical protein LOC285500 |
| -2.90 | ALOX12P2 | arachidonate 12-lipoxygenase pseudogene 2 |
| -2.90 | ID2 /// ID2B | inhibitor of DNA binding 2, dominant negative h |
| 2.90 | RAB36 | RAB36, member RAS oncogene family |
| -2.90 | GSTO2 | glutathione S-transferase omega 2 |
| 2.90 | EPS8 | epidermal growth factor receptor pathway subs |
| -2.90 | TPM1 | tropomyosin 1 (alpha) |
| 2.90 | RRAGD | Ras-related GTP binding D |
| 2.90 | STON1 | Stonin 1 |
| 2.90 | — | CDNA clone IMAGE:5303499 |
| 2.90 | TP53AP1 | TP53 activated protein 1 |
| 2.90 | FYN | FYN oncogene related to SRC, FGR, YES |
| 2.90 | TMEM106C | transmembrane protein 106C |
| -2.90 | FOXO1A | forkhead box O1A (rhabdomyosarcoma) |
| -2.90 | ERBB3 | v-erb-b2 erythroblastic leukemia viral oncogene |
| 2.90 | LOC441204 | hypothetical locus LOC441204 |
| 2.89 | ABCB4 | ATP-binding cassette, sub-family B (MDR/TAP |
| 2.89 | — | Full length insert cDNA clone ZD53C10 |
| 2.89 | GPRIN1 | G protein regulated inducer of neurite outgrowt |
| -2.89 | — | Transcribed locus |
| -2.89 | CDS1 | CDP-diacylglycerol synthase (phosphatidate c |
| -2.88 | H2AFJ | H2A histone family, member J |
| -2.88 | F12 | coagulation factor XII (Hageman factor) |
| 2.88 | — | — |
| -2.88 | MAFB | v-maf musculoaponeurotic fibrosarcoma oncog |
| 2.88 | — | — |
| -2.88 | THY1 | Thy-1 cell surface antigen |
| 2.88 | — | Transcribed locus |
| 2.88 | POU3F3 | POU domain, class 3, transcription factor 3 |
| 2.88 | COMMD10 | COMM domain containing 10 |
| 2.87 | HS6ST2 | heparan sulfate 6-O-sulfotransferase 2 |
| 2.87 | — | — |
| 2.87 | TTC3 | tetratricopeptide repeat domain 3 |

| Value | Symbol | Description |
|---|---|---|
| 2.56 | — | — |
| 2.56 | HECTD2 | HECT domain containing 2 |
| -2.56 | — | — |
| 2.56 | GLCE | UDP-glucuronic acid epimerase |
| 2.56 | — | CDNA FLJ37333 fis, clone BRAMY2020106 |
| -2.56 | CHODL | chondrolectin |
| -2.56 | SLC2A3 | solute carrier family 2 (facilitated glucose trans |
| -2.56 | LOC284242 | hypothetical protein LOC284242 |
| 2.56 | LOC91316 | similar to bK246H3.1 (immunoglobulin lambda- |
| 2.56 | ID3 | inhibitor of DNA binding 3, dominant negative h |
| 2.56 | C19orf20 | chromosome 19 open reading frame 20 |
| 2.56 | SERHL2 | Serine hydrolase-like 2 |
| 2.56 | MTCH2 | mitochondrial carrier homolog 2 (C. elegans) |
| -2.55 | — | — |
| 2.55 | — | — |
| -2.55 | — | — |
| -2.55 | FLJ36848 | hypothetical LOC647115 |
| -2.55 | STYK1 | serine/threonine/tyrosine kinase 1 /// serine/thre |
| 2.55 | — | — |
| 2.55 | DZIP1 | DAZ interacting protein 1 |
| 2.55 | WNT5B | wingless-type MMTV integration site family, me |
| -2.55 | FAM118B | Family with sequence similarity 118, member B |
| 2.55 | P2RY8 | purinergic receptor P2Y, G-protein coupled, 8 |
| -2.55 | — | — |
| 2.55 | FAM13C1 | family with sequence similarity 13, member C1 |
| -2.54 | CXCL6 | chemokine (C-X-C motif) ligand 6 (granulocyte |
| 2.54 | PIK3R3 | phosphoinositide-3-kinase, regulatory subunit 3 |
| 2.54 | — | — |
| 2.54 | IQCE | IQ motif containing E |
| 2.54 | RAGE | renal tumor antigen |
| -2.54 | SFN | stratifin |
| -2.54 | MATK | megakaryocyte-associated tyrosine kinase |
| 2.54 | TXNDC13 | thioredoxin domain containing 13 |
| 2.54 | IGSF6 | immunoglobulin superfamily, member 6 |
| 2.54 | FAM89B | family with sequence similarity 89, member B |
| 2.54 | EPM2AIP1 | EPM2A (laforin) interacting protein 1 |
| -2.54 | FLJ90757 | hypothetical protein LOC440465 |
| 2.53 | TMED4 | transmembrane emp24 protein transport domai |
| -2.53 | — | — |
| -2.53 | C9orf61 | chromosome 9 open reading frame 61 |
| 2.53 | — | Clone TUA8 Cri-du-chat region mRNA |
| 2.53 | — | — |
| 2.53 | NFATC4 | nuclear factor of activated T-cells, cytoplasmic, |
| -2.53 | PMAIP1 | phorbol-12-myristate-13-acetate-induced protei |
| -2.53 | FGFR4 | fibroblast growth factor receptor 4 |
| 2.53 | HOXA6 | homeobox A6 |
| 2.53 | EMP2 | epithelial membrane protein 2 |
| -2.53 | CNTNAP2 | contactin associated protein-like 2 |
| -2.53 | — | — |
| -2.53 | PAWR | PRKC, apoptosis, WT1, regulator |
| -2.53 | DDX25 | DEAD (Asp-Glu-Ala-Asp) box polypeptide 25 |
| 2.52 | FLJ90757 | hypothetical protein LOC440465 |
| 2.52 | LRRC8C | leucine rich repeat containing 8 family, member |
| 2.52 | ABCB1 /// ABCB4 | ATP-binding cassette, sub-family B (MDR/TAP |
| 2.52 | — | — |
| -2.52 | EFEMP1 | EGF-containing fibulin-like extracellular matrix |
| -2.52 | CTSL2 | Cathepsin L2 |
| -2.52 | S100A10 | S100 calcium binding protein A10 |
| -2.52 | CAV2 | caveolin 2 |
| 2.52 | C5orf24 | chromosome 5 open reading frame 24 |
| -2.51 | — | Transcribed locus |
| -2.51 | TMEM64 | Transmembrane protein 64 |
| 2.51 | SIAT7E | ST6 (alpha-N-acetyl-neuraminyl-2,3-beta-galac |
| -2.51 | RP13-36C9.1 /// RP | cancer/testis antigen CT45-2 /// cancer/testis a |
| -2.51 | FKBP4 | FK506 binding protein 4, 59kDa |
| 2.51 | — | — |
| 2.51 | NRIP1 | nuclear receptor interacting protein 1 |
| -2.51 | NME3 | non-metastatic cells 3, protein expressed in |
| 2.51 | HOXA4 | homeobox A4 |
| 2.51 | RBPMS | RNA binding protein with multiple splicing |
| -2.51 | ALMS1 | Alstrom syndrome 1 |
| -2.51 | — | — |
| -2.51 | LOC286044 | hypothetical protein LOC286044 |
| -2.51 | SLITRK4 | SLIT and NTRK-like family, member 4 |
| -2.51 | FAM107A | family with sequence similarity 107, member A |
| 2.51 | — | — |
| -2.50 | ADD2 | adducin 2 (beta) |
| 2.50 | — | CDNA FLJ35137 fis, clone PLACE6009419 |
| 2.50 | — | — |

Appendix 1

| Value | Gene | Description |
|---|---|---|
| -2.87 | — | — |
| 2.87 | LOC285771 | hypothetical protein LOC285771 |
| 2.87 | CRYGC | crystallin, gamma C |
| 2.87 | MCTP1 | Multiple C2-domains with two transmembrane |
| -2.87 | PLEKHC1 | pleckstrin homology domain containing, family |
| -2.87 | LOC138255 | OTTHUMP00000021439 |
| -2.87 | C7orf34 | chromosome 7 open reading frame 34 |
| -2.87 | — | — |
| 2.87 | RP5-875H10.1 | SAM domain containing 1 |
| 2.87 | CAMK2D | Calcium/calmodulin-dependent protein kinase |
| 2.87 | LMO3 | LIM domain only 3 (rhombotin-like 2) |
| 2.87 | RHOBTB3 | Rho-related BTB domain containing 3 |
| -2.87 | UTX | ubiquitously transcribed tetratricopeptide repea |
| 2.87 | ZNF343 | zinc finger protein 343 |
| 2.87 | DNAJC18 | DnaJ (Hsp40) homolog, subfamily C, member |
| 2.87 | FAM125B | family with sequence similarity 125, member B |
| -2.86 | TAF4B | TAF4b RNA polymerase II, TATA box binding |
| 2.86 | — | — |
| 2.86 | THSD7A | thrombospondin, type I, domain containing 7A |
| -2.86 | LMO7 | LIM domain 7 |
| -2.86 | MMP15 | matrix metallopeptidase 15 (membrane-inserte |
| -2.86 | FLJ11286 | hypothetical protein FLJ11286 |
| 2.86 | EDG1 | endothelial differentiation, sphingolipid G-prote |
| -2.86 | — | — |
| 2.86 | SECP43 | tRNA selenocysteine associated protein |
| -2.86 | PCTK3 | PCTAIRE protein kinase 3 |
| 2.86 | AUTS2 | Autism susceptibility candidate 2 |
| 2.86 | TPPP | brain-specific protein p25 alpha |
| -2.86 | C10orf75 | Chromosome 10 open reading frame 75 |
| 2.86 | CELSR2 | cadherin, EGF LAG seven-pass G-type recepto |
| -2.85 | LOC284561 | hypothetical protein LOC284561 |
| -2.85 | PLP2 | proteolipid protein 2 (colonic epithelium-enriche |
| -2.85 | SLC2A3 | solute carrier family 2 (facilitated glucose trans |
| 2.85 | LIX1L | Lix1 homolog (mouse)-like |
| -2.85 | LOC440338 | hypothetical gene supported by AJ002784 |
| 2.85 | MBD2 | methyl-CpG binding domain protein 2 |
| -2.85 | RABGAP1L | RAB GTPase activating protein 1-like |
| -2.85 | MB | myoglobin |
| -2.85 | MOCOS | Molybdenum cofactor sulfurase |
| 2.85 | C6orf118 | chromosome 6 open reading frame 118 |
| -2.84 | TncRNA | trophoblast-derived noncoding RNA |
| -2.84 | SPAG4 | sperm associated antigen 4 |
| -2.84 | ATP1A2 | ATPase, Na+/K+ transporting, alpha 2 (+) poly |
| 2.84 | EPHB2 | EPH receptor B2 |
| 2.84 | FLJ14213 | hypothetical protein FLJ14213 |
| 2.84 | FMN2 | formin 2 |
| -2.84 | C21orf30 | chromosome 21 open reading frame 30 |
| 2.84 | VASH1 | vasohibin 1 |
| 2.84 | SLC1A4 | solute carrier family 1 (glutamate/neutral amino |
| -2.84 | LOC54103 | hypothetical protein LOC54103 |
| -2.84 | — | — |
| -2.84 | NFE2L3 | nuclear factor (erythroid-derived 2)-like 3 |
| 2.84 | LOC219688 | hypothetical protein LOC219688 |
| 2.84 | GRM3 | glutamate receptor, metabotropic 3 |
| 2.84 | SEMA6D | sema domain, transmembrane domain (TM), a |
| 2.84 | FRY | furry homolog (Drosophila) |
| -2.83 | — | — |
| 2.83 | — | — |
| 2.83 | MAP1A | microtubule-associated protein 1A |
| -2.83 | KIAA0040 | KIAA0040 |
| -2.83 | TNFAIP2 | tumor necrosis factor, alpha-induced protein 2 |
| 2.83 | KIF5A | Kinesin family member 5A |
| 2.83 | PALLD | Palladin, cytoskeletal associated protein |
| 2.83 | PTX3 | pentraxin-related gene, rapidly induced by IL-1 |
| 2.83 | CAPZA1 | Capping protein (actin filament) muscle Z-line, |
| -2.83 | — | — |
| 2.83 | UGT2B15 /// UGT2 | UDP glucuronosyltransferase 2 family, polypep |
| -2.83 | WBSCR17 | Williams-Beuren syndrome chromosome regio |
| 2.83 | TTC3 | tetratricopeptide repeat domain 3 |
| -2.82 | — | — |
| 2.82 | GNAZ | guanine nucleotide binding protein (G protein), |
| 2.82 | RNF175 | ring finger protein 175 |
| -2.82 | CDS1 | CDP-diacylglycerol synthase (phosphatidate c |
| -2.82 | — | Similar to hypothetical protein LOC284701 |
| -2.82 | RAB43 | RAB43, member RAS oncogene family |
| -2.82 | CD19 | CD19 molecule |
| -2.82 | ZNF785 | zinc finger protein 785 |
| -2.82 | — | — |
| 2.82 | HBE1 | hemoglobin, epsilon 1 /// hemoglobin, epsilon |
| -2.50 | DSG2 | Desmoglein 2 |
| -2.50 | PPP2R1B | protein phosphatase 2 (formerly 2A), regulatory |
| -2.50 | SKIL | SKI-like |
| -2.49 | USP28 | ubiquitin specific peptidase 28 |
| 2.49 | EME2 | Essential meiotic endonuclease 1 homolog 2 (S |
| 2.49 | PCDH7 | BH-protocadherin (brain-heart) |
| -2.49 | SEMA6A | sema domain, transmembrane domain (TM), ar |
| 2.49 | NPAS3 | neuronal PAS domain protein 3 |
| -2.49 | HPN | hepsin (transmembrane protease, serine 1) |
| -2.49 | — | Transcribed locus |
| -2.48 | MYO6 | myosin VI |
| -2.48 | SHANK2 | SH3 and multiple ankyrin repeat domains 2 |
| 2.48 | GNAZ | guanine nucleotide binding protein (G protein), |
| 2.48 | SPON1 | spondin 1, extracellular matrix protein |
| 2.48 | SSFA2 | sperm specific antigen 2 |
| 2.48 | CYP26B1 | cytochrome P450, family 26, subfamily B, polyp |
| 2.48 | — | — |
| -2.48 | GPR160 | G protein-coupled receptor 160 |
| 2.48 | — | — |
| 2.48 | — | — |
| 2.48 | HS6ST2 | heparan sulfate 6-O-sulfotransferase 2 |
| 2.47 | LOC222070 | hypothetical protein LOC222070 |
| 2.47 | — | — |
| 2.47 | COL11A1 | collagen, type XI, alpha 1 |
| -2.47 | TMBIM1 | transmembrane BAX inhibitor motif containing |
| 2.47 | RPS23 | ribosomal protein S23 |
| 2.47 | — | — |
| -2.47 | PWCR1 | Prader-Willi syndrome chromosome region 1 |
| 2.47 | GRASP | GRP1 (general receptor for phosphoinositides |
| 2.47 | CNTNAP4 | contactin associated protein-like 4 |
| 2.47 | IL13RA1 | interleukin 13 receptor, alpha 1 |
| -2.47 | PARD3B | Par-3 partitioning defective 3 homolog B (C. ele |
| -2.47 | SLC7A3 | solute carrier family 7 (cationic amino acid tran |
| 2.46 | LOC399951 | hypothetical LOC399951 |
| 2.46 | ELAC1 | elaC homolog 1 (E. coli) |
| 2.46 | PCDHGA3 | protocadherin gamma subfamily A, 3 |
| -2.46 | THBS2 | thrombospondin 2 |
| -2.46 | LOC389023 | hypothetical gene supported by BC032913; BC |
| -2.46 | GABRA5 /// LOC72 | gamma-aminobutyric acid (GABA) A receptor, a |
| 2.46 | FAM125B | family with sequence similarity 125, member B |
| 2.46 | — | — |
| 2.46 | STK17A | Serine/threonine kinase 17a (apoptosis-inducin |
| 2.46 | RIN2 | Ras and Rab interactor 2 |
| -2.46 | FGD5 | FYVE, RhoGEF and PH domain containing 5 |
| -2.46 | ITFG2 | Integrin alpha FG-GAP repeat containing 2 |
| -2.46 | — | — |
| -2.46 | SLC6A15 | solute carrier family 6, member 15 |
| 2.46 | RSPO3 | R-spondin 3 homolog (Xenopus laevis) |
| 2.46 | RIMBP2 | RIMS binding protein 2 |
| 2.46 | — | — |
| 2.45 | NEDD9 | neural precursor cell expressed, developmenta |
| 2.45 | FLJ31485 | hypothetical gene supported by AK056047; AK |
| 2.45 | SH3BP5 | SH3-domain binding protein 5 (BTK-associated |
| 2.45 | PIK3R3 | phosphoinositide-3-kinase, regulatory subunit 3 |
| -2.45 | ZNF204 | zinc finger protein 204 |
| 2.45 | JAKMIP2 | janus kinase and microtubule interacting protei |
| 2.45 | KLHL13 | kelch-like 13 (Drosophila) |
| 2.44 | TENC1 | tensin like C1 domain containing phosphatase |
| 2.44 | ZNF529 | Zinc finger protein 529 |
| 2.44 | ENDOGL1 | endonuclease G-like 1 |
| -2.44 | BCL11B | B-cell CLL/lymphoma 11B (zinc finger protein) |
| -2.44 | — | — |
| 2.44 | — | — |
| 2.44 | ITGA11 | integrin, alpha 11 |
| -2.44 | MT1M | metallothionein 1M |
| -2.44 | TAGLN | transgelin |
| 2.44 | — | — |
| 2.44 | TTC3 | tetratricopeptide repeat domain 3 |
| -2.44 | PLA2G2A | phospholipase A2, group IIA (platelets, synovia |
| 2.44 | ULK2 | Unc-51-like kinase 2 (C. elegans) |
| 2.44 | — | CDNA clone IMAGE:5303499 |
| -2.43 | — | — |
| 2.43 | USP46 | Ubiquitin specific peptidase 46 |
| -2.43 | DIAPH2 | diaphanous homolog 2 (Drosophila) |
| -2.43 | — | — |
| -2.43 | — | — |
| -2.43 | — | — |
| 2.43 | HDAC9 | histone deacetylase 9 |
| 2.43 | — | — |

Appendix 1

| | | | | |
|---|---|---|---|---|
| -2.82 | — | — | -2.43 RLN2 | relaxin 2 |
| -2.82 | — | — | 2.43 GPRIN1 | G protein regulated inducer of neurite outgrowth |
| 2.82 | EFCBP2 | EF-hand calcium binding protein 2 | 2.43 LANCL2 | LanC lantibiotic synthetase component C-like 2 |
| -2.82 | IGFBP3 | insulin-like growth factor binding protein 3 | -2.43 olfactory receptor, f | CDNA FLJ11504 fis, clone HEMBA1002119 |
| -2.82 | CHES1 | checkpoint suppressor 1 | -2.43 LOC642893 | Similar to Calponin-2 (Calponin H2, smooth mu |
| 2.82 | — | CDNA FLJ42688 fis, clone BRAMY3002120 | 2.43 PCDHGB7 | protocadherin gamma subfamily B, 7 |
| 2.81 | — | — | -2.43 PAWR | PRKC, apoptosis, WT1, regulator |
| -2.81 | TMEM46 | transmembrane protein 46 | -2.43 TULP2 | tubby like protein 2 |
| 2.81 | DKFZP564D166 | putative ankyrin-repeat containing protein | -2.42 | — |
| -2.81 | CD55 | CD55 molecule, decay accelerating factor for c | 2.42 FJX1 | four jointed box 1 (Drosophila) |
| -2.81 | UTX | ubiquitously transcribed tetratricopeptide repea | 2.42 TMEM106C | transmembrane protein 106C |
| -2.80 | ARL17P1 /// LOC64 | ADP-ribosylation factor-like 17 pseudogene 1 / | 2.42 — | — |
| -2.80 | RPP25 | ribonuclease P 25kDa subunit | 2.42 C10orf56 | chromosome 10 open reading frame 56 |
| 2.80 | — | CDNA FLJ31066 fis, clone HSYRA2001153 | 2.42 ST6GALNAC5 | ST6 (alpha-N-acetyl-neuraminyl-2,3-beta-galac |
| 2.80 | PRRT1 | proline-rich transmembrane protein 1 | -2.42 | — |
| 2.80 | ZFHX4 | zinc finger homeodomain 4 | 2.42 | — |
| -2.80 | RASGRP2 | RAS guanyl releasing protein 2 (calcium and D | 2.42 CHN2 | chimerin (chimaerin) 2 |
| 2.80 | ABCC4 | ATP-binding cassette, sub-family C (CFTR/MR | -2.41 SERPINI1 | serpin peptidase inhibitor, clade I (neuroserpin) |
| -2.80 | B3GNT1 | UDP-GlcNAc:betaGal beta-1,3-N-acetylglucosa | 2.41 | — |
| -2.80 | — | — | 2.41 BMP1 | bone morphogenetic protein 1 |
| 2.80 | — | — | 2.41 RALGDS | ral guanine nucleotide dissociation stimulator |
| 2.80 | — | CDNA clone IMAGE:4811557 | -2.41 | — |
| -2.80 | TMC4 | transmembrane channel-like 4 | -2.41 LASS4 | LAG1 homolog, ceramide synthase 4 (S. cerevi |
| 2.80 | ALDH5A1 | aldehyde dehydrogenase 5 family, member A1 | -2.41 FLJ30672 | hypothetical protein FLJ30672 |
| -2.80 | IFI16 | interferon, gamma-inducible protein 16 | 2.41 | — |
| 2.80 | SOSTDC1 | sclerostin domain containing 1 | 2.41 | — |
| 2.80 | HHIP | hedgehog interacting protein | 2.41 FLJ37644 | hypothetical gene supported by AK094963 |
| 2.79 | PAX3 | paired box gene 3 (Waardenburg syndrome 1) | 2.41 TTC3 | tetratricopeptide repeat domain 3 |
| 2.79 | SNCA | synuclein, alpha (non A4 component of amyloid | -2.41 TNFRSF8 | tumor necrosis factor receptor superfamily, mer |
| 2.79 | ANGPTL2 | angiopoietin-like 2 | 2.41 | — |
| 2.79 | ACACA | Acetyl-Coenzyme A carboxylase alpha | 2.41 TMEM112 | transmembrane protein 112 |
| 2.79 | LOC651466 | Similar to retinoic acid receptor responder (taz | -2.41 BAIAP2L1 | BAI1-associated protein 2-like 1 |
| 2.79 | MPPED2 | metallophosphoesterase domain containing 2 | -2.41 HHEX | homeobox, hematopoietically expressed |
| -2.79 | CHST2 | carbohydrate (N-acetylglucosamine-6-O) sulfot | 2.41 | — |
| -2.79 | ZNF747 | zinc finger protein 747 | 2.41 HS6ST2 | heparan sulfate 6-O-sulfotransferase 2 |
| 2.79 | AYTL1 | acyltransferase like 1 | 2.40 LOC283874 | hypothetical protein LOC283874 |
| 2.79 | ERBB4 | v-erb-a erythroblastic leukemia viral oncogene | 2.40 | — |
| 2.79 | CASKIN1 | CASK interacting protein 1 | 2.40 HS6ST2 | heparan sulfate 6-O-sulfotransferase 2 |
| 2.79 | DCHS1 | dachsous 1 (Drosophila) | 2.40 TNS1 | Tensin 1 /// Tensin 1 |
| -2.79 | LMO7 | LIM domain 7 | -2.40 FAM124B | family with sequence similarity 124B |
| 2.79 | --- | — | 2.40 LOC730069 /// LOC | similar to nuclear receptor binding factor 2 /// sin |
| 2.79 | MYLK | myosin, light polypeptide kinase | -2.40 GABARAPL1 | GABA(A) receptor-associated protein like 1 |
| -2.78 | HRLP5 | H-rev107-like protein 5 | 2.40 | — |
| -2.78 | ADCY2 | adenylate cyclase 2 (brain) | 2.40 KMO | kynurenine 3-monooxygenase (kynurenine 3-h |
| 2.78 | NCAM1 | Neural cell adhesion molecule 1 | 2.40 | — |
| 2.78 | — | — | -2.40 MMP24 | matrix metallopeptidase 24 (membrane-insertec |
| 2.78 | TFAP2A | Transcription factor AP-2 alpha (activating enh | 2.40 | CDNA clone IMAGE:3919515 /// CDNA clone II |
| 2.78 | CBX8 | chromobox homolog 8 (Pc class homolog, Dros | 2.40 | Homo sapiens, clone IMAGE:3618365, mRNA |
| -2.77 | DBC1 | deleted in bladder cancer 1 | 2.40 CRIP2 | cysteine-rich protein 2 |
| 2.77 | C9orf72 | chromosome 9 open reading frame 72 | -2.40 KRT7 | keratin 7 |
| -2.77 | PPFIBP2 | PTPRF interacting protein, binding protein 2 (li | 2.40 | — |
| -2.77 | --- | — | 2.40 | Clone TESTIS-814 mRNA sequence |
| 2.77 | SERAC1 | serine active site containing 1 | 2.40 | — |
| 2.77 | --- | — | -2.40 ICA1 | islet cell autoantigen 1, 69kDa |
| -2.77 | MSTP9 | macrophage stimulating, pseudogene 9 | 2.39 B3GALNT1 | beta-1,3-N-acetylgalactosaminyltransferase 1 ( |
| -2.77 | FLNB | filamin B, beta (actin binding protein 278) | 2.39 FLJ37562 | hypothetical protein FLJ37562 |
| 2.77 | --- | CDNA clone IMAGE:5275948 | 2.39 — | Full length insert cDNA clone YZ38E04 |
| -2.77 | --- | — | -2.39 — | — |
| 2.77 | C5orf15 | Chromosome 5 open reading frame 15 | 2.39 TIMP3 | TIMP metallopeptidase inhibitor 3 (Sorsby fund |
| -2.77 | GSTZ1 | glutathione transferase zeta 1 (maleylacetoace | 2.39 PCDHGA12 /// PCE | protocadherin gamma subfamily A, 12 /// protoc |
| -2.77 | CDC42EP1 | CDC42 effector protein (Rho GTPase binding) | 2.39 ADCY6 | adenylate cyclase 6 |
| -2.77 | KCNK1 | potassium channel, subfamily K, member 1 | -2.39 ELF3 | E74-like factor 3 (ets domain transcription facto |
| -2.77 | FGF12 | fibroblast growth factor 12 | 2.39 CD248 | CD248 molecule, endosialin |
| 2.77 | PHC2 | polyhomeotic homolog 2 (Drosophila) | -2.39 — | CDNA FLJ34677 fis, clone LIVER2002660 |
| 2.77 | DNAI1 | dynein, axonemal, intermediate chain 1 | 2.39 PGCP | plasma glutamate carboxypeptidase |
| -2.76 | KLKB1 | kallikrein B, plasma (Fletcher factor) 1 | 2.39 — | — |
| 2.76 | MCTP1 | multiple C2 domains, transmembrane 1 | 2.39 TTC30B | tetratricopeptide repeat domain 30B |
| -2.76 | TPM1 | tropomyosin 1 (alpha) | 2.39 SLC35D1 | solute carrier family 35 (UDP-glucuronic acid/U |
| -2.76 | — | — | 2.39 TTC3 | tetratricopeptide repeat domain 3 |
| -2.76 | SAV1 | salvador homolog 1 (Drosophila) | 2.38 NIN | ninein (GSK3B interacting protein) |
| 2.76 | — | CDNA FLJ10151 fis, clone HEMBA1003402 | 2.38 SUV39H2 | suppressor of variegation 3-9 homolog 2 (Dros |
| -2.75 | TMEPAI | transmembrane, prostate androgen induced RN | -2.38 — | Transcribed locus |
| -2.75 | ETS1 | v-ets erythroblastosis virus E26 oncogene hom | -2.38 PRB3 | proline-rich protein BstNI subfamily 3 |
| -2.75 | SEMA6B | sema domain, transmembrane domain (TM), a | -2.38 MYH14 | myosin, heavy polypeptide 14 |
| -2.75 | — | — | 2.38 IRX5 | iroquois homeobox protein 5 |
| -2.75 | CHES1 | checkpoint suppressor 1 | -2.38 GPR98 | G protein-coupled receptor 98 |
| 2.75 | PRR3 | proline rich 3 | 2.38 C9orf93 | Chromosome 9 open reading frame 93 |
| -2.75 | DLC1 | deleted in liver cancer 1 | -2.38 VASH2 | vasohibin 2 |
| -2.75 | GNPTAB | N-acetylglucosamine-1-phosphate transferase, | -2.38 KIAA1906 | KIAA1906 protein |

Appendix 1

| Value | Symbol | Description |
|---|---|---|
| -2.75 | PDE5A | phosphodiesterase 5A, cGMP-specific |
| -2.74 | TRIM14 | tripartite motif-containing 14 |
| -2.74 | 6-Sep | septin 6 |
| 2.74 | CD47 | CD47 molecule |
| 2.74 | LOC283400 | hypothetical protein LOC283400 |
| 2.74 | SMYD2 | SET and MYND domain containing 2 |
| -2.74 | — | — |
| 2.74 | SSPN | sarcospan (Kras oncogene-associated gene) |
| 2.74 | — | — |
| 2.74 | RPL31 /// LOC2852 | ribosomal protein L31 /// similar to ribosomal pr |
| 2.74 | TTC3 | tetratricopeptide repeat domain 3 |
| 2.74 | — | — |
| -2.74 | SH3GL3 | SH3-domain GRB2-like 3 |
| -2.74 | UTX | ubiquitously transcribed tetratricopeptide repea |
| 2.74 | DPF1 | D4, zinc and double PHD fingers family 1 |
| -2.74 | — | — |
| 2.73 | KITLG | KIT ligand |
| 2.73 | APLP1 | amyloid beta (A4) precursor-like protein 1 |
| -2.73 | TMEM92 | transmembrane protein 92 |
| 2.73 | MAP1B | microtubule-associated protein 1B |
| -2.73 | SLC43A3 | solute carrier family 43, member 3 |
| 2.73 | ABCC9 | ATP-binding cassette, sub-family C (CFTR/MR |
| 2.73 | — | . |
| 2.73 | ZNF529 | Zinc finger protein 529 |
| -2.73 | ZADH1 | zinc binding alcohol dehydrogenase, domain c |
| -2.73 | KYNU | kynureninase (L-kynurenine hydrolase) |
| -2.73 | KLK8 | kallikrein-related peptidase 8 |
| -2.72 | ZNF452 | zinc finger protein 452 |
| 2.72 | MAPK1 | Mitogen-activated protein kinase 1 |
| 2.72 | STMN4 | stathmin-like 4 /// stathmin-like 4 |
| 2.72 | TMEM178 | transmembrane protein 178 |
| 2.72 | PAK3 | p21 (CDKN1A)-activated kinase 3 |
| 2.72 | MAPRE3 | microtubule-associated protein, RP/EB family, |
| -2.72 | TMEM63A | transmembrane protein 63A |
| 2.72 | NAV3 | neuron navigator 3 |
| -2.72 | SERPINI1 | serpin peptidase inhibitor, clade I (neuroserpin) |
| -2.72 | — | CDNA FLJ33993 fis, clone DFNES2007757 |
| -2.72 | IFI44 | Interferon-induced protein 44 /// Homo sapiens |
| -2.72 | LOC152195 | hypothetical protein LOC152195 |
| -2.72 | RUNX3 | runt-related transcription factor 3 |
| 2.72 | HOXA4 | homeobox A4 |
| -2.72 | POSTN | periostin, osteoblast specific factor |
| 2.72 | — | — |
| -2.71 | — | — |
| 2.71 | CENTD1 | centaurin, delta 1 |
| 2.71 | FAM55C | family with sequence similarity 55, member C |
| -2.71 | RPS24 | Ribosomal protein S24 |
| 2.71 | C6orf174 | chromosome 6 open reading frame 174 |
| -2.71 | SLCO1B1 | solute carrier organic anion transporter family, |
| 2.71 | MAN2A1 | mannosidase, alpha, class 2A, member 1 |
| 2.71 | NRIP1 | nuclear receptor interacting protein 1 |
| -2.71 | ANXA1 | annexin A1 |
| -2.71 | — | — |
| 2.71 | TTC3 | tetratricopeptide repeat domain 3 |
| -2.70 | MNS1 | meiosis-specific nuclear structural 1 |
| 2.70 | FLJ25477 | Hypothetical protein FLJ25477 |
| 2.70 | — | — |
| -2.70 | C10orf95 | Chromosome 10 open reading frame 95 |
| 2.70 | DKFZp313A2432 | hypothetical protein DKFZp313A2432 |
| 2.70 | POU3F4 | POU domain, class 3, transcription factor 4 |
| 2.70 | PHC2 | polyhomeotic homolog 2 (Drosophila) |
| 2.69 | KIAA0523 | KIAA0523 protein |
| -2.69 | TBC1D8 | TBC1 domain family, member 8 (with GRAM d |
| -2.69 | RBPMS | RNA binding protein with multiple splicing |
| 2.69 | AK1 | adenylate kinase 1 |
| 2.69 | — | — |
| -2.69 | PRICKLE1 | prickle homolog 1 (Drosophila) |
| -2.69 | SLC43A3 | solute carrier family 43, member 3 |
| 2.69 | DPYSL4 | dihydropyrimidinase-like 4 |
| -2.69 | — | — |
| 2.69 | DKFZp313A2432 | hypothetical protein DKFZp313A2432 |
| -2.69 | — | Transcribed locus, moderately similar to XP_0 |
| 2.69 | — | CDNA FLJ30383 fis, clone BRACE2008102 |
| -2.68 | GPR | putative G protein coupled receptor |
| -2.68 | CREB3L4 | cAMP responsive element binding protein 3-lik |
| 2.68 | — | CDNA FLJ31660 fis, clone NT2RI2004410 |
| -2.68 | SYT6 | Synaptotagmin VI |
| 2.68 | OSBPL10 | oxysterol binding protein-like 1C |
| -2.68 | ZSCAN2 | zinc finger and SCAN domain containing 2 |
| 2.38 | KIAA1702 | KIAA1702 protein |
| -2.37 | — | — |
| -2.37 | LOC92558 | hypothetical protein LOC92558 |
| 2.37 | ZNF345 | zinc finger protein 345 |
| 2.37 | — | — |
| 2.37 | ZIC1 | Zic family member 1 (odd-paired homolog, Dro |
| 2.37 | CD99L2 | CD99 molecule-like 2 |
| -2.37 | IPW | imprinted in Prader-Willi syndrome |
| -2.37 | — | — |
| -2.37 | RBPMS | RNA binding protein with multiple splicing |
| -2.37 | SLC7A5 | solute carrier family 7 (cationic amino acid tran |
| -2.37 | TJP3 | tight junction protein 3 (zona occludens 3) |
| 2.37 | SCML1 | Sex comb on midleg-like 1 (Drosophila) |
| -2.37 | VIL2 | villin 2 (ezrin) |
| -2.37 | ITM2A | integral membrane protein 2A |
| -2.37 | TEAD4 | TEA domain family member 4 |
| 2.37 | MGC39900 | hypothetical protein MGC39900 |
| -2.36 | STYK1 | serine/threonine/tyrosine kinase 1 |
| 2.36 | TRIO | Triple functional domain (PTPRF interacting) |
| 2.36 | — | CDNA FLJ33772 fis, clone BRSSN2000175 |
| 2.36 | — | CDNA FLJ25106 fis, clone CBR01467 |
| -2.36 | — | Transcribed locus |
| -2.36 | FOXO1A | forkhead box O1A (rhabdomyosarcoma) |
| -2.36 | — | — |
| 2.36 | VPS24 | vacuolar protein sorting 24 (yeast) |
| 2.36 | FABP7 | fatty acid binding protein 7, brain |
| -2.35 | UST | uronyl-2-sulfotransferase |
| 2.35 | PTPRC | protein tyrosine phosphatase, receptor type, C |
| 2.35 | PLEKHO1 | pleckstrin homology domain containing, family |
| -2.35 | GCHFR | GTP cyclohydrolase I feedback regulator |
| -2.35 | LDB2 | LIM domain binding 2 |
| 2.35 | — | — |
| 2.35 | ANKRD25 | ankyrin repeat domain 25 |
| 2.35 | — | — |
| 2.35 | FBN2 | fibrillin 2 (congenital contractural arachnodactyl |
| -2.35 | CCDC69 | coiled-coil domain containing 69 |
| 2.35 | ZNF70 | Zinc finger protein 70 |
| 2.35 | MIA | melanoma inhibitory activity |
| 2.35 | — | — |
| 2.35 | FABP3 | fatty acid binding protein 3, muscle and heart (r |
| 2.35 | HHIP | hedgehog interacting protein |
| 2.35 | BBS5 | Bardet-Biedl syndrome 5 |
| 2.35 | MXRA5 | matrix-remodelling associated 5 |
| -2.34 | RAB11FIP4 | RAB11 family interacting protein 4 (class II) /// |
| -2.34 | — | — |
| -2.34 | UTX | ubiquitously transcribed tetratricopeptide repea |
| -2.34 | TESK2 | testis-specific kinase 2 |
| -2.34 | WDR44 | WD repeat domain 44 |
| 2.34 | LOC150759 | hypothetical protein LOC150759 |
| 2.34 | EMP2 | epithelial membrane protein 2 |
| 2.34 | — | Transcribed locus, weakly similar to NP_00101 |
| -2.33 | HMHA1 | histocompatibility (minor) HA-1 |
| -2.33 | CYP2E1 | cytochrome P450, family 2, subfamily E, polyp |
| -2.33 | SMPDL3B | sphingomyelin phosphodiesterase, acid-like 3B |
| 2.33 | LCP2 | lymphocyte cytosolic protein 2 (SH2 domain co |
| 2.33 | RBBP9 | retinoblastoma binding protein 9 |
| 2.33 | C14orf126 | chromosome 14 open reading frame 126 |
| 2.33 | POLH | polymerase (DNA directed), eta |
| 2.33 | FRMD3 | FERM domain containing 3 |
| 2.33 | SMYD3 | SET and MYND domain containing 3 |
| 2.33 | DKFZP564D166 | putative ankyrin-repeat containing protein |
| 2.33 | — | — |
| 2.33 | OAS2 | 2'-5'-oligoadenylate synthetase 2, 69/71kDa |
| 2.32 | LOC645722 | hypothetical LOC645722 |
| 2.32 | | 11-Sep Septin 11 |
| -2.32 | GABARAPL1 /// GA | GABA(A) receptor-associated protein like 1 /// |
| -2.32 | AP1S3 | adaptor-related protein complex 1, sigma 3 sub |
| 2.32 | SNAP25 | Synaptosomal-associated protein, 25kDa |
| 2.32 | — | — |
| 2.32 | CST3 | cystatin C (amyloid angiopathy and cerebral he |
| 2.32 | FZD2 | frizzled homolog 2 (Drosophila) |
| 2.32 | — | CDNA FLJ25488 fis, clone CBR00232 |
| 2.32 | — | MRNA; cDNA DKFZp586F2224 (from clone DK |
| 2.32 | CHST3 | carbohydrate (chondroitin 6) sulfotransferase 3 |
| -2.32 | KIAA1107 | KIAA1107 |
| 2.32 | CORO1A | coronin, actin binding protein, 1A |
| 2.32 | FAS | Fas (TNF receptor superfamily, member 6) |
| -2.32 | — | — |
| -2.32 | VIL2 | villin 2 (ezrin) |

Appendix 1

| Value | Gene | Description |
|---|---|---|
| -2.68 | TPD52 | tumor protein D52 |
| 2.68 | MAP2K5 | Mitogen-activated protein kinase kinase 5 |
| 2.68 | KIAA0101 | KIAA0101 /// KIAA0101 |
| -2.68 | COL1A2 | Collagen, type I, alpha 2 |
| -2.68 | PTRF | polymerase I and transcript release factor |
| -2.68 | — | — |
| -2.68 | — | Transcribed locus |
| 2.68 | KCNJ8 | potassium inwardly-rectifying channel, subfami |
| -2.67 | ZBTB3 | zinc finger and BTB domain containing 3 |
| -2.67 | ADAMTSL1 | ADAMTS-like 1 |
| -2.67 | GPSM3 | G-protein signalling modulator 3 (AGS3-like, C. |
| 2.67 | — | — |
| -2.67 | SEMA6A | Sema domain, transmembrane domain (TM), a |
| 2.67 | C14orf162 | chromosome 14 open reading frame 162 |
| -2.67 | RGL3 | ral guanine nucleotide dissociation stimulator-li |
| 2.67 | — | Transcribed locus |
| 2.67 | — | — |
| 2.67 | PNMA2 | paraneoplastic antigen MA2 |
| 2.67 | RHOBTB3 | Rho-related BTB domain containing 3 |
| 2.67 | — | CDNA clone IMAGE:5263177 |
| -2.67 | LOC286044 | hypothetical protein LOC286044 |
| 2.67 | DOK6 | docking protein 6 |
| 2.67 | SYDE2 | synapse defective 1, Rho GTPase, homolog 2 |
| 2.67 | PHTF1 | Putative homeodomain transcription factor 1 |
| 2.67 | — | — |
| -2.66 | — | — |
| 2.66 | B3GNT5 | UDP-GlcNAc:betaGal beta-1,3-N-acetylglucosa |
| -2.66 | — | — |
| 2.66 | PLEKHB1 | pleckstrin homology domain containing, family |
| -2.66 | MATN1 | Matrilin 1, cartilage matrix protein |
| 2.66 | — | Similar to leucine rich repeat containing 10 |
| 2.66 | — | — |
| -2.66 | — | — |
| 2.66 | GP1BB /// SEPT5 | glycoprotein Ib (platelet), beta polypeptide /// se |
| -2.66 | MYO5C | myosin VC |
| 2.66 | PCDH19 | protocadherin 19 |
| 2.66 | BAALC | brain and acute leukemia, cytoplasmic |
| 2.66 | ASE-1 | CD3E antigen, epsilon polypeptide associated |
| -2.66 | CPT1A | carnitine palmitoyltransferase 1A (liver) |
| -2.65 | PLSCR1 | phospholipid scramblase 1 |
| -2.65 | SOX17 | SRY (sex determining region Y)-box 17 |
| 2.65 | — | Homo sapiens, clone IMAGE:4940467, mRNA |
| 2.65 | TFDP2 | Transcription factor Dp-2 (E2F dimerization pa |
| -2.65 | LOC401312 | LOC401318 |
| 2.65 | COPB2 | Coatomer protein complex, subunit beta 2 (bet |
| -2.65 | SPP1 | secreted phosphoprotein 1 (osteopontin, bone |
| 2.65 | LOC283012 | hypothetical protein LOC283012 |
| 2.65 | AP3M1 | adaptor-related protein complex 3, mu 1 subun |
| -2.65 | SKIL | SKI-like oncogene |
| -2.65 | HMCN1 | hemicentin 1 |
| -2.65 | CGNL1 | Cingulin-like 1 |
| 2.65 | TP53AP1 | TP53 activated protein 1 |
| 2.65 | HHAT | hedgehog acyltransferase |
| -2.65 | TPM1 | tropomyosin 1 (alpha) |
| 2.64 | TMEM2 | transmembrane protein 2 |
| 2.64 | BCL2 | B-cell CLL/lymphoma 2 |
| 2.64 | PCDHB10 | protocadherin beta 10 |
| -2.64 | H1F0 | H1 histone family, member 0 |
| -2.64 | — | — |
| -2.64 | — | — |
| 2.64 | HOXB5 | homeobox B5 |
| -2.64 | RBP1 | retinol binding protein 1, cellular |
| -2.64 | TTMB | cDNA DKFZp434C184 gene |
| 2.64 | PARP11 | poly (ADP-ribose) polymerase family, member |
| -2.64 | — | — |
| -2.64 | TJP2 | tight junction protein 2 (zona occludens 2) |
| 2.63 | PRO1073 | PRO1073 protein |
| 2.63 | CTGF | connective tissue growth factor |
| 2.63 | LOC400954 | similar to echinoderm microtubule associated p |
| -2.63 | FURIN | furin (paired basic amino acid cleaving enzyme |
| 2.63 | — | — |
| -2.63 | — | Full-length cDNA clone CL0BB018ZE07 of Neu |
| 2.63 | CXXC4 | CXXC finger 4 |
| 2.63 | PHF20L1 | PHD finger protein 20-like 1 |
| 2.63 | SOAT1 | sterol O-acyltransferase (acyl-Coenzyme A: ch |
| -2.63 | PIPOX | pipecolic acid oxidase |
| 2.63 | NEFL | neurofilament, light polypeptide 68kDa |
| -2.62 | CPS1 | carbamoyl-phosphate synthetase 1, mitochond |
| 2.62 | SCRN3 | secernin 3 |
| -2.32 | DNAJB6 /// LOC387 | DnaJ (Hsp40) homolog, subfamily B, member 6 |
| 2.32 | — | — |
| 2.31 | RHOBTB1 | Rho-related BTB domain containing 1 |
| 2.31 | — | — |
| 2.31 | IGSF4 | Immunoglobulin superfamily, member 4 |
| -2.31 | C1orf61 | chromosome 1 open reading frame 61 |
| 2.31 | ERCC5 | Excision repair cross-complementing rodent rep |
| -2.31 | — | — |
| 2.31 | DLC1 | deleted in liver cancer 1 |
| 2.31 | DUSP6 | dual specificity phosphatase 6 |
| -2.31 | G0S2 | G0/G1switch 2 |
| 2.31 | — | — |
| 2.31 | LRRN3 | leucine rich repeat neuronal 3 |
| -2.31 | MCAM | melanoma cell adhesion molecule |
| 2.31 | PDE4D | phosphodiesterase 4D, cAMP-specific (phosph |
| -2.31 | FLJ36748 | hypothetical protein FLJ36748 |
| -2.31 | — | — |
| -2.31 | — | — |
| 2.31 | SMEK2 | SMEK homolog 2, suppressor of mek1 (Dictyos |
| 2.31 | — | — |
| 2.31 | NCOA5 | nuclear receptor coactivator 5 |
| -2.31 | ZNF483 | Zinc finger protein 483 |
| -2.30 | UGP2 | UDP-glucose pyrophosphorylase 2 |
| 2.30 | — | — |
| 2.30 | SOX11 | SRY (sex determining region Y)-box 11 |
| -2.30 | — | — |
| 2.30 | PHC2 | Polyhomeotic homolog 2 (Drosophila) |
| 2.30 | TFDP2 | Transcription factor Dp-2 (E2F dimerization par |
| 2.30 | — | — |
| 2.30 | NCOA6 | nuclear receptor coactivator 6 |
| -2.30 | CCL3 /// CCL3L1 | chemokine (C-C motif) ligand 3 /// chemokine (C |
| -2.30 | SDHALP2 | succinate dehydrogenase complex, subunit A, 1 |
| 2.30 | IGSF4 | immunoglobulin superfamily, member 4 |
| -2.30 | DUSP6 | dual specificity phosphatase 6 |
| -2.30 | FKBP4 | FK506 binding protein 4, 59kDa |
| 2.30 | FAM43A | family with sequence similarity 43, member A |
| 2.30 | — | — |
| 2.30 | CHST3 | carbohydrate (chondroitin 6) sulfotransferase 3 |
| 2.30 | MGC17403 | hypothetical protein MGC17403 |
| 2.30 | — | CDNA FLJ36544 fis, clone TRACH2006378 |
| 2.30 | TRGC2 /// TRGV9 | T cell receptor gamma constant 2 /// T cell rece |
| 2.30 | TCF12 | Transcription factor 12 (HTF4, helix-loop-helix t |
| -2.29 | STMN2 | stathmin-like 2 |
| -2.29 | TMEM63A | transmembrane protein 63A |
| -2.29 | ARNTL2 | aryl hydrocarbon receptor nuclear translocator- |
| 2.29 | C10orf56 | chromosome 10 open reading frame 56 |
| 2.29 | PUNC | Putative neuronal cell adhesion molecule |
| 2.29 | DATF1 | death associated transcription factor 1 |
| 2.29 | C7orf44 | chromosome 7 open reading frame 44 |
| -2.29 | — | CDNA FLJ11918 fis, clone HEMBB1000272 |
| -2.29 | GRPR | gastrin-releasing peptide receptor |
| -2.29 | SLC2A3 | Solute carrier family 2 (facilitated glucose trans |
| -2.29 | FAM62B | family with sequence similarity 62 (C2 domain c |
| -2.29 | PTHR2 | parathyroid hormone receptor 2 |
| 2.29 | NRG2 | neuregulin 2 |
| 2.29 | FCAR | Fc fragment of IgA, receptor for |
| 2.29 | LOXL1 | lysyl oxidase-like 1 |
| 2.28 | ST5 | suppression of tumorigenicity 5 |
| 2.28 | — | — |
| 2.28 | LPIN2 | lipin 2 |
| -2.28 | MGC20983 | hypothetical protein MGC20983 |
| -2.28 | STEAP2 | six transmembrane epithelial antigen of the pro |
| -2.28 | GPR176 | G protein-coupled receptor 176 |
| -2.28 | — | — |
| 2.28 | — | — |
| 2.28 | EDNRA | Endothelin receptor type A |
| 2.28 | EDG2 | endothelial differentiation, lysophosphatidic acid |
| -2.28 | SLC2A3 | solute carrier family 2 (facilitated glucose trans |
| 2.28 | — | — |
| -2.28 | KIAA1543 | KIAA1543 |
| 2.28 | KIF26B | kinesin family member 26B |
| 2.28 | — | — |
| 2.28 | ANKRD6 | ankyrin repeat domain 6 |
| -2.28 | — | Transcribed locus, moderately similar to XP_51 |
| 2.28 | GAS2 | growth arrest-specific 2 |
| 2.28 | ARID5B | AT rich interactive domain 5B (MRF1-like) |
| 2.28 | ABCB1 | ATP-binding cassette, sub-family B (MDR/TAP) |
| -2.28 | ADD2 | Adducin 2 (beta) |
| 2.28 | — | — |

Appendix 1

| | | | |
|---|---|---|---|
| 2.62 — | — | 2.27 TRAM1L1 | translocation associated membrane protein 1-li |
| 2.62 — | — | -2.27 — | — |
| 2.62 OXR1 | oxidation resistance 1 | 2.27 FLJ37562 | hypothetical protein FLJ37562 |
| -2.62 CCL5 | chemokine (C-C motif) ligand 5 | 2.27 MSRB3 | Methionine sulfoxide reductase B3 |
| -2.62 EDN1 | endothelin 1 | 2.27 CSPG5 | chondroitin sulfate proteoglycan 5 (neuroglycar |
| 2.62 FBXL16 | F-box and leucine-rich repeat protein 16 | -2.27 UTX | ubiquitously transcribed tetratricopeptide repea |
| -2.62 DDT | D-dopachrome tautomerase | 2.27 SDC1 | syndecan 1 |
| -2.62 ARRB1 | arrestin, beta 1 | 2.27 LOC162073 | hypothetical protein LOC162073 |
| 2.62 C11orf70 | chromosome 11 open reading frame 70 | 2.27 TRGC2 /// TRGV9 /. | T cell receptor gamma constant 2 /// T cell rece |
| 2.62 FLJ42709 | Hypothetical gene supported by AK124699 | 2.27 — | Transcribed locus, weakly similar to NP_00101 |
| 2.62 — | — | 2.27 ZC3H12C | zinc finger CCCH-type containing 12C |
| 2.62 FJX1 | four jointed box 1 (Drosophila) | 2.27 BCL2 | B-cell CLL/lymphoma 2 |
| 2.62 C14orf152 | chromosome 14 open reading frame 152 | 2.27 TTC28 | tetratricopeptide repeat domain 28 |
| -2.62 PRKCQ | protein kinase C, theta | -2.27 — | — |
| -2.62 WIPI1 | WD repeat domain, phosphoinositide interactin | 2.27 RGS5 | regulator of G-protein signalling 5 |
| -2.62 BARX1 | BarH-like homeobox 1 | -2.27 ABCA1 | ATP-binding cassette, sub-family A (ABC1), me |
| 2.62 MAPK10 | mitogen-activated protein kinase 10 | 2.27 RRAGB | Ras-related GTP binding B |
| -2.61 PLEKHC1 | pleckstrin homology domain containing, family | -2.27 TFAP2C | transcription factor AP-2 gamma (activating enl |
| -2.61 — | — | 2.27 NRCAM | neuronal cell adhesion molecule |
| 2.61 PDCD8 | Programmed cell death 8 (apoptosis-inducing f | -2.26 AP1S3 | adaptor-related protein complex 1, sigma 3 sub |
| -2.61 HCK | hemopoietic cell kinase | -2.26 LOC196996 | Hypothetical protein LOC196996 |
| -2.61 SAT1 | spermidine/spermine N1-acetyltransferase 1 | 2.25 ZNF533 | zinc finger protein 533 |
| -2.61 KLF8 | Kruppel-like factor 8 | 2.26 VPS24 | vacuolar protein sorting 24 homolog (S. cerevis |
| 2.61 UGCGL2 | UDP-glucose ceramide glucosyltransferase-lik | 2.26 SEMA3C | sema domain, immunoglobulin domain (Ig), sho |
| -2.61 LLGL2 | lethal giant larvae homolog 2 (Drosophila) | 2.26 — | Transcribed locus |
| 2.61 RSNL2 | restin-like 2 | 2.26 FLJ39198 | Hypothetical protein LOC643763 |
| -2.61 — | Transcribed locus | -2.26 L1TD1 | LINE-1 type transposase domain containing 1 |
| -2.61 — | — | -2.26 FAM124A | family with sequence similarity 124A |
| -2.61 IGFBP4 | insulin-like growth factor binding protein 4 | -2.26 ATF3 | activating transcription factor 3 |
| 2.61 FLJ90757 | hypothetical protein LOC440465 | 2.26 LOC347475 | hypothetical gene supported by BC017958 |
| -2.61 — | — | 2.26 ARSB | arylsulfatase B |
| -2.60 HLA-G | HLA-G histocompatibility antigen, class I, G | -2.26 — | — |
| 2.60 — | — | 2.26 — | — |
| -2.60 HRASLS3 | HRAS-like suppressor 3 | -2.26 ABCC13 | ATP-binding cassette, sub-family C (CFTR/MRI |
| -2.60 IGSF1 | immunoglobulin superfamily, member 1 | 2.26 PCDH18 | protocadherin 18 |
| 2.60 C20orf58 | chromosome 20 open reading frame 58 | -2.26 COL5A3 | collagen, type V, alpha 3 |
| 2.60 PAK7 | p21(CDKN1A)-activated kinase 7 | 2.26 SHC4 | SHC (Src homology 2 domain containing) famil |
| 2.60 — | — | 2.26 DNAJC1 | DnaJ (Hsp40) homolog, subfamily C, member ' |
| -2.60 ASPHD1 | aspartate beta-hydroxylase domain containing | 2.25 — | — |
| 2.60 — | cDNA clone IMAGE:5288757 | 2.25 ASXL1 | additional sex combs like 1 (Drosophila) |
| 2.60 AKR1C2 | aldo-keto reductase family 1, member C2 (dihy | 2.25 RGS3 | regulator of G-protein signalling 3 |
| 2.60 GNG11 | guanine nucleotide binding protein (G protein), | -2.25 RPRM | reprimo, TP53 dependent G2 arrest mediator c |
| -2.60 LOC728473 | hypothetical protein LOC728473 | -2.25 — | — |
| -2.60 LOC692247 | hypothetical locus LOC692247 | 2.25 PON2 | Paraoxonase 2 |
| -2.59 C1orf38 | chromosome 1 open reading frame 38 | -2.25 GPR64 | G protein-coupled receptor 64 |
| 2.59 FAS | Fas (TNF receptor superfamily, member 6) | 2.25 — | — |
| -2.59 DUSP10 | dual specificity phosphatase 10 | 2.25 — | — |
| 2.59 | 3-Sep septin 3 | 2.25 KLHDC8B | kelch domain containing 8B |
| 2.59 TTC3 | tetratricopeptide repeat domain 3 | 2.25 ARHGAP5 | Rho GTPase activating protein 5 |
| -2.59 RHBDF2 | rhomboid 5 homolog 2 (Drosophila) | -2.25 AARS | alanyl-tRNA synthetase |
| 2.59 NMNAT2 | nicotinamide nucleotide adenylyltransferase 2 | -2.25 JAK3 | Janus kinase 3 (a protein tyrosine kinase, leuko |
| -2.59 KIAA0513 | KIAA0513 | 2.25 SH3-domain GRB2- | SH3-domain GRB2-like pseudogene 3 |
| -2.59 CTH | cystathionase (cystathionine gamma-lyase) | 2.25 — | Transcribed locus |
| -2.59 SILV | silver homolog (mouse) | 2.24 SARM1 | sterile alpha and TIR motif containing 1 |
| 2.59 — | Transcribed locus | 2.24 PHF10 | PHD finger protein 10 |
| 2.59 FAT3 | FAT tumor suppressor homolog 3 (Drosophila) | 2.24 FLJ41603 | FLJ41603 protein |
| -2.59 LOC201895 | hypothetical protein LOC201895 | 2.24 NAP1L5 | nucleosome assembly protein 1-like 5 |
| -2.59 SLC16A3 | solute carrier family 16, member 3 (monocarbo | 2.24 SCHIP1 | schwannomin interacting protein 1 |
| 2.58 ANKRD20A1 /// C2 | ankyrin repeat domain 20 family, member A1 / | 2.24 TIMP2 | TIMP metallopeptidase inhibitor 2 |
| 2.58 SLC6A16 | Solute carrier family 6, member 16 | -2.24 — | — |
| 2.58 — | — | 2.24 — | — |
| -2.58 DNMT3B | DNA (cytosine-5-)-methyltransferase 3 beta | -2.24 — | — |
| -2.58 — | — | -2.24 MT1X | metallothionein 1X |
| 2.58 PAK3 | P21 (CDKN1A)-activated kinase 3 | 2.24 — | — |
| -2.58 GADD45B | growth arrest and DNA-damage-inducible, beta | -2.24 RMST | rhabdomyosarcoma 2 associated transcript (no |
| -2.58 C8orf42 | chromosome 8 open reading frame 42 | -2.24 MUC3A | mucin 3A, cell surface associated |
| -2.58 IQGAP2 | IQ motif containing GTPase activating protein 2 | -2.24 JARID2 | jumonji, AT rich interactive domain 2 |
| 2.58 RPS23 | ribosomal protein S23 | -2.24 LOC692247 | hypothetical locus LOC692247 |
| -2.58 — | — | -2.24 CNGA1 | cyclic nucleotide gated channel alpha 1 |
| 2.58 — | Transcribed locus | -2.23 SEZ6L2 | seizure related 6 homolog (mouse)-like 2 |
| 2.58 ZNF771 | zinc finger protein 771 | 2.23 — | MRNA; cDNA DKFZp667B0924 (from clone DK |
| 2.58 — | — | 2.23 — | — |
| 2.57 ASIP | Agouti signaling protein, nonagouti homolog (m | 2.23 CD47 | CD47 molecule |
| -2.57 KYNU | kynureninase (L-kynurenine hydrolase) | 2.23 — | Full length insert cDNA clone ZD83H10 |
| 2.57 — | — | 2.23 HOXB5 | homeobox B5 |
| -2.57 — | — | 2.23 — | CDNA: FLJ22256 fis, clone HRC02860 |
| -2.57 — | — | -2.23 EGF | epidermal growth factor (beta-urogastrone) |
| 2.57 TMEM5 | transmembrane protein 5 | -2.23 — | — |
| 2.57 HS6ST2 | heparan sulfate 6-O-sulfotransferase 2 | 2.23 SOCS6 | suppressor of cytokine signaling 6 |

Appendix 1

| | | | | |
|---|---|---|---|---|
| -2.57 | NF2 | neurofibromin 2 (bilateral acoustic neuroma) | -2.23 TMEM112 | transmembrane protein 112 |
| -2.57 | FLJ35934 | FLJ35934 protein | -2.23 PHC1 | polyhomeotic homolog 1 (Drosophila) |
| 2.57 | WDR52 | WD repeat domain 52 | -2.23 — | — |
| 2.57 | PREX1 | phosphatidylinositol 3,4,5-trisphosphate-depen | 2.23 RAB36 | RAB36, member RAS oncogene family |
| 2.57 | MGC45564 | GTPase activating Rap/RanGAP domain-like 1 | 2.23 EPHB2 | EPH receptor B2 |
| -2.57 | TRIM37 | tripartite motif-containing 37 | -2.22 PDCD2L | programmed cell death 2-like /// programmed c |
| -2.57 | MYD88 | myeloid differentiation primary response gene | 2.22 — | Transcribed locus, weakly similar to XP_49845: |
| 2.57 | KIAA1462 | KIAA1462 | 2.22 FOXP2 | forkhead box P2 |
| 2.56 | — | — | 2.22 CX3CL1 | chemokine (C-X3-C motif) ligand 1 |
| 2.56 | SLC6A8 | solute carrier family 6 (neurotransmitter transp | -2.22 AIM1 | absent in melanoma 1 |
| -2.56 | TKT | transketolase (Wernicke-Korsakoff syndrome) | -2.22 FKBP1B | FK506 binding protein 1B, 12.6 kDa |
| 2.56 | DST | Dystonin | -2.22 RTP1 | receptor (chemosensory) transporter protein 1 |
| -2.56 | SDC4 | syndecan 4 (amphiglycan, ryudocan) | 2.22 PREX1 | phosphatidylinositol 3,4,5-trisphosphate-depen |
| -2.56 | ZNF671 | zinc finger protein 671 | -2.22 EPB41L4B | erythrocyte membrane protein band 4.1 like 4B |
| -2.56 | TES | testis derived transcript (3 LIM domains) | 2.22 — | Transcribed locus |
| -2.56 | EDNRB | endothelin receptor type B | 2.22 — | MRNA; cDNA DKFZp761L1121 (from clone DK |
| 2.56 | STAMBPL1 | STAM binding protein-like 1 | 2.22 FLJ25476 | FLJ25476 protein |
| -2.56 | BOK | BCL2-related ovarian killer | 2.22 SEPT6 /// N-PAC | septin 6 /// cytokine-like nuclear factor n-pac |
| -2.56 | ZIC3 | Zic family member 3 heterotaxy 1 (odd-paired | -2.22 CXCL1 | chemokine (C-X-C motif) ligand 1 (melanoma g |
| -2.56 | DHRS2 | dehydrogenase/reductase (SDR family) memb | -2.22 RANBP1 | RAN binding protein 1 |
| 2.56 | PLSCR1 | phospholipid scramblase 1 | 2.22 ARHGAP15 | Rho GTPase activating protein 15 |
| -2.56 | PDE5A | phosphodiesterase 5A, cGMP-specific | 2.22 NUB1 | Negative regulator of ubiquitin-like proteins 1 |
| 2.56 | FLJ90757 | hypothetical protein LOC440465 | 2.21 RNF175 | ring finger protein 175 |
| 2.56 | EYA1 | eyes absent homolog 1 (Drosophila) | 2.21 EMILIN3 | elastin microfibril interfacer 3 |
| 2.56 | RAB9B | RAB9B, member RAS oncogene family | 2.21 TMEM178 | transmembrane protein 178 |
| 2.56 | — | — | -2.21 PCNXL2 | pecanex-like 2 (Drosophila) |
| 2.55 | — | — | -2.21 ZNF57 | zinc finger protein 57 |
| 2.55 | — | Homo sapiens, clone IMAGE:4214654, mRNA | -2.21 ITM2A | integral membrane protein 2A |
| -2.55 | CHURC1 | churchill domain containing 1 | 2.21 — | Transcribed locus |
| 2.55 | IFNAR1 | interferon (alpha, beta and omega) receptor 1 | -2.21 — | — |
| 2.55 | — | — | 2.21 IGFBP5 | insulin-like growth factor binding protein 5 |
| 2.55 | DHRS9 | dehydrogenase/reductase (SDR family) memb | 2.21 C12orf46 | chromosome 12 open reading frame 46 |
| 2.55 | — | CDNA clone IMAGE:3919515 /// CDNA clone I | 2.21 FLJ10357 | hypothetical protein FLJ10357 |
| 2.55 | — | — | -2.21 RP11-298P3.3 | CG016 |
| 2.55 | TOX | thymus high mobility group box protein TOX | 2.21 — | MRNA; cDNA DKFZp686D0673 (from clone DI |
| 2.55 | DPP4 | dipeptidyl-peptidase 4 (CD26, adenosine deam | 2.21 MGC16703 | alpha tubulin-like |
| -2.55 | CD55 | CD55 molecule, decay accelerating factor for c | 2.21 COL1A2 | collagen, type I, alpha 2 |
| -2.55 | — | — | 2.21 KIAA1644 | KIAA1644 protein |
| -2.55 | TGFBR2 | transforming growth factor, beta receptor II (70 | 2.21 SRR | serine racemase |
| 2.55 | — | Transcribed locus | 2.20 — | — |
| 2.54 | ZNF436 | zinc finger protein 436 | 2.20 CD47 | CD47 molecule |
| 2.54 | — | — | 2.20 — | CDNA clone IMAGE:4842353 |
| -2.54 | CTSL2 | Cathepsin L2 | 2.20 PARVA | parvin, alpha |
| 2.54 | IGFBPL1 | Insulin-like growth factor binding protein-like 1 | -2.20 LOC643194 | Hypothetical LOC643194 |
| 2.54 | EXOSC6 | Exosome component 6 | 2.20 MARCKS | myristoylated alanine-rich protein kinase C sub |
| -2.54 | GABRA5 /// LOC72 | gamma-aminobutyric acid (GABA) A receptor, | -2.20 COL9A3 | collagen, type IX, alpha 3 |
| -2.54 | — | — | -2.20 — | CDNA clone IMAGE:4733238 |
| -2.54 | — | — | -2.20 — | — |
| 2.54 | TAS2R10 | taste receptor, type 2, member 10 | 2.20 LST1 | leukocyte specific transcript 1 |
| 2.54 | PCBP4 | poly(rC) binding protein 4 | 2.20 PDE4D | phosphodiesterase 4D, cAMP-specific (phosph |
| -2.54 | ST6GAL1 | ST6 beta-galactosamide alpha-2,6-sialyltranfer | -2.20 GPC4 | glypican 4 |
| -2.53 | CNN1 | calponin 1, basic, smooth muscle | -2.20 RRAS2 | related RAS viral (r-ras) oncogene homolog 2 |
| 2.53 | — | — | -2.20 USP53 | Ubiquitin specific peptidase 53 |
| 2.53 | PON2 | paraoxonase 2 | 2.20 KIAA0101 | KIAA0101 |
| -2.53 | ACVR1C | activin A receptor, type IC | -2.20 OCLN /// NAIP | occludin /// similar to Occludin |
| 2.53 | FBXW8 | F-box and WD-40 domain protein 8 | -2.20 IL1B | interleukin 1, beta |
| 2.53 | RUFY3 | RUN and FYVE domain containing 3 | 2.20 KIFC3 | Kinesin family member C3 |
| 2.53 | — | — | 2.20 — | Transcribed locus, strongly similar to XP_5240: |
| -2.53 | TNFRSF12A | tumor necrosis factor receptor superfamily, me | 2.20 — | — |
| 2.53 | PAPPA | pregnancy-associated plasma protein A, pappa | -2.19 — | — |
| 2.53 | DLL3 | delta-like 3 (Drosophila) | 2.19 FCHSD2 | FCH and double SH3 domains 2 |
| 2.53 | — | MRNA; cDNA DKFZp686D0673 (from clone DI | -2.19 SEMA6B | sema domain, transmembrane domain (TM), a |
| 2.53 | TTMA | two transmembrane domain family member A | -2.19 EFHC2 | EF-hand domain (C-terminal) containing 2 |
| 2.53 | — | — | -2.19 CXCL12 | chemokine (C-X-C motif) ligand 12 (stromal cel |
| 2.53 | — | — | -2.19 EBF2 | early B-cell factor 2 |
| -2.52 | LOC644242 | Hypothetical protein LOC644242 | -2.19 CUL4A | Cullin 4A |
| 2.52 | ID4 | inhibitor of DNA binding 4, dominant negative h | -2.19 SLC35F2 | solute carrier family 35, member F2 |
| 2.52 | TIGA1 | TIGA1 | -2.19 KIAA1661 | KIAA1661 protein |
| -2.52 | LLGL2 | lethal giant larvae homolog 2 (Drosophila) | 2.19 — | — |
| -2.52 | RASGRP2 | RAS guanyl releasing protein 2 (calcium and D | 2.19 — | — |
| -2.52 | MMP14 | matrix metallopeptidase 14 (membrane-inserte | 2.19 POLR3GL | polymerase (RNA) III (DNA directed) polypeptic |
| -2.52 | SLCO4C1 | solute carrier organic anion transporter family, | -2.19 DSG2 | desmoglein 2 |
| 2.52 | PIK3R3 | phosphoinositide-3-kinase, regulatory subunit 3 | -2.19 F12 | coagulation factor XII (Hageman factor) |
| -2.52 | — | — | -2.19 JARID2 | Jumonji, AT rich interactive domain 2 |
| -2.52 | — | — | 2.18 — | — |
| 2.52 | LOC222070 | hypothetical protein LOC222070 | 2.18 SFRS6 | splicing factor, arginine/serine-rich 6 |
| 2.52 | GPR153 | G protein-coupled receptor 153 | -2.18 — | — |
| -2.52 | GADD45B | growth arrest and DNA-damage-inducible, beta | -2.18 ST14 | suppression of tumorigenicity 14 (colon carcino |
| 2.52 | — | CDNA FLJ38345 fis, clone FCBBF3028671 | 2.18 HUNK | hormonally upregulated Neu-associated kinase |

Appendix 1

| Value | Gene | Description | Value | Gene | Description |
|---|---|---|---|---|---|
| 2.52 | TXNDC4 | thioredoxin domain containing 4 (endoplasmic | -2.18 | IRX4 | iroquois homeobox protein 4 |
| 2.52 | RRAGD | Ras-related GTP binding D | -2.18 | CTSL2 | Cathepsin L2 |
| -2.52 | ID2 | inhibitor of DNA binding 2, dominant negative H | 2.18 | THBD | thrombomodulin |
| -2.52 | LGALS3 | lectin, galactoside-binding, soluble, 3 (galectin | 2.18 | — | — |
| -2.52 | MDFI | MyoD family inhibitor | -2.18 | ZNF788 | zinc finger family member 788 |
| -2.52 | CUL4A | Cullin 4A | -2.18 | FA2H | fatty acid 2-hydroxylase |
| 2.52 | TOX | thymus high mobility group box protein TOX | 2.18 | SEC31B | SEC31 homolog B (S. cerevisiae) |
| 2.52 | LOC389073 | similar to RIKEN cDNA D630023F18 | -2.18 | SLC2A3 | solute carrier family 2 (facilitated glucose trans| |
| -2.52 | — | — | 2.18 | INPP4B | inositol polyphosphate-4-phosphatase, type II, |
| -2.52 | TRPM4 | transient receptor potential cation channel, sub | -2.18 | — | — |
| -2.52 | PRKCB1 | Protein kinase C, beta 1 | -2.18 | CCL4 | chemokine (C-C motif) ligand 4 |
| 2.52 | MGC26733 | hypothetical protein MGC26733 | 2.18 | SP100 | SP100 nuclear antigen |
| 2.52 | TTC3 | tetratricopeptide repeat domain 3 | 2.18 | PRSS23 | protease, serine, 23 |
| 2.52 | KIAA1545 | KIAA1545 protein | 2.18 | GABRR1 | gamma-aminobutyric acid (GABA) receptor, rh|
| 2.52 | APCDD1 | adenomatosis polyposis coli down-regulated 1 | 2.18 | NIN | ninein (GSK3B interacting protein) |
| -2.51 | FZD8 | frizzled homolog 8 (Drosophila) /// frizzled hom | -2.17 | BCL11B | B-cell CLL/lymphoma 11B (zinc finger protein) |
| 2.51 | NCAM1 | Neural cell adhesion molecule 1 | -2.17 | USP28 | ubiquitin specific peptidase 28 |
| -2.51 | PITPNM2 | phosphatidylinositol transfer protein, membran | 2.17 | CCDC32 | coiled-coil domain containing 32 |
| -2.51 | SNAI1 | snail homolog 1 (Drosophila) | 2.17 | CD99L2 | CD99 molecule-like 2 |
| -2.51 | GABARAPL1 | GABA(A) receptor-associated protein like 1 | 2.17 | FAM46A | family with sequence similarity 46, member A |
| 2.51 | — | — | 2.17 | FLJ42709 | hypothetical gene supported by AK124699 |
| 2.51 | SHANK3 | SH3 and multiple ankyrin repeat domains 3 | -2.17 | — | — |
| -2.51 | — | Homo sapiens, clone IMAGE:4047715, mRNA | -2.17 | CORO2A | coronin, actin binding protein, 2A |
| -2.51 | MYLIP | myosin regulatory light chain interacting protei | -2.17 | — | Transcribed locus, strongly similar to NP_0031! |
| -2.51 | PTGIS | prostaglandin I2 (prostacyclin) synthase /// pro$ | 2.17 | CD47 | CD47 molecule /// CD47 molecule |
| -2.51 | DDIT4L | DNA-damage-inducible transcript 4-like | 2.17 | ENPP2 | ectonucleotide pyrophosphatase/phosphodiest|
| -2.51 | — | — | 2.17 | — | — |
| 2.51 | — | — | 2.17 | AQP1 | aquaporin 1 (Colton blood group) |
| 2.51 | LOC345630 | similar to fibrillarin | 2.17 | KIAA1641 | KIAA1641 |
| -2.51 | PNRC1 | proline-rich nuclear receptor coactivator 1 | -2.17 | GAD1 /// LASS6 | glutamate decarboxylase 1 (brain, 67kDa) /// L/ |
| 2.51 | SMEK2 | SMEK homolog 2, suppressor of mek1 (Dictyo$ | -2.16 | — | CDNA FLJ32963 fis, clone TESTI2008405 |
| 2.51 | CCNE2 | cyclin E2 | 2.16 | — | — |
| 2.50 | SLITRK5 | SLIT and NTRK-like family, member 5 | 2.16 | SLC16A14 | solute carrier family 16, member 14 (monocarb|
| -2.50 | BTBD7 | BTB (POZ) domain containing 7 | 2.16 | CABLES1 | Cdk5 and Abl enzyme substrate 1 |
| 2.50 | TXNL2 | Thioredoxin-like 2 | 2.16 | QKI | quaking homolog, KH domain RNA binding (mc |
| -2.50 | MYCBP | c-myc binding protein | -2.16 | — | — |
| -2.50 | ACOX1 | acyl-Coenzyme A oxidase 1, palmitoyl | 2.16 | RAB40B | RAB40B, member RAS oncogene family |
| -2.50 | TMOD1 | tropomodulin 1 | 2.16 | ITPR1 | inositol 1,4,5-triphosphate receptor, type 1 |
| 2.50 | NME5 | non-metastatic cells 5, protein expressed in (nu | 2.16 | SLIT2 | slit homolog 2 (Drosophila) |
| 2.50 | GPSM2 | G-protein signalling modulator 2 (AGS3-like, C. | 2.16 | RGS12 | regulator of G-protein signalling 12 |
| 2.50 | HGSNAT | heparan-alpha-glucosaminide N-acetyltransfer$ | -2.16 | MYO6 | myosin VI |
| -2.50 | IQGAP1 | IQ motif containing GTPase activating protein 1 | 2.16 | — | — |
| -2.50 | — | — | 2.16 | — | — |
| 2.50 | MXRA7 | matrix-remodelling associated 7 | -2.16 | MFAP3L | microfibrillar-associated protein 3-like |
| -2.49 | — | Transcribed locus | 2.16 | — | — |
| -2.49 | OVOL1 | ovo-like 1(Drosophila) | -2.16 | TOMM40 | Translocase of outer mitochondrial membrane |
| 2.49 | CUL3 | cullin 3 | 2.16 | CUEDC1 | CUE domain containing 1 |
| -2.49 | SPRY1 | sprouty homolog 1, antagonist of FGF signaling | 2.16 | MTX1 | Metaxin 1 |
| 2.49 | ARHGAP6 | Rho GTPase activating protein 6 | -2.15 | — | — |
| -2.49 | — | — | -2.15 | SNRPN | small nuclear ribonucleoprotein polypeptide N |
| -2.49 | — | CDNA clone IMAGE:4799094 | -2.15 | TBC1D1 | TBC1 (tre-2/USP6, BUB2, cdc16) domain famil |
| 2.49 | — | — | -2.15 | ARNTL2 | aryl hydrocarbon receptor nuclear translocator-|
| -2.49 | — | — | 2.15 | RTN1 | reticulon 1 |
| 2.49 | DYNC2H1 | dynein, cytoplasmic 2, heavy chain 1 | -2.15 | — | Similar to hypothetical protein LOC284701 |
| 2.49 | ZNF638 | Zinc finger protein 638 | -2.15 | PPM1B | protein phosphatase 1B (formerly 2C), magnes |
| -2.49 | — | — | -2.15 | GNPTAB | N-acetylglucosamine-1-phosphate transferase, |
| 2.49 | — | Homo sapiens, clone IMAGE:4480133, mRNA | -2.15 | ZNF429 | Zinc finger protein 429 |
| 2.49 | — | — | 2.15 | SARM1 | sterile alpha and TIR motif containing 1 |
| 2.49 | — | — | -2.15 | TMC4 | transmembrane channel-like 4 |
| 2.49 | EXOSC6 | Exosome component 6 | 2.15 | ZNF124 | zinc finger protein 124 |
| -2.49 | — | CDNA clone IMAGE:4638753 | 2.15 | SRrp35 | Serine-arginine repressor protein (35 kDa) |
| 2.49 | — | — | -2.15 | FLJ35848 | hypothetical protein FLJ35848 |
| -2.48 | — | Full length insert cDNA YH97G12 | 2.15 | C12orf38 | chromosome 12 open reading frame 38 |
| -2.48 | — | — | 2.15 | C20orf82 | chromosome 20 open reading frame 82 |
| -2.48 | SMPDL3B | sphingomyelin phosphodiesterase, acid-like 3B | -2.15 | CG018 | hypothetical gene CG018 |
| 2.48 | KCNJ8 | potassium inwardly-rectifying channel, subfami | -2.15 | TBC1D8 | TBC1 domain family, member 8 (with GRAM dc |
| 2.48 | CDO1 | cysteine dioxygenase, type | -2.15 | — | Transcribed locus |
| 2.48 | — | — | -2.15 | RRP22 | RAS-related on chromosome 22 |
| -2.48 | WDHD1 | WD repeat and HMG-box DNA binding protein | 2.15 | KLRC3 | killer cell lectin-like receptor subfamily C, memt |
| 2.48 | PTPRO | protein tyrosine phosphatase, receptor type, C | -2.15 | — | — |
| 2.48 | — | — | 2.15 | KIFAP3 | kinesin-associated protein 3 |
| 2.48 | TTC28 | tetratricopeptide repeat domain 28 | 2.15 | SPON1 | spondin 1, extracellular matrix protein |
| -2.48 | ROR1 | receptor tyrosine kinase-like orphan receptor 1 | 2.15 | PTPRC | protein tyrosine phosphatase, receptor type, C |
| -2.48 | CHES1 | checkpoint suppressor 1 | 2.14 | KBTBD9 | kelch repeat and BTB (POZ) domain containing |
| -2.48 | LMTK3 | lemur tyrosine kinase 3 | 2.14 | MGC39900 | hypothetical protein MGC3990C |
| -2.48 | SERPINB9 | serpin peptidase inhibitor, clade B (ovalbumin), | -2.14 | LOC645745 | metallothionein 1H-like protein |
| -2.48 | GATM | glycine amidinotransferase (L-arginine:glycine | -2.14 | MGAT4C | mannosyl (alpha-1,3-)-glycoprotein beta-1,4-N-|
| -2.48 | PCOLCE | procollagen C-endopeptidase enhancer | 2.14 | — | CDNA clone IMAGE:5311619 |
| 2.48 | LONRF2 | LON peptidase N-terminal domain and ring fing | 2.14 | NAP1L5 | nucleosome assembly protein 1-like 5 |

Appendix 1

| Value | Symbol | Description |
|---|---|---|
| 2.48 | SLC45A1 | solute carrier family 45, member 1 |
| 2.48 | — | — |
| -2.48 | SIPA1 | signal-induced proliferation-associated gene 1 |
| 2.48 | EMP1 | Epithelial membrane protein 1 |
| 2.48 | MKRN3 | makorin, ring finger protein, 3 |
| -2.47 | JPH3 | junctophilin 3 |
| 2.47 | TCF12 | Transcription factor 12 (HTF4, helix-loop-helix |
| -2.47 | GALC | galactosylceramidase |
| -2.47 | P2RX5 | purinergic receptor P2X, ligand-gated ion chan |
| -2.47 | CLCN5 /// PCYT1B | chloride channel 5 (nephrolithiasis 2, X-linked, |
| 2.47 | — | Homo sapiens, clone IMAGE:4346533, mRNA |
| 2.47 | BVES | blood vessel epicardial substance |
| -2.47 | PRICKLE1 | Prickle-like 1 (Drosophila) |
| -2.47 | LOC57228 | small trans-membrane and glycosylated protein |
| -2.47 | RASEF | RAS and EF-hand domain containing |
| -2.47 | LOC728215 /// LOC | similar to transmembrane protein 28 /// similar |
| -2.47 | — | — |
| 2.47 | — | — |
| 2.47 | LOC654342 | Similar to lymphocyte-specific protein 1 |
| 2.46 | PCAF | p300/CBP-associated factor |
| 2.46 | RFX2 | regulatory factor X, 2 (influences HLA class II |
| -2.46 | CLDN3 | claudin 3 |
| 2.46 | STXBP4 | syntaxin binding protein 4 |
| -2.46 | — | Full-length cDNA clone CL0BB018ZE07 of Neu |
| 2.46 | VEGFC | vascular endothelial growth factor C |
| 2.46 | FAS | Fas (TNF receptor superfamily, member 6) |
| -2.46 | — | — |
| 2.46 | NAALAD2 | N-acetylated alpha-linked acidic dipeptidase 2 |
| -2.46 | BCL3 | B-cell CLL/lymphoma 3 |
| 2.46 | — | — |
| -2.46 | LTB4DH | leukotriene B4 12-hydroxydehydrogenase |
| -2.46 | C1orf183 | chromosome 1 open reading frame 183 |
| 2.46 | UBE2J1 | ubiquitin-conjugating enzyme E2, J1 (UBC6 ho |
| -2.45 | — | — |
| -2.45 | AGMAT | agmatine ureohydrolase (agmatinase) |
| -2.45 | BICD1 | bicaudal D homolog 1 (Drosophila) |
| -2.45 | GAD1 /// LASS6 | glutamate decarboxylase 1 (brain, 67kDa) /// L |
| -2.45 | GADD45B | growth arrest and DNA-damage-inducible, beta |
| 2.45 | PDE4D | phosphodiesterase 4D, cAMP-specific (phosph |
| 2.45 | — | CDNA clone IMAGE:5288757 |
| -2.45 | ADAMTS19 | ADAM metallopeptidase with thrombospondin |
| -2.45 | — | — |
| -2.45 | LOC643287 | similar to prothymosin, alpha (gene sequence |
| -2.45 | GCHFR | GTP cyclohydrolase I feedback regulator |
| 2.45 | — | Full length insert cDNA YH77E09 |
| -2.45 | CD40 | CD40 molecule, TNF receptor superfamily men |
| 2.45 | LOC127003 | similar to CG5435-PA |
| 2.45 | — | Cri-du-chat region mRNA, clone NIBB11 |
| 2.45 | MAP2K5 | mitogen-activated protein kinase kinase 5 |
| 2.45 | RUFY3 | RUN and FYVE domain containing 3 |
| -2.45 | GRB14 | growth factor receptor-bound protein 14 |
| -2.45 | — | CDNA clone IMAGE:4819775 |
| -2.45 | TMEPAI | transmembrane, prostate androgen induced RI |
| -2.45 | — | — |
| 2.45 | MGC14289 | similar to RIKEN cDNA 1200014N16 gene |
| 2.45 | FAT3 | FAT tumor suppressor homolog 3 (Drosophila) |
| 2.45 | — | — |
| 2.44 | PROX1 | prospero-related homeobox 1 |
| 2.44 | IFIT5 | interferon-induced protein with tetratricopeptide |
| -2.44 | GABRB3 | Gamma-aminobutyric acid (GABA) A receptor, |
| -2.44 | — | — |
| 2.44 | MLR1 | transcription factor MLR1 |
| -2.44 | NF2 | neurofibromin 2 (bilateral acoustic neuroma) |
| 2.44 | CPEB1 | cytoplasmic polyadenylation element binding p |
| -2.44 | IPW | imprinted in Prader-Willi syndrome |
| -2.44 | RAB15 | RAB15, member RAS oncogene family |
| -2.44 | ARHGEF10 | Rho guanine nucleotide exchange factor (GEF) |
| -2.44 | SORL1 | sortilin-related receptor, L(DLR class) A repeat |
| 2.44 | KIAA0984 | KIAA0984 protein |
| -2.44 | TncRNA | trophoblast-derived noncoding RNA |
| 2.44 | C6orf134 | chromosome 6 open reading frame 134 |
| -2.44 | MCAM | melanoma cell adhesion molecule |
| 2.44 | ARID5B | AT rich interactive domain 5B (MRF1-like) |
| 2.44 | — | Transcribed locus |
| 2.43 | — | Full-length cDNA clone CS0DJ013YP06 of T c |
| 2.43 | WARS2 | Tryptophanyl tRNA synthetase 2 (mitochondria |
| 2.43 | SLC1A3 | solute carrier family 1 (glial high affinity glutam |
| -2.43 | SYT17 | synaptotagmin XVII |
| 2.43 | CELSR1 | cadherin, EGF LAG seven-pass G-type recept |
| 2.14 | — | Clone 23555 mRNA sequence |
| 2.14 | — | — |
| -2.14 | C10orf95 | Chromosome 10 open reading frame 95 |
| 2.14 | CAMK2N1 | calcium/calmodulin-dependent protein kinase II |
| -2.14 | CPO | carboxypeptidase O |
| -2.14 | TBX5 | T-box 5 |
| 2.14 | — | — |
| 2.14 | — | — |
| 2.14 | NBPF14 /// NBPF11 | neuroblastoma breakpoint family, member 14 / |
| -2.14 | — | — |
| 2.14 | — | — |
| -2.14 | GABARAPL1 | GABA(A) receptor-associated protein like 1 |
| 2.14 | DUSP6 | dual specificity phosphatase 6 |
| 2.13 | SSBP2 | single-stranded DNA binding protein 2 |
| 2.13 | C3orf54 | chromosome 3 open reading frame 54 |
| -2.13 | RMST | Rhabdomyosarcoma 2 associated transcript (n |
| 2.13 | THBS3 | thrombospondin 3 |
| 2.13 | LONP2 | Lon peptidase 2, peroxisomal |
| -2.13 | — | — |
| -2.13 | LOC727729 | similar to gamma-aminobutyric acid (GABA) A |
| -2.13 | LOH11CR2A | loss of heterozygosity, 11, chromosomal region |
| -2.13 | — | — |
| 2.13 | — | — |
| 2.13 | TBC1D9 | TBC1 domain family, member 9 (with GRAM d |
| 2.13 | CKLFSF3 | chemokine-like factor superfamily 3 |
| -2.12 | RHOF | ras homolog gene family, member F (in filopodi |
| 2.12 | C21orf34 | Chromosome 21 open reading frame 34 |
| 2.12 | PTHLH | parathyroid hormone-like hormone |
| -2.12 | DUSP5 | dual specificity phosphatase 5 |
| 2.12 | GPRASP1 | G protein-coupled receptor associated sorting |
| -2.12 | ADD2 | adducin 2 (beta) |
| -2.12 | P2RX2 | purinergic receptor P2X, ligand-gated ion chan |
| 2.12 | FLJ90757 | hypothetical protein LOC440465 |
| -2.12 | ZNF589 | zinc finger protein 589 |
| 2.12 | MLLT4 | Myeloid/lymphoid or mixed-lineage leukemia (tr |
| 2.12 | — | — |
| 2.12 | — | — |
| 2.12 | LYST | lysosomal trafficking regulator |
| -2.11 | TRIM37 | tripartite motif-containing 37 |
| 2.11 | CCR1 | chemokine (C-C motif) receptor 1 |
| -2.11 | FKBP1B | FK506 binding protein 1B, 12.6 kDa |
| -2.11 | GLS2 | glutaminase 2 (liver, mitochondrial) |
| 2.11 | PIK3R1 | phosphoinositide-3-kinase, regulatory subunit 1 |
| -2.11 | BTN3A3 | butyrophilin, subfamily 3, member A3 |
| 2.11 | ITPR1 | inositol 1,4,5-triphosphate receptor, type 1 |
| 2.11 | FYN | FYN oncogene related to SRC, FGR, YES |
| -2.11 | IFITM2 | interferon induced transmembrane protein 2 (1- |
| 2.11 | NAV3 | neuron navigator 3 |
| 2.11 | NRP2 | Neuropilin 2 |
| 2.11 | BMP1 | bone morphogenetic protein 1 |
| -2.11 | — | — |
| -2.11 | TMEPAI | transmembrane, prostate androgen induced RI |
| -2.11 | — | — |
| -2.11 | LOC201895 | Hypothetical protein LOC201895 |
| -2.11 | — | — |
| -2.11 | — | Transcribed locus |
| 2.11 | NCAM1 | Neural cell adhesion molecule 1 |
| 2.11 | — | — |
| -2.10 | PDPN | podoplanin |
| 2.10 | GPR161 | G protein-coupled receptor 161 |
| -2.10 | — | — |
| 2.10 | — | CDNA FLJ38252 fis, clone FCBBF3000269 |
| 2.10 | ZNF423 | zinc finger protein 423 |
| 2.10 | CALCRL | calcitonin receptor-like |
| 2.10 | TANC | TPR domain, ankyrin-repeat and coiled-coil-cor |
| -2.10 | PIK3CB | phosphoinositide-3-kinase, catalytic, beta polyp |
| -2.10 | HSPB8 | heat shock 22kDa protein 8 |
| -2.10 | ZNF560 | zinc finger protein 560 |
| 2.10 | — | Transcribed locus |
| -2.10 | OVOL1 | ovo-like 1(Drosophila) |
| 2.10 | PAK3 | P21 (CDKN1A)-activated kinase 3 |
| 2.10 | UBE2J1 | ubiquitin-conjugating enzyme E2, J1 (UBC6 ho |
| 2.10 | SOX11 | SRY (sex determining region Y)-box 11 |
| -2.10 | — | — |
| -2.10 | — | — |
| 2.10 | SULT1C2 | sulfotransferase family, cytosolic, 1C, member |
| -2.10 | FRAT1 | frequently rearranged in advanced T-cell lymph |
| -2.10 | — | — |
| 2.10 | — | — |

Appendix 1

| Value | Symbol | Description |
|---|---|---|
| 2.43 | NPAS3 | neuronal PAS domain protein 3 |
| -2.43 | PPP1R1C | protein phosphatase 1, regulatory (inhibitor) su |
| 2.43 | CYP4V2 | cytochrome P450, family 4, subfamily V, polype |
| -2.43 | CNFN | cornifelin /// cornifelin |
| 2.43 | VAPB | VAMP (vesicle-associated membrane protein)- |
| 2.43 | — | Homo sapiens, clone IMAGE:4214654, mRNA |
| -2.43 | CPT1A | carnitine palmitoyltransferase 1A (liver) |
| -2.43 | DSG2 | Desmoglein 2 |
| -2.43 | C1orf85 | Chromosome 1 open reading frame 85 |
| -2.43 | KRT7 | keratin 7 |
| -2.43 | MYO1D | myosin ID |
| 2.43 | ZDHHC14 | zinc finger, DHHC-type containing 14 |
| 2.43 | — | Transcribed locus |
| 2.42 | FRZB | Frizzled-related protein |
| 2.42 | ANKRD6 | ankyrin repeat domain 6 |
| 2.42 | KIAA0523 | KIAA0523 protein |
| -2.42 | GAS7 | growth arrest-specific 7 |
| -2.42 | ZNF429 | Zinc finger protein 429 |
| -2.42 | OSTF1 | osteoclast stimulating factor 1 |
| 2.42 | DKK3 | dickkopf homolog 3 (Xenopus laevis) |
| -2.42 | USP28 | ubiquitin specific peptidase 28 |
| 2.42 | — | — |
| -2.42 | DSG2 | desmoglein 2 |
| -2.42 | PHC1 | polyhomeotic homolog 1 (Drosophila) |
| -2.42 | HBP1 | HMG-box transcription factor 1 |
| -2.42 | — | — |
| 2.42 | FAM89B | family with sequence similarity 89, member B |
| -2.42 | PYGL | phosphorylase, glycogen; liver (Hers disease, |
| -2.42 | CHGA | chromogranin A (parathyroid secretory protein |
| -2.42 | ZNF718 | zinc finger protein 718 |
| -2.42 | CAV2 | caveolin 2 |
| 2.42 | MGC40405 | Zinc finger, SWIM-type containing 6 |
| 2.42 | EME2 | Essential meiotic endonuclease 1 homolog 2 |
| 2.42 | SOX11 | SRY (sex determining region Y)-box 11 |
| -2.42 | IRF6 | interferon regulatory factor 6 |
| 2.42 | — | Transcribed locus |
| -2.41 | HMG4L | high-mobility group (nonhistone chromosomal) |
| 2.41 | TGFB1I4 | TSC22 domain family, member 1 |
| -2.41 | UNC5B | unc-5 homolog B (C. elegans) |
| 2.41 | ST7 | suppression of tumorigenicity 7 |
| 2.41 | — | — |
| 2.41 | SLC44A5 | solute carrier family 44, member 5 |
| -2.41 | CCL5 | chemokine (C-C motif) ligand 5 /// chemokine ( |
| 2.41 | — | — |
| -2.41 | GPR176 | G protein-coupled receptor 176 |
| 2.41 | LOC283859 | hypothetical protein LOC283859 |
| -2.41 | KIAA0746 | KIAA0746 protein |
| -2.41 | CACNA2D3 | calcium channel, voltage-dependent, alpha 2/d |
| 2.41 | — | CDNA FLJ35508 fis, clone SMINT2011958 |
| 2.41 | — | — |
| 2.40 | C1orf102 | chromosome 1 open reading frame 102 |
| 2.40 | FARP1 | FERM, RhoGEF (ARHGEF) and pleckstrin dor |
| -2.40 | — | — |
| 2.40 | — | — |
| 2.40 | DCX | doublecortex; lissencephaly, X-linked (double |
| -2.40 | RAB15 | RAB15, member RAS oncogene family |
| 2.40 | DCLRE1C | DNA cross-link repair 1C (PSO2 homolog, S. c |
| 2.40 | — | CDNA clone IMAGE:5263177 |
| -2.40 | FLJ10404 | hypothetical protein FLJ10404 |
| 2.40 | MBNL2 | Muscleblind-like 2 (Drosophila) |
| -2.39 | HERC5 | hect domain and RLD 5 |
| -2.39 | PCDHB14 | Protocadherin beta 14 |
| 2.39 | D2HGDH | D-2-hydroxyglutarate dehydrogenase |
| 2.39 | — | — |
| 2.39 | — | — |
| -2.39 | USP44 | ubiquitin specific peptidase 44 |
| 2.39 | EP400 | E1A binding protein p400 |
| 2.39 | CHST3 | carbohydrate (chondroitin 6) sulfotransferase |
| -2.39 | PHLDA1 | pleckstrin homology-like domain, family A, mer |
| 2.39 | GPR161 | G protein-coupled receptor 161 |
| -2.39 | — | — |
| 2.39 | ATP8A2 | ATPase, aminophospholipid transporter-like, C |
| -2.39 | RASIP1 | Ras interacting protein 1 |
| 2.39 | LOC730069 /// LOC | similar to nuclear receptor binding factor 2 /// s |
| -2.39 | — | MRNA; cDNA DKFZp686P18215 (from clone D |
| 2.39 | DPP4 | dipeptidyl-peptidase 4 (CD26, adenosine dean |
| -2.38 | HSPB8 | heat shock 22kDa protein 8 |
| -2.38 | HLA-DRB1 /// HLA-I | major histocompatibility complex, class II, DR |
| 2.38 | ASXL1 | additional sex combs like 1 (Drosophila) |
| 2.10 | FLJ30990 | hypothetical protein FLJ30990 |
| -2.10 | — | — |
| 2.10 | — | — |
| -2.09 | SLC39A14 | solute carrier family 39 (zinc transporter), mem |
| -2.09 | — | — |
| 2.09 | MECP2 | methyl CpG binding protein 2 (Rett syndrome) |
| 2.09 | ITGAM | integrin, alpha M (complement component 3 re |
| 2.09 | NAIP /// LOC72851 | NLR family, apoptosis inhibitory protein /// simil |
| 2.09 | — | — |
| 2.09 | TBX15 | T-box 15 |
| 2.09 | PAM | peptidylglycine alpha-amidating monooxygenas |
| 2.09 | FLJ10357 | hypothetical protein FLJ10357 |
| -2.09 | — | — |
| -2.09 | — | — |
| 2.09 | LOC150166 | hypothetical protein LOC150166 |
| 2.09 | TRGC2 /// TRGV9 | T cell receptor gamma constant 2 /// T cell rece |
| 2.09 | — | — |
| 2.09 | TCF3 | Transcription factor 3 (E2A immunoglobulin enl |
| 2.09 | LOX | lysyl oxidase |
| -2.09 | PAK1 | p21/Cdc42/Rac1-activated kinase 1 (STE20 ho |
| 2.09 | TGFB2 | Transforming growth factor, beta 2 |
| 2.09 | RNF130 | Ring finger protein 130 |
| 2.09 | FAM118A /// LOC7 | Family with sequence similarity 118, member A |
| 2.09 | POLR2J2 | DNA directed RNA polymerase II polypeptide J |
| 2.09 | SLC6A16 | Solute carrier family 6, member 16 |
| 2.09 | KLHL22 | kelch-like 22 (Drosophila) |
| -2.09 | TMEM63A | transmembrane protein 63A |
| 2.09 | — | CDNA FLJ37884 fis, clone BRSTN2012451 |
| 2.09 | — | — |
| 2.08 | CUEDC1 | CUE domain containing 1 |
| -2.08 | OLFML2A | olfactomedin-like 2A |
| 2.08 | FBXW8 | F-box and WD-40 domain protein 8 |
| 2.08 | GSN | gelsolin (amyloidosis, Finnish type) |
| -2.08 | KIAA0040 | KIAA0040 |
| -2.08 | — | —. |
| -2.08 | GAD1 /// LASS6 | glutamate decarboxylase 1 (brain, 67kDa) /// L |
| -2.08 | — | |
| 2.08 | PDGFC | platelet derived growth factor C |
| -2.08 | SNRPN /// SNURF | small nuclear ribonucleoprotein polypeptide N / |
| 2.08 | POLH | Polymerase (DNA directed), eta |
| 2.08 | — | — |
| -2.08 | KCNK1 | potassium channel, subfamily K, member 1 |
| -2.08 | DDT | D-dopachrome tautomerase |
| 2.08 | MEF2C | MADS box transcription enhancer factor 2, poly |
| -2.08 | MRS2L | MRS2-like, magnesium homeostasis factor (S. |
| 2.08 | — | |
| 2.08 | WIPF1 | WAS/WASL interacting protein family, member |
| 2.08 | KBTBD11 | kelch repeat and BTB (POZ) domain containing |
| -2.07 | HELLS | helicase, lymphoid-specific |
| 2.07 | — | — |
| 2.07 | PCBP4 | poly(rC) binding protein 4 |
| 2.07 | — | LOC440156 |
| -2.07 | SEZ6L2 | seizure related 6 homolog (mouse)-like 2 |
| 2.07 | TIMP2 | TIMP metallopeptidase inhibitor 2 |
| 2.07 | CACNB3 | calcium channel, voltage-dependent, beta 3 su |
| -2.07 | MCAM | melanoma cell adhesion molecule |
| -2.07 | FLJ32549 | hypothetical protein FLJ32549 |
| -2.07 | — | — |
| -2.07 | LOC727769 | Hypothetical protein LOC727769 |
| 2.07 | LCE3D | late cornified envelope 3D /// late cornified enve |
| 2.07 | — | — |
| 2.07 | — | — |
| 2.07 | CD99L2 | CD99 molecule-like 2 |
| 2.07 | DKFZp547K054 | hypothetical protein DKFZp547K054 |
| -2.06 | ARFGEF1 | ADP-ribosylation factor guanine nucleotide-exc |
| -2.06 | DENND1C | DENN/MADD domain containing 1C |
| 2.06 | PCDH17 | protocadherin 17 |
| 2.06 | SLC6A16 | solute carrier family 6, member 16 |
| -2.06 | RRAS2 | related RAS viral (r-ras) oncogene homolog 2 |
| -2.06 | UBE3C | Ubiquitin protein ligase E3C |
| -2.06 | OCEL1 | occludin/ELL domain containing 1 |
| 2.06 | NETO2 | neuropilin (NRP) and tolloid (TLL)-like 2 |
| -2.06 | HSPA2 | heat shock 70kDa protein 2 |
| 2.06 | SSBP2 | single-stranded DNA binding protein 2 |
| 2.06 | NME5 | non-metastatic cells 5, protein expressed in (nu |
| 2.06 | RECK | reversion-inducing-cysteine-rich protein with ka |
| 2.06 | SHANK3 | SH3 and multiple ankyrin repeat domains 3 |
| 2.06 | RIN3 | Ras and Rab interactor 3 |
| -2.06 | — | — |

Appendix 1

| | | | | |
|---|---|---|---|---|
| -2.38 | VANGL1 | vang-like 1 (van gogh, Drosophila) | 2.06 | FIGNL1 | fidgetin-like 1 |
| -2.38 | ANKRD6 | ankyrin repeat domain 6 | -2.06 | SLCO4A1 | solute carrier organic anion transporter family, |
| -2.38 | CTH | cystathionase (cystathionine gamma-lyase) | -2.06 | — | — |
| -2.38 | DGKA | diacylglycerol kinase, alpha 80kDa | 2.06 | — | — |
| -2.38 | DNAJB6 /// LOC387 | DnaJ (Hsp40) homolog, subfamily B, member | 2.06 | — | — |
| -2.38 | BCL9L | B-cell CLL/lymphoma 9-like | -2.06 | — | — |
| 2.38 | NNMT | nicotinamide N-methyltransferase | 2.06 | TLR4 | toll-like receptor 4 /// toll-like receptor 4 |
| 2.38 | FLJ13391 | hypothetical protein FLJ13391 | 2.06 | TMEM142B | transmembrane protein 142B |
| 2.38 | FLJ14503 | hypothetical protein FLJ14503 | -2.05 | ZNF589 | zinc finger protein 589 |
| 2.38 | — | — | 2.05 | — | — |
| 2.38 | COPB2 | Coatomer protein complex, subunit beta 2 (bet | -2.05 | ERICH1 | glutamate-rich 1 |
| -2.38 | NUDT7 | nudix (nucleoside diphosphate linked moiety X) | 2.05 | LST1 | leukocyte specific transcript 1 |
| -2.38 | AMT | aminomethyltransferase | -2.05 | — | — |
| -2.38 | LOC150051 | hypothetical LOC150051 | 2.05 | — | — |
| 2.38 | CDC42 | cell division cycle 42 (GTP binding protein, 25k | -2.05 | — | — |
| 2.38 | SCD5 | stearoyl-CoA desaturase 5 | 2.05 | WFIKKN1 | WAP, follistatin/kazal, immunoglobulin, kunitz a |
| -2.38 | GSDMDC1 | Gasdermin domain containing 1 | 2.05 | BTBD6 | BTB (POZ) domain containing 6 |
| -2.37 | CHES1 | checkpoint suppressor 1 | -2.05 | — | CDNA FLJ43172 fis, clone FCBBF3007242 |
| 2.37 | SLC6A16 | solute carrier family 6, member 16 | 2.05 | LOC389129 | similar to CG9996-PA |
| 2.37 | — | Transcribed locus | -2.05 | COCH | coagulation factor C homolog, cochlin (Limulus |
| -2.37 | PPP1R13L | protein phosphatase 1, regulatory (inhibitor) su | 2.05 | FMN2 | formin 2 |
| 2.37 | PDE10A | phosphodiesterase 10A | 2.05 | LZIC | Leucine zipper and CTNNBIP1 domain contain |
| -2.37 | ATXN3 | ataxin 3 | 2.05 | CXCR7 | chemokine (C-X-C motif) receptor 7 |
| -2.37 | LOC389440 | hypothetical LOC389440 | 2.05 | — | — |
| 2.37 | ABCC4 | ATP-binding cassette, sub-family C (CFTR/MR | -2.05 | PCK2 | phosphoenolpyruvate carboxykinase 2 (mitoch |
| 2.37 | SPA17 | Sperm autoantigenic protein 17 | -2.05 | AMY1A /// SSBP1 | amylase, alpha 1A; salivary /// single-stranded |
| -2.37 | — | — | -2.05 | MAFK | v-maf musculoaponeurotic fibrosarcoma oncog |
| -2.37 | BTD | biotinidase | -2.05 | VASH2 | vasohibin 2 |
| -2.37 | VASH2 | vasohibin 2 | 2.05 | DYNC2H1 | dynein, cytoplasmic 2, heavy chain 1 |
| -2.37 | HFE | Hemochromatosis | 2.05 | FRMD6 | FERM domain containing 6 |
| 2.37 | C18orf8 | Chromosome 18 open reading frame 8 | -2.04 | CPLX1 | complexin 1 |
| 2.36 | — | CDNA FLJ37023 fis, clone BRACE2010828 | -2.04 | GLIPR1L1 | GLI pathogenesis-related 1 like 1 |
| -2.36 | HLA-F | major histocompatibility complex, class I, F | 2.04 | PDE3B | Phosphodiesterase 3B, cGMP-inhibited |
| -2.36 | — | Mesenchymal stem cell protein DSC96 | 2.04 | COBLL1 | COBL-like 1 |
| -2.36 | NFKBIA | nuclear factor of kappa light polypeptide gene | 2.04 | ZNF584 | zinc finger protein 584 |
| -2.36 | LOC730432 | similar to serine/threonine/tyrosine interacting | 2.04 | VEGFC | vascular endothelial growth factor C |
| -2.36 | — | — | -2.04 | EML2 | echinoderm microtubule associated protein like |
| 2.36 | PAPPA | pregnancy-associated plasma protein A, pappa | 2.04 | NPAS3 | Neuronal PAS domain protein 3 |
| 2.36 | RGMB | RGM domain family, member B | 2.04 | NBPF1 /// NBPF10 | neuroblastoma breakpoint family, member 1 /// |
| -2.36 | GRPR | gastrin-releasing peptide receptor | 2.04 | LOC113386 | similar to envelope protein |
| -2.36 | BSPRY | B-box and SPRY domain containing | -2.04 | — | — |
| 2.36 | SLC30A7 | Solute carrier family 30 (zinc transporter), mem | 2.04 | — | — |
| 2.36 | SH3BP5 | SH3-domain binding protein 5 (BTK-associated | -2.04 | MRS2L | MRS2-like, magnesium homeostasis factor (S. |
| -2.36 | SNRPN /// SNURF | small nuclear ribonucleoprotein polypeptide N | 2.04 | PUNC | putative neuronal cell adhesion molecule |
| 2.36 | FLJ25967 | Hypothetical gene supported by AK098833 | 2.04 | UBE2J1 | ubiquitin-conjugating enzyme E2, J1 (UBC6 ho |
| -2.36 | SORBS1 | sorbin and SH3 domain containing 1 | 2.04 | PLXNA2 | plexin A2 |
| -2.36 | RNASE1 | ribonuclease, RNase A family, 1 (pancreatic) | 2.04 | NID2 | nidogen 2 (osteonidogen) |
| 2.36 | DENND2A | DENN/MADD domain containing 2A | -2.04 | ITGB4 | integrin, beta 4 |
| -2.35 | — | — | 2.04 | PCDHB11 | protocadherin beta 11 |
| 2.35 | IKZF1 | IKAROS family zinc finger 1 (Ikaros) | 2.04 | STS | steroid sulfatase (microsomal), arylsulfatase C, |
| 2.35 | ABAT | 4-aminobutyrate aminotransferase | 2.04 | — | — |
| 2.35 | TBC1D8 | TBC1 domain family, member 8 (with GRAM d | 2.03 | — | — |
| 2.35 | CPLX1 | complexin 1 | 2.03 | DMRTA2 | DMRT-like family A2 |
| -2.35 | CYP2E1 | cytochrome P450, family 2, subfamily E, polype | -2.03 | TMEM63A | transmembrane protein 63A |
| -2.35 | STEAP2 | six transmembrane epithelial antigen of the pro | 2.03 | KIDINS220 | Kinase D-interacting substance of 220 kDa |
| 2.35 | — | Transcribed locus | 2.03 | RRAGD | Ras-related GTP binding D |
| 2.35 | — | — | -2.03 | BAMBI | BMP and activin membrane-bound inhibitor hor |
| 2.35 | — | Full-length cDNA clone CS0DF032YA11 of Fet | -2.03 | APOBEC3C | apolipoprotein B mRNA editing enzyme, catalyt |
| 2.35 | FLJ10159 | Hypothetical protein FLJ10159 | 2.03 | TTLL3 | tubulin tyrosine ligase-like family, member 3 |
| -2.35 | NBL1 | neuroblastoma, suppression of tumorigenicity | -2.03 | — | CDNA FLJ12909 fis, clone NT2RP2004400 |
| -2.34 | MGC24665 | hypothetical protein MGC24665 | 2.03 | GLT28D1 | glycosyltransferase 28 domain containing 1 |
| 2.34 | AKR1C1 | aldo-keto reductase family 1, member C1 (dihy | 2.03 | PHF20L1 | PHD finger protein 20-like 1 |
| -2.34 | EML2 | Echinoderm microtubule associated protein like | -2.03 | STAU2 | Staufen, RNA binding protein, homolog 2 (Dros |
| 2.34 | DKFZp762A217 | hypothetical protein DKFZp762A217 | -2.03 | GPRC5B | G protein-coupled receptor, family C, group 5, |
| 2.34 | PGAP1 | GPI deacylase | 2.03 | LOC387895 | Hypothetical gene supported by BC040060 |
| -2.34 | MRPL52 | mitochondrial ribosomal protein L52 | 2.03 | IPO9 | Importin 9 |
| -2.34 | — | — | 2.03 | — | CDNA FLJ35137 fis, clone PLACE6009419 |
| -2.34 | USP28 | ubiquitin specific peptidase 28 | 2.03 | SERTAD4 | SERTA domain containing 4 |
| 2.34 | ARTS-1 | type 1 tumor necrosis factor receptor shedding | 2.03 | MDH1B | malate dehydrogenase 1B, NAD (soluble) |
| -2.34 | UST | uronyl-2-sulfotransferase | 2.03 | SKAP2 | src kinase associated phosphoprotein 2 |
| -2.34 | HCLS1 | hematopoietic cell-specific Lyn substrate 1 | 2.03 | HMGCLL1 | 3-hydroxymethyl-3-methylglutaryl-Coenzyme A |
| 2.34 | DOCK11 | dedicator of cytokinesis 11 | 2.02 | TGFBR3 | transforming growth factor, beta receptor III (be |
| -2.34 | UGT3A1 | UDP glycosyltransferase 3 family, polypeptide | 2.02 | EPDR1 | ependymin related protein 1 (zebrafish) |
| 2.34 | CHST3 | carbohydrate (chondroitin 6) sulfotransferase 3 | 2.02 | — | — |
| -2.34 | CADPS | Ca2+-dependent secretion activator | -2.02 | SH2B3 | SH2B adaptor protein 3 |
| -2.34 | CDX4 | caudal type homeobox transcription factor 4 | -2.02 | LOC729440 /// LOC | hypothetical protein LOC729440 /// hypothetica |
| 2.34 | SEMA6D | sema domain, transmembrane domain (TM), a | -2.02 | ARFGEF1 | ADP-ribosylation factor guanine nucleotide-exc |
| 2.33 | ATP10D | ATPase, Class V, type 10D | -2.02 | — | CDNA FLJ29007 fis, clone STM04662, highly s |
| 2.33 | RNF182 | ring finger protein 182 | -2.02 | — | Transcribed locus, weakly similar to XP_50931 |

Appendix 1

| | | | | |
|---|---|---|---|---|
| 2.33 — | — | | 2.02 — | — |
| 2.33 FLJ37562 | hypothetical protein FLJ37562 | | 2.02 EPHB3 | EPH receptor B3 |
| -2.33 COCH | coagulation factor C homolog, cochlin (Limulus | | 2.02 PANX1 | Pannexin 1 |
| -2.33 P2RX2 | purinergic receptor P2X, ligand-gated ion chan | | 2.02 — | — |
| -2.33 — | — | | 2.02 — | Full-length cDNA clone CS0DD001YA12 of Ne |
| 2.33 ABCA2 | ATP-binding cassette, sub-family A (ABC1), m | | 2.02 ROR2 | receptor tyrosine kinase-like orphan receptor 2 |
| 2.33 TAIP-2 | TGF-beta induced apoptosis protein 2 | | -2.02 BTD | biotinidase |
| -2.33 TUBA1 | tubulin, alpha 1 | | 2.02 — | — |
| 2.33 SUV39H2 | suppressor of variegation 3-9 homolog 2 (Dros | | -2.02 EXOSC5 | exosome component 5 |
| -2.33 — | — | | 2.02 CXCL14 | chemokine (C-X-C motif) ligand 14 |
| -2.33 HLA-F | major histocompatibility complex, class I, F | | -2.02 GCH1 | GTP cyclohydrolase 1 (dopa-responsive dystor |
| -2.33 LTB4DH | Leukotriene B4 12-hydroxydehydrogenase | | -2.02 — | — |
| -2.33 BMP2 | bone morphogenetic protein 2 | | -2.01 SOX13 | SRY (sex determining region Y)-box 13 |
| 2.33 KLHL8 | Kelch-like 8 (Drosophila) | | 2.01 RCBTB2 | regulator of chromosome condensation (RCC1 |
| 2.33 — | CDNA FLJ11655 fis, clone HEMBA1004554 | | -2.01 MGC4172 | short-chain dehydrogenase/reductase |
| -2.33 TJP3 | tight junction protein 3 (zona occludens 3) | | 2.01 ZNF336 | zinc finger protein 336 |
| 2.33 — | — | | 2.01 DCPS | Decapping enzyme, scavenger |
| 2.33 PLXNA1 | plexin A1 | | -2.01 — | — |
| -2.32 HIVEP2 | human immunodeficiency virus type I enhance | | 2.01 TNS1 | tensin 1 /// tensin 1 |
| 2.32 ERCC5 | Excision repair cross-complementing rodent re | | 2.01 PCAF | p300/CBP-associated factor |
| -2.32 — | Transcribed locus | | 2.01 RNF182 | ring finger protein 182 |
| -2.32 KIAA1815 | KIAA1815 | | 2.01 MDFIC | MyoD family inhibitor domain containing /// Myc |
| -2.32 C14orf151 | chromosome 14 open reading frame 151 /// ch | | -2.01 KIAA0367 | KIAA0367 |
| 2.32 C11orf41 | chromosome 11 open reading frame 41 | | 2.01 TMEM44 | transmembrane protein 44 |
| -2.32 UGP2 | UDP-glucose pyrophosphorylase 2 | | -2.01 SAT1 | spermidine/spermine N1-acetyltransferase 1 |
| 2.32 — | Transcribed locus | | 2.01 TNFRSF10D | tumor necrosis factor receptor superfamily, me |
| -2.32 — | — | | 2.01 — | — |
| 2.32 MCPH1 | Microcephaly, primary autosomal recessive 1 | | 2.01 TNFAIP6 | tumor necrosis factor, alpha-induced protein 6 |
| 2.32 — | — | | -2.01 DKFZP564I1171 | DKFZP564I1171 protein |
| -2.31 PPP2R2B | protein phosphatase 2 (formerly 2A), regulatory | | 2.01 — | — |
| -2.31 olfactory receptor, f | CDNA FLJ11504 fis, clone HEMBA1002119 | | 2.01 — | — |
| -2.31 GABRB3 | gamma-aminobutyric acid (GABA) A receptor, | | -2.00 TRDN | triadin |
| 2.31 — | — | | 2.00 HOXB13 | homeobox B13 |
| 2.31 KLHL8 | kelch-like 8 (Drosophila) | | -2.00 SYN2 | Synapsin II |
| -2.31 SEPHS1 | selenophosphate synthetase 1 | | 2.00 FLJ16008 | FLJ16008 protein |
| -2.31 — | — | | 2.00 TMEM112 | transmembrane protein 112 |
| 2.31 TRIO | Triple functional domain (PTPRF interacting) | | 2.00 IL13RA1 | interleukin 13 receptor, alpha 1 |
| 2.31 FYN | FYN oncogene related to SRC, FGR, YES | | -2.00 RAB11FIP4 | RAB11 family interacting protein 4 (class II) |
| -2.31 THRB | thyroid hormone receptor, beta (erythroblastic | | 2.00 KLHDC5 | kelch domain containing 5 |
| 2.31 PSTPIP2 | proline-serine-threonine phosphatase interactin | | -2.00 INADL | InaD-like (Drosophila) |
| 2.31 CX3CL1 | chemokine (C-X3-C motif) ligand 1 | | 2.00 — | Full length insert cDNA YH77E09 |
| -2.31 KCNS3 | potassium voltage-gated channel, delayed-rect | | -2.00 — | CDNA FLJ39613 fis, clone SKNSH2009357 |
| 2.31 — | Full-length cDNA clone CS0DC015YK09 of Ne | | -2.00 FOXL2 | forkhead box L2 |
| 2.31 — | — | | 2.00 PALLD | Palladin, cytoskeletal associated protein |
| -2.31 — | — | | 2.00 C7orf6 | Sterile alpha motif domain containing 9-like |
| -2.31 SLC7A10 | solute carrier family 7, (neutral amino acid tran | | 2.00 ATBF1 | AT-binding transcription factor 1 |
| 2.31 DOCK11 | dedicator of cytokinesis 11 | | 2.00 EGR2 | early growth response 2 (Krox-20 homolog, Dr |
| 2.31 NMNAT2 | nicotinamide nucleotide adenylyltransferase 2 | | 2.00 — | — |
| -2.30 GLIPR1L1 | GLI pathogenesis-related 1 like 1 | | -2.00 — | Homo sapiens, clone IMAGE:4414697, mRNA |
| -2.30 METTL7A | methyltransferase like 7A | | | |
| -2.30 AP4S1 | adaptor-related protein complex 4, sigma 1 subunit | | | |
| 2.30 — | — | | | |
| -2.30 — | — | | | |
| 2.30 SMOC1 | SPARC related modular calcium binding 1 | | | |
| -2.30 C10orf118 | chromosome 10 open reading frame 118 | | | |
| -2.30 PTTG1IP | Pituitary tumor-transforming 1 interacting protein | | | |
| 2.30 — | — | | | |
| 2.30 PTD004 | GTP-binding protein PTD004 /// GTP-binding protein PTD004 | | | |
| -2.30 TNS3 | tensin 3 | | | |
| -2.30 PRICKLE1 | prickle homolog 1 (Drosophila) | | | |
| -2.30 EPHA7 | EPH receptor A7 | | | |
| 2.30 KBTBD11 | kelch repeat and BTB (POZ) domain containing 11 | | | |
| -2.30 — | — | | | |
| -2.30 BEST2 | bestrophin 2 | | | |
| 2.30 SLFNL1 | schlafen-like 1 | | | |
| -2.30 LRRTM1 | leucine rich repeat transmembrane neuronal 1 | | | |
| 2.30 — | — | | | |
| -2.30 SYT6 | synaptotagmin VI | | | |
| 2.30 — | — | | | |
| -2.30 DMXL2 | Dmx-like 2 | | | |
| -2.30 FOXO1A | forkhead box O1A (rhabdomyosarcoma) | | | |
| -2.30 LOC342892 | Hypothetical protein LOC342892 | | | |
| 2.30 FAM59B | family with sequence similarity 59, member B | | | |
| -2.29 TDRD7 | tudor domain containing 7 | | | |
| -2.29 SLC1A1 | solute carrier family 1 (neuronal/epithelial high affinity glutamate transporter, system Xag), member | | | |
| -2.29 TRAPPC6A | trafficking protein particle complex 6A | | | |
| 2.29 SIAT7E | ST6 (alpha-N-acetyl-neuraminyl-2,3-beta-galactosyl-1,3)-N-acetylgalactosaminide alpha-2,6-sialyltransferase | | | |
| 2.29 SH3-domain GRB2- | SH3-domain GRB2-like pseudogene 3 | | | |
| 2.29 ABHD12 | abhydrolase domain containing 12 | | | |

Appendix 1

| | | |
|---|---|---|
| 2.29 | — | — |
| 2.29 | C13orf18 | chromosome 13 open reading frame 18 |
| 2.29 | PPM1E | protein phosphatase 1E (PP2C domain containing) |
| -2.29 | IQGAP1 | IQ motif containing GTPase activating protein 1 |
| 2.29 | TMEM2 | Transmembrane protein 2 |
| 2.29 | HPCAL4 | hippocalcin like 4 |
| 2.29 | ACCN2 | amiloride-sensitive cation channel 2, neuronal |
| 2.29 | C6orf89 | chromosome 6 open reading frame 89 |
| 2.29 | — | Transcribed locus |
| 2.29 | ABHD3 | abhydrolase domain containing 3 |
| -2.29 | PINK1 | PTEN induced putative kinase 1 |
| -2.29 | LLGL2 | Lethal giant larvae homolog 2 (Drosophila) |
| 2.29 | ARL5B | ADP-ribosylation factor-like 5B |
| -2.29 | — | — |
| 2.29 | — | — |
| -2.29 | C21orf88 | chromosome 21 open reading frame 88 |
| 2.28 | EXOC3 | exocyst complex component 3 |
| -2.28 | ACTN1 | actinin, alpha 1 |
| 2.28 | PIK3R3 | phosphoinositide-3-kinase, regulatory subunit 3 (p55, gamma) |
| 2.28 | PPM1E | protein phosphatase 1E (PP2C domain containing) |
| 2.28 | CREM | cAMP responsive element modulator |
| -2.28 | RBPMS | RNA binding protein with multiple splicing |
| -2.28 | ST7 | suppression of tumorigenicity 7 |
| 2.28 | — | — |
| -2.28 | PNPLA4 | patatin-like phospholipase domain containing 4 |
| 2.28 | STK17A | Serine/threonine kinase 17a (apoptosis-inducing) |
| -2.28 | ETV4 | ets variant gene 4 (E1A enhancer binding protein, E1AF) /// ets variant gene 4 (E1A enhancer binding protein, E1AF |
| 2.28 | MGC21644 | Hypothetical protein MGC21644 |
| 2.28 | DZIP1 | DAZ interacting protein 1 |
| 2.28 | RTN1 | reticulon 1 |
| 2.28 | ZNF710 /// DOCK4 | Zinc finger protein 710 /// MRNA full length insert cDNA clone EUROIMAGE 375854 /// Dedicator of cytokinesis 4 |
| -2.28 | C11orf32 | chromosome 11 open reading frame 32 |
| -2.28 | ZNF589 | zinc finger protein 589 |
| -2.28 | — | — |
| 2.27 | FARSLB | phenylalanine-tRNA synthetase-like, beta subunit |
| 2.27 | CD47 | CD47 molecule |
| -2.27 | — | CDNA clone IMAGE:5311608 |
| -2.27 | RRBP1 | ribosome binding protein 1 homolog 180kDa (dog) |
| 2.27 | LOC643187 | Similar to ankyrin repeat domain 20A |
| 2.27 | FLJ37562 | hypothetical protein FLJ37562 |
| 2.27 | — | — |
| -2.27 | PARVB | parvin, beta |
| 2.27 | POLR3GL | polymerase (RNA) III (DNA directed) polypeptide G (32kD)-like |
| -2.27 | C1orf38 | chromosome 1 open reading frame 38 |
| 2.27 | YAF2 | YY1 associated factor 2 |
| -2.27 | — | — |
| 2.27 | VAPA | VAMP (vesicle-associated membrane protein)-associated protein A, 33kDa |
| 2.27 | — | — |
| -2.27 | ARHGAP28 | Rho GTPase activating protein 28 |
| 2.27 | — | — |
| 2.27 | ELOVL2 | elongation of very long chain fatty acids (FEN1/Elo2, SUR4/Elo3, yeast)-like 2 |
| -2.26 | RASL11B | RAS-like, family 11, member B |
| 2.26 | — | CDNA clone IMAGE:4842353 |
| 2.26 | NRIP1 | nuclear receptor interacting protein 1 |
| 2.26 | LSDP5 | lipid storage droplet protein 5 |
| 2.26 | LOC650392 | Full-length cDNA clone CS0DF015YK23 of Fetal brain of Homo sapiens (human) /// Hypothetical protein LOC650392 |
| -2.26 | TNFRSF21 | tumor necrosis factor receptor superfamily, member 21 |
| -2.26 | MAPK13 | mitogen-activated protein kinase 13 |
| 2.26 | — | — |
| 2.26 | CELSR2 | cadherin, EGF LAG seven-pass G-type receptor 2 (flamingo homolog, Drosophila) |
| -2.26 | ID2 /// ID2B | inhibitor of DNA binding 2, dominant negative helix-loop-helix protein /// inhibitor of DNA binding 2B, dominant negative helix-lo |
| -2.26 | — | — |
| -2.26 | HNRPM | heterogeneous nuclear ribonucleoprotein M |
| 2.26 | — | Transcribed locus |
| -2.26 | DCP2 | DCP2 decapping enzyme homolog (S. cerevisiae) |
| 2.26 | CACNG4 | calcium channel, voltage-dependent, gamma subunit 4 |
| 2.26 | DFNA5 | deafness, autosomal dominant 5 |
| 2.26 | — | CDNA clone IMAGE:5311370 |
| 2.26 | COL11A1 | collagen, type XI, alpha 1 |
| -2.26 | MUC3A | mucin 3A, cell surface associated |
| 2.26 | DDX19 | DEAD (Asp-Glu-Ala-As) box polypeptide 19B |
| -2.25 | PCNXL2 | pecanex-like 2 (Drosophila) |
| -2.25 | ELL3 | elongation factor RNA polymerase II-like 3 |
| 2.25 | ELOVL2 | elongation of very long chain fatty acids (FEN1/Elo2, SUR4/Elo3, yeast)-like 2 |
| 2.25 | — | Homo sapiens, clone IMAGE:5242623 |
| -2.25 | — | — |
| -2.25 | CX62 | connexin 62 |
| -2.25 | DTWD2 | DTW domain containing 2 |
| 2.25 | COL11A1 | collagen, type XI, alpha 1 |

Appendix 1

| | | |
|---|---|---|
| 2.25 | — | — |
| -2.25 | AIG1 | Androgen-induced 1 |
| 2.25 | ZDHHC21 | zinc finger, DHHC-type containing 21 |
| 2.25 | NOG | Noggin |
| -2.25 | FLJ20674 | hypothetical protein FLJ20674 |
| 2.25 | SPAG9 | sperm associated antigen 9 |
| -2.24 | NFIB | nuclear factor I/B |
| -2.24 | MYO5B | myosin VB |
| 2.24 | VEPH1 | ventricular zone expressed PH domain homolog 1 (zebrafish) |
| 2.24 | TP53AP1 | TP53 activated protein 1 |
| -2.24 | HLA-G | HLA-G histocompatibility antigen, class I, G |
| -2.24 | — | — |
| 2.24 | NUP98 | nucleoporin 98kDa |
| -2.24 | SLC9A7 | solute carrier family 9 (sodium/hydrogen exchanger), member 7 |
| 2.24 | MIB1 | mindbomb homolog 1 (Drosophila) |
| -2.24 | DKFZP564O0823 | DKFZP564O0823 protein |
| -2.24 | — | — |
| 2.24 | — | CDNA clone IMAGE:5288594 |
| 2.24 | SMARCD3 | SWI/SNF related, matrix associated, actin dependent regulator of chromatin, subfamily d, member 3 |
| -2.24 | SHANK2 | SH3 and multiple ankyrin repeat domains 2 |
| -2.24 | — | — |
| -2.24 | — | — |
| 2.24 | LOC200169 | hypothetical protein LOC200169 |
| 2.24 | LOC642732 /// LOC | similar to CG10721-PA /// similar to CG10721-PA |
| -2.23 | — | — |
| 2.23 | ENPEP | glutamyl aminopeptidase (aminopeptidase A) |
| -2.23 | PLEKHC1 | pleckstrin homology domain containing, family C (with FERM domain) member 1 |
| 2.23 | MDH1B | malate dehydrogenase 1B, NAD (soluble) |
| -2.23 | ZNF217 | zinc finger protein 217 |
| -2.23 | — | Mesenchymal stem cell protein DSC96 |
| 2.23 | SLC8A3 | Solute carrier family 8 (sodium-calcium exchanger), member 3 |
| 2.23 | VPS24 | vacuolar protein sorting 24 (yeast) |
| 2.23 | — | — |
| 2.23 | PLCL2 | phospholipase C-like 2 |
| -2.23 | — | — |
| 2.23 | KIAA1715 | KIAA1715 |
| 2.23 | LRIG1 | leucine-rich repeats and immunoglobulin-like domains 1 /// leucine-rich repeats and immunoglobulin-like domains 1 |
| -2.23 | C1GALT1 | core 1 synthase, glycoprotein-N-acetylgalactosamine 3-beta-galactosyltransferase, |
| -2.23 | FAM124A | family with sequence similarity 124A |
| 2.23 | — | LOC440309 |
| 2.23 | C1orf62 | chromosome 1 open reading frame 62 |
| 2.23 | LOC92482 | hypothetical protein LOC92482 |
| -2.22 | — | Transcribed locus |
| 2.22 | NIN | ninein (GSK3B interacting protein) |
| 2.22 | FLJ42709 | hypothetical gene supported by AK124699 |
| -2.22 | C14orf156 | chromosome 14 open reading frame 156 /// chromosome 14 open reading frame 156 |
| 2.22 | LOC283012 | hypothetical protein LOC283012 |
| -2.22 | FLRT2 | fibronectin leucine rich transmembrane protein 2 |
| 2.22 | PPIL6 | peptidylprolyl isomerase (cyclophilin)-like 6 |
| 2.22 | SCCPDH | saccharopine dehydrogenase (putative) |
| -2.22 | PINK1 | PTEN induced putative kinase 1 |
| -2.22 | USP28 | ubiquitin specific peptidase 28 |
| 2.22 | TTC23 | tetratricopeptide repeat domain 23 |
| 2.22 | DCX | doublecortex; lissencephaly, X-linked (doublecortin) |
| 2.22 | SEC31B | SEC31 homolog B (S. cerevisiae) |
| 2.22 | EMID1 | EMI domain containing 1 |
| 2.22 | TFDP2 | Transcription factor Dp-2 (E2F dimerization partner 2) |
| -2.22 | LOC730432 | similar to serine/threonine/tyrosine interacting protein |
| 2.22 | ACSBG2 | Acyl-CoA synthetase bubblegum family member 2 |
| 2.21 | GRK5 | G protein-coupled receptor kinase 5 |
| 2.21 | MAGED4 | melanoma antigen family D, 4 /// melanoma antigen family D, 4 |
| 2.21 | BAIAP2 | BAI1-associated protein 2 |
| 2.21 | ZNF585A | zinc finger protein 585A |
| -2.21 | — | — |
| -2.21 | TERT | telomerase reverse transcriptase |
| 2.21 | ZNF710 /// DOCK4 | Zinc finger protein 710 /// MRNA full length insert cDNA clone EUROIMAGE 375854 /// Dedicator of cytokinesis 4 |
| 2.21 | — | — |
| 2.21 | — | — |
| 2.21 | — | — |
| 2.21 | IQCE | IQ motif containing E |
| 2.21 | DLL1 | delta-like 1 (Drosophila) |
| -2.21 | ARFGEF1 | ADP-ribosylation factor guanine nucleotide-exchange factor 1(brefeldin A-inhibited |
| -2.21 | LOC497257 | Hypothetical LOC497257 |
| -2.21 | AOX1 | aldehyde oxidase 1 |
| 2.21 | CLASP1 | Cytoplasmic linker associated protein 1 |
| -2.21 | — | Homo sapiens, Similar to LOC169932, clone IMAGE:4499203, mRNA |
| -2.21 | HLA-DRB1 /// LOC7 | major histocompatibility complex, class II, DR beta 1 /// major histocompatibility complex, class II, DR beta 1 /// hypothetical pr |
| -2.21 | VSIG1 | V-set and immunoglobulin domain containing 1 |
| 2.21 | — | — |

Appendix 1

| | | |
|---|---|---|
| -2.21 | WDHD1 | WD repeat and HMG-box DNA binding protein 1 |
| 2.21 | — | — |
| -2.20 | PCSK1 | proprotein convertase subtilisin/kexin type 1 |
| -2.20 | STARD8 | START domain containing 8 |
| 2.20 | RERG | RAS-like, estrogen-regulated, growth inhibitor |
| 2.20 | CYP7B1 | cytochrome P450, family 7, subfamily B, polypeptide 1 |
| -2.20 | ESRRG | estrogen-related receptor gamma |
| 2.20 | — | Transcribed locus |
| -2.20 | CR1 | complement component (3b/4b) receptor 1 (Knops blood group) |
| 2.20 | FZD3 | frizzled homolog 3 (Drosophila) |
| 2.20 | PFAAP5 | Phosphonoformate immuno-associated protein 5 |
| 2.20 | — | — |
| -2.20 | NEDD4L | neural precursor cell expressed, developmentally down-regulated 4-like |
| 2.20 | — | Homo sapiens, clone IMAGE:4431109, mRNA |
| 2.20 | C21orf34 | Chromosome 21 open reading frame 34 |
| 2.20 | — | — |
| 2.20 | GPR153 | G protein-coupled receptor 153 |
| 2.20 | SRGAP3 | SLIT-ROBO Rho GTPase activating protein 3 |
| 2.20 | — | — |
| 2.20 | MAPK8IP1 | mitogen-activated protein kinase 8 interacting protein 1 |
| -2.20 | CHES1 | checkpoint suppressor 1 |
| -2.20 | FRAT1 | frequently rearranged in advanced T-cell lymphomas |
| -2.20 | L2HGDH | L-2-hydroxyglutarate dehydrogenase |
| 2.19 | CXorf6 | chromosome X open reading frame 6 |
| 2.19 | — | CDNA FLJ45995 fis, clone SKNMC2003639 |
| 2.19 | — | CDNA FLJ37494 fis, clone BRAWH2015385 |
| 2.19 | — | — |
| -2.19 | ZNF649 | zinc finger protein 649 |
| -2.19 | — | — |
| -2.19 | SLFN5 | schlafen family member 5 |
| 2.19 | CUEDC1 | CUE domain containing 1 |
| -2.19 | LOC400713 | zinc finger-like |
| -2.19 | TBX5 | T-box 5 |
| 2.19 | — | — |
| 2.19 | LOC440934 | Hypothetical gene supported by BC008048 |
| -2.19 | TPD52 | tumor protein D52 |
| 2.19 | IGSF9 | immunoglobulin superfamily, member 9 |
| -2.19 | — | — |
| 2.19 | NRTN | neurturin |
| 2.19 | ODF2 | outer dense fiber of sperm tails 2 |
| 2.19 | BEX1 | brain expressed, X-linked 1 |
| -2.19 | CABYR | calcium binding tyrosine-(Y)-phosphorylation regulated (fibrousheathin 2 |
| -2.19 | — | — |
| -2.19 | ITSN2 | intersectin 2 |
| -2.19 | EML2 | echinoderm microtubule associated protein like 2 |
| 2.19 | — | — |
| -2.19 | GCH1 | GTP cyclohydrolase 1 (dopa-responsive dystonia) |
| -2.19 | C10orf118 | chromosome 10 open reading frame 118 |
| 2.19 | — | Clone IMAGE:26186, mRNA sequence |
| 2.19 | SLC35D1 | solute carrier family 35 (UDP-glucuronic acid/UDP-N-acetylgalactosamine dual transporter), member D1 |
| 2.19 | — | MRNA; cDNA DKFZp564E143 (from clone DKFZp564E143) |
| -2.19 | OCEL1 | occludin/ELL domain containing 1 |
| -2.19 | PAK1 | p21/Cdc42/Rac1-activated kinase 1 (STE20 homolog, yeast) |
| 2.19 | ARTS-1 | type 1 tumor necrosis factor receptor shedding aminopeptidase regulator |
| 2.19 | MTX1 | Metaxin 1 |
| 2.19 | EPB41L5 | erythrocyte membrane protein band 4.1 like 5 /// erythrocyte membrane protein band 4.1 like 5 |
| 2.18 | — | — |
| -2.18 | NEFH | neurofilament, heavy polypeptide 200kDa |
| 2.18 | C13orf12 | chromosome 13 open reading frame 12 |
| 2.18 | SLC1A6 | solute carrier family 1 (high affinity aspartate/glutamate transporter), member 6 |
| 2.18 | — | Similar to hypothetical protein |
| 2.18 | DDR1 | discoidin domain receptor family, member 1 |
| 2.18 | H2AFY2 | H2A histone family, member Y2 |
| -2.18 | RRAS2 | related RAS viral (r-ras) oncogene homolog 2 |
| -2.18 | INHBE | inhibin, beta E |
| 2.18 | — | Transcribed locus |
| 2.18 | VIM | vimentin |
| -2.18 | SOCS2 | suppressor of cytokine signaling 2 |
| 2.18 | TFAP2B | transcription factor AP-2 beta (activating enhancer binding protein 2 beta) |
| 2.18 | C13orf18 | chromosome 13 open reading frame 18 |
| 2.18 | — | — |
| -2.17 | ITM2C | integral membrane protein 2C /// integral membrane protein 2C |
| 2.17 | LOX | lysyl oxidase |
| 2.17 | DDR1 | discoidin domain receptor family, member 1 |
| 2.17 | NCOA6 | nuclear receptor coactivator 6 |
| 2.17 | SKAP2 | src kinase associated phosphoprotein 2 |
| 2.17 | FLJ32745 | hypothetical protein FLJ32745 |
| 2.17 | GLT28D1 | glycosyltransferase 28 domain containing 1 |
| 2.17 | RAB7L1 | RAB7, member RAS oncogene family-like 1 |

Appendix 1

| | | |
|---|---|---|
| -2.17 | ETS2 | v-ets erythroblastosis virus E26 oncogene homolog 2 (avian) |
| -2.17 | RHOF | ras homolog gene family, member F (in filopodia) |
| 2.17 | GBX2 | gastrulation brain homeobox 2 |
| 2.17 | — | — |
| 2.17 | RALGDS | ral guanine nucleotide dissociation stimulator |
| 2.17 | — | — |
| -2.17 | CD44 | CD44 molecule (Indian blood group) |
| 2.17 | ALPK2 | alpha-kinase 2 |
| -2.17 | — | — |
| 2.17 | — | MRNA; cDNA DKFZp686F1844 (from clone DKFZp686F1844) |
| -2.17 | PXN | paxillin |
| 2.17 | DLEU2 /// DLEU2L | deleted in lymphocytic leukemia, 2 /// deleted in lymphocytic leukemia 2-like |
| 2.17 | PHF10 | PHD finger protein 10 |
| 2.16 | — | — |
| 2.16 | ARSB | arylsulfatase B |
| 2.16 | SLC16A6 /// LOC44 | solute carrier family 16 (monocarboxylic acid transporters), member 6 /// similar to solute carrier family 16, member 6; monocai |
| 2.16 | SYTL2 | synaptotagmin-like 2 |
| -2.16 | — | — |
| -2.16 | STYX /// LOC73043 | serine/threonine/tyrosine interacting protein /// similar to serine/threonine/tyrosine interacting protein |
| 2.16 | PPM1L | Protein phosphatase 1 (formerly 2C)-like |
| 2.16 | ZNF584 | zinc finger protein 584 |
| -2.16 | — | Transcribed locus |
| 2.16 | LANCL2 | LanC lantibiotic synthetase component C-like 2 (bacterial) |
| 2.16 | FREM1 | FRAS1 related extracellular matrix 1 |
| 2.16 | CYFIP2 | cytoplasmic FMR1 interacting protein 2 /// cytoplasmic FMR1 interacting protein 2 |
| 2.16 | SMYD2 | SET and MYND domain containing 2 |
| -2.16 | SIVA1 | SIVA1, apoptosis-inducing factor |
| -2.16 | ARHGEF10 | Rho guanine nucleotide exchange factor (GEF) 10 |
| -2.16 | GPX7 | glutathione peroxidase 7 |
| -2.16 | DACT2 | dapper, antagonist of beta-catenin, homolog 2 (Xenopus laevis) |
| 2.16 | TEX261 | testis expressed sequence 261 |
| -2.16 | CAV2 | caveolin 2 |
| -2.16 | MCAM | melanoma cell adhesion molecule |
| 2.16 | LSM11 | LSM11, U7 small nuclear RNA associated |
| -2.16 | TOMM7 /// LOC201 | translocase of outer mitochondrial membrane 7 homolog (yeast) /// hypothetical protein LOC201725 |
| -2.15 | NPM3 | nucleophosmin/nucleoplasmin, 3 |
| -2.15 | CA4 | carbonic anhydrase IV |
| 2.15 | RBBP9 | retinoblastoma binding protein 9 |
| -2.15 | — | — |
| -2.15 | — | — |
| 2.15 | CDH2 | cadherin 2, type 1, N-cadherin (neuronal) |
| -2.15 | TA-NFKBH | T-cell activation NFKB-like protein |
| 2.15 | RGS20 | regulator of G-protein signalling 20 |
| 2.15 | — | Transcribed locus |
| -2.15 | — | — |
| -2.15 | HLA-G | HLA-G histocompatibility antigen, class I, G |
| 2.15 | PAM | peptidylglycine alpha-amidating monooxygenase |
| -2.15 | RABGAP1L | RAB GTPase activating protein 1-like |
| -2.15 | HLA-DRB1 | Major histocompatibility complex, class II, DR beta 1 |
| 2.15 | KCNAB1 | potassium voltage-gated channel, shaker-related subfamily, beta member 1 |
| 2.15 | CCNE2 | cyclin E2 |
| -2.15 | SOX4 | SRY (sex determining region Y)-box 4 |
| 2.15 | ENTPD4 | ectonucleoside triphosphate diphosphohydrolase 4 |
| 2.15 | ABHD3 | Abhydrolase domain containing 3 |
| 2.15 | EIF1 | eukaryotic translation initiation factor 1 |
| 2.14 | CALCRL | calcitonin receptor-like |
| -2.14 | BCL6B | B-cell CLL/lymphoma 6, member B (zinc finger protein) |
| -2.14 | — | — |
| -2.14 | MGLL | monoglyceride lipase /// monoglyceride lipase |
| -2.14 | — | — |
| 2.14 | EPB41L4A | erythrocyte membrane protein band 4.1 like 4A |
| 2.14 | — | — |
| -2.14 | TPD52 | tumor protein D52 |
| -2.14 | KIAA1333 | KIAA1333 |
| -2.14 | CXCL1 | chemokine (C-X-C motif) ligand 1 (melanoma growth stimulating activity, alpha) |
| 2.14 | — | — |
| -2.14 | CD109 | CD109 molecule |
| -2.14 | GCNT2 /// SPTLC3 | glucosaminyl (N-acetyl) transferase 2, I-branching enzyme (I blood group) /// serine palmitoyltransferase, long chain base subt |
| 2.14 | CUEDC1 | CUE domain containing 1 |
| 2.14 | NUCB2 | nucleobindin 2 |
| 2.14 | CBX4 | chromobox homolog 4 (Pc class homolog, Drosophila) |
| 2.14 | DDHD2 | DDHD domain containing 2 |
| 2.14 | — | — |
| 2.14 | — | — |
| 2.14 | NPAS3 | Neuronal PAS domain protein 3 |
| 2.14 | — | — |
| 2.14 | FLJ31818 | hypothetical protein FLJ31818 |
| 2.14 | ANAPC7 | anaphase promoting complex subunit 7 |
| -2.13 | KIAA1333 | KIAA1333 |

Appendix 1

| | | |
|---|---|---|
| -2.13 | ARFGEF1 | ADP-ribosylation factor guanine nucleotide-exchange factor 1(brefeldin A-inhibited) |
| 2.13 | CACNG4 | calcium channel, voltage-dependent, gamma subunit 4 |
| 2.13 | COTL1 | Coactosin-like 1 (Dictyostelium) |
| -2.13 | IL20RB | interleukin 20 receptor beta |
| -2.13 | CYP1B1 | cytochrome P450, family 1, subfamily B, polypeptide 1 |
| -2.13 | CLDN11 | claudin 11 (oligodendrocyte transmembrane protein) |
| 2.13 | — | — |
| -2.13 | DNAJC15 | DnaJ (Hsp40) homolog, subfamily C, member 15 |
| -2.13 | ARFGEF1 | ADP-ribosylation factor guanine nucleotide-exchange factor 1(brefeldin A-inhibited) |
| -2.13 | EPHX1 | epoxide hydrolase 1, microsomal (xenobiotic) |
| 2.13 | TRIM73 | tripartite motif-containing 73 |
| -2.13 | SOX4 | SRY (sex determining region Y)-box 4 |
| 2.13 | HOXB2 | homeobox B2 |
| 2.13 | RGMB | RGM domain family, member B |
| 2.13 | — | — |
| 2.13 | COTL1 | coactosin-like 1 (Dictyostelium) |
| -2.13 | MGC20983 | hypothetical protein MGC20983 |
| 2.13 | — | — |
| 2.13 | — | — |
| -2.13 | — | — |
| -2.13 | — | Transcribed locus |
| 2.13 | TRPS1 | trichorhinophalangeal syndrome I |
| 2.13 | MOCS2 | Molybdenum cofactor synthesis 2 |
| 2.13 | — | Transcribed locus |
| -2.13 | LOC646561 | similar to WW45 protein |
| 2.13 | — | Transcribed locus, weakly similar to XP_525597.1 similar to neuronal pentraxin receptor isoform 2 [Pan troglodytes |
| -2.12 | SLC16A3 | solute carrier family 16, member 3 (monocarboxylic acid transporter 4) |
| -2.12 | LOC221442 | hypothetical protein LOC221442 |
| -2.12 | TTC9 | tetratricopeptide repeat domain 9 |
| -2.12 | SHB | Src homology 2 domain containing adaptor protein B |
| 2.12 | PPOX | protoporphyrinogen oxidase |
| 2.12 | WASF3 | WAS protein family, member 3 |
| 2.12 | SLCO3A1 | Solute carrier organic anion transporter family, member 3A1 |
| 2.12 | — | cDNA clone IMAGE:4797645 |
| 2.12 | ZFP90 | Zinc finger protein 90 homolog (mouse) |
| -2.12 | USP53 | Ubiquitin specific peptidase 53 |
| 2.12 | 6-Mar | membrane-associated ring finger (C3HC4) 6 |
| -2.12 | CDKN3 | cyclin-dependent kinase inhibitor 3 (CDK2-associated dual specificity phosphatase) |
| -2.12 | ZFYVE21 | zinc finger, FYVE domain containing 21 |
| 2.12 | — | — |
| -2.12 | ACTN3 | actinin, alpha 3 |
| 2.12 | C6orf65 | chromosome 6 open reading frame 65 |
| 2.12 | DBNDD2 | Dysbindin (dystrobrevin binding protein 1) domain containing 2 |
| 2.12 | FAM49A | family with sequence similarity 49, member A /// family with sequence similarity 49, member A |
| 2.12 | — | — |
| -2.11 | KIAA1529 | KIAA1529 |
| -2.11 | NFIB | nuclear factor I/B |
| 2.11 | SLC16A9 | solute carrier family 16, member 9 (monocarboxylic acid transporter 9) |
| -2.11 | NDRG2 | NDRG family member 2 |
| -2.11 | ZAR1 /// LOC65195 | zygote arrest 1 /// similar to zygote arrest 1 |
| 2.11 | DDR1 | discoidin domain receptor family, member 1 |
| -2.11 | — | — |
| 2.11 | FZD1 | frizzled homolog 1 (Drosophila) |
| 2.11 | TNRC4 | trinucleotide repeat containing 4 |
| 2.11 | UBE2J1 | ubiquitin-conjugating enzyme E2, J1 (UBC6 homolog, yeast) |
| 2.11 | POLR2J2 | DNA directed RNA polymerase II polypeptide J-related gene |
| 2.11 | FBN1 | fibrillin 1 |
| 2.11 | RIT1 | Ras-like without CAAX 1 |
| 2.11 | — | Transcribed locus |
| -2.11 | ZNF589 | zinc finger protein 589 |
| 2.11 | — | — |
| -2.10 | PLA2G12A | phospholipase A2, group XIIA |
| 2.10 | SLC44A5 | solute carrier family 44, member 5 |
| 2.10 | LIG4 | ligase IV, DNA, ATP-dependent |
| 2.10 | DDR1 | discoidin domain receptor family, member 1 |
| -2.10 | LMO6 | LIM domain only 6 |
| 2.10 | TMEM112 | transmembrane protein 112 |
| 2.10 | FHL1 | four and a half LIM domains 1 |
| 2.10 | SFXN3 | Sideroflexin 3 |
| 2.10 | CALML4 | calmodulin-like 4 |
| 2.10 | ASXL1 | additional sex combs like 1 (Drosophila) |
| 2.10 | TTC13 | tetratricopeptide repeat domain 13 |
| 2.10 | DCLRE1C | DNA cross-link repair 1C (PSO2 homolog, S. cerevisiae) |
| -2.10 | — | — |
| -2.10 | PCDHA9 /// PCDHA | protocadherin alpha 9 /// protocadherin alpha subfamily C, 2 /// protocadherin alpha subfamily C, 1 /// protocadherin alpha 13 |
| -2.10 | HLA-DMA | major histocompatibility complex, class II, DM alpha |
| -2.10 | LYN | v-yes-1 Yamaguchi sarcoma viral related oncogene homolog /// v-yes-1 Yamaguchi sarcoma viral related oncogene homolog |
| -2.10 | PPM1A | protein phosphatase 1A (formerly 2C), magnesium-dependent, alpha isoform |
| 2.10 | GFRA1 | GDNF family receptor alpha 1 |

Appendix 1

| Value | Symbol | Description |
|---|---|---|
| 2.10 | RHOBTB1 | Rho-related BTB domain containing 1 |
| 2.10 | DKK3 | dickkopf homolog 3 (Xenopus laevis) |
| -2.09 | RASEF | RAS and EF-hand domain containing |
| -2.09 | — | — |
| -2.09 | EHD4 | EH-domain containing 4 |
| -2.09 | GATA2 | GATA binding protein 2 |
| 2.09 | KIAA1702 | KIAA1702 protein |
| -2.09 | ARHGAP26 | Rho GTPase activating protein 26 |
| -2.09 | MMP24 | matrix metallopeptidase 24 (membrane-inserted) |
| 2.09 | PCDHB14 | protocadherin beta 14 |
| -2.09 | C21orf63 | chromosome 21 open reading frame 63 |
| 2.09 | LRRC37A2 | leucine rich repeat containing 37, member A2 |
| 2.09 | LRRC49 | leucine rich repeat containing 49 |
| -2.09 | — | — |
| 2.09 | — | Cri-du-chat region mRNA, clone NIBB11 |
| 2.09 | QRSL1 | glutaminyl-tRNA synthase (glutamine-hydrolyzing)-like 1 |
| -2.09 | SERPINF1 | serpin peptidase inhibitor, clade F (alpha-2 antiplasmin, pigment epithelium derived factor), member 1 |
| 2.09 | TSGA10 | Testis specific, 10 |
| 2.09 | C3orf50 | chromosome 3 open reading frame 50 |
| 2.09 | KLF3 | Kruppel-like factor 3 (basic) |
| 2.09 | FAM89B | family with sequence similarity 89, member B |
| 2.09 | SLC1A6 | solute carrier family 1 (high affinity aspartate/glutamate transporter), member 6 |
| 2.09 | C11orf17 /// NUAK2 | chromosome 11 open reading frame 17 /// chromosome 11 open reading frame 17 /// NUAK family, SNF1-like kinase, 2 /// NU/ |
| -2.08 | TRAF1 | TNF receptor-associated factor 1 |
| 2.08 | KIF1B | Kinesin family member 1B |
| -2.08 | ITPK1 | inositol 1,3,4-triphosphate 5/6 kinase |
| 2.08 | MECP2 | methyl CpG binding protein 2 (Rett syndrome) |
| 2.08 | FZD9 | frizzled homolog 9 (Drosophila) |
| -2.08 | FER1L3 | fer-1-like 3, myoferlin (C. elegans) |
| 2.08 | — | — |
| 2.08 | — | — |
| -2.08 | LGMN | legumain |
| -2.08 | SLCO4A1 | solute carrier organic anion transporter family, member 4A1 |
| -2.08 | — | — |
| 2.08 | SACS | spastic ataxia of Charlevoix-Saguenay (sacsin) |
| 2.08 | DPYD | dihydropyrimidine dehydrogenase |
| 2.08 | KIAA0644 | KIAA0644 gene product |
| 2.08 | — | — |
| -2.08 | NPY1R | neuropeptide Y receptor Y1 |
| 2.08 | — | Clone 23555 mRNA sequence |
| 2.08 | — | CDNA FLJ37884 fis, clone BRSTN2012451 |
| 2.08 | ST6GALNAC5 | ST6 (alpha-N-acetyl-neuraminyl-2,3-beta-galactosyl-1,3)-N-acetylgalactosaminide alpha-2,6-sialyltransferase 5 /// ST6 (alpha-l |
| -2.08 | CDKN3 | cyclin-dependent kinase inhibitor 3 (CDK2-associated dual specificity phosphatase) |
| 2.08 | — | MRNA; cDNA DKFZp564P073 (from clone DKFZp564P073) |
| 2.08 | — | — |
| -2.08 | CDC14B | CDC14 cell division cycle 14 homolog B (S. cerevisiae) |
| -2.08 | A2BP1 | ataxin 2-binding protein 1 |
| 2.07 | SRrp35 | Serine-arginine repressor protein (35 kDa) |
| -2.07 | ZNF114 | zinc finger protein 114 |
| 2.07 | — | — |
| 2.07 | — | — |
| 2.07 | — | — |
| 2.07 | PAOX | polyamine oxidase (exo-N4-amino) |
| 2.07 | — | — |
| 2.07 | CD47 | CD47 molecule /// CD47 molecule |
| 2.07 | FOXP1 | forkhead box P1 |
| -2.07 | NUMB | numb homolog (Drosophila) |
| 2.07 | WIPF1 | WAS/WASL interacting protein family, member 1 |
| 2.07 | TMEM22 | transmembrane protein 22 |
| -2.07 | ETV4 | ets variant gene 4 (E1A enhancer binding protein, E1AF) |
| -2.07 | MAP4K1 | mitogen-activated protein kinase kinase kinase kinase 1 |
| -2.07 | SLC12A6 | solute carrier family 12 (potassium/chloride transporters), member 6 |
| -2.07 | ANXA11 | annexin A11 |
| 2.07 | SPOCK1 | sparc/osteonectin, cwcv and kazal-like domains proteoglycan (testican) 1 |
| -2.07 | PLSCR4 | phospholipid scramblase 4 |
| -2.07 | WIPI1 | WD repeat domain, phosphoinositide interacting 1 |
| 2.07 | C10orf58 | chromosome 10 open reading frame 58 |
| 2.07 | RUFY3 | RUN and FYVE domain containing 3 |
| 2.06 | TUSC4 | tumor suppressor candidate 4 |
| 2.06 | — | — |
| -2.06 | PCDHA9 /// PCDHA | protocadherin alpha 9 /// protocadherin alpha subfamily C, 2 /// protocadherin alpha subfamily C, 1 /// protocadherin alpha 13 // |
| 2.06 | CD47 | CD47 molecule |
| 2.06 | — | CDNA FLJ40823 fis, clone TRACH2011093 |
| 2.06 | REV3L | REV3-like, catalytic subunit of DNA polymerase zeta (yeast) |
| 2.06 | NUDT4 /// NUDT4P | nudix (nucleoside diphosphate linked moiety X)-type motif 4 /// nudix (nucleoside diphosphate linked moiety X)-type motif 4 ps |
| 2.06 | — | — |
| 2.06 | SAPS3 | SAPS domain family, member 3 |
| 2.06 | — | — |
| 2.06 | CCDC99 | Coiled-coil domain containing 99 |

Appendix 1

| | | |
|---|---|---|
| 2.06 | TMEM107 | transmembrane protein 107 /// transmembrane protein 107 |
| -2.06 | ROD1 | ROD1 regulator of differentiation 1 (S. pombe) |
| -2.06 | ZMYM6 | zinc finger, MYM-type 6 |
| 2.06 | GTF2IRD2 | GTF2I repeat domain containing 2 |
| 2.06 | ZNF346 | Zinc finger protein 346 |
| 2.06 | GRIK2 | glutamate receptor, ionotropic, kainate 2 |
| 2.06 | FLJ22028 | hypothetical protein FLJ22028 |
| -2.05 | — | — |
| -2.05 | ALDH1A3 | Aldehyde dehydrogenase 1 family, member A3 |
| -2.05 | PKP3 | plakophilin 3 |
| -2.05 | AIG1 | Androgen-induced 1 |
| -2.05 | NQO1 | NAD(P)H dehydrogenase, quinone 1 |
| 2.05 | — | — |
| -2.05 | — | — |
| 2.05 | IQCE | IQ motif containing E |
| 2.05 | CEP290 | centrosomal protein 290kDa |
| 2.05 | IGSF4 | immunoglobulin superfamily, member 4 |
| -2.05 | FAM91A2 | family with sequence similarity 91, member A2 |
| -2.05 | MYCBP | c-myc binding protein |
| -2.05 | CES1 | carboxylesterase 1 (monocyte/macrophage serine esterase 1) |
| 2.05 | HNRPR | heterogeneous nuclear ribonucleoprotein R |
| 2.05 | XPA | xeroderma pigmentosum, complementation group A |
| 2.05 | — | — |
| 2.05 | RNF130 | Ring finger protein 130 |
| -2.05 | TRIB1 | tribbles homolog 1 (Drosophila) |
| 2.05 | — | — |
| 2.05 | — | — |
| -2.05 | PLS1 | plastin 1 (I isoform) |
| -2.05 | RGS10 | regulator of G-protein signalling 10 |
| -2.05 | SEMA4A | sema domain, immunoglobulin domain (Ig), transmembrane domain (TM) and short cytoplasmic domain, (semaphorin) 4A |
| 2.05 | — | CDNA clone IMAGE:4801297 |
| 2.05 | M11S1 | membrane component, chromosome 11, surface marker 1 |
| -2.04 | PFKP | phosphofructokinase, platelet |
| -2.04 | BMPR1A | Bone morphogenetic protein receptor, type IA |
| 2.04 | NRCAM | Neuronal cell adhesion molecule |
| -2.04 | ASL | argininosuccinate lyase |
| 2.04 | KIAA1377 | KIAA1377 protein |
| -2.04 | NFIB | nuclear factor I/B |
| -2.04 | NINJ2 | Ninjurin 2 |
| -2.04 | BFSP1 | beaded filament structural protein 1, filensin |
| -2.04 | — | — |
| 2.04 | MSI1 | musashi homolog 1 (Drosophila) |
| 2.04 | — | Transcribed locus |
| 2.04 | — | — |
| 2.04 | — | CDNA FLJ36544 fis, clone TRACH2006378 |
| -2.04 | P4H-4 | hypoxia-inducible factor prolyl 4-hydroxylase |
| -2.04 | STYK1 | serine/threonine/tyrosine kinase 1 /// serine/threonine/tyrosine kinase 1 |
| -2.04 | — | Transcribed locus |
| 2.04 | INSM1 | insulinoma-associated 1 |
| -2.04 | SNRPN | small nuclear ribonucleoprotein polypeptide N |
| 2.04 | PCGF5 | polycomb group ring finger 5 |
| 2.04 | MDSRP | myelodysplastic syndromes relative |
| 2.04 | SLC25A30 | Solute carrier family 25, member 30 |
| 2.04 | CRB1 | crumbs homolog 1 (Drosophila) |
| -2.03 | CD74 | CD74 molecule, major histocompatibility complex, class II invariant chain |
| -2.03 | — | — |
| 2.03 | TFAP2A | transcription factor AP-2 alpha (activating enhancer binding protein 2 alpha) |
| 2.03 | — | — |
| 2.03 | ABHD14A | abhydrolase domain containing 14A |
| 2.03 | — | — |
| -2.03 | CAPN1 | calpain 1, (mu/I) large subunit |
| 2.03 | HS3ST3B1 | heparan sulfate (glucosamine) 3-O-sulfotransferase 3B1 |
| 2.03 | — | — |
| -2.03 | MXRA5 | matrix-remodelling associated 5 |
| 2.03 | NEDD9 | neural precursor cell expressed, developmentally down-regulated 9 |
| 2.03 | E2F2 | E2F transcription factor 2 |
| 2.03 | RAB3IP | RAB3A interacting protein (rabin3) |
| -2.03 | COL4A3BP | Collagen, type IV, alpha 3 (Goodpasture antigen) binding protein |
| 2.03 | VASH1 | Vasohibin 1 |
| 2.03 | PITPNC1 | phosphatidylinositol transfer protein, cytoplasmic 1 |
| -2.03 | SLC44A1 | solute carrier family 44, member 1 |
| -2.03 | NDUFA1 | NADH dehydrogenase (ubiquinone) 1 alpha subcomplex, 1, 7.5kDa |
| 2.03 | CXorf57 | chromosome X open reading frame 57 |
| 2.03 | — | — |
| -2.03 | LOC284242 | hypothetical protein LOC284242 |
| -2.03 | NEB | Nebulin |
| 2.03 | MEGF10 | multiple EGF-like-domains 10 |
| -2.02 | FLJ20449 | hypothetical protein FLJ20449 |
| -2.02 | PWCR1 | Prader-Willi syndrome chromosome region 1 |

Appendix 1

| | | |
|---|---|---|
| 2.02 | VPS24 | vacuolar protein sorting 24 homolog (S. cerevisiae) |
| -2.02 | WDR59 | WD repeat domain 59 |
| 2.02 | DTX4 | deltex 4 homolog (Drosophila) |
| 2.02 | HECTD2 | HECT domain containing 2 |
| 2.02 | PBK | PDZ binding kinase |
| 2.02 | SOX11 | SRY (sex determining region Y)-box 11 |
| -2.02 | SYN2 | synapsin II |
| 2.02 | FBS1 | Fibrosin 1 |
| -2.02 | GMPR2 | guanosine monophosphate reductase 2 |
| -2.02 | FER1L3 | fer-1-like 3, myoferlin (C. elegans) |
| -2.02 | — | CDNA clone IMAGE:4819775 |
| 2.02 | WWC1 | WW and C2 domain containing 1 |
| 2.02 | SNRPE | small nuclear ribonucleoprotein polypeptide E |
| 2.02 | — | — |
| -2.02 | AHNAK | AHNAK nucleoprotein (desmoyokin) |
| 2.02 | — | Transcribed locus |
| -2.02 | CTSC | cathepsin C |
| 2.02 | KIAA0101 | KIAA0101 |
| 2.02 | DERA | 2-deoxyribose-5-phosphate aldolase homolog (C. elegans) |
| 2.02 | LOC441440 | hypothetical LOC441440 |
| -2.01 | PDE5A | phosphodiesterase 5A, cGMP-specific |
| 2.01 | — | CDNA: FLJ22256 fis, clone HRC02860 |
| -2.01 | DKFZP564I1171 | DKFZP564I1171 protein |
| 2.01 | SLIT2 | slit homolog 2 (Drosophila) |
| 2.01 | — | — |
| 2.01 | LOC645722 | hypothetical LOC645722 |
| 2.01 | — | — |
| -2.01 | VAMP1 | vesicle-associated membrane protein 1 (synaptobrevin 1) |
| 2.01 | — | — |
| 2.01 | CDK5R1 | cyclin-dependent kinase 5, regulatory subunit 1 (p35) |
| 2.01 | — | — |
| -2.01 | CST4 | cystatin S |
| 2.01 | NBPF1 | neuroblastoma breakpoint family, member 1 |
| -2.01 | C11orf67 | chromosome 11 open reading frame 67 |
| -2.01 | FLJ35848 | hypothetical protein FLJ35848 |
| 2.01 | — | CDNA clone IMAGE:4831311 |
| 2.01 | FZD2 | frizzled homolog 2 (Drosophila) |
| 2.01 | — | — |
| -2.01 | SORBS1 | sorbin and SH3 domain containing 1 |
| 2.01 | NEBL | nebulette |
| -2.01 | — | — |
| 2.01 | LONP2 | Lon peptidase 2, peroxisomal |
| 2.01 | DKFZp313A2432 | hypothetical protein DKFZp313A2432 |
| -2.01 | CD164 | CD164 molecule, sialomucin |
| 2.01 | — | — |
| 2.01 | — | — |
| 2.01 | FAM33A | family with sequence similarity 33, member A |
| 2.00 | ITGB8 | integrin, beta 8 |
| 2.00 | SMARCA4 | SWI/SNF related, matrix associated, actin dependent regulator of chromatin, subfamily a, member 4 |
| 2.00 | ZDHHC21 | zinc finger, DHHC-type containing 21 |
| -2.00 | KLHL24 | kelch-like 24 (Drosophila) |
| 2.00 | SLC6A16 | Solute carrier family 6, member 16 |
| 2.00 | — | — |
| 2.00 | SLC35F1 | solute carrier family 35, member F1 |
| -2.00 | DNAJB6 | DnaJ (Hsp40) homolog, subfamily B, member 6 |
| -2.00 | SIGIRR | single immunoglobulin and toll-interleukin 1 receptor (TIR) domain |
| -2.00 | MNAT1 | menage a trois homolog 1, cyclin H assembly factor (Xenopus laevis) |
| 2.00 | COL11A1 | collagen, type XI, alpha 1 |
| 2.00 | TNRC9 | trinucleotide repeat containing 9 |
| -2.00 | — | — |
| -2.00 | LOC388237 /// LOC | similar to kidney-specific protein (KS) /// similar to nuclear pore complex interacting protein /// similar to kidney-specific protein |
| -2.00 | — | — |
| -2.00 | SP110 | SP110 nuclear body protein |
| -2.00 | C20orf59 | chromosome 20 open reading frame 59 |
| 2.00 | HS2ST1 | heparan sulfate 2-O-sulfotransferase 1 |
| 2.00 | IPO9 | Importin 9 |
| -2.00 | C20orf39 | chromosome 20 open reading frame 39 |
| -2.00 | — | — |
| 2.00 | ACCN2 | amiloride-sensitive cation channel 2, neuronal |
| 2.00 | WDR42A | WD repeat domain 42A |
| 2.00 | PIP5K1B | phosphatidylinositol-4-phosphate 5-kinase, type I, beta |
| 2.00 | EFHC1 | EF-hand domain (C-terminal) containing 1 |
| -2.00 | RCN3 | reticulocalbin 3, EF-hand calcium binding domain |
| 2.00 | — | Clone FLB8310 PRO2225 |
| 2.00 | TCF12 | transcription factor 12 (HTF4, helix-loop-helix transcription factors 4) |
| -2.00 | DTX2 | deltex homolog 2 (Drosophila) |
| 2.00 | RAB32 | RAB32, member RAS oncogene family |
| 2.00 | — | — |
| -2.00 | MFAP3L | microfibrillar-associated protein 3-like |

Appendix 1 er 1 type 1 and type 1-like), transmembrane domain (TM) and short cytoplasmic domain, (semaphorin) 5E
nber 10b
gulated (fibrousheathin 2
member 2A1

// erythrocyte membrane protein band 4.1 like !

-activated protein kinase 1C

-associated 2 iae)
 elegans)

evisiae)

ium-activated channel, subfamily N, member 2
otein e L, 7.6kDa
isiae) /// vacuolar protein sorting 37 homolog B (S. cerevisiae a disease (laforin Zp564C203)
ene homolog (avian)

mber 2 roblastoma of Homo sapiens (human)
ubfamily C, 2 /// protocadherin alpha subfamily C, 1 /// protocadherin alpha 13 /// protocadherin alpha 12 /// protocadherin alpha 11 /// protocadherin alpha 10 //

Appendix 1 to nuclear pore complex interacting protein /// similar to kidney-specific protein (KS) /// similar to kidney-specific protein (KS yeast)
56), gamma isoform
arboxylate transporter), member 3

-like te region mRNA fragment

-gulated (fibrousheathin 2
nber 12A

Appendix 1

| MMC P0 | | |
|---|---|---|
| Est Log Ratio | Gene Symbol | Gene Descriptor |
| -10.18 | LEFTY1 | left-right determination factor 1 |
| 9.80 | — | |
| 8.53 | HOXA1 | homeobox A1 |
| 8.42 | — | |
| 7.74 | — | |
| 7.53 | — | |
| -7.30 | LEFTY2 | left-right determination factor 2 |
| 7.12 | GPR177 | G protein-coupled receptor 177 |
| 7.09 | LOC145786 | hypothetical protein LOC145786 |
| 7.05 | CYP1B1 | cytochrome P450, family 1, subfamily B, polypeptide 1 |
| 7.01 | — | |
| 7.00 | MSX1 | msh homeobox 1 |
| 6.85 | HOXB8 | homeobox B8 |
| 6.78 | HOXC6 | homeobox C6 |
| 6.78 | ATP6V0D2 | ATPase, H+ transporting, lysosomal 38kDa, V0 subunit d2 |
| 6.68 | AGTRL1 | angiotensin II receptor-like 1 |
| -6.66 | DPPA5 | developmental pluripotency associated 5 |
| 6.60 | CYP1A1 | cytochrome P450, family 1, subfamily A, polypeptide 1 |
| 6.56 | GPR56 | G protein-coupled receptor 56 |
| 6.53 | — | Homo sapiens, clone IMAGE:5019307, mRNA |
| -6.50 | DPPA3 | developmental pluripotency associated 3 |
| 6.46 | — | |
| 6.44 | HOXB6 | Homeo box B6 |
| 6.36 | — | |
| 6.34 | CDX2 | caudal type homeobox transcription factor 2 |
| 6.33 | — | Homo sapiens, clone IMAGE:5019307, mRNA |
| 6.26 | HOXD4 | homeobox D4 |
| 6.20 | HOXB3 | homeobox B3 |
| 6.19 | — | |
| 6.16 | — | |
| 6.15 | DLX5 | distal-less homeobox 5 |
| 6.12 | COL2A1 | collagen, type II, alpha 1 (primary osteoarthritis, spondyloepiphyseal dysplasia, congenital |
| 6.11 | TFAP2B | transcription factor AP-2 beta (activating enhancer binding protein 2 beta) |
| 6.09 | — | |
| 6.08 | CDX1 | caudal type homeobox transcription factor 1 |
| 6.05 | TFAP2A | transcription factor AP-2 alpha (activating enhancer binding protein 2 alpha) |
| 6.05 | NYD-SP14 | NYD-SP14 protein |
| 6.02 | HOXB6 | homeobox B6 |
| 5.99 | HAND1 | heart and neural crest derivatives expressed 1 |
| 5.91 | LIX1 | Lix1 homolog (mouse) |
| 5.89 | — | |
| -5.89 | PAX6 | paired box gene 6 (aniridia, keratitis) |
| -5.87 | LOC136288 | hypothetical protein LOC136288 |
| 5.81 | — | CDNA FLJ12425 fis, clone MAMMA1003104 |
| 5.81 | GRHL3 | grainyhead-like 3 (Drosophila) |
| 5.76 | — | |
| 5.72 | LEF1 | lymphoid enhancer-binding factor 1 |
| 5.67 | RSPO3 | R-spondin 3 homolog (Xenopus laevis) |
| 5.66 | DKFZP686A01247 | hypothetical protein |
| 5.65 | ZNF750 | zinc finger protein 750 |
| 5.65 | — | CDNA FLJ33981 fis, clone DFNES2004608 |
| 5.60 | — | |
| -5.60 | CAV1 | caveolin 1, caveolae protein, 22kDa |
| 5.57 | — | Transcribed locus |
| 5.55 | — | |
| 5.51 | — | |
| 5.48 | DKFZP686A01247 | hypothetical protein |
| 5.47 | FBXL21 | F-box and leucine-rich repeat protein 21 |
| 5.46 | CYP1B1 | cytochrome P450, family 1, subfamily B, polypeptide 1 |
| 5.44 | WNT6 | wingless-type MMTV integration site family, member 6 |
| 5.43 | TCBA1 | T-cell lymphoma breakpoint associated target 1 |
| 5.41 | MSX2 | msh homeobox 2 |
| -5.40 | PPP1R16B | protein phosphatase 1, regulatory (inhibitor) subunit 16B |
| 5.38 | WNT8A | wingless-type MMTV integration site family, member 8A |
| 5.37 | — | |
| 5.32 | VGLL1 | vestigial like 1 (Drosophila) |
| 5.31 | HOXD3 | homeobox D3 |
| 5.30 | LOC284530 | hypothetical protein LOC284530 |
| -5.29 | HBA2 | hemoglobin, alpha 2 /// hemoglobin, alpha 2 |

Appendix 1

| | | |
|---|---|---|
| 5.26 | LOC729620 | Hypothetical protein LOC729620 |
| 5.25 | — | — |
| -5.24 | LOC153469 | hypothetical protein LOC153469 |
| -5.24 | HBA1 /// HBA2 | hemoglobin, alpha 1 /// hemoglobin, alpha 2 |
| 5.24 | CYP1B1 | cytochrome P450, family 1, subfamily B, polypeptide 1 |
| -5.21 | CYP26A1 | cytochrome P450, family 26, subfamily A, polypeptide 1 |
| 5.21 | FGFBP1 | fibroblast growth factor binding protein 1 |
| 5.20 | KIAA1462 | KIAA1462 |
| 5.14 | COL2A1 | collagen, type II, alpha 1 (primary osteoarthritis, spondyloepiphyseal dysplasia, congenital |
| 5.12 | YAF2 | YY1 associated factor 2 |
| -5.11 | SCNN1B | sodium channel, nonvoltage-gated 1, beta (Liddle syndrome) |
| 5.11 | PAX2 | paired box gene 2 |
| -5.10 | PRDM14 | PR domain containing 14 |
| 5.08 | LEF1 | lymphoid enhancer-binding factor 1 |
| 5.08 | ATP12A | ATPase, H+/K+ transporting, nongastric, alpha polypeptide |
| 5.03 | PRTG | protogenin homolog (Gallus gallus) |
| 5.03 | TNFRSF19 | tumor necrosis factor receptor superfamily, member 19 |
| 5.02 | FOXF1 | forkhead box F1 |
| 4.97 | DKFZP686A01247 | hypothetical protein |
| 4.97 | EPSTI1 | Epithelial stromal interaction 1 (breast) |
| -4.93 | — | Transcribed locus |
| 4.92 | CYP1B1 | cytochrome P450, family 1, subfamily B, polypeptide 1 |
| -4.91 | GPR64 | G protein-coupled receptor 64 |
| -4.90 | UTF1 | undifferentiated embryonic cell transcription factor 1 |
| 4.88 | SNAI2 | snail homolog 2 (Drosophila) |
| -4.87 | GLS2 | glutaminase 2 (liver, mitochondrial) |
| 4.86 | C12orf46 | chromosome 12 open reading frame 46 |
| 4.84 | — | — |
| 4.82 | — | — |
| 4.80 | MBNL2 | muscleblind-like 2 (Drosophila) |
| 4.80 | — | — |
| 4.79 | NTF3 | neurotrophin 3 |
| 4.79 | PKNOX2 | PBX/knotted 1 homeobox 2 |
| 4.75 | GAB2 | GRB2-associated binding protein 2 |
| 4.75 | — | — |
| 4.73 | HOP | homeodomain-only protein /// homeodomain-only protein |
| -4.69 | GNA14 | guanine nucleotide binding protein (G protein), alpha 14 |
| 4.69 | FAM70A | family with sequence similarity 70, member A |
| -4.69 | LOC388638 | hypothetical LOC388638 |
| 4.67 | FLJ20366 | hypothetical protein FLJ20366 |
| 4.65 | GREM1 | gremlin 1, cysteine knot superfamily, homolog (Xenopus laevis) |
| 4.63 | — | — |
| 4.61 | LAMB4 | laminin, beta 4 |
| 4.61 | HOXB7 | homeobox B7 |
| 4.60 | MSX2 | msh homeobox 2 |
| 4.60 | — | — |
| 4.58 | HOXB5 | Homeobox B5 |
| 4.58 | — | — |
| 4.58 | — | Transcribed locus |
| -4.58 | THBS2 | thrombospondin 2 |
| 4.55 | — | — |
| 4.55 | HOXD1 | homeobox D1 |
| -4.54 | C10orf96 | chromosome 10 open reading frame 96 |
| 4.53 | ARL4C | ADP-ribosylation factor-like 4C |
| 4.53 | WNT5B | wingless-type MMTV integration site family, member 5B /// wingless-type MMTV integration site family, member 5B |
| 4.52 | PRRX1 | Paired related homeobox 1 |
| 4.52 | DNMBP | Dynamin binding protein |
| -4.51 | PPP1R16B | protein phosphatase 1, regulatory (inhibitor) subunit 16B |
| -4.51 | LOC202451 | hypothetical protein LOC202451 |
| 4.51 | FBXL21 | F-box and leucine-rich repeat protein 21 |
| 4.50 | PRRX1 | paired related homeobox 1 |
| 4.50 | SMYD2 | SET and MYND domain containing 2 |
| 4.48 | ARL4C | ADP-ribosylation factor-like 4C |
| 4.47 | C4orf18 | chromosome 4 open reading frame 18 |
| -4.44 | ARGBP2 | Sorbin and SH3 domain containing 2 |
| 4.44 | — | — |
| -4.43 | OR2H1 | Olfactory receptor, family 2, subfamily H, member 1 |
| 4.33 | KCNJ13 | potassium inwardly-rectifying channel, subfamily J, member 13 |
| 4.33 | — | — |
| 4.33 | HOXB7 | homeobox B7 |
| 4.33 | HAPLN1 | hyaluronan and proteoglycan link protein 1 |
| 4.32 | GREM1 | gremlin 1, cysteine knot superfamily, homolog (Xenopus laevis) |
| 4.32 | COMMD1 | Copper metabolism (Murr1) domain containing 1 |
| 4.31 | HOXB7 | homeobox B7 |
| 4.29 | T | T, brachyury homolog (mouse) |
| 4.27 | FLJ25477 | Hypothetical protein FLJ25477 |
| 4.26 | — | — |
| 4.25 | MBNL3 | muscleblind-like 3 (Drosophila) |
| -4.25 | FZD5 | frizzled homolog 5 (Drosophila) |

Appendix 1

| | | |
|---|---|---|
| 4.25 | HAPLN1 | hyaluronan and proteoglycan link protein 1 |
| 4.23 | RGS4 | regulator of G-protein signalling 4 |
| -4.21 | — | — |
| -4.19 | NANOG | Nanog homeobox |
| 4.18 | HOXA5 | homeobox A5 |
| -4.17 | ST8SIA1 | ST8 alpha-N-acetyl-neuraminide alpha-2,8-sialyltransferase 1 |
| 4.16 | WDR78 | WD repeat domain 78 |
| 4.15 | FLJ39155 | hypothetical protein FLJ39155 |
| -4.10 | KIAA1244 | KIAA1244 |
| 4.09 | — | . |
| -4.08 | HBA1 /// HBA2 | hemoglobin, alpha 1 /// hemoglobin, alpha 1 /// hemoglobin, alpha 2 /// hemoglobin, alpha 2 |
| -4.08 | AKR1C3 | aldo-keto reductase family 1, member C3 (3-alpha hydroxysteroid dehydrogenase, type II |
| -4.08 | — | CDNA FLJ12557 fis, clone NT2RM4000783 |
| 4.06 | — | — |
| -4.06 | DDX43 | DEAD (Asp-Glu-Ala-Asp) box polypeptide 43 |
| 4.06 | MESP1 | mesoderm posterior 1 homolog (mouse) /// mesoderm posterior 1 homolog (mouse) |
| 4.06 | WNT5A | Wingless-type MMTV integration site family, member 5A |
| 4.06 | PAMCI | peptidylglycine alpha-amidating monooxygenase COOH-terminal interactor |
| 4.06 | — | Transcribed locus |
| 4.03 | LOC284033 | hypothetical protein LOC284033 |
| 4.02 | — | — |
| 4.01 | — | — |
| 4.01 | CDH11 | cadherin 11, type 2, OB-cadherin (osteoblast) |
| 3.98 | HOXA9 | homeobox A9 |
| 3.98 | DAZ1 /// DAZ3 /// D. | deleted in azoospermia 1 /// deleted in azoospermia 3 /// deleted in azoospermia 2 /// deleted in azoospermia 4 |
| 3.98 | HOXC9 | homeobox C9 |
| 3.97 | DACH1 | dachshund homolog 1 (Drosophila) |
| -3.96 | CER1 | cerberus 1, cysteine knot superfamily, homolog (Xenopus laevis) |
| 3.96 | PLA2G2A | phospholipase A2, group IIA (platelets, synovial fluid) |
| 3.95 | FLJ25694 | hypothetical protein FLJ25694 |
| 3.95 | GPR56 | G protein-coupled receptor 56 |
| 3.95 | DLX6 | distal-less homeo box 6 |
| -3.93 | — | — |
| 3.93 | LOC283537 | hypothetical protein LOC283537 |
| 3.92 | LOC440925 | Hypothetical gene supported by AK123485 |
| 3.91 | TNNC1 | troponin C type 1 (slow) |
| 3.91 | GPATC2 | G patch domain containing 2 |
| 3.91 | FLJ39609 | Hypothetical protein FLJ39609 |
| 3.90 | HOXB9 | homeobox B9 |
| 3.90 | — | Homo sapiens, clone IMAGE:6155889, mRNA |
| 3.90 | DAZ1 /// DAZ3 /// D. | deleted in azoospermia 1 /// deleted in azoospermia 3 /// deleted in azoospermia 2 /// deleted in azoospermia 4 |
| 3.90 | TFAP2A | transcription factor AP-2 alpha (activating enhancer binding protein 2 alpha) |
| -3.89 | — | — |
| -3.88 | CAV1 | caveolin 1, caveolae protein, 22kDa |
| -3.88 | MOG | myelin oligodendrocyte glycoprotein |
| 3.88 | KIAA1462 | KIAA1462 |
| -3.86 | PYGM | phosphorylase, glycogen; muscle (McArdle syndrome, glycogen storage disease type V |
| 3.85 | — | — |
| 3.85 | WDR52 | WD repeat domain 52 |
| 3.84 | DAZ1 /// DAZ3 /// D. | deleted in azoospermia 1 /// deleted in azoospermia 3 /// deleted in azoospermia 2 /// deleted in azoospermia 4 |
| -3.83 | EVI1 | ecotropic viral integration site 1 |
| -3.81 | MMP9 | matrix metallopeptidase 9 (gelatinase B, 92kDa gelatinase, 92kDa type IV collagenase) |
| 3.80 | WNT5A | wingless-type MMTV integration site family, member 5A |
| 3.80 | TOR1AIP2 | torsin A interacting protein 2 |
| 3.80 | HCRTR2 | hypocretin (orexin) receptor 2 |
| 3.80 | LHFP | lipoma HMGIC fusion partner |
| 3.80 | FAM123A | family with sequence similarity 123A |
| -3.79 | FZD5 | frizzled homolog 5 (Drosophila) /// frizzled homolog 5 (Drosophila) |
| 3.79 | TBC1D9 | TBC1 domain family, member 9 (with GRAM domain) |
| 3.78 | EYA2 | eyes absent homolog 2 (Drosophila) |
| 3.77 | BAALC | brain and acute leukemia, cytoplasmic |
| 3.77 | — | — |
| 3.76 | — | — |
| 3.76 | KIAA0895 | KIAA0895 protein |
| 3.75 | SERPINA1 | serpin peptidase inhibitor, clade A (alpha-1 antiproteinase, antitrypsin), member 1 |
| 3.73 | — | MRNA; cDNA DKFZp779M2422 (from clone DKFZp779M2422) |
| -3.72 | CALB1 | calbindin 1, 28kDa |
| 3.72 | CREBBP | CREB binding protein (Rubinstein-Taybi syndrome) |
| 3.71 | IMPG1 | interphotoreceptor matrix proteoglycan 1 |
| -3.71 | FLI1 | Friend leukemia virus integration 1 |
| 3.70 | — | — |
| 3.70 | IFIT5 | interferon-induced protein with tetratricopeptide repeats 5 |
| 3.70 | SLITRK6 | SLIT and NTRK-like family, member 6 |
| 3.70 | HPGD | Hydroxyprostaglandin dehydrogenase 15-(NAD |
| -3.69 | — | — |
| 3.68 | DAZ1 /// DAZ3 /// D. | deleted in azoospermia 1 /// deleted in azoospermia 3 /// deleted in azoospermia 2 /// deleted in azoospermia 4 |
| 3.66 | FZD10 | frizzled homolog 10 (Drosophila) |
| 3.66 | — | — |
| 3.64 | HOXD4 | homeobox D4 |

Appendix 1

| | | |
|---|---|---|
| -3.63 | HBA1 /// HBA2 | hemoglobin, alpha 1 /// hemoglobin, alpha 1 /// hemoglobin, alpha 2 /// hemoglobin, alpha 2 |
| 3.63 | — | — |
| -3.63 | ARGBP2 | Sorbin and SH3 domain containing 2 |
| 3.63 | — | — |
| 3.63 | ZNF287 | zinc finger protein 287 |
| 3.62 | — | — |
| 3.62 | SOX3 | SRY (sex determining region Y)-box 3 |
| 3.62 | TCEA3 | transcription elongation factor A (SII), 3 |
| 3.61 | COL3A1 | collagen, type III, alpha 1 (Ehlers-Danlos syndrome type IV, autosomal dominant |
| 3.60 | WNT5A | wingless-type MMTV integration site family, member 5A /// wingless-type MMTV integration site family, member 5A |
| -3.60 | RMST | rhabdomyosarcoma 2 associated transcript (non-coding RNA) |
| 3.60 | MLLT3 | myeloid/lymphoid or mixed-lineage leukemia (trithorax homolog, Drosophila); translocated to, 3 |
| -3.58 | — | — |
| 3.58 | SOX3 | SRY (sex determining region Y)-box 3 |
| -3.58 | GDF3 | growth differentiation factor 3 |
| 3.57 | — | Transcribed locus |
| 3.57 | MCOLN3 | mucolipin 3 |
| -3.57 | — | — |
| 3.56 | PSCD1 | Pleckstrin homology, Sec7 and coiled-coil domains 1(cytohesin 1) |
| -3.55 | DAAM2 | Dishevelled associated activator of morphogenesis 2 |
| 3.54 | NRP1 | neuropilin 1 |
| 3.54 | GAD1 | glutamate decarboxylase 1 (brain, 67kDa) |
| 3.53 | KIAA1822L | KIAA1822-like |
| 3.53 | — | — |
| 3.53 | HOXA10 | homeobox A10 |
| 3.53 | MAPK1 | Mitogen-activated protein kinase 1 |
| 3.51 | PPP3R1 | Protein phosphatase 3 (formerly 2B), regulatory subunit B, 19kDa, alpha isoform (calcineurin B, type I |
| 3.51 | SLIT2 | slit homolog 2 (Drosophila) |
| 3.51 | COL3A1 | collagen, type III, alpha 1 (Ehlers-Danlos syndrome type IV, autosomal dominant |
| 3.50 | HOXA3 | Homeo box A3 |
| 3.50 | — | — |
| -3.50 | LOC157627 | hypothetical protein LOC157627 |
| 3.49 | CLDN4 | claudin 4 |
| 3.49 | TEX10 | Testis expressed sequence 10 |
| 3.47 | TMPRSS13 | transmembrane protease, serine 13 |
| 3.46 | — | CDNA FLJ34826 fis, clone NT2NE2008803 |
| 3.46 | DLX6 | distal-less homeo box 6 |
| 3.45 | SLC6A15 | solute carrier family 6, member 15 |
| -3.45 | — | — |
| 3.45 | MTHFD1L | Methylenetetrahydrofolate dehydrogenase (NADP+ dependent) 1-like |
| 3.45 | GUCY1A3 | guanylate cyclase 1, soluble, alpha 3 |
| 3.44 | DAZ1 /// DAZ3 /// D. | deleted in azoospermia 1 /// deleted in azoospermia 3 /// deleted in azoospermia 2 /// deleted in azoospermia 4 |
| -3.44 | C10orf90 | chromosome 10 open reading frame 90 |
| 3.44 | UPK2 | uroplakin 2 |
| 3.44 | PLAGL1 | pleiomorphic adenoma gene-like 1 |
| -3.43 | NODAL | nodal homolog (mouse) |
| -3.43 | C20orf54 | chromosome 20 open reading frame 54 |
| 3.42 | ARL4C | ADP-ribosylation factor-like 4C |
| 3.42 | D2HGDH | D-2-hydroxyglutarate dehydrogenase |
| -3.41 | KBTBD9 | kelch repeat and BTB (POZ) domain containing 9 |
| 3.41 | LHFP | Lipoma HMGIC fusion partner |
| -3.41 | — | Transcribed locus |
| 3.41 | ALCAM | Activated leukocyte cell adhesion molecule |
| 3.41 | CA12 | carbonic anhydrase XII |
| 3.41 | SBF2 | SET binding factor 2 |
| 3.41 | HOXC5 | homeobox C5 |
| 3.41 | — | MRNA; cDNA DKFZp779F2345 (from clone DKFZp779F2345) |
| -3.40 | RASGRP2 | RAS guanyl releasing protein 2 (calcium and DAG-regulated) |
| -3.39 | INDO | indoleamine-pyrrole 2,3 dioxygenase |
| -3.39 | KCTD4 | potassium channel tetramerisation domain containing 4 |
| 3.39 | ID4 | inhibitor of DNA binding 4, dominant negative helix-loop-helix protein |
| 3.39 | — | — |
| -3.39 | — | MRNA; cDNA DKFZp313A1040 (from clone DKFZp313A1040) |
| 3.39 | CTNND1 | Catenin (cadherin-associated protein), delta 1 |
| 3.38 | ALPK2 | alpha-kinase 2 |
| -3.38 | AK3 | Adenylate kinase 3-like 1 |
| 3.37 | FLJ32447 | hypothetical protein LOC151278 |
| 3.35 | EME2 | Essential meiotic endonuclease 1 homolog 2 (S. pombe) |
| -3.34 | GPR | putative G protein coupled receptor |
| 3.34 | DMRT1 | doublesex and mab-3 related transcription factor 1 |
| 3.33 | FOLR1 | folate receptor 1 (adult) |
| 3.33 | CREBL1 /// TNXB | cAMP responsive element binding protein-like 1 /// cAMP responsive element binding protein-like 1 /// tenascin XB /// tenascin |
| -3.31 | CALB1 | calbindin 1, 28kDa |
| 3.31 | — | — |
| 3.31 | — | — |
| 3.31 | — | CDNA FLJ34815 fis, clone NT2NE2007786 |
| 3.31 | LOC220686 | Hypothetical protein LOC220686 |
| -3.31 | ETS1 | v-ets erythroblastosis virus E26 oncogene homolog 1 (avian) |
| 3.31 | ISL1 | ISL1 transcription factor, LIM/homeodomain, (islet-1) |

Appendix 1

| Value | Symbol | Description |
|---|---|---|
| -3.30 | EBF2 | Early B-cell factor 2 |
| 3.30 | LY6G6D | lymphocyte antigen 6 complex, locus G6C |
| 3.29 | C20orf32 | chromosome 20 open reading frame 32 |
| -3.28 | DEPDC6 | DEP domain containing 6 |
| -3.28 | IL15 | interleukin 15 |
| 3.28 | PICALM | Phosphatidylinositol binding clathrin assembly protein |
| 3.28 | CSF2RA | colony stimulating factor 2 receptor, alpha, low-affinity (granulocyte-macrophage |
| 3.28 | WWOX | WW domain containing oxidoreductase |
| 3.27 | SLITRK6 | SLIT and NTRK-like family, member 6 |
| -3.27 | MYC | v-myc myelocytomatosis viral oncogene homolog (avian) |
| -3.26 | — | |
| -3.26 | KLK10 | kallikrein-related peptidase 10 |
| 3.26 | ZNF436 | zinc finger protein 436 |
| 3.26 | ID3 | inhibitor of DNA binding 3, dominant negative helix-loop-helix protein |
| -3.25 | — | Nucleoporin (GYLZ-RCC18) mRNA, GYLZ-RCC18-NUP2 allele |
| 3.25 | HOXC4 | homeobox C4 |
| 3.25 | ITGB8 | integrin, beta 8 |
| -3.25 | ATP2A3 | ATPase, Ca++ transporting, ubiquitous |
| -3.25 | TLE2 | transducin-like enhancer of split 2 (E(sp1) homolog, Drosophila) |
| 3.25 | — | — |
| -3.24 | ETS1 | v-ets erythroblastosis virus E26 oncogene homolog 1 (avian) |
| 3.23 | TANC2 | tetratricopeptide repeat, ankyrin repeat and coiled-coil containing 2 |
| 3.21 | KCNV1 | potassium channel, subfamily V, member 1 |
| 3.20 | PCDH8 | protocadherin 8 |
| 3.20 | RDHE2 | retinal short chain dehydrogenase reductase isoform 1 |
| 3.20 | — | MRNA; cDNA DKFZp686L042 (from clone DKFZp686L042) |
| 3.18 | PTCHD1 | Patched domain containing 1 |
| -3.18 | PRSS2 | protease, serine, 2 (trypsin 2) |
| 3.17 | TGFBI | transforming growth factor, beta-induced, 68kDa |
| -3.17 | IGSF21 | immunoglobin superfamily, member 21 |
| 3.17 | PKNOX2 | PBX/knotted 1 homeobox 2 |
| -3.16 | LOC202451 | hypothetical protein LOC202451 |
| 3.16 | — | — |
| -3.16 | — | Homo sapiens, clone IMAGE:4047715, mRNA |
| -3.16 | ADAMTSL1 | ADAMTS-like 1 |
| 3.16 | — | — |
| 3.15 | KIAA1731 | KIAA1731 |
| 3.15 | — | — |
| 3.14 | PPP1R7 | Protein phosphatase 1, regulatory subunit 7 |
| 3.13 | TBX6 | T-box 6 |
| 3.12 | CXCL14 | chemokine (C-X-C motif) ligand 14 |
| 3.12 | ABCC6 | ATP-binding cassette, sub-family C (CFTR/MRP), member 6 |
| -3.11 | LOC645619 /// LOC | similar to Adenylate kinase isoenzyme 4, mitochondrial (ATP-AMP transphosphorylase) /// similar to Adenylate kinase isoenzym |
| 3.11 | CDH10 | cadherin 10, type 2 (T2-cadherin) |
| 3.11 | TWIST1 | twist homolog 1 (acrocephalosyndactyly 3; Saethre-Chotzen syndrome) (Drosophila |
| 3.11 | — | MRNA; cDNA DKFZp761A1121 (from clone DKFZp761A1121) |
| 3.11 | NRIP1 | nuclear receptor interacting protein 1 |
| -3.10 | TMEPAI | transmembrane, prostate androgen induced RNA |
| 3.08 | PLA2G7 | phospholipase A2, group VII (platelet-activating factor acetylhydrolase, plasma) /// phospholipase A2, group VII (platelet-activa |
| 3.07 | SPON1 | spondin 1, extracellular matrix protein |
| 3.07 | HHAT | hedgehog acyltransferase |
| 3.07 | CLTC | Clathrin, heavy chain (Hc) |
| 3.07 | SOAT1 | sterol O-acyltransferase (acyl-Coenzyme A: cholesterol acyltransferase) |
| 3.07 | CDH11 | cadherin 11, type 2, OB-cadherin (osteoblast) |
| 3.07 | FRMD4B | FERM domain containing 4B |
| 3.06 | — | — |
| 3.05 | HOXB4 | homeobox B4 |
| 3.05 | LOC130576 | hypothetical protein LOC130576 |
| 3.04 | RBMS1 | RNA binding motif, single stranded interacting protein 1 |
| 3.04 | PDGFRB | platelet-derived growth factor receptor, beta polypeptide |
| 3.04 | — | — |
| -3.04 | — | — |
| 3.04 | KIAA1772 | KIAA1772 |
| 3.04 | D2HGDH | D-2-hydroxyglutarate dehydrogenase |
| -3.03 | HSD11B1 | Hydroxysteroid (11-beta) dehydrogenase 1 |
| 3.02 | — | — |
| -3.02 | SOX2 | SRY (sex determining region Y)-box 2 |
| -3.02 | OTX2 | orthodenticle homolog 2 (Drosophila) |
| 3.02 | ZFHX1B | zinc finger homeobox 1b |
| 3.01 | OSBPL10 | oxysterol binding protein-like 1C |
| -3.00 | PITX2 | paired-like homeodomain transcription factor 2 |
| -3.00 | — | — |
| -3.00 | ZSCAN2 | zinc finger and SCAN domain containing 2 |
| 2.99 | — | — |
| 2.99 | — | — |
| 2.99 | — | — |
| -2.98 | — | — |
| 2.98 | HPGD | hydroxyprostaglandin dehydrogenase 15-(NAD) |
| 2.97 | ZDHHC21 | zinc finger, DHHC-type containing 21 |

Appendix 1

| Value | Symbol | Description |
|---|---|---|
| 2.97 | ZBTB16 | zinc finger and BTB domain containing 16 |
| 2.97 | — | — |
| -2.96 | LCK | lymphocyte-specific protein tyrosine kinase |
| 2.95 | LRRC4 | leucine rich repeat containing 4 |
| -2.95 | — | — |
| 2.95 | NFIC | nuclear factor I/C (CCAAT-binding transcription factor) |
| 2.94 | RGS12 | regulator of G-protein signalling 12 |
| 2.93 | APCDD1 | adenomatosis polyposis coli down-regulated 1 |
| 2.93 | ATP6V0D2 | ATPase, H+ transporting, lysosomal 38kDa, V0 subunit d2 |
| 2.93 | DSCR6 | Down syndrome critical region gene 6 |
| 2.93 | — | PRO1412 |
| 2.93 | ID4 | inhibitor of DNA binding 4, dominant negative helix-loop-helix protein |
| 2.93 | LOC284600 | hypothetical protein LOC284600 |
| 2.92 | LOC285758 | hypothetical protein LOC285758 |
| -2.92 | DDAH1 | Dimethylarginine dimethylaminohydrolase 1 |
| 2.92 | TFAP2B | transcription factor AP-2 beta (activating enhancer binding protein 2 beta) |
| 2.92 | SPON1 | spondin 1, extracellular matrix protein |
| 2.92 | MEIS2 | Meis1, myeloid ecotropic viral integration site 1 homolog 2 (mouse) |
| -2.92 | DPPA2 | developmental pluripotency associated 2 |
| 2.91 | PDE4D | Phosphodiesterase 4D, cAMP-specific (phosphodiesterase E3 dunce homolog, Drosophila) |
| -2.90 | — | Transcribed locus |
| 2.90 | HOXB5 | homeobox B5 |
| -2.90 | GLS2 | glutaminase 2 (liver, mitochondrial) |
| 2.90 | BNIPL | BCL2/adenovirus E1B 19kD interacting protein like |
| -2.90 | TIMP4 | TIMP metallopeptidase inhibitor 4 |
| 2.89 | CITED2 | Cbp/p300-interacting transactivator, with Glu/Asp-rich carboxy-terminal domain, 2 |
| 2.89 | TMEM112 | Transmembrane protein 112 |
| 2.89 | EFNA1 | ephrin-A1 |
| -2.89 | IL15 | interleukin 15 |
| 2.89 | LOC144363 | Hypothetical protein LOC144363 |
| 2.88 | RASGRP1 | RAS guanyl releasing protein 1 (calcium and DAG-regulated) |
| 2.88 | PLAGL1 | pleiomorphic adenoma gene-like 1 |
| -2.87 | FAM124A | family with sequence similarity 124A |
| -2.87 | TMEM46 | transmembrane protein 46 |
| -2.87 | BDNF | brain-derived neurotrophic factor |
| -2.87 | — | Transcribed locus |
| 2.87 | HOXA9 | homeobox A9 |
| -2.87 | — | CDNA clone IMAGE:5311608 |
| 2.87 | ARHGEF17 | Rho guanine nucleotide exchange factor (GEF) 17 |
| 2.86 | — | — |
| -2.86 | — | Homo sapiens, Similar to otoconin 90, clone IMAGE:4044247, mRNA |
| -2.86 | ATP2A3 | ATPase, Ca++ transporting, ubiquitous |
| -2.86 | — | — |
| 2.86 | UNC5C | unc-5 homolog C (C. elegans) |
| 2.85 | FCHSD2 | FCH and double SH3 domains 2 |
| -2.84 | — | — |
| -2.84 | SOX17 | SRY (sex determining region Y)-box 17 |
| 2.84 | — | — |
| -2.83 | GLB1L3 | galactosidase, beta 1 like 3 |
| -2.83 | ETV1 | ets variant gene 1 |
| 2.83 | KCNAB1 | potassium voltage-gated channel, shaker-related subfamily, beta member 1 |
| 2.82 | PDCD8 | Programmed cell death 8 (apoptosis-inducing factor) |
| 2.82 | SPON1 | spondin 1, extracellular matrix protein |
| 2.82 | RASGEF1B | RasGEF domain family, member 1B |
| 2.82 | MME | membrane metallo-endopeptidase (neutral endopeptidase, enkephalinase) |
| -2.82 | HHEX | homeobox, hematopoietically expressed |
| 2.82 | LHFP | Lipoma HMGIC fusion partner |
| 2.82 | CSF2RA | colony stimulating factor 2 receptor, alpha, low-affinity (granulocyte-macrophage |
| -2.81 | TFPI2 | tissue factor pathway inhibitor 2 |
| 2.81 | HPGD | hydroxyprostaglandin dehydrogenase 15-(NAD) |
| 2.81 | DAZ1 /// DAZ3 /// D. | deleted in azoospermia 1 /// deleted in azoospermia 3 /// deleted in azoospermia 2 /// deleted in azoospermia 4 |
| 2.80 | ELF2 | E74-like factor 2 (ets domain transcription factor) |
| 2.80 | CITED2 | Cbp/p300-interacting transactivator, with Glu/Asp-rich carboxy-terminal domain, 2 |
| 2.80 | FLJ22965 | hypothetical protein FLJ22965 |
| -2.80 | — | Full-length cDNA clone CS0DF012YD09 of Fetal brain of Homo sapiens (human) |
| -2.80 | — | Surfactant associated protein F mRNA, partial sequence |
| -2.79 | GALNT3 | UDP-N-acetyl-alpha-D-galactosamine:polypeptide N-acetylgalactosaminyltransferase 3 (GalNAc-T3 |
| 2.78 | ITPR1 | inositol 1,4,5-triphosphate receptor, type 1 |
| -2.78 | TLE2 | transducin-like enhancer of split 2 (E(sp1) homolog, Drosophila) |
| 2.77 | TBX3 | T-box 3 (ulnar mammary syndrome) |
| -2.77 | ATP2A3 | ATPase, Ca++ transporting, ubiquitous |
| 2.77 | — | — |
| -2.77 | SOX2 | SRY (sex determining region Y)-box 2 |
| 2.77 | CCR7 | chemokine (C-C motif) receptor 7 /// chemokine (C-C motif) receptor 7 |
| -2.76 | MUC3B | mucin 3B, cell surface associated |
| -2.76 | — | — |
| 2.76 | — | — |
| 2.76 | PBX1 | Pre-B-cell leukemia transcription factor 1 |
| 2.75 | LEF1 | lymphoid enhancer-binding factor 1 |

Appendix 1

| | | |
|---|---|---|
| 2.75 | SGCG | sarcoglycan, gamma (35kDa dystrophin-associated glycoprotein) |
| 2.75 | SMURF1 | SMAD specific E3 ubiquitin protein ligase 1 |
| 2.74 | TAX1BP3 | Tax1 (human T-cell leukemia virus type I) binding protein 3 |
| 2.74 | HLXB9 | homeobox HB9 |
| 2.74 | ID4 | Inhibitor of DNA binding 4, dominant negative helix-loop-helix protein |
| 2.73 | — | — |
| 2.73 | GPR103 | G protein-coupled receptor 103 |
| 2.73 | — | — |
| -2.73 | CCDC81 | coiled-coil domain containing 81 |
| -2.73 | RHOH | Ras homolog gene family, member H |
| -2.73 | LRRK1 | Leucine-rich repeat kinase 1 |
| 2.72 | KIAA1462 | KIAA1462 |
| 2.71 | — | — |
| -2.71 | FZD8 | frizzled homolog 8 (Drosophila) /// frizzled homolog 8 (Drosophila) |
| -2.71 | FAM124A | family with sequence similarity 124A |
| 2.71 | ATP6V0D2 | ATPase, H+ transporting, lysosomal 38kDa, V0 subunit d2 |
| -2.70 | — | — |
| 2.70 | PACSIN2 | Protein kinase C and casein kinase substrate in neurons 2 |
| 2.69 | FREM2 | FRAS1 related extracellular matrix protein 2 |
| 2.69 | IFI16 | interferon, gamma-inducible protein 16 |
| 2.68 | — | — |
| -2.68 | — | — |
| 2.68 | HBE1 | hemoglobin, epsilon 1 /// hemoglobin, epsilon 1 |
| 2.68 | HOXA7 | homeobox A7 |
| -2.68 | MUC4 | mucin 4, cell surface associated |
| 2.68 | — | — |
| 2.68 | HPGD | hydroxyprostaglandin dehydrogenase 15-(NAD) |
| 2.68 | EGR1 | early growth response 1 |
| -2.68 | — | — |
| -2.67 | HTR3A | 5-hydroxytryptamine (serotonin) receptor 3A |
| 2.67 | SMYD2 | SET and MYND domain containing 2 |
| -2.67 | TERF1 | telomeric repeat binding factor (NIMA-interacting) 1 |
| 2.66 | EFCBP2 | EF-hand calcium binding protein 2 |
| -2.66 | — | — |
| 2.66 | — | — |
| -2.66 | DPPA4 | developmental pluripotency associated 4 |
| 2.65 | LOC347475 | hypothetical gene supported by BC017955 |
| 2.65 | — | — |
| 2.65 | GAD1 /// LASS6 | glutamate decarboxylase 1 (brain, 67kDa) /// LAG1 homolog, ceramide synthase 6 (S. cerevisiae) |
| 2.65 | NHEJ1 | Nonhomologous end-joining factor 1 |
| 2.65 | NCALD | neurocalcin delta /// neurocalcin delta |
| -2.65 | KLF4 | Kruppel-like factor 4 (gut) |
| 2.65 | — | Transcribed locus |
| 2.65 | DKK1 | dickkopf homolog 1 (Xenopus laevis) |
| -2.64 | TERF1 | telomeric repeat binding factor (NIMA-interacting) 1 |
| 2.64 | C8orf48 | chromosome 8 open reading frame 48 |
| 2.64 | PLXNA2 | plexin A2 |
| -2.64 | CPT1A | carnitine palmitoyltransferase 1A (liver) |
| 2.64 | SUHW4 | suppressor of hairy wing homolog 4 (Drosophila) |
| 2.63 | — | — |
| 2.63 | — | — |
| 2.63 | — | — |
| 2.63 | FAM38B | family with sequence similarity 38, member B |
| -2.63 | — | — |
| 2.63 | — | — |
| 2.63 | SUZ12P | Suppressor of zeste 12 homolog pseudogene |
| 2.62 | YAF2 | YY1 associated factor 2 |
| -2.62 | OR10C1 | olfactory receptor, family 10, subfamily C, member 1 |
| 2.62 | AVEN | Apoptosis, caspase activation inhibitor |
| 2.62 | RUNX1 | runt-related transcription factor 1 (acute myeloid leukemia 1; aml1 oncogene) |
| -2.61 | FOXA2 | forkhead box A2 |
| 2.61 | ITPR1 | inositol 1,4,5-triphosphate receptor, type 1 |
| -2.61 | FAT4 | FAT tumor suppressor homolog 4 (Drosophila) |
| -2.60 | — | — |
| 2.60 | DNASE1 | Deoxyribonuclease I |
| -2.60 | — | Transcribed locus |
| 2.60 | DERA | 2-deoxyribose-5-phosphate aldolase homolog (C. elegans) |
| -2.59 | PIM2 | pim-2 oncogene |
| -2.59 | TNFSF11 | tumor necrosis factor (ligand) superfamily, member 11 |
| 2.59 | — | — |
| -2.59 | TMEPAI | transmembrane, prostate androgen induced RNA |
| -2.59 | C17orf76 | chromosome 17 open reading frame 76 |
| -2.59 | DPPA4 | developmental pluripotency associated 4 |
| -2.58 | — | — |
| -2.58 | LOC728473 | hypothetical protein LOC728473 |
| 2.58 | TCF8 | transcription factor 8 (represses interleukin 2 expression) |
| 2.58 | — | Full-length cDNA clone CS0DI029YM01 of Placenta Cot 25-normalized of Homo sapiens (human) |
| -2.58 | NR5A2 | nuclear receptor subfamily 5, group A, member 2 |
| -2.58 | — | — |

Appendix 1

| | | |
|---|---|---|
| -2.58 | — | — |
| | 2.58 FZD1 | frizzled homolog 1 (Drosophila) |
| | 2.57 SAPS3 | SAPS domain family, member 3 |
| | 2.57 DLC1 | deleted in liver cancer 1 |
| | 2.57 MME | membrane metallo-endopeptidase (neutral endopeptidase, enkephalinase) |
| | 2.56 SRCAP | Snf2-related CBP activator protein |
| | 2.56 CA12 | carbonic anhydrase XII |
| | 2.56 MLLT3 | myeloid/lymphoid or mixed-lineage leukemia (trithorax homolog, Drosophila); translocated to, 3 |
| -2.56 | HBA1 | hemoglobin, alpha 1 /// hemoglobin, alpha 1 |
| | 2.56 NME5 | non-metastatic cells 5, protein expressed in (nucleoside-diphosphate kinase) |
| -2.56 | ELAVL2 | ELAV (embryonic lethal, abnormal vision, Drosophila)-like 2 (Hu antigen B) |
| | 2.55 SKAP2 | src kinase associated phosphoprotein 2 |
| 2.54 | — | — |
| 2.54 | — | — |
| | 2.54 SPON1 | spondin 1, extracellular matrix protein |
| -2.54 | HLA-DPB2 | major histocompatibility complex, class II, DP beta 2 (pseudogene) |
| 2.54 | — | — |
| -2.54 | CAV2 | caveolin 2 |
| | 2.53 MYO5B | myosin VB |
| -2.53 | OSBPL10 | oxysterol binding protein-like 10 |
| | 2.53 SYDE2 | synapse defective 1, Rho GTPase, homolog 2 (C. elegans) |
| -2.52 | WNT3 | wingless-type MMTV integration site family, member 3 |
| 2.52 | — | — |
| | 2.52 SDHALP2 | succinate dehydrogenase complex, subunit A, flavoprotein pseudogene 2 |
| | 2.52 CA12 | carbonic anhydrase XII |
| | 2.52 HMX1 | homeobox (H6 family) 1 |
| | 2.52 FZD1 | frizzled homolog 1 (Drosophila) |
| | 2.52 CDRT4 | CMT1A duplicated region transcript 4 |
| | 2.51 IFI16 | interferon, gamma-inducible protein 16 |
| 2.51 | — | — |
| | 2.51 SOX9 | SRY (sex determining region Y)-box 9 (campomelic dysplasia, autosomal sex-reversal |
| 2.51 | — | — |
| | 2.51 PGF | placental growth factor, vascular endothelial growth factor-related protein |
| | 2.51 NOV | nephroblastoma overexpressed gene |
| -2.50 | EBF2 | early B-cell factor 2 |
| | 2.50 C5orf15 | Chromosome 5 open reading frame 15 |
| -2.50 | MOG | myelin oligodendrocyte glycoprotein |
| -2.50 | SOX17 | SRY (sex determining region Y)-box 17 |
| | 2.50 PRSS23 | protease, serine, 23 |
| 2.49 | — | MRNA; cDNA DKFZp547C018 (from clone DKFZp547C018) |
| | 2.49 KRT19 | keratin 19 |
| | 2.49 AKAP13 | A kinase (PRKA) anchor protein 13 |
| | 2.48 CENTG2 | Centaurin, gamma 2 |
| 2.48 | — | — |
| -2.48 | — | Homo sapiens, Similar to otoconin 90, clone IMAGE:4285317, mRNA |
| | 2.48 DACH1 | dachshund homolog 1 (Drosophila) |
| 2.47 | — | — |
| | 2.47 CLIC5 | chloride intracellular channel 5 |
| -2.47 | THY1 | Thy-1 cell surface antigen |
| 2.47 | — | CDNA FLJ40174 fis, clone TESTI2016996 |
| -2.47 | LOC439949 | hypothetical gene supported by AY007155 |
| -2.46 | — | — |
| | 2.46 GADD45A | growth arrest and DNA-damage-inducible, alpha |
| | 2.46 IGF2 /// INS-IGF2 | insulin-like growth factor 2 (somatomedin A) /// insulin- insulin-like growth factor 2 |
| | 2.46 HS6ST2 | heparan sulfate 6-O-sulfotransferase 2 |
| | 2.46 DLL1 | delta-like 1 (Drosophila) |
| -2.46 | TGFB2 | transforming growth factor, beta 2 |
| | 2.45 FOXP1 | Forkhead box P1 |
| | 2.45 ZBTB38 | zinc finger and BTB domain containing 38 |
| | 2.45 GAS1 | growth arrest-specific 1 |
| | 2.45 MBNL2 | muscleblind-like 2 (Drosophila) |
| | 2.45 GSN | gelsolin (amyloidosis, Finnish type) |
| -2.45 | MYRIP | myosin VIIA and Rab interacting protein |
| -2.45 | BTBD11 | BTB (POZ) domain containing 11 |
| -2.44 | — | — |
| 2.44 | — | — |
| -2.44 | CCNA1 | cyclin A1 |
| 2.44 | — | — |
| 2.44 | — | — |
| -2.44 | DLC1 | deleted in liver cancer 1 |
| 2.44 | — | — |
| | 2.44 HS6ST2 | heparan sulfate 6-O-sulfotransferase 2 |
| 2.43 | — | — |
| | 2.43 C18orf30 | chromosome 18 open reading frame 30 |
| -2.43 | TFPI2 | tissue factor pathway inhibitor 2 |
| -2.43 | AK3L1 | adenylate kinase 3-like 1 |
| | 2.43 SKAP2 | src kinase associated phosphoprotein 2 |
| 2.43 | — | CDNA FLJ42313 fis, clone TRACH2019425 |
| | 2.42 PHTF1 | Putative homeodomain transcription factor 1 |

Appendix 1

| | | |
|---|---|---|
| 2.42 | HOXD8 | Homeobox D8 |
| -2.42 | HBA1 /// HBA2 | hemoglobin, alpha 1 /// hemoglobin, alpha 1 /// hemoglobin, alpha 2 /// hemoglobin, alpha 2 |
| -2.42 | GPR176 | G protein-coupled receptor 176 |
| 2.42 | NRIP1 | nuclear receptor interacting protein 1 |
| 2.42 | MMP2 | matrix metallopeptidase 2 (gelatinase A, 72kDa gelatinase, 72kDa type IV collagenase) |
| -2.41 | FAM124A | Family with sequence similarity 124A |
| -2.41 | DHDH | dihydrodiol dehydrogenase (dimeric) |
| -2.41 | — | Transcribed locus |
| 2.41 | MCOLN3 | mucolipin 3 |
| 2.41 | CCDC92 | coiled-coil domain containing 92 |
| -2.41 | — | — |
| 2.41 | CXCL14 | chemokine (C-X-C motif) ligand 14 |
| 2.41 | DYNC1I1 | dynein, cytoplasmic 1, intermediate chain 1 |
| 2.41 | TACSTD2 | tumor-associated calcium signal transducer 2 |
| -2.41 | TNMD | tenomodulin |
| -2.40 | FLJ22662 | hypothetical protein FLJ22662 |
| 2.40 | — | — |
| -2.40 | SOX2 | SRY (sex determining region Y)-box 2 |
| 2.40 | — | — |
| 2.40 | KIAA1267 | KIAA1267 |
| 2.40 | PRR16 | proline rich 16 |
| 2.40 | FZD2 | frizzled homolog 2 (Drosophila) |
| -2.40 | — | CDNA FLJ32963 fis, clone TESTI2008405 |
| -2.39 | LOC157627 | hypothetical protein LOC157627 |
| 2.39 | ID2 /// ID2B | inhibitor of DNA binding 2, dominant negative helix-loop-helix protein /// inhibitor of DNA binding 2B, dominant negative helix-lc |
| 2.39 | CAMK2D | Calcium/calmodulin-dependent protein kinase (CaM kinase) II delta |
| -2.38 | HHEX | homeobox, hematopoietically expressed |
| -2.38 | ANGPT1 | angiopoietin 1 |
| 2.37 | HS6ST2 | heparan sulfate 6-O-sulfotransferase 2 |
| 2.37 | — | — |
| 2.37 | GATA3 | GATA binding protein 3 |
| 2.37 | FOXF2 | forkhead box F2 |
| -2.36 | LAMC3 | laminin, gamma 3 |
| 2.36 | — | — |
| 2.36 | — | — |
| 2.36 | EME2 | Essential meiotic endonuclease 1 homolog 2 (S. pombe) |
| 2.36 | — | — |
| 2.36 | IFI16 | interferon, gamma-inducible protein 16 |
| 2.36 | RNASEL | ribonuclease L (2',5'-oligoisoadenylate synthetase-dependent) |
| 2.35 | — | — |
| 2.35 | — | — |
| -2.35 | CAV2 | caveolin 2 |
| 2.35 | — | — |
| 2.35 | — | — |
| -2.34 | TMEPAI | transmembrane, prostate androgen induced RNA |
| -2.34 | PNMA2 | paraneoplastic antigen MA2 |
| -2.34 | SYT4 | synaptotagmin IV |
| -2.34 | DDX25 | DEAD (Asp-Glu-Ala-Asp) box polypeptide 25 |
| 2.33 | — | LOC441801 |
| 2.33 | — | — |
| -2.32 | HESX1 | homeobox, ES cell expressed 1 |
| -2.32 | CPT1A | carnitine palmitoyltransferase 1A (liver) |
| 2.32 | WDR60 | WD repeat domain 60 |
| 2.32 | PKNOX2 | PBX/knotted 1 homeobox 2 |
| 2.32 | LY6K | lymphocyte antigen 6 complex, locus K |
| 2.31 | CA12 | carbonic anhydrase XII |
| 2.31 | ZNF585A | zinc finger protein 585A |
| 2.31 | — | CDNA FLJ11723 fis, clone HEMBA1005314 |
| 2.31 | KCNAB2 | potassium voltage-gated channel, shaker-related subfamily, beta member 2 |
| 2.31 | SKAP2 | src kinase associated phosphoprotein 2 |
| -2.31 | TMEM63A | transmembrane protein 63A |
| 2.31 | TBX3 | T-box 3 (ulnar mammary syndrome) |
| 2.30 | DKK3 | dickkopf homolog 3 (Xenopus laevis) |
| 2.30 | — | — |
| -2.30 | KIF5A | Kinesin family member 5A |
| -2.29 | LOC153277 | hypothetical protein LOC153277 |
| -2.29 | DBC1 | deleted in bladder cancer 1 |
| 2.29 | — | — |
| 2.29 | PCSK6 | proprotein convertase subtilisin/kexin type 6 |
| -2.29 | — | — |
| 2.29 | PPP1R14C | protein phosphatase 1, regulatory (inhibitor) subunit 14C |
| -2.29 | USP44 | ubiquitin specific peptidase 44 |
| -2.29 | QPCT | glutaminyl-peptide cyclotransferase (glutaminyl cyclase) |
| 2.29 | JUB | jub, ajuba homolog (Xenopus laevis) |
| 2.28 | KIAA1267 | KIAA1267 |
| 2.28 | — | MRNA; cDNA DKFZp564G212 (from clone DKFZp564G212) |
| -2.28 | — | — |
| 2.28 | CAMK2N1 | calcium/calmodulin-dependent protein kinase II inhibitor 1 |
| 2.28 | ARNT2 | aryl-hydrocarbon receptor nuclear translocator 2 |

Appendix 1

| Value | Gene | Description |
|---|---|---|
| 2.28 | NRXN2 | neurexin 2 |
| 2.27 | — | CDNA FLJ38181 fis, clone FCBBF1000125 |
| 2.27 | — | — |
| -2.27 | CRYGD | crystallin, gamma D |
| 2.27 | KIAA0999 | KIAA0999 protein |
| 2.27 | SMYD3 | SET and MYND domain containing 3 |
| -2.26 | MAN1C1 | mannosidase, alpha, class 1C, member 1 |
| 2.26 | MLLT3 | myeloid/lymphoid or mixed-lineage leukemia (trithorax homolog, Drosophila); translocated to, 3 |
| 2.26 | NRXN3 | neurexin 3 |
| -2.25 | — | — |
| 2.25 | COL6A3 | collagen, type VI, alpha 3 |
| -2.25 | ATCAY | ataxia, cerebellar, Cayman type (caytaxin) |
| -2.25 | CXCL5 | chemokine (C-X-C motif) ligand 5 |
| -2.25 | TMEM63A | transmembrane protein 63A |
| -2.24 | NR5A2 | nuclear receptor subfamily 5, group A, member 2 |
| 2.24 | KLHL8 | Kelch-like 8 (Drosophila) |
| -2.24 | MB | myoglobin |
| 2.24 | — | Full length insert cDNA clone YT94E02 |
| -2.24 | PIPOX | pipecolic acid oxidase |
| 2.23 | EPN3 | epsin 3 |
| 2.23 | FST | follistatin |
| 2.23 | PRSS23 | protease, serine, 23 |
| -2.23 | — | CDNA FLJ26031 fis, clone PNC08078 |
| 2.23 | COL4A6 | collagen, type IV, alpha 6 |
| -2.23 | TDGF1 /// TDGF3 | teratocarcinoma-derived growth factor 1 /// teratocarcinoma-derived growth factor 3, pseudogene |
| 2.22 | NEBL | nebulette |
| -2.22 | CXCL5 | chemokine (C-X-C motif) ligand 5 |
| 2.22 | — | — |
| 2.22 | KIAA0644 | KIAA0644 gene product |
| 2.21 | SEMA3C | sema domain, immunoglobulin domain (Ig), short basic domain, secreted, (semaphorin) 3C |
| 2.21 | AHNAK | AHNAK nucleoprotein (desmoyokin) |
| 2.21 | FBN2 | fibrillin 2 (congenital contractural arachnodactyly) |
| -2.21 | TMEM132D | transmembrane protein 132D |
| -2.20 | LCK | lymphocyte-specific protein tyrosine kinase |
| 2.20 | — | — |
| -2.20 | — | CDNA clone IMAGE:4792693 |
| 2.20 | TMEM47 | transmembrane protein 47 |
| 2.20 | NAV2 | neuron navigator 2 |
| 2.20 | — | — |
| -2.20 | EDIL3 | EGF-like repeats and discoidin I-like domains 3 |
| 2.20 | NMNAT2 | nicotinamide nucleotide adenylyltransferase 2 |
| -2.19 | SKIL | SKI-like |
| 2.19 | — | CDNA clone IMAGE:3162229 |
| 2.19 | KIAA1462 | KIAA1462 |
| -2.19 | JAZF1 | JAZF zinc finger 1 |
| 2.19 | CD1D | CD1d molecule /// CD1d molecule |
| -2.18 | — | CDNA FLJ36544 fis, clone TRACH2006378 |
| 2.18 | — | — |
| 2.18 | — | Transcribed locus, weakly similar to XP_520634.1 PREDICTED: similar to naked cuticle homolog 1; naked cuticle-1; Dvl-bindir |
| 2.18 | TBX6 | T-box 6 |
| 2.18 | — | — |
| -2.17 | — | — |
| 2.17 | — | — |
| 2.17 | KIAA0101 | KIAA0101 /// KIAA0101 |
| -2.17 | MUC4 | mucin 4, cell surface associated |
| 2.17 | SLIT3 | slit homolog 3 (Drosophila) |
| -2.16 | ALDH1A1 | aldehyde dehydrogenase 1 family, member A1 |
| -2.16 | ACSM3 | acyl-CoA synthetase medium-chain family member 3 |
| 2.16 | — | — |
| 2.16 | LRRC4C | leucine rich repeat containing 4C |
| -2.16 | HRASLS3 | HRAS-like suppressor 3 |
| -2.16 | — | Homo sapiens, clone IMAGE:5245578, mRNA |
| 2.16 | ZC3H12C | zinc finger CCCH-type containing 12C |
| -2.15 | P2RX5 | purinergic receptor P2X, ligand-gated ion channel, 5 |
| 2.15 | DKK3 | dickkopf homolog 3 (Xenopus laevis) |
| 2.15 | — | — |
| -2.15 | CHST9 | carbohydrate (N-acetylgalactosamine 4-0) sulfotransferase 9 /// carbohydrate (N-acetylgalactosamine 4-0) sulfotransferase 9 |
| 2.15 | NEBL | nebulette |
| -2.15 | ADCY2 | adenylate cyclase 2 (brain) |
| 2.15 | GRLF1 | Glucocorticoid receptor DNA binding factor 1 |
| -2.14 | CYP2E1 | cytochrome P450, family 2, subfamily E, polypeptide 1 |
| 2.14 | — | CDNA FLJ30128 fis, clone BRACE1000124 |
| -2.14 | — | — |
| 2.14 | SMARCA4 | SWI/SNF related, matrix associated, actin dependent regulator of chromatin, subfamily a, member 4 |
| 2.13 | ENTH | enthoprotin |
| -2.13 | CHGA | chromogranin A (parathyroid secretory protein 1) |
| -2.13 | DPYSL3 | dihydropyrimidinase-like 3 |
| -2.13 | BEST2 | bestrophin 2 |
| 2.13 | FNDC5 | fibronectin type III domain containing 5 |

Appendix 1

| | | |
|---|---|---|
| 2.13 | BBP | TM2 domain containing 1 |
| 2.12 | ATP2B4 | ATPase, Ca++ transporting, plasma membrane 4 |
| 2.12 | PIAS1 | Protein inhibitor of activated STAT, 1 |
| 2.12 | — | — |
| -2.12 | MYCT1 | myc target 1 |
| 2.12 | NNMT | nicotinamide N-methyltransferase |
| 2.12 | — | — |
| 2.12 | ZNF407 | Zinc finger protein 407 |
| 2.11 | TMPRSS11E /// LO | transmembrane protease, serine 11E /// similar to transmembrane protease, serine 11E |
| 2.11 | KLHL13 | kelch-like 13 (Drosophila) |
| 2.11 | — | — |
| 2.11 | PALLD | palladin, cytoskeletal associated protein |
| -2.11 | SLC1A3 | solute carrier family 1 (glial high affinity glutamate transporter), member 3 |
| -2.11 | — | — |
| -2.11 | — | — |
| -2.11 | RMST | Rhabdomyosarcoma 2 associated transcript (non-coding RNA) |
| 2.10 | — | — |
| -2.10 | SPRY1 | sprouty homolog 1, antagonist of FGF signaling (Drosophila) |
| 2.10 | — | — |
| 2.10 | EPHB3 | EPH receptor B3 |
| -2.10 | PHC1 | polyhomeotic homolog 1 (Drosophila) |
| -2.10 | FAM111B | Family with sequence similarity 111, member B |
| -2.10 | GRPR | gastrin-releasing peptide receptor |
| 2.10 | FLRT3 | fibronectin leucine rich transmembrane protein 3 |
| -2.09 | — | — |
| -2.09 | NRK | Nik related kinase |
| 2.09 | LOC387895 | Hypothetical gene supported by BC040060 |
| 2.09 | DOCK11 | dedicator of cytokinesis 11 |
| 2.09 | — | CDNA clone IMAGE:4328048 |
| 2.09 | TGFA | transforming growth factor, alpha |
| -2.08 | — | C33.6 unnamed HERV-H protein |
| 2.08 | CRABP2 | cellular retinoic acid binding protein 2 |
| 2.08 | APBA2 | amyloid beta (A4) precursor protein-binding, family A, member 2 (X11-like) |
| 2.08 | FLRT3 | fibronectin leucine rich transmembrane protein 3 |
| 2.08 | SCD5 | stearoyl-CoA desaturase 5 |
| -2.08 | TMEM63A | transmembrane protein 63A |
| -2.07 | — | — |
| -2.07 | FOXO1A | forkhead box O1A (rhabdomyosarcoma) |
| 2.07 | — | Transcribed locus |
| 2.07 | — | — |
| -2.07 | RBMS3 | RNA binding motif, single stranded interacting protein |
| 2.07 | CNKSR3 | CNKSR family member 3 |
| 2.07 | C5orf24 | chromosome 5 open reading frame 24 |
| -2.07 | HEY2 | hairy/enhancer-of-split related with YRPW motif 2 |
| 2.06 | C13orf18 | chromosome 13 open reading frame 18 |
| 2.06 | — | — |
| 2.06 | ZNF638 | Zinc finger protein 638 |
| 2.06 | LOC730069 /// LOC | similar to nuclear receptor binding factor 2 /// similar to nuclear receptor binding factor 2 |
| 2.06 | TIFA | TRAF-interacting protein with a forkhead-associated domain |
| -2.06 | GARNL4 | GTPase activating Rap/RanGAP domain-like 4 |
| -2.06 | NR5A2 | nuclear receptor subfamily 5, group A, member 2 |
| 2.05 | BMI1 | B lymphoma Mo-MLV insertion region (mouse) |
| -2.05 | TUBB6 | tubulin, beta 6 |
| 2.05 | SLITRK6 | SLIT and NTRK-like family, member 6 |
| 2.05 | KIAA0101 | KIAA0101 |
| -2.05 | DNAJC12 | DnaJ (Hsp40) homolog, subfamily C, member 12 |
| -2.05 | JAZF1 | JAZF zinc finger 1 |
| -2.05 | ZNF483 | Zinc finger protein 483 |
| 2.04 | LYPD6 | LY6/PLAUR domain containing 6 |
| 2.04 | SYT7 | synaptotagmin VII |
| 2.03 | STT3B | STT3, subunit of the oligosaccharyltransferase complex, homolog B (S. cerevisiae) |
| -2.03 | LMO3 | LIM domain only 3 (rhombotin-like 2) |
| 2.03 | CHD6 | chromodomain helicase DNA binding protein 6 |
| -2.03 | POLR3G | polymerase (RNA) III (DNA directed) polypeptide G (32kD) |
| 2.03 | PLAGL1 | pleiomorphic adenoma gene-like 1 |
| -2.03 | ANTXR1 | anthrax toxin receptor 1 |
| -2.03 | VSNL1 | visinin-like 1 |
| 2.03 | CRH | corticotropin releasing hormone |
| 2.03 | — | CDNA clone IMAGE:5288757 |
| -2.02 | — | CDNA FLJ12624 fis, clone NT2RM4001754 |
| 2.02 | KIAA1546 | KIAA1546 |
| 2.02 | BMP5 | bone morphogenetic protein 5 |
| -2.02 | THY1 | Thy-1 cell surface antigen |
| 2.02 | CSF2RA | colony stimulating factor 2 receptor, alpha, low-affinity (granulocyte-macrophage |
| 2.02 | IQCE | IQ motif containing E |
| -2.02 | SIX2 | sine oculis homeobox homolog 2 (Drosophila) |
| -2.02 | DPPA4 | developmental pluripotency associated 4 |
| 2.02 | DOCK11 | dedicator of cytokinesis 11 |
| -2.01 | GAP43 | growth associated protein 43 |

Appendix 1

| | | |
|---|---|---|
| 2.01 | CHST11 | Carbohydrate (chondroitin 4) sulfotransferase 11 |
| 2.01 | GAD1 /// LASS6 | glutamate decarboxylase 1 (brain, 67kDa) /// LAG1 homolog, ceramide synthase 6 (S. cerevisiae |
| 2.01 | FREM1 | FRAS1 related extracellular matrix 1 |
| 2.00 | — | — |
| -2.00 | — | — |
| 2.00 | NR2F2 | nuclear receptor subfamily 2, group F, member 2 |
| -2.00 | TSHZ3 | teashirt family zinc finger 3 |
| 2.00 | HPGD | hydroxyprostaglandin dehydrogenase 15-(NAD | us dystrc
domain 1
ide N-ace
G (with Rh eptidase member 9

(C-C mo taining 12

Appendix 2

Microarray Data for Isl1 Multipotent Progenator (IMP) Formation

Formation of Isl1 Multipotent Progenators (IMPs) following treatment of hESCs (BG02) with Wnt3a (25ng/ml) and BMP4 (100ng/ml) in defined media for 6 days. mRNA samples were taken at time 0 (untreated hESCs) and 1, 2, 3, 4 and 6 days, following treatment, for microarray analysis. The following table is a summary of the microarray analysis showing fold changes as log2 ratios. Affymetrix Human Genome U133 Plus 2.0 Array chips were used for this experiment. The following table only shows those genes that changed by at least 2 logs at 6 days (IMP cells) relative to untreated hESCs. Other information was omitted from the table.

Appendix 2

| Wnt+BMP 24hr 3E2 A-LR | Wnt+BMP 48hr 3E3 A-LR | Wnt+BMP 72hr 3E4 A-LR | Wnt+BMP 96hr 3E5 A-LR | Wnt+BMP 144hr 3E6 A-LR | Gene Symbol | Gene Descriptor | SeqDerivedFrom |
|---|---|---|---|---|---|---|---|
| 0.00 | 0.00 | 2.00 | 6.93 | 8.36 | COL3A1 | collagen, type III, alpha 1 (Ehlers-Danlos | AU144167 |
| 0.87 | 3.05 | 5.73 | 7.97 | 8.08 | IGFBP3 | insulin-like growth factor binding protein | M31159 |
| 3.29 | 6.25 | 6.65 | 7.84 | 7.88 | ACTC1 | actin, alpha, cardiac muscle 1 | NM_005159 |
| 0.00 | 0.00 | 1.58 | 6.33 | 7.80 | COL3A1 | collagen, type III, alpha 1 (Ehlers-Danlos | AI813758 |
| -0.21 | 0.84 | 4.76 | 6.64 | 7.68 | IGF2 /// INS-IGF2 | insulin-like growth factor 2 (somatomedin | X07868 |
| 2.86 | 6.56 | 7.41 | 7.57 | 7.27 | HAND1 | heart and neural crest derivatives expres | NM_004821 |
| 3.45 | 6.29 | 6.99 | 7.35 | 6.37 | GPR177 | G protein-coupled receptor 177 | AA775681 |
| -0.68 | -1.00 | -3.28 | -5.07 | -7.16 | HESRG | embryonic stem cell related protein | BF223023 |
| 0.00 | 0.00 | 0.00 | 4.70 | 7.16 | COL3A1 | collagen, type III, alpha 1 (Ehlers-Danlos | AF130082 |
| -4.29 | -6.50 | -7.12 | -7.12 | -7.12 | LEFTY1 | left-right determination factor 1 | NM_020997 |
| 0.21 | 1.87 | 4.38 | 6.91 | 7.11 | IGFBP3 | insulin-like growth factor binding protein | BF340228 |
| 0.18 | 0.00 | 2.69 | 6.26 | 7.01 | COL6A3 | collagen, type VI, alpha 3 | NM_004369 |
| -0.35 | -1.54 | -4.74 | -5.63 | -6.98 | NANOG | Nanog homeobox | NM_024865 |
| 0.00 | 0.00 | 3.20 | 5.14 | 6.83 | LUM | lumican | NM_002345 |
| 5.07 | 5.67 | 6.44 | 6.80 | 6.57 | MSX1 | msh homeobox 1 | NM_002448 |
| 2.46 | 5.42 | 6.20 | 6.62 | 5.52 | GPR177 | G protein-coupled receptor 177 | AL534095 |
| 4.91 | 5.56 | 6.47 | 6.59 | 5.64 | MSX2 | msh homeobox 2 | D31771 |
| 3.15 | 4.37 | 2.33 | 2.90 | 6.32 | CXCL14 | chemokine (C-X-C motif) ligand 14 | NM_004887 |
| 0.26 | 3.24 | 5.59 | 6.14 | 6.25 | SNAI2 | snail homolog 2 (Drosophila) | AI572079 |
| 0.00 | 0.31 | 3.94 | 5.49 | 6.18 | GABRP | gamma-aminobutyric acid (GABA) A rece | NM_014211 |
| -0.92 | -2.57 | -4.99 | -6.17 | -6.17 | GDF3 | growth differentiation factor 3 | NM_020634 |
| -1.98 | -3.75 | -4.95 | -6.16 | -6.16 | SOX2 | SRY (sex determining region Y)-box 2 | AI669815 |
| 4.36 | 4.81 | 5.76 | 6.15 | 5.78 | MSX2 | msh homeobox 2 | D89377 |
| 2.99 | 4.34 | 2.24 | 2.95 | 6.11 | CXCL14 | chemokine (C-X-C motif) ligand 14 | AF144103 |
| 0.74 | 1.30 | 3.06 | 5.25 | 5.92 | PMP22 | peripheral myelin protein 22 | L03203 |
| 1.30 | 3.91 | 5.38 | 5.81 | 4.78 | AGTRL1 | angiotensin II receptor-like 1 | X89271 |
| -2.97 | -4.41 | -5.49 | -5.80 | -5.80 | SOX2 | SRY (sex determining region Y)-box 2 | L07335 |
| 1.69 | 3.24 | 3.89 | 4.87 | 5.79 | COL5A1 | collagen, type V, alpha 1 | AI130969 |
| 1.43 | 4.62 | 5.42 | 5.63 | 5.77 | COLEC12 | collectin sub-family member 12 /// collecti | NM_030781 |
| -1.13 | -2.13 | -3.11 | -4.64 | -5.77 | CALB1 | calbindin 1, 28kDa | AW014927 |
| -0.76 | -1.02 | -1.93 | -3.37 | -5.74 | | Homo sapiens, Similar to otoconin 90, dc | BC015108 |
| 0.00 | 0.00 | 4.09 | 5.71 | 4.07 | C8orf4 | chromosome 8 open reading frame 4 | NM_020130 |
| -0.98 | -2.31 | -3.09 | -5.03 | -5.71 | CALB1 | calbindin 1, 28kDa | NM_004929 |
| 1.41 | 3.81 | 5.71 | 5.62 | 5.10 | LOC145786 | Hypothetical protein LOC145786 | AA912476 |
| -0.26 | -1.56 | -2.93 | -3.84 | -5.69 | PTPRZ1 | protein tyrosine phosphatase, receptor-ty | NM_002851 |
| -3.27 | -5.63 | -5.63 | -4.88 | -4.29 | LEFTY2 | left-right determination factor 2 | NM_003240 |
| 1.34 | 0.99 | 0.66 | 3.22 | 5.59 | TGFBI | transforming growth factor, beta-induced, | NM_000358 |
| -1.35 | 2.55 | 5.21 | 5.59 | 5.37 | TMEM88 | transmembrane protein 88 | AL544576 |
| 0.53 | 2.88 | 5.01 | 5.57 | 5.30 | ISL1 | ISL1 transcription factor, LIM/homeodom | NM_002202 |
| 0.59 | -0.53 | -1.07 | 3.55 | 5.55 | NMU | neuromedin U | NM_006681 |
| 3.97 | 4.81 | 5.46 | 5.54 | 4.77 | GATA3 | GATA binding protein 3 | BC003070 |
| 1.55 | 4.55 | 5.09 | 5.51 | 4.88 | RHOBTB3 | Rho-related BTB domain containing 3 | N21138 |
| 0.00 | 2.40 | 5.09 | 5.51 | 3.54 | SPARCL1 | SPARC-like 1 (mast9, hevin) | NM_004684 |
| 2.71 | 3.90 | 4.94 | 5.45 | 5.15 | TBX3 | T-box 3 (ulnar mammary syndrome) | NM_016569 |
| 1.42 | 4.55 | 5.45 | 4.94 | 4.91 | C9orf19 | chromosome 9 open reading frame 19 | H92988 |
| 2.58 | 5.42 | 5.22 | 4.12 | 0.52 | ATP12A | ATPase, H+/K+ transporting, nongastric, | NM_001676 |
| 3.00 | 4.37 | 5.42 | 5.25 | 4.65 | TFAP2A | transcription factor AP-2 alpha (activating | BF343007 |
| 1.38 | 3.07 | 3.42 | 4.42 | 5.40 | COL5A1 | collagen, type V, alpha 1 | AI983428 |
| 2.08 | 4.61 | 5.06 | 5.39 | 4.85 | RHOBTB3 | Rho-related BTB domain containing 3 | NM_014899 |
| 0.98 | 3.32 | 5.38 | 5.32 | 4.96 | LOC145786 | hypothetical protein LOC145786 | AV699825 |
| 2.02 | 4.53 | 5.22 | 5.38 | 4.77 | GPR177 | G protein-coupled receptor 177 | AL534095 |
| 2.49 | 4.28 | 5.36 | 3.65 | 1.79 | LOC387763 | hypothetical LOC387763 | AW276078 |
| 1.45 | 1.25 | 1.62 | 3.63 | 5.36 | COL1A1 | collagen, type I, alpha 1 | K01228 |
| 2.05 | 2.55 | 4.49 | 5.33 | 5.18 | CDH11 | cadherin 11, type 2, OB-cadherin (osteob | D21254 |
| 0.00 | 0.00 | 2.12 | 4.31 | 5.33 | IGF2 /// INS-IGF2 | insulin-like growth factor 2 (somatomedin | NM_000612 |
| 0.00 | 0.00 | 0.86 | 4.32 | 5.31 | RSPO2 | R-spondin 2 homolog (Xenopus laevis) | BC027938 |
| 0.03 | 2.03 | 4.91 | 5.30 | 4.88 | DOK4 | docking protein 4 | BC003541 |
| -0.59 | 1.79 | 3.44 | 5.06 | 5.29 | C9orf135 | chromosome 9 open reading frame 135 | AI768674 |
| 0.00 | 0.49 | 3.29 | 5.00 | 5.28 | IGFBP5 | insulin-like growth factor binding protein 5 | AW007532 |
| 0.00 | 1.17 | 3.78 | 4.83 | 5.25 | MYL4 | myosin, light chain 4, alkali; atrial, embry | X58851 |
| -0.62 | -0.47 | 3.49 | 4.42 | 5.23 | | gb:AI671581 /DB_XREF=gi:4851312 /DB | AI671581 |
| 0.85 | 4.44 | 5.22 | 4.99 | 4.61 | C9orf19 | chromosome 9 open reading frame 19 | AA284532 |
| 1.65 | 3.27 | 3.55 | 4.55 | 5.19 | COL5A1 | collagen, type V, alpha 1 | N30339 |
| -0.11 | 0.64 | 1.96 | 4.06 | 5.19 | LOXL1 | lysyl oxidase-like 1 | NM_005576 |
| 1.75 | 3.03 | 4.34 | 5.17 | 4.93 | TBX3 | T-box 3 (ulnar mammary syndrome) | AI806338 |
| 1.16 | -1.76 | -3.26 | 5.15 | 4.74 | PMAIP1 | phorbol-12-myristate-13-acetate-induced | NM_021127 |
| -0.20 | 1.79 | 4.54 | 5.10 | 4.37 | DOK4 | docking protein 4 | NM_018110 |
| 0.70 | 3.24 | 4.68 | 5.09 | 4.16 | HAPLN1 | hyaluronan and proteoglycan link protein | NM_001884 |
| 1.13 | 4.04 | 4.65 | 5.08 | 4.58 | RHOBTB3 | Rho-related BTB domain containing 3 | AK023621 |
| 1.82 | 3.86 | 4.23 | 5.08 | 4.73 | RGS5 | regulator of G-protein signalling 5 | AF159570 |
| 3.28 | 4.01 | 4.97 | 5.06 | 4.60 | DLX2 | distal-less homeobox 2 | NM_004405 |
| 0.03 | 3.43 | 4.90 | 4.65 | 4.28 | HAPLN1 | hyaluronan and proteoglycan link protein | U43328 |
| 0.02 | 0.80 | 3.68 | 4.62 | 5.04 | MYL4 | myosin, light chain 4, alkali; atrial, embry | M36172 |
| -0.70 | -0.99 | -1.49 | -1.97 | -5.02 | HIST1H2BD | Histone cluster 1, H2bd | AI435590 |
| 1.40 | 1.13 | 2.51 | 4.73 | 5.01 | DKK1 | dickkopf homolog 1 (Xenopus laevis) | NM_012242 |
| 0.49 | 1.29 | 1.96 | 3.45 | 5.00 | CRABP1 | cellular retinoic acid binding protein 1 | NM_004378 |
| 1.75 | 4.20 | 4.77 | 5.00 | 4.41 | RHOBTB3 | Rho-related BTB domain containing 3 | BE620739 |
| -0.48 | -0.57 | -1.02 | -2.12 | -4.99 | LOC642559 | POU domain, class 5, transcription factor | AF268617 |
| 0.52 | 3.45 | 4.66 | 4.65 | 4.98 | SEMA6D | sema domain, transmembrane domain (T | AL036088 |
| -0.65 | -1.52 | 2.09 | 3.99 | 4.97 | NID2 | nidogen 2 (osteonidogen) | NM_007361 |
| -0.49 | -1.41 | -2.37 | -3.49 | -4.96 | ZNF206 | zinc finger protein 206 | NM_032805 |
| -0.73 | 2.85 | 4.32 | 4.96 | 4.96 | TIMP4 | TIMP metallopeptidase inhibitor 4 | NM_003256 |
| -0.46 | -0.43 | -0.82 | -1.84 | -4.95 | LOC645682 | POU domain, class 5, transcription factor | AF268613 |

Appendix 2

| C1 | C2 | C3 | C4 | C5 | Symbol | Description | Accession |
|---|---|---|---|---|---|---|---|
| -1.42 | -2.50 | -4.56 | -4.94 | -4.02 | CDCA7L | cell division cycle associated 7-like | AK022955 |
| 0.71 | 1.78 | -3.64 | 4.93 | 4.81 | CXCR7 | chemokine (C-X-C motif) receptor 7 | AI817041 |
| 0.50 | 1.01 | -4.16 | 4.93 | -4.80 | NODAL | nodal homolog (mouse) | AI050866 |
| 0.00 | 0.00 | 2.13 | 4.07 | 4.91 | PITX1 | paired-like homeodomain transcription fa NM_002653 |
| 2.43 | 3.60 | 3.59 | 4.56 | 4.90 | AHNAK | AHNAK nucleoprotein (desmoyokin) | BG287862 |
| 0.89 | 2.09 | 3.30 | 4.90 | 4.68 | FLRT3 | fibronectin leucine rich transmembrane pr N71923 |
| 1.30 | 0.86 | -0.90 | -2.97 | -4.90 | | Transcribed locus | AW014743 |
| 0.00 | 1.18 | 3.72 | 4.89 | 3.75 | SESN3 | sestrin 3 | BF685808 |
| -0.75 | -2.51 | -2.80 | -2.92 | -4.89 | VSNL1 | visinin-like 1 | AF039555 |
| -0.70 | -0.16 | -1.58 | -2.92 | -4.87 | C14orf29 | chromosome 14 open reading frame 29 | BE502594 |
| 2.93 | 2.99 | 4.49 | 4.86 | 4.69 | LEF1 | lymphoid enhancer-binding factor 1 | AF288571 |
| 0.00 | 0.06 | 3.13 | 4.86 | 4.76 | MEIS2 | Meis1, myeloid ecotropic viral integration NM_020149 |
| -0.52 | 0.34 | -2.19 | -2.79 | -4.85 | | Homo sapiens, Similar to otoconin 90, cl AI950472 |
| 0.53 | 1.26 | 1.60 | 2.68 | 4.85 | PRSS23 | protease, serine, 23 | AW471145 |
| 2.28 | 3.25 | 4.65 | 4.81 | 4.34 | | Transcribed locus | AA934610 |
| 0.86 | 2.16 | 3.39 | 4.81 | 4.46 | FLRT3 | fibronectin leucine rich transmembrane pr NM_013281 |
| -0.30 | 0.30 | 1.21 | 3.58 | 4.80 | KCTD12 | potassium channel tetramerisation domai AA551075 |
| -0.37 | -0.86 | -2.49 | 3.19 | -4.79 | TDGF1 /// TDGF3 | teratocarcinoma-derived growth factor 1 / NM_003212 |
| 0.00 | 0.00 | 1.80 | 3.91 | 4.78 | IGF2 /// INS-IGF2 | insulin-like growth factor 2 (somatomedin M17863 |
| 4.78 | 3.79 | 2.27 | 1.54 | 0.18 | EOMES | eomesodermin homolog (Xenopus laevis) NM_005442 |
| -0.58 | -2.25 | -4.77 | -4.77 | 4.77 | NANOG | Nanog homeobox | AW137517 |
| -0.31 | 2.95 | 4.40 | 4.75 | 3.88 | | gb:AU144114 /DB_XREF=gi:11005635 /l AU144114 |
| -0.58 | -1.69 | -2.44 | -3.38 | -4.74 | SFRP2 | secreted frizzled-related protein 2 | AW003584 |
| -0.09 | -1.34 | -3.10 | -4.29 | -4.74 | CBR3 | carbonyl reductase 3 | NM_001236 |
| -0.91 | -3.86 | -4.72 | -4.72 | -4.72 | UTF1 | undifferentiated embryonic cell transcripti NM_003577 |
| -0.66 | 0.23 | 3.36 | 4.64 | 4.71 | EPAS1 | endothelial PAS domain protein | AF052094 |
| 0.00 | -2.67 | -4.29 | -4.70 | 4.20 | HOXB6 | homeobox B6 | NM_018952 |
| -1.32 | -1.82 | -2.47 | -3.55 | -4.70 | GPR160 | G protein-coupled receptor 160 | BC000181 |
| -1.49 | -1.14 | -1.55 | -2.63 | -4.70 | DPPA2 | developmental pluripotency associated 2 AI204212 |
| 0.00 | 0.00 | 3.86 | 4.70 | 3.86 | | Transcribed locus | R71596 |
| 1.59 | 1.07 | 1.76 | 3.27 | 4.69 | COL1A1 | collagen, type I, alpha 1 | BE221212 |
| 0.00 | 0.00 | 0.00 | 2.14 | 4.68 | AQP1 | aquaporin 1 (Colton blood group) | AL518391 |
| 0.00 | 0.00 | 0.00 | 1.66 | 4.68 | ACTA2 | actin, alpha 2, smooth muscle, aorta | NM_001613 |
| 1.22 | 2.29 | 2.15 | 3.26 | 4.66 | PRSS23 | protease, serine, 23 | NM_007173 |
| 0.20 | 0.61 | 0.90 | 3.39 | 4.66 | KCTD12 | potassium channel tetramerisation domai AI718937 |
| 1.70 | 3.35 | 4.43 | 4.64 | 4.14 | TBX3 | T-box 3 (ulnar mammary syndrome) | N29712 |
| 0.99 | 1.54 | 2.89 | 4.64 | 4.48 | SCUBE3 | signal peptide, CUB domain, EGF-like 3 AI733234 |
| 0.00 | 2.71 | 3.85 | 4.64 | 3.80 | | gb:AI760252 /DB_XREF=gi:5175919 /DB AI760252 |
| 0.18 | -0.84 | -1.19 | -2.55 | -4.63 | FOXH1 | forkhead box H1 | AI636647 |
| 2.31 | 4.63 | 4.26 | 3.79 | 2.47 | ENPEP | glutamyl aminopeptidase (aminopeptidas L12468 |
| -1.08 | -1.28 | -3.05 | -4.06 | -4.62 | PCSK9 | proprotein convertase subtilisin/kexin typ W92036 |
| 1.02 | 1.62 | 3.51 | 4.62 | 4.31 | CDH11 | cadherin 11, type 2, OB-cadherin (osteob NM_001797 |
| -0.34 | -0.34 | -0.72 | -1.09 | -4.62 | POU5F1 /// POU5l | POU domain, class 5, transcription factor NM_002701 |
| -1.20 | -2.78 | -3.01 | -3.35 | -4.61 | VSNL1 | visinin-like 1 | NM_003385 |
| -0.11 | -0.71 | -2.62 | -3.80 | 4.61 | | Transcribed locus | BF057809 |
| -0.20 | -2.35 | -3.51 | -4.61 | -4.58 | SFRP2 | secreted frizzled-related protein 2 | AF311912 |
| 0.00 | 1.78 | 4.31 | 4.12 | 4.60 | LRRC32 | leucine rich repeat containing 32 | NM_005512 |
| 0.00 | 1.59 | 4.21 | 4.58 | 3.97 | DOK4 | docking protein 4 | BF591163 |
| -0.42 | -1.43 | -1.87 | -2.62 | -4.57 | ZNF206 | zinc finger protein 206 | NM_032805 |
| -1.23 | -1.53 | 0.52 | 2.12 | 4.56 | MGC14376 | hypothetical protein MGC14376 | AF070569 |
| -0.40 | -0.37 | -0.70 | -1.78 | -4.55 | POU5F1 /// POU5l | POU domain, class 5, transcription factor AF268615 |
| 0.00 | 1.00 | 3.59 | 4.55 | 0.68 | DIO3 | deiodinase, iodothyronine, type II | NM_001362 |
| 1.26 | 3.18 | 3.65 | 4.54 | 4.10 | RGS5 | regulator of G-protein signalling 5 | AI183997 |
| -0.65 | 0.45 | 2.96 | 4.24 | 4.51 | MYL4 | myosin, light chain 4, alkali; atrial, embryc AF116676 |
| -1.03 | 0.83 | 2.03 | 3.65 | 4.49 | NELL2 | NEL-like 2 (chicken) /// NEL-like 2 (chicke NM_006159 |
| 1.68 | 2.21 | 3.53 | 4.47 | 3.82 | CAMK2N1 | calcium/calmodulin-dependent protein kir NM_018584 |
| 0.00 | 0.00 | 1.35 | 3.07 | 4.44 | RGS4 | regulator of G-protein signalling 4 | AL514445 |
| -0.64 | -0.83 | -1.79 | -2.79 | -4.44 | | gb:AV731490 /DB_XREF=gi:10840911 /l AV731490 |
| -0.82 | 1.51 | 3.32 | 4.25 | 4.43 | POLR3G | polymerase (RNA) III (DNA directed) poly BF062139 |
| 0.33 | 3.03 | 3.43 | 4.42 | 3.92 | UPK1B /// RGS5 | uroplakin 1B /// regulator of G-protein sig AF493929 |
| 1.51 | 3.05 | 3.46 | 4.08 | 4.41 | GATA6 | GATA binding protein 6 | D87811 |
| -0.30 | -2.37 | -4.40 | -4.40 | 4.40 | FGF4 | fibroblast growth factor 4 (heparin secretc BF510715 |
| 0.76 | 3.52 | 4.39 | 4.24 | 1.64 | YPEL2 | yippee-like 2 (Drosophila) | BE502982 |
| 1.59 | 3.57 | 4.04 | 4.38 | 2.67 | BMP4 | bone morphogenetic protein 4 | D30751 |
| -0.29 | 0.64 | 3.27 | 4.38 | 3.83 | PDGFRA | platelet-derived growth factor receptor, al NM_006206 |
| 2.30 | 2.02 | 2.67 | 4.38 | 2.74 | ID2 /// ID2B | inhibitor of DNA binding 2, dominant neg: AI819238 |
| 1.31 | 2.73 | 3.24 | 4.33 | 3.43 | TBC1D9 | TBC1 domain family, member 9 (with GR AI348094 |
| 1.35 | -2.68 | -4.32 | -4.32 | -4.32 | | Transcribed locus | AI554075 |
| 0.30 | -1.29 | 3.25 | 3.25 | 3.77 | | MRNA; cDNA DKFZp313B1017 (from clc BE883841 |
| 2.59 | 3.80 | 4.28 | 2.92 | 1.79 | ID4 | inhibitor of DNA binding 4, dominant neg: U16153 |
| 2.46 | 3.35 | 4.25 | 4.28 | 3.98 | EFNA1 | ephrin-A1 | NM_004428 |
| -0.52 | -1.21 | -2.67 | -3.40 | -4.26 | HES6 | hairy and enhancer of split 6 (Drosophila AW249678 |
| -1.28 | -2.77 | -3.94 | -4.26 | -3.52 | LOC645619 /// LO similar to Adenylate kinase isoenzyme 4, AI653169 |
| 2.17 | 3.02 | 3.11 | 3.73 | 4.25 | IL6ST | interleukin 6 signal transducer (gp130, or AL049265 |
| -0.62 | -1.47 | -4.05 | -4.25 | -3.19 | LOC91461 | hypothetical protein BC007901 | BF528878 |
| 1.51 | 3.31 | 4.25 | 3.95 | 3.33 | WNT5A | wingless-type MMTV integration site fami AI968085 |
| 1.71 | 1.31 | 2.49 | 4.24 | 4.01 | APCDD1 | adenomatosis polyposis coli down-regula N48299 |
| -1.10 | -2.22 | -3.98 | -4.24 | -4.24 | LCK | lymphocyte-specific protein tyrosine kina: NM_005356 |
| 1.69 | 2.74 | 3.36 | 4.24 | 2.68 | ARL4C | ADP-ribosylation factor-like 4C | AW450363 |
| 1.31 | 2.69 | 4.23 | 4.12 | 2.91 | TMEM54 | transmembrane protein 54 | AL545105 |
| 2.28 | 3.25 | 4.23 | 3.97 | 2.81 | GATA3 | GATA binding protein 3 | AI796169 |
| 0.22 | 0.42 | 1.55 | 3.17 | 4.23 | TNS1 | tensin 1 /// tensin 1 | AL046979 |
| 0.00 | 0.00 | 1.72 | 4.22 | 2.30 | RASGRP1 | RAS guanyl releasing protein 1 (calcium NM_005739 |
| 0.34 | 0.29 | 0.68 | 1.83 | 4.22 | DLK1 | delta-like 1 homolog (Drosophila) | U15979 |
| 0.84 | 1.27 | 4.17 | 3.21 | 4.21 | FN1 | fibronectin 1 | AJ276395 |
| 3.62 | 3.80 | 4.20 | 3.37 | 2.62 | ID4 | inhibitor of DNA binding 4, dominant neg: AW157094 |
| 1.56 | 3.01 | 3.54 | 3.91 | 4.20 | FZD5 | frizzled homolog 5 (Drosophila) /// frizzlec NM_030804 |

Appendix 2

| | | | | | | Gene | Description | Accession |
|---|---|---|---|---|---|---|---|---|
| 0.00 | 1.26 | | 3.92 | 4.19 | | 3.09 | PLA2G2A | phospholipase A2, group IIA (platelets, s) NM_000300 |
| 4.17 | 3.19 | | 1.08 | 0.73 | | 0.00 | SP5 | Sp5 transcription factor | AI380207 |
| 3.37 | 3.28 | | 4.16 | 3.79 | | 2.75 | ID2 /// ID2B | inhibitor of DNA binding 2, dominant neg D13891 |
| 0.00 | 0.00 | | 0.00 | 0.00 | | 4.15 | EGFL6 | EGF-like-domain, multiple 6 | NM_015507 |
| 2.24 | 4.04 | | 4.15 | 3.94 | | 3.24 | DLC1 | deleted in liver cancer 1 | AF026219, |
| 0.00 | 1.15 | | 2.80 | 4.14 | | 3.07 | RPESP | RPE-spondin | AW662373 |
| 0.97 | 3.49 | | 4.13 | 3.97 | | 1.60 | FAM123A | family with sequence similarity 123A | N66614 |
| 0.49 | 1.69 | | 3.02 | 4.11 | | 3.97 | POSTN | periostin, osteoblast specific factor | D13665 |
| 0.00 | 0.00 | | 2.59 | 4.07 | | 4.11 | ZNF503 | zinc finger protein 503 | AA603467 |
| 1.05 | 3.29 | | 4.09 | 4.06 | | 3.22 | FAM89A | family with sequence similarity 89, memb AI130705 |
| 0.00 | 0.00 | | 2.30 | 4.09 | | 3.83 | SLC39A2 | solute carrier family 39 (zinc transporter), NM_014579 |
| 0.00 | 0.47 | | 0.00 | 1.32 | | 4.08 | ARHGDIB | Rho GDP dissociation inhibitor (GDI) bet NM_001175 |
| -0.71 | -1.75 | | -2.64 | -2.80 | | -4.07 | MYC | v-myc myelocytomatosis viral oncogene NM_002467 |
| 0.28 | 0.27 | | 1.84 | 3.33 | | 4.07 | ADAMTS9 | ADAM metallopeptidase with thrombospc AL832835 |
| 0.94 | 2.36 | | 2.90 | 4.06 | | 3.34 | SLCO2A1 | solute carrier organic anion transporter fa NM_005630 |
| 0.00 | 0.82 | | 2.57 | 4.06 | | 2.94 | RPESP | RPE-spondin | AW662373 |
| 3.54 | 4.05 | | 3.96 | 2.87 | | 0.57 | | Transcribed locus | BF110534 |
| 0.00 | 0.00 | | 0.00 | 2.76 | | 4.04 | CRHBP | corticotropin releasing hormone binding p NM_001882 |
| -0.92 | -0.41 | | -1.80 | 2.51 | | -4.04 | CBR1 | carbonyl reductase 1 | BC002511 |
| 2.82 | 3.53 | | 4.04 | 3.29 | | 0.75 | PRKD1 | protein kinase D1 | NM_002742 |
| 0.86 | 0.44 | | 2.21 | 3.65 | | 4.03 | MXRA5 | matrix-remodelling associated 5 | AF245505 |
| 0.00 | 0.08 | | 1.35 | 3.24 | | 4.01 | C11orf9 | chromosome 11 open reading frame 9 | NM_013279 |
| -1.49 | -1.92 | | -1.21 | 1.65 | | -4.00 | PRODH | proline dehydrogenase (oxidase) 1 | AA074145 |
| 0.00 | 0.03 | | 0.27 | 0.00 | | 4.00 | MYO10 | Myosin X | BC041694 |
| 0.00 | 0.00 | | 0.58 | 2.41 | | 3.99 | | Transcribed locus | R33750 |
| -1.26 | -1.77 | | -1.91 | -3.27 | | -3.99 | SP8 | Sp8 transcription factor | BF447038 |
| 0.45 | 2.03 | | 2.86 | 3.89 | | 3.99 | PALLD | palladin, cytoskeletal associated proteir | AU157932 |
| 0.00 | 0.00 | | 0.42 | 3.09 | | 3.99 | CLEC1B | C-type lectin domain family 1, member E NM_016509 |
| 0.00 | 1.86 | | 3.36 | 3.99 | | 2.12 | WNT6 | wingless-type MMTV integration site fami AY009401 |
| 0.83 | 2.27 | | 2.70 | 3.16 | | 3.98 | IRX3 | iroquois homeobox protein 3 | AI681917 |
| -1.26 | 1.09 | | 0.11 | 0.87 | | 3.98 | | cDNA FLJ35259 fis, clone PROST20042 AA483467 |
| 0.00 | 0.00 | | -2.35 | 3.97 | | 3.71 | IGFBP5 | insulin-like growth factor binding protein 5 AW157548 |
| 1.28 | 3.96 | | 3.48 | 3.13 | | 1.68 | ENPEP | glutamyl aminopeptidase (aminopeptidas NM_001977 |
| 0.33 | 0.50 | | 3.10 | 3.94 | | 3.92 | GAS1 | growth arrest-specific 1 | NM_002048 |
| 0.90 | 3.03 | | 3.89 | 3.94 | | 3.42 | KRT19 | keratin 19 | NM_002276 |
| 0.00 | 1.52 | | 3.94 | 3.15 | | 0.00 | CLIC5 | chloride intracellular channel 5 | AL049313 |
| 0.59 | 2.54 | | 3.94 | 3.78 | | 1.51 | KCNK12 | potassium channel, subfamily K, member NM_022055 |
| 3.12 | 3.60 | | 3.93 | 3.41 | | 2.32 | SAMD11 | sterile alpha motif domain containing 11 | AK054643 |
| 1.07 | 0.75 | | 2.90 | 3.93 | | 3.06 | ADAMTS9 | ADAM metallopeptidase with thrombospc AI431730 |
| 2.25 | 2.44 | | 2.28 | 3.06 | | 3.92 | CAPN2 | calpain 2, (m/II) large subunit | M23254 |
| 0.74 | 0.39 | | 1.27 | 2.28 | | 3.92 | IMPAD1 | inositol monophosphatase domain contai NM_017813 |
| 0.74 | 1.82 | | 3.20 | 3.64 | | 3.90 | ALCAM | activated leukocyte cell adhesion molecu BF242905 |
| 0.90 | 1.54 | | 2.11 | 3.56 | | 3.90 | HS3ST1 | heparan sulfate (glucosamine) 3-O-sulfot NM_005114 |
| 1.12 | 1.35 | | -2.54 | 3.68 | | -3.90 | POLR3G | polymerase (RNA) III (DNA directed) poly NM_006467 |
| 0.88 | 1.94 | | 2.72 | 3.59 | | 3.89 | PALLD | palladin, cytoskeletal associated proteir | NM_016081 |
| 1.65 | 3.81 | | 3.89 | 3.53 | | 2.83 | DLC1 | deleted in liver cancer 1 | AA524250 |
| 2.18 | 2.32 | | 2.70 | 3.88 | | 3.88 | CR1 /// CR1L /// LC | complement component (3b/4b) receptor BE552138 |
| 3.65 | 3.88 | | 3.64 | 2.83 | | 2.19 | ID3 | inhibitor of DNA binding 3, dominant neg NM_002167 |
| -0.24 | 0.74 | | 1.98 | 2.79 | | 3.88 | | Homo sapiens, Similar to otoconin 90, clc BC020935 |
| 1.40 | -2.49 | | -3.48 | 3.88 | | 3.26 | | gb:AI566130 /DB_XREF=gi:4524582 /DE AI566130 |
| 0.00 | 0.00 | | 0.00 | 1.10 | | 3.87 | SLN | sarcolipin | NM_003063 |
| 0.00 | 0.00 | | 0.59 | 2.07 | | 3.87 | TMEM100 | transmembrane protein 100 | NM_018286 |
| 0.00 | 0.00 | | 2.90 | 3.87 | | 2.94 | ACPP | acid phosphatase, prostate | NM_001099 |
| -0.60 | -2.26 | | -3.86 | -3.86 | | -3.66 | HLA-DPB2 | major histocompatibility complex, class II, BF057731 |
| -1.03 | -2.02 | | -3.73 | -3.86 | | -3.71 | LOC439949 | hypothetical gene supported by AY00715 AW193600 |
| 0.57 | 0.49 | | 1.49 | 2.91 | | 3.86 | | gb:AK093435.1 /DB_XREF=gi:21752304 AK093435 |
| 1.57 | 1.39 | | 0.88 | 2.66 | | 3.86 | PCDH7 | BH-protocadherin (brain-heart) | NM_002589 |
| 0.57 | 0.50 | | 1.65 | 3.27 | | 3.86 | ATP7B | ATPase, Cu++ transporting, beta polyper NM_000053 |
| 0.00 | 0.86 | | 2.19 | 3.72 | | 3.86 | TNFRSF19 | tumor necrosis factor receptor superfamil BF432648 |
| 0.91 | 2.46 | | 2.38 | 2.80 | | 3.86 | UBE2J1 | ubiquitin-conjugating enzyme E2, J1 (UB AF161502 |
| 0.00 | 0.22 | | 3.22 | 3.85 | | 3.69 | LOC400043 | hypothetical gene supported by BC00935 AL520272 |
| -0.32 | 0.63 | | 3.08 | 3.84 | | 3.71 | PCDH17 | protocadherin 17 | NM_014459 |
| -0.32 | -1.26 | | -2.00 | -3.13 | | -3.84 | CKMT1B /// CKMT | creatine kinase, mitochondrial 1B /// creat NM_020990 |
| -0.79 | -1.64 | | -2.65 | -3.84 | | -1.91 | GALNT3 | UDP-N-acetyl-alpha-D-galactosamine:po BF063271 |
| 0.00 | 0.02 | | 0.91 | 3.50 | | 3.83 | NRP1 | neuropilin 1 | BE620457 |
| 0.87 | 1.81 | | 3.37 | 3.83 | | 3.20 | ARHGAP29 | Rho GTPase activating protein 29 | NM_004815 |
| 1.26 | 3.20 | | 2.99 | 3.83 | | 3.25 | COL11A1 | collagen, type XI, alpha 1 | NM_001854 |
| -0.75 | -1.64 | | -2.27 | -2.58 | | -3.83 | DPPA4 | developmental pluripotency associated 4 NM_018189 |
| -3.04 | -3.35 | | -3.82 | -2.80 | | 1.54 | ID4 | Inhibitor of DNA binding 4, dominant neg AV646610 |
| 0.00 | 0.00 | | 0.00 | 1.74 | | 3.82 | GUCY1A3 | guanylate cyclase 1, soluble, alpha 3 | AI719730 |
| 0.99 | 2.36 | | 3.08 | 3.81 | | 3.77 | GATA4 | GATA binding protein 4 | AV700724 |
| 0.00 | 2.64 | | 3.55 | 3.80 | | 3.78 | PSTPIP2 | proline-serine-threonine phosphatase int NM_024430 |
| -0.74 | -1.53 | | -3.64 | -3.80 | | -2.44 | THY1 | Thy-1 cell surface antigen | AL161958 |
| 0.35 | 1.57 | | 2.70 | 3.80 | | 3.57 | CCDC92 | coiled-coil domain containing 92 | NM_025140 |
| 0.00 | 0.00 | | 1.41 | 3.09 | | 3.80 | HOXD10 | homeobox D10 | AW299531 |
| 0.37 | 0.58 | | 0.48 | 2.26 | | 3.79 | EGFLAM | EGF-like, fibronectin type III and laminin ( BF114725 |
| 0.00 | 0.18 | | 0.53 | 3.21 | | 3.79 | TEK | TEK tyrosine kinase, endothelial (venous NM_000459 |
| 0.00 | 0.25 | | 0.47 | 0.93 | | 3.78 | TFPI | tissue factor pathway inhibitor (lipoproteir AF021834 |
| -0.43 | -0.41 | | 1.87 | 2.97 | | 3.77 | HAS3 | hyaluronan synthase 3 | AF232772 |
| 0.74 | 2.49 | | 3.77 | 3.77 | | 2.39 | ATP2B4 | ATPase, Ca++ transporting, plasma merr AW517686 |
| 1.24 | 1.63 | | 1.78 | 2.80 | | 3.76 | PARVA | parvin, alpha | NM_018222 |
| 0.95 | 2.51 | | 3.76 | 3.52 | | 2.41 | ATP2B4 | ATPase, Ca++ transporting, plasma merr AW517686 |
| 0.00 | 0.00 | | 0.00 | 2.70 | | 3.76 | C20orf82 | chromosome 20 open reading frame 82 | AI816793 |
| -1.10 | 1.47 | | 1.90 | 2.49 | | -3.76 | HRASLS3 | HRAS-like suppressor 3 | BC001387 |
| 0.00 | 0.00 | | 1.52 | 3.69 | | 3.76 | ODAM | odontogenic, ameloblast asssociatec | NM_017855 |
| 0.00 | 0.55 | | 1.97 | 3.76 | | 3.74 | C12orf46 | chromosome 12 open reading frame 46 | AI051248 |
| 3.76 | 3.66 | | 1.73 | 1.72 | | 0.27 | T | T, brachyury homolog (mouse) | NM_003181 |

Appendix 2

| | | | | | Symbol | Description | Accession |
|---|---|---|---|---|---|---|---|
| -2.41 | -3.40 | -3.76 | -3.76 | -3.76 | PIM2 | pim-2 oncogene | NM_006875 |
| -0.76 | -2.66 | -3.60 | -3.75 | -3.75 | AK3L1 | adenylate kinase 3-like 1 | AK026966 |
| -1.04 | -1.33 | -2.53 | -3.70 | -3.75 | PMAIP1 | phorbol-12-myristate-13-acetate-induced | AI857639 |
| -1.45 | -2.39 | -3.13 | -3.75 | -3.74 | ARL4C | ADP-ribosylation factor-like 4C | BG435404 |
| -0.20 | -1.74 | -2.56 | -3.66 | -3.75 | PALLD | palladin, cytoskeletal associated protein | AK025843 |
| -3.05 | -3.74 | -3.22 | -2.42 | -1.52 | GRHL3 | grainyhead-like 3 (Drosophila) | AL137763 |
| 0.00 | -2.21 | -3.43 | -3.44 | -3.73 | FOXF1 | forkhead box F1 | NM_001451 |
| -2.33 | -2.95 | -3.73 | -3.73 | -3.73 | PRDM14 | PR domain containing 14 | NM_024504 |
| 0.74 | 0.42 | -0.12 | -2.17 | -3.73 | CCDC4 | coiled-coil domain containing 4 | AA833830 |
| 0.03 | 2.91 | 3.71 | 3.67 | 1.21 | FAM123A | Family with sequence similarity 123A | BE046923 |
| 1.10 | 2.61 | 3.71 | 3.55 | 2.84 | TFAP2A | transcription factor AP-2 alpha (activating) | NM_003220 |
| -0.36 | -1.44 | -2.99 | -3.41 | -3.71 | SEPHS1 | Selenophosphate synthetase 1 | AI885670 |
| 0.70 | 1.94 | 2.42 | 2.70 | 3.70 | COBLL1 | COBL-like 1 | NM_014900 |
| -1.36 | -1.56 | -2.75 | -3.32 | -3.70 | GPR176 | G protein-coupled receptor 176 | AA526584 |
| -1.01 | -1.76 | -3.47 | -3.70 | -2.95 | FGFBP3 | fibroblast growth factor binding protein 3 | AI628573 |
| -1.07 | -1.05 | -2.49 | -1.88 | -3.69 | SLC16A10 | solute carrier family 16, member 10 (aron) | N30257 |
| -3.49 | -3.69 | -0.19 | -1.45 | -1.03 | SERPINE1 | serpin peptidase inhibitor, clade E (nexin) | NM_000602 |
| 0.42 | -0.35 | -0.64 | -1.18 | -3.68 | SCNN1A | sodium channel, nonvoltage-gated 1 alph | NM_001038 |
| 1.60 | 2.26 | 2.43 | 2.84 | 3.68 | IL6ST | Interleukin 6 signal transducer (gp130, or) | AW242916 |
| 0.00 | 0.17 | 0.00 | 1.79 | 3.68 | TWIST1 | twist homolog 1 (acrocephalosyndactyly) | X99268 |
| -0.44 | -1.83 | -2.81 | -3.00 | -3.68 | ZNF483 | Zinc finger protein 483 | BC036488 |
| -0.87 | -2.68 | -3.13 | -3.53 | -3.68 | GLB1L3 | galactosidase, beta 1 like 3 | BC040605 |
| -1.16 | -1.23 | -1.96 | -3.55 | -3.67 | TNRC9 | trinucleotide repeat containing 9 | AK025084 |
| 3.67 | 3.01 | 0.69 | 0.15 | -0.82 | MIXL1 | Mix1 homeobox-like 1 (Xenopus laevis) | AF211891 |
| 1.84 | 3.67 | 2.68 | 1.55 | 0.00 | MESP1 | mesoderm posterior 1 homolog (mouse) | BC006219 |
| 0.00 | 2.06 | 2.36 | 3.67 | 2.75 | LOC728473 | hypothetical protein LOC728473 | N63706 |
| -1.33 | -3.25 | -3.31 | -3.17 | -3.66 | ETV1 | ets variant gene 1 | BE881590 |
| -1.36 | -2.45 | -3.66 | -3.66 | -3.66 | PIPOX | pipecolic acid oxidase | AF136970 |
| 0.00 | 0.00 | 0.75 | 3.24 | 3.66 | HOXC6 | homeobox C6 | NM_004503 |
| 3.03 | 3.23 | 2.96 | 3.66 | 2.89 | WNT5B | wingless-type MMTV integration site famil | NM_030775 |
| 1.10 | 1.24 | 1.71 | 3.24 | 3.65 | TGFB1I1 | transforming growth factor beta 1 induced | BC001830 |
| 0.05 | -0.05 | -1.38 | -2.48 | -3.64 | CD200 | CD200 molecule | AF063591 |
| -1.30 | -1.32 | -2.21 | -3.08 | -3.64 | TNRC9 | trinucleotide repeat containing 9 | AK027006 |
| 3.03 | 3.64 | 2.89 | 3.09 | 2.24 | CYP1B1 | cytochrome P450, family 1, subfamily B, | NM_000104 |
| 1.42 | 2.82 | 3.64 | 3.62 | 3.46 | WNT5A | wingless-type MMTV integration site famil | NM_003392 |
| -1.11 | -0.85 | -2.34 | -3.64 | -3.64 | GNAS | GNAS complex locus | AF107846 |
| 0.00 | 3.64 | 3.51 | 3.16 | 0.00 | MYST2 /// LOC28 | MYST histone acetyltransferase 2 /// Hyp | AI521166 |
| 0.60 | 0.98 | 0.00 | 1.56 | 3.63 | TIMP3 | TIMP metallopeptidase inhibitor 3 (Sorsb) | NM_000362 |
| 0.00 | 0.65 | 2.18 | 3.63 | 3.12 | SCUBE3 | signal peptide, CUB domain, EGF-like 3 | BE674338 |
| 0.99 | 2.95 | 3.63 | 2.97 | 2.26 | TACSTD2 | tumor-associated calcium signal transduc | J04152 |
| 0.26 | 0.20 | 0.00 | 0.00 | 3.63 | HMGA2 | high mobility group AT-hook 2 | U29113 |
| 0.00 | 2.23 | 3.63 | 2.62 | 1.44 | PENK | proenkephalin | NM_006211 |
| -0.82 | -1.03 | -1.65 | -2.15 | -3.63 | HIST1H2BD | Histone cluster 1, H2bd | AI435590 |
| 0.00 | 0.00 | 0.00 | 1.36 | 3.63 | AQP1 | aquaporin 1 (Colton blood group) | NM_000385 |
| -0.60 | -0.63 | -1.61 | -2.48 | -3.62 | CYP2S1 | cytochrome P450, family 2, subfamily S, | AF335278 |
| -1.48 | -0.82 | -1.00 | -2.30 | -3.62 | PAG1 | phosphoprotein associated with glycosph | AK000680 |
| 0.53 | 1.42 | 1.33 | 3.00 | 3.60 | PLAGL1 | pleiomorphic adenoma gene-like 1 | BG547855 |
| -0.96 | 0.33 | -1.07 | 1.76 | 3.60 | KIF1A | kinesin family member 1A | BG473130 |
| 0.33 | 0.43 | 1.30 | 2.28 | 3.60 | EDG3 | endothelial differentiation, sphingolipid G- | AA534817 |
| 0.00 | 0.00 | 3.06 | 3.60 | 3.47 | HGF | hepatocyte growth factor (hepapoietin A) | X16323 |
| 0.28 | 1.46 | 2.20 | 3.24 | 3.60 | MXRA8 /// LOC72 | matrix-remodelling associated 8 /// similar | AW888223 |
| 0.00 | 2.03 | 3.40 | 3.59 | 3.52 | SEMA6D | sema domain, transmembrane domain (T | AK022831 |
| -0.77 | -0.72 | -2.02 | -2.67 | -3.59 | ADCY2 | adenylate cyclase 2 (brain) | AU149572 |
| -0.69 | -1.32 | -3.58 | -3.56 | -2.59 | THY1 | Thy-1 cell surface antigen | AL558479 |
| 0.56 | 2.66 | 3.58 | 3.13 | 0.50 | FAM123A | family with sequence similarity 123A | NM_152704 |
| 2.73 | 3.58 | 2.92 | 3.30 | 2.20 | CYP1B1 | cytochrome P450, family 1, subfamily B, | AU154504 |
| 0.00 | 0.00 | 0.00 | 0.45 | 3.57 | NRP1 | neuropilin 1 | AF145712 |
| 0.00 | 0.00 | 2.25 | 3.17 | 3.56 | SMTNL2 | smoothelin-like 2 | AI193973 |
| 0.12 | 0.55 | 1.43 | 2.74 | 3.56 | FBN1 | fibrillin 1 | NM_000138 |
| 0.49 | 0.47 | 1.11 | 2.54 | 3.56 | COL6A2 | collagen, type VI, alpha 2 | AY029208 |
| 0.00 | 0.00 | 1.03 | 3.55 | 2.98 | C1orf105 | chromosome 1 open reading frame 105 | AL035295 |
| 0.27 | 0.31 | 0.00 | 0.00 | 3.53 | ING3 | inhibitor of growth family, member 3 | AF161419 |
| 0.95 | 2.93 | 2.70 | 3.53 | 2.99 | COL11A1 | collagen, type XI, alpha 1 | J04177 |
| -0.39 | -1.36 | -2.71 | -2.98 | -3.53 | ETV4 | ets variant gene 4 (E1A enhancer binding) | BC007242 |
| 1.71 | 2.46 | 3.18 | 3.53 | 3.53 | USP44 | ubiquitin specific peptidase 44 | AL136825 |
| 0.36 | 0.38 | 2.01 | 2.85 | 3.53 | ENDOD1 | endonuclease domain containing 1 | AF131747 |
| 0.00 | 0.00 | 3.04 | 3.53 | 2.59 | RGS13 | regulator of G-protein signalling 13 | AF030107 |
| 0.00 | 0.00 | 0.00 | 1.72 | 3.53 | COL3A1 | Collagen, type III, alpha 1 (Ehlers-Danlos) | AU146808 |
| 2.61 | 3.53 | 2.65 | 2.91 | 1.56 | MYOCD | myocardin | AI452798 |
| 0.00 | 0.00 | 0.00 | 2.27 | 3.53 | RSPO3 | R-spondin 3 homolog (Xenopus laevis) | BF589322 |
| 0.00 | 0.79 | 2.31 | 3.52 | 3.41 | POSTN | periostin, osteoblast specific factor | AY140646 |
| -2.34 | -2.68 | -3.52 | -3.52 | -3.52 | | gb:AW196940 /DB_XREF=gi:6476092 /D | AW196940 |
| 0.89 | 1.47 | 2.27 | 3.06 | 3.51 | EFEMP2 | EGF-containing fibulin-like extracellular m | AB030655 |
| 2.84 | 3.51 | 3.32 | 2.29 | 0.12 | CA12 | carbonic anhydrase XII | NM_001218 |
| 0.50 | -0.01 | 0.79 | -1.48 | -3.51 | GABRB3 | gamma-aminobutyric acid (GABA) A rece | AI693153 |
| -0.45 | -0.99 | -1.59 | -3.39 | -3.51 | UGT8 | UDP glycosyltransferase 8 (UDP-galacto: | N22272 |
| -0.78 | -0.32 | -1.25 | -2.20 | -3.51 | SYT1 | synaptotagmin I | AV723167 |
| 0.00 | 1.36 | 2.87 | 3.11 | 3.51 | SLC40A1 | solute carrier family 40 (iron-regulated tra | AL136944 |
| -0.35 | -0.50 | -1.49 | -2.12 | -3.50 | ZIC3 | Zic family member 3 heterotaxy 1 (odd-p | NM_003413 |
| 0.00 | 0.55 | 2.76 | 3.50 | 3.46 | HOXB3 | homeobox B3 | AW510657 |
| -1.20 | -2.25 | -3.00 | -3.50 | -2.58 | AK3L1 | adenylate kinase 3-like 1 | NM_013410 |
| 1.57 | 3.22 | 3.28 | 3.24 | 3.50 | LHFP | lipoma HMGIC fusion partner | NM_005780 |
| 0.00 | 0.00 | 2.67 | 3.50 | 3.35 | MEIS1 | Meis1, myeloid ecotropic viral integration | NM_002398 |
| 0.00 | 0.51 | 2.77 | 3.50 | 1.69 | PPARG | peroxisome proliferator-activated recepto | NM_015869 |
| 0.00 | 0.00 | 2.68 | 3.47 | 3.49 | PCDH17 | protocadherin 17 | N69091 |
| 0.00 | 0.80 | 0.83 | 1.49 | 3.49 | SPON1 | spondin 1, extracellular matrix protein | AI885290 |
| -0.62 | -1.34 | -3.49 | -3.49 | -3.49 | PNMA2 | paraneoplastic antigen MA2 | AB020690 |

Appendix 2

| Col1 | Col2 | Col3 | Col4 | Col5 | Symbol | Description | Accession |
|---|---|---|---|---|---|---|---|
| -2.15 | -3.08 | -3.49 | -3.49 | -3.49 | LOC728176 | hypothetical protein LOC728176 | AA758105 |
| 0.16 | 0.21 | -1.17 | -2.47 | -3.48 | SPP1 | secreted phosphoprotein 1 (osteopontin, | M83248 |
| -0.98 | 1.73 | 1.50 | 2.01 | -3.47 | TGFBR3 | transforming growth factor, beta receptor | NM_003243 |
| -0.31 | -0.55 | -1.16 | -1.86 | -3.47 | ST6GAL1 | ST6 beta-galactosamide alpha-2,6-sialylt | AI743792 |
| -0.31 | 1.57 | 3.01 | 3.47 | 2.08 | TANC2 | tetratricopeptide repeat, ankyrin repeat a | BF115054 |
| -0.97 | 1.05 | 0.92 | 1.14 | -3.47 | GLDC | glycine dehydrogenase (decarboxylating | NM_000170 |
| -0.80 | -1.78 | -2.66 | -3.47 | -3.47 | SCGB3A2 | secretoglobin, family 3A, member 2 | BG540454 |
| 0.65 | 0.84 | 2.16 | 2.83 | -3.47 | ATP2B1 | ATPase, Ca++ transporting, plasma mem | L14561 |
| 1.14 | 2.30 | -1.71 | 2.39 | -3.47 | UBE2J1 | ubiquitin-conjugating enzyme E2, J1 (UB | AF151039 |
| 0.00 | 0.63 | 2.49 | 2.93 | 3.46 | LIX1 | Lix1 homolog (mouse) | N29837 |
| -0.13 | 0.78 | 1.67 | 2.56 | 3.45 | CAPN6 | calpain 6 | NM_014289 |
| 1.64 | 2.03 | 2.32 | 2.95 | 3.45 | | Transcribed locus | AI743880 |
| -1.34 | -2.06 | -2.16 | -2.63 | -3.45 | JARID2 | jumonji, AT rich interactive domain 2 | NM_004973 |
| 0.00 | 0.90 | 3.10 | 3.45 | 1.91 | KRT7 | keratin 7 | BC002700 |
| -0.10 | 0.57 | 2.75 | 3.28 | 3.44 | FREM2 | FRAS1 related extracellular matrix protei | N66307 |
| 0.00 | 0.00 | 0.00 | 1.70 | 3.44 | PRRX1 | paired related homeobox 1 | AA775472 |
| 0.07 | -0.46 | 0.41 | 1.82 | 3.44 | EFEMP1 | EGF-containing fibulin-like extracellular m | AI826799 |
| 1.35 | 0.88 | 1.72 | 3.44 | 1.68 | | cDNA clone IMAGE:4800096 | BE644809 |
| 0.76 | 1.34 | 1.73 | 2.46 | 3.44 | RGL1 | ral guanine nucleotide dissociation stimul | AF186779 |
| 0.03 | -0.42 | -1.83 | 2.55 | 3.44 | GARNL4 | GTPase activating Rap/RanGAP domain | AK000478 |
| -1.17 | 1.67 | 3.44 | 3.44 | 3.44 | | CDNA FLJ12624 fis, clone NT2RM40017 | AK022686 |
| 0.67 | 1.33 | -0.40 | 2.24 | 3.44 | DCAMKL1 | doublecortin and CaM kinase-like 1 | NM_004734 |
| -2.94 | -1.58 | 2.04 | 2.39 | 3.44 | C10orf75 | Chromosome 10 open reading frame 75 | AU151788 |
| 1.36 | -2.82 | 3.43 | 2.89 | 0.75 | HPGD | hydroxyprostaglandin dehydrogenase 15 | AL574184 |
| 0.62 | 1.14 | 2.77 | 3.43 | 1.09 | PRLR | Prolactin receptor | AA843963 |
| 0.00 | 0.00 | 2.56 | 3.43 | 3.19 | | Transcribed locus | AI754693 |
| 1.46 | 1.09 | 1.71 | 3.05 | 3.43 | FOSL2 | FOS-like antigen 2 | AI670662 |
| -0.38 | 0.42 | 1.66 | 3.43 | 2.77 | CTHRC1 | collagen triple helix repeat containing | AA584310 |
| 2.58 | 3.43 | 2.86 | 2.23 | 0.77 | CA12 | carbonic anhydrase XII | AL050025 |
| 2.71 | 3.43 | 2.59 | 3.06 | 3.01 | EMILIN2 | elastin microfibril interfacer 2 /// elastin m | AF270513 |
| 1.19 | 1.04 | 0.00 | 0.77 | 3.41 | RASD1 | RAS, dexamethasone-induced 1 | AF069506 |
| 0.70 | -0.51 | 2.76 | 3.41 | 2.96 | CEBPA | CCAAT/enhancer binding protein (C/EBP | NM_004364 |
| -2.38 | -2.68 | 2.96 | -2.97 | 3.41 | PYCR2 | pyrroline-5-carboxylate reductase family, | AL561868 |
| 0.92 | 1.30 | 1.68 | 2.42 | 3.41 | SSFA2 | sperm specific antigen 2 | NM_006751 |
| 2.40 | 2.40 | 2.97 | 3.41 | 2.88 | FER1L3 | fer-1-like 3, myoferlin (C. elegans) | NM_013451 |
| 1.22 | 2.53 | 3.20 | 3.18 | 3.40 | TACC1 | transforming, acidic coiled-coil containing | AB029026 |
| 1.16 | 2.37 | 2.65 | 3.40 | 2.86 | BMP2 | bone morphogenetic protein 2 | NM_001200 |
| -0.57 | -1.72 | -2.54 | -3.13 | -3.40 | PLA2G3 | phospholipase A2, group III | NM_015715 |
| 0.55 | 1.83 | 2.29 | 3.40 | 2.92 | RGS5 | regulator of G-protein signalling 5 | NM_025226 |
| 2.42 | 2.92 | 3.39 | 3.40 | 1.43 | TMPRSS11E /// LC | transmembrane protease, serine 11E /// s | NM_014058 |
| -0.45 | -1.07 | 2.57 | 2.91 | 3.40 | ADD2 | adducin 2 (beta) | NM_017488 |
| -0.12 | -0.86 | 1.23 | 2.34 | -3.40 | FOXH1 | forkhead box H1 | NM_003923 |
| 0.00 | -2.72 | 3.39 | 0.76 | 0.00 | CFC1 /// LOC6532 | cripto, FRL-1, cryptic family 1 /// similar tc | AF312769 |
| -1.08 | 2.68 | 3.32 | 3.39 | 3.07 | FER1L3 | fer-1-like 3, myoferlin (C. elegans) | AF207990 |
| 2.21 | 2.85 | 2.89 | 2.87 | 3.38 | GATA2 | GATA binding protein 2 | AL563460 |
| 0.14 | -1.26 | 1.91 | 2.78 | 3.37 | C6orf145 | chromosome 6 open reading frame 145 | AK024828 |
| -0.54 | -1.36 | 3.29 | -3.37 | 2.35 | THY1 | Thy-1 cell surface antigen | AA218868 |
| -0.05 | -0.34 | -0.21 | -1.16 | 3.37 | C11orf32 | chromosome 11 open reading frame 32 | AV728268 |
| 0.08 | -1.11 | 3.18 | 3.24 | 3.36 | ETV4 | ets variant gene 4 (E1A enhancer binding | U35622 |
| 0.92 | 0.73 | 1.29 | 2.45 | 3.36 | IMPAD1 | inositol monophosphatase domain contai | AI302253 |
| 0.46 | -0.17 | 2.36 | 3.36 | -2.35 | GAP43 | growth associated protein 43 | NM_002045 |
| 0.00 | 0.98 | 2.52 | 3.36 | 2.56 | DLX5 | distal-less homeobox 5 | NM_005221 |
| 1.64 | 3.36 | 3.27 | 1.36 | -1.73 | CLDN10 | claudin 10 | NM_006984 |
| 1.41 | 2.70 | 3.35 | 3.32 | 2.27 | SEMA3C | sema domain, immunoglobulin domain (I | NM_006379 |
| 0.99 | 1.18 | 0.80 | 3.01 | 3.34 | ANKRD38 | ankyrin repeat domain 38 | AA456955 |
| 1.88 | 3.15 | 2.53 | 1.89 | 3.33 | MFAP4 | microfibrillar-associated protein 4 | R72286 |
| 1.25 | 2.01 | 2.68 | 2.97 | 3.32 | MMP2 | matrix metallopeptidase 2 (gelatinase A, | NM_004530 |
| -1.72 | -3.32 | -2.95 | -2.93 | -1.31 | DEPDC6 | DEP domain containing 6 | NM_022783 |
| 2.33 | 2.72 | 3.00 | 3.32 | 3.32 | IGFBP7 | insulin-like growth factor binding protein 7 | NM_001553 |
| 2.65 | 3.32 | 2.60 | 3.04 | 1.89 | CYP1B1 | cytochrome P450, family 1, subfamily B, | AU144855 |
| 0.00 | 1.41 | 3.32 | 2.56 | 0.00 | CLIC5 | chloride intracellular channel 5 | NM_016929 |
| 0.05 | 1.95 | 2.43 | 3.32 | 2.38 | EPSTI1 | epithelial stromal interaction 1 (breast) | AA633203 |
| 1.62 | 2.04 | 3.32 | 3.16 | 2.61 | DLX1 | distal-less homeobox 1 | BF060783 |
| -1.43 | -1.75 | -2.33 | -3.30 | -3.30 | TNRC9 | trinucleotide repeat containing 9 | U80736 |
| 0.00 | 0.00 | 1.27 | 2.61 | 3.30 | PRDM6 | PR domain containing 6 | AF272898 |
| -0.71 | -1.38 | 2.49 | 2.77 | 3.30 | | Transcribed locus | AU149490 |
| -0.27 | 0.02 | 1.04 | -1.83 | 3.30 | GABRB3 | gamma-aminobutyric acid (GABA) A rece | BE502537 |
| 0.64 | 1.23 | 1.36 | 2.00 | 3.30 | PARVA | parvin, alpha | AF237771 |
| 0.00 | 0.81 | 2.65 | 3.09 | 3.29 | LIX1 | Lix1 homolog (mouse) | AW136983 |
| 0.79 | -2.20 | 1.62 | 3.28 | 2.69 | TncRNA | trophoblast-derived noncoding RNA | AV699657 |
| 0.00 | 0.15 | 0.00 | 0.67 | 3.28 | ARHGDIB | Rho GDP dissociation inhibitor (GDI) beta | AF498927 |
| 0.00 | -1.06 | -2.13 | -2.88 | -3.28 | MAN1C1 | mannosidase, alpha, class 1C, member 1 | NM_020379 |
| 0.00 | 0.00 | 0.37 | 1.63 | 3.28 | HOP | homeodomain-only protein /// homeodom | AB059408 |
| -0.96 | -0.97 | -1.86 | -2.55 | -3.27 | SYNGR3 | synaptogyrin 3 | NM_004209 |
| 0.00 | 0.00 | 1.33 | 3.07 | 3.27 | ADAMTS18 | ADAM metallopeptidase with thrombospc | AI733120 |
| -0.17 | -0.56 | -1.41 | -2.76 | -3.27 | GRB14 | growth factor receptor-bound protein 14 | NM_004490 |
| 0.54 | -0.65 | 1.88 | -2.97 | 3.27 | | gb:AI961235 /DB_XREF=gi:5753948 /DB | AI961235 |
| 3.01 | 3.27 | 3.10 | 2.40 | 2.24 | ID4 | Inhibitor of DNA binding 4, dominant neg | AL022726 |
| 0.92 | 1.28 | 0.28 | 1.39 | 3.27 | MICAL2 | microtubule associated monoxygenase, c | BE965029 |
| -0.11 | 0.78 | 0.94 | -0.34 | 3.27 | SLC7A3 | solute carrier family 7 (cationic amino aci | AI963203 |
| 0.31 | 2.30 | 2.80 | 3.26 | 3.23 | IL6ST | interleukin 6 signal transducer (gp130, or | AB015706 |
| 0.98 | 1.62 | 2.31 | 2.55 | 3.26 | EPHB3 | EPH receptor B3 | X75208 |
| 0.99 | 2.36 | 1.73 | 3.26 | 2.75 | | CDNA FLJ26120 fis, clone SYN00415 | AI355441 |
| -0.15 | -0.62 | 1.53 | -2.12 | -3.26 | ABHD9 | abhydrolase domain containing 9 | NM_024794 |
| -0.27 | -0.07 | -1.00 | -1.51 | -3.25 | GABRB3 | gamma-aminobutyric acid (GABA) A rece | AI478781 |
| -1.03 | -1.80 | -3.06 | -3.25 | -2.35 | C18orf17 | Chromosome 18 open reading frame 17 | AI871745 |
| 1.61 | 2.80 | 3.25 | 2.95 | 0.31 | HPGD | hydroxyprostaglandin dehydrogenase 15 | NM_000860 |

Appendix 2

| | | | | | Symbol | Description | Accession |
|---|---|---|---|---|---|---|---|
| 0.00 | 1.21 | 2.33 | 3.25 | -3.12 | GPR56 | G protein-coupled receptor 56 | AL554008 |
| -0.06 | 0.93 | 2.52 | 3.25 | 0.68 | MAGI3 | membrane associated guanylate kinase, | AI692181 |
| 1.19 | -2.20 | -3.24 | -3.24 | -3.24 | FAM124A | Family with sequence similarity 124A | AA151659 |
| 1.09 | 3.24 | 1.51 | 1.00 | -0.12 | CLDN11 | claudin 11 (oligodendrocyte transmembra | AW264204 |
| 1.92 | -3.04 | -3.24 | 1.79 | -1.35 | DPYSL3 | dihydropyrimidinase-like 3 | NM_001387 |
| 0.00 | 0.32 | 2.94 | 3.24 | 2.70 | CST1 | cystatin SN | NM_001898 |
| 1.86 | 2.53 | 2.63 | 3.23 | 2.98 | IGFBP7 | insulin-like growth factor binding protein 7 | NM_001553 |
| 0.88 | 1.39 | 2.44 | 3.06 | 3.23 | ALCAM | activated leukocyte cell adhesion molecu | AA156721 |
| 0.58 | -0.96 | -2.63 | 3.23 | -2.22 | ADD2 | adducin 2 (beta) | AW002864 |
| 2.62 | -2.58 | 2.73 | 3.23 | 2.65 | RHOB | ras homolog gene family, member B | AI263909 |
| 1.26 | -2.64 | 2.32 | 2.83 | 3.23 | UBE2J1 | ubiquitin-conjugating enzyme E2, J1 (UB | NM_016021 |
| 0.00 | 0.00 | 0.00 | 0.42 | 3.23 | DCN | decorin | AF138300 |
| 2.45 | 2.35 | 1.83 | 2.91 | 3.22 | FLRT2 | fibronectin leucine rich transmembrane p | NM_013231 |
| -0.33 | 0.87 | -1.34 | 1.27 | 3.22 | EMP2 | epithelial membrane protein 2 | AI089325 |
| 3.01 | 2.61 | 0.77 | 1.20 | 3.22 | CD44 | CD44 molecule (Indian blood group) | BE903880 |
| 0.30 | 2.04 | 2.95 | 3.09 | -3.22 | FN1 | fibronectin 1 | X02761 |
| 1.83 | 1.86 | 2.09 | 2.67 | 3.22 | LOC162073 | Hypothetical protein LOC162073 | AA490685 |
| 2.28 | 3.03 | 3.21 | 2.16 | 1.72 | KLF4 | Kruppel-like factor 4 (gut) | BF514079 |
| 0.46 | 1.26 | 0.29 | 1.17 | 3.21 | TIMP3 | TIMP metallopeptidase inhibitor 3 (Sorsb | BF347089 |
| 1.68 | 2.63 | 3.21 | 2.89 | 2.28 | HMX1 | homeobox (H6 family) 1 | NM_018942 |
| 2.50 | -3.21 | 2.70 | 2.26 | 0.58 | CA12 | carbonic anhydrase XII | BF752277 |
| 0.00 | -2.15 | 3.10 | 3.20 | 2.55 | ALPK2 | alpha-kinase 2 | BE551416 |
| -2.76 | 3.20 | -3.20 | -3.20 | 3.20 | RMST | rhabdomyosarcoma 2 associated transcri | BE468066 |
| -0.79 | 1.13 | -2.00 | 2.26 | 3.20 | MAL2 | mal, T-cell differentiation protein 2 | AL117612 |
| -0.34 | 0.69 | -0.50 | 1.25 | -3.20 | SORL1 | sortilin-related receptor, L(DLR class) A r | NM_003105 |
| 1.09 | 1.36 | -1.47 | 1.79 | 3.20 | | gb:AW193698 /DB_XREF=gi:6472397 /D | AW193698 |
| 0.03 | -3.20 | 2.19 | 2.01 | 2.41 | MYL7 | myosin, light chain 7, regulatory | NM_021223 |
| -0.54 | 1.28 | -2.18 | 3.19 | -2.75 | KIAA1804 | mixed lineage kinase 4 | AI809005 |
| -0.29 | 0.22 | 3.19 | 2.79 | 2.22 | PDCD4 | programmed cell death 4 (neoplastic tran | N92498 |
| 0.00 | 1.07 | 1.84 | 3.19 | 2.25 | ENTPD4 | ectonucleoside triphosphate diphosphohy | BC034477 |
| 3.19 | -3.16 | 3.05 | 2.22 | 1.47 | GUCY1B3 | guanylate cyclase 1, soluble, beta 3 | W93728 |
| -0.06 | 0.92 | 2.55 | 3.19 | 2.03 | HOXB2 | homeobox B2 | NM_002145 |
| 0.00 | 0.00 | 2.37 | 3.19 | 2.43 | CLSTN2 | calsyntenin 2 | NM_022131 |
| 1.42 | -2.26 | -3.07 | 3.19 | 3.19 | LCK | lymphocyte-specific protein tyrosine kinas | U07236 |
| 2.17 | 2.97 | 0.98 | 1.40 | 3.19 | ANXA1 | annexin A1 | NM_000700 |
| 0.00 | 0.00 | 0.21 | 2.87 | 3.19 | VTCN1 | V-set domain containing T cell activation | NM_024626 |
| -0.26 | 0.24 | -0.96 | 2.44 | -3.19 | KCNS3 | potassium voltage-gated channel, delaye | NM_002252 |
| -0.72 | -1.47 | -1.70 | 1.82 | -3.18 | EPHA1 | EPH receptor A1 | NM_005232 |
| 0.00 | 0.17 | 2.07 | 3.17 | 3.18 | SULF1 | sulfatase 1 | BE500977 |
| -0.70 | 0.24 | 2.30 | 3.18 | 1.22 | SMARCA2 | SWI/SNF related, matrix associated, actir | AW131754 |
| 0.83 | 1.71 | 2.27 | 3.11 | 3.18 | COL4A6 | collagen, type IV, alpha 6 | AI889941 |
| 0.00 | 0.00 | 0.00 | 0.03 | 3.17 | MBD2 | methyl-CpG binding domain protein 2 | AF072242 |
| -1.25 | -1.25 | -1.11 | 1.12 | -3.17 | CCDC80 | coiled-coil domain containing 80 | AW303375 |
| -0.22 | 0.51 | 1.87 | 3.17 | 1.30 | C21orf105 | chromosome 21 open reading frame 105 | BC005107 |
| 0.14 | 0.40 | 2.14 | 3.17 | 1.51 | TRPM7 | transient receptor potential cation channe | BE044733 |
| 1.54 | 1.18 | 0.78 | 2.44 | 3.17 | ZC3HAV1L | zinc finger CCCH-type, antiviral 1-like | AI188445 |
| -0.48 | -1.11 | -2.13 | 3.16 | -1.36 | GPRC5B | G protein-coupled receptor, family C, grou | NM_016235 |
| 0.25 | 0.21 | 0.87 | 2.04 | 3.16 | IMPAD1 | inositol monophosphatase domain contai | AW628838 |
| 1.23 | 1.75 | 2.00 | 3.03 | 3.16 | LIX1L | Lix1 homolog (mouse)-like | AW500180 |
| 0.54 | 2.45 | 3.01 | 3.16 | 2.77 | SP6 | Sp6 transcription factor | AI817264 |
| -0.08 | 1.93 | 1.10 | 1.65 | 3.16 | PRSS35 | protease, serine, 35 | AL574912 |
| 0.40 | 1.04 | 2.26 | 2.61 | 3.16 | VASH2 | vasohibin 2 | NM_024749 |
| -0.35 | -0.38 | 0.55 | 1.45 | 3.16 | CABYR | calcium binding tyrosine-(Y)-phosphoryla | AF295039 |
| -2.30 | -1.37 | 1.62 | 2.19 | 3.16 | PLP1 | proteolipid protein 1 (Pelizaeus-Merzbach | BC002665 |
| 2.69 | 3.16 | 2.77 | 2.74 | 1.46 | COL13A1 | collagen, type XIII, alpha 1 | M33653 |
| 0.40 | 1.36 | 2.03 | 3.15 | 1.90 | ENTPD4 | ectonucleoside triphosphate diphosphohy | AB002390 |
| -1.57 | -1.45 | 1.56 | 2.39 | -3.15 | GRTP1 | growth hormone regulated TBC protein 1 | BF001483 |
| 0.05 | 1.40 | 1.16 | 2.93 | 3.15 | TPM1 | Tropomyosin 1 (alpha) | AI521618 |
| 1.27 | 2.35 | 2.96 | 3.15 | 1.95 | FBN2 | fibrillin 2 (congenital contractural arachno | NM_001999 |
| -0.74 | -0.94 | -0.78 | 1.33 | -3.15 | FAM46B | family with sequence similarity 46, memb | AA531023 |
| 0.12 | 0.89 | 2.11 | 2.98 | 3.15 | ATP2B1 | ATPase, Ca++ transporting, plasma merr | M95541 |
| 0.00 | 0.94 | 2.35 | 2.20 | 3.14 | FOXF2 | forkhead box F2 | NM_001452 |
| 1.36 | -2.62 | 3.14 | 2.83 | 0.13 | HPGD | hydroxyprostaglandin dehydrogenase 15- | J05594 |
| 0.08 | -0.53 | 0.13 | -0.09 | 3.14 | MNAB | Membrane associated DNA binding prote | BF972355 |
| 2.58 | 3.14 | 2.61 | 2.47 | 2.81 | FST | follistatin | BF438173 |
| -0.23 | 0.02 | 0.97 | 2.36 | 3.13 | IMPAD1 | inositol monophosphatase domain contai | BF674724 |
| 2.51 | 3.13 | 2.42 | 2.08 | 2.08 | FAM43A | family with sequence similarity 43, memb | AW264102 |
| 1.75 | 1.45 | 1.34 | 1.89 | 3.13 | SLC35D1 | solute carrier family 35 (UDP-glucuronic a | N80922 |
| 1.98 | 2.19 | 0.79 | 2.14 | 3.13 | THBS1 | thrombospondin 1 | NM_003246 |
| -0.11 | 0.31 | -0.03 | -0.61 | -3.12 | NTS | neurotensin | NM_006183 |
| 0.16 | 0.33 | -0.67 | 1.93 | -3.12 | ITGB1BP3 | integrin beta 1 binding protein 3 | NM_014446 |
| -0.73 | -2.07 | -3.12 | 3.12 | -3.12 | GNA14 | guanine nucleotide binding protein (G prc | NM_004297 |
| 0.00 | 0.08 | 1.64 | 3.12 | 1.99 | RIN2 | Ras and Rab interactor 2 | AL136924 |
| 0.07 | 0.63 | 2.05 | 2.05 | 3.12 | CCDC3 | coiled-coil domain containing 3 | AL136562 |
| 0.00 | 0.24 | -3.04 | 3.12 | -1.12 | GPR126 | G protein-coupled receptor 126 | AL033377 |
| 1.35 | -1.55 | -1.95 | 2.67 | -3.12 | GNG4 | guanine nucleotide binding protein (G prc | NM_004485 |
| 0.00 | 0.00 | 0.65 | 1.84 | 3.12 | | Transcribed locus | BF055200 |
| -0.11 | -1.02 | 0.31 | 0.75 | -3.11 | TIMP3 | TIMP metallopeptidase inhibitor 3 (Sorsb | U67195 |
| 0.00 | 0.73 | 2.82 | 3.11 | 1.48 | LOC124976 | hypothetical protein LOC124976 | AL568674 |
| 2.05 | 3.11 | 0.57 | -0.41 | -1.98 | CTGF | connective tissue growth factor | M92934 |
| -0.74 | -1.47 | -1.79 | 2.07 | 3.11 | DPPA4 | developmental pluripotency associated 4 | AK022821 |
| 1.62 | 1.65 | 3.11 | 3.03 | 0.82 | GCLM | glutamate-cysteine ligase, modifier subur | AI753488 |
| 2.27 | -3.10 | -3.10 | -3.10 | -3.10 | SOX2 | SRY (sex determining region Y)-box 2 | AW007161 |
| 0.66 | 1.40 | 2.56 | 2.98 | 3.10 | OAF | OAF homolog (Drosophila) | BG033561 |
| 1.12 | 1.26 | 2.14 | 2.81 | -3.10 | BMI1 | B lymphoma Mo-MLV insertion region (m | NM_005180 |
| 0.00 | 0.81 | 1.01 | 2.46 | 3.10 | FBLN2 | fibulin 2 | NM_001998 |
| -0.85 | -1.31 | -2.48 | -2.99 | -3.10 | ENO2 | enolase 2 (gamma, neuronal) | NM_001975 |

Appendix 2

| | | | | | Gene | Description | Accession |
|---|---|---|---|---|---|---|---|
| -0.34 | -0.36 | -0.51 | -1.63 | -3.10 | CRLF1 | cytokine receptor-like factor 1 | NM_004750 |
| 0.61 | 2.22 | 2.61 | 3.10 | 2.61 | LOC130576 | hypothetical protein LOC130576 | BF060747 |
| 0.00 | 0.00 | 1.39 | 2.48 | 3.10 | KIAA0644 | KIAA0644 gene product | AV724192 |
| 0.29 | 0.91 | 1.77 | 2.54 | 3.09 | SETBP1 | SET binding protein 1 | NM_015559 |
| 1.51 | 2.09 | 3.09 | 3.09 | 2.14 | CHST9 | carbohydrate (N-acetylgalactosamine 4-0 | AF332473 |
| 0.19 | 0.20 | 1.21 | 1.57 | 3.09 | KIAA0746 | KIAA0746 protein | AB018289 |
| 1.39 | 0.61 | 2.57 | 3.09 | 1.92 | CAV1 | caveolin 1, caveolae protein, 22kDa | NM_001753 |
| 0.01 | 0.54 | 1.77 | 1.79 | 3.09 | RAB17 | RAB17, member RAS oncogene family | NM_022449 |
| 1.16 | 2.22 | 3.09 | 3.01 | 2.99 | SMAD6 | SMAD family member 6 | NM_005585 |
| -1.66 | -2.70 | 3.08 | 2.05 | 1.69 | DPYSL3 | dihydropyrimidinase-like 3 | W72516 |
| 2.63 | 3.08 | 2.87 | 2.68 | -1.96 | PCDH10 | protocadherin 10 | AI640307 |
| -1.08 | 2.01 | 3.08 | 3.08 | 3.08 | FAM124A | family with sequence similarity 124A | D59502 |
| 1.93 | 0.29 | 1.92 | 3.08 | 2.21 | ADAMTS9 | ADAM metallopeptidase with thrombospc | AF488803 |
| 1.52 | 1.70 | 3.08 | 2.92 | 0.57 | | Full-length cDNA clone CS0CAP007YJ17 | AA630626 |
| 2.16 | 3.08 | 2.32 | 1.21 | 0.62 | TMEM154 | transmembrane protein 154 | AA806283 |
| -0.25 | 0.13 | 2.08 | 3.08 | 2.94 | GPR124 | G protein-coupled receptor 124 | BF511315 |
| 0.88 | 1.82 | 3.03 | 3.07 | 2.51 | NRIP1 | nuclear receptor interacting protein 1 | AI824012 |
| 2.53 | 3.06 | 0.62 | 1.04 | 0.82 | SERPINE1 | serpin peptidase inhibitor, clade E (nexin, | AL574210 |
| 0.00 | 0.00 | 0.00 | 0.45 | 3.06 | | Transcribed locus | AI141861 |
| 1.41 | 2.88 | 3.06 | 2.94 | 1.69 | TNC | tenascin C (hexabrachion) | NM_002160 |
| 0.76 | -0.31 | 1.60 | 2.03 | 3.06 | IL17RD | interleukin 17 receptor D | AW007080 |
| 1.80 | 2.42 | 3.01 | 3.06 | 2.03 | KAL1 | Kallmann syndrome 1 sequence | NM_000216 |
| 1.93 | 2.40 | 2.87 | 3.06 | 2.98 | | MRNA; cDNA DKFZp779M2422 (from cl | AI197932 |
| 0.00 | 0.00 | 0.00 | 2.34 | 3.05 | PITX1 | paired-like homeodomain transcription fa | U70370 |
| 1.05 | 1.56 | 0.34 | 1.50 | 3.05 | THBS1 | thrombospondin 1 | BF055462 |
| 1.53 | 1.94 | 2.75 | 3.05 | 2.36 | DMN | desmuslin | AK026420 |
| -0.39 | 0.65 | 2.41 | 3.05 | 2.81 | SOX9 | SRY (sex determining region Y)-box 9 (c | AI382146 |
| 0.00 | 0.00 | 0.00 | 1.30 | 3.05 | CXCR4 | chemokine (C-X-C motif) receptor 4 | AJ224869 |
| 0.00 | 0.00 | 0.00 | 0.00 | 3.04 | CDC42 | cell division cycle 42 (GTP binding protei | R37654 |
| -0.69 | 1.56 | -2.28 | -2.44 | 3.04 | PRKCQ | protein kinase C, theta | L01087 |
| 0.00 | 0.03 | 0.65 | 2.78 | 3.04 | SDK1 | sidekick homolog 1 (chicken) | AL042166 |
| 1.49 | 2.88 | 3.04 | 2.96 | 1.84 | CITED2 | Cbp/p300-interacting transactivator, with | AF109161 |
| 0.06 | 0.40 | 2.21 | 3.03 | 1.96 | GAP43 | growth associated protein 43 | AF279774 |
| 0.50 | 2.39 | 3.03 | 2.50 | 0.33 | HPGD | hydroxyprostaglandin dehydrogenase 15 | U63296 |
| 0.00 | 0.00 | 2.12 | 2.97 | 3.03 | PCDH17 | protocadherin 17 | AU119437 |
| -0.80 | 2.56 | 2.78 | 3.03 | 3.03 | GPR64 | G protein-coupled receptor 64 | NM_005756 |
| 0.56 | 1.99 | 2.55 | 3.03 | 2.98 | WIPF1 | WAS/WASL interacting protein family, me | AW058622 |
| 1.07 | 2.04 | 1.63 | 2.05 | 3.02 | UBE2J1 | ubiquitin-conjugating enzyme E2, J1 (UB) | AW500009 |
| -0.13 | 0.07 | 1.61 | 2.37 | 3.02 | C10orf56 | chromosome 10 open reading frame 56 | AA131324 |
| 0.00 | 0.00 | 1.82 | 3.02 | 2.73 | KIAA1914 | KIAA1914 | AW138743 |
| 0.00 | 0.26 | 0.00 | 0.12 | 3.02 | TNNT2 | troponin T type 2 (cardiac) | X79857 |
| 0.27 | 1.94 | 2.75 | 2.92 | 3.01 | FN1 | fibronectin 1 /// fibronectin 1 | BC005858 |
| 0.00 | 0.75 | 2.27 | 3.01 | 2.21 | ATP10D | ATPase, Class V, type 10D | AI478147 |
| 0.99 | 2.38 | 2.54 | 2.76 | 3.01 | GREM2 | gremlin 2, cysteine knot superfamily, hor | NM_022469 |
| 0.79 | 1.24 | 0.03 | 1.82 | 3.01 | GAL | galanin | AL556409 |
| 1.55 | 1.77 | 2.35 | 3.01 | -2.39 | | C33.6 unnamed HERV-H protein | U92816 |
| -0.73 | -0.67 | -0.68 | 1.25 | 3.01 | PLS1 | plastin 1 (I isoform) | NM_002670 |
| 0.00 | 0.00 | 0.00 | 0.00 | 3.01 | TNNI1 | troponin I type 1 (skeletal, slow) | NM_003281 |
| 0.68 | 0.43 | -1.11 | -1.88 | 3.01 | KIF1A | kinesin family member 1A | AL533416 |
| 0.89 | 2.75 | 3.01 | 2.42 | 3.01 | GAS7 | growth arrest-specific 7 | BE439987 |
| -0.80 | 0.89 | -1.32 | -1.28 | 3.01 | ASXL1 | additional sex combs like 1 (Drosophila) | AI829840 |
| 0.00 | 0.57 | -0.97 | -1.65 | 3.01 | ZHX1 | zinc fingers and homeoboxes 1 | AI123518 |
| -1.18 | 1.82 | 2.32 | 3.00 | 2.70 | LECT1 | leukocyte cell derived chemotaxin 1 | NM_007015 |
| 1.43 | 1.34 | 1.93 | 3.00 | 2.46 | ZNF703 | zinc finger protein 703 | BG290193 |
| -0.04 | -0.04 | 1.34 | -2.41 | 3.00 | | Hypothetical protein (ORF1), clone 0027! | BF672169 |
| -0.59 | 1.38 | 2.02 | -2.75 | 2.99 | PRKCQ | protein kinase C, theta | AL137145 |
| -2.04 | 2.99 | 1.31 | 0.92 | 1.00 | METTL7A | methyltransferase like 7A | NM_014033 |
| 0.00 | 1.23 | 1.53 | 2.98 | 2.54 | MBNL2 | muscleblind-like 2 (Drosophila) | BE328496 |
| -1.62 | 1.70 | 1.28 | 2.21 | 2.98 | COMMD7 | COMM domain containing 7 | AW451792 |
| 0.17 | 0.86 | 2.64 | 2.98 | 1.61 | GPR157 | G protein-coupled receptor 157 | AK026883 |
| -2.72 | 2.98 | 1.77 | 0.08 | -0.01 | GAD1 /// LASS6 | glutamate decarboxylase 1 (brain, 67kDa | NM_013445 |
| 0.27 | 2.01 | 2.45 | 2.97 | 2.98 | IL6ST /// MAGEA4 | interleukin 6 signal transducer (gp130, or | BE856546 |
| 0.00 | 0.00 | 2.24 | 2.98 | 2.65 | BOC | Boc homolog (mouse) | W72626 |
| -0.85 | 0.80 | 2.41 | 2.98 | 2.69 | LYPD6 | LY6/PLAUR domain containing 6 | AA227842 |
| 0.94 | -1.09 | 0.81 | 1.80 | 2.98 | ST3GAL1 | ST3 beta-galactoside alpha-2,3-sialyltran | NM_003033 |
| 0.38 | 0.24 | 1.47 | 2.50 | 2.98 | KCNMA1 | potassium large conductance calcium-act | U11058 |
| 0.07 | 1.35 | -0.99 | 1.72 | 2.97 | PDGFRB | platelet-derived growth factor receptor, b | NM_002609 |
| 1.91 | -2.26 | -2.21 | 2.97 | 2.97 | CR1L | complement component (3b/4b) receptor | BE552138 |
| -0.08 | 0.08 | 2.97 | 2.50 | 2.08 | EDNRB | endothelin receptor type B | NM_000115 |
| 0.03 | -0.99 | 1.84 | 2.50 | 2.97 | ZIC2 | Zic family member 2 (odd-paired homoloc | AF193855 |
| 0.00 | 0.00 | 0.00 | 0.00 | 2.97 | MMP1 | matrix metallopeptidase 1 (interstitial coll | NM_002421 |
| 0.00 | 0.00 | 0.00 | 0.89 | 2.97 | NR2F2 | nuclear receptor subfamily 2, group F, me | AL037401 |
| 1.86 | 2.97 | 1.40 | 2.32 | 0.11 | SERPINB9 | serpin peptidase inhibitor, clade B (ovalb | AI986192 |
| 0.00 | 0.00 | 1.01 | 2.40 | 2.97 | | Full length insert cDNA clone YT94E02 | AI912571 |
| 0.87 | -1.31 | 1.68 | 2.47 | 2.96 | EFEMP2 | EGF-containing fibulin-like extracellular n | NM_016938 |
| 1.64 | -2.24 | -1.92 | -2.14 | 2.96 | MAP2K6 | mitogen-activated protein kinase kinase 6 | NM_002758 |
| 1.52 | 2.66 | 2.35 | 2.90 | 2.96 | UBE2J1 | ubiquitin-conjugating enzyme E2, J1 (UB) | AL562528 |
| 0.77 | 0.66 | 0.65 | 1.65 | 2.96 | PAG1 | phosphoprotein associated with glycosph | AI860212 |
| 1.29 | 2.96 | 2.72 | 1.81 | 0.64 | LEPREL1 | leprecan-like 1 | NM_018192 |
| -0.05 | 0.42 | -0.87 | 1.54 | 2.96 | GABRB3 | gamma-aminobutyric acid (GABA) A rece | NM_000814 |
| -0.38 | 0.37 | -1.49 | 2.24 | 2.96 | C6orf32 | chromosome 6 open reading frame 32 | NM_015854 |
| -1.13 | -0.97 | 1.48 | 1.62 | 2.96 | LOC728342 | Hypothetical protein LOC728342 | BE542563 |
| 0.54 | 0.30 | 0.10 | -0.51 | -2.96 | LDB2 | LIM domain binding 2 | NM_001290 |
| -1.59 | -1.55 | 1.74 | -1.96 | 2.96 | IER5L | immediate early response 5-like | BF110608 |
| 0.00 | 0.00 | 1.38 | 2.70 | 2.96 | SOX7 | SRY (sex determining region Y)-box 7 | AI808807 |
| 0.28 | 1.23 | 2.36 | 2.89 | 2.95 | FAM114A1 | family with sequence similarity 114, mem | W87456 |
| 0.11 | 0.85 | 1.72 | 2.59 | 2.95 | LOC284262 | hypothetical protein LOC284262 | BF739885 |

Appendix 2

| Value | Symbol | Description | Accession |
|---|---|---|---|
| 0.69 | ABCG2 | ATP-binding cassette, sub-family G (WHI | AF098951 |
| 2.95 | PIM1 | pim-1 oncogene /// pim-1 oncogene | M24779 |
| 2.94 | SPHK1 | sphingosine kinase 1 | NM_021972 |
| 2.75 | PLXNA2 | plexin A2 | AI668418 |
| 2.20 | COMMD3 | COMM domain containing 3 | NM_012071 |
| 2.94 | CHEK2 | CHK2 checkpoint homolog (S. pombe) | BC004207 |
| 2.94 | KDELR3 | KDEL (Lys-Asp-Glu-Leu) endoplasmic re | NM_006855 |
| 2.93 | KLHDC8B | kelch domain containing 8B | AI160540 |
| 2.93 | LAYN | layilin | BE856341 |
| 2.93 | SVEP1 | sushi, von Willebrand factor type A, EGF | AA716107 |
| 2.93 | DNMT3B | DNA (cytosine-5-)-methyltransferase 3 b | NM_006892 |
| 0.81 | DKK3 | dickkopf homolog 3 (Xenopus laevis) | AU148057 |
| 2.21 | SOX9 | SRY (sex determining region Y)-box 9 (c | NM_000346 |
| 1.95 | ENTPD4 | ectonucleoside triphosphate diphosphohy | NM_004901 |
| 2.93 | PPIC | peptidylprolyl isomerase C (cyclophilin C | NM_000943 |
| 2.32 | IFI16 | interferon, gamma-inducible protein 16 | AF208043 |
| 2.93 | OLFM1 | olfactomedin 1 | R38389 |
| 2.92 | HTRA1 | HtrA serine peptidase 1 | NM_002775 |
| 2.92 | BAMBI | BMP and activin membrane-bound inhibit | NM_012342 |
| 2.92 | QKI | quaking homolog, KH domain RNA bindir | AL031781 |
| 1.24 | TRPM7 | transient receptor potential cation channe | AF346629 |
| 2.92 | SMARCA2 | SWI/SNF related, matrix associated, acti | T51136 |
| 1.65 | CITED2 | Cbp/p300-interacting transactivator, with | NM_006079 |
| 2.92 | LOC286167 | hypothetical protein LOC286167 | AV721528 |
| 2.76 | ATP2B1 | ATPase, Ca++ transporting, plasma mem | AW576457 |
| 2.91 | ITGB8 | integrin, beta 8 | BF513121 |
| 2.91 | CDC42EP1 | CDC42 effector protein (Rho GTPase bin | NM_007061 |
| 2.91 | HOXB7 | homeobox B7 | NM_004502 |
| 2.91 | ELP4 | elongation protein 4 homolog (S. cerevisi | NM_019040 |
| 2.91 | RIT1 | Ras-like without CAAX 1 | AL037450 |
| 2.91 | C16orf72 | Chromosome 16 open reading frame 72 | AW503390 |
| 2.91 | GDA | guanine deaminase | AF019638 |
| 2.91 | CREB3L1 | cAMP responsive element binding proteir | AF055009 |
| 2.90 | MATN2 | matrilin 2 | NM_002380 |
| 2.90 | L1TD1 | LINE-1 type transposase domain containi | NM_019079 |
| 1.80 | NPPB | natriuretic peptide precursor B | NM_002521 |
| 1.42 | FEZ2 | fasciculation and elongation protein zeta | AI685892 |
| 2.19 | DAB2 | disabled homolog 2, mitogen-responsive | BC003064 |
| 2.89 | C20orf19 | chromosome 20 open reading frame 19 | NM_018474 |
| 2.89 | HOXA13 | homeobox A13 | BG289306 |
| 2.89 | CD200 | CD200 molecule | H23979 |
| 1.96 | ALDH1A2 | aldehyde dehydrogenase 1 family, memb | AB015228 |
| 2.89 | C20orf118 | Chromosome 20 open reading frame 118 | AV715309 |
| 2.89 | EMP2 | epithelial membrane protein 2 | AV686514 |
| 2.63 | ETV1 | ets variant gene 1 | NM_004956 |
| 2.89 | MAN1A1 | Mannosidase, alpha, class 1A, member 1 | BG287153 |
| 2.89 | FST | follistatin | NM_006350 |
| 2.89 | C1orf187 | chromosome 1 open reading frame 187 | BC021286 |
| 2.89 | ENTPD3 | ectonucleoside triphosphate diphosphohy | NM_001248 |
| 2.34 | TP53INP1 | tumor protein p53 inducible nuclear prote | AW341649 |
| 1.73 | WNT5B | wingless-type MMTV integration site fami | AW007350 |
| 2.64 | BMP2 | bone morphogenetic protein 2 | AA583044 |
| 1.04 | CDH10 | cadherin 10, type 2 (T2-cadherin) | NM_006727 |
| 2.88 | NRP2 | neuropilin 2 | AF280546 |
| 2.88 | PHC1 | polyhomeotic homolog 1 (Drosophila) | AI554106 |
| 1.99 | TEAD1 | TEA domain family member 1 (SV40 tran | AW771935 |
| 2.22 | HSPB8 | heat shock 22kDa protein 8 | AF133207 |
| 0.00 | CD1D | CD1d molecule /// CD1d molecule | NM_001766 |
| 2.87 | LOC285401 | hypothetical protein LOC285401 | BC043407 |
| 2.87 | STMN2 | stathmin-like 2 | BF967657 |
| 1.66 | FLNC | filamin C, gamma (actin binding protein 2 | NM_001458 |
| 2.87 | CABYR | calcium binding tyrosine-(Y)-phosphoryla | NM_012189 |
| 2.87 | EPHB3 | EPH receptor B3 | NM_004443 |
| 2.32 | | MRNA; cDNA DKFZp313B1017 (from clo | AW376955 |
| 1.92 | TAGLN | transgelin | NM_003186 |
| 2.66 | RGS4 | regulator of G-protein signalling 4 | BC000737 |
| 1.87 | TAGLN | transgelin | BC010946 |
| 2.86 | MALAT1 | Metastasis associated lung adenocarcino | AI475544 |
| 2.86 | MMP9 | matrix metallopeptidase 9 (gelatinase B, | NM_004994 |
| 2.86 | PARVA | parvin, alpha | BG107577 |
| 2.65 | HOXA10 | homeobox A10 | BF792917 |
| 2.85 | C8orf72 | chromosome 8 open reading frame 72 | AW264082 |
| 0.39 | DKK3 | dickkopf homolog 3 (Xenopus laevis) | NM_013253 |
| 1.51 | FLJ39609 | Hypothetical protein FLJ39609 | CA447406 |
| 2.80 | CTNND2 | catenin (cadherin-associated protein), de | AF035302 |
| 2.65 | PON2 | paraoxonase 2 | NM_000305 |
| 2.65 | CHAC1 | ChaC, cation transport regulator homolog | NM_024111 |
| 1.56 | SOX8 | SRY (sex determining region Y)-box 8 | BF527050 |
| 2.85 | THBS1 | thrombospondin 1 | AV726673 |
| 2.85 | CCDC80 | coiled-coil domain containing 80 | AA570507 |
| 2.84 | GMDS | GDP-mannose 4,6-dehydratase | NM_001500 |
| 1.68 | SLC16A3 | solute carrier family 16, member 3 (mono | NM_004207 |
| 1.34 | HTRA3 | HtrA serine peptidase 3 | AI828007 |
| 1.62 | ARL4C | ADP-ribosylation factor-like 4C | BC001051 |
| 2.84 | PDZRN3 | PDZ domain containing RING finger 3 | AL569804 |
| 1.88 | ACADL | acyl-Coenzyme A dehydrogenase, long c | AI367275 |
| 2.83 | FGFR4 | fibroblast growth factor receptor 4 | NM_002011 |

Appendix 2

| | | | | | Symbol | Description | Accession |
|---|---|---|---|---|---|---|---|
| 0.00 | 0.64 | 2.83 | 2.83 | 0.78 | PRELP | proline/arginine-rich end leucine-rich rep$_e$ | NM_002725 |
| -0.01 | 1.47 | 2.54 | 2.83 | 2.76 | FMOD | fibromodulin | NM_002023 |
| 0.27 | 1.53 | 0.04 | 1.33 | 2.82 | MFAP5 | microfibrillar associated protein 5 | U37283 |
| 0.00 | 0.00 | 0.71 | 2.82 | 1.93 | LOC387758 | similar to RIKEN cDNA 1110018M03 | AI802391 |
| -1.90 | 2.13 | 2.61 | 2.48 | 2.82 | PYCR2 | pyrroline-5-carboxylate reductase family, | NM_013328 |
| 1.26 | 0.74 | 0.00 | 0.75 | 2.82 | SFRS2IP | Splicing factor, arginine/serine-rich 2, int$_e$ | AA679858 |
| -0.52 | -0.43 | 1.59 | 2.59 | 2.82 | NEFL | neurofilament, light polypeptide 68kD$_a$ | BF055311 |
| 0.00 | 0.00 | 0.00 | 1.53 | 2.82 | VEGFC | vascular endothelial growth factor C | U58111 |
| 0.00 | 0.00 | 1.65 | 2.20 | 2.82 | C10orf56 | chromosome 10 open reading frame 56 | AK024784 |
| 2.82 | 2.40 | 0.72 | 0.70 | 0.18 | | CDNA FLJ34677 fis, clone LIVER200266 | AA524609 |
| 0.71 | 1.01 | 1.29 | 2.00 | 2.81 | | MRNA full length insert cDNA clone EUR | BE500942 |
| 0.15 | 0.14 | 0.52 | 1.49 | 2.81 | FGF13 | fibroblast growth factor 13 | NM_004114 |
| -0.70 | 0.74 | 1.65 | 2.63 | 2.81 | ZNF641 | zinc finger protein 641 | AV700302 |
| 1.60 | 2.55 | 2.71 | 2.81 | 1.97 | C8orf72 | chromosome 8 open reading frame 72 | BE672313 |
| -0.79 | 1.34 | 2.04 | 2.81 | 2.81 | UGT8 | UDP glycosyltransferase 8 (UDP-galacto: | NM_003360 |
| 0.00 | 0.00 | 1.10 | 1.65 | 2.81 | C6orf32 | chromosome 6 open reading frame 32 | AB002384 |
| -0.64 | 0.23 | 2.17 | 2.81 | 0.87 | BCL6 | B-cell CLL/lymphoma 6 (zinc finger protei | NM_001706 |
| -0.45 | 0.40 | 1.74 | 2.81 | 2.22 | DKFZP586H2123 | regeneration associated muscle protease | AI671185 |
| -0.50 | 0.64 | 1.11 | 2.81 | 2.17 | ENC1 | ectodermal-neural cortex (with BTB-like c | AF010314 |
| -0.92 | -0.88 | 1.05 | 1.23 | 2.81 | | gb:AW118997 /DB_XREF=gi:6087581 / | DAW118997 |
| -0.85 | 0.00 | -0.12 | 1.40 | 2.80 | CTH | cystathionase (cystathionine gamma-lyas | NM_001902 |
| -0.07 | 0.44 | -2.27 | 2.33 | 2.80 | HEY1 | hairy/enhancer-of-split related with YRPV | NM_012258 |
| -0.99 | 0.38 | 1.62 | -2.27 | 2.80 | FGFR4 | fibroblast growth factor receptor 4 | AF202063 |
| 0.00 | 0.32 | 0.00 | 0.15 | 2.80 | STXBP6 | syntaxin binding protein 6 (amisyn | N21096 |
| 1.97 | 1.04 | 1.90 | 2.80 | 2.80 | CAV1 | caveolin 1, caveolae protein, 22kD$_a$ | AU147399 |
| -0.07 | 0.84 | 0.49 | 1.46 | 2.80 | CSRP1 | cysteine and glycine-rich protein 1 | NM_004078 |
| 0.07 | 0.29 | 0.67 | 0.28 | 2.79 | SCC-112 | SCC-112 protein | AW991219 |
| 0.09 | 1.84 | 2.57 | 2.75 | 2.79 | FN1 | fibronectin 1 | AF130095 |
| 0.00 | 0.00 | 1.71 | 2.58 | 2.79 | HOXB7 | homeobox B7 | S49765 |
| 1.93 | 2.50 | 1.95 | 1.83 | 2.79 | TERF1 | telomeric repeat binding factor (NIMA-int$_e$ | NM_017489 |
| -0.62 | 1.40 | 2.19 | 2.78 | 2.49 | PGBD5 | piggyBac transposable element derived 5 | NM_024554 |
| 2.07 | 2.78 | 2.25 | 1.30 | 0.91 | | MRNA; cDNA DKFZp564C203 (from clor | AL049245 |
| 1.13 | 1.71 | -2.78 | -2.30 | -1.99 | ETV5 | ets variant gene 5 (ets-related molecule) | NM_004454 |
| 0.00 | 0.00 | 0.00 | 0.00 | 2.78 | EMP1 | epithelial membrane protein 1 | NM_001423 |
| 0.56 | 2.75 | 2.78 | 1.86 | 0.58 | C1orf61 | chromosome 1 open reading frame 61 | NM_006365 |
| 0.27 | 1.57 | 2.78 | 2.78 | 1.82 | MBNL3 | muscleblind-like 3 (Drosophila) | NM_018388 |
| 0.00 | 0.46 | 2.38 | 2.78 | 1.18 | C1orf213 | chromosome 1 open reading frame 213 | AW298597 |
| 1.45 | 2.77 | 2.23 | 0.60 | 0.00 | TTC29 | tetratricopeptide repeat domain 29 | AF345910 |
| 1.41 | 0.23 | 2.03 | 2.77 | 2.51 | FEZ1 | fasciculation and elongation protein zeta | NM_005103 |
| -0.48 | 0.58 | 0.40 | 1.29 | 2.77 | SPON1 | spondin 1, extracellular matrix protein | AB018305 |
| 1.49 | 0.73 | 1.32 | 2.54 | 2.77 | HGSNAT | heparan-alpha-glucosaminide N-acetyltra | NM_025070 |
| 0.00 | 0.64 | 1.54 | 2.03 | 2.77 | PDLIM3 | PDZ and LIM domain 3 | AF002280 |
| 1.73 | 1.36 | 1.21 | 2.77 | 1.58 | TMEM16D | transmembrane protein 16D | BF589515 |
| 0.82 | 0.60 | 0.90 | 1.49 | 2.77 | BMP1 | bone morphogenetic protein 1 | NM_006129 |
| 2.77 | 1.62 | 0.07 | 0.00 | 0.00 | GAD1 | glutamate decarboxylase 1 (brain, 67kDa | NM_000817 |
| 0.00 | 0.00 | 1.14 | 2.76 | 2.42 | | CDNA FLJ12425 fis, clone MAMMA1003 | AW070250 |
| 1.55 | 2.09 | 2.76 | 1.34 | 1.07 | MEGF10 | multiple EGF-like-domains 10 | AU144892 |
| 0.78 | 0.25 | 0.97 | 1.95 | 2.76 | GALNT10 | UDP-N-acetyl-alpha-D-galactosamine:po | BE906572 |
| 0.00 | 0.00 | 0.21 | 1.89 | 2.76 | MCHR1 | melanin-concentrating hormone receptor | AI934819 |
| 0.11 | 0.86 | 1.71 | 2.25 | 2.76 | CD99 | CD99 molecule | U82164 |
| -0.68 | -1.23 | 1.67 | 2.64 | 2.76 | NGFRAP1L1 | NGFRAP1-like 1 | AV726956 |
| 0.02 | 1.82 | 2.54 | 2.73 | 2.76 | FN1 | fibronectin 1 | AK026737 |
| 2.05 | 2.75 | 2.37 | 2.04 | 2.22 | FST | follistatin | NM_013409 |
| 0.05 | 1.15 | 1.60 | 2.75 | 0.46 | SLC16A6 | solute carrier family 16, member 6 (mono | AI873273 |
| 1.98 | 2.75 | 1.38 | 2.24 | 1.43 | | gb:AW263497 /DB_XREF=gi:6640313 / | DAW263497 |
| 0.00 | 0.00 | 0.00 | 0.26 | 2.74 | C4orf18 | chromosome 4 open reading frame 18 | AF260333 |
| 1.32 | 1.97 | 1.41 | 1.48 | 2.74 | | Transcribed locus | BF724178 |
| 0.15 | -0.23 | -0.04 | 1.02 | 2.74 | COL1A1 | collagen, type I, alpha 1 | Y15916 |
| -0.87 | 1.49 | 2.44 | 2.74 | 2.59 | RNF125 | ring finger protein 125 | AI969697 |
| -0.18 | 0.85 | 1.28 | 1.55 | 2.74 | MAN1A1 | mannosidase, alpha, class 1A, member 1 | NM_005907 |
| -1.18 | -1.45 | -1.42 | 1.47 | 2.74 | PAK1 /// VDP | p21/Cdc42/Rac1-activated kinase 1 (STE | NM_003715 |
| -0.14 | -0.57 | -1.41 | 1.94 | 2.74 | OCIAD2 | OCIA domain containing 2 | BG291649 |
| 0.07 | 0.37 | 2.30 | 2.46 | 2.74 | HEY1 | hairy/enhancer-of-split related with YRPV | R61374 |
| -0.83 | -1.40 | -2.35 | 2.74 | 2.28 | PDZD4 | PDZ domain containing 4 | BC002606 |
| 0.00 | -0.27 | 0.54 | 0.92 | 2.73 | TBX2 | T-box 2 | U28049 |
| -0.45 | 0.39 | 2.21 | 2.73 | 0.90 | SMARCA2 | SWI/SNF related, matrix associated, actir | AV725365 |
| -0.35 | -1.15 | -2.35 | 2.73 | 2.72 | SEPHS1 | selenophosphate synthetase 1 | AV682679 |
| 0.11 | 1.48 | 1.97 | 2.73 | 1.72 | DNAJC15 | DnaJ (Hsp40) homolog, subfamily C, me$_r$ | NM_013238 |
| 0.00 | 0.00 | 1.26 | 2.73 | 2.57 | LOC338758 | hypothetical protein LOC338758 | AI377324 |
| -0.97 | -0.95 | -2.42 | 2.73 | 1.41 | ELAVL2 | ELAV (embryonic lethal, abnormal vision, | AL161628 |
| 0.00 | 1.53 | 2.73 | 2.40 | 0.00 | | Full-length cDNA clone CS0DI029YM01 $_t$ | AI224578 |
| 0.57 | 0.32 | 0.92 | 1.18 | 2.73 | PLAT | plasminogen activator, tissue | NM_000930 |
| 0.00 | 0.55 | 2.18 | 2.73 | 2.50 | LYPD6 | LY6/PLAUR domain containing 6 | AL535224 |
| 0.96 | -2.23 | -2.72 | 2.03 | 1.28 | EFHD1 | EF-hand domain family, member D1 | BC002449 |
| 0.30 | 1.09 | 2.27 | 2.72 | 1.68 | GRHL1 | grainyhead-like 1 (Drosophila) | BE566136 |
| 0.47 | 0.52 | 1.80 | 2.47 | 2.72 | TUBA1 | tubulin, alpha 1 | AL565074 |
| 0.00 | 0.00 | 1.26 | 2.72 | 1.62 | ChGn | chondroitin beta1,4 N-acetylgalactosamir | NM_018371 |
| -0.03 | -0.16 | -0.40 | 1.62 | 2.72 | PYCARD | PYD and CARD domain containing | BC004470 |
| 1.56 | -1.62 | -2.36 | 2.72 | 2.72 | GPR176 | G protein-coupled receptor 176 | NM_007223 |
| -0.64 | -0.29 | 1.05 | 1.24 | 2.72 | CYYR1 | cysteine/tyrosine-rich 1 | H06649 |
| 2.71 | 2.20 | 1.35 | 2.09 | 1.96 | BHLHB2 | basic helix-loop-helix domain containing, | NM_003670 |
| 1.31 | 2.31 | 2.71 | 2.60 | 1.86 | NAV2 /// LOC7304 | neuron navigator 2 /// similar to neuron n$_a$ | AK001892 |
| 2.18 | 1.16 | -0.04 | 1.21 | 2.71 | KIAA1702 | KIAA1702 protein | AK027074 |
| 1.58 | -2.26 | 1.69 | 1.51 | 2.71 | TERF1 | telomeric repeat binding factor (NIMA-int$_e$ | AI347136 |
| -0.45 | -0.94 | -1.53 | -2.63 | 2.71 | NPM3 | nucleophosmin/nucleoplasmin, 3 | NM_006993 |
| -0.01 | -0.02 | 1.17 | 2.09 | 2.71 | PPIC | peptidylprolyl isomerase C (cyclophilin C | BE962749 |
| 0.00 | 0.00 | 0.00 | 2.12 | 2.71 | TNS1 | Tensin 1 /// Tensin 1 | AL046979 |

Appendix 2

| | | | | | Symbol | Description | Accession |
|---|---|---|---|---|---|---|---|
| -0.81 | -0.60 | -1.29 | -2.71 | -2.71 | CDA | cytidine deaminase | NM_001785 |
| -1.29 | -1.74 | -2.05 | -1.87 | -2.71 | OTX2 | orthodenticle homolog 2 (Drosophila) | BE779765 |
| -2.26 | -2.44 | -2.71 | -2.70 | -2.09 | ID2 | inhibitor of DNA binding 2, dominant neg: | NM_002166 |
| -0.10 | -1.24 | -2.09 | -1.98 | -2.71 | GATA5 | GATA binding protein 5 | N72525 |
| -0.96 | -0.85 | -1.60 | -2.70 | -2.70 | PAX6 | paired box gene 6 (aniridia, keratitis) | NM_000280 |
| -1.55 | -2.70 | -2.21 | -1.41 | 0.00 | CA12 | carbonic anhydrase XII | BC000278 |
| -0.45 | -1.29 | -2.31 | -2.59 | -2.70 | MT1X | metallothionein 1X | NM_002450 |
| 0.00 | -1.08 | -1.35 | -1.76 | -2.70 | COBLL1 | COBL-like 1 | BF002844 |
| -1.23 | -1.57 | -2.04 | -2.26 | -2.70 | C20orf118 | Chromosome 20 open reading frame 118 | BF437747 |
| 0.00 | 0.00 | 0.71 | 2.05 | -2.70 | KIAA0644 | KIAA0644 gene product | NM_014817 |
| -0.79 | -1.38 | -2.20 | -1.74 | -2.70 | PHC1 /// LOC6534 | polyhomeotic homolog 1 (Drosophila) /// | NM_004426 |
| 0.91 | 0.10 | 0.07 | -0.13 | -2.70 | | Full length insert cDNA clone ZB81B12 | N95440 |
| 0.41 | 1.01 | 2.57 | 2.70 | -2.30 | ST3GAL6 | ST3 beta-galactoside alpha-2,3-sialyltran | AB022918 |
| 0.00 | 0.00 | 1.71 | -2.06 | -2.69 | HGF | hepatocyte growth factor (hepapoietin A) | M77227 |
| 0.00 | 0.00 | 0.00 | 0.00 | -2.69 | CDC42 | cell division cycle 42 (GTP binding protei | M35543 |
| -0.40 | -0.84 | -0.76 | -0.70 | -2.69 | HIBCH | 3-hydroxyisobutyryl-Coenzyme A hydrola | NM_014362 |
| -0.99 | -1.05 | -1.48 | -2.14 | -2.69 | FRAT2 | frequently rearranged in advanced T-cell | AB045118 |
| 0.00 | 0.00 | 0.81 | 2.13 | -2.69 | HOXD11 | homeobox D11 | NM_021192 |
| 1.12 | 1.68 | 2.69 | 2.60 | 1.90 | NRIP1 | nuclear receptor interacting protein 1 | NM_003489 |
| 2.00 | 2.69 | 2.18 | 2.38 | -2.60 | ANXA3 | annexin A3 | M63310 |
| -2.60 | -1.88 | -1.79 | -2.09 | -2.68 | C7orf46 | chromosome 7 open reading frame 46 | BE220330 |
| -1.93 | -1.65 | -2.38 | -2.68 | -2.53 | STMN2 | stathmin-like 2 | NM_007029 |
| -0.29 | 0.40 | 0.63 | 1.96 | -2.68 | COL4A2 | collagen, type IV, alpha 2 | AA909035 |
| -0.93 | -1.76 | -2.14 | -2.56 | -2.68 | C20orf118 | Chromosome 20 open reading frame 118 | AA603344 |
| -0.39 | -1.45 | -1.50 | -2.56 | -2.68 | MT1G | metallothionein 1G | NM_005950 |
| -0.69 | 0.88 | 2.07 | 2.68 | -1.73 | SLC7A2 | solute carrier family 7 (cationic amino aci | AA876372 |
| -1.28 | -1.93 | -2.68 | -2.68 | -1.92 | CHST9 | carbohydrate (N-acetylgalactosamine 4-0 | AF239821 |
| 0.76 | 1.22 | 2.02 | -2.60 | -2.68 | SEPHS1 | selenophosphate synthetase 1 | BC000941 |
| 0.12 | -0.56 | -2.12 | -2.23 | -2.67 | ALDH3A2 | aldehyde dehydrogenase 3 family, memb | L47162 |
| -1.15 | -0.71 | -2.42 | -2.29 | -2.67 | SOHLH2 | spermatogenesis and oogenesis specific | BC013944 |
| 0.00 | 0.00 | 0.00 | 0.13 | -2.67 | DSC3 | desmocollin 3 | NM_001941 |
| 0.27 | 0.25 | -2.19 | -2.67 | -2.67 | GABRA5 | gamma-aminobutyric acid (GABA) A rece | NM_000810 |
| 0.42 | 2.03 | 1.84 | 2.67 | -2.47 | DAB2 | disabled homolog 2, mitogen-responsive | NM_001343 |
| 0.36 | 0.90 | 1.27 | 1.28 | -2.67 | EMP2 | epithelial membrane protein 2 | NM_001424 |
| 0.00 | 0.00 | 0.53 | 2.24 | -2.66 | MAB21L2 | mab-21-like 2 (C. elegans) | AF262032 |
| 0.53 | 0.52 | 0.08 | 0.39 | -2.66 | SPTBN1 | spectrin, beta, non-erythrocytic 1 | AW593244 |
| -0.94 | 0.98 | 2.22 | 2.66 | -2.24 | STON1 | stonin 1 | BG434174 |
| 1.00 | 2.05 | 2.66 | 2.48 | -1.99 | NAV2 | neuron navigator 2 | AU137607 |
| -0.48 | -0.81 | -1.63 | -1.55 | -2.66 | MYO5C | myosin VC | NM_018728 |
| 2.49 | 2.66 | 0.38 | 0.79 | 0.27 | SERPINE2 | Serpin peptidase inhibitor, clade E (nexin | AA703280 |
| 0.60 | 1.08 | 1.85 | 2.39 | -2.65 | MRC2 | mannose receptor, C type 2 | AB014609 |
| -0.69 | -0.69 | -1.84 | -2.65 | -2.65 | ITGA7 | integrin, alpha 7 | AK022548 |
| -0.21 | -0.32 | -0.11 | -0.71 | -2.65 | WBSCR17 | Williams-Beuren syndrome chromosome | AI972623 |
| 0.01 | -0.25 | -1.25 | -2.65 | -1.81 | KIFAP3 | kinesin-associated protein 3 | NM_014970 |
| 0.00 | 0.00 | 0.00 | 0.42 | -2.65 | CDH11 | Cadherin 11, type 2, OB-cadherin (osteol | AI040305 |
| -0.21 | -0.70 | -0.47 | -0.88 | -2.65 | TDRKH | tudor and KH domain containing | AF227192 |
| 1.00 | 1.81 | 1.65 | 1.66 | -2.65 | KIAA0101 | KIAA0101 /// KIAA0101 | BC005832 |
| -1.01 | -2.64 | -2.64 | -2.64 | -2.64 | THBS2 | thrombospondin 2 | NM_003247 |
| -1.05 | -0.46 | -2.64 | 2.00 | 0.00 | ARHGAP28 | Rho GTPase activating protein 28 | NM_030672 |
| 0.46 | 0.10 | -1.45 | -2.62 | -2.64 | SH3BP5 | SH3-domain binding protein 5 (BTK-asso | AL562152 |
| -0.12 | 0.59 | 1.04 | 1.04 | -2.64 | FAM46A | family with sequence similarity 46, memb | AW246673 |
| -0.38 | -0.57 | -1.15 | -1.89 | -2.64 | DNAJB6 | DnaJ (Hsp40) homolog, subfamily B, mer | BC002446 |
| 0.00 | 0.00 | 1.17 | 2.27 | -2.64 | SULF1 | sulfatase 1 | AI479175 |
| 0.00 | 0.00 | 1.31 | 2.64 | 1.28 | LCMT1 | Leucine carboxyl methyltransferase 1 | BC024748 |
| 0.00 | 0.00 | 0.00 | 1.68 | -2.63 | RGS1 | regulator of G-protein signalling 1 | S59049 |
| 0.61 | 1.27 | 1.29 | 1.97 | -2.63 | TPM1 | tropomyosin 1 (alpha) | NM_000366 |
| 0.68 | 1.64 | 0.01 | -1.53 | -2.63 | SOX3 | SRY (sex determining region Y)-box 3 | AI824954 |
| 0.51 | 1.83 | 1.85 | 2.63 | -2.06 | DAB2 | disabled homolog 2, mitogen-responsive | AF188298 |
| 1.19 | 2.16 | 2.63 | 2.29 | -1.51 | C13orf18 | chromosome 13 open reading frame 18 | AI129310 |
| 0.36 | 2.63 | 1.83 | 2.13 | -1.13 | RBM24 | RNA binding motif protein 24 | AI677701 |
| 0.00 | 1.19 | 2.56 | 2.63 | -2.43 | SEMA6D | sema domain, transmembrane domain (T | AK022747 |
| -1.57 | -1.59 | -2.62 | -1.96 | -1.13 | PCSK5 | proprotein convertase subtilisin/kexin typ | NM_006200 |
| 0.00 | 0.00 | -1.05 | 2.27 | -2.62 | ZFHX1B | zinc finger homeobox 1b | NM_014795 |
| 0.48 | -0.62 | -2.62 | -1.95 | -2.62 | | gb:BF222929 /DB_XREF=gi:11130106 /L | BF222929 |
| -1.14 | -2.33 | -2.28 | -1.94 | -2.62 | CHST4 | carbohydrate (N-acetylglucosamine 6-O) | NM_005769 |
| 1.98 | 2.01 | 1.12 | 1.94 | -2.62 | AXL | AXL receptor tyrosine kinase | NM_021913 |
| 0.00 | 0.00 | 0.00 | 0.34 | -2.62 | GFRA3 | GDNF family receptor alpha 3 | AA694259 |
| 0.77 | 1.38 | 1.27 | 1.51 | -2.62 | COL1A2 | collagen, type I, alpha 2 | NM_000089 |
| 0.27 | 0.05 | 0.00 | 0.00 | -2.62 | TAGLN | Transgelin | AI082237 |
| -0.13 | -0.72 | -1.92 | -2.62 | -1.67 | D4S234E | DNA segment on chromosome 4 (unique | NM_014392 |
| -0.20 | 0.59 | 0.93 | 1.74 | -2.62 | DACT3 | dapper, antagonist of beta-catenin, homo | AI809234 |
| -0.60 | -0.59 | -0.59 | -1.61 | -2.53 | GYLTL1B | glycosyltransferase-like 1B | AW272738 |
| -0.48 | -0.26 | 0.21 | -0.24 | -2.62 | MNAB | membrane associated DNA binding prote | BF972355 |
| -0.76 | 0.61 | 1.98 | 2.22 | -2.62 | ZNF124 | zinc finger protein 124 | AB046850 |
| -0.81 | 1.49 | 0.68 | 1.83 | -2.61 | GPRC5A | G protein-coupled receptor, family C, grou | NM_003979 |
| 0.81 | 2.61 | 2.45 | 1.52 | -0.37 | SERPINB9 | serpin peptidase inhibitor, clade B (ovalbu | L40378 |
| 0.00 | 0.00 | 0.00 | 0.39 | -2.61 | FNDC3B | fibronectin type III domain containing 3B | AW058617 |
| 0.00 | 0.69 | 1.27 | 1.58 | -2.61 | PGF | placental growth factor, vascular endothe | BC001422 |
| 0.00 | 0.00 | 0.00 | 0.00 | -2.61 | DCN | decorin | AF138303 |
| -0.94 | -1.01 | -0.91 | -1.43 | -2.61 | USP28 | ubiquitin specific peptidase 28 | NM_020886 |
| -1.20 | -1.33 | -2.10 | -2.50 | -2.61 | | Transcribed locus | AI740721 |
| -1.67 | -2.57 | -2.60 | -2.60 | -2.60 | FZD5 | frizzled homolog 5 (Drosophila) | NM_003468 |
| 0.00 | -1.37 | -2.31 | -2.24 | -2.60 | GADD45G | growth arrest and DNA-damage-inducible | NM_006705 |
| -0.32 | -1.38 | -2.25 | -2.60 | -2.53 | MT1X | metallothionein 1X | NM_005952 |
| 0.93 | 2.27 | 2.03 | 2.60 | -1.43 | | gb:AI188161 /DB_XREF=gi:3739370 /DB | AI188161 |
| 0.00 | -2.17 | -2.60 | -2.02 | -2.33 | CLDN4 | claudin 4 | NM_001305 |
| 0.68 | 2.00 | 1.87 | 2.60 | -2.53 | DAB2 | disabled homolog 2, mitogen-responsive | N21202 |

Appendix 2

| | | | | | Gene | Description | Accession |
|---|---|---|---|---|---|---|---|
| 1.02 | -1.38 | 1.89 | 2.60 | 2.21 | LIPG | lipase, endothelial | NM_006033 |
| 0.00 | 0.41 | 2.09 | 2.60 | 1.40 | SHD | Src homology 2 domain containing transf | AW452918 |
| 0.93 | 1.12 | 0.98 | 1.14 | 2.59 | IDS | iduronate 2-sulfatase (Hunter syndrome) | NM_006123 |
| 0.65 | 0.41 | 0.89 | 2.05 | 2.59 | ARHGEF3 | Rho guanine nucleotide exchange factor | NM_019555 |
| 1.51 | 2.08 | 1.68 | 2.59 | 2.23 | ITGAV | Integrin, alpha V (vitronectin receptor, alp | AA228366 |
| 0.00 | 0.00 | 0.90 | 2.59 | 1.11 | UNC5C | unc-5 homolog C (C. elegans) | NM_003728 |
| 0.00 | 1.30 | 1.87 | 2.30 | 2.59 | GATA4 | GATA binding protein 4 | D78260 |
| 0.00 | 0.00 | 0.00 | 0.29 | 2.59 | DSC3 | desmocollin 3 | AI797281 |
| 1.77 | 1.66 | 1.47 | 1.59 | 2.59 | PAK1 /// VDP | p21/Cdc42/Rac1-activated kinase 1 (STE | BE875592 |
| 1.03 | 2.59 | 2.51 | 0.90 | 0.30 | CD55 | CD55 molecule, decay accelerating facto | NM_000574 |
| 0.20 | 0.35 | 1.66 | 2.59 | 2.57 | SH3BP5 | SH3-domain binding protein 5 (BTK-asso | NM_004844 |
| -0.26 | 0.73 | 1.63 | 2.47 | 2.59 | SLCO4A1 | solute carrier organic anion transporter fa | NM_016354 |
| 1.19 | -0.88 | -2.59 | 2.59 | 2.59 | NODAL | nodal homolog (mouse) | AI670948 |
| -0.43 | 1.06 | 2.24 | 2.59 | 0.95 | FUT8 | fucosyltransferase 8 (alpha (1,6) fucosylt | NM_004480 |
| 0.80 | 1.23 | 1.37 | 1.67 | 2.59 | SETD7 | SET domain containing (lysine methyltrar | AK024846 |
| 0.36 | 1.62 | 2.07 | 2.19 | 2.59 | NEDD9 | neural precursor cell expressed, developi | AL136139 |
| -0.50 | -1.51 | -1.86 | -2.27 | -2.58 | MT1F | metallothionein 1F (functional) | BF246115 |
| -0.57 | 1.32 | 1.60 | 1.59 | 2.58 | KIAA0528 | KIAA0528 | AB011100 |
| 0.48 | 1.25 | -2.41 | -2.58 | -2.58 | CAMKV | CaM kinase-like vesicle-associated | NM_024046 |
| 0.00 | 0.00 | 0.00 | 0.00 | 2.58 | DCN | decorin | AF138302 |
| 0.00 | 0.00 | 0.00 | 1.07 | 2.58 | NR2F2 | nuclear receptor subfamily 2, group F, me | M64497 |
| 0.41 | 0.50 | 1.52 | 1.99 | 2.58 | RGS3 | regulator of G-protein signalling 3 | NM_021106 |
| 0.51 | 1.45 | 2.35 | 2.58 | 1.54 | GATA3 | GATA binding protein 3 | AI796169 |
| 1.27 | 1.95 | 2.01 | 2.52 | 2.58 | NDRG1 | N-myc downstream regulated gene 1 | NM_006096 |
| -0.03 | 1.64 | 1.59 | -2.53 | -2.58 | MT1H | metallothionein 1H | NM_005951 |
| -1.08 | 1.61 | -2.57 | -2.57 | -2.57 | EDG7 | Endothelial differentiation, lysophosphatic | AW274018 |
| 0.00 | 0.00 | 0.09 | 1.38 | 2.57 | ARHGAP29 | Rho GTPase activating protein 29 | AL833445 |
| 1.49 | 0.35 | 1.04 | 1.84 | SFRP1 | secreted frizzled-related protein 1 | AF017987 | |
| 0.36 | -0.63 | 1.97 | -2.57 | -2.57 | CPT1A | carnitine palmitoyltransferase 1A (liver) | BF001714 |
| 0.00 | 0.00 | 0.00 | 1.46 | 2.57 | TNS1 | tensin 1 | AF116610 |
| 0.00 | 0.32 | 1.17 | 2.57 | 1.61 | | Full length insert cDNA clone ZB94A08 | W04694 |
| 0.55 | -0.47 | -1.19 | -2.57 | 1.83 | FOXC1 | forkhead box C1 | NM_001453 |
| 0.00 | 0.12 | 1.74 | 2.36 | 2.56 | MYL4 | myosin, light chain 4, alkali; atrial, embryo | X52005 |
| -0.02 | -0.02 | 0.82 | 2.10 | 2.56 | EGR1 | Early growth response 1 | AI459194 |
| 2.56 | 2.45 | 0.28 | 0.29 | 0.00 | CDX1 | caudal type homeobox transcription facto | NM_001804 |
| -0.79 | 1.65 | -1.20 | -0.93 | 2.56 | C20orf19 | chromosome 20 open reading frame 19 | AI806322 |
| -0.67 | 0.69 | 0.89 | 1.92 | 2.56 | GNG2 | guanine nucleotide binding protein (G pr | AK026424 |
| -0.34 | -0.29 | 0.77 | 2.31 | 2.56 | NAALAD2 | N-acetylated alpha-linked acidic dipeptid | AJ012370 |
| -0.17 | 0.77 | 1.65 | 2.50 | 2.56 | DYNC1I1 | dynein, cytoplasmic 1, intermediate chain | NM_004411 |
| -0.11 | 1.23 | 2.16 | 2.58 | 1.47 | RNF43 | ring finger protein 43 | NM_017763 |
| 0.03 | -0.22 | -1.66 | -1.64 | 2.56 | MRS2L | MRS2-like, magnesium homeostasis fact | AI631209 |
| 0.00 | 0.00 | 0.00 | 0.60 | 2.56 | KYNU | kynureninase (L-kynurenine hydrolase) | D55639 |
| 0.00 | 0.00 | 0.00 | 0.00 | 2.55 | NELF | Nasal embryonic LHRH factor | AI767962 |
| 1.27 | 0.53 | 0.32 | 0.86 | 2.55 | JMJD4 | jumonji domain containing 4 | NM_023007 |
| 0.00 | 0.00 | 0.00 | 1.23 | 2.55 | RGS4 | regulator of G-protein signalling 4 | NM_005613 |
| 0.48 | 0.91 | 1.92 | 2.55 | 1.57 | SH3PXD2A | SH3 and PX domains 2A | W93554 |
| -1.23 | -1.10 | -0.79 | -2.03 | -2.54 | RGMA | RGM domain family, member A | AL136826 |
| -0.62 | -0.55 | -1.23 | 1.83 | 2.54 | | Homo sapiens, clone IMAGE:4401608, m | AK022793 |
| 0.02 | 1.18 | 1.63 | 2.24 | 2.54 | LOXL2 | lysyl oxidase-like 2 | NM_002318 |
| 1.23 | 2.41 | 1.88 | 2.14 | 2.54 | SLIT2 | Slit homolog 2 (Drosophila) | AI692523 |
| 0.00 | 1.15 | 0.99 | 2.15 | 2.54 | EHD2 | EH-domain containing 2 | AI417917 |
| 0.85 | 1.38 | 1.15 | 1.60 | 2.54 | SMARCD3 | SWI/SNF related, matrix associated, acti | NM_003078 |
| -1.11 | 0.32 | 0.60 | 2.54 | 1.45 | MALAT1 | metastasis associated lung adenocarcino | AF132202 |
| -0.25 | 0.41 | 0.15 | -1.16 | -2.54 | CTH | cystathionase (cystathionine gamma-lyas | AL354872 |
| -0.08 | 0.00 | 0.00 | 1.63 | 2.54 | PCDH7 | BH-protocadherin (brain-heart) | NM_002589 |
| 0.00 | 0.03 | 1.76 | 2.54 | 0.52 | CNTN4 | contactin 4 | R42166 |
| -0.19 | -0.43 | -0.99 | 1.08 | 2.54 | MYCN | v-myc myelocytomatosis viral related onc | BC002712 |
| 2.09 | -2.54 | -2.54 | 2.54 | 2.54 | | CDNA FLJ12557 fis, clone NT2RM40007 | AU148706 |
| -2.51 | 2.47 | 1.94 | 1.40 | GUCY1B3 | guanylate cyclase 1, soluble, beta 3 | AF020340 | |
| 0.00 | 0.31 | 1.99 | 2.54 | 2.12 | PRSS12 | Protease, serine, 12 (neurotrypsin, motor | AI810767 |
| -1.25 | 0.41 | 0.69 | 2.54 | 1.48 | MALAT1 | metastasis associated lung adenocarcino | AW005982 |
| 0.04 | 0.29 | 1.57 | 2.54 | 1.30 | FLJ10916 | hypothetical protein FLJ10916 | NM_018271 |
| -0.45 | -1.12 | 2.22 | 2.15 | -2.53 | | CDNA FLJ37658 fis, clone BRHIP20105 | BG547864 |
| -0.13 | 0.36 | 1.36 | 1.81 | 2.53 | CTSB | cathepsin B | NM_001908 |
| 0.12 | 1.36 | 2.53 | 2.15 | 1.24 | FEZ2 | fasciculation and elongation protein zeta | AL117593 |
| -0.36 | 1.04 | 1.86 | 2.50 | 2.53 | FAM114A1 | family with sequence similarity 114, mem | AI742174 |
| -0.26 | -0.19 | 0.56 | 1.02 | 2.53 | AYTL1 | acyltransferase like 1 | AA789296 |
| -1.32 | -1.63 | -1.22 | -1.40 | -2.53 | FOXO1A | forkhead box O1A (rhabdomyosarcoma) | AW117498 |
| 0.53 | 0.54 | 1.63 | 2.53 | 1.72 | GAB2 | GRB2-associated binding protein 2 | NM_012296 |
| 0.00 | 0.00 | 0.00 | 0.01 | 2.53 | SST | somatostatin | NM_001048 |
| -0.18 | 0.34 | 0.64 | 1.40 | 2.53 | PRICKLE1 | prickle homolog 1 (Drosophila) | AA404269 |
| 0.75 | 1.10 | 0.49 | 1.95 | 2.53 | LOC730125 | Hypothetical protein LOC730125 | AU151635 |
| -0.06 | 0.91 | 1.69 | 2.53 | 1.83 | PPFIBP2 | PTPRF interacting protein, binding protei | AI692180 |
| -0.05 | -0.50 | 2.03 | 2.53 | -2.34 | ALDH3A2 | aldehyde dehydrogenase 3 family, memb | BC002430 |
| -0.58 | 1.22 | 1.84 | 1.87 | 2.53 | JAZF1 | JAZF zinc finger 1 | AL047908 |
| 0.54 | 0.49 | 1.21 | 2.53 | 1.76 | RBMS3 | RNA binding motif, single stranded intera | AA428240 |
| 0.00 | 1.03 | 1.50 | 1.84 | 2.53 | | Transcribed locus | AI801626 |
| -0.17 | 0.35 | 0.68 | 1.33 | 2.53 | MORC4 | MORC family CW-type zinc finger 4 | NM_024657 |
| -0.69 | -1.06 | -1.94 | -2.05 | -2.53 | PCNXL2 | pecanex-like 2 (Drosophila) | BC008300 |
| -0.82 | -1.32 | 1.45 | 2.06 | -2.52 | NSBP1 | nucleosomal binding protein 1 | BC005342 |
| -2.52 | -2.52 | -2.52 | -2.52 | -2.52 | LOC157627 | hypothetical protein LOC157627 | AL832535 |
| 0.76 | 1.03 | 1.08 | 2.02 | 2.52 | DYNLT3 | dynein, light chain, Tctex-type 3 | NM_006520 |
| -0.07 | 0.53 | 2.06 | 2.52 | 1.91 | JMJD3 | jumonji domain containing 3 | AB002344 |
| -1.09 | -1.55 | -2.52 | -2.52 | 2.52 | PPP1R16B | protein phosphatase 1, regulatory (inhibit | AB020630 |
| 0.82 | -1.20 | 2.15 | 2.52 | 2.15 | DNAJC6 | DnaJ (Hsp40) homolog, subfamily C, mer | AV729634 |
| -0.48 | -1.18 | -2.04 | -2.11 | -2.52 | GDAP1 | ganglioside-induced differentiation-assoc | BF002104 |
| 1.20 | 0.61 | 1.31 | 1.89 | 2.52 | | gb:AI754928 /DB_XREF=gi:5133192 /DB | AI754928 |

Appendix 2

| | | | | | Symbol | Description | Accession |
|---|---|---|---|---|---|---|---|
| -1.19 | -1.77 | -2.52 | -2.34 | -2.17 | ETV5 | ets variant gene 5 (ets-related molecule) | BF060791 |
| -1.31 | -1.91 | -2.52 | -2.52 | -2.52 | C9orf135 | chromosome 9 open reading frame 135 | AW014133 |
| 0.11 | 1.40 | 1.84 | 2.51 | 2.08 | IFI16 | interferon, gamma-inducible protein 16 | NM_005531 |
| -1.25 | 1.67 | 1.95 | 2.50 | 2.51 | NRP2 | neuropilin 2 | AI819729 |
| 0.22 | 0.54 | 2.20 | 2.37 | 2.51 | ST3GAL6 | ST3 beta-galactoside alpha-2,3-sialyltran | AI989567 |
| 2.51 | 2.22 | 0.00 | 0.00 | 2.00 | GREM1 | gremlin 1, cysteine knot superfamily, hom | NM_013372 |
| 0.00 | 0.00 | 1.83 | 2.51 | 0.37 | SLC8A1 | solute carrier family 8 (sodium/calcium ex | AI741439 |
| -0.05 | 0.15 | 1.74 | 2.51 | 1.79 | NPNT | nephronectin | AL138410 |
| 2.20 | 2.47 | 2.51 | 2.36 | 1.56 | NAV2 | neuron navigator 2 | NM_018162 |
| -1.10 | 0.08 | 1.68 | 2.51 | 0.52 | SMARCA2 | SWI/SNF related, matrix associated, actin | NM_003070 |
| 0.98 | 1.21 | 2.50 | 2.23 | 0.20 | GCLM | glutamate-cysteine ligase, modifier subun | NM_002061 |
| 0.00 | 0.16 | 1.98 | 2.50 | 1.95 | PRSS12 | protease, serine, 12 (neurotrypsin, motop | NM_003619 |
| 0.54 | 1.94 | 2.50 | 1.99 | 1.13 | BTG2 | BTG family, member 2 | NM_006763 |
| 0.00 | 0.25 | 1.79 | 2.50 | 1.61 | CAMK2N1 | calcium/calmodulin-dependent protein kin | AW162846 |
| 0.20 | 0.20 | 1.66 | 2.13 | 2.50 | INA | internexin neuronal intermediate filament | NM_004692 |
| -1.02 | 1.06 | 1.53 | -1.65 | 2.50 | PIF1 | PIF1 5'-to-3' DNA helicase homolog (S. c | AF108138 |
| -0.79 | 1.63 | 1.51 | 2.01 | -2.50 | JARID2 | jumonji, AT rich interactive domain 2 | BG029530 |
| 0.51 | 1.59 | 2.31 | 2.49 | -0.71 | ETS2 | v-ets erythroblastosis virus E26 oncogen | AL575509 |
| -1.72 | 1.96 | 1.99 | 2.49 | 2.18 | EPB41L3 | erythrocyte membrane protein band 4.1-li | AI770004 |
| 0.00 | 0.20 | 0.55 | 1.89 | 2.49 | PLAGL1 | pleiomorphic adenoma gene-like 1 | NM_002656 |
| -1.59 | 1.63 | 1.96 | 1.87 | 2.49 | GATA2 | GATA binding protein 2 | BC002557 |
| 1.73 | 2.23 | 1.04 | 0.59 | 2.49 | CD44 | CD44 molecule (Indian blood group) | NM_000610 |
| -0.23 | 0.04 | 1.56 | 2.49 | 2.49 | SLC38A5 | solute carrier family 38, member 5 | BG325630 |
| 0.12 | 0.61 | 0.54 | 1.26 | 2.49 | CAST | calpastatin | AF327443 |
| 0.84 | 0.32 | 0.09 | 1.17 | 2.49 | IL17D | interleukin 17D | BE856748 |
| -1.54 | 1.85 | 2.49 | -1.70 | -2.25 | TMEM63A | transmembrane protein 63A | AB007958 |
| -0.63 | 0.16 | 0.33 | 1.05 | 2.49 | C10orf32 | chromosome 10 open reading frame 32 | AI147621 |
| 0.12 | 0.16 | -0.60 | 2.22 | 2.48 | IGSF8 | immunoglobulin superfamily, member 8 | BC004108 |
| 0.00 | 0.00 | 0.00 | 1.42 | 2.48 | FLJ20701 | hypothetical protein FLJ20701 /// hypothe | NM_017933 |
| 0.66 | 0.93 | 2.48 | 2.16 | 1.56 | FAM11A | family with sequence similarity 11, memb | AW300965 |
| -0.75 | 1.59 | 2.14 | 2.40 | 2.48 | MT1F | metallothionein 1F (functional | M10943 |
| 1.61 | 1.28 | 1.90 | 2.48 | 2.16 | PROCR | protein C receptor, endothelial (EPCR | NM_006404 |
| 0.06 | 0.13 | 0.62 | 2.48 | 1.37 | CALM2 | Calmodulin 2 (phosphorylase kinase, delt | BF591288 |
| 1.52 | 1.07 | 0.23 | 1.14 | 2.48 | KLHDC5 | kelch domain containing 5 | AU146850 |
| 0.43 | 0.80 | 1.68 | 2.03 | 2.48 | P4HA2 | procollagen-proline, 2-oxoglutarate 4-dio | NM_004199 |
| -0.08 | -0.69 | -0.83 | 1.33 | 2.48 | FLJ20273 | RNA-binding protein | NM_019027 |
| 1.62 | 1.95 | 1.96 | 2.05 | 2.48 | ELF4 | E74-like factor 4 (ets domain transcription | U32645 |
| 0.22 | 0.39 | 1.30 | 2.42 | 2.48 | | CDNA FLJ38181 fis, clone FCBBF10001 | AW207243 |
| -1.79 | 1.43 | -1.18 | 1.74 | 2.48 | SILV | silver homolog (mouse) | U01874 |
| -0.32 | 0.39 | 0.68 | 1.38 | 2.47 | RABGAP1L | RAB GTPase activating protein 1-like | NM_014857 |
| -0.26 | 0.03 | -0.15 | -1.22 | 2.47 | | gb:AW274503 /DB_XREF=gi:6661533 /D | AW274503 |
| 0.60 | -1.04 | -0.72 | 0.44 | 2.47 | DAB1 /// OMA1 | disabled homolog 1 (Drosophila) /// OMA | AI927931 |
| 0.87 | 2.47 | 1.32 | 1.48 | 0.29 | | Transcribed locus | AI093327 |
| 1.35 | 2.47 | -2.47 | -2.47 | 2.47 | ETV1 | ets variant gene 1 | X87175 |
| 0.11 | 0.28 | 0.67 | -0.83 | 2.47 | KIAA1509 | KIAA1509 | AB040942 |
| 1.32 | 2.15 | 2.08 | 2.47 | -1.44 | LRIG1 | leucine-rich repeats and immunoglobulin- | AB050468 |
| 0.05 | 0.60 | 1.26 | 1.88 | 2.47 | CTSB | cathepsin B | NM_001908 |
| 0.00 | 1.10 | 2.12 | 2.47 | 1.79 | TMOD1 | tropomodulin 1 | BC002660 |
| 2.25 | 0.94 | -0.29 | 0.57 | 2.47 | NUP98 | nucleoporin 98kDa | U41815 |
| 0.52 | 0.39 | -0.76 | 1.93 | 2.47 | IFI30 | interferon, gamma-inducible protein 30 | NM_006332 |
| 0.94 | 1.06 | 0.55 | -0.71 | 2.47 | YBX2 | Y box binding protein 2 | NM_015982 |
| -0.67 | 0.03 | -0.03 | -0.22 | 2.47 | HMMR | hyaluronan-mediated motility receptor (R | NM_012485 |
| 0.00 | 0.88 | 1.02 | 2.47 | 2.07 | BACE1 | beta-site APP-cleaving enzyme 1 | AF190725 |
| -1.88 | 1.25 | -1.02 | 1.05 | 2.47 | CCBL1 | cysteine conjugate-beta lyase; cytoplasm | NM_004059 |
| 0.76 | 0.55 | 1.44 | 1.79 | 2.46 | PDLIM4 | PDZ and LIM domain 4 | AI254547 |
| 0.61 | 0.77 | 1.34 | 1.38 | 2.46 | PPP3CC | protein phosphatase 3 (formerly 2B), cat | S46622 |
| -0.87 | 0.70 | 0.91 | -1.33 | 2.46 | AARS | alanyl-tRNA synthetase | NM_001605 |
| -0.58 | -1.24 | 1.38 | 1.55 | 2.46 | PSIP1 | PC4 and SFRS1 interacting protein 1 | NM_004682 |
| 0.51 | 0.69 | 1.12 | 1.56 | 2.46 | GPRC5C | G protein-coupled receptor, family C, gro | NM_022036 |
| -0.55 | 0.98 | 1.31 | 2.45 | 1.99 | MALAT1 | metastasis associated lung adenocarcino | W80468 |
| 0.00 | 1.24 | 2.06 | 2.31 | 2.45 | TACC1 | transforming, acidic coiled-coil containing | BC041391 |
| -1.12 | -1.34 | 2.45 | 1.84 | 1.61 | RASL11B | RAS-like, family 11, member B | NM_023940 |
| -0.42 | -1.03 | -0.70 | -1.03 | 2.45 | ZCCHC7 | zinc finger, CCHC domain containing 7 | BG291039 |
| -0.34 | 0.43 | 1.06 | 1.80 | 2.45 | FKBP7 | FK506 binding protein 7 | AF100751 |
| 1.80 | 1.14 | 0.61 | 1.27 | 2.45 | EMP3 | epithelial membrane protein 3 | NM_001425 |
| -0.52 | -1.33 | -2.45 | 1.90 | 2.45 | PPP1R16B | protein phosphatase 1, regulatory (inhibit | AB020630 |
| 0.05 | 0.66 | 2.45 | 1.90 | 1.63 | FAM11A | family with sequence similarity 11, memb | BC022405 |
| -2.25 | 2.45 | 1.39 | 0.43 | -0.12 | GAD1 /// LASS6 | glutamate decarboxylase 1 (brain, 67kDa | NM_013445 |
| -0.78 | 1.42 | 2.45 | 2.45 | 2.45 | IL15 | interleukin 15 | NM_000585 |
| 0.82 | 1.51 | 2.10 | 2.37 | 2.45 | TACC1 | transforming, acidic coiled-coil containing | NM_006283 |
| -0.61 | 1.01 | 1.40 | 1.76 | 2.45 | MYEF2 | myelin expression factor 2 | BG179854 |
| -0.21 | 0.18 | 1.71 | 2.45 | 2.34 | | gb:AA401256 /DB_XREF=gi:2055145 /DI | AA401256 |
| 0.51 | 0.25 | -0.16 | -0.76 | 2.45 | B3GNT7 | UDP-GlcNAc:betaGal beta-1,3-N-acetylg | CA503291 |
| -0.33 | 0.48 | -1.92 | -2.38 | -2.44 | PSAT1 | phosphoserine aminotransferase 1 | NM_021154 |
| 0.70 | 1.00 | 1.22 | 2.02 | 2.44 | MGC24039 | hypothetical protein MGC24039 | AL137364 |
| 1.22 | 2.44 | 1.83 | 1.73 | 2.44 | MYL9 | myosin, light chain 9, regulatory | NM_006097 |
| 0.66 | 1.16 | 1.78 | 2.44 | 2.33 | PUNC | putative neuronal cell adhesion molecul | AW204060 |
| -0.83 | -1.76 | -2.01 | -1.52 | 2.44 | TMEM63A | transmembrane protein 63A | AW510783 |
| 0.24 | 0.92 | 0.82 | 1.52 | 2.44 | | CDNA clone IMAGE:4402981 | BC015343 |
| -0.22 | 0.52 | 1.48 | 1.96 | 2.44 | LOXL2 | lysyl oxidase-like 2 | BE251211 |
| -0.93 | -1.16 | 1.42 | 1.63 | 2.44 | LRRC20 | leucine rich repeat containing 20 | NM_018205 |
| 0.76 | -0.72 | 0.07 | 0.16 | 2.44 | | CDNA FLJ31093 fis, clone IMR32100016 | AW771952 |
| 2.24 | 2.44 | 2.06 | 1.24 | 0.89 | SERTAD4 | SERTA domain containing 4 | AL035414 |
| 1.01 | 2.14 | 2.43 | 2.05 | 1.98 | SLC16A3 | solute carrier family 16, member 3 (mono | AL513917 |
| 2.17 | 2.43 | 1.40 | 1.69 | 1.57 | HEG1 | HEG homolog 1 (zebrafish) | AI148659 |
| 0.00 | 0.00 | 1.24 | 2.33 | 2.43 | SULF1 | sulfatase 1 | AW043713 |
| 1.42 | 2.43 | 1.35 | 0.12 | 1.54 | CD44 | CD44 molecule (Indian blood group) | BC004372 |

Appendix 2

| | | | | | Gene | Description | Accession |
|---|---|---|---|---|---|---|---|
| 0.10 | -0.67 | -2.16 | -2.43 | 2.18 | ALDH3A2 | aldehyde dehydrogenase 3 family, memb | NM_000382 |
| 0.68 | -0.78 | -0.57 | -0.96 | 2.43 | BCL11A | B-cell CLL/lymphoma 11A (zinc finger pr | AF080216 |
| 1.53 | 1.33 | 1.53 | 2.43 | 1.43 | TMTC1 | transmembrane and tetratricopeptide rep | BF109231 |
| -0.63 | -1.58 | 1.21 | 2.43 | 2.43 | SLAIN1 | SLAIN motif family, member 1 | AV730849 |
| -0.53 | 0.20 | 2.06 | 2.43 | 0.90 | SMARCA2 | SWI/SNF related, matrix associated, actir | AI535683 |
| 2.43 | -1.61 | -0.66 | -0.44 | 1.80 | STC1 | stanniocalcin 1 | AI300520 |
| -0.84 | -0.51 | 0.25 | 2.04 | 2.43 | PAQR8 | progestin and adipoQ receptor family mer | AI655524 |
| 2.43 | 1.49 | 0.50 | 0.52 | 0.35 | VANGL1 | vang-like 1 (van gogh, Drosophila) | BF509230 |
| -0.24 | 0.70 | 2.19 | 2.43 | 1.35 | CLCN5 | chloride channel 5 (nephrolithiasis 2, X-li | NM_000084 |
| 0.00 | 0.00 | 1.73 | 2.42 | 2.28 | MEIS1 | Meis1, myeloid ecotropic viral integration | AL832770 |
| 2.42 | 2.24 | 1.76 | -1.04 | 1.36 | PDE4A | phosphodiesterase 4A, cAMP-specific (pl | NM_006202 |
| 0.00 | 0.00 | 0.00 | 0.57 | 2.42 | COL1A1 | collagen, type I, alpha 1 | AI743621 |
| 0.85 | 0.93 | 0.42 | 0.94 | 2.42 | MAP1A | microtubule-associated protein 1A | AW296788 |
| -0.75 | 0.31 | 0.90 | 1.73 | 2.42 | FXYD6 | FXYD domain containing ion transport re | NM_022003 |
| -0.64 | 0.09 | 0.83 | 2.42 | 2.33 | MLLT3 | myeloid/lymphoid or mixed-lineage leuker | AV756536 |
| 0.00 | -1.44 | 2.31 | 2.42 | 2.05 | WNT5A | Wingless-type MMTV integration site fam | AI703321 |
| 0.45 | -0.94 | 1.50 | 1.81 | 2.42 | | Transcribed locus, strongly similar to XP_ | AV687517 |
| 0.33 | 0.19 | 1.16 | 1.95 | 2.42 | TSHZ1 | teashirt family zinc finger 1 | AF039698 |
| -0.24 | 0.01 | 0.73 | 1.38 | 2.42 | ALPL | alkaline phosphatase, liver/bone/kidney | X14174 |
| -0.14 | -0.72 | 0.85 | 1.57 | 2.42 | PITPNC1 | phosphatidylinositol transfer protein, cyto | NM_012417 |
| 0.00 | 0.84 | 1.31 | 2.42 | 1.98 | LOC254057 | hypothetical protein LOC254057 | AI635756 |
| 0.18 | 0.31 | 2.42 | 2.11 | 1.68 | LOC92482 | hypothetical protein LOC9248; | AV728606 |
| 0.00 | 0.00 | 2.16 | 2.42 | 2.40 | | gb:AI432195 /DB_XREF=gi:4308483 /DE | AI432195 |
| -0.56 | -1.38 | -2.18 | -2.41 | 2.41 | ZBTB3 | zinc finger and BTB domain containing 3 | NM_024784 |
| -0.29 | 0.43 | 1.90 | 2.41 | 0.30 | NMNAT2 | nicotinamide nucleotide adenylyltransfera | AF288395 |
| 1.50 | 2.40 | 2.41 | 2.39 | 2.09 | ETV1 | ets variant gene 1 | AC004857 |
| 0.47 | 1.12 | 2.41 | 2.04 | 1.98 | SGPP1 | sphingosine-1-phosphate phosphatase 1 | BE880703 |
| 0.05 | 0.12 | 0.27 | 1.00 | 2.41 | BMP1 | bone morphogenetic protein 1 | NM_001199 |
| -0.41 | -0.41 | 2.41 | 1.91 | -0.28 | ARHGAP28 | Rho GTPase activating protein 28 | NM_030672 |
| 2.09 | 2.41 | 1.63 | 1.41 | 1.52 | HEG1 | HEG homolog 1 (zebrafish) | AA121502 |
| -2.14 | -0.92 | 1.30 | 2.41 | 1.74 | TFRC | transferrin receptor (p90, CD71) | N76327 |
| 0.50 | 0.44 | 0.66 | 2.41 | 2.07 | ENC1 | ectodermal-neural cortex (with BTB-like c | NM_003633 |
| -0.33 | -0.95 | 1.83 | 2.41 | 2.41 | UNC5D | Unc-5 homolog D (C. elegans) | AI802048 |
| 0.41 | -0.48 | 2.27 | 2.41 | 1.39 | C18orf4 | chromosome 18 open reading frame 4 | AK021539 |
| -0.50 | 1.11 | 1.39 | 1.81 | 2.41 | FLJ22662 | hypothetical protein FLJ2266; | NM_024829 |
| 0.64 | -0.54 | 1.30 | 1.68 | 2.41 | | gb:AA130132 /DB_XREF=gi:1691190 /DI | AA130132 |
| 0.79 | 1.17 | 1.43 | 1.92 | 2.40 | SPSB1 | splA/ryanodine receptor domain and SO( | AF131840 |
| 1.38 | -1.37 | 2.40 | 2.22 | 1.28 | MATR3 | Matrin 3 | BG283790 |
| 0.07 | -0.11 | 0.68 | 2.04 | 2.40 | ANKS1A | ankyrin repeat and sterile alpha motif don | AI990523 |
| 0.00 | 0.00 | 0.91 | 2.40 | 2.33 | EPAS1 | endothelial PAS domain protein 1 | NM_001430 |
| 0.72 | 1.62 | 1.68 | 2.40 | 1.70 | PTPRM | protein tyrosine phosphatase, receptor ty | BC029442 |
| 0.00 | 1.26 | 1.57 | 2.40 | 1.78 | NOG | Noggin | AL575177 |
| 0.00 | 0.05 | 0.58 | -1.21 | 2.40 | GCNT2 | glucosaminyl (N-acetyl) transferase 2, I-b | BF059748 |
| 0.00 | 0.96 | -1.72 | 2.40 | 0.91 | LOC729620 | Hypothetical protein LOC72962( | AI393695 |
| 0.66 | 0.05 | 0.03 | 0.96 | 2.40 | EPM2AIP1 | EPM2A (laforin) interacting protein 1 | BF432224 |
| 0.26 | 0.47 | 0.95 | 1.43 | 2.40 | | Transcribed locus | AW265065 |
| 0.00 | 0.95 | 2.25 | 2.40 | 0.90 | LOC645431 | hypothetical protein LOC645431 | AI654093 |
| 0.00 | 0.43 | 1.25 | 2.39 | 1.34 | CALM2 | Calmodulin 2 (phosphorylase kinase, dell | AV763524 |
| -0.84 | -0.60 | -0.96 | -1.19 | 2.39 | STRBP | spermatid perinuclear RNA binding protei | BC002693 |
| 0.74 | 1.20 | 1.84 | 2.39 | 1.32 | ANXA4 | annexin A4 | NM_001153 |
| -0.20 | 0.17 | -0.71 | 1.56 | 2.39 | PPAP2C | phosphatidic acid phosphatase type 2C | AF047760 |
| 0.71 | 0.84 | 1.08 | 1.25 | 2.39 | PPP3CC | protein phosphatase 3 (formerly 2B), cata | NM_005605 |
| 0.42 | -1.06 | 1.79 | 1.48 | 2.39 | LAMP2 | lysosomal-associated membrane protein | NM_013995 |
| 0.71 | -2.39 | 2.28 | 2.14 | 1.87 | CPZ | carboxypeptidase Z /// carboxypeptidase | BC006393 |
| 1.45 | -1.36 | -0.30 | 0.01 | 2.39 | LOC729777 /// LO | similar to Peroxisomal coenzyme A dipho | AI927954 |
| 1.23 | -1.74 | 1.97 | 2.28 | 2.39 | ITGAV | integrin, alpha V (vitronectin receptor, alp | AI093579 |
| -0.15 | 0.76 | 2.38 | 2.17 | 1.31 | ARHGAP28 | Rho GTPase activating protein 28 | AI935647 |
| 0.00 | 1.20 | 1.89 | 2.38 | 1.79 | PRKCH | protein kinase C, eta | NM_024064 |
| -0.64 | 2.38 | 2.38 | 2.38 | 2.38 | VENTX | VENT homeobox homolog (Xenopus laev | NM_014468 |
| 1.68 | 1.22 | 1.45 | 2.38 | 1.52 | ODZ4 | odz, odd Oz/ten-m homolog 4 (Drosophil: | BF112171 |
| 0.54 | -0.95 | 2.38 | 2.38 | 2.38 | TNFRSF8 | tumor necrosis factor receptor superfamil | NM_001243 |
| 0.85 | 1.12 | 1.46 | 2.38 | 2.37 | CRTC3 | CREB regulated transcription coactivator | NM_022769 |
| 0.00 | 0.55 | 1.81 | 2.37 | 1.84 | JMJD3 | jumonji domain containing 3 | AA521267 |
| 1.37 | 1.28 | 1.02 | 1.74 | 2.37 | PTPN21 | Protein tyrosine phosphatase, non-recept | N21442 |
| -0.45 | -0.29 | -0.69 | -1.49 | 2.37 | NEDD4L | neural precursor cell expressed, developr | AI357376 |
| -0.71 | -0.95 | -0.99 | -1.40 | -2.37 | USP28 | ubiquitin specific peptidase 28 | AB040948 |
| 0.20 | 0.76 | 1.52 | 1.98 | 2.37 | CD99 | CD99 molecule | NM_002414 |
| 0.17 | 0.56 | 0.83 | 2.37 | 1.80 | MALAT1 | metastasis associated lung adenocarcino | BE708432 |
| 0.00 | 0.39 | 1.22 | 2.33 | 2.37 | CHD9 | chromodomain helicase DNA binding pro | BG538482 |
| 2.03 | 2.37 | 2.05 | 1.28 | 0.80 | SERTAD4 | SERTA domain containing 4 | AU146709 |
| 0.44 | 1.47 | 1.91 | 2.37 | 1.97 | KALRN | kalirin, RhoGEF kinase | AL137629 |
| 0.34 | -0.10 | -0.28 | 0.19 | 2.37 | KIAA0141 | KIAA0141 | AA181172 |
| 0.55 | 0.53 | 0.64 | 2.06 | 2.37 | EGFR | Epidermal growth factor receptor (erythro | BE878463 |
| -0.54 | 0.91 | -1.69 | 2.03 | 2.36 | DISP1 | dispatched homolog 1 (Drosophila) | AK023679 |
| -0.08 | 0.28 | 1.30 | 2.36 | 1.44 | TOM1L2 | target of myb1-like 2 (chicken) | AV751731 |
| 0.25 | 0.18 | 0.49 | 1.61 | 2.36 | RHOBTB1 | Rho-related BTB domain containing 1 | AB018283 |
| -0.24 | -0.54 | -1.06 | -1.27 | 2.36 | IPW | imprinted in Prader-Willi syndrome | AI872541 |
| 0.01 | 0.03 | 1.08 | 1.10 | -2.35 | KIAA0746 | KIAA0746 protein | AA522514 |
| -0.89 | 2.35 | -0.80 | 0.09 | -1.30 | DUSP6 | dual specificity phosphatase 6 | BC003143 |
| 0.00 | 0.42 | 1.79 | 2.35 | 0.16 | CSF2RA | colony stimulating factor 2 receptor, alph: | NM_006140 |
| 0.06 | -0.36 | 1.07 | 1.42 | -2.35 | HELZ /// OVOS2 // | helicase with zinc finger /// ovostatin 2 /// | AW594320 |
| 0.00 | 0.00 | 1.11 | 2.35 | 0.36 | BCL6 | B-cell CLL/lymphoma 6 (zinc finger protei | AW264036 |
| 1.47 | 0.88 | 1.16 | 1.95 | -2.35 | CTNNB1 | Catenin (cadherin-associated protein), be | AW362945 |
| -0.19 | -0.45 | -0.72 | -1.19 | -2.35 | PPM1B | protein phosphatase 1B (formerly 2C), m: | AF136972 |
| 0.50 | 0.31 | 0.67 | 1.23 | 2.35 | PON2 | paraoxonase 2 | AF001602 |
| -1.72 | 1.34 | 1.34 | -1.24 | -2.35 | TMEM108 | transmembrane protein 108 | BC000568 |
| -1.06 | -1.97 | -2.35 | -2.12 | -1.28 | MTSS1 | metastasis suppressor 1 | NM_014751 |

Appendix 2

| | | | | | Symbol | Description | Accession |
|---|---|---|---|---|---|---|---|
| 0.95 | 1.92 | 2.33 | 2.35 | 1.53 | C13orf18 | chromosome 13 open reading frame 18 | NM_025113 |
| 0.90 | 0.74 | 0.72 | 0.19 | 2.35 | PCOLCE | procollagen C-endopeptidase enhancer | NM_002593 |
| 0.58 | 2.33 | 2.35 | 2.35 | 2.35 | | CDNA FLJ37467 fis, clone BRAWH2011! | AI369234 |
| 0.32 | 0.49 | 0.97 | 2.35 | 1.52 | OBSL1 | obscurin-like 1 | BF446688 |
| 0.82 | 1.13 | 2.09 | 2.34 | 1.32 | SLC6A15 | solute carrier family 6, member 15 | AK022853 |
| 2.04 | 2.34 | 1.97 | 2.34 | 2.19 | MCOLN3 | mucolipin 3 | AI636080 |
| 0.00 | 0.00 | 0.58 | 1.88 | 2.34 | | Transcribed locus | BG252802 |
| 1.32 | 1.69 | 1.80 | 2.18 | 2.34 | ZYG11A | zyg-11 homolog A (C. elegans) | AW243917 |
| -0.21 | -0.32 | -0.83 | -1.29 | -2.34 | GART | phosphoribosylglycinamide formyltransfer | NM_000819 |
| -0.57 | -0.98 | -1.10 | -1.29 | -2.34 | PAK1 | p21/Cdc42/Rac1-activated kinase 1 (STE | U51120 |
| 1.68 | 2.34 | 1.51 | 0.08 | 0.61 | ELL2 | elongation factor, RNA polymerase II, 2 | AI924426 |
| 0.00 | 0.00 | 0.00 | 0.94 | 2.34 | PRRX1 | paired related homeobox 1 | NM_006902 |
| 0.00 | 0.00 | 0.00 | 1.23 | 2.34 | ADAMTS9 | ADAM metallopeptidase with thrombospo | AF086069 |
| 0.45 | 1.38 | 1.24 | 2.34 | 2.08 | NRP2 | Neuropilin 2 | AK024680 |
| -0.55 | -0.80 | -2.12 | -2.30 | -2.34 | ITGA6 | integrin, alpha 6 | AV733308 |
| 0.26 | 0.99 | 1.91 | 2.34 | 1.05 | ANXA4 | annexin A4 | BC000182 |
| 0.00 | 0.00 | 2.34 | 2.30 | 1.55 | FN1 | fibronectin 1 | AJ276395 |
| -0.01 | -0.01 | 0.06 | 0.22 | 2.34 | RAD23B | RAD23 homolog B (S. cerevisiae) | AF262027 |
| 0.56 | -0.49 | -2.33 | -1.91 | -1.83 | | Clone 23700 mRNA sequence | AI097640 |
| 0.00 | 1.01 | 2.33 | 2.13 | 1.87 | TBX3 | T-box 3 (ulnar mammary syndrome) | U69556 |
| 2.33 | 1.93 | 0.37 | 1.02 | 1.07 | EXT1 | Exostoses (multiple) 1 | AA480392 |
| 0.16 | 1.11 | 2.33 | 2.33 | -0.98 | SLC6A15 | solute carrier family 6, member 15 | NM_018057 |
| 2.33 | 2.17 | 1.39 | 1.27 | 1.30 | SHB | Src homology 2 domain containing adapt | BU685917 |
| 1.83 | 1.68 | 2.33 | 1.47 | -0.83 | C20orf39 | chromosome 20 open reading frame 39 | NM_024893 |
| -1.20 | -1.88 | -1.07 | -1.52 | 2.33 | | CDNA FLJ36559 fis, clone TRACH20092 | AI016316 |
| 1.22 | 1.62 | 1.85 | 2.33 | 1.66 | TMEM2 | transmembrane protein 2 | NM_013390 |
| 0.09 | -0.53 | -1.70 | -2.03 | -2.33 | SCLY | selenocysteine lyase | AA911739 |
| 0.60 | 0.68 | -0.08 | -0.55 | -2.33 | C4orf34 | chromosome 4 open reading frame 34 | BE972723 |
| -0.58 | 0.81 | -0.90 | -1.34 | -2.33 | GCA | grancalcin, EF-hand calcium binding prot | NM_012196 |
| 0.06 | 0.34 | 1.06 | 1.89 | 2.32 | FBLN1 | fibulin 1 | Z95331 |
| 0.00 | 1.18 | 2.32 | 1.81 | 0.09 | DLX4 | distal-less homeobox 4 | NM_001934 |
| -0.46 | -1.16 | -1.94 | -1.18 | -2.32 | EFCAB4A | EF-hand calcium binding domain 4A | AI683694 |
| 0.22 | 0.60 | 1.18 | 1.57 | 2.32 | PHC2 | polyhomeotic homolog 2 (Drosophila) | NM_004427 |
| 2.32 | 2.25 | 0.68 | 0.08 | -0.68 | C1orf97 | chromosome 1 open reading frame 97 /// | BC005997 |
| 2.32 | -1.33 | -0.39 | 0.87 | 1.46 | SFRP1 | secreted frizzled-related protein 1 | NM_003012 |
| 0.19 | -0.08 | 1.92 | 2.17 | 2.12 | FGF2 | fibroblast growth factor 2 (basic) | M27968 |
| 0.23 | 1.23 | 2.12 | 2.32 | -2.32 | | Transcribed locus | AI768826 |
| 1.28 | 1.80 | 2.32 | 1.84 | 0.88 | COL9A2 | collagen, type IX, alpha 2 | AI733465 |
| 0.83 | 2.32 | 2.04 | 1.90 | 1.63 | GAS7 | growth arrest-specific 7 | NM_003644 |
| 0.00 | 0.94 | 2.32 | 1.72 | 0.80 | ATP2B4 | ATPase, Ca++ transporting, plasma mer | NM_001684 |
| 0.17 | 0.80 | 0.73 | 1.26 | 2.32 | CDK6 | cyclin-dependent kinase 6 | AW274756 |
| -0.13 | 1.04 | 2.17 | 2.32 | 0.99 | FUT8 | fucosyltransferase 8 (alpha (1,6) fucosylt | AB049740 |
| 1.27 | 2.32 | 1.28 | 1.51 | 1.66 | SULF2 | sulfatase 2 | AL133001 |
| 0.13 | 0.11 | 1.43 | 2.31 | 2.26 | | septin 8 | D86957 |
| 0.00 | 0.00 | 0.00 | 0.51 | 2.31 | 8-Sep | CDNA FLJ25106 fis, clone CBR01467 | W61005 |
| 0.00 | 0.00 | 1.23 | 2.00 | 2.31 | HOXA11 | homeobox A11 | H94842 |
| -0.43 | 0.33 | 1.44 | 1.91 | 2.31 | TMEM51 | transmembrane protein 51 | NM_018022 |
| -1.26 | -1.18 | -1.66 | -2.31 | -0.35 | ELMO1 | engulfment and cell motility 1 | NM_014800 |
| -0.79 | -0.77 | -2.31 | -2.31 | -2.31 | INHBE | inhibin, beta E | BC005161 |
| -1.09 | -0.88 | -1.38 | -1.96 | -2.31 | | Homo sapiens, clone IMAGE:5241654, rr | Z83851 |
| 0.65 | 0.79 | -1.13 | 1.28 | 2.31 | RAB3IP | RAB3A interacting protein (rabin3) | BC002556 |
| 0.61 | 0.72 | 1.33 | 1.85 | 2.31 | TFPI | tissue factor pathway inhibitor (lipoprotei | BF511231 |
| 0.00 | 0.00 | 0.07 | 2.28 | 2.31 | HOXA9 | homeobox A9 | U41813 |
| 1.15 | 0.75 | 0.53 | 1.72 | 2.31 | GNAS | GNAS complex locus | AI693143 |
| 1.07 | 2.22 | 1.65 | 0.66 | 2.31 | DKK3 | Dickkopf homolog 3 (Xenopus laevis) | AL569601 |
| 0.00 | 0.00 | 0.00 | 0.34 | 2.31 | C20orf75 | chromosome 20 open reading frame 75 | BC019612 |
| 0.00 | 0.00 | 0.00 | 0.67 | 1.95 | TGFB2 | Transforming growth factor, beta 2 | AU145950 |
| 0.74 | -0.03 | 2.21 | 2.30 | 1.79 | MAFB | v-maf musculoaponeurotic fibrosarcoma | NM_005461 |
| -0.42 | 0.19 | 0.81 | 1.26 | 2.30 | TFPI | tissue factor pathway inhibitor (lipoprotei | AF021834 |
| -1.64 | -2.30 | -2.30 | -2.30 | -2.30 | NLRP7 | NLR family, pyrin domain containing 7 | AA565499 |
| -1.30 | -1.29 | -2.12 | -2.30 | -2.30 | GNG4 | guanine nucleotide binding protein (G prc | AF493872 |
| 1.23 | 1.67 | 1.68 | 2.30 | 1.93 | EPB41L3 | erythrocyte membrane protein band 4.1-li | BC006141 |
| -0.14 | -0.32 | 1.92 | 2.30 | 1.89 | NEFL | neurofilament, light polypeptide 68kDa | AL537457 |
| -0.06 | -0.26 | -0.10 | 0.28 | -2.30 | AUH | AU RNA binding protein/enoyl-Coenzym | NM_001698 |
| 0.37 | 1.10 | 1.96 | 1.91 | 2.30 | SRC | v-src sarcoma (Schmidt-Ruppin A-2) viral | AK024281 |
| 0.07 | -0.35 | -0.79 | -1.67 | -2.30 | MMP25 | matrix metallopeptidase 25 | NM_022718 |
| 1.00 | 2.30 | 0.59 | -0.27 | 0.27 | ACTG2 | actin, gamma 2, smooth muscle, enteric | NM_001615 |
| 0.83 | 1.62 | 2.29 | 2.10 | 1.08 | FMR1 | fragile X mental retardation 1 | AA830884 |
| 0.53 | 2.29 | 1.64 | 2.22 | 2.19 | PPFIBP1 | PTPRF interacting protein, binding protei | AI962377 |
| -1.13 | -1.59 | -2.04 | -2.29 | -1.26 | CLU | clusterin | M25915 |
| 0.00 | 0.00 | 0.86 | 2.29 | 2.29 | IGFBP5 | insulin-like growth factor binding protein | R73554 |
| 0.19 | -0.38 | 1.49 | 2.29 | 2.29 | | gb:BF510692 /DB_XREF=gi:11593990 /L | BF510692 |
| 0.01 | 0.97 | 2.16 | 2.29 | 2.15 | LPGAT1 | lysophosphatidylglycerol acyltransferase | BC034621 |
| 0.69 | 0.82 | 0.59 | 1.30 | 2.29 | GPSM1 | G-protein signalling modulator 1 (AGS3-li | AI242661 |
| -0.31 | -1.02 | -2.29 | -1.10 | -0.74 | RPS24 | Ribosomal protein S24 | AK094613 |
| 1.49 | 2.29 | 0.02 | -1.30 | -0.63 | TFPI2 | tissue factor pathway inhibitor 2 | AL574096 |
| -0.54 | -0.37 | -0.52 | -0.66 | -2.29 | MLSTD1 | male sterility domain containing 1 | NM_018099 |
| 0.09 | 0.58 | 0.34 | -1.74 | -2.29 | COL4A1 | collagen, type IV, alpha 1 | NM_001845 |
| 0.02 | -0.09 | 0.83 | 1.20 | 2.28 | NME7 | non-metastatic cells 7, protein expressed | AI094560 |
| 1.27 | 1.64 | 0.42 | 0.11 | 2.28 | PTRF | polymerase I and transcript release facto | BC004295 |
| 0.36 | 1.40 | 1.40 | 1.47 | 2.28 | LNPEP | leucyl/cystinyl aminopeptidase | AA767440 |
| 0.90 | 0.45 | 0.84 | 1.63 | 2.28 | EGLN1 | egl nine homolog 1 (C. elegans) | AL117352 |
| 0.00 | 0.00 | 0.00 | 2.19 | 2.28 | HTR1E | 5-hydroxytryptamine (serotonin) receptor | NM_000865 |
| 1.27 | 1.47 | 1.36 | 1.63 | 2.28 | | gb:AW474898 /DB_XREF=gi:7045004 /D | AW474898 |
| 0.00 | 0.76 | 1.45 | 2.28 | 1.46 | TBC1D9 | TBC1 domain family, member 9 (with GR | BE646554 |
| 0.00 | 0.00 | 0.00 | 0.54 | 0.75 | FAM46A | family with sequence similarity 46, memb | AL078599 |
| 0.00 | 0.73 | 0.00 | 0.01 | 0.66 | ANXA8 /// ANXA8L | annexin A8 /// annexin A8-like 1 /// simila | NM_001630 |

Appendix 2

| | | | | | Symbol | Description | Accession |
|---|---|---|---|---|---|---|---|
| 0.70 | 1.80 | 2.28 | 0.40 | 1.36 | SGK | serum/glucocorticoid regulated kinase | NM_005627 |
| 1.22 | 1.50 | 1.77 | 2.28 | 2.28 | PPM1E | protein phosphatase 1E (PP2C domain c | R40892 |
| 0.32 | -0.04 | -0.33 | -0.30 | 2.28 | FARS2 | phenylalanine-tRNA synthetase 2 (mitoct | NM_006567 |
| 0.44 | 0.66 | 1.73 | 2.06 | 2.28 | PPP1R9B | protein phosphatase 1, regulatory subuni | BF508705 |
| -0.12 | -0.78 | -1.27 | 1.69 | 2.28 | FAM119A | family with sequence similarity 119, mem | AI625022 |
| 0.28 | 0.89 | 1.28 | 1.74 | 2.28 | FKBP9 | FK506 binding protein 9, 63 kDa | AL050187 |
| 0.01 | 0.47 | 0.30 | 0.82 | 2.27 | GPR161 | G protein-coupled receptor 161 | AI743151 |
| 0.47 | 1.22 | 1.81 | 2.27 | 2.00 | TEAD1 | TEA domain family member 1 (SV40 tran | AI590088 |
| 1.51 | 0.82 | 0.45 | 0.80 | 2.27 | CBX4 | chromobox homolog 4 (Pc class homolog | AI570531 |
| -0.31 | -0.31 | 0.33 | 0.11 | 2.27 | STC1 | stanniocalcin 1 | U46768 |
| 0.36 | 0.45 | 1.04 | 0.83 | 2.27 | RIT1 | Ras-like without CAAX 1 | AA417878 |
| 0.00 | 0.48 | 2.27 | 1.87 | 1.57 | FBN2 | fibrillin 2 (congenital contractural arachno | X62009 |
| 0.59 | 0.96 | 0.94 | 1.87 | 2.27 | EHD2 | EH-domain containing 2 | AI417917 |
| 0.72 | -0.77 | -1.00 | 0.96 | 2.27 | FAM111A | family with sequence similarity 111, mem | NM_022074 |
| 0.51 | 0.45 | -0.79 | -1.41 | 2.27 | GART | phosphoribosylglycinamide formyltransfer | BE966876 |
| 0.63 | -0.08 | -0.87 | -0.07 | 2.27 | FAM36A | family with sequence similarity 36, memb | AA831192 |
| 0.56 | 0.77 | 0.66 | 2.27 | 1.86 | PRO1073 | PRO1073 protein | AF113016 |
| -0.38 | -0.59 | -0.58 | -0.70 | 2.27 | NME1 | Non-metastatic cells 1, protein (NM23A) | AL133577 |
| 0.17 | -0.85 | 1.29 | 2.19 | 2.27 | LOC645745 | metallothionein 1H-like protein | AF333388 |
| 1.82 | 2.27 | 1.38 | 0.31 | 0.85 | CRIP2 | cysteine-rich protein 2 | U36190 |
| 0.76 | 0.36 | -0.92 | 1.05 | 2.27 | POLR2J2 | DNA directed RNA polymerase II polypep | AW205664 |
| 1.59 | 1.31 | 0.28 | 1.89 | 2.27 | OBFC2A | oligonucleotide/oligosaccharide-binding f | AU157541 |
| 1.52 | 1.69 | 1.89 | 2.27 | 1.96 | EPB41L3 | erythrocyte membrane protein band 4.1-li | NM_012307 |
| 1.04 | 0.99 | 0.71 | 1.47 | 2.27 | | MRNA; cDNA DKFZp667B0924 (from clo | AI216690 |
| -0.10 | -0.54 | 0.96 | 1.37 | 2.26 | TP53INP2 | tumor protein p53 inducible nuclear prote | AL109824 |
| -0.27 | -0.10 | -0.52 | 1.67 | 2.26 | IFITM1 | interferon induced transmembrane protei | AA749101 |
| 1.14 | 1.12 | 0.09 | 0.66 | 2.26 | SFXN3 | sideroflexin 3 | M95929 |
| 1.76 | 2.19 | 0.79 | -0.65 | 2.26 | COCH | coagulation factor C homolog, cochlin (Li | BC007230 |
| 2.26 | 2.09 | 1.00 | 0.48 | 1.21 | VGLL3 | vestigial like 3 (Drosophila) | AI754423 |
| 1.03 | 0.51 | 0.05 | 0.85 | 2.26 | MGC21874 | transcriptional adaptor 2 (ADA2 homolog. | AI859834 |
| 1.19 | -1.57 | -1.67 | 2.26 | 0.43 | SOCS3 | suppressor of cytokine signaling 3 | BG035761 |
| -0.37 | -1.24 | -1.52 | 1.65 | 2.25 | ZNF649 | zinc finger protein 649 | BC005368 |
| -0.08 | 0.13 | 1.47 | 2.26 | 2.13 | H6PD | hexose-6-phosphate dehydrogenase (glu | AW138757 |
| -0.28 | -0.45 | -0.15 | 1.15 | 2.26 | PTN | pleiotrophin (heparin binding growth factc | AL565812 |
| 0.00 | 0.00 | 0.00 | 0.87 | 2.26 | EDG1 | endothelial differentiation, sphingolipid G | NM_001400 |
| 0.65 | 0.91 | 0.75 | 1.76 | 2.26 | MYLK | myosin, light chain kinase | AA526844 |
| 2.25 | -0.92 | -0.48 | 0.89 | 1.39 | WSB1 /// LOC654 | WD repeat and SOCS box-containing 1 / | BF111821 |
| 0.90 | 2.25 | 1.83 | 1.36 | 1.40 | CRIP1 /// GALK2 | cysteine-rich protein 1 (intestinal) /// galac | NM_001311 |
| 0.21 | 0.45 | 0.38 | 1.21 | 2.25 | CAST | calpastatin | NM_001750 |
| 0.00 | 0.43 | 1.82 | 2.15 | 2.25 | FREM1 | FRAS1 related extracellular matrix 1 | AI824037 |
| 0.00 | 0.00 | 0.50 | 0.84 | 2.25 | SENP6 | SUMO1/sentrin specific peptidase 6 | AK001406 |
| 0.00 | 0.00 | 0.00 | 0.82 | 2.25 | PLAC1 | placenta-specific 1 | NM_021796 |
| 0.00 | 0.00 | 0.84 | 1.74 | 2.25 | CAPN6 | calpain 6 | NM_014289 |
| -2.04 | 2.25 | 2.06 | 1.64 | 1.78 | TGFB1 | transforming growth factor, beta 1 (Camu | BC000125 |
| 0.00 | 0.00 | 0.00 | 2.25 | 1.96 | LOC286191 | Hypothetical protein LOC286191 | AW451999 |
| -0.40 | -0.79 | -1.25 | -1.39 | 2.25 | GMDS | GDP-mannose 4,6-dehydratase | AI762113 |
| -0.30 | -0.91 | -2.25 | 1.82 | 1.93 | PSMB10 | proteasome (prosome, macropain) subur | NM_002801 |
| -0.22 | -0.81 | -0.62 | -1.16 | 2.25 | ZNF165 | zinc finger protein 165 | NM_003447 |
| 0.45 | 0.93 | 1.14 | 1.28 | 2.25 | SRrp35 | CDNA FLJ14459 fis, clone HEMBB10024 | AA889416 |
| -1.71 | 1.30 | 0.79 | 2.25 | 1.95 | FJX1 | four jointed box 1 (Drosophila) | NM_014344 |
| 0.31 | 1.69 | -2.25 | 1.30 | 0.50 | CD55 | CD55 molecule, decay accelerating facto | BC001288 |
| -0.73 | 1.90 | -1.72 | 1.85 | 2.25 | GPM6B | glycoprotein M6B | N63576 |
| 0.53 | 1.41 | 1.32 | 1.95 | 2.25 | TPM1 | tropomyosin 1 (alpha) | M19267 |
| 0.41 | 0.20 | -0.58 | 1.36 | 2.24 | FOXA3 | forkhead box A3 | R99562 |
| 0.55 | -0.47 | 0.62 | 0.21 | 2.24 | PSMB2 | proteasome (prosome, macropain) subur | BC000268 |
| 1.91 | 2.24 | 2.24 | 2.24 | 2.24 | INSM1 | insulinoma-associated 1 | NM_002196 |
| 1.69 | 2.12 | 2.24 | 1.31 | 0.00 | SGCG | sarcoglycan, gamma (35kDa dystrophin- | NM_000231 |
| 0.28 | 0.51 | 1.05 | 1.45 | 2.24 | PITX2 | paired-like homeodomain transcription fa | NM_000325 |
| -0.96 | -0.90 | -0.58 | -0.90 | 2.24 | ADRBK2 | adrenergic, beta, receptor kinase 2 | AI651212 |
| 0.00 | 0.00 | 0.00 | 0.12 | 2.24 | | CDNA FLJ31660 fis, clone NT2RI200441 | AL137310 |
| 1.02 | 1.81 | 2.24 | 1.88 | 0.41 | PPAPDC1A | phosphatidic acid phosphatase type 2 do | BF130943 |
| -0.53 | 0.88 | 2.24 | 2.03 | 2.11 | JPH1 | junctophilin 1 | AI202201 |
| 2.24 | -0.70 | 0.04 | 1.28 | 1.15 | LOC728177 /// LO | hypothetical protein LOC728177 /// hypot | AI761675 |
| -0.48 | -0.71 | -1.24 | 1.59 | 2.24 | SLC43A1 | solute carrier family 43, member 1 | NM_003627 |
| 0.00 | 1.10 | 1.48 | 2.23 | 1.86 | IFI16 | interferon, gamma-inducible protein 16 | BG256677 |
| 0.24 | -0.32 | 1.02 | 1.86 | 2.23 | TSHZ1 | teashirt family zinc finger 1 | W60810 |
| 1.37 | 2.23 | 1.08 | 0.10 | 1.26 | CD44 | CD44 molecule (Indian blood group) | AI493245 |
| -0.43 | 0.41 | 1.77 | 2.23 | 1.52 | CLCN5 | chloride channel 5 (nephrolithiasis 2, X-li | AA218974 |
| 0.72 | 1.53 | -2.23 | 2.23 | 2.23 | ATP2A3 | ATPase, Ca++ transporting, ubiquitous | Y15724 |
| 0.37 | 0.20 | 1.94 | 2.23 | 1.26 | THRB | thyroid hormone receptor, beta (erythrobl | BG494007 |
| 0.00 | 0.00 | 0.09 | -2.23 | 1.70 | CXCR7 | Chemokine (C-X-C motif) receptor 7 | BE552368 |
| -0.13 | 0.52 | 1.51 | 1.87 | 2.23 | KDELR3 | KDEL (Lys-Asp-Glu-Leu) endoplasmic re | NM_016657 |
| -0.50 | -1.23 | -2.13 | -2.23 | 2.23 | GDAP1 | ganglioside-induced differentiation-assoc | N46350 |
| 0.00 | 0.42 | 1.43 | 2.23 | 0.23 | NMNAT2 | nicotinamide nucleotide adenylyltransfera | H90656 |
| 0.24 | 0.25 | 0.85 | 1.53 | 2.22 | COL6A2 | collagen, type VI, alpha 2 | AL531750 |
| -0.10 | -0.16 | 0.21 | -0.17 | -2.22 | STAU2 | staufen, RNA binding protein, homolog 2 | AK002152 |
| 1.71 | 1.81 | 1.57 | 1.90 | 2.22 | WTIP | Wilms tumor 1 interacting protein | BF111298 |
| 0.12 | 0.00 | 1.63 | 2.22 | 1.00 | CAMK2N1 | calcium/calmodulin-dependent protein kir | N75559 |
| 1.18 | 1.60 | -2.10 | 2.22 | -2.22 | ZDHHC22 | zinc finger, DHHC-type containing 22 | AI363193 |
| -0.52 | 0.66 | 0.91 | 1.31 | 2.22 | HRSP12 | heat-responsive protein 12 | N54448 |
| 2.14 | 2.22 | 1.95 | 1.16 | 0.60 | | gb:AI276403 /DB_XREF=gi:3898677 /DB | AI276403 |
| 0.73 | 1.14 | 1.66 | 2.22 | 1.45 | | MRNA; cDNA DKFZp566M0947 (from clc | AI288759 |
| -0.34 | -0.69 | -1.17 | -1.49 | 2.22 | JAZF1 | JAZF zinc finger 1 | AI990891 |
| -0.65 | 0.01 | 0.10 | -0.44 | 2.22 | S100A4 | S100 calcium binding protein A4 | NM_002961 |
| 0.37 | 0.00 | 1.24 | 2.18 | 2.22 | FOSL2 | FOS-like antigen 2 | N36408 |
| 0.09 | -0.44 | 1.43 | 2.22 | 2.22 | PRIMA1 | proline rich membrane anchor 1 | AI823845 |
| -0.61 | -1.50 | -2.22 | -2.22 | -2.22 | NR5A2 | nuclear receptor subfamily 5, group A, m | AF228413 |

Appendix 2

| | | | | | Symbol | Description | Accession |
|---|---|---|---|---|---|---|---|
| 0.19 | 0.07 | 0.66 | 0.74 | 2.22 | TXNDC13 | thioredoxin domain containing 13 | BF572868 |
| 0.00 | 0.95 | 0.60 | 2.22 | 1.40 | TncRNA | trophoblast-derived noncoding RNA | AU155361 |
| 1.73 | 2.22 | 1.53 | 1.03 | 0.01 | SERPINB9 | serpin peptidase inhibitor, clade B (ovalbu | BC002538 |
| 0.22 | 1.29 | 1.12 | 1.80 | 2.22 | TPM1 | tropomyosin 1 (alpha) | NM_000366 |
| 0.00 | 0.00 | 0.47 | 1.89 | 2.22 | HOXA10 | homeobox A10 | AI375919 |
| -0.28 | -0.57 | -1.83 | -2.22 | -1.18 | D4S234E | DNA segment on chromosome 4 (unique | BC001745 |
| 0.29 | 0.36 | 1.20 | 2.22 | 0.79 | FAM38B | family with sequence similarity 38, memb | NM_022068 |
| 0.00 | 0.00 | 0.00 | 0.52 | 2.21 | MSRB3 | methionine sulfoxide reductase B3 | AW027333 |
| -0.05 | -0.41 | -1.63 | -2.21 | -1.88 | ITGA6 | integrin, alpha 6 | NM_000210 |
| -0.21 | -0.53 | -1.23 | -1.71 | -2.21 | EIF4E3 | eukaryotic translation initiation factor 4E | AI935522 |
| -1.85 | -2.21 | -1.65 | -1.61 | -0.47 | PPP2R2B | protein phosphatase 2 (formerly 2A), regu | AA974416 |
| -0.43 | -0.72 | -1.97 | -2.21 | -1.50 | SH2B3 | SH2B adaptor protein 3 | NM_005475 |
| 0.00 | 0.00 | 0.16 | 0.66 | 2.21 | CXCR4 | chemokine (C-X-C motif) receptor 4 /// ch | AF348491 |
| 1.58 | -1.62 | -1.53 | -2.21 | -2.21 | KIAA1155 | KIAA1155 protein | AB032981 |
| -0.40 | -1.27 | -1.70 | -2.21 | -2.19 | | gb:AF078844.1 /DB_XREF=gi:6683748 / | AF078844 |
| -0.57 | -0.84 | -2.21 | -1.98 | -0.66 | FADS3 | fatty acid desaturase 3 | AC004770 |
| -0.74 | 0.04 | 1.62 | 2.21 | 0.37 | NMNAT2 | nicotinamide nucleotide adenylyltransfera | NM_170706 |
| 0.00 | 1.64 | 2.21 | 1.85 | 0.00 | GPR83 | G protein-coupled receptor 83 | BE670361 |
| 0.81 | 1.25 | -1.69 | -2.21 | 1.94 | ASXL1 | additional sex combs like 1 (Drosophila) | N64780 |
| 0.78 | -0.06 | -1.34 | -1.85 | -2.21 | NETO1 | neuropilin (NRP) and tolloid (TLL)-like 1 | NM_138966 |
| -0.62 | -0.47 | -0.43 | -0.79 | -2.21 | KIAA0586 | KIAA0586 | NM_014749 |
| 0.00 | 0.00 | 0.28 | 1.06 | 2.21 | TGM2 | transglutaminase 2 (C polypeptide, protei | AL031651 |
| 0.11 | 0.33 | 0.52 | 1.70 | 2.20 | COL4A2 | collagen, type IV, alpha 2 | X05610 |
| -0.17 | -1.06 | -1.94 | -2.20 | -1.54 | RASGEF1A | RasGEF domain family, member 1A | BF446578 |
| -0.63 | -1.13 | -2.20 | -2.20 | -2.20 | MAGI2 | membrane associated guanylate kinase, | AB014605 |
| 0.10 | 1.24 | 2.18 | 2.20 | 0.84 | TRIM38 | tripartite motif-containing 38 | AU157590 |
| -0.27 | -0.57 | -0.80 | -0.83 | -2.20 | PMS1 | PMS1 postmeiotic segregation increased | BG434893 |
| -2.20 | -2.20 | -2.20 | -2.20 | -2.20 | C10orf96 | chromosome 10 open reading frame 96 | BC044830 |
| 1.25 | 0.98 | -0.86 | -1.63 | -2.20 | PPP2R2C | protein phosphatase 2 (formerly 2A), regu | AI669212 |
| 0.30 | 0.91 | 1.46 | 1.94 | 2.20 | | Homo sapiens, clone IMAGE:3618365, m | BC004287 |
| 0.77 | 0.62 | 2.20 | 1.18 | 0.49 | MAP3K8 | mitogen-activated protein kinase kinase k | NM_005204 |
| 1.14 | 0.30 | 0.12 | 0.97 | 2.20 | ZNF70 | Zinc finger protein 70 | N62996 |
| 0.19 | 0.22 | -1.25 | 1.96 | -2.20 | CCND2 | cyclin D2 | AW026491 |
| 1.10 | 2.15 | 2.20 | 1.94 | 2.18 | GAS7 | growth arrest-specific 7 | NM_005890 |
| 0.63 | 0.66 | -0.19 | 0.34 | -2.20 | LOC440900 | Hypothetical LOC440900 | AA977481 |
| -0.91 | -2.20 | -0.34 | -0.16 | -0.98 | DUSP6 | dual specificity phosphatase 6 | BC005047 |
| -0.89 | -1.08 | -1.38 | -1.98 | -2.19 | | gb:BE813017 /DB_XREF=gi:10245251 /t | BE813017 |
| -0.19 | 0.30 | -0.20 | -0.79 | -2.19 | GLOXD1 | glyoxalase domain containing 1 | AI653050 |
| -0.66 | -2.19 | -1.72 | -1.38 | -1.99 | SPRY1 | sprouty homolog 1, antagonist of FGF sig | BF508662 |
| 0.27 | 1.09 | 1.98 | 2.19 | 1.57 | CTSL2 | cathepsin L2 | AF070448 |
| 0.00 | 0.00 | 1.75 | 2.19 | 0.85 | ACPP | acid phosphatase, prostate | AI659898 |
| -0.82 | -0.91 | -0.97 | -1.29 | -2.19 | ANKRD28 | ankyrin repeat domain 28 | AI081194 |
| 0.00 | 0.74 | 2.19 | 1.54 | 1.44 | TRPV2 | transient receptor potential cation channe | NM_015930 |
| 0.33 | 0.49 | 1.72 | 1.56 | 2.19 | TICAM2 | toll-like receptor adaptor molecule 2 | AI423165 |
| -0.42 | -0.71 | -0.81 | -0.85 | -2.19 | CHES1 | checkpoint suppressor 1 | NM_005197 |
| -0.37 | 0.27 | -0.15 | -0.63 | -2.19 | | gb:AW197495 /DB_XREF=gi:6476725 /D | AW197495 |
| -0.95 | 0.96 | -1.08 | -1.00 | -2.19 | JMJD2C | jumonji domain containing 2C | AB037901 |
| 0.00 | 0.58 | -0.70 | -1.32 | -2.19 | FLJ20273 | RNA-binding protein | AW241742 |
| -1.43 | 2.19 | 1.98 | 1.62 | 0.45 | NTF3 | neurotrophin 3 | NM_002527 |
| 0.38 | 0.38 | 0.09 | 1.07 | 2.19 | C16orf72 | Chromosome 16 open reading frame 72 | W58461 |
| -0.59 | 1.36 | -2.19 | -1.57 | -1.73 | ARSE | arylsulfatase E (chondrodysplasia puncta | NM_000047 |
| -1.87 | -2.18 | -1.08 | -0.91 | -1.52 | AASS | aminoadipate-semialdehyde synthase | AF229180 |
| 0.68 | 0.62 | 0.98 | 2.01 | 2.18 | GALNT6 | UDP-N-acetyl-alpha-D-galactosamine:po | NM_007210 |
| -0.94 | 1.44 | -2.03 | -2.18 | -1.11 | CLU | clusterin | M25915 |
| 0.91 | 0.54 | 0.00 | 0.19 | 2.18 | MGC10850 | hypothetical protein MGC10850 | BC004284 |
| 1.00 | 1.51 | 2.14 | 2.05 | 2.18 | | Transcribed locus | AI374739 |
| 0.20 | -0.83 | -0.98 | 1.60 | 2.18 | CECR2 | Cat eye syndrome chromosome region, c | BE551781 |
| 1.06 | 0.97 | 1.95 | 2.18 | 2.08 | FRMD6 | FERM domain containing 6 | AL040051 |
| -1.36 | -2.18 | -0.69 | 0.15 | 0.31 | KCNN2 | potassium intermediate/small conductanc | NM_021614 |
| -0.46 | 0.00 | 0.66 | 1.01 | 2.18 | ATP1B1 | ATPase, Na+/K+ transporting, beta 1 pol | BC000006 |
| -1.06 | -1.06 | -0.75 | 0.58 | 2.18 | METTL7A | methyltransferase like 7A | BC004492 |
| 0.45 | 0.67 | 1.23 | 2.18 | 0.97 | TMTC2 | transmembrane and tetratricopeptide rep | AI765006 |
| 0.43 | 0.70 | 1.35 | 1.86 | 2.18 | ADAM9 | ADAM metallopeptidase domain 9 (meltri | NM_003816 |
| 0.33 | 0.00 | 0.63 | 1.50 | 2.18 | HIPK3 | Homeodomain interacting protein kinase | AV693403 |
| 0.00 | 1.15 | 2.18 | 2.10 | 1.77 | SMAD6 | SMAD family member 6 | AI628464 |
| -0.93 | 0.67 | 2.07 | 2.18 | 1.75 | LIFR | leukemia inhibitory factor receptor alpha | AI680541 |
| 0.02 | 0.32 | 1.13 | 2.18 | 1.08 | | CDNA FLJ36544 fis, clone TRACH20063 | AW298235 |
| 1.56 | 2.18 | 2.16 | 1.59 | 1.67 | RHOU | ras homolog gene family, member U | AL096776 |
| 0.22 | 0.60 | -0.05 | -0.68 | -2.18 | SLC7A8 | solute carrier family 7 (cationic amino aci | AL365347 |
| 0.76 | 1.65 | 1.76 | 2.18 | 2.02 | ZBTB38 | zinc finger and BTB domain containing 38 | NM_024724 |
| -1.32 | -1.32 | -0.22 | -0.22 | -2.18 | STC1 | Stanniocalcin 1 | AW003173 |
| -0.10 | 0.52 | 1.84 | 2.18 | 1.34 | LEPR | leptin receptor | U50748 |
| -0.35 | -0.63 | 1.30 | 2.16 | 1.22 | CUL7 | cullin 7 | NM_014780 |
| 2.11 | 2.18 | 1.45 | -0.16 | 1.21 | NEFM | neurofilament, medium polypeptide 150kl | NM_005382 |
| 0.00 | 0.00 | 0.00 | 0.71 | 2.18 | | CDNA FLJ25106 fis, clone CBR01467 | AW138886 |
| 0.13 | 0.52 | 0.80 | 1.48 | 2.18 | CTSB | cathepsin B | W47179 |
| 0.02 | 0.25 | 0.03 | 0.58 | 2.18 | CAST | calpastatin | AA195244 |
| 0.88 | 0.66 | 1.33 | 1.31 | 2.17 | ARRDC3 | arrestin domain containing 3 | AB037797 |
| 0.00 | 0.00 | 0.00 | 1.06 | 2.17 | APOA1 | apolipoprotein A-I | NM_000039 |
| 1.64 | 1.77 | 0.87 | 2.00 | 2.17 | NEXN | nexilin (F actin binding protein) | NM_144570 |
| 2.17 | 1.48 | -0.10 | 0.10 | -0.33 | VANGL1 | vang-like 1 (van gogh, Drosophila) | R85437 |
| 1.32 | 1.44 | 1.56 | 2.17 | 1.93 | BMPR2 | bone morphogenetic protein receptor, typ | AI457436 |
| 0.00 | 0.00 | 0.00 | 0.00 | 2.17 | TM4SF1 | transmembrane 4 L six family member 1 | AI346835 |
| 0.12 | 0.77 | -1.41 | -1.88 | -2.17 | TANC1 | tetratricopeptide repeat, ankyrin repeat ar | AB051515 |
| -1.09 | -1.07 | -1.20 | -1.69 | -2.17 | ARRB2 | arrestin, beta 2 | NM_004313 |
| -0.71 | 1.00 | -0.83 | -1.41 | -2.17 | GSTO2 | glutathione S-transferase omega 2 | AL162742 |
| 0.00 | 1.10 | -1.73 | 2.17 | 1.57 | | Homo sapiens, clone IMAGE:5019307, m | BF593636 |

Appendix 2

| | | | | | Symbol | Description | Accession |
|---|---|---|---|---|---|---|---|
| 0.00 | 0.90 | 2.01 | 2.17 | 1.05 | HOXA1 | homeobox A1 | S79910 |
| 0.28 | 0.37 | -0.91 | -0.97 | -2.17 | | CDNA FLJ33569 fis, clone BRAMY2010 | BG413612 |
| 0.67 | 1.27 | 2.16 | 2.17 | 1.11 | IRS1 | insulin receptor substrate 1 | NM_005544 |
| -1.28 | 1.09 | -0.50 | 1.16 | -2.17 | LMCD1 | LIM and cysteine-rich domains 1 | NM_014583 |
| -0.00 | 0.00 | 0.74 | 1.86 | -2.17 | KLK6 | kallikrein-related peptidase 6 | NM_002774 |
| -0.57 | -0.36 | -0.84 | 1.32 | -2.17 | GART | phosphoribosylglycinamide formyltransfer | AF008655 |
| 0.05 | -0.51 | -0.83 | -1.22 | -2.17 | ARRB1 | arrestin, beta 1 | NM_004041 |
| 1.56 | 1.90 | 2.07 | 2.17 | 1.12 | SOCS3 | suppressor of cytokine signaling 3 | AI244908 |
| 0.00 | 0.40 | 0.16 | 2.16 | 0.67 | MBNL2 | Muscleblind-like 2 (Drosophila) | AF339768 |
| -0.52 | -1.15 | -0.40 | 0.39 | -2.16 | RPUSD3 | RNA pseudouridylate synthase domain c | AI125996 |
| 0.35 | 0.69 | 1.44 | 2.16 | 2.16 | POLR3GL | polymerase (RNA) III (DNA directed) poly | BC004355 |
| -0.45 | 1.23 | -1.08 | -1.69 | -2.16 | MPP2 | membrane protein, palmitoylated 2 (MAG | NM_005374 |
| 0.87 | 1.02 | 0.68 | 2.16 | 1.71 | MALAT1 | metastasis associated lung adenocarcino | AI446756 |
| -0.84 | -0.98 | -1.01 | -1.55 | -2.16 | L2HGDH | L-2-hydroxyglutarate dehydrogenase /// L | BC006117 |
| -1.08 | -0.93 | -1.45 | 1.82 | -2.16 | PGM2L1 | phosphoglucomutase 2-like 1 | AV724329 |
| 0.53 | 0.63 | 1.94 | 2.16 | 1.31 | EYA2 | eyes absent homolog 2 (Drosophila) | U71207 |
| 2.16 | 1.75 | 0.86 | 1.06 | 0.73 | GADD45B | growth arrest and DNA-damage-inducible | NM_015675 |
| 0.15 | 0.84 | 2.16 | 1.93 | 1.58 | SGPP1 | sphingosine-1-phosphate phosphatase 1 | NM_030791 |
| -0.25 | -0.38 | -0.55 | -1.12 | -2.16 | PRKCI | protein kinase C, iota | AI689429 |
| 0.30 | 0.25 | 0.87 | 1.90 | 2.16 | MGC24039 | hypothetical protein MGC24039 | AU144041 |
| -0.44 | 0.57 | 0.73 | 1.00 | -2.16 | C3orf59 | chromosome 3 open reading frame 59 | AU157304 |
| 0.61 | 0.81 | 0.72 | 0.86 | 2.15 | CHES1 | checkpoint suppressor 1 | NM_018589 |
| -0.03 | 1.13 | 1.76 | 2.15 | 2.07 | PRKCH | protein kinase C, eta | NM_006255 |
| 0.11 | 0.48 | 0.04 | 0.35 | 2.15 | SSFA2 | Sperm specific antigen 2 | AL556611 |
| 0.15 | 1.18 | 0.61 | 1.72 | 2.15 | KIRREL | kin of IRRE like (Drosophila) | NM_018240 |
| 0.00 | 0.00 | 0.00 | 0.00 | 2.15 | GUCY1A3 | Guanylate cyclase 1, soluble, alpha 3 | BF002625 |
| 0.13 | -0.09 | 1.33 | 1.73 | 2.15 | MRS2L | MRS2-like, magnesium homeostasis fact | AF052167 |
| -0.35 | 2.13 | 2.15 | -2.15 | -2.15 | LOC202451 | hypothetical protein LOC202451 | AI979261 |
| 0.00 | 0.48 | 0.18 | 1.51 | 2.15 | H2AFY | H2A histone family, member Y | AW291297 |
| 0.00 | 0.48 | 0.00 | 0.27 | 2.15 | IL11 | interleukin 11 | NM_000641 |
| -0.34 | 0.18 | 1.11 | 1.60 | 2.15 | CTSB | cathepsin B | AA130998 |
| -0.59 | -0.42 | -0.40 | -0.56 | -2.15 | FBXL7 | F-box and leucine-rich repeat protein 7 | AU145127 |
| 2.15 | 1.70 | 0.00 | 0.00 | 0.00 | GREM1 | gremlin 1, cysteine knot superfamily, hom | AF154054 |
| 0.00 | 0.29 | 0.65 | 1.70 | 2.15 | BACE1 | beta-site APP-cleaving enzyme 1 | NM_012104 |
| 1.95 | 2.15 | 1.74 | 1.52 | 0.16 | NOTUM | notum pectinacetylesterase homolog (Dr | AL574571 |
| 1.24 | 1.21 | 2.15 | 1.13 | -0.79 | EPHB1 | EPH receptor B1 | AI674183 |
| -0.70 | -0.29 | -0.72 | -1.15 | -2.15 | RAB3B | RAB3B, member RAS oncogene family | BE552383 |
| -0.66 | -0.98 | -1.59 | 1.85 | -2.15 | MYEF2 | myelin expression factor 2 | N50034 |
| 0.54 | 0.33 | -0.14 | -0.39 | -2.15 | HMMR | hyaluronan-mediated motility receptor (R | U29343 |
| 0.32 | 1.13 | 1.18 | 2.15 | 1.21 | PTPRM | protein tyrosine phosphatase, receptor ty | NM_002845 |
| 0.13 | -0.34 | -0.66 | -0.96 | -2.14 | | CDNA FLJ30437 fis, clone BRACE20090 | R43746 |
| 0.03 | 0.01 | -1.14 | -1.11 | -2.14 | | CDNA FLJ33569 fis, clone BRAMY2010 | BE783065 |
| 0.12 | 0.49 | 0.00 | 1.73 | 2.14 | DDR2 | Discoidin domain receptor family, membe | W73819 |
| 1.79 | 1.42 | -0.17 | 0.71 | 2.14 | ADORA1 | adenosine A1 receptor | NM_000674 |
| 0.39 | 0.33 | 0.71 | 1.36 | 2.14 | INPP1 | inositol polyphosphate-1-phosphatase | NM_002194 |
| 0.00 | 0.75 | 1.88 | 2.14 | 0.72 | VIT | vitrin | AI817458 |
| -0.73 | -0.73 | -0.73 | 0.43 | -2.14 | CDC42EP5 | CDC42 effector protein (Rho GTPase bin | AW084544 |
| 0.37 | 0.17 | -1.70 | -2.14 | -2.14 | STEAP1 | six transmembrane epithelial antigen of t | NM_012449 |
| 2.14 | 1.23 | 0.00 | 0.00 | 0.11 | LOC648987 | hypothetical LOC648987 | AI056871 |
| -0.21 | -0.65 | -0.49 | -0.49 | -2.14 | LIG3 | ligase III, DNA, ATP-dependent | NM_013975 |
| 0.15 | -0.42 | -0.06 | 0.11 | 2.14 | WDR7 | WD repeat domain 7 | AB011113 |
| 0.37 | 0.18 | -1.49 | -2.14 | -1.69 | SLC7A11 | solute carrier family 7, (cationic amino ac | AB040875 |
| 1.89 | 1.86 | 2.14 | 1.99 | 1.48 | SDK2 | sidekick homolog 2 (chicken) | N23651 |
| 0.90 | 0.90 | 2.14 | 1.97 | -1.93 | LPGAT1 | lysophosphatidylglycerol acyltransferase | NM_014873 |
| -0.51 | -0.96 | -2.03 | -2.14 | -1.92 | ZNF589 | zinc finger protein 589 | AF114817 |
| -0.70 | 0.25 | 1.36 | 1.97 | 2.14 | EFNB2 | ephrin-B2 | U16797 |
| 0.17 | 0.64 | 0.58 | 1.57 | 2.14 | COL4A1 | collagen, type IV, alpha 1 | AI922605 |
| 0.20 | 0.75 | 2.07 | 2.14 | 1.08 | TNFAIP3 | tumor necrosis factor, alpha-induced prot | NM_006290 |
| 0.08 | 0.27 | 0.85 | 1.78 | 2.14 | ANGPTL2 | angiopoietin-like 2 | AF007150 |
| -0.43 | 0.24 | 1.92 | 2.13 | 0.37 | C15orf29 | Chromosome 15 open reading frame 29 | AU144048 |
| 0.62 | 1.63 | 1.92 | 1.84 | 2.13 | RHOC | ras homolog gene family, member C | NM_005167 |
| -1.51 | -1.46 | 1.29 | -0.17 | -2.13 | WDR27 | WD repeat domain 27 | AI016894 |
| 0.29 | 0.62 | 1.30 | 1.93 | 2.13 | C5orf24 | chromosome 5 open reading frame 24 | AV707506 |
| 0.36 | -1.13 | -1.54 | -2.13 | -2.13 | NAP1L2 | nucleosome assembly protein 1-like 2 | NM_021963 |
| -0.05 | 0.52 | 1.50 | 2.13 | 1.71 | LAMB1 | laminin, beta 1 /// laminin, beta 1 | M20206 |
| 0.94 | 0.93 | 1.05 | 2.13 | 1.45 | CEP72 /// TMEM1 | centrosomal protein 72kDa /// transmemb | AI949760 |
| -0.86 | 1.00 | 1.56 | 2.10 | 2.13 | LOC730259 | hypothetical protein LOC730259 | AA725362 |
| -1.43 | 0.89 | -1.67 | 0.77 | -2.13 | CDCA7 | cell division cycle associated 7 | AI277642 |
| 0.59 | 0.74 | -0.53 | 0.59 | -2.13 | SUDS3 | suppressor of defective silencing 3 homo | AK026749 |
| -0.90 | -1.39 | -1.08 | 1.09 | -2.13 | THYN1 | thymocyte nuclear protein 1 | NM_014174 |
| 0.12 | 0.00 | 0.01 | 1.27 | 2.13 | PAG1 | phosphoprotein associated with glycosph | BF589359 |
| 0.00 | 0.00 | 1.07 | 2.13 | 0.07 | CFH /// CFHR1 | complement factor H /// complement fact | X56210 |
| 0.58 | 0.82 | 1.06 | 2.13 | 1.91 | CTNNB1 | catenin (cadherin-associated protein), be | AF130085 |
| -1.01 | 0.07 | 2.13 | 2.12 | 1.81 | MAFB | v-maf musculoaponeurotic fibrosarcoma | AW135013 |
| 0.51 | 1.21 | 1.11 | 1.45 | 2.13 | COL1A2 | collagen, type I, alpha 2 | AA788711 |
| 0.00 | 0.00 | -1.01 | 1.29 | 2.12 | HGF | hepatocyte growth factor (hepapoietin A) | U46010 |
| -1.57 | -0.92 | -1.57 | -1.71 | -2.12 | LQK1 | LQK1 hypothetical protein short isoform | N51468 |
| 1.15 | 1.76 | 0.63 | 1.65 | 2.12 | | CDNA FLJ31353 fis, clone MESAN20002 | AI801777 |
| -0.49 | -0.26 | -1.13 | 1.76 | -2.12 | ASRGL1 | asparaginase like 1 | NM_025080 |
| 1.08 | 1.17 | 1.74 | 2.12 | 1.64 | NDRG2 | NDRG family member 2 | NM_016250 |
| 0.91 | 0.29 | 2.12 | 1.11 | -2.12 | FGF2 | fibroblast growth factor 2 (basic) | NM_002006 |
| 0.00 | 0.77 | 0.72 | 1.46 | 2.12 | COL18A1 | collagen, type XVIII, alpha 1 | NM_030582 |
| -0.04 | 0.92 | 1.33 | 1.54 | -2.12 | MPZL1 | myelin protein zero-like 1 | AF239756 |
| 0.00 | 0.00 | 0.31 | 2.12 | 1.12 | DIO3OS | deiodinase, iodothyronine, type III opposi | AF305836 |
| -0.01 | 0.39 | 1.06 | 1.64 | 2.12 | TPST1 | tyrosylprotein sulfotransferase 1 | NM_003596 |
| -0.83 | 0.69 | -0.41 | -0.79 | -2.12 | C14orf115 | chromosome 14 open reading frame 115 | NM_018228 |
| 0.01 | 0.96 | 1.83 | 2.04 | 2.12 | BACE1 | beta-site APP-cleaving enzyme 1 | AI653425 |

Appendix 2

| | | | | | | | |
|---|---|---|---|---|---|---|---|
| 0.22 | 0.22 | -0.33 | -1.33 | -2.12 | MN1 | meningioma (disrupted in balanced transl | NM_002430 |
| -0.17 | 0.37 | 0.88 | 1.48 | 2.12 | CTSB | cathepsin B | AA020826 |
| 0.53 | -0.71 | -2.12 | -2.12 | -2.12 | | MRNA; cDNA DKFZp686L0310 (from clo | AL832136 |
| -0.59 | -1.13 | -2.12 | -2.08 | 0.18 | P2RY1 | Purinergic receptor P2Y, G-protein coupl | AK026659 |
| 0.00 | 0.00 | 0.25 | 0.89 | 2.11 | ZHX1 | zinc fingers and homeoboxes 1 | AF195766 |
| 1.18 | -0.14 | -1.00 | -1.35 | -2.11 | LOC728262 | Hypothetical protein LOC728262 | BF057027 |
| 0.70 | 1.10 | 1.10 | 1.88 | 2.11 | FLRT2 | fibronectin leucine rich transmembrane p | AF169676 |
| -0.22 | -0.31 | -1.31 | -1.77 | -2.11 | ZNF169 | zinc finger protein 169 | AI693543 |
| -0.50 | -0.87 | -0.59 | -1.11 | -2.11 | MAP7 | microtubule-associated protein 7 | AJ242502 |
| -0.19 | -0.78 | -2.11 | 0.54 | -1.32 | C13orf25 | chromosome 13 open reading frame 25 | AA256157 |
| 0.00 | 0.70 | 1.65 | 2.11 | 1.89 | NCAM1 | neural cell adhesion molecule 1 | AA126505 |
| 0.99 | 0.86 | 1.78 | 2.11 | 0.59 | MED12 | mediator of RNA polymerase II transcripti | BC004354 |
| 1.55 | 1.16 | 1.38 | 1.08 | 2.11 | ZNF777 | zinc finger protein 777 | NM_015694 |
| -0.74 | -0.81 | -0.67 | -0.85 | -2.11 | TFB1M | transcription factor B1, mitochondria | AI341648 |
| 1.24 | 1.31 | 0.79 | 2.05 | 2.11 | LEPR | Leptin receptor | AU151151 |
| 1.23 | 1.03 | -0.99 | 1.54 | 2.11 | TFDP2 | transcription factor Dp-2 (E2F dimerizatio | BG034328 |
| 0.76 | 1.06 | 1.50 | 1.26 | 2.11 | BCL9L | B-cell CLL/lymphoma 9-like | AL353962 |
| 1.50 | 0.81 | 0.12 | 0.97 | 2.11 | KLHDC5 | kelch domain containing 5 | AI334297 |
| 0.16 | 0.20 | -0.45 | -0.67 | -2.11 | MAGI1 | membrane associated guanylate kinase, | AI141556 |
| -0.59 | -1.03 | -2.11 | -2.11 | -2.11 | PPP1R1A | protein phosphatase 1, regulatory (inhibit | NM_006741 |
| 0.54 | 1.41 | 1.90 | 2.11 | 1.73 | DERA | 2-deoxyribose-5-phosphate aldolase hom | NM_015954 |
| 0.62 | 0.85 | 1.15 | 1.40 | 2.11 | RAI1 | retinoic acid induced 1 | BF984830 |
| 1.48 | 2.11 | 1.57 | 1.01 | 0.41 | SERPINE2 | serpin peptidase inhibitor, clade E (nexin, | AL541302 |
| 0.16 | -0.05 | -1.51 | -2.11 | -1.41 | DBNDD1 | dysbindin (dystrobrevin binding protein 1) | AK022644 |
| 1.75 | 2.10 | 0.55 | -0.61 | -1.75 | COCH | coagulation factor C homolog, cochlin (Li | AA669336 |
| -0.48 | -0.06 | 1.22 | 2.10 | 1.40 | SLC22A18 | solute carrier family 22 (organic cation tr | NM_002555 |
| 0.00 | 0.00 | 0.00 | 0.00 | 2.10 | PRR16 | proline rich 16 | NM_016644 |
| -2.08 | -2.10 | -2.10 | -2.10 | -2.10 | CHODL | chondrolectin | NM_024944 |
| 1.35 | 1.55 | 1.47 | 2.10 | 2.03 | JUB | jub, ajuba homolog (Xenopus laevis) | NM_032876 |
| 0.29 | 0.00 | 0.54 | 1.41 | 2.10 | LMO2 | LIM domain only 2 (rhombotin-like 1) | NM_005574 |
| 1.95 | 2.10 | 0.93 | 1.44 | 1.41 | DKFZp761P0423 | Homolog of rat pragma of Rnd2 | AI494291 |
| 0.58 | -0.78 | -2.05 | -2.10 | -1.13 | FLVCR | feline leukemia virus subgroup C cellular | AK001419 |
| 0.33 | 0.37 | 0.40 | 0.42 | 2.10 | NRP2 | neuropilin 2 | AF280546 |
| 0.00 | 0.00 | 0.00 | 0.48 | 2.10 | RGC32 | response gene to complement 32 | NM_014059 |
| 0.10 | 0.74 | 1.55 | 2.10 | 1.84 | TMBIM1 | transmembrane BAX inhibitor motif conta | NM_022152 |
| 1.04 | 1.45 | 2.02 | 2.10 | 0.86 | DSCR1 | Down syndrome critical region gene 1 | NM_004414 |
| 0.00 | 0.00 | 0.00 | 0.00 | 2.10 | EPC1 | Enhancer of polycomb homolog 1 (Droso | W93523 |
| 0.00 | 0.00 | 0.00 | 1.07 | 2.10 | C20orf75 | chromosome 20 open reading frame 75 | BC019612 |
| 0.20 | 0.63 | 1.56 | 2.10 | 1.79 | LAMB1 | laminin, beta 1 | NM_002291 |
| -0.78 | -1.15 | -1.14 | -1.30 | -2.10 | FABP7 | fatty acid binding protein 7, brain | NM_001446 |
| 0.00 | 0.00 | 1.35 | 1.52 | 2.10 | HGF | hepatocyte growth factor (hepapoietin A; | M77227 |
| 0.00 | 0.11 | 1.58 | 2.10 | 1.18 | THRB | thyroid hormone receptor, beta (erythrobl | BF431989 |
| -1.33 | -0.31 | -1.35 | -2.10 | -2.10 | | Transcribed locus | AI962352 |
| 0.51 | 1.15 | 0.58 | 0.60 | 2.10 | CCNE2 | cyclin E2 | NM_004702 |
| -0.48 | -0.81 | -0.98 | -1.30 | -2.10 | FAM126A | family with sequence similarity 126, mem | AB030241 |
| 1.18 | 1.52 | 1.03 | 2.10 | 1.06 | IRS1 | Insulin receptor substrate 1 | BG403162 |
| -0.34 | 0.47 | 0.84 | 2.10 | 1.17 | PTPRD | protein tyrosine phosphatase, receptor ty | N73931 |
| 0.80 | 1.33 | 1.92 | 2.10 | 2.02 | HAS2 | hyaluronan synthase 2 | NM_005328 |
| 0.00 | 0.00 | 0.88 | 2.09 | 0.00 | FLJ45983 | FLJ45983 protein | AI631850 |
| -1.53 | -1.05 | -0.61 | -0.71 | -2.09 | | CDNA FLJ30156 fis, clone BRACE20004 | BF969544 |
| 0.24 | 0.82 | 1.63 | 1.49 | 2.09 | CDKN1C | Cyclin-dependent kinase inhibitor 1C (p57 | N33167 |
| -0.20 | 0.42 | 2.02 | 2.09 | 1.25 | ZFP36L1 | zinc finger protein 36, C3H type-like 1 | BE620915 |
| -0.36 | 1.56 | 2.09 | 2.07 | 1.62 | DSC2 | desmocollin 2 | BF196457 |
| -0.59 | -0.59 | -1.24 | -1.56 | -2.09 | KATNB1 | katanin p80 (WD repeat containing) subu | NM_005886 |
| 0.84 | -0.02 | 0.96 | 1.17 | 2.09 | C5orf33 | chromosome 5 open reading frame 33 | H94910 |
| -0.77 | 0.55 | 0.22 | 1.32 | 2.09 | SLC7A8 | solute carrier family 7 (cationic amino aci | AL365343 |
| 0.05 | -0.92 | -1.08 | -1.46 | -2.09 | CABC1 | chaperone, ABC1 activity of bc1 complex | NM_020247 |
| -0.83 | -0.50 | 1.52 | -1.54 | -2.09 | RRAGD | Ras-related GTP binding D | AF272036 |
| 0.14 | 1.51 | 0.99 | 2.09 | 2.03 | PRO1073 | PRO1073 protein | NM_014086 |
| -0.32 | -0.05 | 1.14 | 2.09 | 1.16 | EPB41L5 | erythrocyte membrane protein band 4.1 li | AB046768 |
| -0.04 | -0.51 | -1.39 | -1.61 | -2.09 | KATNB1 | katanin p80 (WD repeat containing) subu | NM_005886 |
| 0.01 | -0.98 | -1.61 | -2.09 | -1.74 | WDR74 | WD repeat domain 74 | NM_018093 |
| -0.75 | 1.33 | 1.72 | 1.62 | 2.09 | HOOK1 | hook homolog 1 (Drosophila) | AA618420 |
| -0.83 | -0.99 | -1.19 | 0.76 | 2.09 | PHF17 | PHD finger protein 17 | AW138134 |
| -0.88 | 0.25 | 0.83 | 2.08 | 1.77 | ST6GALNAC3 | ST6 (alpha-N-acetyl-neuraminyl-2,3-beta | AW963951 |
| 0.66 | 0.54 | 0.87 | 0.96 | 2.08 | GALNACT-2 | chondroitin sulfate GalNAcT-2 | NM_018590 |
| -0.21 | 0.44 | 0.80 | 0.22 | -2.08 | FAM100B | family with sequence similarity 100, mem | AA831661 |
| 2.00 | 2.08 | 1.22 | 1.79 | 1.99 | | CDNA clone IMAGE:5301910 | AI803010 |
| 0.10 | 1.25 | 1.36 | 1.68 | 2.08 | LOC727936 | similar to CG9996-PA | AI452595 |
| 2.08 | 1.04 | -0.25 | -0.73 | -0.20 | PHF15 | PHD finger protein 15 | AI735639 |
| 0.10 | -0.42 | -0.59 | -1.97 | 2.08 | ALDH1A3 | aldehyde dehydrogenase 1 family, memb | NM_000693 |
| 0.21 | 0.53 | 1.95 | 2.08 | 1.64 | ZFP36L1 | zinc finger protein 36, C3H type-like 1 | BG250310 |
| 0.39 | 0.47 | 1.62 | 1.80 | 2.08 | | gb:AW576195 /DB_XREF=gi:7247734 /D | AW576195 |
| -0.58 | -1.21 | -1.25 | -1.51 | -2.08 | PAK1 | p21/Cdc42/Rac1-activated kinase 1 (STE | AU154408 |
| 0.77 | 1.24 | 1.39 | 1.59 | 2.08 | VASN | vasorin | BE741869 |
| 0.29 | -0.46 | 1.54 | -2.08 | -0.55 | HSPC111 | hypothetical protein HSPC111 | NM_016391 |
| 0.29 | 0.33 | -0.18 | -0.21 | 2.08 | TPM3 | tropomyosin 3 | AY004867 |
| 0.70 | 1.45 | 1.69 | 2.08 | 0.48 | SPSB4 | splA/ryanodine receptor domain and SOC | AL563476 |
| 1.03 | 0.45 | 0.28 | 1.28 | 2.08 | RUFY3 | RUN and FYVE domain containing 3 | AI871641 |
| 0.51 | 0.29 | 1.01 | 1.62 | 2.08 | CHD9 | chromodomain helicase DNA binding pro | AI742305 |
| 0.91 | 0.83 | 1.48 | 2.07 | 1.84 | FURIN | furin (paired basic amino acid cleaving er | NM_002569 |
| 0.57 | 0.68 | 1.56 | 2.07 | 1.81 | CTSL | cathepsin L | NM_001912 |
| -0.19 | -0.52 | -0.55 | -0.90 | -2.07 | HSD17B4 | hydroxysteroid (17-beta) dehydrogenase | NM_000414 |
| 0.57 | 1.04 | 1.87 | 1.39 | 2.07 | SNAI1 | snail homolog 1 (Drosophila) | NM_005985 |
| -0.51 | -0.16 | -1.29 | -1.89 | -2.07 | KIF5C | kinesin family member 5C | NM_004522 |
| -0.91 | -0.99 | -0.34 | -0.84 | 2.07 | GRB7 | growth factor receptor-bound protein 7 | AB008790 |
| 0.00 | 0.00 | 0.00 | 0.00 | 2.07 | MGC26963 | hypothetical protein MGC26963 | AI963083 |

Appendix 2

| | | | | | Symbol | Description | Accession |
|---|---|---|---|---|---|---|---|
| -1.35 | -0.96 | -1.71 | -2.07 | -2.07 | FAM113B | family with sequence similarity 113, mem | BF056901 |
| 0.13 | -0.58 | 1.99 | 1.67 | -2.07 | SLC1A6 | solute carrier family 1 (high affinity aspart | BC028721 |
| 2.07 | 1.65 | 0.71 | 0.94 | -1.15 | TCF7 | transcription factor 7 (T-cell specific, HMC | NM_003202 |
| 0.18 | 0.63 | 1.94 | 2.07 | -0.14 | ANKRD15 | ankyrin repeat domain 15 | D79994 |
| 0.32 | 0.78 | 1.95 | 2.07 | 1.28 | SYBL1 | synaptobrevin-like 1 | NM_005638 |
| 0.05 | 0.88 | 1.18 | 2.07 | 1.42 | ATBF1 | AT-binding transcription factor 1 | NM_006885 |
| 0.00 | 0.00 | 0.56 | 1.80 | 2.07 | ANKRD43 | ankyrin repeat domain 43 | AI744123 |
| 0.40 | 2.07 | -0.16 | -0.58 | 0.58 | ACTA1 | actin, alpha 1, skeletal muscle | NM_001100 |
| -0.41 | 0.09 | 1.35 | 1.84 | 2.07 | LAMA1 | laminin, alpha 1 | AI990816 |
| 0.57 | 0.75 | 0.31 | 0.84 | 2.07 | SLC7A6 | solute carrier family 7 (cationic amino aci | AI660619 |
| 0.69 | 0.21 | -0.19 | 1.14 | -2.07 | B3GNT7 | UDP-GlcNAc:betaGal beta-1,3-N-acetylg | CA503291 |
| 0.30 | 0.98 | 2.07 | 1.52 | 0.25 | PNRC1 | proline-rich nuclear receptor coactivator 1 | AF279899 |
| 0.16 | -0.16 | 0.56 | 1.03 | -2.07 | RRM2 | ribonucleotide reductase M2 polypeptide | BC001886 |
| 0.29 | 1.25 | 2.07 | 1.93 | 1.46 | STARD10 | START domain containing 10 | AF151810 |
| -0.03 | 0.46 | -0.52 | -1.05 | -2.07 | OIP5 | Opa interacting protein 5 | BE045993 |
| 0.41 | -1.16 | 2.07 | 2.07 | -2.07 | KIAA0523 | KIAA0523 protein | AB011095 |
| 0.52 | 0.80 | 1.46 | 2.07 | 0.68 | WWC3 | WWC family member 3 | NM_018458 |
| 0.17 | 0.70 | 2.07 | 1.87 | 1.47 | PVT1 | Pvt1 oncogene homolog, MYC activator ( | BG200951 |
| 1.06 | 1.62 | 1.82 | 2.07 | 1.97 | | MRNA; cDNA DKFZp566M0947 (from cl | BG402859 |
| 0.00 | 0.00 | 0.29 | 1.83 | -2.07 | MLLT3 | myeloid/lymphoid or mixed-lineage leuke | NM_004529 |
| -0.79 | -0.76 | -0.68 | -1.36 | -2.06 | MAP7 | microtubule-associated protein 7 | T62571 |
| 0.56 | 0.56 | 0.31 | 0.82 | -2.06 | CD248 | CD248 molecule, endosialin | NM_020404 |
| 0.82 | 2.06 | 0.46 | -0.18 | 0.72 | STAC | SH3 and cysteine rich domain | NM_003149 |
| 0.32 | -0.50 | 1.06 | 1.20 | -2.06 | ARRB1 | arrestin, beta 1 | BE207758 |
| 0.37 | 0.94 | 1.46 | 2.06 | 0.71 | WWC3 | WWC family member 3 | AB033106 |
| 1.00 | 0.95 | 1.53 | 1.63 | 2.06 | SLC12A2 | solute carrier family 12 (sodium/potassiun | NM_001046 |
| 0.38 | 1.03 | 1.05 | 2.06 | 1.87 | C9orf3 | chromosome 9 open reading frame 3 | BG036668 |
| 1.55 | 1.08 | 1.10 | 1.31 | -2.06 | IDS | iduronate 2-sulfatase (Hunter syndrome) | NM_000202 |
| -0.16 | 0.90 | 0.47 | -2.06 | 1.81 | TncRNA | trophoblast-derived noncoding RNA | BE675516 |
| -1.12 | -0.35 | 1.07 | 0.27 | -2.06 | KLHL24 | kelch-like 24 (Drosophila) | AL120021 |
| -0.16 | -0.27 | 1.50 | 2.07 | 2.03 | DENND1A | DENN/MADD domain containing 1A | AB046828 |
| 2.06 | 0.87 | 0.54 | 1.08 | 1.68 | EXOSC6 | Exosome component 6 | AI701408 |
| -1.13 | 1.39 | 1.13 | 1.45 | 2.06 | IDS | iduronate 2-sulfatase (Hunter syndrome) | AI926544 |
| 0.19 | 0.98 | 1.38 | 2.06 | 1.61 | NRP2 | neuropilin 2 | N90777 |
| -0.53 | -0.61 | -0.30 | -0.84 | -2.06 | EPB41L5 | erythrocyte membrane protein band 4.1 li | AI652872 |
| 0.35 | 1.19 | 1.07 | 2.02 | 2.06 | DNAJC15 | DnaJ (Hsp40) homolog, subfamily C, mer | AI091398 |
| -0.31 | -0.22 | 0.13 | 0.53 | -2.06 | KIAA1913 | KIAA1913 | AA088177 |
| 0.12 | 1.12 | 1.58 | 1.93 | 2.05 | KDELC2 | KDEL (Lys-Asp-Glu-Leu) containing 2 | AL548941 |
| 0.00 | 0.00 | 0.00 | 0.00 | 2.05 | C6orf62 | Chromosome 6 open reading frame 62 | AW972292 |
| -2.05 | -1.79 | -1.21 | -1.06 | -1.77 | GUCA1A | guanylate cyclase activator 1A (retina) | L36861 |
| 0.56 | 1.12 | 1.50 | 1.97 | 2.05 | PLOD2 | procollagen-lysine, 2-oxoglutarate 5-diox | NM_000935 |
| -0.35 | 0.00 | 0.37 | 1.07 | 2.05 | PRICKLE1 | Prickle homolog 1 (Drosophila) | AA206141 |
| 1.12 | 2.05 | 1.70 | 0.92 | 0.00 | CA12 | carbonic anhydrase XII | BC001012 |
| 0.30 | -0.62 | -0.31 | -0.37 | -2.05 | LIG3 | ligase III, DNA, ATP-dependent | NM_002311 |
| 0.00 | 0.43 | 0.94 | 1.86 | 2.05 | ADCY6 | adenylate cyclase 6 | AF250226 |
| 0.39 | 0.36 | 1.79 | 2.05 | 1.16 | NUDT15 | nudix (nucleoside diphosphate linked moi | NM_018283 |
| -0.67 | 0.58 | 1.18 | 1.25 | 2.05 | MMP14 | matrix metallopeptidase 14 (membrane-in | AU149305 |
| -2.05 | 1.84 | 1.37 | 1.31 | 1.50 | GRK5 | G protein-coupled receptor kinase 5 | NM_005308 |
| -0.20 | 0.80 | 2.05 | 1.68 | 1.28 | SEPP1 | selenoprotein P, plasma, 1 | NM_005410 |
| -0.03 | -0.29 | 1.79 | 2.05 | 1.66 | CHRNA5 | cholinergic receptor, nicotinic, alpha 5 | NM_000745 |
| 0.18 | 0.32 | 0.75 | 0.51 | 2.05 | TXNDC4 | thioredoxin domain containing 4 (endopla | BF439241 |
| 1.05 | 0.66 | 0.10 | 0.15 | 2.05 | LOC401805 | hypothetical gene supported by NM_144; | BF681162 |
| 0.00 | 0.00 | 0.00 | 1.13 | 2.05 | LOC654342 | Similar to lymphocyte-specific protein 1 | BF195104 |
| 0.60 | 1.10 | 1.38 | 2.05 | 1.77 | SPSB1 | splA/ryanodine receptor domain and SO( | NM_025106 |
| 0.86 | 0.54 | 0.35 | 0.81 | 2.05 | LOC146517 | hypothetical protein LOC146517 | AW299653 |
| 0.00 | 0.00 | 0.00 | 1.15 | 2.05 | FBN1 | fibrillin 1 | AI264196 |
| 0.25 | 0.97 | 0.47 | 0.55 | 2.05 | S100A16 | S100 calcium binding protein A16 | AA045184 |
| 0.52 | 1.23 | 1.74 | 2.05 | 1.10 | FIGN | Fidgetin | BG109695 |
| 0.48 | 0.91 | 0.93 | 0.80 | 2.05 | OGFRL1 | opioid growth factor receptor-like 1 | NM_024576 |
| 0.50 | 1.20 | 1.67 | 2.05 | 1.78 | FGD4 | FYVE, RhoGEF and PH domain containin | AI949549 |
| 0.36 | 0.03 | 1.48 | 1.55 | 2.05 | RAB38 | RAB38, member RAS oncogene family | NM_022337 |
| 0.00 | 0.00 | 0.00 | 1.07 | 2.05 | H2AFY | H2A histone family, member Y | AF044286 |
| -0.12 | 0.30 | 0.81 | 1.01 | 2.05 | CTSZ | cathepsin Z | AF073890 |
| -1.09 | -0.66 | -1.35 | -1.89 | -2.05 | | CDNA FLJ32963 fis, clone TESTI200840 | AK057525 |
| 1.05 | 1.90 | 2.05 | 1.58 | -0.72 | PREX1 | phosphatidylinositol 3,4,5-trisphosphate-c | BF308645 |
| -0.08 | 0.70 | 1.07 | 1.73 | 2.05 | ADAM9 | ADAM metallopeptidase domain 9 (meltri | AF495383 |
| 0.03 | 0.45 | 0.86 | 0.57 | 2.04 | SPARC | secreted protein, acidic, cysteine-rich (os | AL575922 |
| -0.70 | -0.65 | 1.64 | 2.04 | -2.04 | ADCY2 | adenylate cyclase 2 (brain) | AA224446 |
| -0.47 | -1.24 | 1.80 | 2.04 | 1.96 | FZD2 | frizzled homolog 2 (Drosophila) | L37882 |
| -0.72 | -0.32 | -0.85 | -1.13 | -2.04 | COMTD1 | catechol-O-methyltransferase domain cor | AI924025 |
| -0.02 | 0.30 | 1.53 | 2.04 | 1.40 | CLCN5 | chloride channel 5 (nephrolithiasis 2, X-lii | AK025562 |
| 0.46 | 0.41 | 0.65 | 1.64 | 2.04 | MFI2 | Antigen p97 (melanoma associated) iden | AI885815 |
| 1.10 | -1.31 | -0.80 | -1.82 | -2.04 | ETV5 | ets variant gene 5 (ets-related molecule) | X76184 |
| 2.02 | 2.04 | 0.86 | 0.51 | -1.12 | ADM | adrenomedullin | NM_001124 |
| 0.27 | 0.70 | 1.89 | 2.04 | 0.96 | TTC7B | tetratricopeptide repeat domain 7B | BE963437 |
| -0.12 | 0.13 | 1.47 | 2.04 | 0.52 | ARHGAP24 | Rho GTPase activating protein 24 | AI743534 |
| 0.43 | 0.23 | 0.64 | 1.19 | 2.04 | ARL2BP | ADP-ribosylation factor-like 2 binding pro | BF244411 |
| -1.42 | 1.85 | 2.04 | 1.76 | 1.13 | PCSK5 | proprotein convertase subtilisin/kexin typ( | NM_006200 |
| 0.59 | 0.96 | 0.06 | 1.28 | 2.04 | FILIP1L | filamin A interacting protein 1-like | NM_014890 |
| -0.45 | -1.14 | -2.04 | -1.66 | -1.36 | C20orf42 | chromosome 20 open reading frame 42 | NM_017671 |
| -0.61 | -0.60 | 1.00 | 1.66 | 2.04 | ZNF788 | zinc finger family member 788 | AI190287 |
| -0.32 | -0.48 | -0.73 | -1.50 | -2.04 | C21orf56 | chromosome 21 open reading frame 56 | AL136871 |
| 0.26 | 0.54 | 0.37 | 1.39 | 2.04 | IFIT5 | interferon-induced protein with tetratricop | N47725 |
| 0.93 | 1.94 | 2.04 | 1.48 | 1.42 | RHOU | ras homolog gene family, member U | AB051826 |
| 0.91 | 1.82 | 1.19 | 1.63 | 2.04 | SLIT2 | slit homolog 2 (Drosophila) | AF055585 |
| -1.11 | 1.00 | 0.00 | 1.38 | 2.04 | OBFC2A | oligonucleotide/oligosaccharide-binding fc | AV734843 |
| 0.96 | 2.04 | 1.18 | 1.57 | 1.37 | EMILIN2 | elastin microfibril interfacer 2 | AL552384 |

Appendix 2

| | | | | | Symbol | Description | Accession |
|---|---|---|---|---|---|---|---|
| -0.33 | 0.05 | 0.00 | 0.36 | -2.04 | | Transcribed locus | AI872374 |
| 0.19 | 0.71 | -1.47 | 2.01 | 2.03 | MAN2B2 | mannosidase, alpha, class 2B, member 2 | AW954107 |
| 0.41 | -0.47 | -2.02 | 2.03 | -1.10 | SORBS1 | sorbin and SH3 domain containing 1 | NM_015385 |
| 0.32 | 1.88 | -2.03 | 1.78 | 2.01 | GAS7 | growth arrest-specific 7 | BC001152 |
| 0.43 | 0.69 | 1.07 | 1.36 | 2.03 | LNPEP | Leucyl/cystinyl aminopeptidase | AA156754 |
| 0.30 | 1.15 | 1.68 | 2.03 | 2.01 | PPP1R3D | protein phosphatase 1, regulatory subunit | AL109928 |
| -0.98 | -1.53 | 1.59 | 1.90 | -2.03 | TBC1D8 | TBC1 domain family, member 8 (with GR | NM_007063 |
| 0.00 | 0.00 | 0.19 | 1.64 | 2.03 | SDK1 | sidekick homolog 1 (chicken) | AF131799 |
| -0.31 | -0.28 | 1.17 | -1.48 | -2.03 | CRMP1 | collapsin response mediator protein 1 | NM_001313 |
| 0.66 | -0.81 | -0.65 | -1.16 | -2.03 | NUP210 | nucleoporin 210kDa | AI867102 |
| 0.57 | -0.26 | 0.31 | 0.97 | 2.03 | CST3 | cystatin C (amyloid angiopathy and ceret | NM_000099 |
| 0.49 | -0.28 | 1.15 | -2.03 | 1.86 | ULK2 | unc-51-like kinase 2 (C. elegans) | BG526973 |
| -0.38 | -0.98 | 1.97 | -2.03 | 1.97 | ZNF589 | zinc finger protein 589 | AF114817 |
| 0.72 | -0.71 | -2.03 | -1.85 | -0.91 | | Transcribed locus | AW206286 |
| 0.33 | 0.44 | 1.05 | 1.07 | 2.03 | CFL2 | cofilin 2 (muscle) | AV726166 |
| 0.04 | -0.54 | -0.60 | -1.16 | -2.03 | EIF2C1 | Eukaryotic translation initiation factor 2C, | AW136032 |
| 1.10 | 1.39 | 2.00 | 1.78 | 2.03 | FZD1 | frizzled homolog 1 (Drosophila) | NM_003505 |
| 1.12 | -1.12 | 1.56 | 1.79 | 2.03 | | gb:AI807356 /DB_XREF=gi:5393922 /DB | AI807356 |
| 0.89 | 0.94 | -1.50 | 2.03 | 0.64 | KIAA1729 | KIAA1729 protein | AW270138 |
| 0.17 | -0.18 | 1.13 | -1.53 | -2.03 | MOSC1 | MOCO sulphurase C-terminal domain con | NM_022746 |
| 0.77 | -0.95 | 1.17 | 1.48 | 2.03 | LOC56757 | hypothetical protein LOC56757 | AI862477 |
| 0.41 | 1.05 | -2.03 | 1.56 | 0.40 | RNF175 | ring finger protein 175 | AW051591 |
| -0.35 | -0.22 | -0.73 | 1.61 | -2.02 | IFITM1 | interferon induced transmembrane proteir | NM_003641 |
| -1.74 | -2.02 | -0.86 | 1.62 | -2.02 | EBF2 | early B-cell factor 2 | NM_022659 |
| 1.00 | 1.92 | 1.47 | 1.43 | 2.02 | ANXA2P2 | annexin A2 pseudogene 2 | M62898 |
| 0.08 | 0.04 | 1.22 | -1.72 | 2.02 | CARD11 | caspase recruitment domain family, mem | AF322641 |
| -0.41 | -0.70 | -0.60 | 0.70 | -2.02 | SUDS3 | suppressor of defective silencing 3 homo | AK024460 |
| -0.63 | -1.46 | -2.02 | 1.87 | 1.77 | | Transcribed locus | AI807950 |
| -0.14 | -0.82 | -0.64 | -0.11 | -2.02 | OMA1 | OMA1 homolog, zinc metallopeptidase (S | AI927931 |
| 0.36 | 1.27 | 0.52 | 2.02 | 2.01 | | CDNA clone IMAGE:6025865 | AA156240 |
| 0.88 | 1.34 | -0.28 | -0.97 | -2.02 | | gb:AA700440 /DB_XREF=gi:2703403 /DB | AA700440 |
| 0.00 | 0.00 | 2.02 | 1.93 | 0.16 | PRELP | proline/arginine-rich end leucine-rich repe | U41344 |
| 0.44 | 1.32 | 2.02 | 1.78 | 0.32 | FMR1 | fragile X mental retardation 1 | AI743037 |
| -0.33 | -0.11 | -0.76 | 1.82 | -2.02 | CKB | creatine kinase, brain | NM_001823 |
| 1.30 | 0.48 | -0.37 | 0.77 | 2.02 | | CDNA FLJ34899 fis, clone NT2NE20185 | AI868039 |
| 0.00 | 0.00 | 1.07 | 2.02 | 1.45 | BOC | Boc homolog (mouse) | AY027658 |
| 0.46 | -0.18 | -1.53 | -2.02 | 2.02 | KIAA0367 | KIAA0367 | AB002365 |
| -0.01 | 0.97 | 1.13 | 2.01 | 2.02 | TTC3 | tetratricopeptide repeat domain 3 | AU131711 |
| 0.10 | 0.24 | 0.00 | 0.24 | 2.02 | LOC285831 | hypothetical protein LOC285831 | AA775731 |
| -1.45 | -0.27 | 1.29 | -1.90 | -2.02 | KIF5C | kinesin family member 5C | BF059313 |
| 0.52 | -0.42 | -1.38 | 1.65 | -2.02 | EIF4E3 | eukaryotic translation initiation factor 4E f | BE465037 |
| 0.53 | 1.30 | 0.77 | 0.86 | 2.02 | CCDC50 | coiled-coil domain containing 50 | AI681307 |
| 0.55 | -0.02 | 0.29 | -0.63 | 2.02 | EXOSC6 | exosome component 6 | NM_058219 |
| -0.26 | -0.87 | -2.02 | 2.00 | 2.01 | ZNF589 | zinc finger protein 589 | NM_016089 |
| -0.58 | -0.38 | -0.39 | -0.43 | 2.02 | CXorf45 | chromosome X open reading frame 45 | NM_024810 |
| 1.56 | -1.32 | -2.02 | 2.02 | -2.02 | EDG7 | endothelial differentiation, lysophosphatic | NM_012152 |
| 0.17 | -0.07 | -0.57 | -0.87 | -2.02 | PWCR1 | Prader-Willi syndrome chromosome regic | AW770748 |
| -0.41 | -0.24 | -0.71 | 1.62 | -2.02 | MGST1 | microsomal glutathione S-transferase 1 | D16947 |
| 0.10 | 0.89 | 1.33 | 2.00 | 2.02 | PLOD2 | procollagen-lysine, 2-oxoglutarate 5-diox | AI754404 |
| 0.90 | 2.02 | 0.00 | 0.00 | 0.00 | | Surfactant associated protein F mRNA, p | T96555 |
| -2.02 | 1.63 | 0.62 | 1.26 | 0.65 | TNFAIP2 | tumor necrosis factor, alpha-induced prot | NM_006291 |
| -0.30 | -0.93 | -1.33 | -1.73 | -2.01 | FLJ20674 | hypothetical protein FLJ20674 | NM_019086 |
| -0.09 | 0.34 | 0.38 | 0.65 | 2.01 | SPON1 | spondin 1, extracellular matrix protein | AB051390 |
| 1.06 | 0.90 | 0.75 | 1.13 | 2.01 | CMTM3 | CKLF-like MARVEL transmembrane dom | AL574900 |
| 0.42 | 0.58 | 0.61 | 0.77 | 2.01 | SCARF2 | scavenger receptor class F, member 2 | AI127800 |
| 0.91 | -0.09 | 0.11 | 0.91 | 2.01 | FAM57A | family with sequence similarity 57, memb | NM_024792 |
| 0.63 | 0.78 | 1.64 | 2.01 | 2.00 | SPPL2A | signal peptide peptidase-like 2A | AI674647 |
| 0.29 | 0.57 | 0.61 | 1.12 | 2.01 | CSGlcA-T | chondroitin sulfate glucuronyltransferase | AA534198 |
| 0.00 | 0.00 | -1.50 | 2.01 | -1.54 | HGF | hepatocyte growth factor (hepapoietin A; | M60718 |
| 1.10 | 1.67 | 1.48 | 1.83 | 2.01 | FAM65A | family with sequence similarity 65, memb | NM_024519 |
| 0.43 | 0.85 | 1.58 | 2.01 | 1.51 | EIF2C4 | Eukaryotic translation initiation factor 2C, | AI669957 |
| 0.00 | 0.00 | 0.54 | 2.01 | 1.34 | TRIM55 | tripartite motif-containing 55 | AW663544 |
| 0.72 | 0.88 | 1.11 | 2.01 | 1.38 | TMTC1 | transmembrane and tetratricopeptide rep | AU151239 |
| 0.06 | -0.26 | -2.01 | -2.01 | -2.01 | PRKAR1B | Protein kinase, cAMP-dependent, regulat | AI632259 |
| 0.78 | 1.27 | 1.79 | 2.01 | 1.47 | FAM83B | Family with sequence similarity 83, meml | AK024927 |
| -0.68 | 0.00 | 0.00 | 1.26 | 2.01 | KIAA1715 | KIAA1715 | AI814587 |
| 0.25 | 2.01 | -0.26 | 1.18 | 1.52 | MYLC2PL | myosin light chain 2, precursor lymphocyt | BC002778 |
| 0.33 | 0.64 | 1.11 | 1.50 | 2.01 | H2AFY | H2A histone family, member Y | NM_004893 |
| -0.39 | -0.62 | -0.57 | -0.96 | -2.01 | RBM35A | RNA binding motif protein 35A | NM_017697 |
| 0.45 | 1.51 | 1.00 | 1.51 | 2.01 | PRO1073 | PRO1073 protein | AA827878 |
| 0.12 | 0.38 | -2.01 | 1.82 | 1.85 | CAB39L | calcium binding protein 39-like | AW242839 |
| -0.17 | -0.49 | -0.60 | -1.04 | -2.01 | MAP7 | microtubule-associated protein 7 | AW242297 |
| 1.10 | -1.12 | -1.34 | 2.01 | -1.72 | BMPR2 | bone morphogenetic protein receptor, typ | AL046696 |
| -0.72 | -2.01 | -2.01 | 2.01 | -2.01 | RASGRP2 | RAS guanyl releasing protein 2 (calcium | AI688812 |
| 1.74 | 2.01 | 1.13 | 0.79 | 0.99 | | MRNA; cDNA DKFZp667B1718 (from clo | AA114166 |
| -0.47 | -1.12 | -1.65 | 1.78 | -2.01 | C3orf28 | chromosome 3 open reading frame 28 | NM_014367 |
| -0.24 | 0.34 | -1.35 | -1.73 | -2.01 | MXD4 | MAX dimerization protein 4 | AA831438 |
| -0.78 | -1.11 | -0.87 | -0.76 | -2.01 | USP32 | ubiquitin specific peptidase 32 /// ubiquitir | AF350251 |
| 2.01 | 1.80 | -0.76 | 1.24 | 0.24 | CAV2 | caveolin 2 | NM_001233 |
| -0.37 | -0.30 | -2.00 | -0.93 | 0.36 | SNAPC4 | small nuclear RNA activating complex, pc | AK023513 |
| 0.00 | 0.76 | 2.00 | 1.43 | 0.00 | SYNPR | synaptoporin | H11380 |
| 2.00 | 1.84 | 1.16 | 0.09 | -0.83 | LYPD1 | LY6/PLAUR domain containing 1 | AL567376 |
| 0.00 | 0.00 | 0.02 | 0.94 | 2.00 | HOXD13 | homeobox D13 | AI971104 |
| 0.37 | -1.25 | 1.57 | 2.00 | 1.66 | NRP2 | neuropilin 2 | AA295257 |
| -0.04 | -0.04 | -2.00 | 1.52 | -1.04 | PDCD4 | programmed cell death 4 (neoplastic tran | NM_014456 |
| -0.62 | -0.76 | -0.96 | -1.10 | -2.00 | SBK1 | SH3-binding domain kinase 1 | AI935915 |
| 0.00 | 0.00 | 0.19 | 1.58 | 2.00 | | Transcribed locus | AI678013 |

Appendix 2

| | | | | | Symbol | Description | Accession |
|---|---|---|---|---|---|---|---|
| -0.12 | -0.31 | 0.77 | 0.62 | -2.00 | WNK3 | WNK lysine deficient protein kinase 3 | H06509 |
| -0.57 | 0.69 | -0.87 | -1.28 | -2.00 | SP4 | Sp4 transcription factor | BF438799 |
| -0.65 | -1.17 | -1.81 | -2.00 | -1.84 | VAV3 | vav 3 oncogene | NM_006113 |
| -0.62 | -1.36 | -1.48 | -2.00 | -1.71 | ICAM3 | intercellular adhesion molecule 3 | NM_002162 |
| -0.49 | 0.41 | -0.63 | -0.69 | -2.00 | CNTNAP2 | contactin associated protein-like 2 | AC005378 |
| 0.92 | 0.12 | -1.09 | -2.00 | -1.53 | | gb:AA780067 /DB_XREF=gi:2839398 /DI | AA780067 |
| -2.00 | 0.00 | 0.00 | 0.83 | -1.17 | FGF18 | Fibroblast growth factor 18 | AI798863 |
| -1.08 | -1.27 | 0.78 | -1.35 | -2.00 | MYADM | myeloid-associated differentiation marker | BE908995 |
| -0.38 | 0.60 | -0.02 | 0.89 | -2.00 | OLFML2A | olfactomedin-like 2A | AL050002 |
| -0.11 | 0.03 | -0.55 | -1.26 | -2.00 | NMI | N-myc (and STAT) interactor | NM_004688 |
| 0.44 | -0.03 | -2.00 | -0.31 | -0.74 | C20orf199 | Chromosome 20 open reading frame 199 | AI625235 |
| 0.64 | 0.69 | 0.68 | 0.87 | -2.00 | SFXN1 | sideroflexin 1 | BF593817 |
| 0.77 | -1.30 | 1.99 | 1.92 | 0.85 | | Transcribed locus | AA993515 |
| -0.49 | -0.93 | -1.20 | -1.55 | -1.99 | ZIK1 | zinc finger protein interacting with K prote | AC003682 |
| 0.26 | -0.49 | 0.13 | 0.91 | -1.99 | CYB5D1 | cytochrome b5 domain containing 1 | NM_144607 |
| 0.43 | 0.64 | 1.77 | 1.99 | -0.95 | MYO5B | myosin VB | AI991160 |
| 0.15 | 0.51 | 0.20 | 0.76 | -1.99 | SLC7A8 | solute carrier family 7 (cationic amino aci | NM_012244 |
| 0.35 | 0.62 | 1.07 | 1.99 | 1.63 | CALD1 | caldesmon 1 | AU147402 |
| 0.11 | -0.45 | 0.23 | 0.90 | -1.99 | WHSC1 | Wolf-Hirschhorn syndrome candidate 1 | AI770166 |
| 0.00 | 0.03 | 0.00 | 0.17 | -1.99 | PDGFC | platelet derived growth factor C | AB033831 |
| -0.44 | 0.19 | 0.35 | -0.05 | -1.99 | SCC-112 | SCC-112 protein | AW991219 |
| 0.00 | 0.00 | 0.18 | 0.51 | -1.99 | | MRNA full length insert cDNA clone EUR | BE620374 |
| 1.02 | 0.08 | 1.99 | 1.46 | -0.47 | MXI1 | MAX interactor 1 /// MAX interactor.1 | NM_005962 |
| -0.21 | 0.70 | -1.38 | 1.57 | -1.99 | PDCD2L | programmed cell death 2-like /// programi | BC006146 |
| 0.34 | -0.26 | -0.70 | -0.32 | -1.99 | THADA | thyroid adenoma associated | AI286226 |
| 0.42 | -1.43 | -1.99 | 1.99 | -1.99 | TMEM132D | transmembrane protein 132D | AW166133 |
| 0.00 | 0.00 | 0.80 | 1.99 | 0.00 | SLC16A6 | solute carrier family 16, member 6 (mono | NM_004694 |
| 1.19 | -0.02 | 1.50 | 0.95 | 1.99 | COL6A1 | collagen, type VI, alpha 1 | BE350145 |
| 1.62 | 1.99 | 1.99 | 1.99 | 1.99 | LHFPL4 | lipoma HMGIC fusion partner-like 4 | AL540045 |
| 0.00 | 0.13 | 1.42 | 1.99 | 1.73 | HOXB5 | homeobox B5 | AI052747 |
| 1.13 | 0.99 | 1.99 | 1.86 | 1.97 | UNC5B | unc-5 homolog B (C. elegans) | AK022859 |
| 0.15 | 0.68 | 1.30 | 1.99 | 1.66 | ALAD | aminolevulinate, delta-, dehydratase | BC000977 |
| -0.04 | 0.08 | 1.01 | 1.99 | 1.68 | C5orf30 | chromosome 5 open reading frame 30 | AL565741 |
| -0.98 | 0.76 | 0.51 | -0.57 | -1.99 | LOC440132 | hypothetical LOC440132 | AA514237 |
| -0.35 | -0.99 | -1.98 | -1.68 | -0.33 | ETS2 | v-ets erythroblastosis virus E26 oncogen | NM_005239 |
| 1.04 | -1.23 | -1.32 | -1.30 | -1.98 | ME2 | malic enzyme 2, NAD(+)-dependent, mitc | M55905 |
| 1.47 | 1.98 | 1.56 | 1.22 | 0.75 | PPM1K | protein phosphatase 1K (PP2C domain c | AV706522 |
| 0.52 | -0.68 | -0.81 | -1.19 | -1.98 | SLC27A5 | solute carrier family 27 (fatty acid transpo | NM_012254 |
| 0.00 | 1.52 | 1.98 | 1.56 | 0.00 | | gb:AI741514 /DB_XREF=gi:5109802 /DB | AI741514 |
| -0.30 | -0.08 | 0.86 | 1.78 | 1.98 | | Transcribed locus | AW021102 |
| 0.20 | 1.63 | 1.98 | 1.06 | 1.24 | CRABP2 | cellular retinoic acid binding protein 2 | NM_001878 |
| 1.26 | 1.98 | 1.02 | 0.46 | 1.59 | CD44 | CD44 molecule (Indian blood group) | M24915 |
| -0.26 | -0.98 | -1.08 | -1.68 | -1.98 | FAM83F | family with sequence similarity 83, memb | BE786265 |
| 0.80 | -1.46 | -1.74 | -1.72 | -1.98 | SLC29A1 | solute carrier family 29 (nucleoside trans | AF079117 |
| 1.98 | 1.56 | 0.86 | 0.57 | 0.48 | FLJ25076 | similar to CG4502-PA | H17038 |
| -1.98 | -1.67 | -0.70 | 0.55 | 1.20 | SFRP1 | secreted frizzled-related protein 1 | AI332407 |
| 0.32 | -1.65 | -1.98 | 1.98 | 1.98 | SPIB | Spi-B transcription factor (Spi-1/PU.1 rela | NM_003121 |
| 0.08 | 0.51 | 1.46 | 1.98 | 1.57 | KIAA0323 | KIAA0323 | AB002321 |
| -1.24 | -0.61 | -1.35 | -1.98 | -1.98 | FGFR4 | fibroblast growth factor receptor 4 | AF359241 |
| -0.78 | 0.27 | 0.84 | 1.98 | 1.45 | MALAT1 | metastasis associated lung adenocarcino | AF001540 |
| 1.21 | 1.23 | 0.44 | 0.18 | 1.98 | PTRF | polymerase I and transcript release facto | AL545542 |
| 1.25 | 1.43 | 1.62 | 1.52 | 1.98 | ELF4 | E74-like factor 4 (ets domain transcriptior | NM_001421 |
| 0.70 | 1.30 | 0.86 | 1.49 | 1.98 | TNFRSF10D | tumor necrosis factor receptor superfamil | AI738556 |
| -0.46 | -0.06 | -0.14 | 1.41 | 1.98 | MID1 | Midline 1 (Opitz/BBB syndrome) | BF055144 |
| 0.20 | 0.16 | 1.43 | 1.98 | 1.31 | MARK1 | MAP/microtubule affinity-regulating kinas | AI183517 |
| 1.17 | 1.98 | 1.41 | 1.68 | 1.90 | MALT1 | mucosa associated lymphoid tissue lymp | AF070528 |
| 0.49 | 1.47 | 0.74 | 1.98 | 1.40 | | gb:BF439579 /DB_XREF=gi:11452017 /D | BF439579 |
| 0.21 | 0.70 | -0.51 | 0.84 | -1.97 | GPHN | gephyrin | NM_020806 |
| 0.45 | 0.97 | -1.31 | -1.97 | -1.73 | ASXL1 | additional sex combs like 1 (Drosophila) | AL034550 |
| 0.31 | 1.28 | 1.97 | 1.44 | 0.28 | MANEA | mannosidase, endo-alpha | NM_024641 |
| 0.11 | 0.16 | 0.39 | 0.46 | -1.97 | VAPA | VAMP (vesicle-associated membrane pro | AL571942 |
| 0.72 | 0.78 | 0.96 | 1.97 | 0.36 | ACOX3 | acyl-Coenzyme A oxidase 3, pristanoy | BF055171 |
| 0.70 | 1.24 | -1.38 | -1.97 | 1.48 | KLHL9 | kelch-like 9 (Drosophila) | AW138594 |
| 0.57 | 1.38 | -1.97 | 0.02 | 1.89 | SPRY4 | Sprouty homolog 4 (Drosophila) | AK024556 |
| -0.11 | -0.79 | -0.92 | -1.16 | -1.97 | CA11 | carbonic anhydrase XI | AB018195 |
| 1.97 | 0.00 | 0.00 | 0.00 | -0.87 | NAV3 | neuron navigator 3 | NM_014903 |
| 0.99 | 1.47 | 0.47 | -1.03 | -1.97 | CCDC50 | coiled-coil domain containing 50 | AI247881 |
| 0.00 | 0.00 | 1.04 | 1.48 | 1.97 | EGR1 | early growth response 1 | NM_001964 |
| 1.38 | 0.26 | -0.60 | -0.23 | -1.97 | LANCL2 | LanC lantibiotic synthetase component C | AJ278245 |
| -0.20 | -0.44 | -0.51 | -1.16 | -1.97 | RBM35A | RNA binding motif protein 35A | BF001941 |
| 0.00 | 0.73 | 0.31 | 1.97 | 0.81 | ADAMTSL4 | ADAMTS-like 4 | AF217974 |
| 0.50 | 1.39 | 1.97 | 1.95 | 1.78 | STARD10 | START domain containing 10 | D60944 |
| 1.17 | 1.57 | 1.92 | 1.97 | 1.83 | TEAD3 | TEA domain family member 3 | AF142482 |
| 0.14 | -0.25 | -1.51 | -1.97 | -1.49 | PHB | prohibitin | NM_002634 |
| 0.00 | 0.00 | 0.00 | 1.97 | 1.04 | LMO1 | LIM domain only 1 (rhombotin 1) | NM_002315 |
| -0.47 | 1.33 | 1.52 | 1.86 | 1.97 | MT1M | metallothionein 1M | AL031602 |
| -0.50 | -0.68 | -0.92 | -1.33 | -1.97 | SBK1 | SH3-binding domain kinase 1 | BF447901 |
| 0.00 | 0.00 | 0.00 | 0.06 | 1.97 | SLITRK6 | SLIT and NTRK-like family, member 6 | AL137517 |
| 1.89 | 1.97 | 0.36 | 1.16 | 1.02 | ACTN1 | actinin, alpha 1 | M95178 |
| 0.20 | -0.32 | -0.45 | -0.42 | -1.97 | SCFD2 | sec1 family domain containing 2 | AW205790 |
| 0.36 | 0.18 | 0.56 | 1.59 | 1.97 | TLK2 | Tousled-like kinase 2 | AW962705 |
| 0.55 | -0.60 | -1.73 | 1.96 | -0.99 | | CDNA FLJ33420 fis, clone BRACE20200 | AA206016 |
| 0.61 | 1.13 | 1.96 | 1.96 | 1.35 | CYP27A1 | cytochrome P450, family 27, subfamily A | NM_000784 |
| -0.97 | -0.03 | 0.03 | 1.96 | 0.20 | AHSA2 | AHA1, activator of heat shock 90kDa pro | AI986239 |
| 1.43 | 1.36 | 0.92 | 1.96 | 1.75 | ITGAV | Integrin, alpha V (vitronectin receptor, alp | AW962458 |
| 0.92 | 0.93 | 0.43 | 1.81 | 1.96 | COL1A2 | Collagen, type I, alpha 2 | AA628535 |
| 1.96 | 0.94 | -0.68 | -0.68 | -0.68 | GAL | galanin | NM_015973 |

The invention claimed is:

1. A method of differentiating primate Pluripotent Stem Cells (pPSCs) into Isl1+ mesoderm cells comprising (a) providing pPSCs; (b) contacting the pPSCs with an effective amount of at least one GSK inhibitor selected from the group consisting of a GSK3 inhibitor and a Wnt protein in a cell differentiation medium for a period sufficient to produce mesendoderm cells; and (c) subsequently contacting the cells obtained from step (b) with an effective amount of a bone morphogenic protein (BMP) and optionally, a GSK inhibitor selected from the group consisting of a GSK3 inhibitor and a Wnt protein for a period sufficient to produce said mesoderm cells; and (d) optionally, isolating said mesoderm cells.

2. The method according to claim 1 wherein said pPSCs are human embryonic stem cells (hESCs).

3. The method according to claim 1 wherein said GSK inhibitor of step (b) or step (c) is selected from the group consisting of
BIO (2'Z,3'E)-6-Bromoindirubin-3'-oxime (GSK3 Inhibitor IX),
BIO-Acetoxime (2'Z,3'E)-6-Bromoindirubin-3'-acetoxime (GSK3 Inhibitor X),
(5-Methyl-1H-pyrazol-3-yl)-(2-phenylquinazolin-4-yl) amine (GSK3-Inhibitor XIII),
Pyridocarbazole-cyclopenadienylruthenium complex (GSK3 Inhibitor XV),
TDZD-8 4-Benzyl-2-methyl-1,2,4-thiadiazolidine-3,5-dione (GSK3β Inhibitor I),
2-Thio(3-iodobenzyl)-5-(1-pyridyl)-[1,3,4]-oxadiazole (GSK3β Inhibitor II),
OTDZT 2,4-Dibenzyl-5-oxothiadiazolidine-3-thione (GSK3β Inhibitor III),
α-4-Dibromoacetophenone (GSK3β Inhibitor VII),
AR-A014418 N-(4-Methoxybenzyl)-N'-(5-nitro-1,3-thiazol-2-yl)urea (GSK-3β Inhibitor VIII),
3-(1-(3-Hydroxypropyl)-1H-pyrrolo[2,3-b]pyridin-3-yl]-4-pyrazin-2-yl-pyrrole-2,5-dione (GSK-3β Inhibitor XI),
TWS119 pyrrolopyrimidine compound (GSK3β Inhibitor XII),
L803 H-KEAPPAPPQSpP-NH₂ or its Myristoylated form (GSK3β Inhibitor XIII),
2-Chloro-1-(4,5-dibromo-thiophen-2-yl)-ethanone (GSK3β Inhibitor VI), and mixtures thereof.

4. The method according to claim 1 wherein said GSK inhibitor of step b) is a Wnt protein.

5. The method according to claim 4 wherein said Wnt protein is selected from the group consisting of Wnt1, Wnt2, Wnt3, Wnt3a, Wnt4, Wnt10, Wnt 14, Wnt14b, Wnt15, Wnt16 and mixtures thereof.

6. The method according to claim 1 wherein said GSK inhibitor of step b) is BIO (2'Z,3'E)-6-Bromoindirubin-3'-oxime (GSK3 Inhibitor IX).

7. The method according to claim 4 wherein said Wnt protein is Wnt3a.

8. The method according to claim 1 wherein said contacting step (b) occurs for a period ranging from about 18 to 72 hours.

9. The method according to claim 1 wherein said bone morphogenic protein is selected from the group consisting of BMP-2, BMP-4, BMP-6, BMP-7 and mixtures thereof.

10. The method according to claim 1 wherein said contacting step (c) occurs for a period ranging from about 3 days to about 9 days.

11. The method according to claim 1 wherein said cell differentiation medium is at least a minimum essential medium plus one or more optional components selected from the group consisting of growth factors, ascorbic acid, glucose, non-essential amino acids, salts (including trace elements), glutamine, insulin, Activin A, transferring and beta mercaptoethanol.

12. The method according to claim 1 wherein said cell differentiation medium is selected from the group consisting of Dulbecco's modified Eagle's medium (DMEM), Knockout Dulbecco's modified Eagle's medium (KO DMEM) and Ham's F12/DMEM basal medium (50:50) further including albumin, antibiotics, trace minerals, ascorbic acid, β-mercaptoethanol, fibroblast growth factor (FGF) and insulin-like growth factor analog (LR-IGF).

13. The method according to claim 1 wherein said cell differentiation medium is DMEM/F12 (50:50) containing effective amounts of proalbumin, pen/strep antibiotic, non-essential amino acids, trace minerals, ascorbic Acid, β-Mercaptoethanol, fibroblast growth factor (FGF), insulin-like growth factor analogue (LR-IGF), Activin A and Heregulin.

14. The method according to claim 1 wherein said GSK inhibitor of step c) is a Wnt protein.

15. The method according to claim 14 wherein said Wnt protein is selected from the group consisting of Wnt1, Wnt2, Wnt3, Wnt3a, Wnt4, Wnt10, Wnt14, Wnt14b, Wnt15, Wnt16 and mixtures thereof.

16. The method according to claim 1 wherein said GSK inhibitor of step c) is BIO (2'Z,3'E)-6-Bromoindirubin-3'-oxime (GSK3 Inhibitor IX).

17. The method according to claim 15 wherein said Wnt protein is Wnt3a.

18. The method according to claim 1 wherein said pPSCs are human induced pluripotent stem cells (hiPSCs).

19. A method of differentiating primate Pluripotent Stem Cells (pPSCs) into Isl1+ mesoderm cells comprising (a) providing pPSCs; (b) contacting the pPSCs with an effective amount of at least one GSK inhibitor selected from the group consisting of a GSK3 inhibitor and a Wnt protein in a cell differentiation medium for a period ranging from about 18 hours to about 72 hours to produce mesendoderm cells; and (c) subsequently contacting the cells obtained from step (b) with an effective amount of a bone morphogenic protein (BMP) and optionally, a GSK inhibitor selected from the group consisting of a GSK3 inhibitor or a Wnt protein for a period of about two days to about 9 days to produce said mesoderm cells; and (d) optionally, isolating said mesoderm cells.

20. A method of producing Isl1+ mesoderm cells from pPSCs comprising culturing said pPSCs in a differentiation medium with an effective amount of a GSK inhibitor in combination with an effective amount of a bone morphogenic protein and optionally, isolating said Isl1+ mesoderm cells.

21. The method according to claim 20 wherein said pPSCs human embryonic stem cells (hESCs).

22. The method according to claim 20 wherein said pPSCs are human induced pluripotent stem cells (hiPSCs).

23. The method according to claim 20 wherein said GSK inhibitor is selected from the group consisting of
BIO (2'Z,3'E)-6-Bromoindirubin-3'-oxime (GSK3 Inhibitor IX),
BIO-Acetoxime (2'Z,3'E)-6-Bromoindirubin-3'-acetoxime (GSK3 Inhibitor X),
(5-Methyl-1H-pyrazol-3-yl)-(2-phenylquinazolin-4-yl) amine (GSK3-Inhibitor XIII),
Pyridocarbazole-cyclopenadienylruthenium complex (GSK3 Inhibitor XV),
TDZD-8 4-Benzyl-2-methyl-1,2,4-thiadiazolidine-3,5-dione (GSK3β Inhibitor I), 2-Thio(3-iodobenzyl)-5-(1-pyridyl)-[1,3,4]-oxadiazole (GSK3β Inhibitor II),
OTDZT 2,4-Dibenzyl-5-oxothiadiazolidine-3-thione (GSK3β Inhibitor III),
α-4-Dibromoacetophenone (GSK3β Inhibitor VII),
AR-A014418 N-(4-Methoxybenzyl)-N'-(5-nitro-1,3-thiazol-2-yl)urea (GSK-3β Inhibitor VIII),
3-(1-(3-Hydroxypropyl)-1H-pyrrolo[2,3-b]pyridin-3-yl]-4-pyrazin-2-yl-pyrrole-2,5-dione (GSK-3β Inhibitor XI),
TWS119 pyrrolopyrimidine compound (GSK3β Inhibitor XII),
L803 H-KEAPPAPPQSpP-NH$_2$ or its Myristoylated form (GSK3β Inhibitor XIII),
2-Chloro-1-(4,5-dibromo-thiophen-2-yl)-ethanone (GSK3β Inhibitor VI), and mixtures thereof.

24. The method according to claim 20 wherein said GSK inhibitor is a Wnt protein.

25. The method according to claim 24 wherein said Wnt protein is selected from the group consisting of Wnt1, Wnt2, Wnt3, Wnt3a, Wnt4, Wnt10, Wnt 14, Wnt14b, Wnt15, Wnt16 and mixtures thereof.

26. The method according to claim 20 wherein said GSK inhibitor is BIO (2'Z,3'E)-6-Bromoindirubin-3'-oxime (GSK3 Inhibitor IX).

27. The method according to claim 24 wherein said Wnt protein is Wnt3a.

28. The method according to claim 24 wherein said bone morphogenic protein is selected from the group consisting of BMP-2, BMP-4, BMP-6, BMP-7 and mixtures thereof.

29. The method according to claim 20 wherein said cell differentiation medium is at least a minimum essential medium plus one or more optional components selected from the group consisting of growth factors, ascorbic acid, glucose, non-essential amino acids, salts (including trace elements), glutamine, insulin, Activin A, transferring and beta mercaptoethanol.

30. The method according to claim 20 wherein said cell differentiation medium is selected from the group consisting of Dulbecco's modified Eagle's medium (DMEM), Knock-out Dulbecco's modified Eagle's medium (KO DMEM) and Ham's F12/DMEM basal medium (50:50) further including albumin, antibiotics, trace minerals, ascorbic acid, beta mercaptoethanol, fibroblast growth factor (FGF) and insulin-like growth factor analog (LR-IGF).

31. The method according to claim 20 wherein said cell differentiation medium is DMEM/F12 (50:50) containing effective amounts of proalbumin, pen/strep antibiotic, non-essential amino acids, trace minerals, ascorbic Acid, β-Mercaptoethanol, fibroblast growth factor (FGF), insulin-like growth factor analogue (LR-IGF), Activin A and Heregulin.

32. A method of differentiating mesendoderm cells into Isl1+ mesoderm cells comprising contacting said mesendoderm cells with an effective amount of a bone morphogenic protein and optionally, a GSK inhibitor in a cell differentiation medium for a period ranging from about 2-9 days to produce Isl1+ mesoderm cells and optionally, isolating said mesoderm cells.

33. The method according to claim 32 wherein said GSK inhibitor is selected from the group consisting of:
BIO (2'Z,3'E)-6-Bromoindirubin-3'-oxime (GSK3 Inhibitor IX),
BIO-Acetoxime (2'Z,3'E)-6-Bromoindirubin-3'-acetoxime (GSK3 Inhibitor X),
(5-Methyl-1H-pyrazol-3-yl)-(2-phenylquinazolin-4-yl)amine (GSK3-Inhibitor XIII),
Pyridocarbazole-cyclopenadienylruthenium complex (GSK3 Inhibitor XV),
TDZD-8 4-Benzyl-2-methyl-1,2,4-thiadiazolidine-3,5-dione (GSK3β Inhibitor I),
2-Thio(3-iodobenzyl)-5-(1-pyridyl)-[1,3,4]-oxadiazole (GSK3β Inhibitor II),
OTDZT 2,4-Dibenzyl-5-oxothiadiazolidine-3-thione (GSK3β Inhibitor III),
α-4-Dibromoacetophenone (GSK3β Inhibitor VII),
AR-A014418 N-(4-Methoxybenzyl)-N'-(5-nitro-1,3-thiazol-2-yl)urea (GSK-3β Inhibitor VIII),
3-(1-(3-Hydroxypropyl)-1H-pyrrolo[2,3-b]pyridin-3-yl]-4-pyrazin-2-yl-pyrrole-2,5-dione (GSK-3β Inhibitor XI),
TWS119 pyrrolopyrimidine compound (GSK3β Inhibitor XII),
L803 H-KEAPPAPPQSpP-NH$_2$ or its Myristoylated form (GSK3β Inhibitor XIII),
2-Chloro-1-(4,5-dibromo-thiophen-2-yl)-ethanone (GSK3β Inhibitor VI), and mixtures thereof.

34. The method according to claim 32 wherein said GSK inhibitor is a Wnt protein.

35. The method according to claim 34 wherein said Wnt protein is selected from the group consisting of Wnt1, Wnt2, Wnt3, Wnt3a, Wnt4, Wnt10, Wnt 14, Wnt14b, Wnt15, Wnt16 and mixtures thereof.

36. The method according to claim 33 wherein said GSK inhibitor is BIO (2'Z,3'E)-6-Bromoindirubin-3'-oxime (GSK3 Inhibitor IX).

37. The method according to claim 35 wherein said Wnt protein is Wnt3a.

38. The method according to claim 32 wherein said contacting step occurs for a period ranging from about 3 to about 6 days.

39. The method according to claim 32 wherein said bone morphogenic protein is selected from the group consisting of BMP-2, BMP-4, BMP-6, BMP-7 and mixtures thereof.

40. The method according to claim 39 wherein said contacting occurs for a period ranging from about 3 days to about 5 days.

* * * * *